(12) United States Patent
Boström et al.

(10) Patent No.: US 8,415,378 B2
(45) Date of Patent: Apr. 9, 2013

(54) ISOXAZOL-3(2H)-ONE ANALOGS AS THERAPEUTIC AGENTS

(75) Inventors: Jonas Boström, Mölndal (SE); Leifeng Cheng, Mölndal (SE); Tomas Fex, Mölndal (SE); Michael Karle, Mölndal (SE); Daniel Pettersen, Mölndal (SE); Peter Schell, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 323 days.

(21) Appl. No.: 12/755,010

(22) Filed: Apr. 6, 2010

(65) Prior Publication Data

US 2010/0261755 A1 Oct. 14, 2010

Related U.S. Application Data

(60) Provisional application No. 61/167,224, filed on Apr. 7, 2009, provisional application No. 61/171,956, filed on Apr. 23, 2009.

(51) Int. Cl.

| | | |
|---|---|---|
| *A01N 43/40* | (2006.01) | |
| *A01N 43/80* | (2006.01) | |
| *A61K 31/445* | (2006.01) | |
| *A61K 31/42* | (2006.01) | |
| *C07D 401/00* | (2006.01) | |
| *C07D 405/00* | (2006.01) | |
| *C07D 409/00* | (2006.01) | |
| *C07D 411/00* | (2006.01) | |
| *C07D 413/00* | (2006.01) | |
| *C07D 417/00* | (2006.01) | |
| *C07D 419/00* | (2006.01) | |
| *C07D 421/00* | (2006.01) | |
| *C07D 261/00* | (2006.01) | |
| *C07D 307/02* | (2006.01) | |
| *C07D 315/00* | (2006.01) | |
| *C07D 407/00* | (2006.01) | |

(52) U.S. Cl.
USPC ........... 514/326; 514/380; 546/209; 548/243; 549/472; 549/475

(58) Field of Classification Search .................. 548/243; 514/380, 326; 546/209; 549/472, 475
See application file for complete search history.

(56) References Cited

U.S. PATENT DOCUMENTS

2008/0081803 A1 4/2008 Butora et al. ............ 514/211.02

FOREIGN PATENT DOCUMENTS

WO WO 95/14683 6/1995

OTHER PUBLICATIONS

Boulton et. al., Tetrahedron, 1964, Pergamon Press Ltd, vol. 20, pp. 2835-2840.*

STN International File Registry; CHEMCATS, RN 884230-75-5 (Aug. 18, 2010).
R.D. Allan et al., "Synthesis of Analogues of GABA. IX* 5-(Aminomethyl)-3-hydroxyfuran-2(5H)-one", Aust. J. Chem. 36:977-981 (1983).
N. Badham et al., "A Practical Synthesis of the PDE4 Inhibitor, SB-207499, from a Cyclohexanone Precursor", Org. Proc. Res. Dev. 7: 101-108 (2003).
R.F. Borne et al., "Synthesis and X-Ray Crystal Structures of Isonipecotinamide Derivatives as Reverse Amide Analogues of Fentanyl", J. Heterocylic Chem. 27: 375-384 (1990).
J.R. Byberg et al., "Synthesis and Biological Activity of a GABA$_A$ Agonist Which Has No Effect on Benzodiazepine Binding and of Structurally Related Glycine Antagonists", Drug Design and Delivery 1: 261-274 (1987).
J.R. Byberg et al., "Conformational Analysis and Molecular Modelling of a Partial GABA$_A$ Agonist and a Glycine Antagonist Related to the GABA$_A$ Agonist, Thip", Drug Design and Delivery 10: 213-229 (1993).

(Continued)

*Primary Examiner* — Sreeni Padmanabhan
*Assistant Examiner* — Sarah Pihonak
(74) *Attorney, Agent, or Firm* — James Kastenmayer

(57) ABSTRACT

I

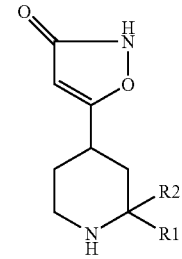

or a pharmaceutically suitable salt thereof, wherein,
$R^1$ and $R^2$ independently are hydrogen, deuterium, aryl, hetero aryl, C1-C8 alkyl, optionally being substituted with one or more substituents independently being $R^3$,
$R^3$ is an aryl, hetero aryl, fluorine(s), a C1-C6 alkyl containing one or more fluorine, a C1-C6 alkyl containing one or more deuterium, a C1-C6 alkyl containing hydroxy, the aryl and heteroaryl optionally being substituted with one or more halogen, a fluorinated alkoxy, a fluorinated alkyl, a sulfonyl, one or more deuterium, a C1-6 alkyl, a C1-6 alkoxy, a nitrile,
or $R^3$ is a C1-6 alkyl optionally substituted with one or more of the following groups: COOR4, OCOR4, CONR5R6, NR5COR6, OR4;
wherein, R4 is a C1-10 alkyl optionally substituted with one or more fluorine, deuterium, alkoxy, arylcarboxylate, alkyl carboxylate;
R5 and R6 are independently selected from hydrogen, alkyl or they may together form a 4-8 membered carbon ring;
or R1 and R2 form a 3-10 membered carbon ring optionally comprising O or N and optionally substituted with a C1-10 alkyl or aryl, hetero aryl optionally substituted with R3.

4 Claims, 13 Drawing Sheets

OTHER PUBLICATIONS

D.L. Comins et al., "Addition of Grignard Reagents to 1-Acyl-4-Methoxypyridinium Salts. An Approach to the Synthesis of Quinolizidinones", Tetrahedron Lett. 27(38): 4549-4552 (1986).

E. Falch et al., "Heteroaryl Analogues of AMPA. 2. Synthesis, Absolute Stereochemistry, Photochemistry, and Structure—Activity Relationships", J. Med. Chem. 41: 2513-2523 (1998).

D. Frolund et al., "Partial $GABA_A$ Receptor Agonists. Synthesis and in Vitro Pharmacology of a Series of Nonannulated Analogs of 4,5,6,7-Tetrahydroisoxazolo[5,4-c]pyridin-3-ol", J. Med. Chem. 38:3287-3296 (1995).

D. Frolund et al., "A Novel Class of Potent 3-Isoxazolol $GABA_A$ Antagonists: Design, Synthesis and Pharmacology", J. Med. Chem. 43: 4930-4933 (2000).

D. Frolund et al., "Novel Class of Potent 4-Arylalkyl 3-Isoxazolol $GABA_A$ Antagonists: Design, Synthesis and Pharmacology", J. Med. Chem. 45: 2454-2468 (2002).

D. Geffken et al., "Zur Cyclisierenden Carbonylierung 3-Hydroxycarbohydroxamsauren mit 1,1'- Carbonyldiimidazol", Liebigs Ann. Chem. 219-225 (1982).

P. Krogsgaard-Larsen et al., "2 Heterocylic Analogues of GABA: Chemistry, Molecular Pharmacology and Therapeutic Aspects", Progress in Medicinal Chemistry 22:67-120 (1985).

P. Krogsgaard-Larsen et al., "Recent Advances in GABA Agonists, Antagonists and Uptake Inhibitors: Structure-Activity Relationships and Therapeutic Potential", Advances in Drug Research 17:381-456 (1988).

A. Metzger et al., "LiCl-Mediated Preparation of Highly Functionalized Benzylic Zinc Chlorides", Org. Lett. 10(6): 1107-1110 (2008).

A. Nazih et al., "Synthesis of (±)-4-Substituted Pipecolinic Acids from 4-Alkylpyridines", Synlett 1337-1338 (1998).

U. Sorensen et al., "A Novel Route to 5-Substituted 3-Isoxazolols Cyclization of N,O-DiBoc β-Keto Hydroxamic Acids Synthesized Via Acyl Meldrum's Acids", J. Org. Chem. 65: 1003-1007 (2000).

P.S. Watson et al., "A Diastereoselective Synthesis of 2,4,-Disubstituted Piperidines: Scaffolds for Drug Discovery", Organic Letters 2(23): 3679-3681 (2000).

* cited by examiner

Figure 1: XRPD pattern for example 55
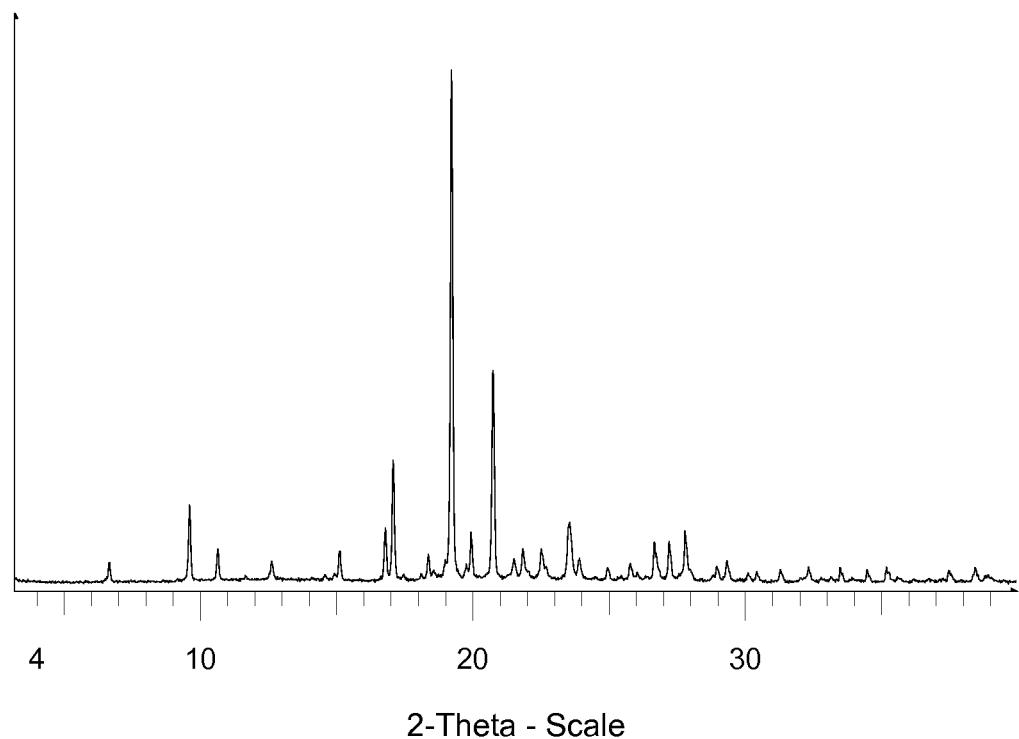

Figure 2: XRPD pattern for example 55 HCl salt
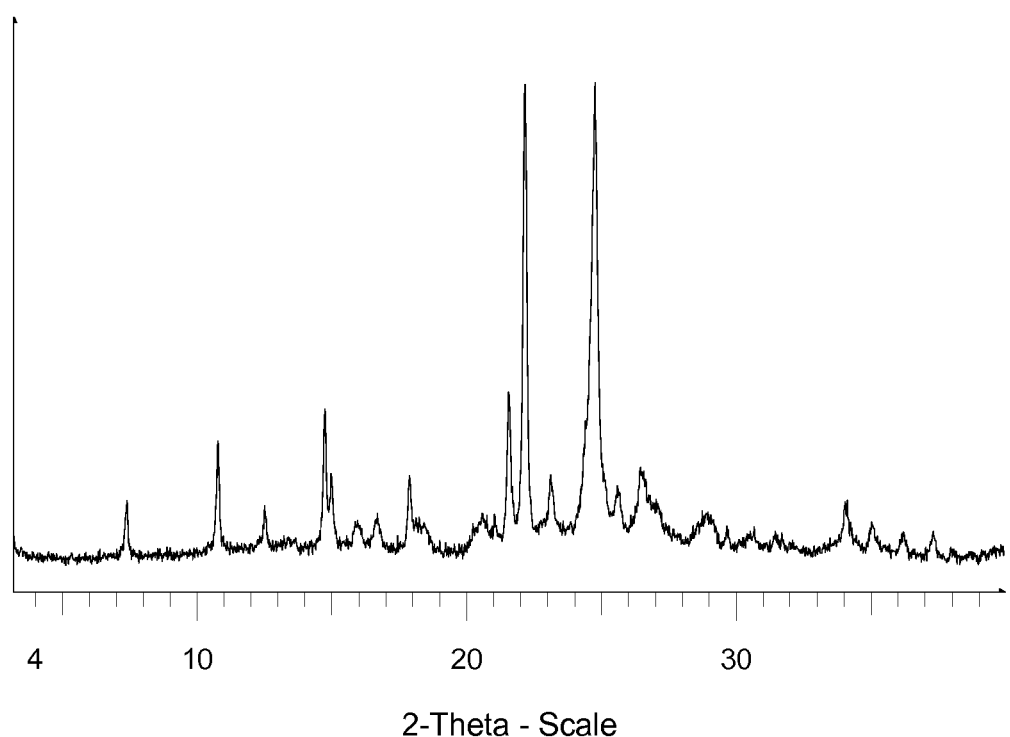

Figure 3: XRPD pattern for example 143
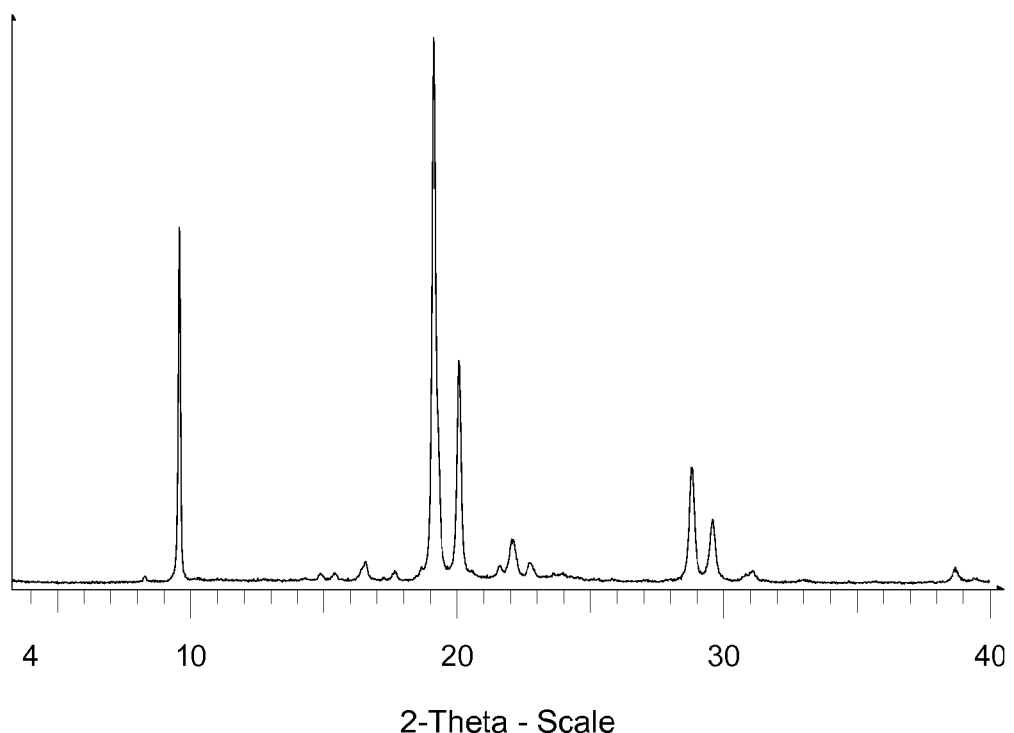

Figure 4: XRPD pattern for example 143 HCl salt
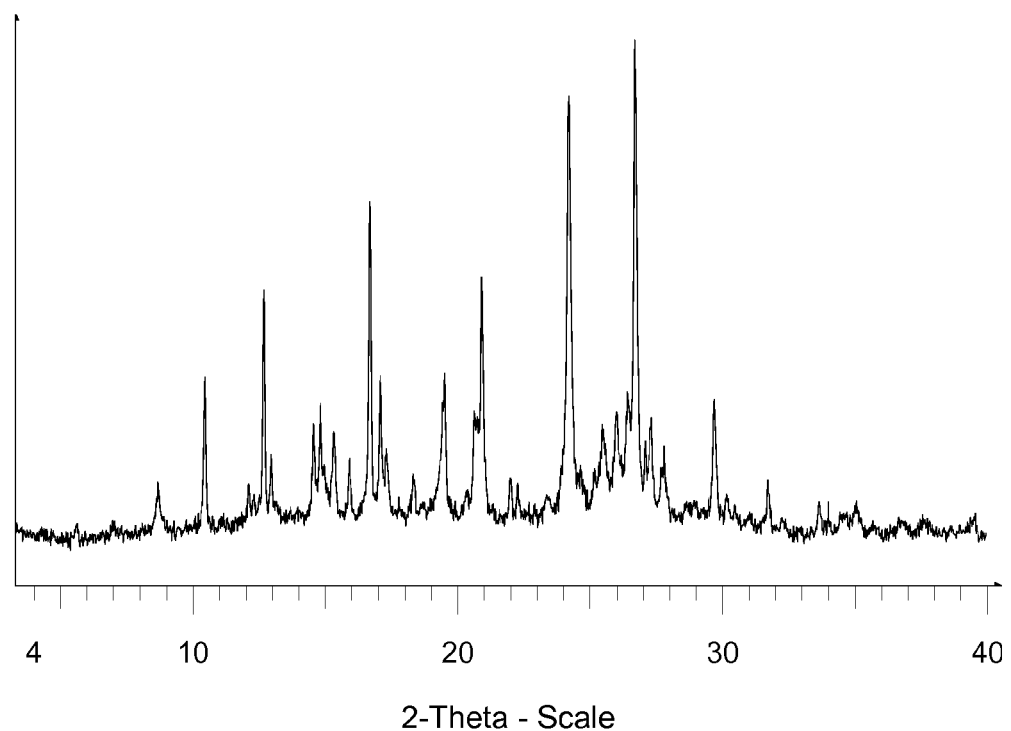

Figure 5: XRPD pattern for example 104
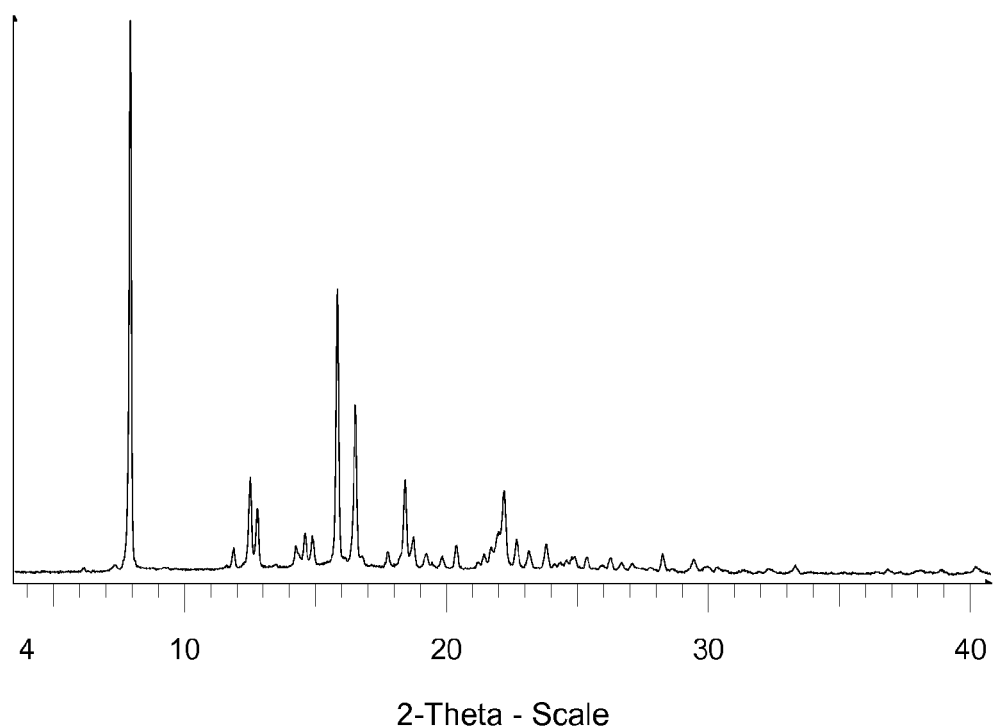

Figure 6: XRPD pattern for example 104 HCl salt
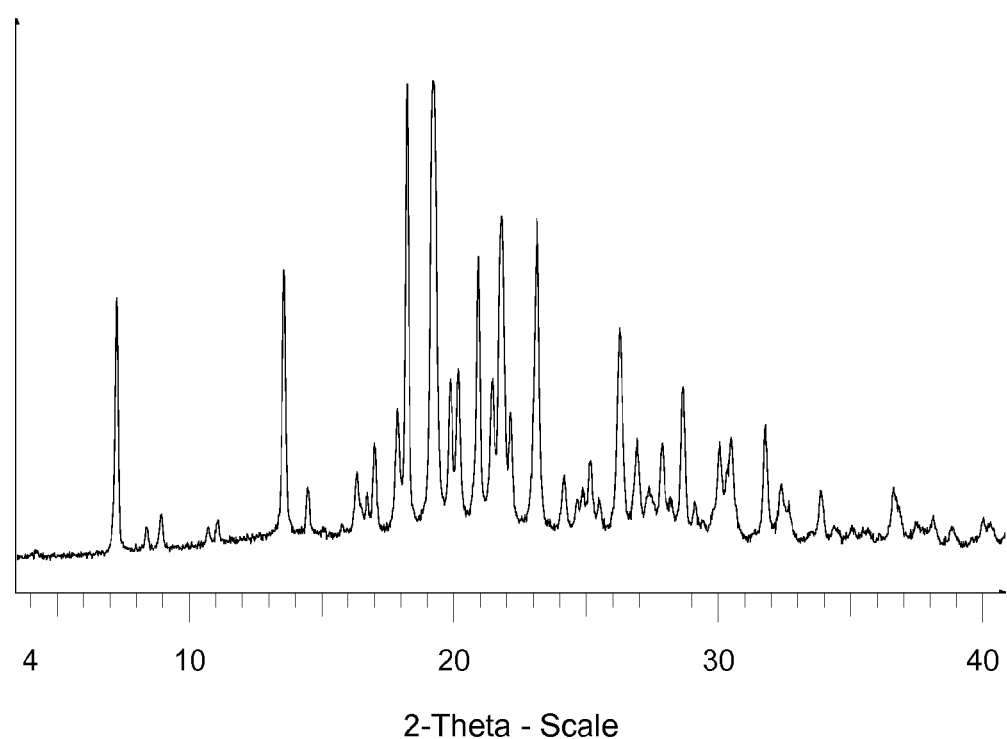

Figure 7: XRPD pattern for example 65
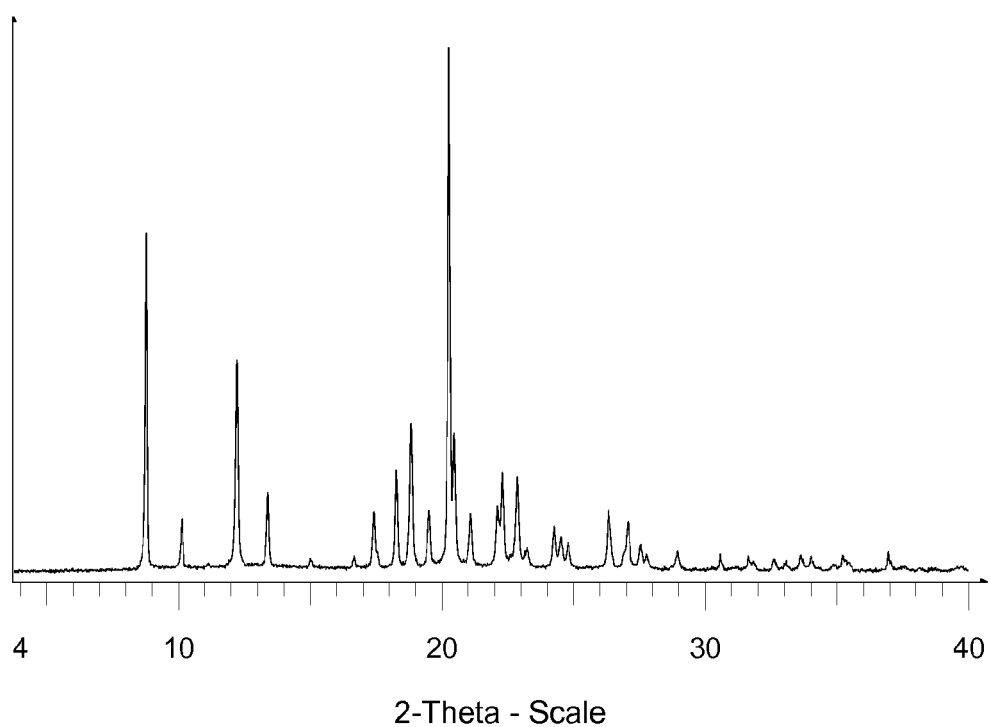

Figure 8: XRPD pattern for example 65 HCl salt
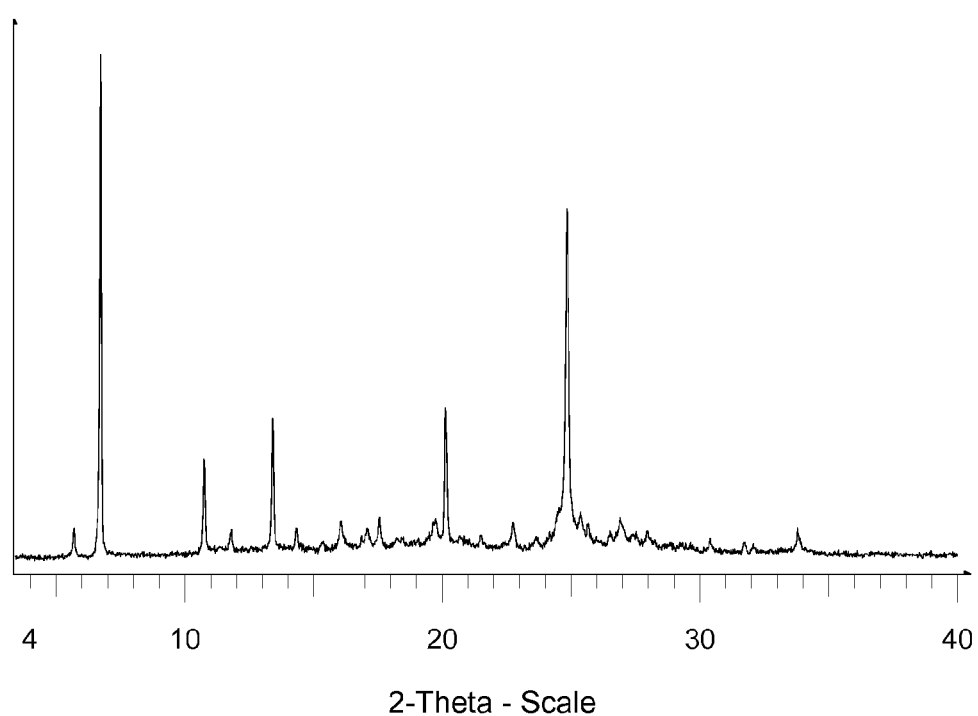

Figure 9: XRPD pattern for example 14
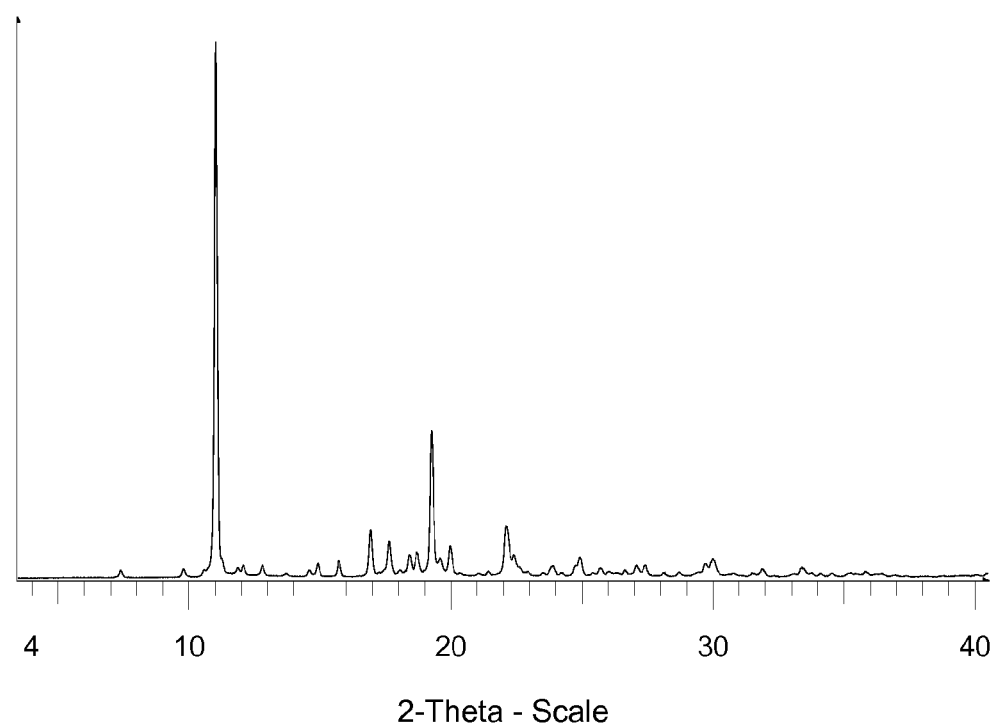

Figure 10: XRPD pattern for example 14 HCl salt
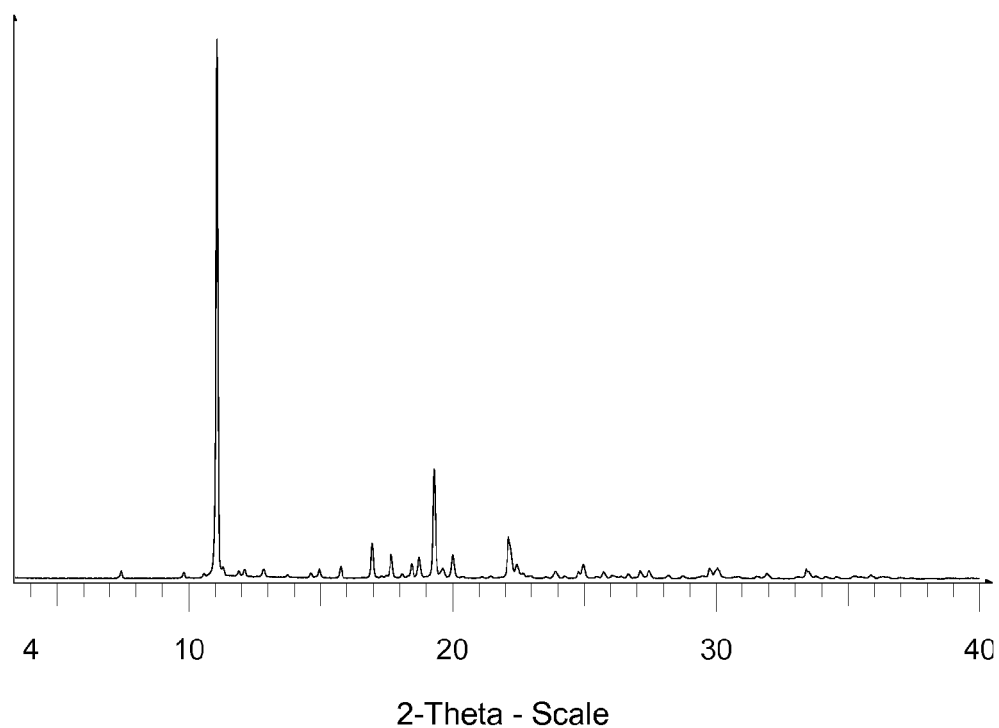

Figure 11: XRPD pattern for example 18 HCl salt
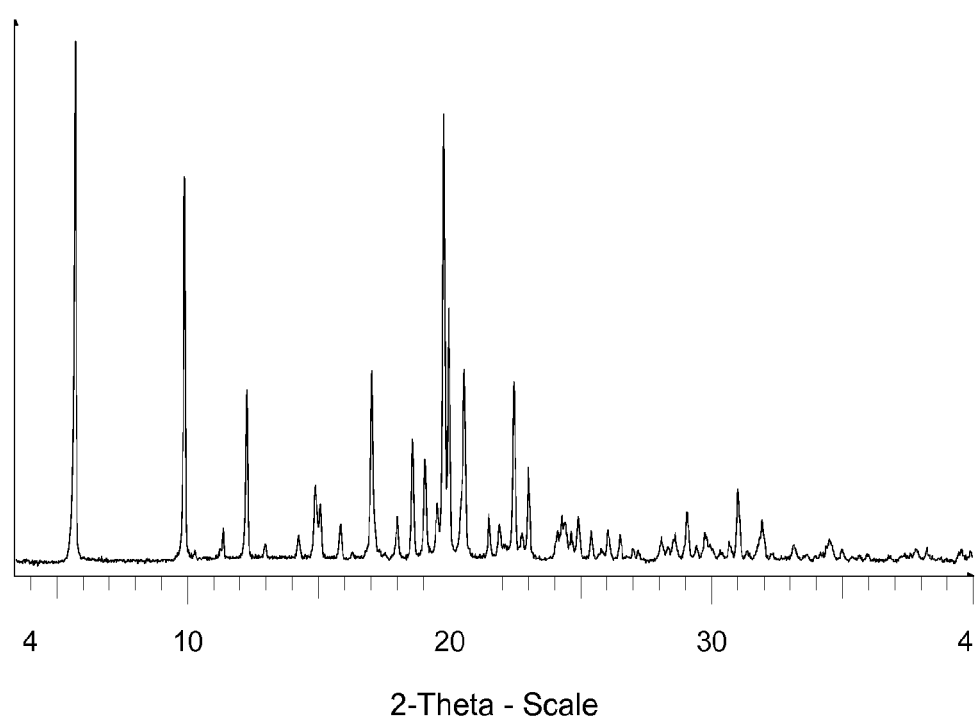

Figure 12: XRPD pattern for example 115
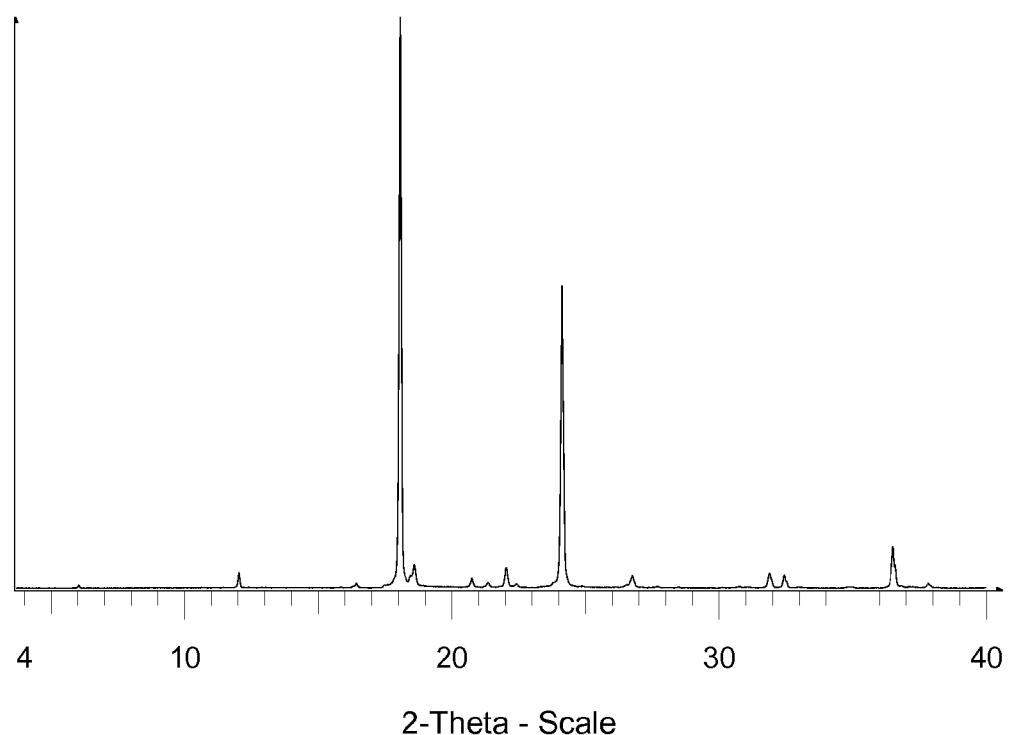

Figure 13: XRPD pattern for example 10 HCl salt
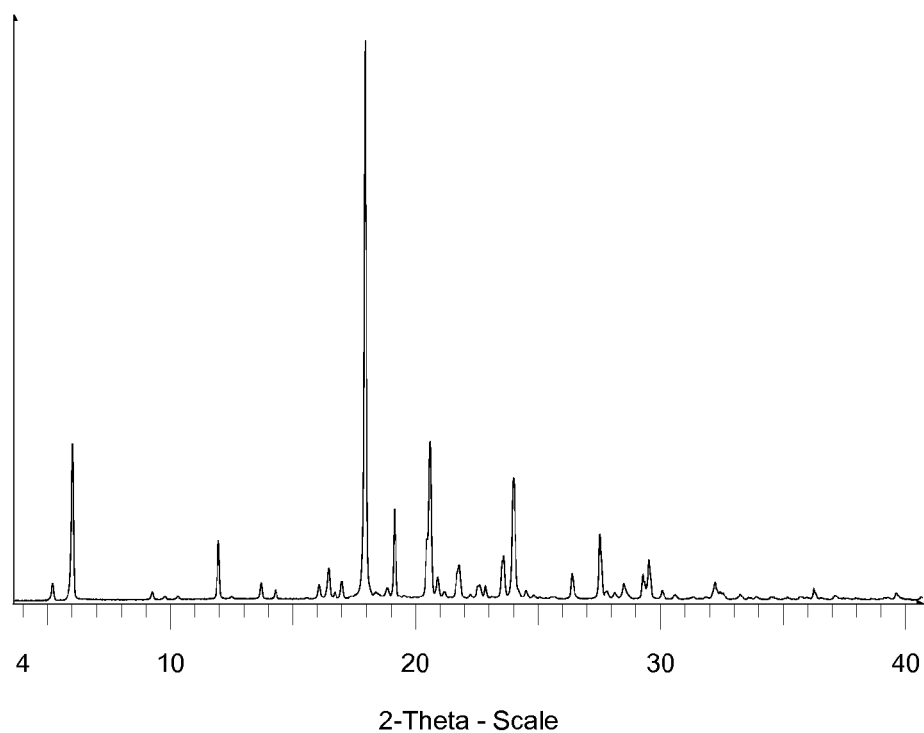

ISOXAZOL-3(2H)-ONE ANALOGS AS THERAPEUTIC AGENTS

This application claims the benefit under 35 U.S.C. 119(e) of U.S. Provisional Application No. 61/167,224, filed Apr. 7, 2009, and U.S. Provisional Application No. 61/171,956, filed Apr. 23, 2009, both of which are herein incorporated by reference in their entirety.

FIELD OF INVENTION

The present invention relates to compounds of formula I, to a pharmaceutical composition comprising them, and to their use in treating fibrinolysis related diseases or conditions, for example inherited bleeding disorders, stroke, menorrhagia and liver diseases and for the treatment of hereditary angioedema.

BACKGROUND

Bleeding is a common clinical problem in trauma, surgery, bleeding disorders, stroke, menorrhagia and liver diseases. Treatment of bleeding includes agents in primary and secondary haemostasis as well as fibrinolysis inhibition.

The fibrinolytic system comprises an inactive zymogen, plasminogen (PLG), that can be activated to the active enzyme plasmin (PLN). PLN degrades insoluble fibrin into soluble fibrin fragments. The result of this activity is the dissolution of the fibrin clot. The activation of plasminogen to plasmin occurs on the clot surface after binding to fibrin. Mediators of the activation are urokinase plasminogen activator (u-PA) or tissue-type plasminogen activator (t-PA).

Activation of the fibrinolytic process can be used to treat thrombotic conditions. Conversely, inhibition of fibrinolysis can be, and is, used for treatment of bleeding conditions. There are several possible targets for the inhibition of fibrinolysis. Activation of plasminogen activator inhibitor 1 (PAI-1), inhibition of u-PA and/or t-PA activity, inhibition of PLN activity and activation of antiplasmin are examples. Specific inhibition of proteolytic sites in tPA, uPA and PLN is difficult. However, bleeding control via inhibition of plasmin(ogen) fibrin binding by lysine analogues has been proven in humans as a safe and effective mechanism of action.

Inhibition of fibrinolysis via a lysine mimetic is a validated concept for reducing blood-loss, without increased risk for thrombotic complications, for instance following surgery, in menorrhagia, haemophilia and von Willebrands disease.

Potential uses of the compounds are to block plasmin-induced proteolysis as a universal pathomechanism propagating cancer, and cardiovascular, inflammatory, and many other diseases.

Antifibrinolytics have also been successfully used to treat hereditary angioedema. In this disease the skin or mucosa around the mouth, throat and tongue rapidly swell up. Swelling can occur at other places like limbs or genitals. For reasons that are not well-understood antifibrinolytics can be used as a prophylaxis or acute treatment of hereditary angioedema.

Tranexamic acid, currently the compound on the market to treat menorrhagia, requires very high and multiple doses and has gastrointestinal side effects. Its use has been described in "Tranexamic acid. A review of its use in surgery and other indications"; Dunn, C. J.; Goa K. L.; Drugs 1999, June 57 (6): 1005-1032.

OBJECT OF THE INVENTION

An object of the invention is to provide for a pharmaceutical compound to prevent or treat excess bleeding, the treatment or prevention therapy having one or more improvements such as enhanced efficacy, selectivity, permeability, duration, less side effects and improved bio availability.

BRIEF DESCRIPTION OF THE DRAWINGS

FIG. 1 shows X-ray powder diffraction pattern of a typical sample of example 55.
FIG. 2 shows X-ray powder diffraction pattern of a typical sample of example 55 HCl salt.
FIG. 3 shows X-ray powder diffraction pattern of a typical sample of example 143.
FIG. 4 shows X-ray powder diffraction pattern of a typical sample of example 143 HCl salt.
FIG. 5 shows X-ray powder diffraction pattern of a typical sample of example 104.
FIG. 6 shows X-ray powder diffraction pattern of a typical sample of example 104 HCl salt.
FIG. 7 shows X-ray powder diffraction pattern of a typical sample of example 65.
FIG. 8 shows X-ray powder diffraction pattern of a typical sample of example 65 HCl salt.
FIG. 9 shows X-ray powder diffraction pattern of a typical sample of example 14.
FIG. 10 shows X-ray powder diffraction pattern of a typical sample of example 14 HCl salt.
FIG. 11 shows X-ray powder diffraction pattern of a typical sample of example 18 HCl salt.
FIG. 12 shows X-ray powder diffraction pattern of a typical sample of example 115.
FIG. 13 shows X-ray powder diffraction pattern of a typical sample of example 10 HCl salt.

DESCRIPTION OF THE INVENTION

The present invention provides for a compound of formula I:

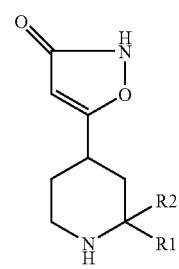

or a pharmaceutically suitable salt thereof, wherein,
R1 and R2 independently are hydrogen, deuterium, aryl, hetero aryl, C1-C8 alkyl, optionally being substituted with one or more substituents independently being R3,
R3 is an aryl, hetero aryl, fluorine(s), a C1-C6 alkyl containing one or more fluorine, a C1-C6 alkyl containing one or more deuterium, a C1-C6 alkyl containing hydroxy, the aryl and heteroaryl optionally being substituted with one or more halogen, a fluorinated alkoxy, a fluorinated alkyl, a sulfonyl, one or more deuterium, a C1-6 alkyl, a C1-6 alkoxy, a nitrile,
or R3 is a C1-6 alkyl optionally substituted with one or more of the following groups: COOR4, OCOR4, CONR5R6, NR5COR6, OR4;

wherein, R4 is a C1-10 alkyl optionally substituted with one or more fluorine, deuterium, alkoxy, arylcarboxylate, alkyl carboxylate R5 and R6 are independently selected from hydrogen, alkyl or they may together form a 4-8 membered carbon ring;

or R1 and R2 form a 3-10 membered carbon ring optionally comprising O or N and optionally substituted with a C1-10 alkyl or aryl, hetero aryl optionally substituted with R3.

According to an embodiment of the invention R1 and R2 can be independently hydrogen, deuterium, hetero aryl, C1-C8 alkyl, optionally being substituted with one or more substituents independently being R3, R3 is an aryl, hetero aryl, fluorine(s), a C1-C6 alkyl containing one or more fluorine, a C1-C6 alkyl containing one or more deuterium, a C1-C6 alkyl containing hydroxy, the aryl and heteroaryl optionally being substituted with one or more halogen, a fluorinated alkoxy, a fluorinated alkyl, a sulfonyl, one or more deuterium, a C1-6 alkyl, a C1-6 alkoxy, a nitrile, or R3 is a C1-6 alkyl optionally substituted with one or more of the following groups: COOR4, OCOR4, CONR5R6, NR5COR6, OR4;

wherein, R4 is a C1-10 alkyl optionally substituted with one or more fluorine, deuterium, alkoxy, arylcarboxylate, alkyl carboxylate;

R5 and R6 are independently selected from hydrogen, alkyl or they may together form a 4-8 membered carbon ring;

or R1 and R2 form a 3-10 membered carbon ring optionally comprising O or N and optionally substituted with a C1-10 alkyl or aryl, hetero aryl optionally substituted with R3.

The word alkyl includes straight alkyls, branched alkyls and 3-8 membered ring-formed alkyls. The word hetero aryl is a variant of a five or six membered ring system with one or more heteroatoms, i.e. not C, selected from N, O, or S.

According to another aspect of the invention there is provided for a compound of formula Ia:

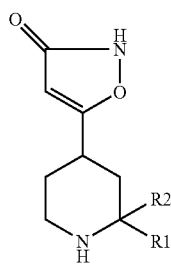

Ia or a pharmaceutically suitable salt thereof, wherein,

R1 and R2 independently are hydrogen, C1-C8 alkyl, optionally being substituted with R3, R3 is an aryl, the aryl optionally being substituted with one or more fluorine, or OR4, R4 is a C1-C6 alkyl.

According to another aspect of the invention it is provided for a compound selected from one or more of the following compounds:

5-((2S,4S)-2-Benzylpiperidin-4-yl)isoxazol-3(2H)-one;
5-((2R,4R)-2-Benzylpiperidin-4-yl)isoxazol-3(2H)-one;
5-((2R,4S)-2-Benzylpiperidin-4-yl)isoxazol-3(2H)-one;
5-((2S,4R)-2-Benzylpiperidin-4-yl)isoxazol-3(2H)-one;
5-((2S,4S)-2-Isobutylpiperidin-4-yl)isoxazol-3(2H)-one;
5-((2S,4R)-2-Isobutylpiperidin-4-yl)isoxazol-3(2H)-one;
5-((2S,4S)-2-Isobutylpiperidin-4-yl)isoxazol-3(2H)-one;
5-((2R,4S)-2-Phenethylpiperidin-4-yl)isoxazol-3(2H)-one;
5-((2S,4R)-2-Phenethylpiperidin-4-yl)isoxazol-3(2H)-one;
5-((2S,4S)-2-Phenethylpiperidin-4-yl)isoxazol-3(2H)-one;
5-((2S,4S)-2-(4-tert-Butylbenzyl)piperidin-4-yl)isoxazol-3(2H)-one;
5-((2R,4S)-2-(4-tert-Butylbenzyl)piperidin-4-yl)isoxazol-3(2H)-one;
5-((2S,4S)-2-Neopentylpiperidin-4-yl)isoxazol-3(2H)-one;
5-((2R,4S)-2-Neopentylpiperidin-4-yl)isoxazol-3(2H)-one;
5-((2R,4S)-2-Methylpiperidin-4-yl)isoxazol-3(2H)-one;
5-((2S,4R)-2-Methylpiperidin-4-yl)isoxazol-3(2H)-one;
5-((2S,4S)-2-Methylpiperidin-4-yl)isoxazol-3(2H)-one;
5-((2S,4S)-2-(2-Methyl-2-phenylpropyl)piperidin-4-yl)isoxazol-3(2H)-one;
5-((2R,4S)-2-(2-Methyl-2-phenylpropyl)piperidin-4-yl)isoxazol-3(2H)-one;
5-((2R,4S)-2-(Cyclohexylmethyl)piperidin-4-yl)isoxazol-3(2H)-one;
5-((2R,4R)-2-(Cyclohexylmethyl)piperidin-4-yl)isoxazol-3(2H)-one;
5-((2S,4S)-2-(Cyclohexylmethyl)piperidin-4-yl)isoxazol-3(2H)-one;
5-((2R,4S)-2-(3,4-Difluorophenyl)piperidin-4-yl)isoxazol-3(2H)-one;
5-(Trans-2-(3,4-difluorophenyl)piperidin-4-yl)isoxazol-3(2H)-one;
5-((2R,4S)-2-(4-Fluorophenyl)piperidin-4-yl)isoxazol-3(2H)-one;
5-(Trans-2-(4-fluorophenyl)piperidin-4-yl)isoxazol-3(2H)-one;
5-((2R,4S)-2-(4-Chlorophenyl)piperidin-4-yl)isoxazol-3(2H)-one;
5-((2S,4R)-2-(4-Chlorophenyl)piperidin-4-yl)isoxazol-3(2H)-one;
5-(Trans-2-(4-chlorophenyl)piperidin-4-yl)isoxazol-3(2H)-one;
5-((2R,4S)-2-(3-(Trifluoromethyl)phenyl)piperidin-4-yl)isoxazol-3(2H)-one;
5-((2S,4R)-2-(3-(Trifluoromethyl)phenyl)piperidin-4-yl)isoxazol-3(2H)-one;
5-(Trans-2-(3-(trifluoromethyl)phenyl)piperidin-4-yl)isoxazol-3(2H)-one;
5-((2R,4S)-2-(4-(Trifluoromethyl)phenyl)piperidin-4-yl)isoxazol-3(2H)-one;
5-((2S,4R)-2-(4-(Trifluoromethyl)phenyl)piperidin-4-yl)isoxazol-3(2H)-one;
5-(Trans-2-(4-(trifluoromethyl)phenyl)piperidin-4-yl)isoxazol-3(2H)-one;
5-((2R,4S)-2-(3-tert-Butylphenyl)piperidin-4-yl)isoxazol-3(2H)-one;
5-(Trans-2-(4-tert-butylphenyl)piperidin-4-yl)isoxazol-3(2H)-one;
5-((2R,4S)-2-(4-(Methylsulfonyl)phenyl)piperidin-4-yl)isoxazol-3(2H)-one;
5-((Trans-2-(4-(methylsulfonyl)phenyl)piperidin-4-yl)isoxazol-3(2H)-one;
5-((2R,4S)-2-(6-(Trifluoromethyl)pyridin-3-yl)piperidin-4-yl)isoxazol-3(2H)-one;
5-(Trans-2-(6-(trifluoromethyl)pyridin-3-yl)piperidin-4-yl)isoxazol-3(2H)-one;
5-((2R,4S)-2-(5-tert-Butylthiophen-2-yl)piperidin-4-yl)isoxazol-3(2H)-one;
5-((2S,4R)-2-(5-tert-Butylthiophen-2-yl)piperidin-4-yl)isoxazol-3(2H)-one;
5-((2R,4S)-2-(2,4-Difluorophenyl)piperidin-4-yl)isoxazol-3(2H)-one;
5-((2R,4S)-2-(4-Chloro-2-fluorophenyl)piperidin-4-yl)isoxazol-3(2H)-one;

5-(Trans-2-(4-chloro-2-fluorophenyl)piperidin-4-yl)isoxazol-3(2H)-one;
5-((2R,4S)-2-(2-Chloro-4-fluorophenyl)piperidin-4-yl)isoxazol-3(2H)-one;
5-(Trans-2-(2-chloro-4-fluorophenyl)piperidin-4-yl)isoxazol-3(2H)-one;
5-((2R,4S)-2-(4-Chloro-3-fluorophenyl)piperidin-4-yl)isoxazol-3(2H)-one;
5-(Trans-2-(4-chloro-3-fluorophenyl)piperidin-4-yl)isoxazol-3(2H)-one;
5-((2R,4S)-2-(2,4-Dichlorophenyl)piperidin-4-yl)isoxazol-3(2H)-one;
5-((2S,4R)-2-(2,4-Dichlorophenyl)piperidin-4-yl)isoxazol-3(2H)-one;
5-((2S,4S)-2-(2,4-Dichlorophenyl)piperidin-4-yl)isoxazol-3(2H)-one;
5-((2R,4R)-2-(2,4-Dichlorophenyl)piperidin-4-yl)isoxazol-3(2H)-one;
5-((2R,4S)-2-(3,5-Dichlorophenyl)piperidin-4-yl)isoxazol-3(2H)-one;
5-((2S,4R)-2-(3,5-Dichlorophenyl)piperidin-4-yl)isoxazol-3(2H)-one;
5-(Trans-2-(3,5-dichlorophenyl)piperidin-4-yl)isoxazol-3(2H)-one;
5-((2R,4S)-2-(2-Fluoro-4-(trifluoromethoxy)phenyl)piperidin-4-yl)isoxazol-3(2H)-one;
5-(Trans-2-(2-fluoro-4-(trifluoromethoxy)phenyl)piperidin-4-yl)isoxazol-3(2H)-one;
5-((2R,4S)-2-(3,4,5-Trifluorophenyl)piperidin-4-yl)isoxazol-3(2H)-one;
5-((2S,4R)-2-(3,4,5-Trifluorophenyl)piperidin-4-yl)isoxazol-3(2H)-one;
5-(Trans-2-(3,4,5-trifluorophenyl)piperidin-4-yl)isoxazol-3(2H)-one;
5-((2R,4S)-2-(2,4,5-Trifluorophenyl)piperidin-4-yl)isoxazol-3(2H)-one;
5-((2S,4S)-2-(2,4,5-Trifluorophenyl)piperidin-4-yl)isoxazol-3(2H)-one;
5-((2R,4S)-2-(4-Chloro-3,5-difluorophenyl)piperidin-4-yl)isoxazol-3(2H)-one;
5-(Trans-2-(4-chloro-3,5-difluorophenyl)piperidin-4-yl)isoxazol-3(2H)-one;
5-((2R,4S)-2-(3-Methyl-4-(trifluoromethyl)phenyl)piperidin-4-yl)isoxazol-3(2H)-one;
5-((2S,4R)-2-(3-Methyl-4-(trifluoromethyl)phenyl)piperidin-4-yl)isoxazol-3(2H)-one;
5-(Trans-2-(3-methyl-4-(trifluoromethyl)phenyl)piperidin-4-yl)isoxazol-3(2H)-one;
5-((2R,4S)-2-(3,5-Difluoro-4-(trifluoromethyl)phenyl)piperidin-4-yl)isoxazol-3(2H)-one;
5-(Trans-2-(3,5-difluoro-4-(trifluoromethyl)phenyl)piperidin-4-yl)isoxazol-3(2H)-one;
5-((2R,4S)-2-(2-Methyl-4-(trifluoromethyl)phenyl)piperidin-4-yl)isoxazol-3(2H)-one;
5-((2R,4S)-2-(2-Fluoro-4-(trifluoromethyl)phenyl)piperidin-4-yl)isoxazol-3(2H)-one;
5-(Trans-2-(2-fluoro-4-(trifluoromethyl)phenyl)piperidin-4-yl)isoxazol-3(2H)-one;
5-((2R,4S)-2-(3-fluoro-4-(trifluoromethyl)phenyl)piperidin-4-yl)isoxazol-3(2H)-one;
5-((2S,4R)-2-(3-Fluoro-4-(trifluoromethyl)phenyl)piperidin-4-yl)isoxazol-3(2H)-one;
5-((2R,4S)-2-Phenylpiperidin-4-yl)isoxazol-3(2H)-one;
5-((2S,4S)-2-Phenylpiperidin-4-yl)isoxazol-3(2H)-one;
5-((2R,4S)-2-Cyclohexylpiperidin-4-yl)isoxazol-3(2H)-one;
5-((2S,4S)-2-Cyclohexylpiperidin-4-yl)isoxazol-3(2H)-one;
5-((2R,4S)-2-(2-Methyl-2H-tetrazol-5-yl)piperidin-4-yl)isoxazol-3(2H)-one;
5-(Trans-2-(2-methyl-2H-tetrazol-5-yl)piperidin-4-yl)isoxazol-3(2H)-one;
5-((2R,4S)-2-(1-Methyl-1H-tetrazol-5-yl)piperidin-4-yl)isoxazol-3(2H)-one;
5-((2R,4S)-2-(Cyclohexyloxymethyl)piperidin-4-yl)isoxazol-3(2H)-one;
5-((2S,4R)-2-(Cyclohexyloxymethyl)piperidin-4-yl)isoxazol-3(2H)-one;
5-(Trans-2-(cyclohexyloxymethyl)piperidin-4-yl)isoxazol-3(2H)-one;
5-((2R,4S)-2-(Difluoromethyl)piperidin-4-yl)isoxazol-3(2H)-one;
5-(Trans-2-(difluoromethyl)piperidin-4-yl)isoxazol-3(2H)-one;
5-((2S,4S)-2-((4,4-Difluorocyclohexyl)methyl)piperidin-4-yl)isoxazol-3(2H)-one;
5-((2R,4R)-2-((4,4-Difluorocyclohexyl)methyl)piperidin-4-yl)isoxazol-3(2H)-one;
5-(Trans-2-((4,4-difluorocyclohexyl)methyl)piperidin-4-yl)isoxazol-3(2H)-one;
5-((2S,4S)-2-(4-Fluorophenethyl)piperidin-4-yl)isoxazol-3(2H)-one;
5-((2R,4R)-2-(4-Fluorophenethyl)piperidin-4-yl)isoxazol-3(2H)-one;
5-(Trans-2-(4-fluorophenethyl)piperidin-4-yl)isoxazol-3(2H)-one;
5-((2S,4S)-2-(3,3-Dimethylbutyl)piperidin-4-yl)isoxazol-3(2H)-one;
5-((2R,4S)-2-(3,3-Dimethylbutyl)piperidin-4-yl)isoxazol-3(2H)-one;
5-((2R,4S)-2-(4-Fluorobenzyl)piperidin-4-yl)isoxazol-3(2H)-one;
5-((2S,4S)-2-(4-Fluorobenzyl)piperidin-4-yl)isoxazol-3(2H)-one;
5-((2R,4S)-2-(3-Fluorobenzyl)piperidin-4-yl)isoxazol-3(2H)-one;
5-((2S,4S)-2-(3-Fluorobenzyl)piperidin-4-yl)isoxazol-3(2H)-one;
5-((2R,4S)-2-(2-Fluorobenzyl)piperidin-4-yl)isoxazol-3(2H)-one;
5-((2S,4S)-2-(2-Fluorobenzyl)piperidin-4-yl)isoxazol-3(2H)-one;
5-((2R,4R)-2-(2-Fluorobenzyl)piperidin-4-yl)isoxazol-3(2H)-one;
5-((2R,4S)-2-(4-(Trifluoromethyl)benzyl)piperidin-4-yl)isoxazol-3(2H)-one;
5-((2S,4S)-2-(4-(Trifluoromethyl)benzyl)piperidin-4-yl)isoxazol-3(2H)-one;
5-((2R,4R)-2-(4-(Trifluoromethyl)benzyl)piperidin-4-yl)isoxazol-3(2H)-one;
5-((2R,4S)-2-(3-(Trifluoromethyl)benzyl)piperidin-4-yl)isoxazol-3(2H)-one;
5-((2S,4R)-2-(3-(Trifluoromethyl)benzyl)piperidin-4-yl)isoxazol-3(2H)-one;
5-(Trans-2-(3-(trifluoromethyl)benzyl)piperidin-4-yl)isoxazol-3(2H)-one;
5-((2R,4S)-2-(2-(Trifluoromethyl)benzyl)piperidin-4-yl)isoxazol-3(2H)-one;
5-((2S,4R)-2-(2-(trifluoromethyl)benzyl)piperidin-4-yl)isoxazol-3(2H)-one;
5-(Trans-2-(2-(trifluoromethyl)benzyl)piperidin-4-yl)isoxazol-3(2H)-one;
5-((2R,4S)-2-(4-(Trifluoromethoxy)benzyl)piperidin-4-yl)isoxazol-3(2H)-one;

5-(Trans-2-(4-(trifluoromethoxy)benzyl)piperidin-4-yl)isoxazol-3(2H)-one;
5-((2R,4S)-2-(4-Chlorobenzyl)piperidin-4-yl)isoxazol-3(2H)-one;
5-(Trans-2-(4-chlorobenzyl)piperidin-4-yl)isoxazol-3(2H)-one;
5-((2R,4S)-2-(4-(Methylsulfonyl)benzyl)piperidin-4-yl)isoxazol-3(2H)-one;
5-((2S,4R)-2-(4-(Methylsulfonyl)benzyl)piperidin-4-yl)isoxazol-3(2H)-one;
5-(Trans-2-(4-(methylsulfonyl)benzyl)piperidin-4-yl)isoxazol-3(2H)-one;
5-((2R,4S)-2-(3,4-Difluorobenzyl)piperidin-4-yl)isoxazol-3(2H)-one;
5-((2S,4R)-2-(3,4-Difluorobenzyl)piperidin-4-yl)isoxazol-3(2H)-one;
5-((2S,4S)-2-(3,4-Difluorobenzyl)piperidin-4-yl)isoxazol-3(2H)-one;
5-((2R,4R)-2-(3,4-Difluorobenzyl)piperidin-4-yl)isoxazol-3(2H)-one;
5-((2R,4S)-2-(2,5-Difluorobenzyl)piperidin-4-yl)isoxazol-3(2H)-one;
5-((2S,4R)-2-(2,5-Difluorobenzyl)piperidin-4-yl)isoxazol-3(2H)-one;
5-(Trans-2-(2,5-difluorobenzyl)piperidin-4-yl)isoxazol-3(2H)-one;
5-((2R,4S)-2-(2,6-Difluorobenzyl)piperidin-4-yl)isoxazol-3(2H)-one;
5-((2S,4R)-2-(2,6-Difluorobenzyl)piperidin-4-yl)isoxazol-3(2H)-one;
5-(Trans-2-(2,6-difluorobenzyl)piperidin-4-yl)isoxazol-3(2H)-one;
5-((2R,4S)-2-(3,5-Difluorobenzyl)piperidin-4-yl)isoxazol-3(2H)-one;
5-((2S,4R)-2-(3,5-Difluorobenzyl)piperidin-4-yl)isoxazol-3(2H)-one;
5-((2S,4S)-2-(3,5-Difluorobenzyl)piperidin-4-yl)isoxazol-3(2H)-one;
5-((2R,4R)-2-(3,5-Difluorobenzyl)piperidin-4-yl)isoxazol-3(2H)-one;
5-((2R,4S)-2-(2,4-Difluorobenzyl)piperidin-4-yl)isoxazol-3(2H)-one;
5-((2S,4R)-2-(2,4-Difluorobenzyl)piperidin-4-yl)isoxazol-3(2H)-one;
5-(Trans-2-(2,4-difluorobenzyl)piperidin-4-yl)isoxazol-3(2H)-one;
5-((2R,4S)-2-(3-Fluoro-5-(trifluoromethyl)benzyl)piperidin-4-yl)isoxazol-3(2H)-one;
5-((2S,4R)-2-(3-Fluoro-5-(trifluoromethyl)benzyl)piperidin-4-yl)isoxazol-3(2H)-one;
5-(Trans-2-(3-fluoro-5-(trifluoromethyl)benzyl)piperidin-4-yl)isoxazol-3(2H)-one;
5-((2R,4S)-2-(3-Fluoro-4-(trifluoromethyl)benzyl)piperidin-4-yl)isoxazol-3(2H)-one;
5-((2S,4R)-2-(3-Fluoro-4-(trifluoromethyl)benzyl)piperidin-4-yl)isoxazol-3(2H)-one;
5-(Trans-2-(3-fluoro-4-(trifluoromethyl)benzyl)piperidin-4-yl)isoxazol-3(2H)-one;
5-((2R,4S)-2-(3,4,5-Trifluorobenzyl)piperidin-4-yl)isoxazol-3(2H)-one;
5-((2S,4R)-2-(3,4,5-Trifluorobenzyl)piperidin-4-yl)isoxazol-3(2H)-one;
5-(Trans-2-(3,4,5-trifluorobenzyl)piperidin-4-yl)isoxazol-3(2H)-one;
5-((2R,4S)-2-(3,5-Di-tert-butylbenzyl)piperidin-4-yl)isoxazol-3(2H)-one;
5-((2S,4R)-2-(3,5-Di-tert-butylbenzyl)piperidin-4-yl)isoxazol-3(2H)-one;
5-(Trans-2-(3,5-di-tert-butylbenzyl)piperidin-4-yl)isoxazol-3(2H)-one;
5-((2R,4S)-2-Benzyl-2,3,4,5,6-d$_5$-piperidin-4-yl)isoxazol-3(2H)-one;
5-((2S,4R)-2-Benzyl-2,3,4,5,6-d$_5$-piperidin-4-yl)isoxazol-3(2H)-one;
5-(Trans-2-benzyl-2,3,4,5,6-d$_5$-piperidin-4-yl)isoxazol-3(2H)-one.

The compounds of formula I may exist in stereoisomeric and/or tautomeric forms. It is to be understood that all enantiomers, diastereomers, racemates, tautomers and mixtures thereof are included within the scope of the invention.

Different isomers may have different biological activity. It may be the case that different compounds of the general formula I may show the highest biological activity with different configuration. For instance for one compound the (2R, 4S) configuration may have the highest biological activity, but for another compound the (2S,4S) may have the highest activity.

According to one aspect of the invention it is provided for a compound of formula II with the following configuration:

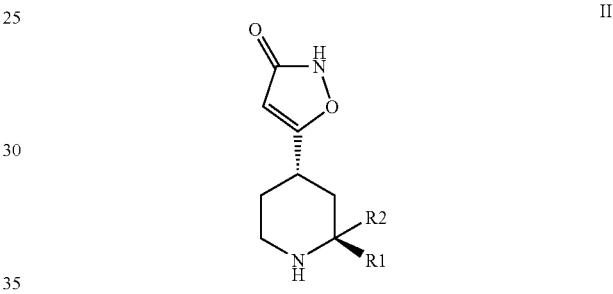

II

According to one aspect of the invention it is provided for a compound of formula III with the following configuration:

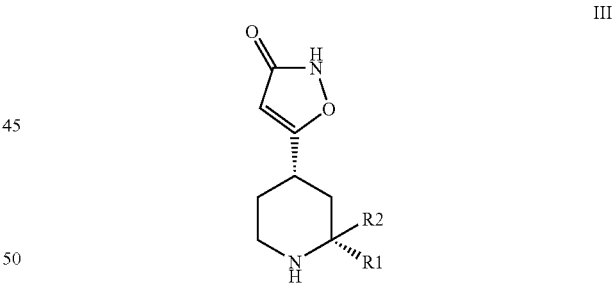

III

According to one aspect of the invention it is provided for a compound of formula IV with the following configuration:

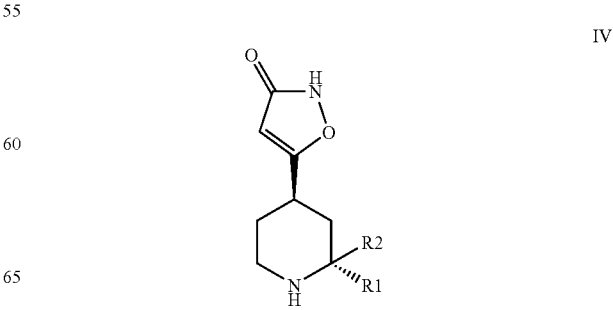

IV

According to one aspect of the invention it is provided for a compound of formula V with the following configuration:

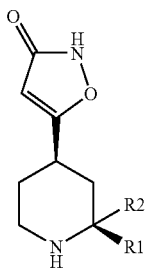

V

According to another aspect of the invention it is provided for a pharmaceutical composition comprising at least one compound and a pharmaceutically acceptable carrier or diluent.

According to another aspect of the invention it is provided for a method for treatment or prophylaxis of a disease or condition, such as heavy bleeding, inherited or acquired bleeding disorders, stroke, menorrhagia and liver diseases, in which modulation of fibrinolysis is beneficial, and for the treatment of hereditary angioedema, comprising administering to a warm-blooded animal in need of such treatment a therapeutically effective amount of at least one compound of formula I. Other areas of use for the compound according to formula I would be in wound healing, reduce blood loss in connection with surgery including dental surgery and for treating patients who are treated with anti-coagulation, for instance in preparation for surgery. The compound may also be used to reduce the blood transfusion needed in different situations. The compound may additionally be used in prophylactic treatment of von Willebrand's disease, haemophilia or in the case of anti-coagulating patients.

According to another aspect of the invention it is provided for a method wherein said disease or condition is selected from inherited bleeding disorders, stroke, menorrhagia and liver diseases.

According to another aspect of the invention it is provided for the treatment or prophylaxis of a disease or condition in which modulation of fibrinolysis is beneficial.

According to another aspect of the invention it is provided for wherein said disease or condition is selected from inherited bleeding disorders, stroke, menorrhagia and liver diseases.

According to another aspect of the invention it is provided for the use of a compound according to the invention in the manufacture of a medicament for the treatment or prophylaxis of a disease or condition in which modulation of fibrinolysis is beneficial.

According to another aspect of the invention it is provided for treatment or prophylaxis wherein said disease is selected from inherited bleeding disorders, stroke, menorrhagia and liver diseases.

Compounds of formula I-V may be prepared by the following route:

Scheme A. Preparation of intermediates

METHOD A

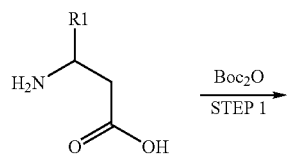

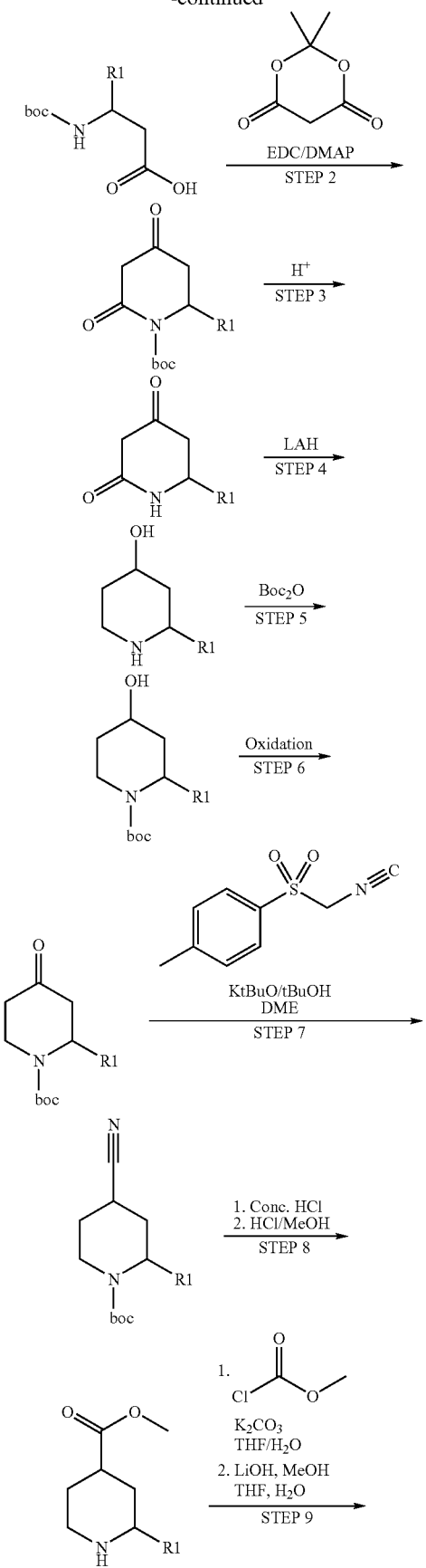

11
-continued
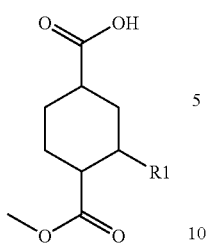
12
-continued
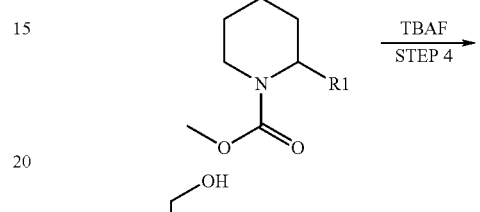
METHOD B
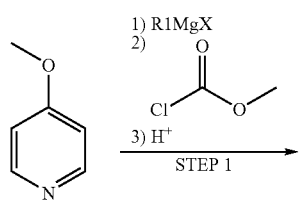
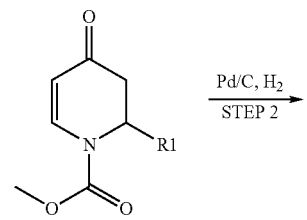
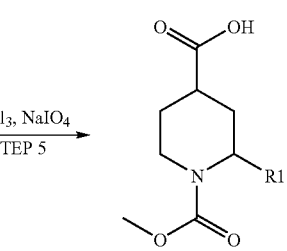
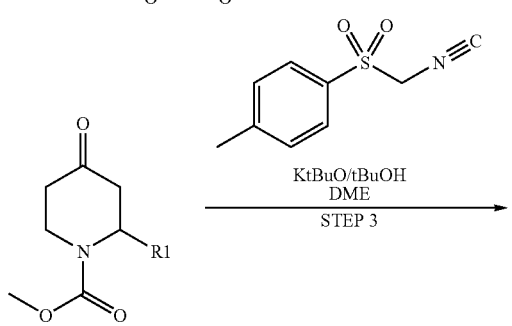
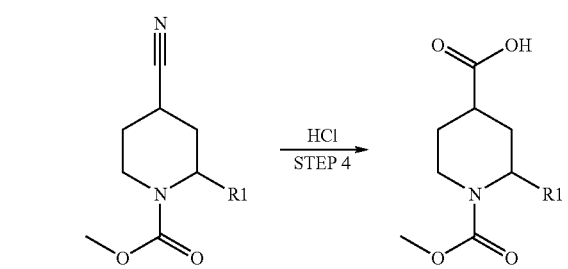
METHOD D
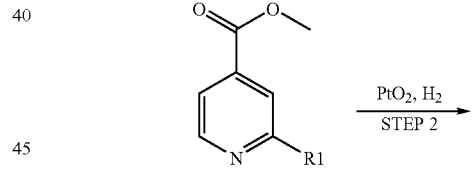
METHOD C
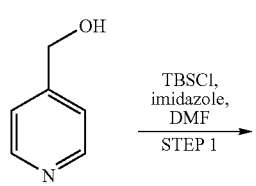
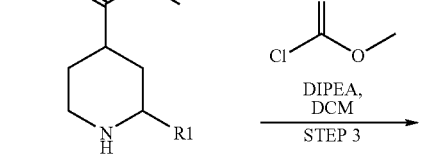
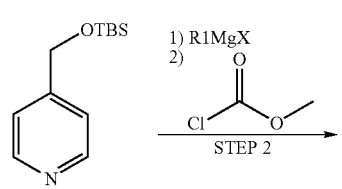
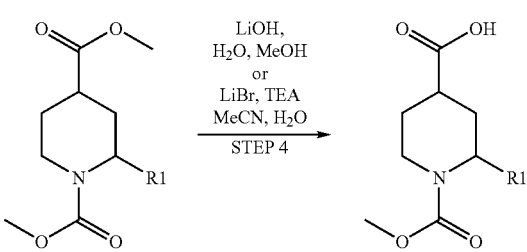

METHOD E
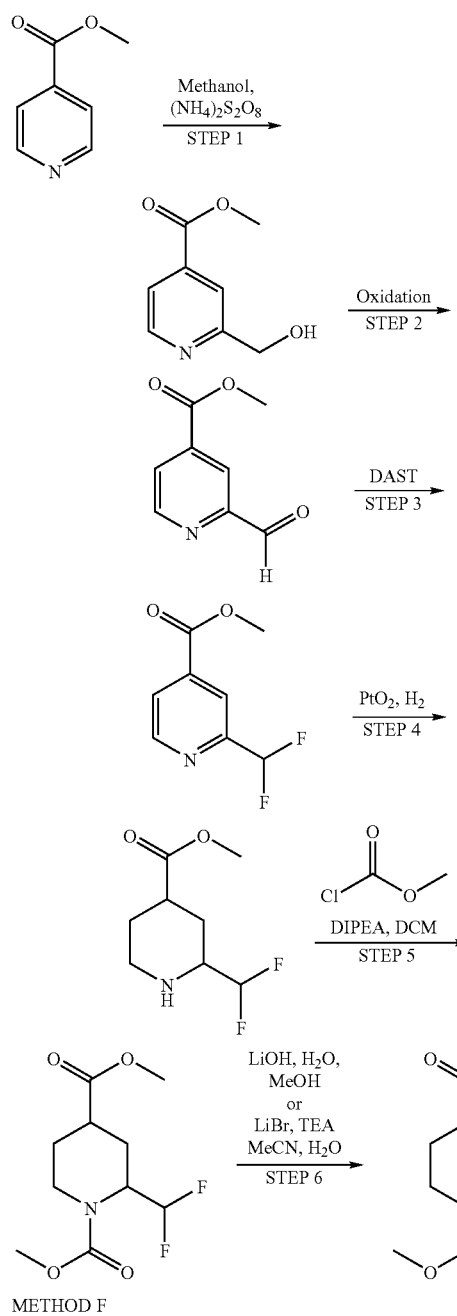
METHOD F
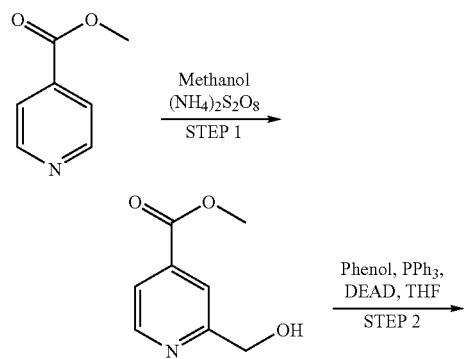
-continued
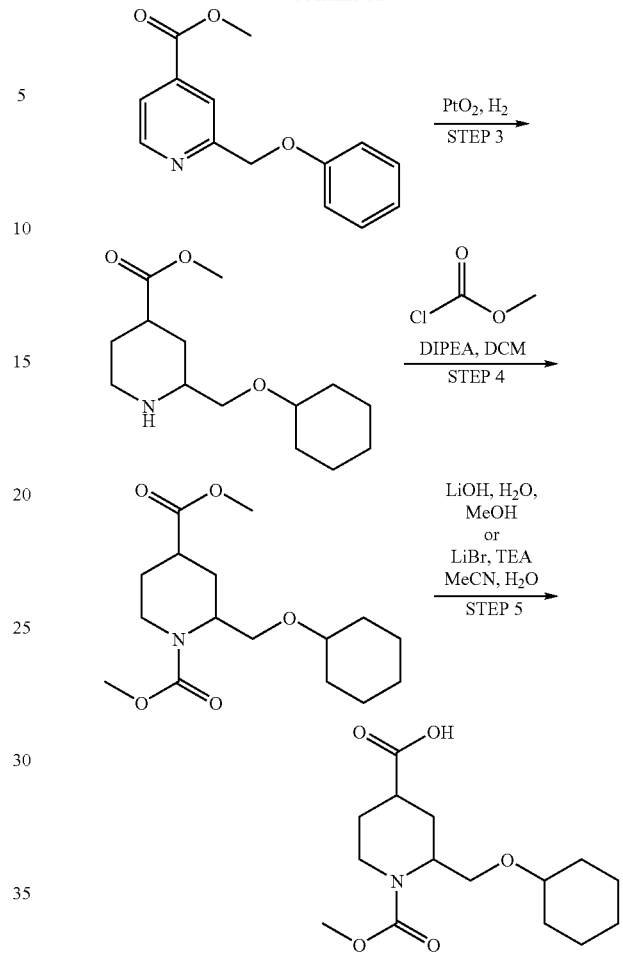
METHOD G
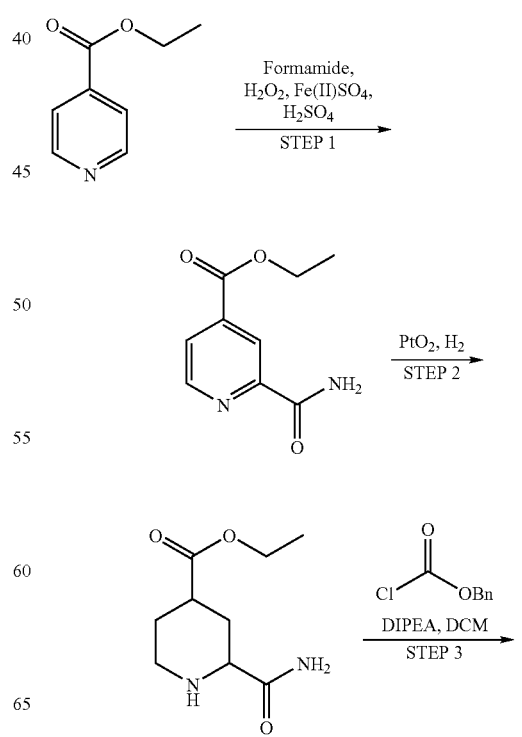

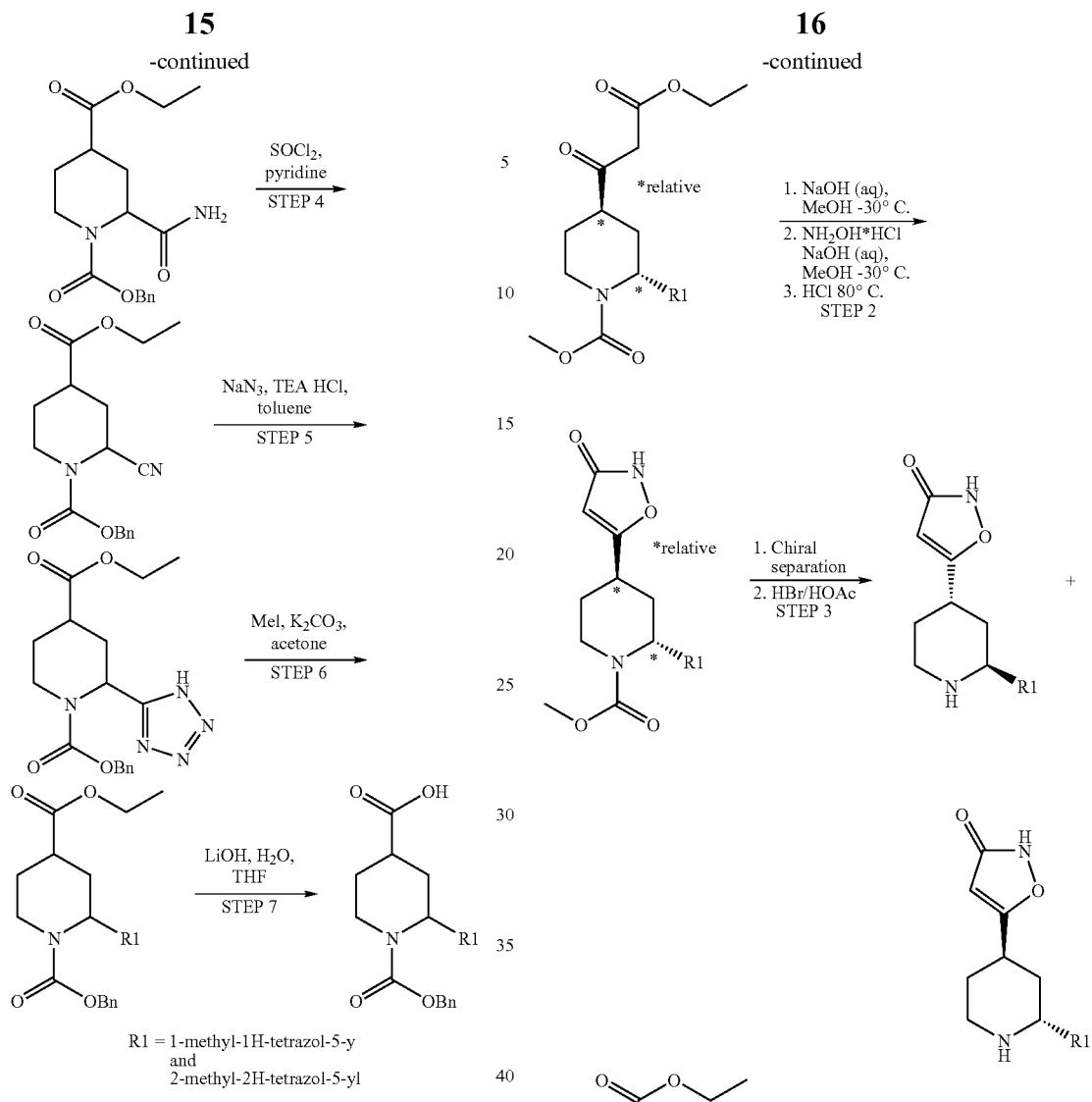
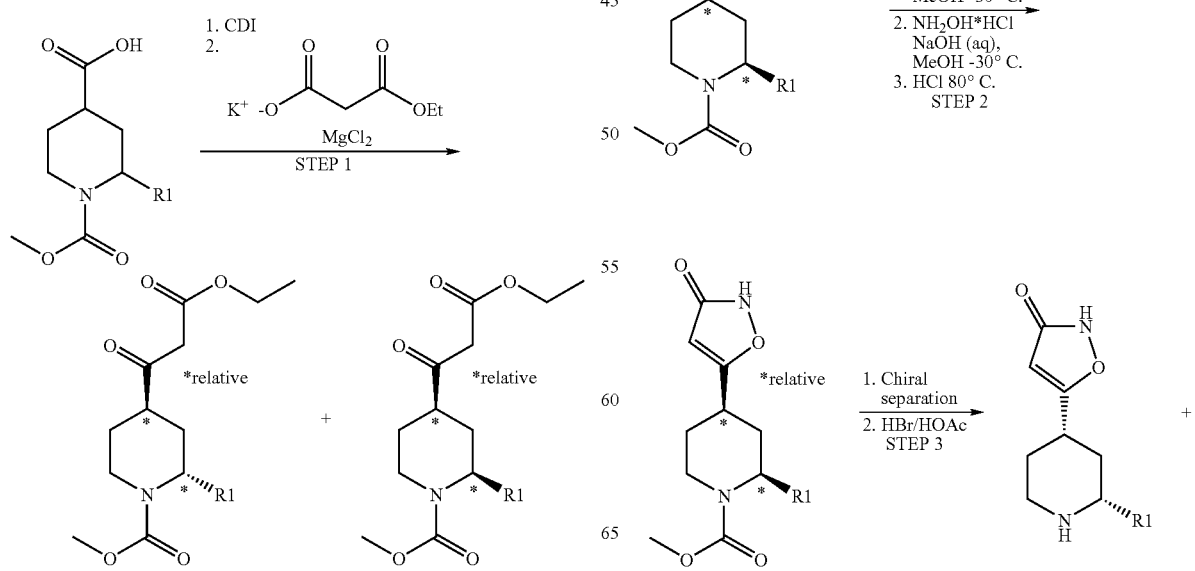
Scheme B. Formation of 5-isoxazol-3-ones

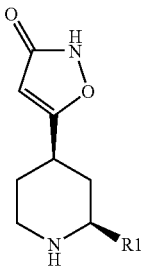

NOTE: Stereochemical assignments marked with asterisks shall be taken to be definitive of the relative configurations of the carbon atoms marked, but not their absolute configurations, unless expressly stated otherwise It will be apparent to the person skilled in the art that the above described processes are not the only way of producing the compounds according to the invention, but that a person skilled in the art may change order of sequences, reaction conditions and other parameters accordingly. Examples of parameters to be varied are using different solvents, acids and bases and temperature and furthermore to protect an amine, hydroxyl or other potentially reactive group. Suitable protecting groups and details of processes for adding and removing such groups are, in general, well known in the art. See, for example, "Protective groups on Organic Synthesis", $3^{rd}$ edition (1999) by Greene and Wuts.

Resolution of the enantiomers could be done at any stage, by using for instance column separation, by recrystallization using a chiral acid or a base. Resolution could be also carried out by enzymatically selective reaction. Alternatively, the enantiomers could be stereospecifically synthesized.

For the uses, methods, medicaments and compositions mentioned herein the amount of formula I-V compound, or pharmaceutically acceptable salts thereof, or mixtures thereof used and the dosage administered may vary with the formula I-V compound, or pharmaceutically acceptable salts, or mixtures thereof employed; and/or the desired mode of administration and/or treatment. However, in general, satisfactory results are obtained when a compound in accordance with formula I-V, or pharmaceutically acceptable salts, or mixtures thereof is administered at a daily dosage of about 0.1 mg to about 400 mg/kg of animal body weight. Such doses may be given in divided doses 1 to 4 times a day or in a sustained release form. For man, the total daily dose may, for example, range of from about 5 mg to about 7,000 mg, and more particularly from about 10 mg to about 1500 mg. Unit dosage forms suitable for oral administration generally comprise, for example, from about 2 mg to about 1,400 mg of at least one compound in accordance with formula I-V, or pharmaceutically acceptable salts, or mixtures thereof admixed with at least one solid and/or liquid pharmaceutical carrier, lubricant, and/or diluent.

The specific dose level and frequency of dosage for any particular subject, however, may vary and generally depends on a variety of factors, including, but not limited to, for example, the bioavailability of the specific formula I-V compound(s), or pharmaceutically acceptable salts, or mixtures thereof in the administered form; metabolic stability and length of action of the specific formula I-V compound(s), or pharmaceutically acceptable salts, or mixtures thereof; species, age, body weight, general health, sex, and diet of the subject; mode and time of administration; rate of excretion; drug combination; and severity of the particular condition.

Compound(s) in accordance with formula I-V, or pharmaceutically acceptable salts, or mixtures thereof may be administered by any means suitable for the condition to be treated and the quantity of formula I-V, or pharmaceutically acceptable salts, or mixtures thereof to be delivered.

Compound(s) in accordance with formula I-V, or pharmaceutically acceptable salts, or mixtures thereof may be administered in the form of a conventional pharmaceutical composition by any route including, but not limited to, for example, orally, intramuscularly, subcutaneously, topically, intranasally, epidurally, intraperitoneally, intrathoracially, intravenously, intrathecally, intracerebroventricularly, through intra uterine device, and by injecting into the joints, by applied in a device such as a patch or a plug for topical treatment such as nose-bleeding.

In one embodiment, the route of administration is orally, intravenously, through intra uterine device or intramuscularly.

A compound of formula I-V, or pharmaceutically acceptable salts, or mixtures thereof may be used on their own or in the form of appropriate medicinal preparations for enteral or parenteral administration.

Acceptable solid pharmaceutical compositions include, but are not limited to, for example, powders, tablets, dispersible granules, capsules, cachets, and suppositories.

In a solid pharmaceutical composition, pharmaceutically acceptable carriers include, but are not limited to, for example, at least one solid, at least one liquid, and mixtures thereof. The solid carrier can also be a diluent, flavouring agent, solubilizer, lubricant, suspending agent, binder, encapsulating material, and/or tablet disintegrating agent. Suitable carriers, include, but are not limited to, for example, magnesium carbonate; magnesium stearate; talc; lactose; sugar; pectin; dextrin; starch; tragacanth; methyl cellulose; sodium carboxymethyl cellulose; a low-melting wax; cocoa butter; and mixtures thereof.

A powder can be prepared by, for example, mixing a finely divided solid with at least one finely divided compound of formula I-V, or pharmaceutically acceptable salts, or mixtures thereof.

A tablet can be prepared by, for example, mixing at least one compound in accordance with formula I-V, or pharmaceutically acceptable salts, or mixtures thereof in suitable proportions with a pharmaceutically acceptable carrier having the necessary binding properties and compacted into the desired shape and size.

A suppository can be prepared by, for example, mixing at least one compound of formula I-V, or pharmaceutically acceptable salts, or mixtures thereof with at least one suitable non-irritating excipient that is liquid at rectal temperature but solid at a temperature below rectal temperature, wherein the non-irritating excipient is first melted and the formula I compound dispersed therein. The molten homogeneous mixture is then poured into convenient sized moulds and allowed to cool and solidify. Exemplary non-irritating excipients include, but are not limited to, for example, cocoa butter; glycerinated gelatine; hydrogenated vegetable oils; mixtures of polyethylene glycols of various molecular weights; and fatty acid esters of polyethylene glycol.

Acceptable liquid pharmaceutical compositions include, but are not limited to, for example, solutions, suspensions, and emulsions.

Exemplary liquid pharmaceutical compositions suitable for parenteral administration include, but are not limited to, for example, sterile water or water propylene glycol solutions of at least one compound in accordance with formula I-V, or pharmaceutically acceptable salts, or mixtures thereof; and aqueous polyethylene glycol solutions of at least one compound in accordance with formula I-V, or pharmaceutically acceptable salts, or mixtures thereof.

Aqueous solutions for oral administration can be prepared by dissolving at least one compound in accordance with formula I-V, or pharmaceutically acceptable salts, or mixtures thereof in water and adding suitable colorants, flavouring agents, stabilizers, and/or thickening agents as desired.

Aqueous suspensions for oral administration can be prepared by dispersing at least one finely divided compound of formula I-V, or pharmaceutically acceptable salts, or mixtures thereof in water together with a viscous material, such as, for example, a natural synthetic gum, resin, methyl cellulose, and sodium carboxymethyl cellulose.

In one embodiment, the pharmaceutical composition contains from about 0.05% to about 99% w (percent by weight) of at least one compound in accordance with formula I-V, or pharmaceutically acceptable salts, or mixtures thereof. All percentages by weight being based on total composition.

In another embodiment, the pharmaceutical composition contains from about 0.10% to about 50% wt (percent by weight) of at least one compound in accordance with formula I-V, or pharmaceutically acceptable salts, or mixtures thereof. All percentages by weight being based on total composition.

Also provided herein is a process for preparing a pharmaceutical composition comprising mixing or compounding the ingredients together and forming the mixed ingredients into tablets or suppositories; encapsulating the ingredients in capsules; or dissolving the ingredients to form injectable solutions.

A compound according to the present invention may be used in combination with other agents to treat the conditions disclosed above. Examples of that are non-steroid anti-inflammatory agents, such as NSAID inhibitors and hormonal treatment, such as progesterone and/or oestrogen, antiplatelet or anti-coagulant agents to prevent side effects, coagulation factors such as factor VII and factor VIII, von Willebrand's factor.

Assay Method

The assay method used for evaluating biological activity of the compounds according to the invention was Clot-lysis buffer assay.

Measurement of inhibition of plasminogen were performed in a 200 µL reaction mixture containing 15 mM HEPES, pH 7.4, 100 mM NaCl, 0.008% Tween-80, 13 µg/mL human Glu-plasminogen (Chromogenix, Italy), 1.7 mg/mL human fibrinogen (Aniara, USA), 0.02 nM human single-chain tissue type plasminogen activator (Biopool, Sweden), 1% DMSO and 0.05 NIH U/mL human thrombin (Sigma, USA).

Tested substance were added to the reaction mixture in 10% DMSO. Reaction was started by the addition of thrombin.

Fibrin formation and degradation were followed in a spectrophotometer at 405 nm for 15 hrs at 37° C.

Biological Activity

Measured according to the Clot-lysis buffer assay described above.

Example 1 showed an $IC_{50}$ value of 2.85 µM. Example 2 showed an $IC_{50}$ value of 169 µM. Example 3 showed an $IC_{50}$ value of 1.16 µM. Example 4 showed an $IC_{50}$ value of 150 µM. Example 5 showed an $IC_{50}$ value of 2.86 µM. Example 6 showed an $IC_{50}$ value of 47.5 µM. Example 7 showed an $IC_{50}$ value of 2.62 µM. Example 8 showed an $IC_{50}$ value of 2.36 µM. Example 9 showed an $IC_{50}$ value of 16.5 µM. Example 10 showed an $IC_{50}$ value of 1.46 µM. Example 11 showed an $IC_{50}$ value of 4.3 µM. Example 12 showed an $IC_{50}$ value of 2.25 µM. Example 13 showed an $IC_{50}$ value of 1.28 µM. Example 14 showed an $IC_{50}$ value of 1.15 µM. Example 15 showed an $IC_{50}$ value of 5.2 µM. Example 16 showed an $IC_{50}$ value of 56.2 µM. Example 17 showed an $IC_{50}$ value of 4.65 µM. Example 18 showed an $IC_{50}$ value of 1.6 µM. Example 19 showed an $IC_{50}$ value of 1.6 µM. Example 20 showed an $IC_{50}$ value of 5.1 µM. Example 21 showed an $IC_{50}$ value of 107 µM. Example 22 showed an $IC_{50}$ value of 1.2 µM. Example 23 showed an $IC_{50}$ value of 1 µM. Example 24 showed an $IC_{50}$ value of 42.8 µM. Example 25 showed an $IC_{50}$ value of 2.5 µM. Example 26 showed an $IC_{50}$ value of 73.8 µM. Example 27 showed an $IC_{50}$ value of 1.5 µM. Example 28 showed an $IC_{50}$ value of 283 µM. Example 29 showed an $IC_{50}$ value of 24 µM. Example 30 showed an $IC_{50}$ value of 0.7 µM. Example 31 showed an $IC_{50}$ value of 33.1 µM. Example 32 showed an $IC_{50}$ value of 23.6 µM. Example 33 showed an $IC_{50}$ value of 1.43 µM. Example 34 showed an $IC_{50}$ value of 150 µM. Example 35 showed an $IC_{50}$ value of 14.4 µM. Example 36 showed an $IC_{50}$ value of 1.9 µM. Example 37 showed an $IC_{50}$ value of 228 µM. Example 38 showed an $IC_{50}$ value of 1.5 µM. Example 39 showed an $IC_{50}$ value of 97.3 µM. Example 40 showed an $IC_{50}$ value of 1.5 µM. Example 41 showed an $IC_{50}$ value of 40.9 µM. Example 42 showed an $IC_{50}$ value of 34.9 µM. Example 43 showed an $IC_{50}$ value of 77.5 µM. Example 44 showed an $IC_{50}$ value of 2.3 µM. Example 45 showed an $IC_{50}$ value of 2.35 µM. Example 46 showed an $IC_{50}$ value of 90.7 µM. Example 47 showed an $IC_{50}$ value of 1.4 µM. Example 48 showed an $IC_{50}$ value of 44.3 µM. Example 49 showed an $IC_{50}$ value of 2 µM. Example 50 showed an $IC_{50}$ value of 5.3 µM. Example 51 showed an $IC_{50}$ value of 0.9 µM. Example 52 showed an $IC_{50}$ value of 1940 µM. Example 53 showed an $IC_{50}$ value of 72.9 µM. Example 54 showed an $IC_{50}$ value of 372 µM. Example 55 showed an $IC_{50}$ value of 0.6 µM. Example 56 showed an $IC_{50}$ value of 43.8 µM. Example 57 showed an $IC_{50}$ value of 40 µM. Example 58 showed an $IC_{50}$ value of 2.1 µM. Example 59 showed an $IC_{50}$ value of 70.7 µM. Example 60 showed an $IC_{50}$ value of 1.9 µM. Example 61 showed an $IC_{50}$ value of 858 µM. Example 62 showed an $IC_{50}$ value of 7.1 µM. Example 63 showed an $IC_{50}$ value of 3.22 µM. Example 64 showed an $IC_{50}$ value of 31.4 µM. Example 65 showed an $IC_{50}$ value of 2.2 µM. Example 66 showed an $IC_{50}$ value of 7.5 µM. Example 67 showed an $IC_{50}$ value of 1.3 µM. Example 68 showed an $IC_{50}$ value of 81.1 µM. Example 69 showed an $IC_{50}$ value of 92.5 µM. Example 70 showed an $IC_{50}$ value of 2.5 µM. Example 71 showed an $IC_{50}$ value of 11.6 µM. Example 72 showed an $IC_{50}$ value of 0.6 µM. Example 73 showed an $IC_{50}$ value of 1.54 µM. Example 74 showed an $IC_{50}$ value of 52.2 µM. Example 75 showed an $IC_{50}$ value of 3.1 µM. Example 76 showed an $IC_{50}$ value of 190 µM. Example 77 showed an $IC_{50}$ value of 8 µM. Example 78 showed an $IC_{50}$ value of 64.2 µM. Example 79 showed an $IC_{50}$ value of 3.3 µM. Example 80 showed an $IC_{50}$ value of 44 µM. Example 81 showed an $IC_{50}$ value of 1.6 µM. Example 82 showed an $IC_{50}$ value of 20.3 µM. Example 83 showed an $IC_{50}$ value of 42 µM. Example 84 showed an $IC_{50}$ value of 1.7 µM. Example 85 showed an $IC_{50}$ value of 173 µM. Example 86 showed an $IC_{50}$ value of 15.6 µM. Example 87 showed an $IC_{50}$ value of 10.7 µM. Example 88 showed an $IC_{50}$ value of 31.2 µM. Example 89 showed an $IC_{50}$ value of 1.5 µM. Example 90 showed an $IC_{50}$ value of 102 µM. Example 91 showed an $IC_{50}$ value of 5.9 µM. Example 92 showed an $IC_{50}$ value of 1.1 µM. Example 93 showed an $IC_{50}$ value of 69.8 µM. Example 94 showed an $IC_{50}$ value of 4.6 µM. Example 95 showed an $IC_{50}$ value of 1.04 µM. Example 96 showed an $IC_{50}$ value of 7.3 µM. Example 97 showed an $IC_{50}$ value of 0.7 µM. Example 98 showed an $IC_{50}$ value of 2.51 µM. Example 99 showed an $IC_{50}$ value of 0.81 µM. Example 100 showed an $IC_{50}$ value of 1.93 µM. Example 101 showed an $IC_{50}$ value of 4.7 µM. Example 102 showed an $IC_{50}$ value of 2.18 µM. Example 103 showed an $IC_{50}$ value of 94 µM. Example 104 showed an $IC_{50}$ value of 1.5 µM. Example 105 showed an $IC_{50}$ value of 7.2 µM. Example 106 showed an $IC_{50}$ value of 88.8 µM. Example 107 showed an $IC_{50}$ value of 1.7 µM. Example 108 showed an $IC_{50}$ value of 70.5 µM. Example 109 showed an $IC_{50}$ value of 5 µM. Example 110 showed an $IC_{50}$ value of 1.2 µM. Example 111 showed an $IC_{50}$ value of 31.3 µM. Example 112 showed an $IC_{50}$ value of 5.5 µM. Example 113 showed an $IC_{50}$ value of 1.1 µM. Example 114 showed an $IC_{50}$ value of 6.5 µM. Example 115 showed an $IC_{50}$ value of 0.8 µM. Example 116 showed an $IC_{50}$ value of 5.6 µM. Example 117 showed an $IC_{50}$ value of 0.8 µM. Example 118 showed an $IC_{50}$ value of 225 µM. Example 119 showed an $IC_{50}$ value of 10.7 µM. Example 120 showed an $IC_{50}$ value of 0.89 µM. Example 121 showed an $IC_{50}$ value of 120 µM. Example 122 showed an $IC_{50}$ value of 4.4 µM. Example 123 showed an $IC_{50}$ value of 147 µM. Example 124 showed an $IC_{50}$ value of 1.2 µM. Example 125 showed an $IC_{50}$ value of 92.9 µM. Example 126 showed an $IC_{50}$ value of 3.6 µM. Example 127 showed an $IC_{50}$ value of 1.4 µM. Example 128 showed an $IC_{50}$ value of 31.4 µM. Example 129 showed an $IC_{50}$ value of 10.2 µM. Example 130 showed an $IC_{50}$ value of 1.1 µM. Example 131 showed an $IC_{50}$ value of 128 µM. Example 132 showed an $IC_{50}$ value of 2.2 µM. Example 133 showed an $IC_{50}$ value of 120 µM. Example 134 showed an $IC_{50}$ value of 0.85 µM. Example 135 showed an $IC_{50}$ value of 69.1 µM. Example 136 showed an $IC_{50}$ value of 4.94 µM. Example 137 showed an $IC_{50}$ value of 1 µM. Example 138 showed an $IC_{50}$ value of 123 µM. Example 139 showed an $IC_{50}$ value of 2.9 µM. Example 140 showed an $IC_{50}$ value of 0.6 µM. Example 141 showed an $IC_{50}$ value of 69.5 µM. Example 142 showed an $IC_{50}$ value of 1.8 µM. Example 143 showed an $IC_{50}$ value of 0.9 µM. Example 144 showed an $IC_{50}$ value of 88.2 µM. Example 145 showed an $IC_{50}$ value of 4.3 µM. Example 146 showed an $IC_{50}$ value of 6.6 µM. Example 147 showed an $IC_{50}$ value of 44.6 µM. Example 148 showed an $IC_{50}$ value of 2.7 µM. Example 149 showed an $IC_{50}$ value of 0.9 µM. Example 150 showed an $IC_{50}$ value of 87 µM. Example 151 showed an $IC_{50}$ value of 7.7 µM.

X-Ray Powder Diffraction

The X-ray powder diffraction (referred to herein as XRPD or XRD) pattern was determined by mounting a sample on a zero background holder, single silicon crystal, and spreading out the sample into a thin layer. Using a Bruker D8 Advance theta-2 theta diffractometer with a VÅNTEC-1 detector, the sample was spun (to improve counting statistics) and irradiated with X-rays generated by a copper tube operated at 30 kV and 50 mA. Automatic variable divergence slits were used.

The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York. X-ray powder diffraction data were not corrected by using an internal reference. Measurements were performed with variable slits.

It will be understood that the 2-theta values of the X-ray powder diffraction pattern may vary slightly from one machine to another and also depending on variations in sample preparation and batch to batch variation, and so the values quoted are not to be construed as absolute. It will also be understood that the relative intensities of peaks may vary depending on orientation effects so that the intensities shown in the XRD trace included herein are illustrative and not intended to be used for absolute comparison.

The compounds may crystallize as ansolvates or solvates (including hydrates and mixed solvates). Solvent molecules may be more or less strongly bound in the structure. Transformations may appear between ansolvates and solvates or between stoicheiometric and non stoicheiometric solvates. Transformations may be either reversible or irreversible. The relative humidity or presence of other solvents is something that may affect the x-ray powder diffraction pattern more or less depending on the amount of solvent present in the structure.

The X-ray powder diffraction pattern of a typical sample of examples 10, 14, 18, 55, 65, 104, 115 and 143 are shown in FIGS. 1-13.

EXAMPLES

List of Abbreviations Used in the Examples

AcOH—ACETIC ACID
CV—COLUMN VOLUME
DME—1,2-DIMETHOXYETHANE
DEE—DIETHYL ETHER
DMF—N,N-DIMETHYLFORMAMIDE
DIPEA—N,N-DIISOPROPYLETHYLAMINE
DCM—DICHLOROMETHANE
dppf—1,1'-BIS(DIPHENYLPHOSPHINO)FERROCENE
DMAP—4-DIMETHYLAMINOPYRIDINE
EDC—1-ETHYL-3-(3-DIMETHYLAMINOPROPYL) CARBODIIMIDE
EtOH—ETHANOL
FA—FORMIC ACID
h—HOUR(S)
min—MINUTE(S)
MTBE—Methyl tert-butylether
IPA—ISOPROPYL ALCOHOL
LAH—LITHIUM ALUMINUM HYDRIDE
TEA—TRIETHYLAMINE
THF—TETRAHYDROFURAN
TBDMSCl—TERT-BUTYLDIMETHYLCHLOROSILANE
TBAF—TETRABUTYLAMMONIUM FLUORIDE
MeOH—METHANOL
EtOAc—ETHYL ACETATE
Ph—PHENYL
satd—SATURATED

PREPARATION OF REFERENCE COMPOUNDS

Reference Compound 1

2-Benzyl-1-(methoxycarbonyl)piperidine-4-carboxylic acid

Step 1: tert-Butyl 2-benzyl-4-cyanopiperidine-1-carboxylate

To a solution of 2-benzyl-4-oxo-piperidine-1-carboxylic acid tert-butyl ester (15 g, 51.8 mmol) (from SYNTECH) in DME (250 mL) under nitrogen atmosphere was simultaneously added toluene-4-sulfonylmethyl isocyanide (15.2 g, 77.7 mmol, in 250 mL DME) and potassium tert-butoxide (156 mL, 1 M in tert-butanol) over 1 h so that the temperature was kept below −10° C. The solution was stirred at −10° C. for 2 h and then allowed to reach room temperature over 16 h. To the reaction mixture was added $H_2O$ (400 mL) and the solution was stirred for 20 min and then extracted with DEE (×3) and EtOAc (×3). The combined organic phases were dried over $Na_2SO_4$ and evaporated. The residue was purified by column chromatography using EtOAc/heptane (10-60% gradient EtOAc) to yield tert-butyl 2-benzyl-4-cyanopiperidine-1-carboxylate (11.85 g, 76%). $^1$H NMR (600 MHz, cdcl$_3$) δ 1.38-1.46 (m, 9H), 1.63-2.14 (m, 4H), 2.62-3.33 (m, 4H), 4.17 (m, 1H), 4.48 (m, 1H), 7.11-7.41 (m, 5H); MS m/z 301 $(M+H)^+$.

Step 2: Methyl 2-benzylpiperidine-4-carboxylate

To tert-butyl 2-benzyl-4-cyanopiperidine-1-carboxylate (11.85 g, 39.5 mmol) was added conc. HCl (43 mL). After 20 min of stirring the solution was transferred to microwave reaction vials and heated to 140° C. for 30 min in single node microwave reactor. The solvents were evaporated. The residue was dissolved in HCl (1.25 M in MeOH, 50 mL) and the suspension was heated under reflux for 1 h. Removal of the solvents resulted in an oil that was taken up in satd $NaHCO_3$ (ca. 80 mL) and further neutralized with solid $NaHCO_3$. The aqueous phase was extracted with DCM (×3) which was dried using a phase separator and evaporated to yield methyl 2-benzylpiperidine-4-carboxylate (7.36 g, 80%) as an oil. $^1$H NMR (600 MHz, CDCl$_3$) δ 1.18-2.40 (m, 5H), 2.47-3.15 (m, 5H), 3.66-2.69 (2 s, tot integral, 3H), 7.15-7.35 (m, 5H); MS m/z 234 $(M+H)^+$.

Step 3: 2-Benzyl-1-(methoxycarbonyl)piperidine-4-carboxylic acid

To a solution of methyl 2-benzylpiperidine-4-carboxylate (7.36 g, 31.55 mmol) and DIPEA (11.02 mL, 63.09 mmol) in DCM (200 mL) was added methyl chloroformate (3.18 mL, 41.01 mmol) in 100 mL DCM over 1 h. The reaction mixture was stirred for 40 min, then washed with satd $NaHCO_3$, dried using a phase separator and evaporated. The residue was dissolved in THF (80 mL) followed by addition of LiOH (1.0 g, 42.0 mmol), MeOH (60 mL) and water (60 mL). The reaction mixture was stirred at room temperature under nitrogen atmosphere for 72 h. After evaporation of solvents, the residue was taken up in water. The pH was adjusted to <2 by addition of HCl (10%). The aqueous phase was then extracted with DCM (×5). The combined organic layers were dried by using a phase separator and evaporated to give 2-benzyl-1-(methoxycarbonyl)piperidine-4-carboxylic acid as an oil. MS m/z 276 $(M-H)^-$.

Reference Compound 2

2-Isobutyl-1-(methoxycarbonyl)piperidine-4-carboxylic acid

Step 1:
3-(tert-Butoxycarbonylamino)-5-methylhexanoic acid

To a solution of DL-β-homo leucine (45 g, 0.31 mol) in 1N NaOH (1 L) at 0° C., a solution of $(Boc)_2O$ (87.8 g, 0.403 mol) in 1,4-dioxane (500 mL) was added dropwise. The reaction mixture was stirred at room temperature overnight, cooled to 0° C. and neutralized with 1 N HCl (ca. 1000 mL). The solid was filtered off and dried under vacuum to yield 3-(tert-butoxycarbonylamino)-5-methylhexanoic acid (48.0 g, 63%) as a solid.

Step 2: tert-Butyl 2-isobutyl-4,6-dioxopiperidine-1-carboxylate

To a stirred solution of 3-(tert-butoxycarbonylamino)-5-methylhexanoic acid (44.0 g, 0.179 mol) in DCM (800 mL) at 0° C., EDC hydrochloride (51.56 g, 0.269 mol), DMAP (32.8 g, 0.269 mol) and Meldrum's acid (25.8 g, 0.179 mol) were added. The reaction mixture was stirred at room temperature for 3 h, washed with 1 N $KHSO_4$ (500 mL), dried over $Na_2SO_4$ and concentrated. The residue was dissolved in dry ethyl acetate (1.5 L) and heated under reflux overnight. The reaction mixture was washed with 1 N $KHSO_4$ (500 mL), brine (500 mL), dried over $Na_2SO_4$ and concentrated. The residue was purified by column chromatography using petroleum ether and EtOAc (65:35) as eluent to yield 3-(tert-butoxycarbonylamino)-5-methylhexanoic acid as a solid (35 g, 72%).

Step 3: 6-Isobutyl-piperidine-2,4-dione

To a solution of tert-butyl 2-isobutyl-4,6-dioxopiperidine-1-carboxylate (30 g, 0.114 mol) in dry 1,4 dioxane (300 mL), HCl (3 M in 1,4 dioxane, 100 mL) was added and stirred at room temperature for 3 h. The reaction mixture was concentrated and purified by crystallization using diethyl ether to yield 6-isobutyl-piperidine-2,4-dione (14 g, 74%) as a white solid.

Step 4: 2-Isobutyl-piperidin-4-ol

To a stirred ice cooled suspension of LAH (16.1 g, 0.414 mol) in THF (100 mL), a solution of 6-isobutyl-piperidine-2,4-dione (14.0 g, 0.083 mol) in THF (100 mL) was added dropwise under $N_2$. The reaction mixture was warmed to room temperature and stirred under $N_2$ for 48 h. The reaction mixture was cooled to 0° C. and quenched with water (16.1 mL), 1 N NaOH (16.1 mL) and water (16.1 mL). The reaction mixture was filtered and the solid was washed with hot THF (100 mL). The filtrate was concentrated to yield 2-isobutyl-piperidin-4-ol as a solid (9 g, crude).

Step 5: tert-Butyl-4-hydroxy-2-isobutylpiperidine-1-carboxylate

2-Isobutyl-piperidin-4-ol (9.0 g, 0.057 mol) was taken up in a 50:50 solution of THF and satd $NaHCO_3$ (100 mL) and the mixture was cooled to 0° C. A solution of $(Boc)_2O$ (13.7 g, 0.063 mol) in THF (50 mL) was added dropwise. The resulting solution was stirred at room temperature overnight. The reaction mixture was concentrated and extracted with EtOAc (100 mL). The organic phase was washed with water (100 mL), brine (100 mL), dried over $Na_2SO_4$ and concentrated. The concentrated product was purified by column chromatography using 20% of EtOAc in petroleum ether to yield a mixture of two compounds. The mixture was further purified by preparative HPLC to yield tert-butyl-4-hydroxy-2-isobutylpiperidine-1-carboxylate as a pale yellow liquid (4.5 g, 39.5%).

Step 6: 2-Isobutyl-4-oxo-piperidine-1-carboxylic acid tert-butyl ester

To a stirred solution of tert-butyl-4-hydroxy-2-isobutylpiperidine-1-carboxylate (4.6 g, 0.018 mol) in DCM (50 mL) at 0° C., 1,1,1-triacetoxy-1,1-dihydro-1,2-benziodoxol-3(1H)-one (9.1 g, 0.02146 mol) was added portionwise and the resulting solution was warmed to room temperature and stirred under N₂ overnight. The reaction mixture was quenched with satd NaHCO₃ solution (50 mL) and was filtered through a Celite® pad. The filtrate was extracted several times with DCM (50 mL), the combined organic phases were washed with water (50 mL), brine (50 mL), dried over Na₂SO₄ and concentrated. The concentrated product was purified by column chromatography using 10% EtOAc in petroleum ether to yield the product with HPLC purity 90%. The impure product was further purified by preparative HPLC to yield 2-isobutyl-4-oxo-piperidine-1-carboxylic acid tert-butyl ester as a liquid (2.1 g, 46%).

Step 7: tert-Butyl 4-cyano-2-isobutylpiperidine-1-carboxylate

The compound was prepared as described in Reference Compound 1, Step 1 from 2-Isobutyl-4-oxo-piperidine-1-carboxylic acid tert-butyl ester (4.55 g, 17.8 mmol), toluene-4-sulfonylmethyl isocyanide (5.2 g, 26.7 mmol) and potassium tert-butoxide (53.4 mL, 1 M in tert-butanol) which yielded crude tert-butyl 4-cyano-2-isobutylpiperidine-1-carboxylate. MS m/z 267 (M+H)⁺.

Step 8: 2-Isobutyl-piperidine-4-carboxylic acid methyl ester

The compound was prepared as described in Reference Compound 1, Step 2 from crude tert-butyl-4-cyano-2-isobutylpiperidine-1-carboxylate (6.43 g, ca 24.2 mmol) which yielded crude 2-isobutyl-piperidine-4-carboxylic acid methyl ester. MS m/z 200 (M+H)⁺.

Step 9: 2-Isobutyl-1-(methoxycarbonyl)piperidine-4-carboxylic acid

The compound was prepared as described in Reference Compound 1, Step 3 from crude 2-isobutyl-piperidine-4-carboxylic acid methyl ester (2.6 g, 13.0 mmol), DIPEA (4.55 mL, 26.1 mmol) and methyl chloroformate (1.31 mL, 17.0 mmol) and subsequently LiOH (1.3 equivalents) which yielded crude 2-isobutyl-1-(methoxycarbonyl)piperidine-4-carboxylic acid. MS m/z 242 (M−H)⁻.

Reference Compound 3

1-(Methoxycarbonyl)-2-phenethylpiperidine-4-carboxylic acid

Step 1: Methyl 4-oxo-2-phenethyl-3,4-dihydropyridine-1(2H)-carboxylate

4-Methoxypyridine (9.30 mL, 91.64 mmol) was dissolved in THF (150 mL) under nitrogen atmosphere and cooled to −15° C. Phenethylmagnesium chloride (93 mL, 93.47 mmol, 1 M in THF) was added dropwise and a suspension was formed. After stirring at −20° C. for 30 minutes methyl chloroformate (9.23 mL, 119.13 mmol) was added over 1 minute. Stirring was continued at −10° C. for 1 h and then HCl (10%) was added. The mixture was stirred for 20 minutes and then concentrated. The aqueous phase was extracted with ether (×2) and the organic phase was dried (MgSO₄) and evaporated to yield methyl 4-oxo-2-phenethyl-3,4-dihydropyridine-1(2H)-carboxylate (21.7 g, 82%) as an oil. ¹H NMR (600 MHz, cdcl₃) δ 1.98 (m, 2H), 2.54 (m, 2H), 2.69 (m, 1H), 2.81 (m, 1H), 3.83 (s, 3H), 4.62 (m, 1H), 5.33 (m, 1H), 7.12-7.38 (m, 5H), 7.72 (m, 1H); MS m/z 260 (M+H)⁺.

Step 2: Methyl 4-oxo-2-phenethylpiperidine-1-carboxylate

Methyl 4-oxo-2-phenethyl-3,4-dihydropyridine-1(2H)-carboxylate (21.7 g, ca 75 mmol) was hydrogenated over Pd/C (5%) in EtOAc at 5 bar for 20 h. The mixture was filtered through a silica plug and then evaporated to give the product as an oil (19.8 g). ¹H NMR (600 MHz, cdcl₃) δ 1.69 (m, 1H), 1.80 (m, 1H), 2.26 (m, 2H), 2.41 (m, 1H), 2.47-2.70 (m, 3H), 3.16 (m, 1H), 3.69 (m, 3H), 4.15-4.48 (br m, 2H), 7.14-7.30 (m, 5H). MS 262 m/z (M+H)⁺.

Step 3: Methyl 4-cyano-2-phenethylpiperidine-1-carboxylate

To a solution of methyl 4-oxo-2-phenethylpiperidine-1-carboxylate (19.8 g, 75.7 mmol) in DME (250 mL) under nitrogen atmosphere was simultaneously added toluene-4-sulfonylmethyl isocyanide (16.6 g, 85.0 mmol, in 250 mL DME) and potassium tert-butoxide (197 mL, 1 M in tert-butanol) over 1 h so that the temperature was kept below −10° C. The mixture was then stirred at −10° C. for 2 h and allowed to reach ambient temperature over 16 h. To the orange reaction mixture was added H₂O (400 mL), it was stirred for 20 minutes and then extracted with ether (×3) and EtOAc (×3). The organic phases were combined, dried over Na₂SO₄ and evaporated to give 24.8 g of residue. Flash chromatography using EtOAc/heptane (30-80% gradient EtOAc) gave the product (13.2 g, 64%) as a mixture of diastereomers (major cis isomer). MS m/z 273 (M+H)⁺. Trans isomer: ¹H NMR (600 MHz, cdcl₃) δ 1.71 (m, 2H), 1.84-2.09 (m, 4H), 2.47-2.68 (m, 2H), 2.71-2.92 (m, 2H), 3.70 (s, 3H), 4.12 (br m, 1H), 4.45 (br m, 1H), 7.01-7.40 (m, 5H). Cis isomer: ¹H NMR (600 MHz, cdcl₃) δ 1.76 (m, 1H), 1.88 (m, 1H), 1.92-2.07 (m, 2H), 2.07-2.15 (m, 1H), 2.24-2.38 (m, 1H), 2.55-2.72 (m, 2H), 2.96 (m, 1H), 3.16-3.29 (m, 1H), 3.69 (s, 3H), 4.10 (m, 1H), 4.35 (m, 1H), 7.15-7.35 (m, 5H).

Step 4: 1-(Methoxycarbonyl)-2-phenethylpiperidine-4-carboxylic acid

To methyl 4-cyano-2-phenethylpiperidine-1-carboxylate (13.2 g, 48.5 mmol) in a microwave reaction vial was added 6 M HCl. The mixture was heated to 100° C. for 30 min in a single node microwave reactor. The aqueous phase was extracted with EtOAc and the resulting organic phase was washed once with 10% HCl, dried over MgSO₄ and evaporated to give crude product 3.47 g. MS m/z 290 (M−H)⁻.

Reference Compound 4

2-(4-tert-Butylbenzyl)-1-(methoxycarbonyl)piperidine-4-carboxylic acid

Step 1: 4-((tert-Butyldimethylsilyloxy)methyl)pyridine

To a solution of pyridin-4-ylmethanol (25.7 g, 0.24 mol) and imidazole (19.8 g, 0.29 mol) in dry DMF (300 mL) and dry DCM (33 mL) under nitrogen atmosphere was added TBDMSCl (42.6 g, 0.29 mol). The solution was stirred for 18 h under which time a precipitate formed. The reaction mixture was concentrated by removal of volatiles (about 100 mL) followed by addition of water (500 mL). The resulting mixture was extracted with 1:1 heptane:EtOAc (200 mL×3). The combined organic phases were washed with brine (×2), dried (MgSO₄), filtered and evaporated to yield 4-((tert-butyldimethylsilyloxy)-methyl)pyridine (51.70 g, 98%) as an oil. $^1$H NMR (600 MHz, cdcl$_3$) δ −0.01 (s, 6H), 0.82 (s, 9H), 4.63 (s, 2H), 7.14 (m, 2H), 8.43 (m, 2H).

Step 2: Methyl 2-(4-tert-butylbenzyl)-4-((tert-butyldimethylsilyloxy)methyl)pyridine-1(2H)-carboxylate To a suspension of 4-(tert-butyldimethylsilyloxy)methyl)pyridine (5.33 g, 23.86 mmol) in THF (50 mL) cooled to −30° C. was added (4-tert-butylbenzyl)magnesium bromide (105 mL, 26.25 mmol, 0.25 M in THF) over 10 minutes. Methyl carbonochloridate (2.443 mL, 31.02 mmol) was added dropwise over 10 minutes. The reaction mixture was allowed to reach 0° C. over 2 h. The organic solvents were evaporated, the reaction mixture was diluted with ethyl acetate, then washed with 1 N HCl and brine. The organic layer was dried over MgSO$_4$ and evaporated to give 9 g crude residue, which was purified in 2 equal portions by automated column chromatography (Biotage, 340 g KP-SIL), eluent: heptane/EtOAc gradient 0-50%, which yielded (6.5 g, 64%) of the product as a clear oil. $^1$H NMR (400 MHz, cdcl$_3$) (complex) δ −0.07-0.21 (m, 6H), 0.9-1.30 (m, 18H), 2.0-7.4 (m, 15H). MS m/z 431 (M+H)$^+$.

Step 3: Methyl 2-(4-tert-butylbenzyl)-4-((tert-butyldimethylsilyloxy)methyl)piperidine-1-carboxylate To a solution of methyl 2-(4-tert-butylbenzyl)-4-((tert-butyldimethylsilyloxy)methyl)-pyridine-1(2H)-carboxylate (6.5 g, 15.13 mmol) in ethyl acetate (50 mL) was added platinum(IV) oxide (0.07 g, 0.31 mmol). The suspension was hydrogenated at 6 bar H$_2$ atmosphere for 20 h. The mixture was filtered through Celite and the solvents were evaporated to give the product (6.27 g, 96%) as an oil. $^1$H NMR (400 MHz, cdcl$_3$) δ −0.07-0.18 (m, 6H), 0.77-1.01 (m, 9H), 1.28-1.37 (m, 9H), 1.36-1.87 (m, 4H), 2.58-2.74 (m, 1H), 2.88-3.06 (m, 2H), 3.40-3.55 (m, 3H), 3.60-3.72 (m, 3H), 3.78-4.10 (m, 2H), 7.14-7.32 (m, 4H). MS m/z 434 (M+H)$^+$.

Step 4: Methyl 2-(4-tert-butylbenzyl)-4-(hydroxymethyl)piperidine-1-carboxylate To a suspension of methyl 2-(4-tert-butylbenzyl)-4-((tert-butyldimethylsilyloxy)methyl)-piperidine-1-carboxylate (6.27 g, 14.46 mmol) in tetrahydrofuran (15 mL) was added tetrabutylammonium fluoride (18.79 mL, 18.79 mmol, 1 M in THF) and the reaction mixture was stirred at room temperature for 90 minutes. The solvents were evaporated, the residue dissolved in ethyl acetate and washed with satd NaHCO$_3$ (×1), then brine (×2). The organic layer was dried over MgSO$_4$ and evaporated. The residue was purified by automated column chromatography (Biotage, (340 g KP-SIL) eluent EtOAc/heptane, gradient 20-90% EtOAc) to yield the product (3.21 g, 70%) as an oil. $^1$H NMR (400 MHz, cdcl$_3$) δ 1.30 (s, 9H), 1.42-1.50 (m, 2H), 1.65-1.91 (m, 2H), 2.68 (m, 1H), 2.89-3.07 (m, 2H), 3.39-3.62 (m, 3H), 3.67 (m, 3H), 3.87 (m 1H), 4.07 (m, 1H), 7.11 (m, 2H), 7.30 (m, 2H). MS m/z 320 (M+H)$^+$.

Step 5: 2-(4-tert-Butylbenzyl)-1-(methoxycarbonyl)piperidine-4-carboxylic acid To a solution of methyl 2-(4-tert-butylbenzyl)-4-(hydroxymethyl)piperidine-1-carboxylate (2.9 g, 9.08 mmol) in carbon tetrachloride (18 mL) was added sodium periodate (5.83 g, 27.24 mmol) and water (27 mL). Acetonitrile (18 mL) was added to this mixture, followed by ruthenium(III) chloride (0.041 g, 0.20 mmol). The resulting biphasic mixture was stirred vigorously at room temperature for 2 h. The reaction mixture was diluted with water and DCM, the aqueous layer was extracted with DCM (×3). The combined organic layers were dried over MgSO$_4$ and evaporated to give the product as an oil (3.0 g, 98%) MS m/z 332 (M−H)$^-$.

Reference Compound 5

1-(Methoxycarbonyl)-2-neopentylpiperidine-4-carboxylic acid

Step 1: Methyl 4-((tert-butyldimethylsilyloxy)methyl)-2-neopentylpyridine-1(2H)-carboxylate The compound was prepared as described in Reference Compound 4, Step 2 starting from 4-(tert-butyldimethylsilyloxy)methyl)pyridine, prepared as described in Reference Compound 4, Step 1, neopentylmagnesium chloride (40.5 mL, 40.5 mmol, 1 M in THF) and methyl carbonochloridate (3.77 mL, 47.9 mmol). The residue was purified by automated flash column chromatography on a Biotage® KP-SIL 340 g column. A gradient of 15:1 to 10:1 heptane:EtOAc was used as mobile phase to give the title compound (9.3 g, 71%): $^1$H NMR (400 MHz, cdcl$_3$) δ −0.00 (s, 3H), 0.09 (s, 3H), 0.87 (s, 18H), 1.09-1.81 (m, 2H), 1.94-2.44 (m, 1H), 3.70 (s, 3H), 4.22-4.90 (m, 2H), 5.12-5.61 (m, 1H), 5.69-5.97 (m, 1H), 6.25-6.79 (m, 1H). MS m/z 354 (M+H)$^+$.

Step 2: Methyl 4-((tert-butyldimethylsilyloxy)methyl)-2-neopentylpiperidine-1-carboxylate The compound was prepared as described in Reference Compound 4, Step 3 starting from methyl 4-((tert-butyldimethylsilyloxy)methyl)-2-neopentylpyridine-1(2H)-carboxylate which resulted in the title compound. MS m/z 358 (M+H)$^+$.

Step 3: Methyl 4-(hydroxymethyl)-2-neopentylpiperidine-1-carboxylate

The compound was prepared as described in Reference Compound 4, Step 4 starting from methyl 4-((tert-butyldimethylsilyloxy)methyl)-2-neopentylpiperidine-1-carboxylate and TBAF (34.2 mL, 34.2 mmol, 1 M in THF). The residue was purified by automated flash column chromatography on a Biotage® KP-SIL 340 g column. A gradient from 30% to 100% EtOAc in heptane was used as eluent, which resulted in the title compound.

Step 5: 1-(Methoxycarbonyl)-2-neopentylpiperidine-4-carboxylic acid

The compound was prepared as described in Reference Compound 4, Step 5 starting from methyl 4-(hydroxymethyl)-2-neopentylpiperidine-1-carboxylate, sodium periodate (15.0 g, 70.3 mmol) and ruthenium(III) chloride (0.11 g, 0.52 mmol), which resulted in the title compound. MS m/z 256 (M−H)$^-$.

Reference Compound 6

1-(Methoxycarbonyl)-2-methylpiperidine-4-carboxylic acid

Step 1: Methyl 4-((tert-butyldimethylsilyloxy)methyl)-2-methylpyridine-1(2H)-carboxylate The compound was prepared as described in Reference Compound 4, Step 2 starting from 4-(tert-butyldimethylsilyloxy)methyl)pyridine, prepared as described in Reference Compound 4, Step 1, methylmagnesium chloride (3 M in THF) (13.1 mL, 39.4 mmol, 1 M in THF) and methyl carbonochloridate (3.61 mL, 46.7 mmol). The residue was purified by column chromatography (Biotage heptane:EtOAc using a gradient 0-15% EtOAc; snap 360 column) which gave the title compound as a slightly yellow oil (2.48 g, 23%): $^1$H NMR (400 MHz, cdcl$_3$) δ −0.03 (d, 6H), 0.66-1.04 (m, 12H), 1.84 (m, 1H), 2.20-2.70 (m, 1H), 3.62 (s, 3H), 4.31 (m, 1H), 5.63 (m, 1H), 5.83 (m, 1H), 6.50 (m, 1H). MS m/z 298 (M+H)$^+$.

Step 2: Methyl 4-((tert-butyldimethylsilyloxy)methyl)-2-methylpiperidine-1-carboxylate The compound was prepared as described in Reference Compound 4, Step 3 starting from methyl 4-((tert-butyldimethylsilyloxy)methyl)-2-methylpyridine-1(2H)-carboxylate which resulted in the title compound. MS m/z 302 (M+H)$^+$.

Step 3: Methyl 4-(hydroxymethyl)-2-methylpiperidine-1-carboxylate

The compound was prepared as described in Reference Compound 4, Step 4 starting from methyl 4-((tert-butyldimethylsilyloxy)methyl)-2-methylpiperidine-1-carboxylate and TBAF (10.65 mL, 10.65 mmol, 1 M in THF). The residue was purified by column chromatography (Biotage 40%-90% gradient EtOAc in heptane, 340 snap column), which resulted in the title compound. $^1$H NMR (400 MHz, cdcl$_3$) δ 0.95-1.42 (m, 3H), 1.68-1.95 (m, 3H), 3.08 (m, 1H), 3.39-3.53 (m, 2H), 3.61 (m, 1H), 3.68 (s, 3H), 3.71-3.87 (m, 1H), 3.87-4.08 (m, 1H), 4.30-4.62 (m, 1H).

Step 5: 1-(Methoxycarbonyl)-2-methylpiperidine-4-carboxylic acid

The compound was prepared as described in Reference Compound 4, Step 5 starting from methyl 4-(hydroxymethyl)-2-methylpiperidine-1-carboxylate, sodium periodate (3.53 g, 16.5 mmol) and ruthenium(III) chloride (0.025 g, 0.12 mmol), which resulted in the title compound. MS m/z 200 (M−H)$^-$.

Reference Compound 7

1-(Methoxycarbonyl)-2-(2-methyl-2-phenylpropyl)piperidine-4-carboxylic acid

Step 1: Methyl 4-((tert-butyldimethylsilyloxy)methyl)-2-(2-methyl-2-phenylpropyl)pyridine-1(2H)-carboxylate The compound was prepared as described in Reference Compound 4, Step 2 starting from 4-(tert-butyldimethylsilyloxy)methyl)pyridine, prepared as described in Reference Compound 4, Step 1, (2-methyl-2-phenylpropyl)magnesium chloride (0.5 M in THF, 93 mL, 46.6 mmol) and methyl carbonochloridate (3.61 mL, 46.7 mmol) to give the product (17.5 g). MS m/z 416 (M+H)$^+$.

Step 2: Methyl 4-((tert-butyldimethylsilyloxy)methyl)-2-(2-methyl-2-phenylpropyl)-piperidine-1-carboxylate The compound was prepared as described in Reference Compound 4, Step 3 starting from crude methyl 4-((tert-butyldimethylsilyloxy)methyl)-2-(2-methyl-2-phenylpropyl)pyridine-1(2H)-carboxylate (17.5 g) which resulted in the titled compound (16.5 g). MS m/z 420 (M+H)$^+$.

Step 3: Methyl 4-(hydroxymethyl)-2-(2-methyl-2-phenylpropyl)piperidine-1-carboxylate The compound was prepared as described in Reference Compound 4, Step 4 starting from crude methyl 4-((tert-butyldimethylsilyloxy)methyl)-2-(2-methyl-2-phenylpropyl)piperidine-1-carboxylate (16.5 g) and TBAF (46.5 mL, 46.6 mmol, 1 M in THF). The residue was purified by column chromatography (Biotage 40-65% gradient EtOAc in heptane, 340 snap column, 2 runs), which resulted in the titled compound. MS m/z 306 (M+H)$^+$.

Step 4: 1-(Methoxycarbonyl)-2-(2-methyl-2-phenylpropyl)piperidine-4-carboxylic acid The compound was prepared as described in Reference Compound 4, Step 5 starting from methyl 4-(hydroxymethyl)-2-(2-methyl-2-phenylpropyl)piperidine-1-carboxylate (8.0 g, 26.2 mmol), sodium periodate (16.8 g, 78.6 mmol) and ruthenium(III) chloride (0.12 g, 0.58 mmol), which resulted in the title compound (7.24 g, 87%). MS m/z 318 (M−H)$^-$.

Reference Compound 8

2-(Cyclohexylmethyl)-1-(methoxycarbonyl)piperidine-4-carboxylic acid

Step 1: Methyl 2-benzylisonicotinate

Methyl 2-chloroisonicotinate (4.29 g, 25 mmol) and Pd(PPh$_3$)$_4$ (1.156 g, 1.00 mmol) were dissolved in THF (60 mL) to give a yellow solution. Then benzylzinc(II) bromide (0.5 M in THF) (75 mL, 37.50 mmol) was added. The resulting brown mixture was warmed to 60° C. in an oil-bath for 18 h. The reaction mixture was quenched by addition of methanol, then diluted with ethyl acetate and washed with satd NH$_4$Cl and water. The combined organic layers were dried over MgSO$_4$ and evaporated. The residue was purified via Biotage, Thompsson 160 g Silica, eluent isocratic heptanes/ethyl acetate 9:1 over 1 CV, then linear gradient 9:1-75:25 over 6 CV. Product containing fractions were evaporated to give methyl 2-benzylisonicotinate as an orange liquid. $^1$H NMR (400 MHz, cdcl$_3$) δ 3.91 (s, 3H), 4.22 (s, 2H), 7.19-7.34 (m, 5H), 7.66 (dd, 1H), 7.69 (d, 1H), 8.70 (d, 1H).

Step 2: Methyl 2-(cyclohexylmethyl)piperidine-4-carboxylate

Methyl 2-benzylisonicotinate (1.29 g, 5.67 mmol) and PtO$_2$ (0.13 g, 0.57 mmol) were added to acetic acid (50 mL). The reaction mixture was hydrogenated in a Büchi hydrogentor at 8 bar at room temperature for 3 days. Methanol (100 mL) was added and the catalyst filtered off. The solvent was evaporated. The crude product was partitioned between Na$_2$CO$_3$ (aq) and ethyl acetate. The organic phase was isolated, dried over Na$_2$SO$_4$, filtered through Celite® and the solvent was evaporated. $^1$H NMR (600 MHz, cdcl$_3$) δ 0.78-0.91 (m, 2H), 1.04-1.27 (m, 5H), 1.27-1.38 (m, 1H), 1.48 (ddd, 2H), 1.63 (dd, 5H), 1.80-1.93 (m, 2H), 2.36 (tt, 1H), 2.51-2.57 (m, 1H), 2.61 (td, 1H), 3.11 (ddd, 1H), 3.64 (s, 3H).

Step 3: Dimethyl 2-(cyclohexylmethyl)piperidine-1,4-dicarboxylate

Methyl 2-(cyclohexylmethyl)piperidine-4-carboxylate (1.79 g, 7.48 mmol), methyl carbonochloridate (1.06 g, 11.2 mmol) and DIPEA (1.93 g, 15.0 mmol) were added to dichloromethane (60 mL) at room temperature and stirred for 2 h. The reaction mixture was diluted with diethylether and washed with water. The organic phase was dried over MgSO$_4$, filtered through Celite® and the solvent was evaporated. Crude product 2.2 g. $^1$H NMR (400 MHz, cdcl$_3$) δ 0.71-0.97 (m, 2H), 1.02-1.28 (m, 5H), 1.38 (dt, 1H), 1.69 (ddd, 6H), 1.98 (ddd, 3H), 2.52-2.61 (m, 1H), 3.01-3.16 (m, 1H), 3.67 (s, 3H), 3.69 (s, 3H), 3.81-3.94 (m, 1H), 4.13-4.31 (m, 1H).

Step 4: 2-(Cyclohexylmethyl)-1-(methoxycarbonyl)piperidine-4-carboxylic acid Dimethyl 2-(cyclohexylmethyl)piperidine-1,4-dicarboxylate (2.20 g, 7.40 mmol) was dissolved in THF (25 mL) and water (25 mL). LiOH (0.266 g, 11.1 mmol) was added and the resulting mixture was stirred at room temperature overnight and heated under reflux for 30 min. The reaction mixture was partitioned between 1 M KHSO$_4$ and diethyl ether. The organic phase was dried (Na$_2$SO$_4$), filtered through Celite® and the solvent was evaporated. The crude product was dissolved again in THF (25 mL) and water (25 mL). LiOH (0.23 g) was added to the reaction flask. The reaction mixture was stirred overnight. The reaction was worked up as above to give the product. $^1$H NMR (600 MHz, cdcl$_3$) δ 0.85 (ddd, 2H), 1.19 (dddd, 5H), 1.38-1.48 (m, 1H), 1.61 (d, 4H), 1.72 (tt, 2H), 1.97 (qd, 3H), 2.56-2.65 (m, 1H), 3.02-3.14 (m, 1H), 3.67 (d, 3H), 3.88 (d, 1H), 4.22 (s, 1H).

Reference Compound 9

2-(3,4-Difluorophenyl)-1-(methoxycarbonyl)piperidine-4-carboxylic acid

Step 1: Methyl 2-(3,4-difluorophenyl)isonicotinate

A mixture of methyl 2-chloroisonicotinate (5 g, 29.14 mmol), 3,4-difluorophenylboronic acid (5.06 g, 32.05 mmol), potassium carbonate (2.416 g, 17.48 mmol) and PdCl$_2$ (dppf) (1.066 g, 1.46 mmol) was stirred in methanol (30 mL) and heated in a single-node microwave reactor at 100° C. for 30 min. The solvent was evaporated in vacuo. DCM (400 mL) and 8% NaHCO$_3$ (aq) (400 mL) were added, shaken and the phases separated. The aqueous phase was extracted with DCM (400 mL). The combined organic phases were dried with a phase separator and evaporated in vacuo. The residue was purified by automated flash chromatography on three Biotage® KP-SIL 100 g columns. A gradient from 5% EtOAc in heptane over 2 CV followed by 5% to 20% of EtOAc in heptane over 9 CV was used as mobile phase. Methyl 2-(3,4-difluorophenyl)isonicotinate (5.82 g, 80%) was isolated as a white solid. $^1$H NMR (400 MHz, cdcl$_3$) δ 4.00 (s, 3H), 7.23-7.33 (m, 1H), 7.76-7.84 (m, 2H), 7.90-8.00 (m, 1H), 8.21-8.27 (m, 1H), 8.82 (dd, 1H).

Step 2: Methyl 2-(3,4-difluorophenyl)piperidine-4-carboxylate hydrochloride Methyl 2-(3,4-difluorophenyl)isonicotinate (5.821 g, 23.36 mmol) was dissolved in hydrogen chloride (1.25 M in MeOH) (37.4 mL, 46.72 mmol) and stirred at room temperature for 30 min. The solvent was evaporated in vacuo. The remaining HCl salt was redissolved in MeOH (20 mL), platinum(IV) oxide (0.159 g, 0.70 mmol) was added and the reaction mixture hydrogenated in a Büchi hydrogenator at 5 bar and room temperature for 6 h. The catalyst was filtered off, washed with MeOH and the filtrate evaporated in vacuo to yield methyl 2-(3,4-difluorophenyl)piperidine-4-carboxylate hydrochloride (6.10 g, 90%) as a pale solid. MS m/z 256 (M+H)$^+$.

Step 3: Dimethyl 2-(3,4-difluorophenyl)piperidine-1,4-dicarboxylate

Methyl 2-(3,4-difluorophenyl)piperidine-4-carboxylate hydrochloride (6.1 g, 20.91 mmol) and DIPEA (9.13 mL, 52.28 mmol) were dissolved in DCM (30 mL). Methyl chloroformate (1.944 mL, 25.09 mmol) was added and the reaction stirred at room temperature for 1.5 h. DCM (170 mL) was added. The organic phase was washed with 0.1 M HCl (2×200 mL), satd NaHCO$_3$ (200 mL), dried with a phase separator and evaporated in vacuo yielding dimethyl 2-(3,4-difluorophenyl)piperidine-1,4-dicarboxylate (6.58 g, 100%) as a dark oil. MS m/z 314 (M+H)$^+$.

Step 4: 2-(3,4-Difluorophenyl)-1-(methoxycarbonyl)piperidine-4-carboxylic acid Dimethyl 2-(3,4-difluorophenyl)piperidine-1,4-dicarboxylate (6.578 g, 21.00 mmol) was dissolved in THF (40 mL) and water (0.800 mL). Lithium bromide (14.59 g, 167.97 mmol) and TEA (11.71 mL, 83.98 mmol) were added and the reaction was stirred at 80° C. for 3 h. The reaction mixture was cooled to room temperature and some solvent evaporated in vacuo. EtOAc (150 mL) and water (150 mL) were added, shaken and the phases separated. The organic phase was extracted with water (150 mL). The combined aqueous phases were acidified with 3 M HCl to pH 1 and extracted with EtOAc (2×300 mL). The combined organic phases were dried with Na$_2$SO$_4$, filtered and evaporated in vacuo to yield 2-(3,4-difluorophenyl)-1-(methoxycarbonyl)piperidine-4-carboxylic acid (5.66 g, 90%) as a light brown oil. MS m/z 298 (M+H)$^+$.

Reference Compound 10

2-(4-Fluorophenyl)-1-(methoxycarbonyl)piperidine-4-carboxylic acid

Step 1: Methyl 2-(4-fluorophenyl)isonicotinate hydrochloride

Methyl 2-chloroisonicotinate (4.5 g, 26.23 mmol), 4-fluorophenylboronic acid (4.51 g, 32.26 mmol), potassium carbonate (2.247 g, 16.26 mmol) and PdCl$_2$ (dppf) (0.380 g, 0.52 mmol) were mixed in methanol (30 mL) in two 20 mL microwave vials. The vials were capped and heated at 100° C. for 10 min in a single node microwave reactor. The solids were removed by filtration and the filtrate evaporated to yield a dark red slurry. To the residue was added HCl (1.25 M in methanol, 100 mL). The mixture was stirred at 45° C. for 4 h, then concentrated. Satd NaHCO$_3$ (100 mL) was added under ice cooling and extracted with DCM (3×100 mL) The combined organic phases were washed with brine, passed through a phase separator and evaporated to yield a brown solid. The crude was dissolved in MTBE (180 mL) and some solids were filtered off. Cooled with ice-water, hydrogen chloride (4 M in dioxane, 10 mL, 40 mmol) was added dropwise during stirring and a suspension was formed. The suspension was stirred at 0° C. for 10 min. The solid was collected by filtration and washed with MTBE to yield methyl 2-(4-fluorophenyl)isonicotinate hydrochloride (6.4 g, 91%) as a beige solid. $^1$H NMR (400 MHz, cd3od) d 4.07 (s, 3H), 7.37-7.51 (m, 2H), 8.02-8.13 (m, 2H), 8.37 (dd, 1H), 8.71 (d, 1H), 8.97 (dd, 1H). MS m/z 232 (M+H)$^+$ Step 2: Methyl 2-(4-fluorophenyl)piperidine-4-carboxylate Methyl 2-(4-fluorophenyl)isonicotinate hydrochloride (6.4 g, 23.91 mmol) was dissolved in methanol (100 mL) and platinum(IV) oxide (0.271 g, 1.20 mmol) added. The resulting mixture was hydrogenated in a Büchi hydrogenator at room temperature and 5 bar for 21 h. The catalyst was filtered off, washed with MeOH and the filtrate evaporated. DCM and satd NaHCO$_3$ were added and the phases separated. The organic layer was washed with brine, passed through a phase separator and evaporated to yield a brown oil. The residue was purified by automated flash chromatography on a Biotage® KP-SIL 100 g column. A gradient from 0% to 5% of MeOH in DCM (containing 1% Et$_3$N) over 10 CV was used as mobile phase and then isocratically eluted with 5% of MeOH in DCM (containing 1% Et$_3$N). Methyl 2-(4-fluorophenyl)piperidine-4-carboxylate (4.2 g, 74%) was isolated. MS m/z 238 (M+H)$^+$ Step 3: Dimethyl 2-(4-fluorophenyl)piperidine-1,4-dicarboxylate Methyl 2-(4-fluorophenyl)piperidine-4-carboxylate (7.4 g, 31.19 mmol) was dissolved in DCM (100 mL) and DIPEA (6.52 mL, 37.43 mmol) added followed by methyl chloroformate (2.95 mL, 37.43 mmol) at 0° C. The solution was stirred at room temperature for 1 h. The reaction mixture washed with 0.1 M HCl and satd NaHCO$_3$. The organic phase was passed through a phase separator and evaporated to yield dimethyl 2-(4-fluorophenyl)piperidine-1,4-dicarboxylate (8.07 g, 97%) as a brown oil. MS m/z 296 (M+H)$^+$ Step 4: 2-(4-Fluorophenyl)-1-(methoxycarbonyl) piperidine-4-carboxylic acid Dimethyl 2-(4-fluorophenyl)piperidine-1,4-dicarboxylate (8.97 g, 30.38 mmol) was dissolved in acetonitrile (60 mL) and water (1.200 mL), then lithium bromide (21.10 g, 243.00 mmol) was added. Triethylamine (16.84 mL, 121.50 mmol) was added and the resulting brown suspension was heated under reflux for 1 h. Water (120 mL) and MTBE (120 mL) were added. The organic phase was extracted with water (2×25 mL). The pooled aqueous layer was acidified to pH 1 with 6 M HCl and extracted with MTBE (2×150 mL). The combined organic layer was washed with water (25 mL), dried over anhydrous Na$_2$SO$_4$ and evaporated. 2-(4-Fluorophenyl)-1-(methoxycarbonyl)piperidine-4-carboxylic acid (8.4 g, 98%) was isolated as a brown oil.

Reference Compound 11

2-(4-Chlorophenyl)-1-(methoxycarbonyl)piperidine-4-carboxylic acid

Step 1: Methyl 2-(4-chlorophenyl)isonicotinate hydrochloride

Methyl 2-bromoisonicotinate (3.39 g, 15.69 mmol), 4-chlorophenylboronic acid (3.68 g, 23.54 mmol), potassium carbonate (3.25 g, 23.54 mmol) and PdCl$_2$ (dppf) (0.341 g, 0.47 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield an orange solid. The solid was dissolved in MTBE, then HCl (4 M in dioxane) was added to give crude methyl 2-(4-chlorophenyl)isonicotinate hydrochloride (4.3 g). MS m/z 248 (M+H)$^+$ Step 2: Methyl 2-(4-chlorophenyl)piperidine-4-carboxylate Methyl 2-(4-chlorophenyl)isonicotinate hydrochloride (4.46 g, 15.69 mmol) was dissolved in MeOH (40 mL) and platinum(IV) oxide (0.356 g, 1.57 mmol) added. The resulting mixture was hydrogenated in a Büchi hydrogenator at room temperature and 5 bar for 1 h. The catalyst was filtered off and washed with MeOH and the eluate evaporated leaving a brown solid. The solid was dissolved in DCM and washed with 1 M K$_2$CO$_3$ and brine. The organic layer was dried through a phase-separator and evaporated. The residue was dissolved in DCM and added onto SCX-2 cation exchange columns (4*10 g columns. Each column was washed with DCM, MeOH and then eluted with NH$_3$/MeOH (1 CV each). The NH$_3$/MeOH layer was evaporated yielding methyl 2-(4-chlorophenyl)piperidine-4-carboxylate (3.13 g, 79%). MS m/z 254 (M+H)$^+$ Step 3: Dimethyl 2-(4-chlorophenyl)piperidine-1,4-dicarboxylate Methyl 2-(4-chlorophenyl)piperidine-4-carboxylate (3.13 g, 12.34 mmol) was dissolved in DCM (50 mL), then DIPEA (5.39 mL, 30.84 mmol) was added. Methyl carbonochloridate (1.360 mL, 17.27 mmol) was added dropwise to the solution. The mixture was stirred at room temperature for 3 h. The mixture was washed with 0.1 M HCl (2*100 mL) and satd NaHCO$_3$ (100 mL), then dried through a phase-separator and evaporated yielding dimethyl 2-(4-chlorophenyl)piperidine-1,4-dicarboxylate (3.97 g, quant.) as an orange oil. MS m/z 312 (M+H)$^+$ Step 4: 2-(4-Chlorophenyl)-1-(methoxycarbonyl) piperidine-4-carboxylic acid Dimethyl 2-(4-chlorophenyl)piperidine-1,4-dicarboxylate (3.97 g, 12.73 mmol) was dissolved into acetonitrile (55 mL) and water (1.1 mL), then lithium bromide (8.85 g, 101.87 mmol) was added. Et$_3$N (7.10 mL, 50.94 mmol) was added and the resulting yellow suspension was heated at reflux for 2 h. Water (100 mL) and MTBE (150 mL) were added. The phases were separated and the organic layer was extracted with water (2×). The pooled water layers were acidified to pH 1 with 3.8 M HCl and extracted with MTBE (2×). The combined organic layer was dried over Na$_2$SO$_4$, filtered and evaporated leaving 2-(4-chlorophenyl)-1-(methoxycarbonyl) piperidine-4-carboxylic acid (3.49 g, 92%) as a yellow semi-solid. MS m/z 298 (M+H)$^+$ Reference Compound 12

1-(Methoxycarbonyl)-2-(3-(trifluoromethyl)phenyl) piperidine-4-carboxylic acid

Step 1: Methyl 2-(3-(trifluoromethyl)phenyl)isonicotinate

Methyl 2-bromoisonicotinate (2.71 g, 12.57 mmol), 3-(trifluoromethyl)phenylboronic acid (3.58 g, 18.85 mmol), potassium carbonate (2.61 g, 18.85 mmol) and $PdCl_2$ (dppf) (0.162 g, 0.25 mmol) were mixed in methanol (30 mL) in two 20 mL microwave vials. The vials were capped and heated at 100° C. for 10 min in a single node microwave reactor. DCM and water were added and the phases separated. The water phase (pH 9) was extracted with DCM and the combined organic phase washed with brine, passed through a phase separator and evaporated to yield a brown solid. The residue was dissolved in DCM and added onto an SCX-2 cation exchange column. The column was washed with DCM, MeOH and then eluted with $NH_3$/MeOH (1 CV each). The $NH_3$/MeOH layer was evaporated yielding methyl 2-(3-(trifluoromethyl)phenyl)isonicotinate (2.6 g, 73%). MS m/z 282 $(M+H)^+$

Step 2: Methyl 2-(3-(trifluoromethyl)phenyl)piperidine-4-carboxylate

Methyl 2-(3-(trifluoromethyl)phenyl)isonicotinate (2.6 g, 9.25 mmol) was dissolved in acetic acid (40 mL) and platinum(IV) oxide (0.210 g, 0.92 mmol) added. The resulting mixture was hydrogenated in a Büchi hydrogenator at room temperature and 5 bar for 3 h. The catalyst was filtered off, washed with MeOH and the eluate evaporated. DCM and 1 M $K_2CO_3$ were added and the phases separated. The organic layer was washed with brine, passed through a phase separator and evaporated to yield methyl 2-(3-(trifluoromethyl)phenyl)piperidine-4-carboxylate (1.4 g, 52%) as a slightly brown oil. MS m/z 288 $(M+H)^+$

Step 3: Dimethyl 2-(3-(trifluoromethyl)phenyl)piperidine-1,4-dicarboxylate

Methyl 2-(3-(trifluoromethyl)phenyl)piperidine-4-carboxylate (1.4 g, 4.87 mmol) was dissolved in DCM (50 mL), then DIPEA (2.128 mL, 12.18 mmol) was added. Methyl chloroformate (0.537 mL, 6.82 mmol) was added dropwise to the solution. The reaction mixture was stirred at room temperature for 4 h, washed with 0.1 M HCl (100 mL) and satd NaHCO3 (100 mL), dried through a phase separator and evaporated yielding dimethyl 2-(3-(trifluoromethyl)phenyl)piperidine-1,4-dicarboxylate (1.7 g, quant.) as an orange oil. MS m/z 346 $(M+H)^+$

Step 4: 1-(Methoxycarbonyl)-2-(3-(trifluoromethyl)phenyl)piperidine-4-carboxylic acid Dimethyl 2-(3-(trifluoromethyl)phenyl)piperidine-1,4-dicarboxylate (1.7 g, 4.92 mmol) was dissolved into acetonitrile (22 mL) and water (0.440 mL), then lithium bromide (3.42 g, 39.38 mmol) was added. $Et_3N$ (2.74 mL, 19.69 mmol) was added and the resulting yellow suspension was heated under reflux for 2 h. Water (50 mL) and MTBE (150 mL) were added. The phases were separated and the organic layer was extracted with water (2 times). The pooled water layers were acidified to pH 1 with 3.8 M HCl and extracted with MTBE (2 times). The combined organic layer was dried over $Na_2SO_4$, filtered and evaporated yielding 1-(methoxycarbonyl)-2-(3-(trifluoromethyl)phenyl)piperidine-4-carboxylic acid (1.48 g, 91%) as a slightly yellow semi-solid. MS m/z 332 $(M+H)^+$

Reference Compound 13

1-(Methoxycarbonyl)-2-(4-(trifluoromethyl)phenyl)piperidine-4-carboxylic acid

Step 1: Methyl 2-(4-(trifluoromethyl)phenyl)isonicotinate

Methyl 2-chloroisonicotinate (5 g, 29.14 mmol), 4-(trifluoromethyl)phenylboronic acid (8.30 g, 43.71 mmol), potassium carbonate (6.04 g, 43.71 mmol) and $PdCl_2$ (dppf) (0.633 g, 0.87 mmol) were mixed in methanol (30 mL) in two 20 mL microwave vials. Two drops of water were added to one of the vials and the vials were capped and heated at 100° C. for 10 min in a single node microwave reactor. The solids were removed by filtration and the filtrate evaporated to yield a dark red slurry. DCM and water were added and the phases separated. The water phase (pH 9) was extracted with DCM and the combined organic phase washed with brine, passed through a phase separator and evaporated to yield a brown solid. The crude was dissolved in MTBE (180 mL) and solids filtered off. Hydrogen chloride (4 M in dioxane, (7.29 mL, 29.14 mmol) was added dropwise during stirring and a suspension was formed. The suspension was stirred at room temperature for 2.5 h. The solid was collected by filtration and washed with MTBE. MTBE and satd $NaHCO_3$ was added to the solid, the organic phase dried ($Na_2SO_4$), filtered and evaporated to yield methyl 2-(4-(trifluoromethyl)phenyl) isonicotinate (5.75 g, 70%) as a beige solid. $^1$H NMR (400 MHz, cdcl$_3$) δ 4.00 (s, 3H), 7.75 (d, 2H), 7.84 (dd, 1H), 8.18 (d, 2H), 8.33 (s, 1H), 8.87 (dd, 1H). MS m/z 282 $(M+H)^+$

Step 2: Methyl 2-(4-(trifluoromethyl)phenyl)piperidine-4-carboxylate

Methyl 2-(4-(trifluoromethyl)phenyl)isonicotinate (4.985 g, 17.73 mmol) was dissolved in acetic acid (45 mL) and platinum(IV) oxide (0.232 g, 1.02 mmol) added. The resulting mixture was hydrogenated in a Büchi hydrogenator at room temperature and 5 bar for 5 h. More platinum(IV) oxide (0.116 g, 0.51 mmol) was added and the hydrogenation continued at 5 bar for 1 h. The catalyst was filtered off and washed with MeOH and the eluate evaporated. DCM and 10% $K_2CO_3$ were added and the phases separated. The organic layer was washed with brine, passed through a phase separator and evaporated to yield methyl 2-(4-(trifluoromethyl)phenyl)piperidine-4-carboxylate (5.04 g, 99%) as a brown oil. MS m/z 288 $(M+H)^+$

Step 3: Dimethyl 2-(4-(trifluoromethyl)phenyl)piperidine-1,4-dicarboxylate

Methyl 2-(4-(trifluoromethyl)phenyl)piperidine-4-carboxylate (4.973 g, 17.31 mmol) was dissolved in DCM (100 mL) and DIPEA (3.62 mL, 20.77 mmol) added followed by methyl carbonochloridate (1.636 mL, 20.77 mmol). The solution was stirred at room temperature for 1 h 45 min. The reaction mixture was washed with 0.1 M HCl and satd $NaHCO_3$. The organic phase was passed through a phase separator and evaporated to yield crude dimethyl 2-(4-(trifluoromethyl)phenyl)piperidine-1,4-dicarboxylate (6.05 g, 101%) as a brown oil. MS m/z 346 $(M+H)^+$

Step 4: 1-(Methoxycarbonyl)-2-(4-(trifluoromethyl)phenyl)piperidine-4-carboxylic acid Dimethyl 2-(4-(trifluoromethyl)phenyl)piperidine-1,4-dicarboxylate (5.996 g, 17.36 mmol) was dissolved in acetonitrile (60 mL) and water (1.200 mL), then lithium bromide (12.06 g, 138.91 mmol) was added. Triethylamine (9.63 mL, 69.46 mmol) was added and the resulting brown suspension was heated under reflux for 1 h. Water and MTBE were added. The organic phase was extracted with water (×2). The combined aqueous layer was acidified to pH 1 with 3.8 M aq HCl and then extracted with MTBE (×2). The combined organic layer was washed with water and evaporated. Trace of water was azeotropically removed by MeCN. 1-(Methoxycarbonyl)-2-(4-(trifluoromethyl)phenyl)piperidine-4-carboxylic acid (5.71 g, 99%) was isolated as a brown oil. MS m/z 332 (M+H)+

Reference Compound 14

2-(3-tert-Butylphenyl)-1-(methoxycarbonyl)piperidine-4-carboxylic acid

Step 1: 2-(3-tert-Butylphenyl)-4,4,5,5-tetramethyl-1,3,2-dioxaborolane

1-Bromo-3-tert-butylbenzene (4.48 g, 21 mmol) was dissolved in DMSO (150 mL) and 4,4,4',4',5,5,5',5'-octamethyl-2,2'-bi(1,3,2-dioxaborolane) (5.87 g, 23.10 mmol), potassium acetate (6.18 g, 63.00 mmol) and Pd(PPh$_3$)$_4$ (1.213 g, 1.05 mmol) added. The resulting brown suspension was heated to 80° C. under nitrogen. After 9 h water and diethyl ether were added and the phases separated. The organic phase was evaporated and water azeotropically removed by MeCN. The residue was purified via Biotage in two runs (0=>20% EtOAc in heptane, 5 CV; Biotage® KP-SIL 340 g column) to yield a yellow oil. Purified again via Biotage (0=>20% EtOAc in heptane, 8 CV; Biotage® KP-SIL 340 g column) 2-(3-tert-Butylphenyl)-4,4,5,5-tetramethyl-1,3,2-dioxaborolane (3.39 g, 62%) was isolated as a yellow oil. $^1$H NMR (600 MHz, cdcl$_3$) δ 1.32 (s, 9H), 1.33 (s, 12H), 7.29 (t, 1H), 7.47-7.50 (m, 1H), 7.61 (d, 1H), 7.81 (s, 1H).

Step 2: Methyl 2-(3-tert-butylphenyl)isonicotinate hydrochloride

Methyl 2-chloroisonicotinate (1.7 g, 9.91 mmol), 2-(3-tert-butylphenyl)-4,4,5,5-tetramethyl-1,3,2-dioxaborolane (3.393 g, 13.04 mmol), potassium carbonate (2.054 g, 14.86 mmol) and PdCl$_2$ (dppf) (0.215 g, 0.30 mmol) were mixed in methanol (14 mL) in a 20 mL microwave vial. The vial was capped and heated at 100° C. for 10 min in a single node microwave reactor. The reaction mixture was suspended in methanol, the solids removed by filtration and the filtrate evaporated to yield a dark red slurry. DCM and water were added and the phases separated. The water phase (pH 9) was extracted with DCM and the combined organic phase washed with brine, passed through a phase separator and evaporated to a brown solid. The solid was dissolved in MTBE (100 mL) and the solids were filtered off. Hydrogen chloride(4 M in dioxane, 3.50 mL, 13.99 mmol) was added dropwise during stirring and a suspension was formed. The suspension was stirred at room temperature for 3 days. The solid was collected by filtration and washed with MTBE to yield methyl 2-(3-tert-butylphenyl)isonicotinate hydrochloride (2.14 g, 70%) as a slightly brown solid. $^1$H NMR (600 MHz, cd$_3$od) δ 1.41 (s, 9H), 4.07 (s, 3H), 7.62 (t, 1H), 7.77-7.80 (m, 2H), 8.00-8.02 (m, 1H), 8.37-8.40 (m, 1H), 8.69-8.71 (m, 1H), 8.94-8.97 (m, 1H).

Step 3: Methyl 2-(3-tert-butylphenyl)piperidine-4-carboxylate

Methyl 2-(3-tert-butylphenyl)isonicotinate hydrochloride (3 g, 9.81 mmol) was dissolved in methanol (100 mL) and platinum(IV) oxide (0.111 g, 0.49 mmol) added. The resulting mixture was hydrogenated in a Büchi hydrogenator at room temperature and 5 bar for 13 h. To the mixture was added platinum(IV) oxide (40 mg), and the mixture was hydrogenated in a Büchi hydrogenator at room temperature and 5 bar for 1 h. The catalyst was filtered off and washed with MeOH and the eluate evaporated. DCM and satd NaHCO$_3$ were added and the phases separated. Washed with brine, passed through a phase separator and evaporated to yield methyl 2-(3-tert-butylphenyl)piperidine-4-carboxylate (2.56 g, 95%) as a brown oil.

Step 4: Dimethyl 2-(3-tert-butylphenyl)piperidine-1,4-dicarboxylate

Methyl 2-(3-tert-butylphenyl)piperidine-4-carboxylate (2.56 g, 9.30 mmol) was dissolved in DCM (100 mL) and DIPEA (2.429 mL, 13.94 mmol) added followed by methyl carbonochloridate (0.9 mL, 11.43 mmol) at 0° C. The solution was stirred at room temperature for 1 h. The reaction mixture was washed with 1 M aq HCl (pH 4) followed by brine, satd NaHCO$_3$. The organic phase was passed through a phase separator and evaporated to yield dimethyl 2-(3-tert-butylphenyl)piperidine-1,4-dicarboxylate (3.17 g, quant.) as a brown oil.

Step 5: 2-(3-tert-Butylphenyl)-1-(methoxycarbonyl)piperidine-4-carboxylic acid

Dimethyl 2-(3-tert-butylphenyl)piperidine-1,4-dicarboxylate (3.17 g, 9.51 mmol) was dissolved in acetonitrile (60 mL) and water (1.200 mL), then lithium bromide (6.61 g, 76.06 mmol) was added in one portion. Triethylamine (5.27 mL, 38.03 mmol) was added and the resulting brown suspension was heated under reflux for 1.5 h. Water (120 mL) and MTBE (120 mL) were added. The organic phase was extracted with water (2×25 mL). The pooled aqueous layer was acidified to pH 1 with 0.5 M HCl (30 mL) and extracted with MTBE (2×150 mL). The combined organic layer was washed with water (25 mL), dried over Na$_2$SO$_4$ and evaporated. 2-(3-tert-Butylphenyl)-1-(methoxycarbonyl)piperidine-4-carboxylic acid (2.73 g, 90%) was isolated as a foam.

Reference Compound 15

2-(4-tert-Butylphenyl)-1-(methoxycarbonyl)piperidine-4-carboxylic acid

Step 1: Methyl 2-(4-tert-butylphenyl)isonicotinate hydrochloride

Methyl 2-chloroisonicotinate (7 g, 40.80 mmol), 4-tert-butylphenylboronic acid (10 g, 56.17 mmol), potassium carbonate (3.5 g, 25.32 mmol) and PdCl$_2$ (dppf) (0.9 g, 1.24 mmol) were mixed in methanol (30 mL) in two equal portions in 20 mL microwave vials. The vials were capped and heated at 100° C. for 10 min in a single node microwave reactor. The solids were removed by filtration and the filtrate evaporated to yield a dark red slurry. DCM and brine were added and the phases separated. The water phase (pH 9) was extracted with DCM and the combined organic phases dried over MgSO$_4$ and evaporated. The crude was dissolved in MTBE (180 mL) and the solids filtered off. Hydrogen chloride (4 M in dioxane, 10.20 mL, 40.80 mmol) was added dropwise during stirring and a suspension was formed. The suspension was stirred at room temperature for 1 h. The solid was collected by filtration and washed with MTBE. Methyl 2-(4-tert-butylphenyl)isonicotinate hydrochloride (9.6 g, 77%) was isolated as a dark brown solid. $^1$H NMR (400 MHz, dmso) δ 1.30 (s, 9H), 3.92 (s, 3H), 7.53 (d, 2H), 7.80 (dd, 1H), 8.04 (d, 2H), 8.29 (s, 1H), 8.85 (d, 1H), 9.86 (br, 1H). MS m/z 270 (M+H)+

Step 2: Methyl 2-(4-tert-butylphenyl)piperidine-4-carboxylate hydrochloride

To a solution of methyl 2-(4-tert-butylphenyl)isonicotinate hydrochloride (9.6 g, 31.39 mmol) in MeOH (100 mL) was added platinum(IV) oxide (0.713 g, 3.14 mmol). The resulting mixture was hydrogenated in a Büchi hydrogenator at 5 bar. After 8 h the reaction mixture was filtered through a diatomeous earth filter carton, the residue washed with methanol, and the filtrate evaporated. Methyl 2-(4-tert-butylphenyl)piperidine-4-carboxylate hydrochloride (9.66 g, 99%) was isolated as a brown solid. $^1$H NMR (400 MHz, dmso) δ 1.26 (s, 9H), 1.88-2.15 (m, 4H), 2.82-2.92 (m, 1H), 3.03-3.16 (m, 1H), 3.27-3.38 (m, 1H), 3.61 (s, 3H), 4.22-4.29 (m, 1H), 7.42-7.53 (m, 4H), 9.43 (br, 2H). MS m/z 276 (M+H)$^+$

Step 3: Dimethyl 2-(4-tert-butylphenyl)piperidine-1,4-dicarboxylate

To a suspension of methyl 2-(4-tert-butylphenyl)piperidine-4-carboxylate hydrochloride (9.66 g, 30.98 mmol) in dichloromethane (100 mL) was added DIPEA (12 mL, 68.89 mmol). The reaction mixture was cooled in an ice-bath and methyl carbonochloridate (2.8 mL, 35.56 mmol) was added dropwise over 5 min. The reaction mixture was stirred for 18 h at room temperature and washed with 3.8 N HCl. The aqueous layer was extracted with DCM. The combined organic layers were dried over MgSO$_4$ and evaporated. Dimethyl 2-(4-tert-butylphenyl)piperidine-1,4-dicarboxylate (10.6 g, quant.) was isolated as a dark brown oil. MS m/z 334 (M+H)$^+$

Step 4: 2-(4-tert-Butylphenyl)-1-(methoxycarbonyl)piperidine-4-carboxylic acid To a solution of dimethyl 2-(4-tert-butylphenyl)piperidine-1,4-dicarboxylate (10.937 g, 32.80 mmol) in MeCN (100 mL) was added lithium bromide (6.58 mL, 262.42 mmol), triethylamine (18.19 mL, 131.21 mmol) and water (2 mL). The resulting mixture was heated under reflux for 3 h, then cooled to room temperature. The solvents were evaporated and the residue dissolved in water. The aqueous layer was washed with MTBE, then acidified by the addition of 3.8 N HCl. The aqueous layer was extracted three times with DCM. The combined organic layers were dried over MgSO$_4$ and evaporated. 2-(4-tert-Butylphenyl)-1-(methoxycarbonyl)piperidine-4-carboxylic acid (9.5 g, 91%) was isolated as a light brown foam. MS m/z 320 (M+H)$^+$

Reference Compound 16

1-(Methoxycarbonyl)-2-(4-(methylsulfonyl)phenyl)piperidine-4-carboxylic acid

Step 1: Methyl 2-(4-(methylsulfonyl)phenyl)isonicotinate

Methyl 2-chloroisonicotinate (5 g, 29.14 mmol), 4-(methylsulfonyl)phenylboronic acid (7.58 g, 37.88 mmol), potassium carbonate (2.416 g, 17.48 mmol) and PdCl$_2$ (dppf) (0.633 g, 0.87 mmol) were dissolved in methanol (30 mL) and divided up in two microwave vials. Each vial was heated to 100° C. in a single node microwave reactor for 35 min. DCM (250 mL) and water (250 mL) were added, shaken and the phases separated. The aqueous phase was extracted with DCM (250 mL). The combined organic phases were washed with brine (500 mL), dried with a phase separator and evaporated in vacuo. The residue was purified by automated flash chromatography on two Biotage® KP-SIL 340 g columns. A gradient of 20-70% EtOAc in heptane over 10 CV and then 70% EtOAc in heptane over 5 CV was used as mobile phase. The product was collected using the wavelength 253 nm. The product fractions were collected and evaporated in vacuo yielding methyl 2-(4-(methylsulfonyl)phenyl)-isonicotinate (5.66 g, 66.7%) as a white solid. $^1$H NMR (600 MHz, CDCl$_3$) δ 3.09 (s, 3H), 3.98 (s, 3H), 7.85 (dd, 1H), 8.05 (d, 2H), 8.25 (d, 2H), 8.34 (s, 1H), 8.86 (t, 1H).

Step 2: Methyl 2-(4-(methylsulfonyl)phenyl)piperidine-4-carboxylate hydrochloride Methyl 2-(4-(methylsulfonyl)phenyl)isonicotinate (5.663 g, 19.44 mmol) was suspended in MeOH (20 mL) and hydrogen chloride (1.25 M in MeOH, 40 mL, 50.00 mmol) was added. The mixture was stirred at room temperature for 20 min and then evaporated in vacuo. The HCl salt was suspended in MeOH (100 mL) and platinum(IV) oxide (0.221 g, 0.97 mmol) added. The mixture was hydrogenated in a Büchi hydrogenator at room temperature and 5 bar for 2 h. The catalyst was filtered off and washed with MeOH. The filtrate was evaporated in vacuo yielding methyl 2-(4-(methylsulfonyl)phenyl)piperidine-4-carboxylate hydrochloride (5.84 g, 90%) as a white solid. MS m/z 298 (M+H)$^+$

Step 3: Dimethyl 2-(4-(methylsulfonyl)phenyl)piperidine-1,4-dicarboxylate

Methyl 2-(4-(methylsulfonyl)phenyl)piperidine-4-carboxylate hydrochloride (5.2 g, 15.58 mmol) and DIPEA (6.78 mL, 38.94 mmol) were dissolved in DCM (40 mL) and methyl carbonochloridate (1.472 mL, 18.69 mmol) added. The reaction was stirred at room temperature for 50 min. DCM (160 mL) was added. The organic phase was washed with 0.1 M HCl (2×200 mL), satd NaHCO$_3$ (200 mL), dried with a phase separator and evaporated in vacuo yielding crude dimethyl 2-(4-(methylsulfonyl)phenyl)piperidine-1,4-dicarboxylate (5.95 g, 108%). MS m/z 356 (M+H)$^+$

Step 4: 1-(Methoxycarbonyl)-2-(4-(methylsulfonyl)phenyl)piperidine-4-carboxylic acid Dimethyl 2-(4-(methylsulfonyl)phenyl)piperidine-1,4-dicarboxylate (5.952 g, 16.75 mmol) was dissolved in acetonitrile (50 mL) and water (1.000 mL), then lithium bromide (11.64 g, 133.98 mmol) added. Triethylamine (9.29 mL, 66.99 mmol) was added and the reaction mixture heated under reflux for 1.5 h. MTBE (150 mL) and water (150 mL) were added, shaken and the phases separated. The organic phase was extracted with water (2×200 mL). The combined aqueous phases were acidified to pH 1 with 3 M HCl and extracted with MTBE (2×500 mL). The combined organic phases were dried with Na$_2$SO$_4$, filtered and evaporated in vacuo yielding 1-(methoxycarbonyl)-2-(4-(methylsulfonyl)phenyl)piperidine-4-carboxylic acid (4.76 g, 83%). MS m/z 342 (M+H)$^+$

Reference Compound 17

1-(Methoxycarbonyl)-2-(6-(trifluoromethyl)pyridin-3-yl)piperidine-4-carboxylic acid

Step 1: Methyl 6'-(trifluoromethyl)-2,3'-bipyridine-4-carboxylate hydrochloride Methyl 2-chloroisonicotinate (3 g, 17.48 mmol), 6-(trifluoromethyl)pyridin-3-yl boronic acid (5.01 g, 26.23 mmol), potassium carbonate (1.450 g, 10.49 mmol) and PdCl$_2$ (dppf) (0.380 g, 0.52 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield an orange solid. The solid was diluted with MTBE, then HCl (4 M in dioxane) was added to give a suspension. The solids were collected by filtration to yield methyl 6'-(trifluoromethyl)-2,3'-bipyridine-4-carboxylate hydrochloride (3.2 g, 57%). MS m/z 283 (M+H)$^+$ Step 2: Methyl 2-(6-(trifluoromethyl)pyridin-3-yl) piperidine-4-carboxylate hydrochloride Methyl 6'-(trifluoromethyl)-2,3'-bipyridine-4-carboxylate hydrochloride (2.5 g, 7.86 mmol) was dissolved in MeOH (20 mL) and platinum(IV) oxide (0.036 g, 0.16 mmol) added. The resulting mixture was hydrogenated in a Büchi hydrogenator at room temperature and 5 bar for 1 h. Additional catalyst was added and the hydrogenation was continued for 1 h. The catalyst was filtered off, washed with MeOH and the eluate evaporated yielding methyl 2-(6-(trifluoromethyl)pyridin-3-yl)piperidine-4-carboxylate hydrochloride (2.2 g, 86%) as a brown solid. MS m/z 289 (M+H)$^+$ Step 3: Dimethyl 2-(6-(trifluoromethyl)pyridin-3-yl) piperidine-1,4-dicarboxylate Methyl 2-(6-(trifluoromethyl)pyridin-3-yl)piperidine-4-carboxylate hydrochloride (3 g, 9.24 mmol) was dissolved in DCM (50 mL) and DIPEA (4.03 mL, 23.10 mmol). Methyl carbonochloridate (1.019 mL, 12.93 mmol) was added dropwise to the solution. The mixture was stirred at room temperature for 10 minutes. The mixture was washed with 0.1 M HCl (2×100 mL) and satd NaHCO$_3$ (100 mL), then dried through a phase-separator and evaporated yielding crude dimethyl 2-(6-(trifluoromethyl)pyridin-3-yl)piperidine-1,4-dicarboxylate (3 g, 94%) as a dark brown oil. MS m/z 347 (M+H)$^+$ Step 4: 1-(Methoxycarbonyl)-2-(6-(trifluoromethyl) pyridin-3-yl)piperidine-4-carboxylic acid Crude dimethyl 2-(6-(trifluoromethyl)pyridin-3-yl)piperidine-1,4-dicarboxylate (2.9 g, 8.38 mmol) was dissolved in acetonitrile (35 mL) and water (0.700 mL), then lithium bromide (2.91 g, 33.50 mmol) was added. Et$_3$N (2.334 mL, 16.75 mmol) was added and the resulting yellow suspension was heated under reflux for 1 h. Water (100 mL) and MTBE (150 mL) were added. The phases were separated and the organic layer was extracted with water (2 times). The pooled water layers were acidified to pH 1 with 3.8 M HCl and extracted into MTBE (2 times). The combined organic layer was dried over Na$_2$SO$_4$, filtered and evaporated yielding crude 1-(methoxycarbonyl)-2-(6-(trifluoromethyl)pyridin-3-yl)piperidine-4-carboxylic acid (2.5 g, 90%) as a slightly yellow solid. MS m/z 333 (M+H)$^+$ Reference Compound 18

2-(5-tert-Butylthiophen-2-yl)-1-(methoxycarbonyl) piperidine-4-carboxylic acid

Step 1: Methyl 2-(5-tert-butylthiophen-2-yl)isonicotinate

Methyl 2-chloroisonicotinate (175 mg, 1.02 mmol), 2-(5-tert-butylthiophen-2-yl)-4,4,5,5-tetramethyl-1,3,2-dioxaborolane (300 mg, 1.13 mmol), K$_2$CO$_3$ (85 mg, 0.61 mmol) and PdCl$_2$ (dppf) (37.3 mg, 0.05 mmol) was stirred in methanol (2 mL) and heated in a single node microwave reactor to 100° C. for 30 min. DCM (50 mL) and water (50 mL) were added, shaken and the phases separated. The aqueous phase was extracted with DCM (50 mL). The combined organic phases were dried with a phase separator and evaporated in vacuo. The residue was purified by automated flash chromatography on a Biotage® KP-SIL 50 g column. A gradient from 5% EtOAc in heptane over 2 CV followed by 5% to 20% of EtOAc in heptane over 9 CV was used as mobile phase. The product was collected using the wavelength 295 nm. The product fractions were collected and evaporated in vacuo yielding methyl 2-(5-tert-butylthiophen-2-yl)isonicotinate (213 mg, 76%). $^1$H NMR (600 MHz, cdcl$_3$) δ 1.41 (s, 9H), 3.96 (s, 3H), 6.85 (d, 1H), 7.50 (s, 1H), 7.61 (d, 1H), 8.13 (s, 1H), 8.64 (d, 1H). MS m/z 276 (M+H)$^+$ Step 2: Methyl 2-(5-tert-butylthiophen-2-yl)piperidine-4-carboxylate hydrochloride Methyl 2-(5-tert-butylthiophen-2-yl)isonicotinate (2.02 g, 7.34 mmol) was dissolved in hydrogen chloride (1.25 M in MeOH, 11.74 mL, 14.67 mmol) and stirred at room temperature for 30 min. The solvent was evaporated in vacuo. The residue was dissolved in MeOH (20 mL), platinum(IV) oxide (0.050 g, 0.22 mmol) added and the reaction mixture hydrogenated in a Büchi hydrogenator at 5 bar and room temperature for 3 h. Additional platinum(IV) oxide (0.050 g, 0.22 mmol) was added and the hydrogenation continued for 3 h. The reaction mixture was filtered through celite, washed with MeOH and the filtrate evaporated in vacuo. The residue was redissolved in MeOH (15 mL) and platinum(IV) oxide (0.167 g, 0.73 mmol) added. Hydrogenation was continued for 3 h. Additional platinum(IV) oxide (0.167 g, 0.73 mmol) was added and the hydrogenation continued for 2 h. The reaction mixture was filtered through celite, washed with MeOH and the filtrate evaporated in vacuo to yield methyl 2-(5-tert-butylthiophen-2-yl)piperidine-4-carboxylate hydrochloride (2.360 g, 101%) as a black oil. MS m/z 282 (M+H)$^+$ Step 3: Dimethyl 2-(5-tert-butylthiophen-2-yl)piperidine-1,4-dicarboxylate Methyl 2-(5-tert-butylthiophen-2-yl)piperidine-4-carboxylate hydrochloride (2.36 g, 7.42 mmol) and DIPEA (3.24 mL, 18.56 mmol) were dissolved in DCM (30 mL). Methyl chloroformate (0.690 mL, 8.91 mmol) was added and the reaction mixture stirred at room temperature for 1 h. DCM (170 mL) was added. The organic phase was washed with 0.1 M HCl (2×200 mL), satd NaHCO$_3$ (200 mL), dried with a phase separator and evaporated in vacuo yielding dimethyl 2-(5-tert-butylthiophen-2-yl)piperidine-1,4-dicarboxylate (2.490 g, 99%) as a dark oil. MS m/z 340 (M+H)$^+$ Step 4: 2-(5-tert-Butylthiophen-2-yl)-1-(methoxycarbonyl)piperidine-4-carboxylic acid Dimethyl 2-(5-tert-butylthiophen-2-yl)piperidine-1,4-dicarboxylate (2.49 g, 7.34 mmol) was dissolved in acetonitrile (20 mL). Water (0.400 mL) and lithium bromide (5.10 g, 58.68 mmol) were added. After 5 min, TEA (4.09 mL, 29.34 mmol) was added and the reaction heated at reflux for 1 h. MTBE (150 mL) and water (150 mL) were added, shaken and the phases separated. The organic phase was extracted with water (150 mL). The combined aqueous phases were acidified with 3 M HCl to pH 1 and extracted with MTBE (2×300 mL). The combined organic phases were dried with Na$_2$SO$_4$, filtered and evaporated in vacuo yielding 2-(5-tert-butylthiophen-2-yl)-1-(methoxycarbonyl)piperidine-4-carboxylic acid (1.125 g, 47.1%) as a white foam. MS m/z 326 (M+H)$^+$ Reference Compound 19

2-(2,4-Difluorophenyl)-1-(methoxycarbonyl)piperidine-4-carboxylic acid

Step 1: Methyl 2-(2,4-difluorophenyl)isonicotinate hydrochloride

Methyl 2-chloroisonicotinate (3 g, 17.48 mmol), 2,4-difluorophenylboronic acid (4.14 g, 26.23 mmol), potassium carbonate (1.812 g, 13.11 mmol) and PdCl$_2$ (dppf) (0.380 g, 0.52 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield a brown solid. The solid was dissolved in MTBE and stirred for 15 minutes, then filtered. The orange MTBE layer was treated with hydrogen chloride (4 M in dioxane, 4.37 mL, 17.48 mmol) and stirred for 1 h at room temperature. The formed solid was collected by filtration. Methyl 2-(2,4-difluorophenyl)isonicotinate hydrochloride (4.0 g, 80%) was isolated as a slightly orange solid. MS m/z 250 (M+H)$^+$ Step 2: Methyl 2-(2,4-difluorophenyl)piperidine-4-carboxylate hydrochloride Methyl 2-(2,4-difluorophenyl)isonicotinate hydrochloride (3.93 g, 13.76 mmol) was dissolved in MeOH (40 mL) and platinum(IV) oxide (0.312 g, 1.38 mmol) added. The resulting mixture was hydrogenated in a Büchi hydrogenator at room temperature and 5 bar for 2 h. The catalyst was filtered off, washed with MeOH and the eluate evaporated leaving methyl 2-(2,4-difluorophenyl)piperidine-4-carboxylate hydrochloride (2.34 g, 58%) as a slightly yellow solid. MS m/z 256 (M+H)$^+$ Step 3: Dimethyl 2-(2,4-difluorophenyl)piperidine-1,4-dicarboxylate Methyl 2-(2,4-difluorophenyl)piperidine-4-carboxylate hydrochloride (2.34 g, 8.02 mmol) was dissolved in DCM (50 mL), then DIPEA (3.50 mL, 20.05 mmol) was added. Methyl carbonochloridate (0.884 mL, 11.23 mmol) was added dropwise to the solution. The mixture was stirred at room temperature for 4 h, washed with 0.1 M HCl (100 mL) and satd NaHCO$_3$ (100 mL), then dried through a phase-separator and evaporated yielding dimethyl 2-(2,4-difluorophenyl)piperidine-1,4-dicarboxylate (2.38 g, 95%) as an orange oil.

Step 4: 2-(2,4-Difluorophenyl)-1-(methoxycarbonyl) piperidine-4-carboxylic acid

Dimethyl 2-(2,4-difluorophenyl)piperidine-1,4-dicarboxylate (2.38 g, 7.60 mmol) was dissolved into acetonitrile (35 mL) and water (0.700 mL), then lithium bromide (5.28 g, 60.77 mmol) was added. Et$_3$N (4.24 mL, 30.39 mmol) was added and the resulting yellow suspension was heated under reflux for 2 h. Water (50 mL) and MTBE (150 mL) were added. The phases were separated and the organic layer was extracted with water (2 times). The pooled water layers were acidified to pH 1 with 3.8 M HCl and extracted with MTBE (2 times). The combined organic layer was dried over Na$_2$SO$_4$, filtered and evaporated yielding 2-(2,4-difluorophenyl)-1-(methoxycarbonyl)piperidine-4-carboxylic acid (2.27, quant.) as a slightly yellow semi-solid. MS m/z 300 (M+H)$^+$ Reference Compound 20

2-(4-Chloro-2-fluorophenyl)-1-(methoxycarbonyl) piperidine-4-carboxylic acid

Step 1: Methyl 2-(4-chloro-2-fluorophenyl)isonicotinate hydrochloride

Methyl 2-chloroisonicotinate (4 g, 23.31 mmol), 4-chloro-2-fluorophenylboronic acid (6.10 g, 34.97 mmol), potassium carbonate (2.416 g, 17.48 mmol) and PdCl$_2$ (dppf) (0.506 g, 0.70 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield a dark-orange solid. The solid was dissolved in MTBE and stirred for 15 minutes, then filtered. The orange MTBE layer was treated with hydrogen chloride (4 M in dioxane, 5.83 mL, 23.31 mmol) and stirred for 1 h at room temperature. The precipitate was collected by filtration to yield methyl 2-(4-chloro-2-fluorophenyl)isonicotinate hydrochloride (7.22 g, quant.) as a slightly orange solid. MS m/z 266 (M+H)$^+$ Step 2: Methyl 2-(4-chloro-2-fluorophenyl)piperidine-4-carboxylate Methyl 2-(4-chloro-2-fluorophenyl)isonicotinate hydrochloride (7.26 g, 24.03 mmol) was dissolved in MeOH (100 mL) and platinum(IV) oxide (0.546 g, 2.40 mmol) added. The resulting mixture was hydrogenated in a Büchi hydrogenator at room temperature and 5 bar for 1 h. The catalyst was filtered off and washed with MeOH and the eluate evaporated yielding methyl 2-(4-chloro-2-fluorophenyl)piperidine-4-carboxylate hydrochloride (7.45 g, quant.) as a brown solid. MS m/z 272 (M+H)$^+$ Step 3: Dimethyl 2-(4-chloro-2-fluorophenyl)piperidine-1,4-dicarboxylate Methyl 2-(4-chloro-2-fluorophenyl)piperidine-4-carboxylate (7.45 g, 27.42 mmol) was dissolved into DCM (120 mL) then DIPEA (11.97 mL, 68.55 mmol) was added. Methyl carbonochloridate (3.02 mL, 38.39 mmol) was added dropwise to the solution. The mixture was stirred at room temperature for 3 h. The mixture was washed with 0.1 M HCl (2×100 mL) and satd NaHCO$_3$ (100 mL), then dried through a phase-separator and evaporated leaving dimethyl 2-(4-chloro-2-fluorophenyl)piperidine-1,4-dicarboxylate (7.77 g, 86%) as an orange oil. MS m/z 330 (M+H)$^+$ Step 4: 2-(4-Chloro-2-fluorophenyl)-1-(methoxycarbonyl)piperidine-4-carboxylic acid Dimethyl 2-(4-chloro-2-fluorophenyl)piperidine-1,4-dicarboxylate (7.77 g, 23.56 mmol) was dissolved into acetonitrile (100 mL) and water (2.000 mL), then lithium bromide (16.37 g, 188.51 mmol) was added. Et₃N (13.14 mL, 94.25 mmol) was added and the resulting yellow suspension was heated under reflux for 2 h. Water (200 mL) and MTBE (300 mL) were added. The phases were separated and the organic layer was extracted with water (2 times). The pooled water layers were acidified to pH 1 with 3.8 M HCl and extracted with MTBE (2 times). The combined organic layer was dried over MgSO₄, filtered and evaporated yielding 2-(4-chloro-2-fluorophenyl)-1-(methoxycarbonyl)piperidine-4-carboxylic acid (7.28 g, 98%) as a yellow semi-solid. MS m/z 316 (M+H)⁺

Reference Compound 21

2-(2-Chloro-4-fluorophenyl)-1-(methoxycarbonyl) piperidine-4-carboxylic acid

Step 1: Methyl 2-(2-chloro-4-fluorophenyl)isonicotinate hydrochloride

Methyl 2-chloroisonicotinate (3.5 g, 20.40 mmol), 2-chloro-4-fluorophenylboronic acid (3.91 g, 22.44 mmol), potassium carbonate (2.114 g, 15.30 mmol) and PdCl₂ (dppf) (0.443 g, 0.61 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield a dark-brown solid. The solid was dissolved in MTBE and stirred for 15 minutes, then filtered. The MTBE layer was treated with hydrogen chloride (4 M in dioxane, 5.10 mL, 20.40 mmol) and stirred for 1 h at room temperature. The precipitate was collected by filtration. Methyl 2-(2-chloro-4-fluorophenyl) isonicotinate (2.350 g, 38.1%) was obtained as a light yellow solid. ¹H NMR (400 MHz, cdcl₃) δ 4.13 (s, 3H), 7.24-7.33 (m, 1H), 7.36 (d, 1H), 7.82-8.03 (m, 1H), 8.34 (s, br., 1H), 8.56 (s, br., 1H), 9.08 (s, br., 1H). MS m/z 266 (M+H)⁺

Step 2: Methyl 2-(2-chloro-4-fluorophenyl)piperidine-4-carboxylate hydrochloride Methyl 2-(2-chloro-4-fluorophenyl)isonicotinate hydrochloride (2.35 g, 7.78 mmol) was dissolved in methanol (50 mL) and platinum(IV) oxide (0.177 g, 0.78 mmol) was added. The reaction mixture was hydrogenated in a Büchi hydrogenator at 5 bar and room temperature for 9 h. The catalyst was removed by filtration and the solvent was evaporated. The residue was dissolved in methanol (50.0 mL) and platinum (IV) oxide (144 mg, 0.63 mmol) was added. Hydrogenation was continued at 5 bar and room temperature for 4 h. The catalyst was removed by filtration and the solvent was evaporated. Crude methyl 2-(2-chloro-4-fluorophenyl)piperidine-4-carboxylate hydrochloride (2.4 g, 100%) was obtained as a yellow solid. MS m/z 272 (M+H)⁺

Step 3: Dimethyl 2-(2-chloro-4-fluorophenyl)piperidine-1,4-dicarboxylate

Methyl 2-(2-chloro-4-fluorophenyl)piperidine-4-carboxylate hydrochloride (2.4 g, 7.79 mmol) was dissolved in dichloromethane (50 mL) to give a colorless solution. DIPEA (3.39 mL, 19.47 mmol) and methyl carbonochloridate (0.736 mL, 9.35 mmol) were added and the mixture was stirred at room temperature for 14 h. 0.1 M HCl was added and the aqueous phase was extracted with DCM. The combined organic layers were filtered through a phase separator and evaporated. Crude 2-(2-chloro-4-fluorophenyl)piperidine-1, 4-dicarboxylate (2.5 g, 97%) was obtained as a yellow oil. MS m/z 330 (M+H)⁺

Step 4: 2-(2-Chloro-4-fluorophenyl)-1-(methoxycarbonyl)piperidine-4-carboxylic acid Dimethyl 2-(2-chloro-4-fluorophenyl)piperidine-1,4-dicarboxylate (2.5 g, 7.58 mmol) was dissolved in acetonitrile (50 mL) and water (1 mL), then lithium bromide (5.27 g, 60.65 mmol) was added. Triethylamine (4.20 mL, 30.33 mmol) was added and the resulting suspension was heated under reflux for 7 h. MTBE (170 mL) and water (90 mL) were added, the phases separated and the organic layer was extracted with water. The combined aqueous layers were acidified with 3.8 M HCl and extracted with EtOAc. The combined organic layers were dried with Na₂SO₄ and evaporated. 2-(2-Chloro-4-fluorophenyl)-1-(methoxycarbonyl)-piperidine-4-carboxylic acid (2.130 g, 89%) was isolated as a brown solid. MS m/z 316 (M+H)⁺

Reference Compound 22

2-(4-Chloro-3-fluorophenyl)-1-(methoxycarbonyl) piperidine-4-carboxylic acid

Step 1: 2-(4-Chloro-3-fluorophenyl)-4,4,5,5-tetramethyl-1,3,2-dioxaborolane 4-bromo-1-chloro-2-fluorobenzene (4 g, 19.10 mmol), 4,4, 4',4',5,5,5',5'-octamethyl-2,2'-bi(1,3,2-dioxaborolane) (5.63 g, 22.15 mmol), PdCl₂ (dppf) (0.691 g, 0.95 mmol) and potassium acetate (3.75 g, 38.20 mmol) were suspended in DMSO (40 mL) and heated to 80° C. for 4 h. The reaction mixture was allowed to cool to room temperature. Diluted with EtOAc (400 mL) and filtered over celite. The organic phase was washed with water (3×500 mL), brine (500 mL), dried with a phase separator and evaporated in vacuo. The residue was purified by automated flash chromatography on 2 Biotage® KP-SIL 100 g columns. A gradient from 0% to 30% of EtOAc in heptane over 15 CV was used as mobile phase. The product was collected using the wavelength 258 nm. 2-(4-Chloro-3-fluorophenyl)-4,4,5,5-tetramethyl-1,3,2-dioxaborolane (2.100 g, 42.9%) was isolated as a colorless oil. ¹H NMR (600 MHz, cdcl₃) δ 1.32 (s, 12H), 7.37 (t, 1H), 7.48 (d, 1H), 7.52 (d, 1H).

Step 2: Methyl 2-(4-chloro-3-fluorophenyl)isonicotinate

Methyl 2-chloroisonicotinate (1.2 g, 6.99 mmol), potassium carbonate (0.580 g, 4.20 mmol) and PdCl₂ (dppf) (0.122 g, 0.17 mmol) were combined in a microwave vial. 2-(4-Chloro-3-fluorophenyl)-4,4,5,5-tetramethyl-1,3,2-dioxaborolane (2.1 g, 8.19 mmol) dissolved in MeOH (15 mL) was added. The reaction mixture was heated in a single node microwave reactor at 100° C. for 15 min. DCM (125 mL) and water (125 mL) were added, shaken and the phases separated. The aqueous phase was extracted with DCM (125 mL). The combined organic phases were washed with brine (250 mL), dried with a phase separator and evaporated in vacuo. The residue was purified by automated flash chromatography on a Biotage® KP-SIL 100 g column. A gradient of 10% EtOAc in heptane over 3 CV and then 10 to 50% EtOAc in heptane over 12 CV was used as mobile phase. The product was collected using the wavelength 253 nm. Methyl 2-(4-chloro-3-fluorophenyl)isonicotinate (1.473 g, 79%) was isolated as a white solid. ¹H NMR (400 MHz, cdcl₃) δ 4.00 (s, 3H), 7.48-7.54 (m, 1H), 7.76-7.83 (m, 2H), 7.88-7.94 (m, 1H), 8.24-8.27 (m, 1H), 8.83 (dd, 1H).

Step 3: Methyl 2-(4-chloro-3-fluorophenyl)piperidine-4-carboxylate hydrochloride Methyl 2-(4-chloro-3-fluorophenyl)isonicotinate (1.473 g, 5.54 mmol) was suspended in MeOH (30 mL) and hydrogen chloride (1.25 M in MeOH, 9.86 mL, 11.09 mmol) was added dropwise during stirring. The solvent was evaporated after 15 min and the HCl salt redissolved in MeOH (10 mL) and platinum(IV) oxide (0.063 g, 0.28 mmol) added. The resulting mixture was hydrogenated in a Büchi hydrogenator at room temperature and 5 bar for 1.5 h. Platinum(IV) oxide (0.038 g, 0.17 mmol) was added and the hydrogenation continued for 1 h. The catalyst was filtered off and washed with MeOH. The solvent was evaporated in vacuo yielding methyl 2-(4-chloro-3-fluorophenyl)piperidine-4-carboxylate hydrochloride (1.639 g, 96%) as a white solid. MS m/z 272 (M+H)⁺

Step 4: Dimethyl 2-(4-chloro-3-fluorophenyl)piperidine-1,4-dicarboxylate

Methyl 2-(4-chloro-3-fluorophenyl)piperidine-4-carboxylate hydrochloride (1.639 g, 5.32 mmol) and DIPEA (2.316 mL, 13.30 mmol) were dissolved in DCM (10 mL). Methyl carbonochloridate (0.503 mL, 6.38 mmol) was added dropwise and the reaction stirred at room temperature for 2 h. The reaction mixture was diluted with DCM (100 mL) and washed with 0.1 M HCl (2×75 mL), sat. NaHCO₃ (100 mL), dried through a phase separator and evaporated in vacuo yielding dimethyl 2-(4-chloro-3-fluorophenyl)piperidine-1,4-dicarboxylate (1.625 g, 93%) as a colorless oil. MS m/z 330 (M+H)⁺

Step 5: 2-(4-Chloro-3-fluorophenyl)-1-(methoxycarbonyl)piperidine-4-carboxylic acid Dimethyl 2-(4-chloro-3-fluorophenyl)piperidine-1,4-dicarboxylate (1.625 g, 4.93 mmol) was dissolved in acetonitrile (20 mL) and water (0.400 mL). lithium bromide (3.42 g, 39.42 mmol) was added. Triethylamine (2.73 mL, 19.71 mmol) was then added and the reaction heated under reflux for 1.5 h. Water (200 mL) and MTBE (150 mL) were added, shaken and the phases separated. The organic phase was extracted with water (2×200 mL). The combined aqueous phases were acidified with 3 M HCl to pH 1 and then extracted with MTBE (2×500 mL). The combined organic phases were dried with Na₂SO₄, filtered and evaporated in vacuo yielding 2-(4-chloro-3-fluorophenyl)-1-(methoxycarbonyl)piperidine-4-carboxylic acid (1.430 g, 92%). MS m/z 314 (M−H)⁻

Reference Compound 23

2-(2,4-Dichlorophenyl)-1-(methoxycarbonyl)piperidine-4-carboxylic acid

Step 1: Methyl 2-(2,4-dichlorophenyl)isonicotinate

Potassium carbonate (1.812 g, 13.11 mmol), methyl 2-chloroisonicotinate (3 g, 17.48 mmol), 2,4-dichlorophenylboronic acid (5.00 g, 26.23 mmol), PdCl₂ (dppf) (0.380 g, 0.52 mmol), and MeOH (30.6 mL) were split in two 20 mL microwave vials and heated to 100° C. for 35 min in a single node microwave reactor. The reaction mixture was diluted with water and DCM, extracted with DCM and evaporated. Purified by automated flash chromatography using 5% EtOAc in heptane ->30% EtOAc over 15 CV at 280 nm. Methyl 2-(2,4-dichlorophenyl)isonicotinate (2.3 g, 47%) was isolated as a white solid. ¹H NMR (400 MHz, cdcl₃) δ 3.98 (s, 3H), 7.37 (dd, 1H), 7.53 (d, 1H), 7.57 (d, 1H), 7.86 (dd, 1H), 8.20 (s, 1H), 8.87 (d, 1H). MS m/z 282 (M+H)⁺

Step 2: Methyl 2-(2,4-dichlorophenyl)piperidine-4-carboxylate hydrochloride

Methyl 2-(2,4-dichlorophenyl)isonicotinate hydrochloride (2.60 g, 8.15 mmol) was dissolved in MeOH (50 mL), added platinum(IV) oxide (0.019 g, 0.08 mmol) and hydrogenated in a Büchi hydrogenator at 5 bar for 90 min. The reaction mixture was filtered and evaporated to give crude methyl 2-(2,4-dichlorophenyl)piperidine-4-carboxylate hydrochloride (2.8 g) as a white solid. MS m/z 288 (M+H)⁺

Step 3: Dimethyl 2-(2,4-dichlorophenyl)piperidine-1,4-dicarboxylate

Methyl 2-(2,4-dichlorophenyl)piperidine-4-carboxylate hydrochloride (2.8 g, 8.63 mmol) was diluted with DCM (24.18 mL). DIPEA (3.76 mL, 21.56 mmol) and methyl carbonochloridate (0.815 mL, 10.35 mmol) were added. The reaction mixture was stirred at room temperature for 30 min, then washed with 3×0.1 M HCl and brine. Filtered through a phase separator. Evaporated to yield dimethyl 2-(2,4-dichlorophenyl)piperidine-1,4-dicarboxylate (2.78 g, 93%) as an oil. MS m/z 346 (M+H)⁺

Step 4: 2-(2,4-dichlorophenyl)-1-(methoxycarbonyl)piperidine-4-carboxylic acid

Dimethyl 2-(2,4-dichlorophenyl)piperidine-1,4-dicarboxylate (2.78 g, 8.03 mmol) was dissolved in acetonitrile (27.1 mL) and water (0.542 mL). Lithium bromide (5.58 g, 64.24 mmol) and triethylamine (4.48 mL, 32.12 mmol) were added and the resulting mixture heated under reflux for 4 h, diluted with Water and MTBE and the organic layer extracted with water. The combined aqueous layers were acidified with 3 M HCl, extracted with MTBE, dried over MgSO₄, filtered and evaporated to give 2-(2,4-dichlorophenyl)-1-(methoxycarbonyl)piperidine-4-carboxylic acid (2.440 g, 91%) as a foam. MS m/z 332 (M+H)⁺

Reference Compound 24

2-(3,5-Dichlorophenyl)-1-(methoxycarbonyl)piperidine-4-carboxylic acid

Step 1: Methyl 2-(3,5-dichlorophenyl)isonicotinate

Potassium carbonate (2.416 g, 17.48 mmol), methyl 2-chloroisonicotinate (5 g, 29.14 mmol), 2-(3,5-dichlorophenyl)-4,4,5,5-tetramethyl-1,3,2-dioxaborolane (10.34 g, 37.88 mmol), PdCl₂ (dppf) (0.633 g, 0.87 mmol), and MeOH (45.7 mL) were split in three 20 mL microwave-vials and heated to 100° C. in a single node microwave reactor for 20 min. The reaction mixture was diluted with water and DCM, the aqueous layer extracted with DCM and the combined organic layers were evaporated. Purified by automated flash chromatography using 5% EtOAc in heptane ->30% EtOAc over 15

CV at 280 nm. Methyl 2-(3,5-dichlorophenyl)isonicotinate (6.1 g, 74%) was isolated as a white powder. $^1$H NMR (400 MHz, cdcl$_3$) δ 4.01 (s, 3H), 7.44 (t, 1H), 7.84 (dd, 1H), 7.96 (d, 2H), 8.23-8.28 (m, 1H), 8.85 (dd, 1H).

Step 2: Methyl 2-(3,5-dichlorophenyl)piperidine-4-carboxylate hydrochloride

Methyl 2-(3,5-dichlorophenyl)isonicotinate hydrochloride (6.88 g, 21.6 mmol) was dissolved in MeOH (50 mL), added platinum(IV) oxide (0.049 g, 0.22 mmol) and hydrogenated in a Büchi hydrogenator at 5 bar for 4 h. Reaction mixture filtered, washed with MeOH until all product had dissolved and evaporated. Methyl 2-(3,5-dichlorophenyl)piperidine-4-carboxylate hydrochloride (4.8 g, 69%) was isolated as a yellowish solid. MS m/z 288 (M+H)$^+$ Step 3: Dimethyl 2-(3,5-dichlorophenyl)piperidine-1,4-dicarboxylate Methyl 2-(3,5-dichlorophenyl)piperidine-4-carboxylate hydrochloride (4.8 g, 14.79 mmol) was dissolved in DCM (41.5 mL) and DIPEA (6.46 mL, 36.97 mmol). Methyl chloroformate (1.374 mL, 17.74 mmol) was added and the reaction mixture was stirred at room temperature for 1 h, then diluted with DCM and washed with 0.3 M HCl and brine. The organic layer was filtered through a phase separator and evaporated to give dimethyl 2-(3,5-dichlorophenyl)-piperidine-1,4-dicarboxylate (5.3 g) as an oil. MS m/z 346 (M+H)$^+$ Step 4: 2-(3,5-Dichlorophenyl)-1-(methoxycarbonyl) piperidine-4-carboxylic acid Dimethyl 2-(3,5-dichlorophenyl)piperidine-1,4-dicarboxylate (5.3 g, 15.31 mmol) was dissolved in acetonitrile (51.7 mL). Water (1.033 mL), lithium bromide (10.64 g, 122.47 mmol) and triethylamine (8.53 mL, 61.24 mmol) were added and the resulting mixture was heated under reflux for 2.5 h. It was diluted with water and MTBE. The aqueous layer was extracted with water. The combined aqueous layers were acidified with 3 M HCl, extracted with MTBE, dried over MgSO$_4$, filtered and evaporated to give 2-(3,5-dichlorophenyl)-1-(methoxycarbonyl)piperidine-4-carboxylic acid (4.60 g, 90%) as a greenish foam. MS m/z 330 (M−H)$^-$ Reference Compound 25

2-(2-Fluoro-4-(trifluoromethoxy)phenyl)-1-(methoxycarbonyl)piperidine-4-carboxylic acid Step 1: 2-(2-Fluoro-4-(trifluoromethoxy)phenyl)-4,4,5,5-tetramethyl-1,3,2-dioxaborolane 1-Bromo-2-fluoro-4-(trifluoromethoxy)benzene (7.41 g, 28.61 mmol) was dissolved in DMSO (50 mL). 4,4,4',4',5,5,5',5'-octamethyl-2,2'-bi(1,3,2-dioxaborolane) (8.43 g, 33.19 mmol), PdCl$_2$ (dppf) (1.035 g, 1.43 mmol) and potassium acetate (5.62 g, 57.22 mmol) were added and the mixture was heated in an oil bath at 80° C. for 15 h. The reaction mixture was diluted with ethyl acetate and washed with water. The organic layer was dried over Na$_2$SO$_4$ and evaporated. The residue was purified by automated flash chromatography on a Biotage® KP-SIL 340 g column. A gradient from 0% to 25% of EtOAc in heptane over 10 CV was used as mobile phase. 2-(2-Fluoro-4-(trifluoromethoxy)phenyl)-4,4,5,5-tetramethyl-1,3,2-dioxaborolane (5.38 g, 61.4%) was obtained as colorless solid.

Step 2: Methyl 2-(2-fluoro-4-(trifluoromethoxy)phenyl)isonicotinate

Methyl 2-chloroisonicotinate (3 g, 17.48 mmol), 2-(2-fluoro-4-(trifluoromethoxy)phenyl)-4,4,5,5-tetramethyl-1,3,2-dioxaborolane (5.37 g, 17.55 mmol), potassium carbonate (1.812 g, 13.11 mmol) and PdCl$_2$ (dppf) (0.380 g, 0.52 mmol) were mixed in methanol (30 mL) in two separate 20 mL microwave vials. The vials were capped and heated at 100° C. for 10 min in a single node microwave reactor. Water and DCM were added and the phases were separated. The aqueous phase was extracted with DCM and the combined organic layers were filtered through a phase separator and evaporated to yield a dark-brown solid. The residue was purified by automated flash chromatography on a Biotage® KP-SIL 340 g column. A gradient from 8:1 to 3:1 of EtOAc in heptane over 10 CV was used as mobile phase. Methyl 2-(2-fluoro-4-(trifluoromethoxy)phenyl)isonicotinate (4.48 g, 81%) was yielded as a colorless solid. $^1$H NMR (600 MHz, cdcl$_3$) δ 3.96 (s, 3H), 7.07 (d, 1H), 7.14 (d, 1H), 7.79-7.84 (m, 1H), 8.03-8.09 (m, 1H), 8.31 (s, 1H), 8.82-8.88 (m, 1H). MS m/z 316 (M+H)$^+$ Step 3: Methyl 2-(2-fluoro-4-(trifluoromethoxy)phenyl)piperidine-4-carboxylate hydrochloride Methyl 2-(2-fluoro-4-(trifluoromethoxy)phenyl)isonicotinate (4.47 g, 14.18 mmol) was dissolved in methanol and hydrogen chloride (1.25 M in methanol, 17.02 mL, 21.27 mmol) was added. The solvent was evaporated and the residue redissolved in methanol (50 mL). Platinum(IV) oxide (0.322 g, 1.42 mmol) was added and the mixture hydrogenated at 5 bar at room temperature for 5 h. The catalyst was filtered off and the solvent was evaporated. Crude methyl 2-(2-fluoro-4-(trifluoromethoxy)phenyl)piperidine-4-carboxylate hydrochloride (4.97 g, 98%) was obtained as a colorless solid. MS m/z 322 (M+H)$^+$ Step 4: Dimethyl 2-(2-fluoro-4-(trifluoromethoxy) phenyl)piperidine-1,4-dicarboxylate Methyl 2-(2-fluoro-4-(trifluoromethoxy)phenyl)piperidine-4-carboxylate hydrochloride (4.97 g, 13.89 mmol) was dissolved in dichloromethane (50 mL) and DIPEA (6.05 mL, 34.73 mmol). Methyl carbonochloridate (1.313 mL, 16.67 mmol) was added and the reaction mixture was stirred at room temperature for 4 h. 0.1 M HCl was added and the aqueous layer extracted with DCM. The combined organic layers were filtered through a phase separator and evaporated. Crude dimethyl 2-(2-fluoro-4-(trifluoromethoxy)phenyl)piperidine-1,4-dicarboxylate (5.39 g, 102%) was obtained as a yellow oil. MS m/z 380 (M+H)$^+$ Step 5: 2-(2-Fluoro-4-(trifluoromethoxy)phenyl)-1-(methoxycarbonyl)piperidine-4-carboxylic acid Dimethyl 2-(2-fluoro-4-(trifluoromethoxy)phenyl)piperidine-1,4-dicarboxylate (5.35 g, 14.10 mmol) was dissolved in acetonitrile (100 mL) and water (2.000 mL), then lithium bromide (9.80 g, 112.84 mmol) was added. Triethylamine (7.82 mL, 56.42 mmol) was added and the resulting suspension was heated under reflux for 7 h. MTBE (350 mL) and water (180 mL) were added, the phases separated and the organic layer was extracted with water. The combined aqueous layers were acidified with 3.8 M HCl and extracted with EtOAc. The combined organic layers were dried with Na$_2$SO$_4$ and evaporated. 2-(2-Fluoro-4-(trifluoromethoxy)phenyl)-1-(methoxycarbonyl)piperidine-4-carboxylic acid (5.09 g, 99%) was yielded as a colorless solid. MS m/z 364 (M−H)$^−$ Reference Compound 26

1-(Methoxycarbonyl)-2-(3,4,5-trifluorophenyl)piperidine-4-carboxylic acid

Step 1: Methyl 2-(3,4,5-trifluorophenyl)isonicotinate

Methyl 2-bromoisonicotinate (4 g, 18.52 mmol), 3,4,5-trifluorophenylboronic acid (4.89 g, 27.77 mmol), potassium carbonate (3.84 g, 27.77 mmol) and PdCl$_2$ (dppf) (0.402 g, 0.56 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield a brown solid. The residue was dissolved in DCM and purified by SCX-2 cation exchange chromatography. Methyl 2-(3,4,5-trifluorophenyl)isonicotinate (2.62 g, 52%) was isolated as a slightly yellow solid. MS m/z 268 (M+H)$^+$ Step 2: Methyl 2-(3,4,5-trifluorophenyl)piperidine-4-carboxylate hydrochloride Methyl 2-(3,4,5-trifluorophenyl)isonicotinate (2.62 g) was dissolved in MTBE, then HCl (4 M in dioxane, 15 mL) was added. The solvents were evaporated to give methyl 2-(3,4,5-trifluorophenyl)isonicotinate hydrochloride (2.94 g, 9.68 mmol), which was dissolved in MeOH (40 mL) and platinum(IV) oxide (0.220 g, 0.97 mmol) added. The resulting mixture was hydrogenated in a Büchi hydrogenator at room temperature and 5 bar for 1 h. The catalyst was filtered off, washed with MeOH and the eluate evaporated yielding methyl 2-(3,4,5-trifluorophenyl)piperidine-4-carboxylate hydrochloride (2.75 g, 92%) as a brown solid. MS m/z 274 (M+H)$^+$ Step 3: Dimethyl 2-(3,4,5-trifluorophenyl)piperidine-1,4-dicarboxylate Methyl 2-(3,4,5-trifluorophenyl)piperidine-4-carboxylate hydrochloride (2.75 g, 8.88 mmol) was dissolved into DCM (50 mL), then DIPEA (3.88 mL, 22.20 mmol) was added. Methyl carbonochloridate (0.979 mL, 12.43 mmol) was added dropwise to the solution. The mixture was stirred at room temperature for 4 h. The mixture was washed with HCl (0.1 M, 100 mL) and satd NaHCO$_3$ (100 mL), then dried through a phase-separator and evaporated yielding dimethyl 2-(3,4,5-trifluorophenyl)piperidine-1,4-dicarboxylate (2.77 g, 94%) as an orange oil.

Step 4: 1-(Methoxycarbonyl)-2-(3,4,5-trifluorophenyl)piperidine-4-carboxylic acid Dimethyl 2-(3,4,5-trifluorophenyl)piperidine-1,4-dicarboxylate (2.77 g, 8.36 mmol) was dissolved in acetonitrile (35 mL) and water (0.700 mL), then lithium bromide (5.81 g, 66.89 mmol) was added. Et$_3$N (4.66 mL, 33.45 mmol) was added and the resulting yellow suspension was heated under reflux for 2 h. Water (50 mL) and MTBE (150 mL) were added. The phases were separated and the organic layer was extracted with water (2 times). The pooled aqueous layers were acidified to pH 1 with 3.8 M HCl and with MTBE (2 times). The combined organic layer was dried over Na$_2$SO$_4$, filtered and evaporated yielding 1-(methoxycarbonyl)-2-(3,4,5-trifluorophenyl)piperidine-4-carboxylic acid (2.23 g, 84%) as a slightly yellow semi-solid. MS m/z 316 (M−H)$^−$ Reference Compound 27

1-(Methoxycarbonyl)-2-(2,4,5-trifluorophenyl)piperidine-4-carboxylic acid

Step 1: Methyl 2-(2,4,5-trifluorophenyl)isonicotinate

Methyl 2-chloroisonicotinate (3.25 g, 18.94 mmol), 2,4,5-trifluorophenylboronic acid (5.00 g, 28.41 mmol), potassium carbonate (3.93 g, 28.41 mmol) and PdCl$_2$ (dppf) (0.411 g, 0.57 mmol) were mixed in methanol (20 mL) in two 20 mL microwave vials. The vials were capped and heated at 100° C. for 10 min in a single node microwave reactor. The reaction mixture was suspended in methanol, filtered and the filtrate evaporated to yield a dark red slurry. DCM and water were added and the phases separated. The water phase (pH 9) was extracted with DCM and the combined organic phase washed with brine, passed through a phase separator and evaporated to yield a brown solid. The crude brown solid was dissolved in MTBE (120 mL) and solids filtered off. Hydrogen chloride (4 M in dioxane, 4.74 mL, 18.94 mmol) was added dropwise and a suspension was formed. The suspension was stirred at room temperature for 45 min. The solid was collected by filtration and washed with MTBE. MTBE and satd NaHCO$_3$ were added. The organic phase was dried over Na$_2$SO$_4$, filtered and evaporated to yield methyl 2-(2,4,5-trifluorophenyl)isonicotinate (1.676 g, 33%) as a beige solid. The MTBE-filtrate was washed with satd NaHCO$_3$, dried over Na$_2$SO$_4$, filtered and evaporated to yield a brown solid. The residue was purified via Biotage (0=>20% EtOAc in heptane, 6 CV; Biotage® KP-SIL 100 g column) to yield methyl 2-(2,4,5-trifluorophenyl)-isonicotinate (0.86 g, 17%) as a white solid. $^1$H NMR (600 MHz, cdcl$_3$) δ 3.97 (s, 3H), 7.00-7.07 (m, 1H), 7.81 (dd, 1H), 7.90-7.97 (m, 1H), 8.32-8.33 (m, 1H), 8.83 (dd, 1H). MS m/z 268 (M+H)$^+$ Step 2: Methyl 2-(2,4,5-trifluorophenyl)piperidine-4-carboxylate Methyl 2-(2,4,5-trifluorophenyl)isonicotinate (2.509 g, 9.39 mmol) was dissolved in acetic acid (25 mL) and platinum(IV) oxide (0.107 g, 0.47 mmol) added. The resulting mixture was hydrogenated in a Büchi hydrogenator at room temperature and 5 bar for 6 h. The catalyst was filtered off, washed with MeOH and the eluate evaporated. DCM and 10% K$_2$CO$_3$ were added and the phases separated. The organic layer was washed with brine, passed through a phase separator and evaporated to yield methyl 2-(2,4,5-trifluorophenyl)piperidine-4-carboxylate (2.434 g, 95%) as a brown oil. MS m/z 274 (M+H)$^+$ Step 3: Dimethyl 2-(2,4,5-trifluorophenyl)piperidine-1,4-dicarboxylate Methyl 2-(2,4,5-trifluorophenyl)piperidine-4-carboxylate (2.232 g, 8.17 mmol) was dissolved in DCM (50 mL) and DIPEA (1.707 mL, 9.80 mmol), then methyl carbonochloridate (0.965 mL, 12.25 mmol) was added. The solution was stirred at room temperature for 1 h. The reaction mixture was washed with 0.1 M HCl and satd NaHCO$_3$, passed through a phase separator and evaporated to yield crude dimethyl 2-(2,4,5-trifluorophenyl)piperidine-1,4-dicarboxylate (2.971 g, quant.) as a brown oil. MS m/z 332 (M+H)$^+$

Step 4: 1-(Methoxycarbonyl)-2-(2,4,5-trifluorophenyl)piperidine-4-carboxylic acid Dimethyl 2-(2,4,5-trifluorophenyl)piperidine-1,4-dicarboxylate (2.971 g, 8.97 mmol) was dissolved in acetonitrile (30 mL) and water (0.600 mL), then lithium bromide (6.23 g, 71.74 mmol) was added. Triethylamine (4.97 mL, 35.87 mmol) was added and the resulting brown suspension was heated under reflux. Water and MTBE were added. The organic phase was extracted with water (×2). The pooled aqueous layer was acidified to pH 1 with 3.8 M HCl and then extracted with MTBE (×2). The combined organic layer was washed with water and evaporated. Traces of water were azeotropically removed by MeCN. 1-(Methoxycarbonyl)-2-(2,4,5-trifluorophenyl)piperidine-4-carboxylic acid (2.388 g, 84%) was isolated as a yellow oil. MS m/z 318 (M+H)$^+$

Reference Compound 28

2-(4-Chloro-3,5-difluorophenyl)-1-(methoxycarbonyl)piperidine-4-carboxylic acid

Step 1: 2-(4-Chloro-3,5-difluorophenyl)-4,4,5,5-tetramethyl-1,3,2-dioxaborolane To 5-Bromo-2-chloro-1,3-difluorobenzene (4.8 g, 21.11 mmol) dissolved in DMSO (40 mL) was added 4,4,4',4',5,5,5',5'-octamethyl-2,2'-bi(1,3,2-dioxaborolane) (6.22 g, 24.48 mmol), PdCl$_2$ (dppf) (0.764 g, 1.06 mmol) and potassium acetate (4.14 g, 42.21 mmol). The reaction mixture was heated in an oil bath at 80° C. for 10 h, then was diluted with ethyl acetate and washed with water. The organic layer was dried over Na$_2$SO$_4$ and evaporated. The residue was purified by automated flash chromatography on a Biotage® KP-SIL 340 g column. A gradient from 0% to 30% of EtOAc in heptane over 10 CV was used as mobile phase. 2-(4-Chloro-3,5-difluorophenyl)-4,4,5,5-tetramethyl-1,3,2-dioxaborolane (4.01 g, 69%) was isolated.

Step 2: Methyl 2-(4-chloro-3,5-difluorophenyl)isonicotinate hydrochloride

Methyl 2-chloroisonicotinate (3.01 g, 17.53 mmol), PdCl$_2$ (dppf) (0.317 g, 0.44 mmol) and potassium carbonate (1.322 mL, 21.91 mmol) were distributed equally over 3 microwave reaction vials. 2-(4-Chloro-3,5-difluorophenyl)-4,4,5,5-tetramethyl-1,3,2-dioxaborolane (4.01 g, 14.61 mmol) was dissolved in methanol (45 mL) to give a colorless solution. The solution was split into 3 equal portions and added to the vials. The vials were capped and heated in a single node microwave reactor at 100° C. for 10 min each. The content of the vials was combined and the solvent evaporated. The residue was dissolved in DCM and washed with water. The organic phase was filtered through a phase separator and evaporated. The residue was dissolved in MTBE and solids were filtered off. Hydrogen chloride (4 M in dioxane, 3.65 mL, 14.61 mmol) was added and the precipitate collected to yield methyl 2-(4-chloro-3,5-difluorophenyl)isonicotinate hydrochloride (1.72 g, 42%) as a solid. $^1$H NMR (400 MHz, cdcl$_3$) δ 4.06 (s, 3H), 7.86 (d, 2H), 8.09 (d, 1H), 8.39 (s, 1H), 8.96 (d, 1H). MS m/z 284 (M+H)$^+$

Step 3: Methyl 2-(4-chloro-3,5-difluorophenyl)piperidine-4-carboxylate

Methyl 2-(4-chloro-3,5-difluorophenyl)isonicotinate hydrochloride (1.94 g, 6.06 mmol) was dissolved in methanol. Platinum(IV) oxide (0.138 g, 0.61 mmol) was added and the mixture was hydrogenated at 5 bar at room temperature in a Büchi hydrogenator for 7 h. The catalyst was removed by filtration and the solvent evaporated. Methyl 2-(4-chloro-3,5-difluoro-phenyl)piperidine-4-carboxylate hydrochloride (1.820 g, 92%) was yielded as a colorless oil. MS m/z 290 (M+H)$^+$

Step 4: Dimethyl 2-(4-chloro-3,5-difluorophenyl)piperidine-1,4-dicarboxylate Methyl 2-(4-chloro-3,5-difluorophenyl)piperidine-4-carboxylate hydrochloride (1.82 g, 5.58 mmol) was dissolved in dichloromethane (50 mL). DIPEA (2.430 mL, 13.95 mmol) and methyl carbonochloridate (0.527 mL, 6.70 mmol) were added and the mixture was stirred at room temperature for 3 h. 0.1 M HCl was added and the aqueous layer was extracted with DCM. The combined organic layers were filtered through a phase separator and evaporated to yield dimethyl 2-(4-chloro-3,5-difluorophenyl)piperidine-1,4-dicarboxylate (1.83 g, 94%). MS m/z 348 (M+H)$^+$

Step 5: 2-(4-Chloro-3,5-difluorophenyl)-1-(methoxycarbonyl)piperidine-4-carboxylic acid Dimethyl 2-(4-chloro-3,5-difluorophenyl)piperidine-1,4-dicarboxylate (1.83 g, 5.26 mmol) was dissolved in acetonitrile (30 mL) and water (0.600 mL), then lithium bromide (3.66 g, 42.10 mmol) was added. Triethylamine (2.92 mL, 21.05 mmol) was added and the resulting suspension was heated under reflux for 4 h. MTBE (100 mL) and water (50 mL) were added, the phases separated and the organic layer was extracted with water. The combined aqueous layers were acidified to pH 1 with 3.8 M HCl and extracted with MTBE. The combined organic layers were dried over Na$_2$SO$_4$ and evaporated to yield 2-(4-chloro-3,5-difluoro-phenyl)-1-(methoxycarbonyl)piperidine-4-carboxylic acid (1.600 g, 91%) as a light yellow solid. MS m/z 332 (M−H)$^-$

Reference Compound 29

1-(Methoxycarbonyl)-2-(3-methyl-4-(trifluoromethyl)phenyl)piperidine-4-carboxylic acid

Step 1: 4,4,5,5-Tetramethyl-2-(3-methyl-4-(trifluoromethyl)phenyl)-1,3,2-dioxaborolane 4-Bromo-2-methyl-1-(trifluoromethyl)benzene (3.3 g, 13.8 mmol), 4,4,4',4',5,5,5',5'-octamethyl-2,2'-bi(1,3,2-dioxaborolane) (4.07 g, 16.01 mmol), potassium acetate (2.71 g, 27.61 mmol) and PdCl$_2$ (dppf) (0.5 g, 0.69 mmol) were combined in DMF (60 mL) and divided into three microwave vials. The reaction mixtures were heated in a single node microwave reactor to 100° C. for 10 min. The reaction mixtures were diluted with ethyl acetate and filtered through celite. The filtrate was washed with water (3×) and brine. The organic layer was isolated, dried over Na$_2$SO$_4$, filtered through celite and the solvent evaporated. Auto mated column chromatography using the Biotage apparatus. Gradient elution using heptane-ethyl acetate, started 0% ethyl acetate up to 30%. 4,4,5,5-Tetramethyl-2-(3-methyl-4-(trifluoromethyl)phenyl)-1,3,2-dioxaborolane (1.66 g, 42%) was isolated. $^1$H NMR (600 MHz, cdcl$_3$) δ 1.33 (s, 12H), 2.47 (s, 3H), 7.57 (d, 1H), 7.66-7.70 (m, 2H).

Step 2: Methyl 2-(3-methyl-4-(trifluoromethyl)phenyl)isonicotinate

Methyl 2-chloroisonicotinate (0.996 g, 5.80 mmol), potassium carbonate (1.042 g, 7.54 mmol), 4,4,5,5-tetramethyl-2-(3-methyl-4-(trifluoromethyl)phenyl)-1,3,2-dioxaborolane (1.66 g, 5.80 mmol) and PdCl$_2$ (dppf) (0.105 g, 0.15 mmol) were mixed in methanol (20 mL) in two microwave vials. The vials were capped and heated at 100° C. for 10 min in a single node microwave reactor. The solution was partitioned between water and ethyl acetate. The organic layer was isolated, dried over Na$_2$SO$_4$, filtered through celite and the solvent was evaporated. Automated column chromatography using the Biotage equipment. Gradient elution using heptane-ethyl acetate, 0% to 50%. Methyl 2-(3-methyl-4-(trifluoromethyl)phenyl)-isonicotinate (1.22 g, 71%) was isolated. $^1$H NMR (600 MHz, cdcl$_3$) δ 2.57 (s, 3H), 3.99 (s, 3H), 7.70 (d, 1H), 7.81 (dd, 1H), 7.91 (d, 1H), 7.98 (s, 1H), 8.29 (s, 1H), 8.84 (d, 1H).

Step 3: Methyl 2-(3-methyl-4-(trifluoromethyl)phenyl)piperidine-4-carboxylate

Methyl 2-(3-methyl-4-(trifluoromethyl)phenyl)isonicotinate (2.32 g, 7.86 mmol) was dissolved in acetic acid (150 mL) and platinum(IV) oxide (36 mg, 0.16 mmol) was added. Hydrogenation in a Büchi hydrogenator at room temperature and 6 bar for 2 h. The catalyst was filtered off. More platinum (IV) oxide was added and hydrogenation continued until starting material was consumed. Catalyst was filtered off and the solvent was evaporated to yield crude methyl 2-(3-methyl-4-(trifluoromethyl)phenyl)piperidine-4-carboxylate (2.60 g, 110%).

Step 4: Dimethyl 2-(3-methyl-4-(trifluoromethyl)phenyl)piperidine-1,4-dicarboxylate Methyl 2-(4-(trifluoromethyl)benzyl)piperidine-4-carboxylate (2.9 g, 9.62 mmol) was dissolved in DIPEA (1.866 g, 14.44 mmol) and dichloromethane (50 mL). Methyl carbonochloridate (1.091 g, 11.55 mmol) was added dropwise and the resulting mixture was stirred at room temperature overnight. 1 M KHSO$_4$ and diethyl ether were added and the phases separated. The organic layer was washed with Na$_2$CO$_3$, dried over MgSO$_4$, filtered through celite and evaporated to yield dimethyl 2-(3-methyl-4-(trifluoromethyl)phenyl)-piperidine-1,4-dicarboxylate (3.09 g, 89%).

Step 5: 1-(Methoxycarbonyl)-2-(3-methyl-4-(trifluoromethyl)phenyl)piperidine-4-carboxylic acid Dimethyl 2-(3-methyl-4-(trifluoromethyl)phenyl)piperidine-1,4-dicarboxylate (3.09 g, 8.60 mmol) was dissolved in acetonitrile (30 mL) and water (0.6 mL), lithium bromide (5.97 g, 68.79 mmol) was added. Triethylamine (3.48 g, 34.40 mmol) was added and the resulting suspension was heated under reflux for 1 h. Water (60 mL) and MTBE were added. The organic phase was extracted with water (×2). To the pooled aqueous layer was added MTBE and the solution was acidified to pH 1 with HCl and then extracted with MTBE (×2). The organic layer was dried over Na$_2$SO$_4$, filtered through celite and the solvent evaporated to yield 1-(methoxycarbonyl)-2-(3-methyl-4-(trifluoromethyl)phenyl)piperidine-4-carboxylic acid (2.65 g, 7.67 mmol).

Reference Compound 30

2-(3,5-Difluoro-4-(trifluoromethyl)phenyl)-1-(methoxycarbonyl)piperidine-4-carboxylic acid Step 1: 2-(3,5-Difluoro-4-(trifluoromethyl)phenyl)-4,4,5,5-tetramethyl-1,3,2-dioxaborolane 5-Bromo-1,3-difluoro-2-(trifluoromethyl)benzene (4.7 g, 18.01 mmol), PdCl$_2$ (dppf) (0.652 g, 0.90 mmol) and potassium acetate (3.53 g, 36.02 mmol) were suspended in MeOH (20 mL), divided in two microwave vials and heated to 120° C. in a single node microwave reactor for 20 min. The reaction mixture was diluted with EtOAc (400 mL), washed with water (400 mL), brine (400 mL), dried with Na$_2$SO$_4$, filtered and evaporated in vacuo. The residue was purified by automated flash chromatography on 2 Biotage® KP-SIL 100 g columns. A gradient from 0% to 30% of EtOAc in heptane over 12 CV was used as mobile phase. The product was collected using the wavelength 265 nm. 2-(3,5-Difluoro-4-(trifluoromethyl)phenyl)-4,4,5,5-tetramethyl-1,3,2-dioxaborolane (3.30 g, 59.5%) was isolated as a white solid. $^1$H NMR (600 MHz, cdcl$_3$) δ 1.32 (s, 12H), 7.37 (d, 2H).

Step 2: Methyl 2-(3,5-difluoro-4-(trifluoromethyl)phenyl)isonicotinate

Methyl 2-chloroisonicotinate (1,838 g, 10.71 mmol), potassium carbonate (0.888 g, 6.43 mmol) and PdCl$_2$ (dppf) (0.233 g, 0.32 mmol) were added to a microwave vial. 2-(3,5-difluoro-4-(trifluoromethyl)phenyl)-4,4,5,5-tetramethyl-1,3,2-dioxaborolane (3.3 g, 10.71 mmol) dissolved in MeOH (15 mL) was added and the reaction heated in a single node microwave reactor at 100° C. for a total of 40 min. DCM (100 mL) and water (100 mL) were added, shaken and the phases separated. The aqueous phase was extracted with DCM (100 mL). The combined organic phases were washed with brine (200 mL), dried with a phase separator and evaporated in vacuo. The residue was purified by automated flash chromatography on a Biotage® KP-SIL 100 g column. A gradient from 5% EtOAc in heptane over 3 CV followed by 5% to 30% of EtOAc in heptane over 9 CV was used as mobile phase. The product was collected using the wavelength 250 nm. Methyl 2-(3,5-difluoro-4-(trifluoromethyl)phenyl)isonicotinate (1.810 g, 53%) was isolated as a white solid. $^1$H NMR (600 MHz, cdcl$_3$) δ 3.99 (s, 3H), 7.74 (d, 2H), 7.86-7.89 (m, 1H), 8.27 (s, 1H), 8.86 (d, 1H).

Step 3: Methyl 2-(3,5-difluoro-4-(trifluoromethyl)phenyl)piperidine-4-carboxylate hydro-chloride Methyl 2-(3,5-difluoro-4-(trifluoromethyl)phenyl)isonicotinate (3.147 g, 9.92 mmol) was dissolved in MeOH (20 mL) and hydrogen chloride (1.25 M in MeOH, 23.81 mL, 29.76 mmol) was added. The reaction was stirred at room temperature for 2 h and evaporated. Methanol (20 mL) and platinum(IV) oxide (0.113 g, 0.50 mmol) was added and the solution hydrogenated in a Büchi hydrogenator at 5 bar and room temperature for 4.5 h. Platinum(IV) oxide (0.113 g, 0.50 mmol) was added and hydrogenation continued for 4 h. The catalyst was filtered off and washed with MeOH. The filtrate was evaporated in vacuo to yield methyl 2-(3,5-difluoro-4-(trifluoromethyl)phenyl)piperidine-4-carboxylate hydrochloride (3.12 g, 87%) as a white solid. MS m/z 324 (M+H)+

Step 4: Dimethyl 2-(3,5-difluoro-4-(trifluoromethyl) phenyl)piperidine-1,4-dicarboxylate Methyl 2-(3,5-difluoro-4-(trifluoromethyl)phenyl)piperidine-4-carboxylate hydrochloride (3.118 g, 8.67 mmol) and DIPEA (3.02 mL, 17.34 mmol) were dissolved in DCM (30 mL). Methyl carbonochloridate (1.024 mL, 13.00 mmol) was added and the reaction stirred at room temperature for 1.5 h. Additional methyl carbonochloridate (0.341 mL, 4.33 mmol) was added and stirring continued for 0.5 h. DCM (170 mL) was added. The organic phase was washed with 0.1 M HCl (2×200 mL), satd NaHCO$_3$ (200 mL), dried with a phase separator and evaporated in vacuo to yield dimethyl 2-(3,5-difluoro-4-(trifluoromethyl)phenyl)-piperidine-1,4-dicarboxylate (2.85 g, 86%) as a colorless oil. MS m/z 382 (M+H)+

Step 5: 2-(3,5-Difluoro-4-(trifluoromethyl)phenyl)-1-(methoxycarbonyl)piperidine-4-carboxylic acid Dimethyl 2-(3,5-difluoro-4-(trifluoromethyl)phenyl)piperidine-1,4-dicarboxylate (2.851 g, 7.48 mmol) was dissolved in acetonitrile (25 mL) and water (2.5 mL), then lithium bromide (5.19 g, 59.82 mmol) was added followed by triethylamine (4.15 mL, 29.91 mmol). The reaction mixture was heated under reflux for 1 h. MTBE (150 mL) and water (150 mL) were added, shaken and the phases separated. The organic phase was extracted with water (2×150 mL). The combined aqueous phases were acidified with 3 M HCl to pH 1 and extracted with MTBE (2×450 mL). The combined organic phases were dried over Na$_2$SO$_4$, filtered and evaporated in vacuo yielding 2-(3,5-difluoro-4-(trifluoromethyl) phenyl)-1-(methoxy-carbonyl)piperidine-4-carboxylic acid (2.363 g, 86%). MS m/z 368 (M+H)+

Reference Compound 31

1-(Methoxycarbonyl)-2-(2-methyl-4-(trifluoromethyl)phenyl)piperidine-4-carboxylic acid Step 1: Methyl 2-(2-methyl-4-(trifluoromethyl)phenyl)isonicotinate hydrochloride Potassium carbonate (2.66 g, 19.23 mmol), methyl 2-chloroisonicotinate (5.5 g, 32.05 mmol), 2-methyl-4-(trifluoromethyl)phenylboronic acid (8.50 g, 41.67 mmol), PdCl$_2$ (dppf) (0.696 g, 0.96 mmol), and MeOH (50.3 mL) were split into three microwave vials and heated in a single node microwave reactor to 100° C. for 20 min. Diluted with DCM, filtered and evaporated. Purified by flash chromatography using 5% EtOAc in heptane ->20% EtOAc over 10 CV at 280 nm. The residue was dissolved in ether and hydrogen chloride (4 M in dioxane, 8.01 mL, 32.05 mmol) was added and the solvents evaporated to yield methyl 2-(2-methyl-4-(trifluoromethyl)phenyl)isonicotinate hydrochloride (9.15 g, 86%) as a white solid. $^1$H NMR (400 MHz, cd$_3$od) δ 2.41 (s, 3H), 4.03 (s, 3H), 7.63-7.76 (m, 3H), 8.27 (dd, 1H), 8.33 (dd, 1H), 8.99 (dd, 1H). MS m/z 296 (M+H)+

Step 2: Methyl 2-(2-methyl-4-(trifluoromethyl)phenyl)piperidine-4-carboxylate hydrochloride Methyl 2-(2-methyl-4-(trifluoromethyl)phenyl)isonicotinate hydrochloride (9 g, 27.13 mmol) was dissolved in MeOH (50 mL), platinum(IV) oxide (0.185 g, 0.81 mmol) was added and the resulting mixture hydrogenated in a Büchi hydrogenator at 5 bar for 5 h. The catalyst was filtered off and the filtrate evaporated to give methyl 2-(2-methyl-4-(trifluoromethyl)phenyl)-piperidine-4-carboxylate hydrochloride (8 g, 87%) as a yellowish solid. MS m/z 302 (M+H)+

Step 3: Dimethyl 2-(2-methyl-4-(trifluoromethyl) phenyl)piperidine-1,4-dicarboxylate Methyl 2-(2-methyl-4-(trifluoromethyl)phenyl)piperidine-4-carboxylate hydrochloride (8.2 g, 24.28 mmol) and DIPEA (10.60 mL, 60.69 mmol) were dissolved in dichloromethane (100 mL). Methyl carbonochloridate (2.257 mL, 29.13 mmol) was added and the reaction stirred at room temperature for 1 h. DCM (100 mL) was added. The organic phase was washed twice with 1 M HCl and water, dried over Na$_2$SO$_4$ and evaporated to yield dimethyl 2-(2-methyl-4-(trifluoromethyl)phenyl)piperidine-1,4-dicarboxylate (8.9 g, quant.). MS m/z 360 (M+H)+

Step 4: 1-(Methoxycarbonyl-2-(2-methyl-4-(trifluromethyl)phenyl)piperidine-4-carboxylic acid Dimethyl 2-(2-methyl-4-(trifluoromethyl)phenyl)piperidine-1,4-dicarboxylate (8.9 g, 24.77 mmol) was dissolved in acetonitrile (80 mL). Water (1.6 mL), lithium bromide (17.21 g, 198.14 mmol), and triethylamine (13.73 mL, 99.07 mmol) were added. The mixture was heated at reflux for 2.5 h. After cooling it was diluted with water and extracted with EtOAc twice and the combined organic layer washed with water. The combined aqueous layer was acidified with 2 M HCl and extracted three times with EtOAc. The combined organic layer was dried over Na$_2$SO$_4$, filtered and evaporated to give crude 1-(methoxycarbonyl)-2-(2-methyl-4-(trifluoromethyl) phenyl)piperidine-4-carboxylic acid (7.79 g, 91%). MS m/z 344 (M−H)−

Reference Compound 32

2-(2-Fluoro-4-(trifluoromethyl)phenyl)-1-(methoxycarbonyl)piperidine-4-carboxylic acid Step 1: Methyl 2-(2-fluoro-4-(trifluoromethyl)phenyl)isonicotinate hydrochloride Methyl 2-chloroisonicotinate (2.8 g, 16.32 mmol), 2-fluoro-4-(trifluoromethyl)phenylboronic acid (5.09 g, 24.48 mmol), potassium carbonate (1.692 g, 12.24 mmol) and PdCl$_2$ (dppf) (0.354 g, 0.49 mmol) were mixed in methanol (30 mL) in two separate 20 mL microwave vials. The vials were capped and heated at 100° C. for 10 min in a single node microwave reactor. Water and DCM were added and the phases were separated. The water phase (pH 9) was extracted with DCM and the combined organic phase washed with brine, passed through a phase separator and evaporated to yield a dark-orange solid. The solid was dissolved in MTBE and stirred for 15 minutes, then filtered. The orange MTBE layer was treated with hydrogen chloride (4 M in dioxane, 4.08 mL, 16.32 mmol) and stirred for 1 h at room temperature. The precipitate was collected by filtration. Methyl 2-(2-fluoro-4-(trifluoromethyl)phenyl)isonicotinate hydrochloride (5.4 g, 99%) was isolated as a slightly orange solid. MS m/z 300 (M+H)+

Step 2: Methyl 2-(2-fluoro-4-(trifluoromethyl)phenyl)piperidine-4-carboxylate hydrochloride Methyl 2-(2-fluoro-4-(trifluoromethyl)phenyl)isonicotinate hydrochloride (5.4 g, 16.09 mmol) was dissolved in MeOH (40 mL) and platinum(IV) oxide (0.365 g, 1.61 mmol) added. The resulting mixture was hydrogenated in a Büchi hydrogenator at room temperature and 5 bar for 2 h. The catalyst was filtered off and washed with MeOH and the eluate evaporated yielding methyl 2-(2-fluoro-4-(trifluoromethyl)phenyl)piperidine-4-carboxylate hydro-chloride (5.1 g, 93%) as a slightly brown solid. MS m/z 306 (M+H)$^+$ Step 3: Dimethyl 2-(2-fluoro-4-(trifluoromethyl) phenyl)piperidine-1,4-dicarboxylate Methyl 2-(2-fluoro-4-(trifluoromethyl)phenyl)piperidine-4-carboxylate hydrochloride (5.50 g, 16.09 mmol) was dissolved in DCM (100 mL), then DIPEA (7.03 mL, 40.23 mmol) was added. Methyl carbonochloridate (1.774 mL, 22.53 mmol) was added dropwise to the solution. The mixture was stirred at room temperature for 4 h. The mixture was washed with 0.1 M HCl (100 mL) and satd NaHCO$_3$ (100 mL), then dried through a phase-separator and evaporated yielding dimethyl 2-(2-fluoro-4-(trifluoromethyl)phenyl)piperidine-1,4-dicarboxylate (5.33 g, 91%) as a brown oil.

Step 4: 2-(2-Fluoro-4-(trifluoromethyl)phenyl)-1-(methoxycarbonyl)piperidine-4-carboxylic acid Dimethyl 2-(2-fluoro-4-(trifluoromethyl)phenyl)piperidine-1,4-dicarboxylate (5.33 g, 14.67 mmol) was dissolved in acetonitrile (35 mL) and water (0.700 mL), then lithium bromide (10.19 g, 117.37 mmol) was added. Et$_3$N (8.18 mL, 58.68 mmol) was added and the resulting yellow suspension was heated under reflux for 1 h. Water (50 mL) and MTBE (150 mL) were added. The phases were separated and the organic layer was extracted with water (2 times). The pooled water layers were acidified to pH 1 with 3.8 M HCl and extracted with MTBE (2 times). The combined organic layer was dried over Na$_2$SO$_4$, filtered and evaporated yielding 2-(2-fluoro-4-(trifluoromethyl)phenyl)-1-(methoxycarbonyl)piperidine-4-carboxylic acid (4.82 g, 94%) as a slightly yellow solid. MS m/z 348 (M−H)$^−$ Reference Compound 33

2-(3-Fluoro-4-(trifluoromethyl)phenyl)-1-(methoxycarbonyl)piperidine-4-carboxylic acid Step 1: 2-(3-Fluoro-4-(trifluoromethyl)phenyl)-4,4,5,5-tetramethyl-1,3,2-dioxaborolane 4-Bromo-2-fluoro-1-(trifluoromethyl)benzene (5.08 g, 20.91 mmol) was dissolved in DMSO (40 mL), then 4,4,4',4',5,5,5',5'-octamethyl-2,2'-bi(1,3,2-dioxaborolane) (6.16 g, 24.25 mmol), PdCl$_2$ (dppf) (0.756 g, 1.05 mmol) and potassium acetate (4.10 g, 41.81 mmol) were added and the mixture was heated in an oil bath at 80° C. for 10 h. The reaction mixture was diluted with ethyl acetate and washed with water. The organic layer was dried with Na$_2$SO$_4$ and evaporated. The residue was purified by automated flash chromatography on a Biotage® KP-SIL 340 g column. A gradient from 0% to 20% of EtOAc in heptane over 10 CV was used as mobile phase. 2-(3-Fluoro-4-(trifluoromethyl)phenyl)-4,4,5,5-tetramethyl-1,3,2-dioxa-borolane (3.72 g, 61%) was isolated.

Step 2: Methyl 2-(3-fluoro-4-(trifluoromethyl)phenyl)isonicotinate

Methyl 2-chloroisonicotinate (2.86 g, 16.67 mmol), PdCl$_2$ (dppf) (0.278 g, 0.38 mmol) and potassium carbonate (1.161 mL, 19.24 mmol) were distributed equally over 3 microwave reaction vials. 2-(3-Fluoro-4-(trifluoromethyl)phenyl)-4,4,5,5-tetramethyl-1,3,2-dioxa-borolane (3.72 g, 12.82 mmol) dissolved in methanol (45 mL) was split into 3 equal portions and added to the vials. The vials were capped and heated in a single node microwave reactor at 100° C. for 10 min each. The contents of the vials was combined and the solvent evaporated. The residue was dissolved in DCM and washed with water. The organic phase was filtered through a phase separator and evaporated. The residue was purified by automated flash chromatography on a Biotage® KP-SIL 340 g column. 7:1 of heptane:EtOAc over 10 CV was used as mobile phase. Crude methyl 2-(3-fluoro-4-(trifluoromethyl)phenyl)isonicotinate (2.92 g, 76%) was isolated. MS m/z 300 (M+H)$^+$ Step 3: Methyl 2-(3-fluoro-4-(trifluoromethyl)phenyl)piperidine-4-carboxylate Methyl 2-(3-fluoro-4-(trifluoromethyl)phenyl)isonicotinate (2.9 g, 9.69 mmol) was dissolved in methanol and hydrogen chloride (1.25 M in methanol, 11.63 mL, 14.54 mmol) was added. The solvent was evaporated and the residue redissolved in methanol (50 mL), platinum(IV) oxide (0.220 g, 0.97 mmol) was added and the reaction mixture was hydrogenated at 5 bar and room temperature in a Büchi hydrogenator for 2 h. The catalyst was removed by filtration and the solvent was evaporated to yield methyl 2-(3-fluoro-4-(trifluoromethyl)phenyl)-piperidine-4-carboxylate hydrochloride (3.12 g, 94%). MS m/z 306 (M+H)$^+$ Step 4: Dimethyl 2-(3-fluoro-4-(trifluoromethyl) phenyl)piperidine-1,4-dicarboxylate 2-(3-Fluoro-4-(trifluoromethyl)phenyl)piperidine-4-carboxylate hydrochloride (3.12 g, 10.22 mmol) was dissolved in dichloromethane (50 mL), then DIPEA (4.45 mL, 25.55 mmol) and methyl carbonochloridate (0.966 mL, 12.26 mmol) were added and the mixture was stirred at room temperature for 3 h. 0.1 M HCl was added and the aqueous layer was extracted with DCM. The combined organic layers were filtered through a phase separator and evaporated to yield dimethyl 2-(3-fluoro-4-(trifluoromethyl)phenyl)piperidine-1,4-dicarboxylate (3.2 g, 86%). MS m/z 364 (M+H)$^+$ Step 5: 2-(3-Fluoro-4-(trifluoromethyl)phenyl)-1-(methoxycarbonyl)piperidine-4-carboxylic acid Dimethyl 2-(3-fluoro-4-(trifluoromethyl)phenyl)piperidine-1,4-dicarboxylate (3.2 g, 8.81 mmol) was dissolved in acetonitrile (40 mL) and water (0.800 mL), then lithium bromide (6.12 g, 70.46 mmol) was added. Triethylamine (4.88 mL, 35.23 mmol) was added and the resulting solution was heated under reflux for 5 h. MTBE (110 mL) and water (60 mL) were added, the phases separated and the organic layer was extracted with water. The combined aqueous layers were acidified to pH 1 with 3.8 M HCl and extracted with MTBE. The combined organic layers were dried with Na$_2$SO$_4$ and evaporated to yield 2-(3-fluoro-4-(trifluoromethyl)phenyl)-1-(methoxycarbonyl)piperidine-4-carboxylic acid (3.07 g, quant.). MS m/z 348 (M−H)$^−$ Reference Compound 34

1-(Methoxycarbonyl)-2-phenylpiperidine-4-carboxylic acid

Step 1: Methyl 2-phenylisonicotinate

Methyl 2-chloroisonicotinate (2.5 g, 14.57 mmol), phenylboronic acid (2.66 g, 21.86 mmol), potassium carbonate (3.02 g, 21.86 mmol) and PdCl$_2$ (dppf) (0.316 g, 0.44 mmol) were mixed in methanol (15 mL) in a 20 mL microwave vial. Two drops of water were added and the vial was capped and heated at 100° C. for 10 min in a single node microwave reactor. The solids were removed by filtration and the filtrate partly evaporated to yield a dark red slurry. DCM and water were added and the phases separated. The water phase (pH 9) was extracted with DCM and the combined organic phase washed with brine, passed through a phase separator and evaporated to yield a dark red oil. The compound was purified via Biotage, SNAP 340 g KP-SIL, eluent isocratic heptane/ethyl acetate 9:1 for 2 CV, then linear gradient heptane/ethyl acetate 9:1 to 6:4 over 5 CV to give methyl 2-phenylisonicotinate (1.83 g, 58%) as a colourless oil. $^1$H NMR (400 MHz, cdcl$_3$) δ 3.98 (s, 3H), 7.39-7.54 (m, 3H), 7.76 (dd, 1H), 8.01-8.09 (m, 2H), 8.29 (s, 1H), 8.82 (d, 1H). MS m/z 214 (M+H)$^+$ Step 2: Methyl 2-phenylpiperidine-4-carboxylate Methyl 2-phenylisonicotinate (1.83 g, 8.58 mmol) was dissolved in acetic acid (20 mL) and platinum(IV) oxide (0.097 g, 0.43 mmol) added. The resulting mixture was hydrogenated in a Büchi hydrogenator at room temperature and 5 bar for 2.5 h. The catalyst was filtered off and washed with MeOH and the eluate evaporated. DCM and 10% K$_2$CO$_3$ were added and the phases separated. The water phase was extracted with DCM and the combined organic phase washed with brine, passed through a phase separator and evaporated to yield crude methyl 2-phenylpiperidine-4-carboxylate (2.131 g) as a yellow oil. MS m/z 220 (M+H)$^+$ Step 3: Dimethyl 2-phenylpiperidine-1,4-dicarboxylate Methyl 2-phenylpiperidine-4-carboxylate (4.33 g, 19.75 mmol) was dissolved in DCM (150 mL) and DIPEA (3.78 mL, 21.72 mmol), then methyl carbonochloridate (1.710 mL, 21.72 mmol) was added. The solution was stirred at room temperature for 1 h 45 min. More DIPEA (1.720 mL, 9.87 mmol) and methyl carbonochloridate (0.777 mL, 9.87 mmol) were added and the reaction continued at room temperature for another 30 min. The reaction mixture was washed with 0.1 M HCl and satd NaHCO$_3$. The organic phase was passed through a phase separator and evaporated to yield dimethyl 2-phenylpiperidine-1,4-dicarboxylate (5.88 g, quant.) as a yellow oil. MS m/z 278 (M+H)$^+$ Step 4: 1-(Methoxycarbonyl)-2-phenylpiperidine-4-carboxylic acid Dimethyl 2-phenylpiperidine-1,4-dicarboxylate (5.88 g, 21.20 mmol) was dissolved in acetonitrile (60 mL) and water (1.2 mL), then lithium bromide (4.25 mL, 169.63 mmol) was added. Triethylamine (11.76 mL, 84.81 mmol) was added and the resulting yellow suspension was heated at reflux for 1 h. Water (60 mL) and MTBE were added. The organic phase was extracted with water (×2). To the pooled aqueous layer was added MTBE and the solution was acidified to pH 1 with 3.8 M aq HCl and then extracted with MTBE (×2). The combined organic layer was washed with water and evaporated. Traces of water were azeotropically removed by MeCN. 1-(Methoxycarbonyl)-2-phenylpiperidine-4-carboxylic acid (5.25 g, 94%) was isolated as a slightly yellow semisolid. MS m/z 264 (M+H)$^+$ Reference Compound 35

2-Cyclohexyl-1-(methoxycarbonyl)piperidine-4-carboxylic acid

Step 1: Methyl 2-cyclohexylpiperidine-4-carboxylate hydrochloride

Methyl 2-phenylisonicotinate (3.182 g, 14.92 mmol) (from reference compound 34, step 1) was dissolved in MeOH (30 mL) and hydrogen chloride (1.25 M in MeOH, 14.33 mL, 17.91 mmol) was added. The solvents were evaporated to give a slightly yellow solid. The residue was dissolved in MeOH (60 mL) and platinum(IV) oxide (0.102 g, 0.45 mmol) was added. The resulting mixture was then hydrogenated in a Büchi hydrogenator at 8 bar for 5 h. More platinum(IV) oxide (121 mg) was added and the hydrogenation continued overnight at 8 bar (15 h). Platinum(IV) oxide (120 mg) was added and the hydrogenation continued at 60 C for 5 hours. Platinum(IV) oxide (120 mg) was added and the hydrogenation was continued at 60 C overnight (15 h). The reaction mixture was filtered through diatomic earth containing filter carton and washed with methanol. The solvents were evaporated and the residue dried in vacuum to give a white solid. The residue was redissolved in MeOH (60 mL). Platinum(IV) oxide (340 mg) was added and the hydrogenation continued at 8 bar, 60 C overnight (22 h). The reaction mixture was filtered through diatomic earth containing filter carton and washed with methanol. The solvents were evaporated and the residue dried in vacuum to give methyl 2-cyclohexylpiperidine-4-carboxylate hydrochloride (3.50 g, 89%) as a white solid. MS m/z 226 (M+H)$^+$ Step 2: Dimethyl 2-cyclohexylpiperidine-1,4-dicarboxylate Methyl chloroformate (1.344 mL, 17.36 mmol) in DCM (50 mL) was added to a solution of methyl 2-cyclohexylpiperidine-4-carboxylate hydrochloride (3.50 g, 13.35 mmol) and DIPEA (1.88 mL, 10.76 mmol) in DCM (100 mL). The reaction solution was stirred for 3 h. 1.88 mL DIPEA and 1.345 mL methyl chloroformate was added and the reaction continued overnight (16 h). The organic phase was washed with satd NaHCO$_3$. The phases were separated and the organic phase dried using a phase separator to give crude dimethyl 2-cyclohexylpiperidine-1,4-dicarboxylate (4.90 g). MS m/z 284 (M+H)$^+$ Step 3: 2-Cyclohexyl-1-(methoxycarbonyl)piperidine-4-carboxylic acid Dimethyl 2-cyclohexylpiperidine-1,4-dicarboxylate (4.90 g, crude) was dissolved in acetonitrile (30 mL) and water (0.600 mL). lithium bromide (9.28 g, 106.80 mmol) and triethylamine (7.40 mL, 53.40 mmol) were added and the mixture was heated under reflux for 2 h. Water (60 mL) and MTBE were added. The organic phase was extracted with water (×2). MTBE was added to the pooled aqueous layer and the solution was acidified to pH 1 with 2 M HCl and then extracted with MTBE (×2). The combined organic layer was dried over Na$_2$SO$_4$ and evaporated to give 2-cyclohexyl-1-(methoxycarbonyl)piperidine-4-carboxylic acid (3.28 g, 91% (over 2 steps)) as a slightly yellow semisolid. MS m/z 270 (M+H)$^+$

Reference Compound 36

1-(Benzyloxycarbonyl)-2-(2-methyl-2H-tetrazol-5-yl)piperidine-4-carboxylic acid

Step 1: Ethyl 2-carbamoylisonicotinate

To a solution of ethyl isonicotinate (10 g, 66.15 mmol) and concentrated sulfuric acid (3.53 mL, 66.15 mmol) in formamide (80 mL, 2012.41 mmol), 30% hydrogen peroxide (2.399 mL, 99.23 mmol) and powdered iron(II) sulfate heptahydrate (27.6 g, 99.23 mmol) were separately and simultaneously added over 15 min with efficient stirring and cooling in an ice-bath. After complete addition the ice bath was removed and stirring was continued for 2 h. Sodium 2-hydroxypropane-1,2,3-tricarboxylate (132 mL, 132.31 mmol) (tris odium citrate) was added and the mixture was brought to pH 8 by addition of satd NaHCO$_3$ The resultant mixture was extracted with DCM three times and the combined organic extracts were washed with cold water, dried over Na$_2$SO$_4$ and evaporated. The solid residue contained a minority of product. The crude product was subjected to the same treatment as above twice more before there was a majority of the desired product in the crude product which was recrystallised from EtOH. Yield: 4.3 g. The mother liquor was purified on Biotage using heptane/EtOAc 80/20-10/90 and gave another 0.8 g of product. Ethyl 2-carbamoylisonicotinate (5.1 g, 40%) was isolated. $^1$H NMR (400 MHz, dmso) δ 1.34 (t, 3H), 4.37 (q, 2H), 7.79 (s, 1H), 8.00 (d, 1H), 8.22 (s, 1H), 8.40 (s, 1H), 8.83 (d, 1H). MS m/z 195 (M+H)$^+$

Step 2: Ethyl 2-carbamoylpiperidine-4-carboxylate hydrochloride

Ethyl 2-carbamoylisonicotinate (4.24 g, 21.83 mmol) was slurried in MeOH (50 mL) and HCl in MeOH (17.47 mL, 21.83 mmol) and platinum(IV) oxide (0.248 g, 1.09 mmol) were added. The mixture was hydrogenated at 5 bar in a Büchi hydrogenation apparatus. After 3 h there were still starting material left. platinum(IV) oxide (0.14 g, 0.62 mmol) was added and the reaction continued for 2 h when platinum(IV) oxide (0.387 g, 1.70 mmol) was added and the reaction was stirred overnight. The reaction mixture was filtered and evaporated to give ethyl 2-carbamoylpiperidine-4-carboxylate hydrochloride (3.93 g, 90%). $^1$H NMR (400 MHz, dmso) δ 1.16 (t, 3H), 1.31-1.63 (m, 2H), 1.86 (d, 1H), 2.26 (d, 1H), 2.54-2.66 (m, 1H), 2.74-2.88 (m, 1H), 3.10-3.19 (m, 1H), 3.47-3.56 (m, 1H), 4.06 (q, 2H), 7.38 (s, 1H), 7.71 (s, 1H). MS m/z 201 (M+H)$^+$

Step 3: 1-Benzyl 4-ethyl 2-carbamoylpiperidine-1,4-dicarboxylate

Ethyl 2-carbamoylpiperidine-4-carboxylate hydrochloride (2 g, 7.86 mmol) was slurried in dichloromethane (25 mL) and DIPEA (3.43 mL, 19.65 mmol) was added followed by benzyl carbonochloridate (1.161 mL, 8.25 mmol) dropwise. The reaction was stirred for 1 h then washed with 25 mL of 2 M HCl and water, dried over Na$_2$SO$_4$ and evaporated. The crude product was purified on a 100 g Biotage column with heptane/EtOAc over 4 CV followed by 100% EtOAc over 10 CV. 1-Benzyl 4-ethyl 2-carbamoylpiperidine-1,4-dicarboxylate (1.99 g, 76%) was isolated. $^1$H NMR (400 MHz, dmso) δ 1.16 (t, 3H), 1.57-1.69 (m, 1H), 1.81-1.92 (m, 1H), 1.95-2.07 (m, 1H), 2.21-2.32 (m, 1H), 2.58-2.67 (m, 1H), 3.29-3.45 (m, 1H), 3.69-3.77 (m, 1H), 3.92-4.06 (m, 2H), 4.34 (t, 1H), 4.99-5.08 (m, 2H), 6.95 (s, 1H), 7.25-7.38 (m, 6H). MS m/z 335 (M+H)$^+$

Step 4: 1-Benzyl 4-ethyl 2-cyanopiperidine-1,4-dicarboxylate

1-Benzyl 4-ethyl 2-carbamoylpiperidine-1,4-dicarboxylate (2.4 g, 7.18 mmol) was dissolved in pyridine (50 mL, 618.21 mmol). The mixture was cooled on an ice bath and SOCl$_2$ (3.14 mL, 43.07 mmol) was added dropwise and left overnight at room temperature. The reaction mixture was evaporated and partitioned between diluted HCl and DCM. The aqueous layer was extracted with DCM and the combined organic layer was washed with water, dried over Na$_2$SO$_4$ and evaporated. Crude 1-benzyl 4-ethyl 2-cyanopiperidine-1,4-dicarboxylate (2.25 g, 99%) was isolated. $^1$H NMR (400 MHz, dmso) δ 1.21 (t, 3H), 1.54-1.66 (m, 1H), 1.98-2.12 (m, 2H), 2.29-2.37 (m, 1H), 2.83-2.91 (m, 1H), 3.04-3.16 (m, 1H), 3.83-3.91 (m, 1H), 4.02-4.18 (m, 2H), 5.13 (s, 2H), 5.25-5.31 (m, 1H), 7.28-7.40 (m, 5H).

Step 5: 1-Benzyl 4-ethyl 2-(1H-tetrazol-5-yl)piperidine-1,4-dicarboxylate

1-Benzyl 4-ethyl 2-cyanopiperidine-1,4-dicarboxylate (2.5 g, 7.90 mmol) was dissolved in toluene (50 mL) and sodium azide (0.822 g, 12.64 mmol) and triethylamine hydrochloride (1.740 g, 12.64 mmol) were added and the mixture was heated at 95° C. overnight. The reaction mixture was allowed to cool to room temperature and was washed with 2 M HCl. The aqueous phase was extracted with EtOAc and the combined organic phase was dried over Na$_2$SO$_4$ and evaporated to yield 1-benzyl 4-ethyl 2-(1H-tetrazol-5-yl)piperidine-1,4-dicarboxylate (2.8 g, 99%). MS m/z 360 (M+H)$^+$

Step 6: 1-Benzyl 4-ethyl 2-(2-methyl-2H-tetrazol-5-yl)piperidine-1,4-dicarboxylate and 1-benzyl 4-ethyl 2-(1-methyl-1H-tetrazol-5-yl)piperidine-1,4-dicarboxylate 1-Benzyl 4-ethyl 2-(1H-tetrazol-5-yl)piperidine-1,4-dicarboxylate (3.45 g, 9.60 mmol) was dissolved in acetone (20 mL) and iodomethane (2.99 mL, 48.00 mmol) and K$_2$CO$_3$ (3.98 g, 28.80 mmol) were added. The mixture was stirred at room temperature for 3 h. The reaction mixture was partitioned between water and EtOAc. The aqueous layer was extracted twice with EtOAc and the combined organic phase was washed with water and evaporated. The crude product was purified on a 100 g Biotage column with heptane/EtOAc 88/12-0/100 over 12 column volumes (CV). 1-Benzyl 4-ethyl 2-(2-methyl-2H-tetrazol-5-yl)piperidine-1,4-dicarboxylate (1.84 g, 51%) and 1-benzyl 4-ethyl 2-(1-methyl-1H-tetrazol-5-yl)piperidine-1,4-dicarboxylate (1.14 g, 32%) were isolated. 2-Methyl-isomer: $^1$H NMR (400 MHz, cdcl$_3$) δ 1.15 (t, 3H), 1.75-1.87 (m, 1H), 2.02-2.11 (m, 1H), 2.27-2.37 (m, 1H), 2.66-2.78 (m, 2H), 3.55-3.65 (m, 1H), 3.75-3.86 (m, 1H), 3.90-3.99 (m, 1H), 4.01-4.09 (m, 1H), 4.25 (s, 3H), 5.13 (q, 2H), 5.55-5.62 (m, 1H), 7.25-7.38 (m, 5H). MS m/z 374 (M+H)$^+$. 3-Methyl-isomer: MS m/z 374 (M+H)$^+$

Step 7: 1-(Benzyloxycarbonyl)-2-(2-methyl-2H-tetrazol-5-yl)piperidine-4-carboxylic acid 1-Benzyl 4-ethyl 2-(2-methyl-2H-tetrazol-5-yl)piperidine-1,4-dicarboxylate (0.92 g, 2.36 mmol) was dissolved in THF (10 mL) and water (10 mL) and LiOH (0.239 g, 9.98 mmol) was added. The mixture was stirred at room temperature for 1 h 10 min and then diluted with water and acidified with 2 M HCl. The aqueous phase was extracted 3 times with EtOAc, the combined organic phase dried over $Na_2SO_4$ and evaporated to yield 1-(benzyloxycarbonyl)-2-(2-methyl-2H-tetrazol-5-yl)piperidine-4-carboxylic acid (828 mg, quant.). $^1$H NMR (400 MHz, $cdcl_3$) δ 1.80-1.91 (m, 1H), 2.01-2.11 (m, 1H), 2.34 (dt, 1H), 2.63-2.79 (m, 2H), 3.55-3.65 (m, 1H), 4.01-4.09 (m, 1H), 4.24 (s, 3H), 5.13 (d, 2H), 5.60 (dd, 1H), 7.27-7.39 (m, 5H). MS m/z 346 $(M+H)^+$ Reference Compound 37

1-(Benzyloxycarbonyl)-2-(1-methyl-1H-tetrazol-5-yl)piperidine-4-carboxylic acid

1-Benzyl 4-ethyl 2-(1-methyl-1H-tetrazol-5-yl)piperidine-1,4-dicarboxylate (1.14 g, 2.93 mmol) (from reference compound 36, step 6) was dissolved in THF (10 mL) and water (10 mL) and LiOH (0.280 g, 11.69 mmol) was added. The mixture was stirred at room temperature for 30 min and then diluted with water and acidified with 2 M HCl. The aqueous phase was extracted 3 times with EtOAc, the combined organic phase dried over $Na_2SO_4$ and evaporated to yield 1-(Benzyloxycarbonyl)-2-(1-methyl-1H-tetrazol-5-yl) piperidine-4-carboxylic acid (990 mg, 98%). $^1$H NMR (400 MHz, $cdcl_3$) δ 1.89-2.01 (m, 1H), 2.15-2.24 (m, 1H), 2.27-2.36 (m, 1H), 2.50-2.61 (m, 1H), 2.78 (p, 1H), 3.68-3.80 (m, 1H), 3.91-4.09 (m, 4H), 5.08 (q, 2H), 5.44 (t, 1H), 7.23-7.39 (m, 5H). MS m/z 346 $(M+H)^+$ Reference Compound 38

2-(Cyclohexyloxymethyl)-1-(methoxycarbonyl)piperidine-4-carboxylic acid

Step 1: Methyl 2-(hydroxymethyl)isonicotinate

The reaction was performed in 2 separate 1000 mL round-bottomed flasks. To a solution of methyl isonicotinate (70 g, 510.44 mmol) and sulfuric acid (2.340 mL, 43.90 mmol) in MeOH (700 mL) under reflux, was added a solution of ammonium peroxydisulfate (210 g, 918.80 mmol) in water (350 mL) over 20 min. The reaction was refluxed for 20 min and was then allowed to cool to room temperature. The solid was filtered off and washed with MeOH. MeOH was removed from the filtrate under reduced pressure and then was neutralised by cautious stepwise addition of solid $Na_2CO_3$ under ice-cooling. The aqueous solution was extracted with ethyl acetate and the combined organic layers were dried with $Na_2SO_4$ and evaporated. The dark-brown residue was treated with cyclohexane (3×300 mL) and the cyclohexane phase was decanted. The remaining dark-brown residue was purified by automated flash chromatography on 2 Biotage® KP-SIL 340 g columns. A gradient from 25% to 100% of EtOAc in heptane over 10 CV was used as mobile phase. Methyl 2-(hydroxymethyl)isonicotinate (27.5 g, 32%) was isolated. $^1$H NMR (400 MHz, $cdcl_3$) δ 3.90 (s, 3H), 4.78 (s, 2H), 7.57-7.90 (m, 2H), 8.64 (s, 1H). MS m/z 168 $(M+H)^+$ Step 2: Methyl 2-(phenoxymethyl)isonicotinate Methyl 2-(hydroxymethyl)isonicotinate (2.232 g, 13.35 mmol) dissolved in THF (15 mL) and phenol (1.426 mL, 16.02 mmol) and triphenylphosphine (3.71 mL, 16.02 mmol) were added. The mixture was cooled to 0° C. (E)-diisopropyl diazene-1,2-dicarboxylate (3.24 g, 16.02 mmol) was added dropwise, the ice-bath removed and the reaction stirred at room temperature for 2 h. The solvent was evaporated and the residue was purified by automated flash chromatography on a Biotage® KP-SIL 340 g column. 4:1 of EtOAc in heptane over 10 CV was used as mobile phase. Methyl 2-(phenoxymethyl)isonicotinate (2.65 g, 82%) was isolated. $^1$H NMR (400 MHz, $cdcl_3$) δ 3.96 (s, 3H), 5.26 (s, 2H), 6.95-7.04 (m, 3H), 7.27-7.34 (m, 2H), 7.76-7.80 (m, 1H), 8.10 (s, 1H), 8.75 (d, 1H). MS m/z 244 $(M+H)^+$ Step 3 Methyl 2-(cyclohexyloxymethyl)piperidine-4-carboxylate Methyl 2-(phenoxymethyl)isonicotinate (2.6 g, 10.69 mmol) was dissolved in acetic acid (50 mL), then platinum (IV) oxide (0.243 g, 1.07 mmol) was added and the mixture hydrogenated in a Büchi hydrogenator at 5 bar and room temperature for 6 h. The catalyst was removed by filtration and the solvent evaporated. The residue was taken up in DCM and the organic phase was washed with satd $NaHCO_3$. The aqueous phase was extracted with DCM and the combined organic phases were filtered through a phase separator and evaporated. Methyl 2-(cyclohexyloxymethyl)piperidine-4-carboxylate (2 g, 73%) was isolated.

Step 4: Dimethyl 2-(cyclohexyloxymethyl)piperidine-1,4-dicarboxylate

Methyl 2-(cyclohexyloxymethyl)piperidine-4-carboxylate (2.13 g, 8.34 mmol) was dissolved in dichloromethane (50 mL). DIPEA (2.034 mL, 11.68 mmol) and methyl carbonochloridate (0.788 mL, 10.01 mmol) were added and the mixture was stirred at room temperature for 3 h. 0.1 M $NH_4Cl$ was added and the aqueous layer was extracted with DCM. The combined organic layers were filtered through a phase separator and evaporated. Dimethyl 2-(cyclohexyloxymethyl)piperidine-1,4-dicarboxylate (2.54 g, 97%) was isolated. MS m/z 314 $(M+H)^+$ Step 5: 2-(Cyclohexyloxymethyl)-1-(methoxycarbonyl)piperidine-4-carboxylic acid Dimethyl 2-(cyclohexyloxymethyl)piperidine-1,4-dicarboxylate (2.54 g, 8.1 mmol) was dissolved in acetonitrile (35 mL) and water (0.7 mL), then lithium bromide (5.63 g, 64.80 mmol) was added. Triethylamine (4.49 mL, 32.40 mmol) was added and the resulting suspension was heated under reflux for 4 h. MTBE (100 mL) and water (50 mL) were added, the phases separated and the organic layer was extracted with water. The combined aqueous layers were acidified to pH 1 with 3.8 M HCl and extracted with MTBE. The combined organic layers were dried with $Na_2SO_4$ and evaporated. 2-(Cyclohexyloxymethyl)-1-(methoxycarbonyl)piperidine-4-carboxylic acid (2.43 g, quant.) was isolated. MS m/z 300 $(M+H)^+$ Reference Compound 39

2-(Difluoromethyl)-1-(methoxycarbonyl)piperidine-4-carboxylic acid

Step 1: Methyl 2-formylisonicotinate

Methyl 2-(hydroxymethyl)isonicotinate (8.36 g, 50 mmol) (from reference compound 38, step 1) was dissolved in dichloromethane (150 mL). Dess-Martin periodinane (25 g, 58.94 mmol) was added and the mixture stirred at room temperature for 2 h 30 min. Sodium sulfothioate (59.3 g, 375.00 mmol) was dissolved in satd NaHCO$_3$ and added to the reaction mixture. The suspension was vigorously stirred at room temperature for 15 min, DCM was added and the phases were separated. The aqueous phase was extracted with DCM twice and the combined organic layers were dried over MgSO$_4$ and evaporated. The residue was purified by automated flash chromatography on a Biotage® KP-SIL 340 g column. Gradient heptanes/EtOAc 80:20 to 65:35 over 5 CV was used as mobile phase. Methyl 2-formylisonicotinate (7 g, 85%) was isolated as an off-white solid. $^1$H NMR (400 MHz, cdcl$_3$) δ 4.00 (s, 3H), 8.09 (dd, 1H), 8.49 (s, 1H), 8.95 (d, 1H), 10.15 (s, 1H). MS m/z 165 (M)+

Step 2: Methyl 2-(difluoromethyl)isonicotinate

Methyl 2-formylisonicotinate (2.51 g, 15.20 mmol) was dissolved in dichloromethane (50 mL) and cooled to 0° C. Diethylaminosulfur trifluoride (DAST) (2.61 mL, 19.76 mmol) was added dropwise. The cooling was removed and the mixture was stirred at room temperature for 2 h. Satd NaHCO$_3$ was added at 0° C. and the phases were separated. The aqueous phase was extracted with DCM. The combined organic phases were filtered through a phase separator and evaporated. The residue was purified by automated flash chromatography on a Biotage® KP-SIL 50 g column. 5:1 of EtOAc in heptane over 10 CV was used as mobile phase. Methyl 2-(difluoromethyl)isonicotinate (2.4 g, 84%) was isolated. $^1$H NMR (400 MHz, cdcl$_3$) δ 4.00 (s, 3H), 6.70 (t, 1H), 7.97 (d, 1H), 8.19 (s, 1H), 8.82 (d, 1H).

Step 3: Methyl 2-(difluoromethyl)piperidine-4-carboxylate

Methyl 2-(difluoromethyl)isonicotinate (2.4 g, 12.82 mmol) was dissolved in acetic acid (40 mL). Platinum(IV) oxide (0.291 g, 1.28 mmol) was added and the mixture was hydrogenated at 5 bar and room temperature for 7 h in a Büchi hydrogenation apparatus. The catalyst was removed by filtration, fresh platinum(IV) oxide (210 mg, 0.92 mmol) was added and the hydrogenation was continued at 5 bar and room temperature for 6 h. The catalyst was removed by filtration and the solvent evaporated. The residue was taken up in DCM and the organic phase was washed with satd NaHCO$_3$. The aqueous phase was extracted with DCM and the combined organic phases were filtered through a phase separator and evaporated. Methyl 2-(difluoromethyl)piperidine-4-carboxylate (1.85 g, 75%) was isolated. MS m/z 194 (M+H)$^+$ Step 4: Dimethyl 2-(difluoromethyl)piperidine-1,4-dicarboxylate Methyl 2-(difluoromethyl)piperidine-4-carboxylate (1.85 g, 9.58 mmol) was dissolved in dichloromethane (50 mL), DIPEA (2.335 mL, 13.41 mmol) and methyl carbonochloridate (0.905 mL, 11.49 mmol) were added and the mixture was stirred at room temperature for 3 h. 0.1 M NH$_4$Cl was added and the aqueous layer was extracted with DCM. The combined organic layers were filtered through a phase separator and evaporated. Crude dimethyl 2-(difluoromethyl)piperidine-1,4-dicarboxylate (2.35 g, 98%) was isolated.

Step 5: 2-(Difluoromethyl)-1-(methoxycarbonyl)piperidine-4-carboxylic acid

Dimethyl 2-(difluoromethyl)piperidine-1,4-dicarboxylate (2.35 g, 9.35 mmol) was dissolved in THF (35 mL) and 1 M lithium hydroxide (12.16 mL, 12.16 mmol) in water was added. The mixture was stirred at room temperature for 3 h, then 1 M HCl and DCM were added and the phases were separated. The aqueous phase was extracted with DCM and the combined organic layers were dried by filtration through a phase separator and evaporated. 2-(Difluoromethyl)-1-(methoxycarbonyl)piperidine-4-carboxylic acid (2.2 g, 99%) was isolated. MS m/z 275 (M–H)$^-$ Reference Compound 40

2-((4,4-Difluorocyclohexyl)methyl-1-(methoxycarbonyl)piperidine-4-carboxylic acid Step 1: (4,4-Difluorocyclohexyl)methanol Ethyl 4,4-difluorocyclohexanecarboxylate (10 g, 52.03 mmol) was dissolved in THF (100 mL) and cooled to 1° C. under nitrogen atmosphere. LAH (57.2 mL, 57.23 mmol) was added dropwise to the solution at a rate to keep the temperature below 10° C. The resulting mixture was allowed to reach 20° C. and stirred at that temperature for approximately 1 h. The reaction mixture was then cooled to 10° C. and quenched carefully by the sequential slow addition of 2.2 mL of water, 2.2 mL of 15 w/v % aqueous NaOH and 6.6 mL of water and stirred for 30 minutes at 20° C. The solids were removed by filtration and washed with THF. The reaction solution was dried over MgSO$_4$ and evaporated in vacuo to give crude (4,4-difluoro-cyclohexyl)methanol (7.22 g, 92%). $^1$H NMR (400 MHz, cdcl$_3$) δ 1.21-1.38 (m, 2H), 1.44 (s, 1H), 1.51-1.90 (m, 5H), 2.04-2.18 (m, 2H), 3.52 (d, 2H).

Step 2: 4-(Bromomethyl)-1,1-difluorocyclohexane (4,4-Difluorocyclohexyl)methanol (7.22 g, 48.08 mmol) and triphenylphosphine (25.2 g, 96.16 mmol) were dissolved in DCM (75 mL) and cooled to 0° C. under nitrogen atmosphere. Carbon tetrabromide (31.9 g, 96.16 mmol) was dissolved in DCM (75 mL) and added to the reaction mixture. The mixture was stirred at room temperature overnight. The solvent was evaporated. Pentane (250 mL) was added to the orange residue, which caused triphenylphosphineoxide to precipitate. The off-white solids were filtered off. The filtrate was evaporated and purified on a ISOLUTE Silica Flash column (50 g). Pentane followed by EtOAc:pentane (1% EtOAc) was used as eluent. 4-(Bromomethyl)-1,1-difluorocyclohexane (5.48 g, 54%) was isolated. $^1$H NMR (400 MHz, cdcl$_3$) δ 1.32-1.46 (m, 2H), 1.64-1.84 (m, 3H), 1.90-1.99 (m, 2H), 2.05-2.18 (m, 2H), 3.31 (d, 2H).

Step 3: ((4,4-Difluorocyclohexyl)methyl)zinc(II) bromide

Zinc powder (1.43 g, 21.87 mmol) was added to a dried flask and was heated at 70° C. under vacuum for 30 minutes. Dry DMA (29 mL) and iodine (0.092 g, 0.37 mmol) were added and the mixture was heated at 70° C. until the red-brown colour had disappeared (approx. 5 minutes). 4-(Bromomethyl)-1,1-difluorocyclohexane (3.1 g, 14.55 mmol) was added and heating was continued for ca. 42 h. The resulting solution was used in the next transformation.

Step 4: Methyl 2-((4,4-difluorocyclohexyl)methyl)isonicotinate

To methyl-2-chloroisonicotinate (1.664 g, 9.7 mmol) and bis(tri-tert-butylphosphine)palladium(0) (198 mg, 0.38 mmol) under nitrogen was added tetrahydrofuran (10 mL). To the resulting solution was added freshly prepared ((4,4-difluorocyclohexyl)methyl)zinc(II) bromide (14.55 mmol, 0.5 M in 29 mL DMA) and the resulting brown mixture heated to 60° C. for 4 h. The reaction mixture was diluted with ethyl acetate and washed with satd NaHCO$_3$ (2 times), satd NH$_4$Cl and brine. The organic layer was dried over MgSO$_4$, filtered and evaporated. The residue was dissolved in DCM and added onto an SCX-2 cation exchange column. The column was washed with DCM, MeOH and then eluted with NH$_3$/MeOH. The NH$_3$/MeOH layer was evaporated leaving methyl 2-((4,4-difluorocyclohexyl)methyl)isonicotinate (2 g, 67%) as a yellow oil. $^1$H NMR (400 MHz, cdcl$_3$) δ 1.30-1.46 (m, 2H), 1.58-1.79 (m, 4H), 1.87-2.14 (m, 3H), 2.82 (d, 2H), 3.96 (s, 3H), 7.65-7.73 (m, 2H), 8.70 (d, 1H). MS m/z 270 (M+H)$^+$ Step 5: Methyl 2-((4,4-difluorocyclohexyl)methyl)piperidine-4-carboxylate hydrochloride Methyl 2-((4,4-difluorocyclohexyl)methyl)isonicotinate (5 g, 18.6 mmol) was treated with HCl (4 M in dioxane) and evaporated to give methyl 2-((4,4-difluorocyclohexyl)methyl)-isonicotinate hydrochloride (5.6 g, 18.32 mmol) which was dissolved in MeOH (100 mL), then platinum(IV) oxide (0.416 g, 1.83 mmol) was added. The mixture was hydrogenated in a Büchi hydrogenator at 5 bar overnight. The catalyst was filtered off and solvents were evaporated yielding methyl 2-((4,4-difluorocyclohexyl)methyl)piperidine-4-carboxylate hydrochloride (5.1 g, 89%). MS m/z 276 (M+H)$^+$ Step 6: Dimethyl 2-((4,4-difluorocyclohexyl)methyl)piperidine-1,4-dicarboxylate Methyl 2-((4,4-difluorocyclohexyl)methyl)piperidine-4-carboxylate hydrochloride (5.1 g, 16.36 mmol) was dissolved in DCM (150 mL), then DIPEA (7.14 mL, 40.89 mmol) was added. Methyl carbonochloridate (1.803 mL, 22.90 mmol) was added dropwise to the solution. The mixture was stirred at room temperature for 2 h. The mixture was washed with 0.1 M HCl (100 mL) and satd NaHCO$_3$ (100 mL), then dried through a phase separator and evaporated yielding crude dimethyl 2-((4,4-difluorocyclohexyl)methyl)piperidine-1,4-dicarboxylate (5.7 g, 105%)

Step 7: 2-((4,4-Difluorocyclohexyl)methyl)-1-(methoxycarbonyl)piperidine-4-carboxylic acid Dimethyl 2-((4,4-difluorocyclohexyl)methyl)piperidine-1,4-dicarboxylate (5.7 g, 17.10 mmol) was dissolved in acetonitrile (75 mL) and water (1.5 mL), then lithium bromide (11.88 g, 136.78 mmol) was added. Et$_3$N (9.53 mL, 68.39 mmol) was added to the solution. The resulting yellow suspension was heated at reflux for 2 h. Water (100 mL) and MTBE (300 mL) were added. The phases were separated and the organic layer was extracted with water (2 times). The pooled water layers were acidified to pH 1 with 3.8 M HCl and extracted with MTBE (2 times). The combined organic layer was dried over Na$_2$SO$_4$, filtered and evaporated to yield 2-((4,4-difluorocyclohexyl)methyl)-1-(methoxycarbonyl)piperidine-4-carboxylic acid (4.82 g, 88%) as a white solid.

Reference Compound 41

2-(4-Fluorophenethyl)-1-(methoxycarbonyl)piperidine-4-carboxylic acid

Step 1: (E)-Methyl 2-(4-fluorostyryl)isonicotinate

Methyl 2-chloroisonicotinate (5.5 g, 32.05 mmol), (E)-4-fluorostyrylboronic acid (7.98 g, 48.08 mmol), potassium phosphate (3.93 mL, 48.08 mmol) and PdCl$_2$ (dppf) (0.464 g, 0.64 mmol) were split into 5 equal portions and each portion was placed in a microwave reaction vessel. The vessels were evacuated and backfilled with nitrogen. Methanol (15 mL) was added to each vessel, the vessels were sealed and heated in a single node microwave reactor at 100° C. for 10 min each. The contents of the vessels was pooled and water and DCM were added, the phases separated and the aqueous layer was extracted with DCM. The combined organic layers were filtered through a phase separator and evaporated. The residue was purified by automated flash chromatography on a Biotage® KP-SIL 340 g column. A gradient from 6:1 to 4:1 of EtOAc in heptane over 15 CV was used as mobile phase. (E)-Methyl 2-(4-fluorostyryl)isonicotinate (3.88 g, 47%) was isolated. $^1$H NMR (400 MHz, cdcl$_3$) δ 3.98 (s, 3H), 7.04-7.18 (m, 3H), 7.52-7.62 (m, 2H), 7.63-7.71 (m, 2H), 7.93 (s, 1H), 8.74 (d, 1H). MS m/z 258 (M+H)$^+$ Step 2: Methyl 2-(4-fluorophenethyl)isonicotinate (E)-methyl 2-(4-fluorostyryl)isonicotinate (3.6 g, 13.99 mmol) was dissolved in methanol (200 mL). Palladium on charcoal (0.149 g, 1.40 mmol) was added and the mixture was hydrogenated at atmospheric pressure and room temperature for 18 h. The catalyst was filtered off and the filtrate was evaporated. Methyl 2-(4-fluorophenethyl)isonicotinate (3.63 g, 99%) was isolated. MS m/z 260 (M+H)$^+$ Step 3: Methyl 2-(4-fluorophenethyl)piperidine-4-carboxylate Methyl 2-(4-fluorophenethyl)isonicotinate (3.8 g, 14.66 mmol) dissolved in acetic acid (150 mL) and platinum(IV) oxide (0.25 g, 1.10 mmol) was added. The mixture was hydrogenated in a Büchi hydrogenation apparatus at 5 bar and room temperature for 5 h. The catalyst was removed by filtration and the solvent was evaporated. The residue was taken up in DCM and washed with satd NaHCO$_3$. The organic phase was filtered through a phase separator and evaporated. Methyl 2-(4-fluorophenethyl)piperidine-4-carboxylate (3.89 g, quant.) was isolated. MS m/z 266 (M+H)$^+$ Step 4: Dimethyl 2-(4-fluorophenethyl)piperidine-1,4-dicarboxylate Methyl 2-(4-fluorophenethyl)piperidine-4-carboxylate (3.89 g, 14.65 mmol) was dissolved in dichloromethane (150 mL). DIPEA (3.06 mL, 17.58 mmol) was added, followed by methyl carbonochloridate (1.615 mL, 20.51 mmol). The mixture was stirred at room temperature for 2 h. 0.1 HCl and DCM were added. The phases were separated and the aqueous phase was extracted with DCM. The combined organic layers were washed with satd NaHCO$_3$, filtered through a phase separator and evaporated. Dimethyl 2-(4-fluorophenethyl)piperidine-1,4-dicarboxylate (3.19 g, 67%) was isolated. MS m/z 324 (M+H)$^+$ Step 5: 2-(4-Fluorophenethyl)-1-(methoxycarbonyl)piperidine-4-carboxylic acid Dimethyl 2-(4-fluorophenethyl)piperidine-1,4-dicarboxylate (3.18 g, 9.83 mmol) was dissolved in acetonitrile (35 mL) and water (0.7 mL) and lithium bromide (6.83 g, 78.67 mmol) was added. Triethylamine (5.45 mL, 39.34 mmol) was added and the resulting suspension was heated under reflux for 5 h. MTBE and water were added, the phases separated and the organic layer was extracted with water. The combined aqueous layers were acidified to pH 1 with 3.8 M HCl and extracted with MTBE. The combined organic layers were washed with water, dried with $Na_2SO_4$ and evaporated. Crude 2-(4-fluorophenethyl)-1-(methoxycarbonyl)piperidine-4-carboxylic acid (4.37 g) was isolated. MS m/z 310 $(M+H)^+$ Reference Compound 42

2-(3,3-Dimethylbutyl)-1-(methoxycarbonyl)piperidine-4-carboxylic acid

Step 1: Methyl 4-((tert-butyldimethylsilyloxy)methyl)-2-(3,3-dimethylbutyl)pyridine-1(2H)-carboxylate 4-((tert-Butyldimethylsilyloxy)methyl)pyridine (5.58 g, 25 mmol) (from reference compound 4, step 1) was dissolved in dry THF (50 mL) under nitrogen and the mixture cooled to −15° C. (3,3-Dimethylbutyl)magnesium chloride (0.5 M in THF) (50 mL, 25 mmol) was added dropwise during 20 min to yield a yellow solution which was stirred at −15° C. for 30 min. Then, methyl carbonochloridate (2.5 mL, 32 mmol) was added during 1 min. The reaction was continued at −15° C. for 30 min and then the mixture was cooled to −60° C. After 2 h the temperature had reached room temperature. Water (20 mL) was added and the solvent evaporated. The aqueous phase was extracted with DCM (×2) and the combined organic phase passed through a phase separator. The solvent was evaporated to yield a yellow oil. The residue was purified via Biotage (0=>10% EtOAc in heptane) to yield methyl 4-((tert-butyldimethylsilyloxy)methyl)-2-(3,3-dimethylbutyl)pyridine-1(2H)-carboxylate (3.67 g, 44%) as a colourless oil. MS m/z 368 $(M+H)^+$ Step 2: Methyl 4-((tert-butyldimethylsilyloxy)methyl-2-(3,3-dimethylbutyl)piperidine-1-carboxylate To a solution of methyl 4-((tert-butyldimethylsilyloxy)methyl)-2-(3,3-dimethylbutyl)-pyridine-1(2H)-carboxylate (3.63 g, 9.87 mmol) in ethyl acetate (60 mL) was platinum (IV) oxide (224 mg, 1 mmol) added. Hydrogenated at 6 bar in a Büchi hydrogenator for 3.5 h. The catalyst was filtered off and the filtrate evaporated to yield methyl 4-((tert-butyl-dimethylsilyloxy)methyl)-2-(3,3-dimethylbutyl)piperidine-1-carboxylate (3.62 g, 99%) as a colourless oil. MS m/z 372 $(M+H)^+$ Step 3: Methyl 2-(3,3-dimethylbutyl)-4-(hydroxymethyl)piperidine-1-carboxylate Methyl 4-((tert-butyldimethylsilyloxy)methyl)-2-(3,3-dimethylbutyl)piperidine-1-carboxylate (3.606 g, 9.7 mmol) was dissolved in THF (50 mL) and TBAF (1M in THF) (13 mL, 13 mmol) added. Stirred at room temperature for 3.5 h. The solvent was evaporated. Redissolved in DCM and washed with satd $NaHCO_3$. The organic phase was passed through a phase separator and evaporated to yield an oil. The residue was purified via Biotage (eluent 30-70% EtOAc in heptane) to yield methyl 2-(3,3-dimethylbutyl)-4-(hydroxymethyl)piperidine-1-carboxylate (2.45 g, 98%) as a colourless oil. MS m/z 258 $(M+H)^+$ Step 4: 2-(3,3-Dimethylbutyl)-1-(methoxycarbonyl)piperidine-4-carboxylic acid Methyl 2-(3,3-dimethylbutyl)-4-(hydroxymethyl)piperidine-1-carboxylate (2.44 g, 9.49 mmol) was dissolved in $CCl_4$ (20 mL) and acetonitrile (20 mL). Sodium periodiate (6.09 g, 28.5 mmol) was added followed by water (30 mL) and ruthenium (III) chloride (43 mg, 0.21 mmol). The resulting suspension was stirred at room temperature for 3 h 50 min. The reaction mixture was diluted with DCM (100 mL) and water (100 mL). The aqueous layer was extracted with DCM (×3) and the combined organic phase passed through a phase separator and evaporated to yield crude 2-(3,3-dimethylbutyl)-1-(methoxycarbonyl)piperidine-4-carboxylic acid (2.42 g, 94%) as a black solid. MS m/z 272 $(M+H)^+$ Reference Compound 43

2-(4-Fluorobenzyl)-1-(methoxycarbonyl)piperidine-4-carboxylic acid

Step 1: Methyl 2-(4-fluorobenzyl)isonicotinate

Methyl 2-chloroisonicotinate (5.6 g, 32.64 mmol) and $Pd(PPh_3)_4$ (0.754 g, 0.65 mmol) were dissolved under nitrogen in THF (100 mL) and (4-fluorobenzyl)zinc(II) chloride (0.5 M in THF) (100 mL, 50.00 mmol) was added. The brown solution was stirred at 60° C. for 19 h. The reaction was quenched by addition of methanol (50.0 mL). The solution was diluted with EtOAc and washed with $NH_4Cl$ (aq) and water. The organic layer was evaporated, dissolved in DCM and washed with $NH_4Cl$ (aq) and then dried by passage through a phase separator. The solvent was evaporated to yield a brown oil. The compound was purified in 2 runs via Biotage, SNAP 340 g KP-SIL, eluent isocratic heptane/ethyl acetate 8:2 for 2 CV, then linear gradient heptane/ethyl acetate 8:2 to 5:5 over 5 CV to yield methyl 2-(4-fluorobenzyl)isonicotinate 7.08 g (88%) as a yellow oil. $^1$H NMR (400 MHz, cdcl$_3$) δ 3.92 (s, 3H), 4.18 (s, 2H), 6.94-7.02 (m, 2H), 7.19-7.27 (m, 2H), 7.65-7.69 (m, 2H), 8.68-8.71 (m, 1H). MS m/z 246 $(M+H)^+$ Step 2: Methyl 2-(4-fluorobenzyl)piperidine-4-carboxylate Methyl 2-(4-fluorobenzyl)isonicotinate (5.06 g, 20.63 mmol) was dissolved in acetic acid (50 mL) and platinum(IV) oxide (0.234 g, 1.03 mmol) added. The resulting mixture was hydrogenated in a Büchi hydrogenator overnight at room temperature and 5 bar. The catalyst was filtered off and washed with MeOH and the eluate evaporated. DCM and 10% $K_2CO_3$ were added and the phases separated. The aqueous phase was extracted with DCM and the combined organic phase washed with brine, passed through a phase separator and evaporated to yield methyl 2-(4-fluorobenzyl)piperidine-4-carboxylate (3.816 g, 73.6%) as a yellow oil. MS m/z 252 $(M+H)^+$ Step 3: Dimethyl 2-(4-fluorobenzyl)piperidine-1,4-dicarboxylate Methyl 2-(4-fluorobenzyl)piperidine-4-carboxylate (4.981 g, 19.82 mmol) was dissolved in DCM (150 mL) and DIPEA (4.14 mL, 23.79 mmol), then methyl carbonochloridate (1.873 mL, 23.79 mmol) was added. The solution was stirred at room temperature for 50 min. More methyl carbonochloridate (a few drops) were added and the reaction continued at room temperature for 1 h. The reaction mixture was washed with 0.1 M HCl and satd $NaHCO_3$. The organic phase was passed through a phase separator and evaporated to yield dimethyl 2-(4-fluorobenzyl)piperidine-1,4-dicarboxylate (5.82 g, 95%) as a yellow oil. MS m/z 310 (M+H)+

Step 4: 2-(4-Fluorobenzyl)-1-(methoxycarbonyl) piperidine-4-carboxylic acid

Dimethyl 2-(4-fluorobenzyl)piperidine-1,4-dicarboxylate (5.797 g, 18.74 mmol) was dissolved in acetonitrile (60 mL) and water (1.2 mL), then lithium bromide (13.02 g, 149.92 mmol) was added. Triethylamine (10.39 mL, 74.96 mmol) was added and the resulting yellow suspension was heated at reflux for 1.5 h. water (60 mL) and MTBE (120 mL) were added. The organic phase was extracted with water (×2). The pooled aqueous layer was acidified to pH 1 with 3.8 M HCl and then extracted with MTBE (×2). The combined organic layer was washed with water and evaporated. Traces of water were azeotropically removed by MeCN. 2-(4-Fluorobenzyl)-1-(methoxycarbonyl)piperidine-4-carboxylic acid (4.43 g, 80%) was isolated as a beige solid. MS m/z 296 (M+H)+

Reference Compound 44

2-(3-Fluorobenzyl)-1-(methoxycarbonyl)piperidine-4-carboxylic acid

Step 1: Methyl 2-(3-fluorobenzyl)isonicotinate

Methyl 2-chloroisonicotinate (5.6 g, 32.64 mmol) and Pd(PPh$_3$)$_4$ (0.754 g, 0.65 mmol) were dissolved in THF (100 mL) under nitrogen and (3-fluorobenzyl)zinc(II) chloride (0.5 M in THF) (100 mL, 50.00 mmol) was added. The brown solution was stirred at 60° C. for 4 h. The reaction was quenched by addition of methanol (50 mL), diluted with EtOAc and washed with NH$_4$Cl. The organic layer was dried over Na$_2$SO$_4$, filtered and evaporated to yield a yellow oil. The compound was purified in 2 runs via Biotage, SNAP 340 g KP-SIL, eluent isocratic heptane/ethyl acetate 8:2 for 2 CV, then linear gradient heptane/ethyl acetate 8:2 to 5:5 over 5 CV to yield methyl 2-(3-fluorobenzyl)isonicotinate (6.766 g, 85%) as a yellow oil. $^1$H NMR (400 MHz, cdcl$_3$) δ 3.93 (s, 3H), 4.21 (s, 2H), 6.88-7.00 (m, 2H), 7.02-7.07 (m, 1H), 7.22-7.30 (m, 1H), 7.66-7.73 (m, 2H), 8.68-8.73 (m, 1H). MS m/z 246 (M+H)+

Step 2: Methyl 2-(3-fluorobenzyl)piperidine-4-carboxylate

Methyl 2-(3-fluorobenzyl)isonicotinate (6.766 g, 27.59 mmol) was dissolved in acetic acid (70 mL) and platinum(IV) oxide (0.313 g, 1.38 mmol) added. The resulting mixture was hydrogenated in a Büchi hydrogenator at room temperature and 5 bar for 4.5 h. More platinum(IV) oxide (0.313 g, 1.38 mmol) was added and the hydrogenation continued at 5 bar for 2 h 40 min. The catalyst was filtered off, washed with MeOH and the eluate evaporated. DCM and 10% K$_2$CO$_3$ were added and the phases separated. The water phase was extracted with DCM and the combined organic phase washed with brine, passed through a phase separator and evaporated to yield crude methyl 2-(3-fluorobenzyl)piperidine-4-carboxylate (7.6 g, 110%) as a brown oil. MS m/z 252 (M+H)+

Step 3: Dimethyl 2-(3-fluorobenzyl)piperidine-1,4-dicarboxylate

Methyl 2-(3-fluorobenzyl)piperidine-4-carboxylate (7.6 g, 30.24 mmol) was dissolved in DCM (200 mL) and DIPEA (6.32 mL, 36.29 mmol), then methyl carbonochloridate (3.3 mL, 41.91 mmol) was added. The solution was stirred at room temperature for 2 h. The reaction mixture was washed with 0.1 M HCl and satd NaHCO$_3$. The organic phase was passed through a phase separator and evaporated to yield dimethyl 2-(3-fluorobenzyl)piperidine-1,4-dicarboxylate (9.30 g, 99%) as a brown oil. MS m/z 310 (M+H)+

Step 4: 2-(3-Fluorobenzyl)-1-(methoxycarbonyl) piperidine-4-carboxylic acid

Dimethyl 2-(3-fluorobenzyl)piperidine-1,4-dicarboxylate (9.153 g, 29.59 mmol) was dissolved in acetonitrile (100 mL) and water (2 mL), then lithium bromide (20.56 g, 236.72 mmol) was added. Triethylamine (16.41 mL, 118.36 mmol) was added and the resulting brown suspension was heated at reflux for 2 h. Water (100 mL) and MTBE (300 mL) were added. The organic phase was extracted with water (×2). The pooled aqueous layer was acidified to pH 1 with 3.8 M HCl and then extracted with MTBE (×2). The combined organic layer was washed with water, dried over Na$_2$SO$_4$, filtered through a Celite containing filter and evaporated. 2-(3-Fluorobenzyl)-1-(methoxycarbonyl)piperidine-4-carboxylic acid (7.07 g, 81%) was isolated as a yellow solid. MS m/z 296 (M+H)+

Reference Compound 45

2-(2-Fluorobenzyl)-1-(methoxycarbonyl)piperidine-4-carboxylic acid

Step 1: Methyl 2-(2-fluorobenzyl)isonicotinate

Methyl 2-chloroisonicotinate (5.2 g, 30.31 mmol) and Pd(PPh$_3$)$_4$ (0.700 g, 0.61 mmol) were dissolved under nitrogen in THF (100 mL) and (2-fluorobenzyl)zinc(II) chloride (0.5 M in THF) (90 mL, 45.00 mmol) was added and the brown solution was stirred at 60° C. for 18 h. The reaction was quenched by addition of methanol (50.0 mL). The solution was diluted with EtOAc, washed with NH$_4$Cl (aq) and dried over Na$_2$SO$_4$, then evaporated. The compound was purified in 2 runs via Biotage, SNAP 340 g KP-SIL, eluent isocratic heptane/ethyl acetate 8:2 for 2 CV, then linear gradient heptane/ethyl acetate 8:2 to 5:5 over 5 CV to give methyl 2-(2-fluorobenzyl)isonicotinate (5.42 g, 73%) as a yellow oil. $^1$H NMR (400 MHz, cdcl$_3$) 3.92 (s, 3H), 4.25 (s, 2H), 7.00-7.13 (m, 2H), 7.18-7.30 (m, 2H), 7.64-7.74 (m, 2H), 8.69 (d, 1H). MS m/z 246 (M+H)+

Step 2: Methyl 2-(2-fluorobenzyl)piperidine-4-carboxylate

Methyl 2-(2-fluorobenzyl)isonicotinate (5.42 g, 22.08 mmol) was dissolved in acetic acid (50 mL) and platinum(IV) oxide (0.251 g, 1.10 mmol) added. The resulting mixture was hydrogenated in a Büchi hydrogenator for 4 h at room temperature and 5 bar. The catalyst was filtered off and washed with MeOH and the eluate evaporated. DCM and 10% K$_2$CO$_3$ were added and the phases separated. The water phase was extracted with DCM and the combined organic phase washed with water, passed through a phase separator and evaporated to yield methyl 2-(2-fluorobenzyl)piperidine-4-carboxylate (4.49 g, 81%) MS m/z 252 (M+H)+

Step 3: Dimethyl 2-(2-fluorobenzyl)piperidine-1,4-dicarboxylate

To a solution of methyl 2-(2-fluorobenzyl)piperidine-4-carboxylate (4.49 g, 17.85 mmol) and DIPEA (9.35 mL, 53.55 mmol) in DCM (100 mL) was added methyl chloroformate (1.798 mL, 23.21 mmol) in DCM (50 mL). The reaction mixture was stirred for 1.5 h. The organic phase was washed with satd NaHCO$_3$. The phases were separated and the organic phase dried using a phase separator to yield crude dimethyl 2-(2-fluorobenzyl)piperidine-1,4-dicarboxylate (6.16 g, 112%). MS m/z 310 (M+H)$^+$ Step 4: 2-(2-Fluorobenzyl)-1-(methoxycarbonyl) piperidine-4-carboxylic acid Dimethyl 2-(2-fluorobenzyl)piperidine-1,4-dicarboxylate (6.16 g, crude) was dissolved in acetonitrile (45 mL) and water (0.9 mL). Lithium bromide (13.84 g, 159.39 mmol) and triethylamine (11.05 mL, 79.69 mmol) were added and the mixture was heated at reflux overnight. Water (90 mL) and MTBE were added. The organic phase was extracted with water (×2). To the pooled aqueous layer was added MTBE and the solution was acidified to pH 1 with 2 M HCl and then extracted with MTBE (×2). The combined organic layer was dried over Na$_2$SO$_4$ and evaporated to give 2-(2-fluorobenzyl)-1-(methoxycarbonyl)piperidine-4-carboxylic acid (4.48 g, 76%) as a slightly yellow semisolid. MS m/z 296 (M+H)$^+$ Reference Compound 46

Cis-1-(methoxycarbonyl)-2-(4-(trifluoromethyl)benzyl)piperidine-4-carboxylic acid Step 1: Methyl 2-(4-(trifluoromethyl)benzyl)isonicotinate Methyl 2-chloroisonicotinate (18 g, 104.91 mmol) and Pd(PPh$_3$)$_4$ (2.43 g, 2.10 mmol) were dissolved in THF (300 mL). (4-Trifluoromethyl)benzyl)zinc(II) chloride (0.5 M in THF) (273 mL, 137 mmol) was added to the yellow solution and the flask was warmed to 60° C. overnight. The reaction mixture was quenched by adding methanol. The solution was diluted with ethyl acetate and washed with NH$_4$Cl (aq) and water. The organic layer was dried with Na$_2$SO$_4$, filtered through celite, and the solvent was evaporated. The crude was chromatographed using the Biotage equipment. Eluent ethyl acetate-heptane, started 0-100 and linear gradient until 100-0. Methyl 2-(4-(trifluoromethyl)benzyl)isonicotinate (11.5 g, 37.1%) was isolated. $^1$H NMR (600 MHz, cdcl$_3$) δ 3.91 (s, 3H), 4.25 (s, 2H), 7.36 (d, 2H), 7.54 (d, 2H), 7.66-7.70 (m, 2H), 8.68 (d, 1H).

Step 2: Methyl 2-(4-(trifluoromethyl)benzyl)piperidine-4-carboxylate

Methyl 2-(4-(trifluoromethyl)benzyl)isonicotinate (11.5 g, 38.95 mmol) was dissolved in acetic acid (200 mL) and methanol (100 mL). Platinum(IV) oxide (0.177 g, 0.78 mmol) was added and the mixture hydrogenated in a Büchi hydrogenator at room temperature and 7 bar for 6 h. The catalyst was filtered off. Fresh platinum(IV) oxide (0.18 g, 0.78 mmol) was added and hydrogenation continued at 9 bar for 7 h. The catalyst was filtered off, the solvent was evaporated and the residue partitioned between ethyl acetate and Na$_2$CO$_3$ (aq). The organic layer was dried over MgSO$_4$, filtered through celite and the solvent evaporated. Methyl 2-(4-(trifluoromethyl)benzyl)piperidine-4-carboxylate (9.5 g, 81%) was isolated.

Step 3: Dimethyl 2-(4-(trifluoromethyl)benzyl)piperidine-1,4-dicarboxylate

Methyl 2-(4-(trifluoromethyl)benzyl)piperidine-4-carboxylate (9.5 g, 31.53 mmol) was dissolved in DIPEA (8.24 mL, 47.29 mmol) and dichloromethane (150 mL). Methyl carbonochloridate (3.58 g, 37.50 mmol) was added dropwise and the reaction mixture was stirred at room temperature for 1 h, diluted with ether and washed with 1 M HCl. The organic layer was washed with Na$_2$CO$_3$ (aq), dried MgSO$_4$, filtered through celite and the solvent was evaporated to yield dimethyl 2-(4-(trifluoromethyl)benzyl)piperidine-1,4-dicarboxylate (10.9 g, 96%).

Step 4: 1-(Methoxycarbonyl)-2-(4-(trifluoromethyl) benzyl)piperidine-4-carboxylic acid Dimethyl 2-(4-(trifluoromethyl)benzyl)piperidine-1,4-dicarboxylate (10.9 g, 30.33 mmol) was dissolved in acetonitrile (80 mL) and water (1.6 mL), then lithium bromide (21.07 g, 242.67 mmol) and triethylamine (16.82 mL, 121.33 mmol) were added and the resulting yellow suspension was heated at reflux. Water (60 mL) and MTBE were added. The organic phase was extracted with water (×2). To the pooled aqueous layer was added MTBE and the solution was acidified to pH 1 with HCl and then extracted with MTBE (×2). The organic layer was dried Na$_2$SO$_4$, filtered through celite and the solvent evaporated to yield 1-(methoxycarbonyl)-2-(4-(trifluoromethyl)benzyl)piperidine-4-carboxylic acid (9.14 g, 87%).

Step 5: Cis-1-(methoxycarbonyl)-2-(4-(trifluoromethyl)benzyl)piperidine-4-carboxylic acid 1-(Methoxycarbonyl)-2-(4-(trifluoromethyl)benzyl)piperidine-4-carboxylic acid (14.65 g, 42.43 mmol) was suspended in MTBE (150 mL) and heated under reflux for 1 min, then stirred at room temperature for 3 days. The solids were isolated and dried under vacuum. Cis-1-(methoxycarbonyl)-2-(4-(trifluoromethyl)benzyl)piperidine-4-carboxylic acid (9.3 g, 63.5%) was isolated. $^1$H NMR (600 MHz, cd$_3$od) δ 1.68-1.77 (m, 1H), 1.90-1.97 (m, 1H), 1.99-2.10 (m, 2H), 2.58-2.64 (m, 1H), 2.83-2.89 (m, 1H), 2.93-3.00 (m, 1H), 3.16-3.31 (m, 1H), 3.43 (s, 3H), 3.86-3.92 (m, 1H), 4.31-4.36 (m, 1H), 7.36 (d, 2H), 7.53 (d, 2H).

Reference Compound 47

1-(Methoxycarbonyl)-2-(4-(trifluoromethyl)benzyl) piperidine-4-carboxylic acid

Step 1: Methyl 4-cyano-2-(4-(trifluoromethyl)benzyl)piperidine-1-carboxylate

To a solution of methyl 4-oxo-2-(4-(trifluoromethyl)benzyl)piperidine-1-carboxylate (8.75 g, 27.75 mmol) (Syngene) in DME (100 mL) under nitrogen was added simultaneously 1-(isocyanomethylsulfonyl)-4-methylbenzene (8.13 g, 41.63 mmol) in 100 mL DME and potassium tert-butoxide (83 mL, 83.26 mmol) (1 M) over 30 min at −20 to −10° C. The solution was stirred at −20° C. for 2 h and then allowed to warm to room temperature overnight. To the orange reaction mixture was added water (200 mL), the solution was stirred for 20 min and then extracted with diethyl ether (3×) and EtOAc (3×). The combined organic phases were washed once with brine and then dried over Na$_2$SO$_4$ and evaporated to yield a brown oil. The oil was purified by flash chromatography on silica gel using a gradient of 20-60% EtOAc in heptane as eluent. Methyl 4-cyano-2-(4-(trifluoromethyl)benzyl)piperidine-1-carboxylate (7.96 g, 87.9%) was isolated as a yellow oil.

Step 2: 1-(Methoxycarbonyl)-2-(4-(trifluoromethyl)benzyl)piperidine-4-carboxylic acid Methyl 4-cyano-2-(4-(trifluoromethyl)benzyl)piperidine-1-carboxylate (2.1 g, 6.44 mmol), hydrogen peroxide (5 mL, 206.78 mmol) and potassium hydroxide (3.61 g, 54.36 mmol) in water (50 mL) were heated to 80° C. overnight. 1 M HCl and EtOAc was added to the reaction mixture. The organic phase was isolated, dried with $Na_2SO_4$, filtered through Celite and the solvent was evaporated to yield 1-(methoxycarbonyl)-2-(4-(trifluoromethyl)benzyl)-piperidine-4-carboxylic acid (1.67 g, 75%).

Reference Compound 48

1-(Methoxycarbonyl)-2-(3-(trifluoromethyl)benzyl)piperidine-4-carboxylic acid

Step 1: Methyl 2-(3-(trifluoromethyl)benzyl)isonicotinate

Methyl 2-chloroisonicotinate (8.1 g, 47.21 mmol) and $Pd(PPh_3)_4$ (1.091 g, 0.94 mmol) were dissolved in THF (150 mL) under nitrogen. (3-Trifluoromethyl)benzyl)zinc(II) chloride (0.5 M in THF) (142 mL, 71 mmol) was added to the orange solution and the flask was warmed to 60° C. overnight. The reaction mixture was quenched by adding methanol (50 mL) and most of the solvent was removed by evaporation. The residue was diluted with ethyl acetate and washed with $NH_4Cl$ (aq) and water. The organic layer was dried with $Na_2SO_4$, filtered through celite, and the solvent was evaporated. The crude was chromatographed using the Biotage equipment. Eluent ethyl acetate-heptane, started 20-80 and linear gradient until 40-60. Methyl 2-(3-(trifluoromethyl)benzyl)isonicotinate (12.83 g, 92%) was isolated. $^1$H NMR (400 MHz, cdcl$_3$) δ 3.93 (s, 3H), 4.27 (s, 2H), 7.37-7.56 (m, 4H), 7.66-7.75 (m, 2H), 8.67-8.76 (m, 1H).

Step 2: Methyl 2-(3-(trifluoromethyl)benzyl)piperidine-4-carboxylate

Methyl 2-(3-(trifluoromethyl)benzyl)isonicotinate (12.83 g, 43.45 mmol) and platinum(IV) oxide (0.197 g, 0.87 mmol) were added to acetic acid (150 mL). The reaction mixture was hydrogenated in a Büchi hydrogenator for 6 h at room temperature and 5 bar. The catalyst was filtered off and fresh platinum(IV) oxide (0.26 g) was added. Hydrogenation was continued overnight at 6 bar. The catalyst was filtered off and the solvent was evaporated. The residue was dissolved in ethyl acetate and washed with $Na_2CO_3$ (aq). The organic layer was isolated, dried over $MgSO_4$, filtered through celite and the solvent evaporated. Crude methyl 2-(3-(trifluoromethyl)benzyl)piperidine-4-carboxylate (14.4 g, 110%) was isolated.

Step 3: Dimethyl 2-(3-(trifluoromethyl)benzyl)piperidine-1,4-dicarboxylate

Methyl 2-(3-(trifluoromethyl)benzyl)piperidine-4-carboxylate (6.0 g, 19.91 mmol) was dissolved in DIPEA (6.94 mL, 39.83 mmol) and dichloromethane (150 mL). Methyl carbonochloridate (2.258 g, 23.90 mmol) was added dropwise. Ether was added and the reaction mixture was washed with 1 M HCl and $Na_2CO_3$ (aq). The organic layer was dried over $MgSO_4$, filtered through celite and the solvent was evaporated to yield dimethyl 2-(3-(trifluoromethyl)benzyl)piperidine-1,4-dicarboxylate (6.1 g, 85%).

Step 4: 1-(Methoxycarbonyl)-2-(3-(trifluoromethyl)benzyl)piperidine-4-carboxylic acid Dimethyl 2-(3-(trifluoromethyl)benzyl)piperidine-1,4-dicarboxylate (6.1 g, 16.98 mmol) and LiBr (11.79 g, 135.8 mmol) were dissolved in acetonitrile (60 mL) and water (1.2 mL). Triethylamine (9.41 mL, 67.90 mmol) was added and the resulting suspension was heated at reflux for 1 h, then cooled to room temperature and stirred overnight. Dissolved between ethyl acetate and 3 M HCl. The water layer was extracted once with ethyl acetate. The combined organic layers were dried over $Na_2SO_4$, filtered through celite and the solvent was evaporated to yield 1-(methoxycarbonyl)-2-(3-(trifluoromethyl)benzyl)piperidine-4-carboxylic acid (5.8 g, 99%).

Reference Compound 49

1-(Methoxycarbonyl)-2-(2-(trifluoromethyl)benzyl)piperidine-4-carboxylic acid

Step 1: (2-(Trifluoromethyl)benzyl)zinc(II) bromide

In a dried flask zinc powder (2.489 g, 38.07 mmol) was suspended in anhydrous tetrahydrofuran (50 mL) under nitrogen. The resulting suspension was warmed to 60° C., then 1,2-dibromoethane (0.126 mL, 1.46 mmol) was added and stirred at that temperature for 15 min. It was cooled to room temperature, then chlorotrimethylsilane (0.149 mL, 1.17 mmol) was added and stirred for 20 min. 1-(Bromomethyl)-2-(trifluoromethyl)benzene (4.46 mL, 29.28 mmol) in THF (2 mL) was added dropwise and stirring was continued at room temperature for 4 h. Stirring was switched off to let the precipitates settle. The supernatant was used in the next transformation.

Step 2: Methyl 2-(2-(trifluoromethyl)benzyl)isonicotinate

Freshly made (2-(trifluoromethyl)benzyl)zinc(II) bromide (8.91 g, 29.28 mmol) in tetrahydrofuran (50 mL) was added to a solution of methyl 2-chloroisonicotinate (3.35 g, 19.52 mmol) and bis(tri-tert-butylphosphine)Pd(0) (0.399 g, 0.78 mmol) in tetrahydrofuran (50 mL) under nitrogen in a dried flask. The resulting red mixture was heated to 60° C. overnight (16 h). After cooling to room temperature, the reaction was quenched by the addition of 10% aq $NH_4Cl$ and diluted with ethyl acetate. After phase separation, the organic layer was washed with brine, dried over $MgSO_4$ and evaporated. The residue was dissolved in 100 mL MTBE. Insolubles were filtered off and the filtrate was evaporated. Purification via Biotage, SNAP 340 g KP-SIL, eluent isocratic heptane/ethyl acetate 8:2 for 1 CV, then linear gradient heptane/ethyl acetate 8:2 to 5:5 over 6 CV to yield methyl 2-(2-(trifluoromethyl)benzyl)isonicotinate (4.61 g, 80%) as a yellow oil. $^1$H NMR (400 MHz, cdcl$_3$) δ 3.91 (s, 3H), 4.43 (s, 2H), 7.28-7.40 (m, 2H), 7.47 (t, 1H), 7.54-7.65 (m, 1H), 7.65-7.72 (m, 2H), 8.71 (d, 1H). MS m/z 296 (M+H)$^+$

Step 3: Methyl 2-(2-(trifluoromethyl)benzyl)piperidine-4-carboxylate

Methyl 2-(2-(trifluoromethyl)benzyl)isonicotinate (4.613 g, 15.62 mmol) was dissolved in acetic acid (40 mL) and platinum(IV) oxide (0.26 g, 1.14 mmol) added. The resulting mixture was hydrogenated in a Büchi hydrogenator for 3 h at room temperature and 5 bar. More platinum(IV) oxide (160 mg) was added and the hydrogenation continued at room temperature at 5 bar for 2 h. The catalyst was filtered off and washed with MeOH and the eluate evaporated. DCM and 10% $K_2CO_3$ were added and the phases separated. The water phase was extracted with DCM and the combined organic phase washed with water, passed through a phase separator and evaporated to yield methyl 2-(2-(trifluoromethyl)benzyl)-piperidine-4-carboxylate (4.20 g, 89%) as a yellow oil. MS m/z 302 $(M+H)^+$

Step 4: Dimethyl 2-(2-(trifluoromethyl)benzyl)piperidine-1,4-dicarboxylate

Methyl chloroformate (1.399 mL, 18.07 mmol) in DCM (40 mL) was added to a solution of methyl 2-(2-(trifluoromethyl)benzyl)piperidine-4-carboxylate (4.19 g, 13.9 mmol) and DIPEA (7.28 mL, 41.69 mmol) in DCM (60 mL). The reaction mixture was stirred for 1.5 h at room temperature, then washed with satd $NaHCO_3$. The phases were separated and the organic phase dried using a phase separator to give crude dimethyl 2-(2-(trifluoromethyl)-benzyl)piperidine-1,4-dicarboxylate (5.42 g, 109%). MS m/z 360 $(M+H)^+$

Step 5: 1-(Methoxycarbonyl)-2-(2-(trifluoromethyl)benzyl)piperidine-4-carboxylic acid Crude dimethyl 2-(2-(trifluoromethyl)benzyl)piperidine-1,4-dicarboxylate (5.42 g, 15.15 mmol) was dissolved in acetonitrile (40 mL) and water (0.800 mL). lithium bromide (9.66 g, 111.20 mmol) and triethylamine (7.71 mL, 55.60 mmol) were added and the mixture was heated at reflux for 1 h 45 min. Water (90 mL) and MTBE were added. The organic phase was extracted with water. To the pooled aqueous layer was added MTBE and the solution was acidified to pH 1 with 2 M HCl and then extracted with MTBE (×2). The combined organic layer was dried over $Na_2SO_4$ and evaporated to give 1-(methoxycarbonyl)-2-(2-(trifluoromethyl)benzyl)piperidine-4-carboxylic acid (4.72 g, 98%) as a slightly yellow semisolid. MS m/z 346 $(M+H)^+$

Reference Compound 50

1-(Methoxycarbonyl)-2-(4-(trifluoromethoxy)benzyl)piperidine-4-carboxylic acid

Step 1: (4-(Trifluoromethoxy)benzyl)zinc(II) bromide

In a dried flask was zinc powder (0.769 g, 11.76 mmol) suspended in anhydrous tetrahydrofuran (20 mL) under nitrogen. The resulting suspension was warmed to 60° C., then 1,2-dibromoethane (0.042 mL, 0.49 mmol) was added and stirred at that temperature for 15 min. It was cooled to room temperature, then chlorotrimethylsilane (0.050 mL, 0.39 mmol) was added and stirred at room temperature for 1 h. Then, 1-(bromomethyl)-4-(trifluoromethoxy)benzene (2.5 g, 9.80 mmol) in tetrahydrofuran (5 mL) was added over 2 min, then stirring continued at room temperature for 22 h. The stirring was switched off to let the solids settle. The supernatant was used in next transformation

Step 2: Methyl 2-(4-(trifluoromethoxy)benzyl)isonicotinate

To a solution of methyl 2-chloroisonicotinate (4.80 g, 28 mmol) and $Pd(PPh_3)_4$ (0.647 g, 0.56 mmol) in tetrahydrofuran (50 mL) under nitrogen in a dried flask was added a freshly prepared solution of (4-(trifluoromethoxy)benzyl)zinc(II) bromide (12.56 g, 39.20 mmol) in tetrahydrofuran (90 mL). The resulting bright yellow mixture was heated to 60° C. for 2 h 30 min, then cooled to room temperature. The reaction was quenched by the addition of 10% aqueous $NH_4Cl$. It was diluted with ethyl acetate. After phase separation, the organic layer was washed with brine, dried over $MgSO_4$ and evaporated. The residue was suspended in 50 mL MTBE and sonicated, then the yellow insolubles were filtered off and washed with MTBE. The volume of the filtrate was increased to ca. 150 mL, then 5 mL MeOH was added, followed by hydrogen chloride (4 M in dioxane) (7.00 mL, 28.00 mmol). A colorless precipitate formed, which then dissolved again. The solvents were evaporated. The residue was dissolved in ca. 15 mL DCM and then MTBE and heptanes were added. An oil had formed that was triturated and after a few minutes a solid started to form. It was sonicated and then stirred at room temperature for 20 min. The formed solid was collected and washed with MTBE and dried. The solid was dissolved in DCM and washed with 10% $K_2CO_3$. After phase separation, the aqueous layer was extracted with DCM. The combined organic layers were dried over $MgSO_4$ and evaporated. Methyl 2-(4-(trifluoromethoxy)benzyl)isonicotinate (8.04 g, 92%) was isolated as a pale yellow oil. $^1H$ NMR (400 MHz, $cdcl_3$) δ 3.93 (s, 3H), 4.22 (s, 2H), 7.11-7.17 (m, 2H), 7.24-7.31 (m, 2H), 7.67-7.72 (m, 2H), 8.68-8.72 (m, 1H). MS m/z 312 $(M+H)^+$

Step 3: Methyl 2-(4-(trifluoromethoxy)benzyl)piperidine-4-carboxylate

To a solution of methyl 2-(4-(trifluoromethoxy)benzyl)isonicotinate (8.04 g, 25.83 mmol) in acetic acid (40 mL) was added platinum(IV) oxide (0.343 g, 1.51 mmol) and the resulting mixture hydrogenated at 5 bar in a Büchi hydrogenator for 5 h. The reaction mixture was filtered through a diatomeous earth filter carton and the catalyst washed with methanol. The solvents were evaporated, the residue dissolved in DCM and washed with 10% $Na_2CO_3$. After phase separation the aqueous layer was extracted with DCM. The combined organic layers were dried over $MgSO_4$ and evaporated. Methyl 2-(4-(trifluoromethoxy)benzyl)piperidine-4-carboxylate (8.19 g, 100%) was isolated as a dark brown oil. MS m/z 318 $(M+H)^+$

Step 4: Dimethyl 2-(4-(trifluoromethoxy)benzyl)piperidine-1,4-dicarboxylate

To a solution of methyl 2-(4-(trifluoromethoxy)benzyl)piperidine-4-carboxylate (8.19 g, 25.81 mmol) in DCM (100 mL) was added DIPEA (5.40 mL, 30.97 mmol) followed by methyl carbonochloridate (2.236 mL, 28.39 mmol). The reaction mixture was stirred at room temperature for 30 min. The solvents were evaporated and the residue partitioned between ethyl acetate and 3.8 M HCl. After phase separation the aqueous layer was extracted with ethyl acetate. The combined organic layers were dried over $MgSO_4$ and evaporated to give a yellow oil. Dimethyl 2-(4-(trifluoromethoxy)benzyl)piperidine-1,4-dicarboxylate (9.72 g, 100%) was isolated. MS m/z 376 $(M+H)^+$

Step 5: 1-(Methoxycarbonyl)-2-(4-(trifluoromethoxy)benzyl)piperidine-4-carboxylic acid To a solution of dimethyl 2-(4-(trifluoromethoxy)benzyl)piperidine-1,4-dicarboxylate (9.72 g, 25.90 mmol) in MeCN (80 mL) and water (1.6 mL) was added lithium bromide (18.2 g, 209.57 mmol) and triethylamine (15 mL, 108.21 mmol). The resulting mixture was heated under reflux for 3 h, then cooled to room temperature. Water and MTBE were added. The organic phase was extracted with water twice. The pooled aqueous layers were adjusted to pH 1 with 3.8 M HCl and then extracted with DCM (3×). The mixture was filtered through a diatomeous earth filter carton. The combined organic layers were dried over $MgSO_4$ and evaporated. 1-(Methoxycarbonyl)-2-(4-(trifluoromethoxy)benzyl)piperidine-4-carboxylic acid (8.75 g, 94%) was isolated as a pale yellow solid. MS m/z 360 (M−H)⁻

Reference Compound 51

2-(4-Chlorobenzyl)-1-(methoxycarbonyl)piperidine-4-carboxylic acid

Step 1: tert-Butyl 2-(4-chlorobenzyl)-4-cyanopiperidine-1-carboxylate

To a solution of tert-butyl 2-(4-chlorobenzyl)-4-oxopiperidine-1-carboxylate (8.737 g, 26.98 mmol) in DME (200 mL) under nitrogen was added simultaneously 1-(isocyanomethyl-sulfonyl)-4-methylbenzene (7.90 g, 40.47 mmol) in 200 mL DME and potassium tert-butoxide (81 mL, 80.94 mmol) over 1 hour so that the temperature never rose above 0° C. The solution was stirred at −20° C. for 2 h and then let to warm to room temperature overnight. Water (200 mL) was added to the orange reaction mixture and the solution was stirred for 20 min and then extracted with 3× diethyl ether and 3× EtOAc. The organic phases were combined and dried over $Na_2SO_4$ and evaporated to give a brown residue. Further purification was done on Biotage (340 g column, 3 runs, heptane/EtOAc, gradient 20-60% EtOAc) to give tert-butyl 2-(4-chlorobenzyl)-4-cyanopiperidine-1-carboxylate (5.54 g, 61%). $^1$H NMR (400 MHz, cdcl₃) δ, 1.21-1.50 (m, 9H), 1.58-2.14 (m, 4H), 2.55-3.27 (m, 4H), 4.06-4.25 (m, 1H), 4.34-4.60 (m, 1H), 7.02-7.34 (m, 4H). MS m/z 235, 237 (M-C5H8O2+H)⁺

Step 2: 2-(4-Chlorobenzyl)piperidine-4-carboxylic acid hydrochloride

Conc. HCl (20 mL, 651.11 mmol) was added to tert-butyl 2-(4-chlorobenzyl)-4-cyanopiperidine-1-carboxylate (5.54 g, 16.55 mmol) and the mixture stirred for 20 minutes. The mixture was transferred to a 20 mL microwave vial. The vial was capped and heated at 140° C. for 30 min in a single node microwave reactor. Concentration of the reaction solution yielded crude 2-(4-chlorobenzyl)piperidine-4-carboxylic acid hydrochloride (5.34 g, 111%). MS m/z 254, 256 (M+H)⁺

Step 3: Methyl 2-(4-chlorobenzyl)piperidine-4-carboxylate

To crude 2-(4-chlorobenzyl)piperidine-4-carboxylic acid hydrochloride (5.34 g, 20.9 mmol) was added HCl (1.25 M in MeOH, 60 mL). The resulting suspension was refluxed for 2 h and then concentrated to give a slightly yellow solid. The residue was taken up in satd $NaHCO_3$ (100 mL). The aqueous phase was extracted with DCM (×3), the combined organic layers dried with a phase separator and evaporated to yield methyl 2-(4-chlorobenzyl)piperidine-4-carboxylate (3.85 g, 87%) as a brown oil. MS m/z 268, 270 (M+H)⁺

Step 4: Dimethyl 2-(4-chlorobenzyl)piperidine-1,4-dicarboxylate

To a solution of methyl 2-(4-chlorobenzyl)piperidine-4-carboxylate (3.72 g, 13.2 mmol) and DIPEA (4.85 mL, 27.78 mmol) in DCM (100 mL) was added methyl chloroformate (1.431 mL, 18.48 mmol) in DCM (50 mL) over 30 minutes. The reaction solution was stirred overnight (16 h). The organic phase was washed with satd $NaHCO_3$, dried using a phase separator and evaporated to yield dimethyl 2-(4-chlorobenzyl)piperidine-1,4-dicarboxylate (4.74 g, 110%) as a yellow oil. MS m/z 326, 328 (M+H)⁺

Step 5: 2-(4-Chlorobenzyl)-1-(methoxycarbonyl)piperidine-4-carboxylic acid

Dimethyl 2-(4-chlorobenzyl)piperidine-1,4-dicarboxylate (4.74 g, 14.55 mmol) was dissolved in tetrahydrofuran (15 mL) followed by addition of LiOH (0.430 g, 17.97 mmol), MeOH (10 mL) and water (10 mL). The reaction mixture was stirred at room temperature overnight. The solvents were evaporated and the residue was taken up in water. The pH was adjusted to <2 by addition of 2 M HCl. The product was poorly soluble and attempts to extract the aqueous phase with DCM and ethyl acetate failed. Instead the mixture was concentrated and then filtered, washed with water and dried to give a yellow solid material. The water phase did contain some product and was extracted with DCM (×3) and dried with a phase separator to give about 500 mg. Crude 2-(4-chlorobenzyl)-1-(methoxycarbonyl)piperidine-4-carboxylic acid (4.27 g, quant.) was isolated. MS m/z 312, 314 (M+H)⁺

Reference Compound 52

1-(Methoxycarbonyl)-2-(4-(methylsulfonyl)benzyl) piperidine-4-carboxylic acid

Step 1: (4-(Methylsulfonyl)benzyl)zinc(II) bromide

Zinc powder (2.81 g, 42.97 mmol) was suspended in THF (50 mL) under nitrogen and heated to 60° C. 1,2-dibromoethane (0.336 g, 1.79 mmol) was added and stirred for 15 min at 60° C. It was cooled to ambient temperature, TMSCl (0.156 g, 1.43 mmol) was added and stirred for 15 min at ambient temperature. 1-(Bromomethyl)-4-(methylsulfonyl)benzene (8.92 g, 35.81 mmol) dissolved in THF (50 mL) was added over 15 min and the resulting mixture was stirred at ambient temperature overnight. Stirring was stopped and the supernatant used in the next reaction.

Step 2: Methyl 2-(4-(methylsulfonyl)benzyl)isonicotinate

Methyl 2-chloroisonicotinate (5.12 g, 29.84 mmol) and $Pd(PPh_3)_4$ (1.379 g, 1.19 mmol) were dissolved in THF (50 mL) under nitrogen. Freshly prepared 4-(methylsulfonyl) benzyl)zinc(II) bromide (11.26 g, 35.81 mmol) in THF (100 mL) was added and the reaction mixture heated to 60° C. for 3 h. Water (20 mL) was added. It was diluted with $NaHCO_3$ (aq) and extracted with diethylether. The organic layer was washed with NaCl (aq), dried over $Na_2SO_4$, filtered and evaporated. Purified using the Biotage equipment. Ethyl acetate and hexane used as eluent. Gradient 0% to 100% of ethyl acetate. Methyl 2-(4-(methylsulfonyl)benzyl)-isonicotinate (8.0 g, 88%) was isolated. $^1$H NMR (600 MHz, cdcl₃)

δ 3.00 (s, 3H), 3.92 (s, 3H), 4.28 (s, 2H), 7.45 (d, 2H), 7.68-7.72 (m, 2H), 7.85 (d, 2H), 8.69 (d, 1H). MS m/z 306 (M+H)$^+$

Step 3: Methyl 2-(4-(methylsulfonyl)benzyl)piperidine-4-carboxylate

Methyl 2-(4-(methylsulfonyl)benzyl)isonicotinate (8.0 g, 26.2 mmol) was dissolved in acetic acid (250 mL). Activated carbon was added and stirred for 30 min. The activated carbon was filtered off. To the solution was added PtO$_2$ (0.119 g, 0.52 mmol) and the reaction mixture hydrogenated in a Büchi hydrogenator overnight at room temperature and 9 bar. The catalyst was filtered off. The solvent was evaporated. The crude was partitioned between Na$_2$CO$_3$ (aq) and ethyl acetate. The organic layer was dried over Na$_2$SO$_4$, filtered through celite and evaporated to yield methyl 2-(4-(methylsulfonyl)benzyl)piperidine-4-carboxylate (5.38 g, 65.9%).

Step 4: Dimethyl 2-(4-(methylsulfonyl)benzyl)piperidine-1,4-dicarboxylate

Methyl 2-(4-(methylsulfonyl)benzyl)piperidine-4-carboxylate (5.88 g, 18.88 mmol) was dissolved in DIPEA (4.93 mL, 28.32 mmol) and dichloromethane (150 mL). Methyl carbonochloridate (2.141 g, 22.66 mmol) was added dropwise and the reaction mixture stirred at room temperature overnight. The solvent was evaporated and the residue partitioned between 1 M KHSO$_4$ and diethyl ether. The organic layer was dried over Na$_2$SO$_4$, filtered through celite and evaporated to yield dimethyl 2-(4-(methylsulfonyl)benzyl)piperidine-1,4-dicarboxylate (5.5 g, 79%).

Step 5: 1-(Methoxycarbonyl)-2-(4-(methylsulfonyl)benzyl)piperidine-4-carboxylic acid Dimethyl 2-(4-(methylsulfonyl)benzyl)piperidine-1,4-dicarboxylate (5.5 g, 14.89 mmol) was dissolved in acetonitrile (50 mL) and water (1 mL), then lithium bromide (10.34 g, 119.10 mmol) and triethylamine (8.25 mL, 59.55 mmol) were added and the resulting suspension was heated at reflux for 2 h. Water and MTBE were added. The organic phase was extracted with water (×2). To the pooled aqueous layer was added ethyl acetate and the solution was acidified to pH 1 with HCl and then extracted with ethyl acetate twice. The organic layer was dried (Na$_2$SO$_4$), filtered through celite and evaporated to yield 1-(methoxycarbonyl)-2-(4-(methylsulfonyl)benzyl)piperidine-4-carboxylic acid (4.2 g, 79%). MS m/z 354 (M−H)$^-$ Reference Compound 53

2-(3,4-Difluorobenzyl)-1-(methoxycarbonyl)piperidine-4-carboxylic acid

Step 1: Methyl 2-(3,4-difluorobenzyl)isonicotinate

Methyl 2-chloroisonicotinate (5.6 g, 32.64 mmol) and Pd(PPh$_3$)$_4$ (0.754 g, 0.65 mmol) were dissolved in THF (100 mL) under nitrogen. (3,4-Difluorobenzyl)zinc(II) bromide (0.5 M in THF) (100 mL, 50.00 mmol) was added and the brown solution was stirred at 60° C. overnight. The reaction was quenched by addition of methanol (50 mL). The solution was diluted with EtOAc and washed with NH$_4$Cl (aq). The organic layer was dried over MgSO$_4$, filtered and evaporated to yield a yellow oil. The compound was purified via Biotage, SNAP 340 g KP-SIL, eluent isocratic heptane/ethyl acetate 8:2 for 2 CV, then linear gradient heptane/ethyl acetate 8:2 to 5:5 over 6 CV to yield methyl 2-(3,4-difluorobenzyl)isonicotinate (7.7 g, 90%) as a yellow oil. $^1$H NMR (400 MHz, cdcl$_3$) δ 3.93 (s, 3H), 4.16 (s, 2H), 6.94-7.01 (m, 1H), 7.02-7.12 (m, 2H), 7.66-7.71 (m, 2H), 8.70 (dd, 1H). MS m/z 264 (M+H)$^+$ Step 2: Methyl 2-(3,4-difluorobenzyl)piperidine-4-carboxylate Methyl 2-(3,4-difluorobenzyl)isonicotinate (7.7 g, 29.25 mmol) was dissolved in acetic acid (75 mL) and platinum(IV) oxide (0.332 g, 1.46 mmol) added. The resulting mixture was hydrogenated in a Büchi hydrogenator at room temperature and 5 bar for 4 h 45 min. More platinum(IV) oxide (0.166 g, 0.73 mmol) was added and the hydrogenation continued at 5 bar for 2 h. More platinum(IV) oxide (0.166 g, 0.73 mmol) was added and the hydrogenation continued at 5 bar for 1 h 20 min. The catalyst was filtered off and washed with MeOH and the eluate evaporated. DCM and 10% K$_2$CO$_3$ were added and the phases separated. The organic layer was washed with brine, passed through a phase separator and evaporated to yield crude methyl 2-(3,4-difluorobenzyl)piperidine-4-carboxylate (8.133 g, 103%) as a brown oil. MS m/z 270 (M+H)$^+$ Step 3: Dimethyl 2-(3,4-difluorobenzyl)piperidine-1,4-dicarboxylate Methyl 2-(3,4-difluorobenzyl)piperidine-4-carboxylate (8.115 g, 30.14 mmol) was dissolved in DCM (200 mL) and DIPEA (6.30 mL, 36.16 mmol), then methyl carbonochloridate (3.3 mL, 41.91 mmol) was added. The solution was stirred at room temperature for 2 h. The reaction mixture was washed with 0.1 M HCl satd NaHCO$_3$. The organic phase was passed through a phase separator and evaporated. The residue was redissolved in ether/pentane, 80/20, the solution washed with 1 M HCl 5 times, then with satd NaHCO$_3$ and brine, dried over MgSO$_4$, filtered and evaporated to yield dimethyl 2-(3,4-difluorobenzyl)piperidine-1,4-dicarboxylate (7.05 g, 71%). MS m/z 328 (M+H)$^+$ Step 4: 2-(3,4-Difluorobenzyl)-1-(methoxycarbonyl)piperidine-4-carboxylic acid Dimethyl 2-(3,4-difluorobenzyl)piperidine-1,4-dicarboxylate (7.010 g, 21.42 mmol) was dissolved in acetonitrile (75 mL) and water (1.5 mL). Lithium bromide (14.88 g, 171.33 mmol) and triethylamine (11.87 mL, 85.66 mmol) were added and the resulting yellow suspension was heated at reflux for 3 h. Water (100 mL) and MTBE (300 mL) were added. The organic phase was extracted with water (×2). The pooled aqueous layer was acidified to pH 1 with 3.8 M HCl and then extracted with MTBE (×2). The combined organic layer was washed with water, dried over Na$_2$SO$_4$, filtered and evaporated to yield 2-(3,4-difluorobenzyl)-1-(methoxycarbonyl)piperidine-4-carboxylic acid (6.62 g, 99%) as a yellow solid. MS m/z 314 (M+H)$^+$ Reference Compound 54

2-(2,5-Difluorobenzyl)-1-(methoxycarbonyl)piperidine-4-carboxylic acid

Step 1: Methyl 2-(2,5-difluorobenzyl)isonicotinate

To a solution of methyl 2-chloroisonicotinate (5.6 g, 32.64 mmol) and Pd(PPh$_3$)$_4$ (0.754 g, 0.65 mmol) in anhydrous THF (100 mL) was added (2,5-difluorobenzyl)zinc(II) bromide (0.5 M in THF) (100 mL, 50.00 mmol) dropwise under nitrogen. The reaction mixture was heated at 60° C. for 15 h. The reaction mixture was quenched by addition of methanol (50 mL) and then filtered. The solvent was evaporated under reduced pressure. The residue was dissolved in ethyl acetate and washed with satd NH$_4$Cl solution and brine, then dried. The solvent was evaporated under reduced pressure. The residue was suspended in ethanol, filtered and the solid washed with ethanol. The filtrate was concentrated. The residue was dissolved in MTBE (150 mL), then HCl (4 M in dioxane, (8.15 mL) and MeOH (7.5 mL) were added. The resulting suspension was stirred for 20 min, the solid collected, washed with MTBE (×2) and air dried. The solid was dissolved in DCM (200 mL) and washed with satd NaHCO$_3$. The organic phase was dried using a phase separator and evaporated to yield methyl 2-(2,5-difluorobenzyl)isonicotinate (6.8 g, 79%). MS m/z 264 (M+H)$^+$ Step 2: Methyl 2-(2,5-difluorobenzyl)piperidine-4-carboxylate A mixture of methyl 2-(2,5-difluorobenzyl)isonicotinate (6.8 g, 25.83 mmol) and platinum(IV) oxide (0.293 g, 1.29 mmol) in acetic acid (68 mL) was hydrogenated in a Büchi hydrogenator at room temperature and 5 bar for 5 h. More PtO$_2$ (190 mg) was added and the hydrogenation continued at room temperature and 5 bar for additional 80 min. The reaction mixture was filtered through Celite and the catalyst was washed with methanol. The filtrate was concentrated, the residue was dissolved in DCM, washed with satd NaHCO$_3$ and the organic layer was dried using a phase separator. The solvent was evaporated under reduced pressure. The residue was dissolved in iso-hexane/ether and filtered. The solvents were evaporated in vacuo to yield methyl 2-(2,5-difluorobenzyl)piperidine-4-carboxylate (6.65 g, 96%). MS m/z 270 (M+H)$^+$ Step 3: Dimethyl 2-(2,5-difluorobenzyl)piperidine-1,4-dicarboxylate To a solution of methyl 2-(2,5-difluorobenzyl)piperidine-4-carboxylate (6.65 g, 24.69 mmol) in DCM (100 mL) and DIPEA (5.16 mL, 29.63 mmol) was added methyl carbonochloridate (2.53 mL, 32.10 mmol) dropwise at room temperature under nitrogen. The reaction mixture was stirred at room temperature for 1 h. The reaction was quenched with 0.15 M HCl (250 mL). The organic phase was separated, washed with satd NaHCO$_3$, dried using a phase separator and evaporated to yield dimethyl 2-(2,5-difluorobenzyl)piperidine-1,4-dicarboxylate (8.1 g, 100%). MS m/z 328 (M+H)$^+$ Step 4: 2-(2,5-Difluorobenzyl)-1-(methoxycarbonyl) piperidine-4-carboxylic acid To a solution of dimethyl 2-(2,5-difluorobenzyl)piperidine-1,4-dicarboxylate (8.08 g, 24.69 mmol) in acetonitrile (85 mL) and water (1.7 mL) was added lithium bromide (4.95 mL, 197.48 mmol) and triethylamine (13.69 mL, 98.74 mmol). The reaction mixture was heated to reflux for 2.5 h, then allowed to cool to room temperature. Water (150 mL) and MTBE (300 mL) was added. The aqueous phase was separated and the organic phase was extracted twice with water. The water phases were combined and 4.0 M HCl was added until a pH of 1 was obtained. The aqueous was extracted with MTBE (300 mL×2). The organic phases were combined, washed with brine, dried with Na$_2$SO$_4$ and evaporated under reduced pressure to give 2-(2,5-difluorobenzyl)-1-(methoxycarbonyl)piperidine-4-carboxylic acid (7.4 g, 96%). MS m/z 314 (M+H)$^+$ Reference Compound 55

2-(2,6-Difluorobenzyl)-1-(methoxycarbonyl)piperidine-4-carboxylic acid

Step 1: Methyl 2-(2,6-difluorobenzyl)isonicotinate

Methyl 2-chloroisonicotinate (5.600 g, 32.64 mmol) and Pd(PPh$_3$)$_4$ (0.754 g, 0.65 mmol) were dissolved in THF (100 mL) under nitrogen and (2,6-difluorobenzyl)zinc(II) bromide (0.5 M in THF, 100 mL, 50.00 mmol) was added and the resulting solution was stirred at 60° C. for 4 h before it was cooled to room temperature and quenched with methanol (50.0 mL). The mixture was diluted with EtOAc and washed with satd NH$_4$Cl. The organic phase was dried with MgSO$_4$, filtered and evaporated. The crude product was dissolved in MTBE (200 mL), solids were filtered off, and HCl (4 M in dioxane, 8.16 mL, 32.64 mmol) was added dropwise. The mixture was stirred for 10 minutes before the precipitate was filtered off, washed with MTBE and dissolved in MTBE/satd NaHCO$_3$. The organic layer was dried with MgSO$_4$, filtered and evaporated to give methyl 2-(2,6-difluorobenzyl)isonicotinate (5.03 g, 58.6%) as a white solid. $^1$H NMR (400 MHz, cdcl$_3$) δ 3.92 (s, 3H), 4.29 (s, 2H), 6.87-6.97 (m, 2H), 7.18-7.29 (m, 1H), 7.61-7.73 (m, 2H), 8.63-8.70 (m, 1H). MS m/z 264 (M+H)$^+$ Step 2: Methyl 2-(2,6-difluorobenzyl)piperidine-4-carboxylate Methyl 2-(2,6-difluorobenzyl)isonicotinate (5.031 g, 19.11 mmol) was dissolved in acetic acid (49 mL) and platinum(IV) oxide (0.217 g, 0.96 mmol) was added. The mixture was hydrogenated in a Büchi hydrogenator at room temperature and 5 bar for 5 h. More platinum(IV) oxide (0.108 g, 0.48 mmol) was added and hydrogenation was continued for 1 h. Additional platinum(IV) oxide (0.108 g, 0.48 mmol) was added and the mixture was again hydrogenated for 1.5 h. More platinum(IV) oxide (0.108 g, 0.48 mmol) was added. After a total of 8.5 h the reaction mixture was filtered through celite and the catalyst was washed with MeOH. The eluate was concentrated and DCM and 1 M K$_2$CO$_3$ were added. The phases were separated and the organic phase was washed with brine before it was dried and concentrated to yield methyl 2-(2,6-difluorobenzyl)piperidine-4-carboxylate (5.01 g, 97%). MS m/z 270 (M+H)$^+$ Step 3: Dimethyl 2-(2,6-difluorobenzyl)piperidine-1,4-dicarboxylate Methyl 2-(2,6-difluorobenzyl)piperidine-4-carboxylate (5.008 g, 18.60 mmol) was dissolved in DCM (121 mL) and DIPEA (3.89 mL, 22.32 mmol) followed by methyl carbonochloridate (2.050 mL, 26.04 mmol) were added. After 3.5 h at room temperature the solution was washed with 0.1 M HCl and satd NaHCO$_3$. The organic phase was dried and concentrated to yield dimethyl 2-(2,6-difluorobenzyl)piperidine-1, 4-dicarboxylate (5.98 g, 98%). MS m/z 328 (M+H)$^+$ Step 4: 2-(2,6-Difluorobenzyl)-1-(methoxycarbonyl) piperidine-4-carboxylic acid Dimethyl 2-(2,6-difluorobenzyl)piperidine-1,4-dicarboxylate (5.98 g, 18.27 mmol) was dissolved in acetonitrile (50 mL) and water (1 mL), then lithium bromide (12.69 g, 146.16 mmol) and triethylamine (10.13 mL, 73.08 mmol) were added. The suspension was heated to reflux for 3.5 h, then water (60 mL) and MTBE (180 mL) were added. The organic phase was extracted with water (×2). The combined water phases were acidified to pH 1 with 3.8 M HCl and extracted with MTBE (×2). The combined organic phases were washed with water, dried with $MgSO_4$, filtered through celite and concentrated to give 2-(2,6-difluorobenzyl)-1-(methoxycarbonyl)piperidine-4-carboxylic acid (4.72 g, 82%) as a light yellow solid. MS m/z 314 $(M+H)^+$ Reference Compound 56

2-(3,5-Difluorobenzyl)-1-(methoxycarbonyl)piperidine-4-carboxylic acid

Step 1: Methyl 2-(3,5-difluorobenzyl)isonicotinate

Methyl 2-chloroisonicotinate (5.600 g, 32.64 mmol) and $Pd(PPh_3)_4$ (0.754 g, 0.65 mmol) were dissolved in THF (100 mL) under nitrogen, then (3,5-difluorobenzyl)zinc(II) chloride (0.5 M in THF, 100 mL, 50.00 mmol) was added and the resulting solution was stirred at 60° C. for 3 h before it was cooled to room temperature and quenched with methanol (50.0 mL). The mixture was diluted with EtOAc and washed with satd $NH_4Cl$. The organic phase was dried and concentrated. The residue was purified by automated flash chromatography on a Biotage® KP-SIL 340 g column, eluent isocratic heptane/EtOAc 8:2 for 2 CV, then a gradient from 20% to 50% of EtOAc in heptane over 6 CV was used as mobile phase. Methyl 2-(3,5-difluorobenzyl)isonicotinate (7.42 g, 86%) was isolated as an oil. $^1$H NMR (400 MHz, $cdcl_3$) δ 3.94 (s, 3H), 4.18 (s, 2H), 6.66 (tt, 1H), 6.74-6.82 (m, 2H), 7.67-7.75 (m, 2H), 8.67-8.75 (m, 1H). MS m/z 264 $(M+H)^+$ Step 2: Methyl 2-(3,5-difluorobenzyl)piperidine-4-carboxylate Methyl 2-(3,5-difluorobenzyl)isonicotinate (7.417 g, 28.18 mmol) was dissolved in acetic acid (72 mL) and platinum(IV) oxide (0.320 g, 1.41 mmol) was added. The mixture was hydrogenated in a Büchi hydrogenator at room temperature and 5 bar for 5 h. The reaction mixture was filtered through celite and the catalyst was washed with MeOH. The eluate was concentrated and DCM and 1 M $K_2CO_3$ were added. The phases were separated and the organic phase was washed with brine before it was dried and concentrated to yield methyl 2-(3,5-difluorobenzyl)piperidine-4-carboxylate (7.08 g, 93%). MS m/z 270 $(M+H)^+$ Step 3: Dimethyl 2-(3,5-difluorobenzyl)piperidine-1,4-dicarboxylate Methyl 2-(3,5-difluorobenzyl)piperidine-4-carboxylate (7.082 g, 26.30 mmol) was dissolved in DCM (170 mL) and DIPEA (5.50 mL, 31.56 mmol), then methyl carbonochloridate (2.88 mL, 36.58 mmol) was added. The reaction mixture was stirred at room temperature for 3 h, then additional methyl carbonochloridate (0.7 mL, 8.89 mmol) was added. The solution was stirred for 30 min then washed with 0.1 M HCl and satd $NaHCO_3$. The organic phase was dried and concentrated to give dimethyl 2-(3,5-difluorobenzyl)piperidine-1,4-dicarboxylate (8.55 g, 99%). MS m/z 328 $(M+H)^+$ Step 4: 2-(3,5-Difluorobenzyl)-1-(methoxycarbonyl)piperidine-4-carboxylic acid Dimethyl 2-(3,5-difluorobenzyl)piperidine-1,4-dicarboxylate (8.459 g, 25.84 mmol) was dissolved in acetonitrile (85 mL) and water (1.7 mL). Lithium bromide (17.95 g, 206.74 mmol) and triethylamine (14.33 mL, 103.37 mmol) were added. The suspension was heated to reflux 1.5 h before water (100 mL) and MTBE (300 mL) were added. The organic phase was extracted with water (×2). The combined water phases were acidified to pH 1 with 3.8 M HCl and extracted with MTBE (×2). The combined organic phases were washed with water, dried with $MgSO_4$, filtered through celite and concentrated. The crude product was redissolved in MTBE and washed with 0.1 M HCl (×2) and water. The organic phase was dried with $MgSO_4$ and concentrated to give 2-(3,5-difluorobenzyl)-1-(methoxycarbonyl)piperidine-4-carboxylic acid (6.88 g, 85%). MS m/z 314 $(M+H)^+$ Reference Compound 57

2-(2,4-Difluorobenzyl)-1-(methoxycarbonyl)piperidine-4-carboxylic acid

Step 1: Methyl 2-(2,4-difluorobenzyl)isonicotinate

Methyl 2-chloroisonicotinate (5.2 g, 30.31 mmol) and $Pd(PPh_3)_4$ (0.700 g, 0.61 mmol) were dissolved in THF (100 mL) under nitrogen and (2,4-difluorobenzyl)zinc(II) chloride (0.5 M in THF, 90 mL, 45.00 mmol) was added and the brown solution was stirred at 60° C. overnight (18 h). The reaction was quenched by addition of methanol (50.0 mL). The solution was diluted with EtOAc and washed with $NH_4Cl$ (aq) and brine and dried over $Na_2SO_4$ to give a red oil. The crude was redissolved in MTBE (200 mL) and solids were filtered off. Hydrogen chloride (4 M in dioxane, 7.58 mL, 30.31 mmol) was added dropwise during stirring and a suspension was formed. The suspension was stirred at room temperature for 15 min. The solid was collected by filtration and washed with MTBE. The solid was dissolved in MTBE/satd $NaHCO_3$. The phases were separated, the organic phase dried over $Na_2SO_4$, filtered and evaporated to yield methyl 2-(2,4-difluorobenzyl)isonicotinate (7.011 g, 88%) as a red oil. 1H NMR (400 MHz, $cdcl_3$) δ 3.93 (s, 3H), 4.20 (s, 2H), 6.77-6.88 (m, 2H), 7.18-7.25 (m, 1H), 7.62-7.73 (m, 2H), 8.69 (dd, 1H). MS m/z 264 $(M+H)^+$ Step 2: Methyl 2-(2,4-difluorobenzyl)piperidine-4-carboxylate Methyl 2-(2,4-difluorobenzyl)isonicotinate (7.011 g, 26.63 mmol) was dissolved in acetic acid (50 mL) and platinum(IV) oxide (0.302 g, 1.33 mmol) added. The resulting mixture was hydrogenated in a Büchi hydrogenator for 4.5 h at room temperature and 5 bar. platinum(IV) oxide (174 mg) was added and the hydrogenation continued at room temperature at 5 bar for 2 h. Additional platinum(IV) oxide (185 mg) was added and the hydrogenation continued at room temperature at 5 bar for 2 h. The catalyst was filtered off and washed with MeOH and the eluate evaporated. DCM and 10% $K_2CO_3$ were added and the phases separated. The water phase was extracted with DCM and the combined organic phase washed with water, passed through a phase separator and evaporated to yield methyl 2-(2,4-difluorobenzyl)-piperidine-4-carboxylate (7.103 g, 99%) as a yellow oil. MS m/z 270 $(M+H)^+$ Step 3: Dimethyl 2-(2,4-difluorobenzyl)piperidine-1,4-dicarboxylate To a solution of methyl 2-(2,4-difluorobenzyl)piperidine-4-carboxylate (7.1 g, 26.37 mmol) in DCM (100 mL) was added DIPEA (6.5 mL, 37.32 mmol) followed by methyl carbonochloridate (2.3 mL, 29.21 mmol) dropwise. After completed addition the reaction mixture was stirred at room temperature for 4 h, then 2 M HCl was added. The organic layer was diluted with MTBE, the biphasic mixture was filtered to remove insolubles and after phase separation the organic layer was washed with brine and satd NaHCO$_3$, dried over MgSO$_4$ and evaporated to give dimethyl 2-(2,4-difluorobenzyl)piperidine-1,4-dicarboxylate (8.51 g, 99%) as a dark oil. MS m/z 328 (M+H)$^+$ Step 4: 2-(2,4-Difluorobenzyl)-1-(methoxycarbonyl)piperidine-4-carboxylic acid To a suspension of lithium bromide (18.06 g, 207.99 mmol) in acetonitrile (80 mL) and water (1.6 mL) was added triethylamine (14.42 mL, 104.00 mmol) followed by dimethyl 2-(2,4-difluorobenzyl)piperidine-1,4-dicarboxylate (8.51 g, 26.00 mmol) in acetonitrile (40 mL). The resulting mixture was heated under reflux for 2 h 30 min, then cooled to room temperature and water and MTBE were added. The organic phase was extracted with water twice. The pooled aqueous layers were adjusted to pH 1 with 3.8 M HCl and then extracted with DCM (3×). The combined organic layers were dried over MgSO$_4$ and evaporated to yield 2-(2,4-difluorobenzyl)-1-(methoxycarbonyl)piperidine-4-carboxylic acid (7.48 g, 92%) as an orange solid. MS m/z 314 (M+H)$^+$ Reference Compound 58

2-(3-Fluoro-5-(trifluoromethyl)benzyl)-1-(methoxycarbonyl)piperidine-4-carboxylic acid Step 1: (3-Fluoro-5-(trifluoromethyl)benzyl)zinc(II) bromide In a dried flask was zinc powder (1.526 g, 23.34 mmol) suspended in anhydrous THF (12.5 mL) under nitrogen. The resulting suspension was warmed to 60° C., then 1,2-dibromoethane (0.084 mL, 0.97 mmol) was added and stirred at that temperature for 15 min. It was cooled to room temperature, then chlorotrimethylsilane (0.099 mL, 0.78 mmol) was added and stirred at room temperature for 20 min. Then, 1-(bromomethyl)-3-fluoro-5-(trifluoromethyl)benzene (5 g, 19.45 mmol) dissolved in anhydrous THF (12.5 mL) was added over 7 min and stirring continued at room temperature for 1 h, then stirring was switched off to let the solids settle. The supernatant was used in the next transformation.

Step 2: Methyl 2-(3-fluoro-5-(trifluoromethyl)benzyl)isonicotinate

Methyl 2-chloroisonicotinate (3.0 g, 17.48 mmol) and Pd(PPh$_3$)$_4$ (0.606 g, 0.52 mmol) were dissolved in THF (50 mL) under nitrogen. Freshly prepared (3-fluoro-5-(trifluoromethyl)benzyl)zinc(II) bromide (5.41 g, 19.45 mmol) in THF (25 mL) was added to the yellow solution and the flask was warmed to 60° C. overnight. The reaction mixture was quenched by adding methanol. The solution was diluted with ethyl acetate and washed with NH$_4$Cl and water. The organic layer was dried with Na$_2$SO$_4$, filtered through celite, and the solvent was evaporated. The residue was chromatographed using the Biotage equipment. Eluent ethyl acetate-heptane, started 20-80 and linear gradient until 60-40. Methyl 2-(3-fluoro-5-(trifluoromethyl)benzyl)isonicotinate (4.1 g, 75% yield) was isolated. $^1$H NMR (400 MHz, cdcl$_3$) δ 3.94 (s, 3H), 4.25 (s, 2H), 7.13-7.22 (m, 2H), 7.33 (s, 1H), 7.69-7.75 (m, 2H), 8.70-8.74 (m, 1H). MS m/z 314 (M+H)$^+$ Step 3: Methyl 2-(3-fluoro-5-(trifluoromethyl)benzyl)piperidine-4-carboxylate To a solution of methyl 2-(3-fluoro-5-(trifluoromethyl)benzyl)isonicotinate (4.5 g, 14.37 mmol) in acetic acid (50 mL) was added platinum(IV) oxide (0.36 g, 1.59 mmol) and the resulting mixture hydrogenated at 5 bar in a Büchi hydrogenator for 3 h 45 min. The reaction mixture was filtered through a diatomeous earth filter carton and the catalyst washed with methanol. The solvents were evaporated, the residue dissolved in DCM and washed with 10% Na$_2$CO$_3$. After phase separation the aqueous layer was extracted with DCM. The combined organic layers were dried over MgSO$_4$ and evaporated. Methyl 2-(3-fluoro-5-(trifluoro-methyl)benzyl)piperidine-4-carboxylate (4.11 g, 90%) was isolated as a pale yellow oil that partially solidified upon standing. MS m/z 320 (M+H)$^+$ Step 4: Dimethyl 2-(3-fluoro-5-(trifluoromethyl)benzyl)piperidine-1,4-dicarboxylate To a solution of methyl 2-(3-fluoro-5-(trifluoromethyl)benzyl)piperidine-4-carboxylate (4.10 g, 12.84 mmol) in DCM (50 mL) cooled in an ice-bath was added DIPEA (3.5 mL, 20.09 mmol) followed by methyl carbonochloridate (1.112 mL, 14.12 mmol). After completed addition the reaction mixture was stirred at room temperature for 2 h. The solvents were evaporated and the residue partitioned between ethyl acetate and 3.8 M HCl. After phase separation the organic layer was washed with brine, then dried over MgSO$_4$ and evaporated to yield crude dimethyl 2-(3-fluoro-5-(trifluoromethyl)benzyl)piperidine-1,4-dicarboxylate (4.94 g, 102%) as a pale yellow oil. MS m/z 378 (M+H)$^+$ Step 5: 2-(3-Fluoro-5-(trifluoromethyl)benzyl)-1-(methoxycarbonyl)piperidine-4-carboxylic acid To a solution of dimethyl 2-(3-fluoro-5-(trifluoromethyl)benzyl)piperidine-1,4-dicarboxylate (4.94 g, 13.09 mmol) in acetonitrile (60 mL) and water (1.2 mL) was added lithium bromide (9.10 g, 104.74 mmol) and triethylamine (7.26 mL, 52.37 mmol). The resulting mixture was heated under reflux for 2 h, then cooled to room temperature. Water was added and acetonitrile removed by evaporation. The aqueous layer was further diluted with water, then washed with MTBE. The organic layer was extracted with water. The combined aqueous layers were acidified with 3.8 M HCl, a colorless precipitate formed. The aqueous layer was extracted with DCM three times. The combined organic layers were dried over MgSO$_4$ and evaporated. 2-(3-Fluoro-5-(trifluoromethyl)benzyl)-1-(methoxycarbonyl)piperidine-4-carboxylic acid (4.58 g, 96%) was isolated as a pale yellow viscous oil. MS m/z 364 (M+H)$^+$ Reference Compound 59

2-(3-Fluoro-4-(trifluoromethyl)benzyl)-1-(methoxycarbonyl)piperidine-4-carboxylic acid Step 1: (3-Fluoro-4-(trifluoromethyl)benzyl)zinc(II) bromide In a dried flask was zinc powder (3.05 g, 46.69 mmol) suspended in anhydrous tetrahydrofuran (25 mL) under nitrogen. The resulting suspension was warmed to 60° C., then 1,2-dibromoethane (0.168 mL, 1.95 mmol) was added and stirred at that temperature for 15 min. It was cooled to room temperature, then chlorotrimethylsilane (0.2 mL, 1.58 mmol) was added and stirred at room temperature for 1 h 15 min. Then, 4-(bromomethyl)-2-fluoro-1-(trifluoromethyl)benzene (10 g, 38.91 mmol) in tetrahydrofuran (5 mL) was added in 6 equal portions every 10 minutes under ice-cooling. After complete addition the ice-bath was removed and the reaction mixture stirred at room temperature for 18 h. Then was stirring switched off to let the solids settle. The supernatant was used in next transformation.

Step 2: Methyl 2-(3-fluoro-4-(trifluoromethyl)benzyl)isonicotinate

To a solution of methyl 2-chloroisonicotinate (5.15 g, 30 mmol) and Pd(PPh$_3$)$_4$ (0.693 g, 0.60 mmol) in tetrahydrofuran (40 mL) under nitrogen in a dried flask was added freshly prepared (3-fluoro-4-(trifluoromethyl)benzyl)zinc(II) bromide (12.55 g, 38.91 mmol) in tetrahydrofuran (50 mL). The resulting bright yellow mixture was heated to 60° C. for 2 h 20 min, then cooled to room temperature. The reaction was quenched by the addition of 10% NH$_4$Cl. It was diluted with ethyl acetate. After phase separation, the organic layer was washed with brine, dried over MgSO$_4$ and evaporated. The residue was suspended in 150 mL MTBE and sonicated, then the yellow insolubles were filtered off and washed with MTBE. The volume of the filtrate was increased to ca. 200 mL, then hydrogen chloride (7.50 mL, 30.00 mmol) (4M in dioxane) was added dropwise. A colorless precipitate formed. The resulting suspension was stirred for ca. 1 h, then sonicated for 2 min. The formed solid was collected and washed with MTBE and dried. The solid was dissolved in DCM and washed with 10% K$_2$CO$_3$. After phase separation, the aqueous layer was extracted with DCM. The combined organic layers were dried over MgSO$_4$ and evaporated. Methyl 2-(3-fluoro-4-(trifluoromethyl)benzyl)isonicotinate (8.26 g, 88%) was isolated as a pale orange oil. $^1$H NMR (400 MHz, cdcl$_3$) δ 3.94 (s, 3H), 4.24 (s, 2H), 7.06-7.18 (m, 2H), 7.52 (t, 1H), 7.69-7.75 (m, 2H), 8.68-8.75 (m, 1H). MS m/z 314 (M+H)$^+$ Step 3: Methyl 2-(3-fluoro-4-(trifluoromethyl)benzyl)piperidine-4-carboxylate To a solution of methyl 2-(3-fluoro-4-(trifluoromethyl)benzyl)isonicotinate (8.26 g, 26.37 mmol) in acetic acid (50 mL) was added platinum(IV) oxide (0.44 g, 1.94 mmol) and the resulting mixture hydrogenated at 5 bar in a Büchi hydrogenator for 8 h. The reaction mixture was filtered through a diatomeous earth filter carton and the catalyst washed with methanol. The solvents were evaporated, the residue dissolved in DCM and washed with 10% Na$_2$CO$_3$. After phase separation the aqueous layer was extracted with DCM. The combined organic layers were dried over MgSO4 and evaporated. Methyl 2-(3-fluoro-4-(trifluoromethyl)-benzyl)piperidine-4-carboxylate (8.4 g, 100%) was isolated as a pale yellow oil that partially solidified upon standing. MS m/z 320 (M+H)$^+$ Step 4: Dimethyl 2-(3-fluoro-4-(trifluoromethyl)benzyl)piperidine-1,4-dicarboxylate To a solution of methyl 2-(3-fluoro-4-(trifluoromethyl) benzyl)piperidine-4-carboxylate (5.96 g, 18.67 mmol) in DCM (100 mL) cooled in an ice-bath added DIPEA (4 mL, 22.96 mmol) followed by methyl carbonochloridate (1.617 mL, 20.53 mmol). After completed addition the reaction mixture was stirred at room temperature for 2 h. The solvents were evaporated and the residue partitioned between ethyl acetate and 3.8 M HCl. After phase separation the organic layer was washed with brine, then dried over MgSO$_4$ and evaporated. Dimethyl 2-(3-fluoro-4-(trifluoromethyl) benzyl)piperidine-1,4-dicarboxylate (7.17 g, 102%) was isolated as a pale yellow oil.

Step 5: 2-(3-Fluoro-4-(trifluoromethyl)benzyl)-1-(methoxycarbonyl)piperidine-4-carboxylic acid To a solution of dimethyl 2-(3-fluoro-4-(trifluoromethyl) benzyl)piperidine-1,4-dicarboxylate (7.17 g, 19.00 mmol) in acetonitrile (60 mL) and water (1.2 mL) was added lithium bromide (13.20 g, 152.02 mmol) and triethylamine (10.54 mL, 76.01 mmol). The resulting mixture was heated under reflux for 2 h, then cooled to room temperature. Water was added and acetonitrile removed by evaporation. The aqueous layer was further diluted with water, then washed with MTBE. The organic layer was extracted with water. The combined aqueous layers were acidified with 3.8 M HCl, a colorless precipitate formed. The solids were extracted with DCM 6 times. The aqueous layer was extracted twice again with DCM. The combined organic layers were dried over MgSO$_4$ and evaporated. 2-(3-Fluoro-4-(trifluoromethyl)benzyl)-1-(methoxycarbonyl)piperidine-4-carboxylic acid (6.56 g, 95%) was isolated as an off-white solid. MS m/z 364 (M+H)$^+$ Reference Compound 60

1-(Methoxycarbonyl)-2-(3,4,5-trifluorobenzyl)piperidine-4-carboxylic acid

Step 1: (3,4,5-Trifluorobenzyl)zinc(II) bromide

Zinc powder (2.62 g, 40.00 mmol) and lithium chloride (1.696 g, 40.00 mmol) were added to a dried flask and heated to 150° C. under vacuum for 30 min. The flask was allowed to reach room temperature. THF (20 mL) and 1,2-dibromoethane (0.115 mL, 1.33 mmol) were added. The mixture was heated until boiling occurred and the flask was then allowed to reach room temperature. Chlorotrimethylsilane (0.034 mL, 0.27 mmol) was added and the mixture was again heated until boiling occurred. The flask was cooled with an ice-bath and 5-(bromomethyl)-1,2,3-trifluorobenzene (6 g, 26.67 mmol) dissolved in THF (5 mL) was then added dropwise. The ice-bath was removed and the reaction stirred at room temperature for 20 h. Solids were allowed to settle and the supernatant used in the next transformation.

Step 2: Methyl 2-(3,4,5-trifluorobenzyl)isonicotinate hydrochloride

Methyl 2-chloroisonicotinate (3.5 g, 20.40 mmol) was dissolved in THF (30 mL) under a nitrogen atmosphere. Bis(tri-tert-butylphosphine)Pd(0) (0.208 g, 0.41 mmol) was added. Freshly made (3,4,5-trifluorobenzyl)zinc(II) bromide (1.06 M in THF) (25.1 mL, 26.65 mmol) was then added and the reaction mixture stirred at 60° C. for 3 h. Water (15 mL) was added and THF was evaporated. The reaction mixture was diluted with satd NaHCO$_3$ and extracted with EtOAc (3×). The combined organic phases were washed with satd NaHCO$_3$, water, NH$_4$Cl and brine, and dried with Na$_2$SO$_4$, filtered and evaporated in vacuo yielding a red oil (5 g). MTBE (70 mL) was added, insolubles filtered off and washed with MTBE (10 mL). To the filtrate was added hydrogen chloride (4 M in dioxane, 5.10 mL, 20.40 mmol) dropwise, an orange precipitate formed. The mixture was cooled with an ice-bath. The precipitate was filtered off, washed with cold MTBE and dried in vacuo yielding methyl 2-(3,4,5-trifluorobenzyl)isonicotinate hydrochloride (4.00 g, 61.7%) as an orange solid. $^1$H NMR (600 MHz, CD$_3$OD) δ 4.02 (s, 3H), 4.45 (s, 2H), 7.13-7.22 (m, 2H), 8.24-8.32 (m, 2H), 8.87-8.93 (m, 1H). MS m/z 282 (M+H)$^+$ Step 3: Methyl 2-(3,4,5-trifluorobenzyl)piperidine-4-carboxylate hydrochloride Methyl 2-(3,4,5-trifluorobenzyl)isonicotinate hydrochloride (4 g, 12.59 mmol) was dissolved in MeOH (45 mL) and platinum(IV) oxide (0.143 g, 0.63 mmol) added. The resulting mixture was hydrogenated in a Büchi hydrogenator at room temperature and 5 bar for 3 h. Additional platinum(IV) oxide (0.029 g, 0.13 mmol) was added and the hydrogenation continued for 20 min. The catalyst was filtered off and washed with MeOH. The filtrate was evaporated in vacuo to yield methyl 2-(3,4,5-trifluorobenzyl)piperidine-4-carboxylate hydrochloride (3.96 g, 97%) as a brown solid. MS m/z 288 (M+H)$^+$ Step 4: Dimethyl 2-(3,4,5-trifluorobenzyl)piperidine-1,4-dicarboxylate Methyl 2-(3,4,5-trifluorobenzyl)piperidine-4-carboxylate hydrochloride (3.957 g, 12.22 mmol) and DIPEA (4.68 mL, 26.89 mmol) were dissolved in DCM (20 mL) and methyl carbonochloridate (1.059 mL, 13.45 mmol) was added. The reaction was stirred at room temperature for 18 h, diluted with DCM (200 mL), washed with 0.1 M HCl (2×200 mL), satd NaHCO3 (200 mL), dried through a phase separator and evaporated in vacuo to yield dimethyl 2-(3,4,5-trifluorobenzyl)piperidine-1,4-dicarboxylate (4.01 g, 95%) as a brown oil. MS m/z 346 (M+H)$^+$ Step 5: 1-(Methoxycarbonyl)-2-(3,4,5-trifluorobenzyl)piperidine-4-carboxylic acid Dimethyl 2-(3,4,5-trifluorobenzyl)piperidine-1,4-dicarboxylate (4.01 g, 11.61 mmol) was dissolved in acetonitrile (40 mL) and water (0.8 mL). Lithium bromide (2.329 mL, 92.90 mmol) was added followed by triethylamine (6.44 mL, 46.45 mmol). The reaction was refluxed for 2 h. The reaction was cooled to room temperature. Water (200 mL) and MTBE (150 mL) were added, shaken and the phases separated. The organic phase was extracted with water (2×150 mL). The combined aqueous phases were acidified with 3 M HCl to pH 1 and then extracted with MTBE (2×400 mL). The combined organic phases were dried with Na$_2$SO$_4$, filtered and evaporated in vacuo to yield 1-(methoxycarbonyl)-2-(3,4,5-trifluoro-benzyl)piperidine-4-carboxylic acid (3.42 g, 89%) as a light brown foam. MS m/z 330 (M−H)$^-$ Reference Compound 61

2-(3,5-Di-tert-butylbenzyl)-1-(methoxycarbonyl) piperidine-4-carboxylic acid

Step 1: (3,5-Di-tert-butylbenzyl)zinc(II) bromide

In a dried flask was zinc powder (2.493 g, 38.13 mmol) suspended in anhydrous tetrahydrofuran (23 mL) under nitrogen. The resulting suspension was warmed to 60° C., then 1,2-dibromoethane (0.137 mL, 1.59 mmol) was added and stirred at that temperature for 15 min. It was cooled to room temperature, then chlorotrimethylsilane (0.161 mL, 1.27 mmol) was added and stirred at room temperature for 45 min. Then, 1-(bromomethyl)-3,5-di-tert-butylbenzene (9 g, 31.77 mmol) dissolved in anhydrous tetrahydrofuran (23.00 mL) was added over 10 min. Stirring continued at room temperature for 16 h, then stirring was switched off to let the solids settle. The supernatant was used in the next transformation.

Step 2: Methyl 2-(3,5-di-tert-butylbenzyl)isonicotinate

To a solution of methyl 2-chloroisonicotinate (4 g, 23.31 mmol) and Pd(PPh$_3$)$_4$ (0.539 g, 0.47 mmol) in tetrahydrofuran (120 mL) under nitrogen in a dried flask was added a freshly prepared solution of (3,5-di-tert-butylbenzyl)zinc(II) bromide (11.08 g, 31.78 mmol) in tetrahydrofuran (46 mL). The resulting bright yellow solution was heated to 60° C. for 35 min, then stirred at room temperature for 1 h. The reaction was quenched by addition of methanol (50 mL). The solution was diluted with EtOAc and washed with NH$_4$Cl. The organic layer was dried over MgSO$_4$, filtered and evaporated to yield a brown oil. The crude was redissolved in MTBE (180 mL) and solids were filtered off. Hydrogen chloride (4 M in dioxane, 6.42 mL, 25.66 mmol) was added dropwise during stirring and a suspension was formed. The suspension was stirred at room temperature for 10 min. The solid was collected by filtration and washed with MTBE. Redissolved in MTBE/satd NaHCO$_3$. The phases were separated, the organic phase dried over Na$_2$SO$_4$, filtered and evaporated to yield methyl 2-(3,5-di-tert-butylbenzyl)isonicotinate (7.132 g, 90%) as a brown oil. $^1$H NMR (600 MHz, cdcl$_3$) δ 1.28 (s, 18H), 3.89 (s, 3H), 4.19 (s, 2H), 7.11 (d, 2H), 7.27 (t, 1H), 7.64 (dd, 1H), 7.71 (s, 1H), 8.68 (d, 1H). MS m/z 340 (M+H)$^+$ Step 3: Methyl 2-(3,5-di-tert-butylbenzyl)piperidine-4-carboxylate Methyl 2-(3,5-di-tert-butylbenzyl)isonicotinate (3.538 g, 10.42 mmol) was dissolved in acetic acid (30 mL) and platinum(IV) oxide (0.118 g, 0.52 mmol) added. The resulting mixture was hydrogenated in a Büchi hydrogenator at room temperature and 5 bar for 5 h 45 min. The catalyst was filtered off and washed with MeOH and the eluate evaporated. DCM and 10% K$_2$CO$_3$ were added and the phases separated. The organic layer was washed with brine, passed through a phase separator and evaporated to yield crude methyl 2-(3,5-di-tert-butylbenzyl)piperidine-4-carboxylate (3.80 g, 106%) as a beige oil. MS m/z 346 (M+H)$^+$ Step 4: Dimethyl 2-(3,5-di-tert-butylbenzyl)piperidine-1,4-dicarboxylate Methyl 2-(3,5-di-tert-butylbenzyl)piperidine-4-carboxylate (3.691 g, 10.68 mmol) was dissolved in DCM (80 mL) and DIPEA (2.233 mL, 12.82 mmol) added followed by methyl carbonochloridate (1.262 mL, 16.02 mmol). The solution was stirred at room temperature for 1.5 h. The reaction mixture was washed with 0.1 M HCl and satd NaHCO$_3$. The organic phase was passed through a phase separator and evaporated to yield dimethyl 2-(3,5-di-tert-butylbenzyl)piperidine-1,4-dicarboxylate (3.91 g, 91%) as a yellow oil. MS m/z 404 (M+H)$^+$

Step 5: 2-(3,5-Di-tert-butylbenzyl)-1-(methoxycarbonyl)piperidine-4-carboxylic acid Dimethyl 2-(3,5-di-tert-butylbenzyl)piperidine-1,4-dicarboxylate (3.886 g, 9.63 mmol) was dissolved in acetonitrile (40 mL) and water (0.8 mL), then lithium bromide (6.69 g, 77.04 mmol) and triethylamine (5.34 mL, 38.52 mmol) were added and the resulting yellow suspension was heated at reflux. After 5 h water (100 mL) and MTBE (250 mL) were added. The organic phase was extracted with water (×2). The pooled aqueous layer was acidified to pH 1 with 3.8 M HCl and then extracted with MTBE (×3). The combined organic layer was washed with water, dried $Na_2SO_4$, filtered and evaporated to yield 2-(3,5-di-tert-butylbenzyl)-1-(methoxycarbonyl)piperidine-4-carboxylic acid (3.723 g, 99%) as a yellow gum. MS m/z 390 (M+H)$^+$

Reference Compound 62

2-Benzyl-2,3,4,5,6-$d_5$-1-(methoxycarbonyl)piperidine-4-carboxylic acid

Step 1: Benzyl-2,3,4,5,6-$d_5$ zinc(II) bromide

In a dried flask was zinc powder (2.4 g, 36.70 mmol) suspended in anhydrous tetrahydrofuran (40 mL) under nitrogen. The resulting suspension was warmed to 60° C., then 1,2-dibromoethane (0.125 mL, 1.45 mmol) was added and stirred at that temperature for 20 min. It was cooled to room temperature, then chlorotrimethylsilane (0.15 mL, 1.18 mmol) was added and stirred at room temperature for 30 min. Then, benzyl-2,3,4,5,6-$d_5$ bromide (5 g, 28.40 mmol) (99.2% deuterated) was added in portions over 30 min, then stirring was continued at room temperature for 18 h. Stirring was switched off to let the precipitate settle. The supernatant was used in the next transformation.

Step 2: Methyl 2-benzyl-2,3,4,5,6-$d_5$ isonicotinate

To a solution of methyl 2-chloroisonicotinate (3.95 g, 23 mmol) and Pd(PPh$_3$)$_4$ (0.532 g, 0.46 mmol) in tetrahydrofuran (40 mL) under nitrogen in a dried flask was added freshly prepared benzyl-2,3,4,5,6-$d_5$ zinc(II) bromide (6.86 g, 28.4 mmol) in tetrahydrofuran (50 mL). The resulting bright yellow mixture was heated to 60° C. for 2 h. After cooling to room temperature, the reaction was quenched by the addition of 10% NH$_4$Cl. It was diluted with ethyl acetate. After phase separation, the organic layer was washed with brine, dried over MgSO$_4$ and evaporated. The residue was suspended in MTBE (50 mL) and sonicated, the yellow insolubles were filtered off and washed with MTBE. The volume of the filtrate was increased to ca. 150 mL, then 5 mL MeOH was added, followed by hydrogen chloride (5.75 mL, 23.00 mmol) (4M in dioxane). A colorless precipitate formed. The mixture was stirred for 10 min, sonicated for 5 min, then the solids were collected and washed with MTBE. The solid was transferred with MeOH into a separation funnel and was diluted with MTBE. Then 10% Na$_2$CO$_3$ was added and vigorously shaken. After phase separation, the organic layer was washed with brine, dried over MgSO$_4$ and evaporated. Methyl 2-benzyl-2,3,4,5,6-$d_5$ isonicotinate (4.78 g, 89%) was isolated as a pale yellow oil. $^1$H NMR (400 MHz, cdcl$_3$) δ 3.92 (s, 3H), 4.23 (s, 2H), 7.65-7.71 (m, 2H), 8.66-8.74 (m, 1H). MS m/z 233 (M+H)$^+$

Step 3: Methyl 2-benzyl-2,3,4,5,6-$d_5$ piperidine-4-carboxylate

Methyl 2-benzyl-2,3,4,5,6-$d_5$ isonicotinate (4.69 g, 20.19 mmol) was dissolved in acetic acid (3 mL) and platinum(IV) oxide (0.364 g, 1.60 mmol) was added. The resulting mixture was hydrogenated in a Büchi hydrogenator at 4 bar for 4 h. The reaction mixture was filtered through a diatomous earth filter carton, washed with methanol and the solvents evaporated. The residue was dissolved in MTBE and washed with satd NaHCO$_3$. Before phase separation, the aqueous phase was adjusted to pH 9 by addition of 10% K$_2$CO$_3$. The organic phase was dried over MgSO$_4$ and evaporated to yield methyl 2-benzyl-2,3,4,5,6-$d_5$ piperidine-4-carboxylate (4.6 g, 96%) as a yellow oil. MS m/z 239 (M+H)$^+$

Step 4: Dimethyl 2-benzyl-2,3,4,5,6-$d_5$ piperidine-1,4-dicarboxylate

To a solution of methyl 2-benzyl-2,3,4,5,6-$d_5$ piperidine-4-carboxylate (4.6 g, 19.30 mmol) and DIPEA (5 mL, 28.71 mmol) in DCM (75 mL) was added methyl carbonochloridate (1.8 mL, 22.86 mmol) dropwise. Stirring continued at room temperature for 45 min, then solvents evaporated. Residue partitioned between MTBE and 1 N HCl. Organic layer washed with brine and satd NaHCO$_3$, then dried over MgSO$_4$ and evaporated to yield dimethyl 2-benzyl-2,3,4,5,6-$d_5$ piperidine-1,4-dicarboxylate (5.55 g, 97%) as a pale yellow oil. MS m/z 297 (M+H)$^+$

Step 5: 2-Benzyl-2,3,4,5,6-$d_5$-1-(methoxycarbonyl) piperidine-4-carb oxylic acid Dimethyl 2-benzyl-2,3,4,5,6-$d_5$ piperidine-1,4-dicarboxylate (5.55 g, 18.73 mmol) was dissolved in acetonitrile (60 mL) and water (1.2 mL), then lithium bromide (13.01 g, 149.81 mmol) and triethylamine (10.38 mL, 74.91 mmol) were added. The resulting yellow suspension was heated under reflux. After 2 h 10 min the reaction mixture was cooled to room temperature, then water and MTBE were added. The organic phase was extracted with water twice. The pooled aqueous layers were adjusted to pH 1 with 3.8 M HCl and then extracted with DCM (3×). The combined organic layers were dried over MgSO$_4$ and evaporated to yield 2-benzyl-2,3,4,5,6-$d_5$-1-(methoxycarbonyl)piperidine-4-carboxylic acid (5.16 g, 98%) as an off-white solid. MS m/z 283 (M+H)$^+$

PREPARATION OF COMPOUND EXAMPLES

Formation of 5-isoxazol-3-ones

Example 1

5-((2S,4S)-2-Benzylpiperidin-4-yl)isoxazol-3(2H)-one

Step 1: Trans-methyl 2-benzyl-4-(3-ethoxy-3-oxopropanoyl)piperidine-1-carboxylate and cis-methyl 2-benzyl-4-(3-ethoxy-3-oxopropanoyl)piperidine-1-carboxylate A suspension of magnesium chloride (3.11 g, 32.66 mmol) and ethyl potassium malonate (8.34 g, 48.99 mmol) in dry THF (70 mL) was stirred under nitrogen atmosphere at 50° C. for 4 h (flask 1). In another flask was added carbonyldiimidazole (6.35 g, 39.19 mmol) portionwise to a suspension of 2-benzyl-1-(methoxycarbonyl)piperidine-4-carboxylic acid (9.057 g, 32.66 mmol) (reference compound 1) in dry THF (70 mL) at 5° C. under nitrogen atmosphere. This reaction mixture was stirred for 1 h at 5° C. (flask 2). The contents of flask 2 was then added dropwise to flask 1 and the resulting mixture was stirred for 24 h. The reaction mixture was concentrated and the residue was partitioned between EtOAc and H$_2$O. The aqueous phase was extracted once with EtOAc and the combined organic phases were washed with H$_2$O, satd Na$_2$CO$_3$ and then dried over Na$_2$SO$_4$ and evaporated to give 11.02 g oil. Purification using automated column chromatography (Biotage) (2 runs—340 g column, grad 10-60% EtOAc/heptane) yielded trans-methyl 2-benzyl-4-(3-ethoxy-3-oxopropanoyl)piperidine-1-carboxylate (6.35 g): $^1$H NMR (600 MHz, cdcl$_3$) δ 1.27 (m, 3H), 1.41-1.66 (m, 3H), 1.70-2.11 (m, 2H), 2.53-3.10 (m, 4H), 3.55 (d, 4H), 4.19 (dd, 3H), 4.42-4.99 (m, 1H), 7.08-7.37 (m, 5H); MS m/z 348 (M+H)$^+$ and cis-methyl 2-benzyl-4-(3-ethoxy-3-oxopropanoyl)piperidine-1-carboxylate (2.15 g): $^1$H NMR (600 MHz, cdcl$_3$) δ 1.25 (m, 3H), 1.61-1.96 (m, 4H), 2.64-2.79 (m, 2H), 2.80-3.10 (m, 2H), 3.44 (s, 2H), 3.63 (s, 3H), 3.84-4.00 (m, 1H), 4.03-4.25 (m, 3H), 7.15-7.42 (m, 5H); MS m/z 348 (M+H)$^+$.

Step 2: Trans-methyl 2-benzyl-4-(3-oxo-2,3-dihydroisoxazol-5-yl)piperidine-1-carboxylate A solution of trans-methyl 2-benzyl-4-(3-ethoxy-3-oxopropanoyl)piperidine-1-carboxylate (6.35 g, 18.3 mmol) in MeOH (2 mL) was added to a solution of NaOH (0.77 g, 19.4 mmol) in MeOH/H$_2$O (15 mL/0.9 mL) at −30° C. After 10 minutes was added a solution of hydroxylamine hydrochloride (2.54 g, 36.6 mmol) and NaOH (1.46 g, 36.6 mmol) in MeOH (18 mL) and H$_2$O (18 mL). Stirring was continued at −30° C. for 30 minutes. The reaction mixture was then poured into concentrated HCl (20 mL) held at 80° C. The solution was stirred for 30 minutes. The organic solvent was evaporated and the aqueous phase extracted with DEE (×3). The organic phase was dried over Na$_2$SO$_4$ and evaporated to give a solid, 3.68 g, which was purified by preparative HPLC on a Kromasil C8 column (10 µm 250×20 ID mm) using a gradient of 20-70% acetonitrile in H$_2$O/MeCN/FA 95/5/0.2 buffer, over 18 minutes with a flow of 19 mL/minutes. Trans-methyl-2-benzyl-4-(3-oxo-2,3-dihydroisoxazol-5-yl)piperidine-1-carboxylate (2.54 g, 54.6%) was isolated as a solid. $^1$H NMR (600 MHz, cdcl$_3$) δ 1.50-2.21 (m, 4H), 2.91 (m, 2H), 3.10 (m, 2H), 3.58 (d, 3H), 4.04-4.41 (m, 1H), 4.43-4.82 (m, 1H), 5.55-5.84 (m, 1H), 7.15-7.30 (m, 5H); MS m/z 317 (M+H)$^+$.

Step 3: (2S,4S)-Methyl 2-benzyl-4-(3-oxo-2,3-dihydroisoxazol-5-yl)piperidine-1-carboxylate Racemic trans-methyl 2-benzyl-4-(3-oxo-2,3-dihydroisoxazol-5-yl)piperidine-1-carboxylate (2.54 g, 8.04 mmol) was subjected to chiral separation using Chiralcel IA, mobile phase heptane/EtOH/FA 80/20/0.4/0.1, which resulted in (2S,4S)-methyl 2-benzyl-4-(3-oxo-2,3-dihydroisoxazol-5-yl)piperidine-1-carboxylate (0.99 g).

Step 4: 5-((2S,4S)-2-Benzylpiperidin-4-yl)isoxazol-3(2H)-one

To (2S,4S)-methyl 2-benzyl-4-(3-oxo-2,3-dihydroisoxazol-5-yl)piperidine-1-carboxylate (0.99 g) was added HBr (33% in HOAc, 20 mL) and the solution was stirred for 8 h. The volatiles were concentrated and the residues purified by preparative HPLC on a XBridge C18 column (10 µm 250×50 ID mm) using a gradient of 0-40% acetonitrile in H$_2$O/MeCN/NH$_3$ 95/5/0.2 buffer over 15 minutes with a flow of 100 mL/minutes. The title compound was isolated (0.62 g, 30%). $^1$H NMR (600 MHz, dmso) δ 1.47 (m, 1H), 1.67-1.83 (m, 3H), 2.51-2.67 (m, 3H), 2.74-2.89 (m, 2H), 3.04-3.15 (m, 1H), 5.67 (s, 1H), 7.21 (m, 5H); [α]$^{20}_D$ +47.0 (MeOH/H$_2$O 1:1, c=1); HRMS Calculated for [C$_{15}$H$_{19}$N$_2$O$_2$]+: 259.1447. Found: 259.1449.

Example 2

5-((2R,4R)-2-Benzylpiperidin-4-yl)isoxazol-3(2H)-one

Step 1: (2R,4R)-Methyl 2-benzyl-4-(3-oxo-2,3-dihydroisoxazol-5-yl)piperidine-1-carboxylate The title compound was obtained in the preparation of Example 1, Step 3 (0.93 g).

Step 2: 5-((2R,4R)-2-Benzylpiperidin-4-yl)isoxazol-3(2H)-one

Following the same procedure as described in Example 1, Step 4 using ((2R,4R)-methyl 2-benzyl-4-(3-oxo-2,3-dihydroisoxazol-5-yl)piperidine-1-carboxylate the title compound (0.55 g, 27%) was obtained. [α]$^{20}_D$ −43.0 (MeOH/H$_2$O 1:1, c=1); HRMS Calculated for [C$_{15}$H$_{19}$N$_2$O$_2$]+: 259.1447. found: 259.1449.

Example 3

5-((2R,4S)-2-Benzylpiperidin-4-yl)isoxazol-3(2H)-one

Step 1: Cis-methyl 2-benzyl-4-(3-oxo-2,3-dihydroisoxazol-5-yl)piperidine-1-carboxylate A solution of cis-methyl 2-benzyl-4-(3-ethoxy-3-oxopropanoyl)piperidine-1-carboxylate (2.15 g, 6.18 mmol) (from Example 1, Step 1) in MeOH (0.75 mL) was added to a solution of NaOH (0.26 g, 6.55 mmol) in MeOH/H$_2$O (5 mL/0.3 mL) at −30° C. After 10 minutes was added a solution of hydroxylamine hydrochloride (0.86 g, 12.4 mmol) and NaOH (0.49 g, 12.4 mmol) in MeOH (6.1 mL) and H$_2$O (6.1 mL). Stirring was continued at −30° C. for 30 minutes. The reaction mixture was then poured into concentrated HCl (7 mL) held at 80° C. The solution was stirred for 30 minutes. The organic solvent was evaporated and the aqueous phase extracted with ether (×3). The combined organic phases were dried over Na$_2$SO$_4$, and evaporated to yield a solid, 2.2 g. The compound was purified by preparative HPLC on a Kromasil C8 column (10 µm 250×20 ID mm) using a gradient of 20-70% acetonitrile in H$_2$O/MeCN/FA 95/5/0.2 buffer, over 18 minutes with a flow of 19 mL/minutes. The title compound was isolated (1.1 g, 57%). $^1$H NMR (600 MHz, cdcl$_3$) δ 1.76-2.15 (m, 4H), 2.63 (m, 1H), 2.82 (m, 1H), 2.87-3.03 (m, 1H), 3.03-3.22 (m, 1H), 3.61 (s, 3H), 3.99 (m, 1H), 4.19-4.33 (m, 1H), 5.71 (s, 1H), 7.01-7.37 (m, 5H). MS m/z 317 (M+H)$^+$.

Step 2: (2R,4S)-Methyl 2-benzyl-4-(3-oxo-2,3-dihydroisoxazol-5-yl)piperidine-1-carboxylate Racemic cis-methyl 2-benzyl-4-(3-oxo-2,3-dihydroisoxazol-5-yl)piperidine-1-carboxylate (1.1 g) was subjected to chiral separation using Chiralcel OD, mobile phase heptane/EtOH/FA 90/10/0.1 at 40° C. which resulted in (2R,4S)-methyl 2-benzyl-4-(3-oxo-2,3-dihydroisoxazol-5-yl)piperidine-1-carboxylate (0.47 g).

Step 3: 5-((2R,4S)-2-Benzylpiperidin-4-yl)isoxazol-3(2H)-one

To (2R,4S)-methyl 2-benzyl-4-(3-oxo-2,3-dihydroisoxazol-5-yl)piperidine-1-carboxylate (0.47 g) was added HBr (33% in HOAc, 10 mL) and the solution was stirred for 16 h. The volatiles were concentrated and the residue purified by preparative HPLC on a XBridge C18 column (10 µm 250×50 ID mm) using a gradient of 0-40% acetonitrile in $H_2O$/MeCN/$NH_3$ 95/5/0.2 buffer over 15 minutes with a flow of 100 mL/minutes. The title compound was isolated (0.26 g, 29%): $^1$H NMR (600 MHz, dmso) δ 1.07 (m, 1H), 1.26-1.45 (m, 1H), 1.75 (m, 2H), 2.53 (m, 2H), 2.58-2.67 (m, 2H), 2.69 (m, 1H), 2.97 (m, 1H), 5.66 (s, 1H), 7.08-7.34 (m, 5H); $[α]^{20}_D$ +67.8 (MeOH/$H_2O$ 1:1, c=1); HRMS Calculated for $[C_{15}H_{19}N_2O_2]$+: 259.1447. found: 259.1442.

Example 4

5-((2S,4R)-2-Benzylpiperidin-4-yl)isoxazol-3(2H)-one

Step 1: (2S,4R)-Methyl 2-benzyl-4-(3-oxo-2,3-dihydroisoxazol-5-yl)piperidine-1-carboxylate The title compound was obtained in Example 3, Step 2 (0.47 g).

Step 2: 5-((2S,4R)-2-Benzylpiperidin-4-yl)isoxazol-3(2H)-one

Following the same procedure as described in Example 3, Step 3 using (2S,4R)-methyl 2-benzyl-4-(3-oxo-2,3-dihydroisoxazol-5-yl)piperidine-1-carboxylate yielded the title compound (0.23 g, 26%); HRMS Calculated for $[C_{15}H_{19}N_2O_2]$+: 259.1447. found: 259.1433.

Example 5

5-((2R,4S)-2-Isobutylpiperidin-4-yl)isoxazol-3(2H)-one

Step 1: Trans-methyl 2-isobutyl-4-(3-ethoxy-3-oxopropanoyl)piperidine-1-carboxylate and cis-methyl 2-isobutyl-4-(3-ethoxy-3-oxopropanoyl)piperidine-1-carboxylate The compounds were prepared as described in Example 1, Step 1 starting from crude 2-isobutyl-1-(methoxycarbonyl)piperidine-4-carboxylic acid (2.28 g, 9.4 mmol) (Reference Compound 2), magnesium chloride (0.95 g, 9.95 mmol), ethyl potassium malonate (2.5 g, 14.9 mmol) and carbonyldiimidazole (1.98 g, 12.2 mmol) which resulted in trans-methyl 2-isobutyl-4-(3-ethoxy-3-oxopropanoyl)piperidine-1-carboxylate (1.60 g, 54%). Trans isomer: $^1$H NMR (500 MHz, cdcl$_3$) δ 0.91 (m, 6H), 1.29 (t, 3H), 1.42-1.98 (m, 6H), 2.48-2.84 (m, 3H), 3.48 (s, 2H), 3.70 (s, 3H), 3.98-4.28 (m, 3H), 4.30-4-60 (m, 1H); MS m/z 314 (M+H)+ and cis-methyl 2-isobutyl-4-(3-ethoxy-3-oxopropanoyl)piperidine-1-carboxylate (0.59 g, 20%). Cis isomer: $^1$H NMR (500 MHz, cdcl$_3$) δ 0.80 (d, 3H), 0.83 (d, 3H), 1.09 (m, 1H), 1.20 (t, 3H), 1.31-1.54 (m, 2H), 1.60 (m, 1H), 1.69-1.86 (m, 2H), 1.98 (m, 1H), 2.56-2.68 (m, 1H), 2.91-3.04 (m, 1H), 3.44 (s, 2H), 3.60 (s, 3H), 3.78 (m, 1H), 4.00-4.17 (m, 3H); MS m/z 314 (M+H)+.

Step 2: Trans-methyl 2-isobutyl-4-(3-oxo-2,3-dihydroisoxazol-5-yl)piperidine-1-carboxylate The compound was prepared as described in Example 1, Step 2 starting from trans-methyl 2-isobutyl-4-(3-ethoxy-3-oxopropanoyl)piperidine-1-carboxylate (1.60 g, 5.0 mmol) which yielded the product (1.02 g, 71%): $^1$H NMR (500 MHz, cdcl$_3$) δ 0.95 (m, 6H), 1.32 (m, 1H), 1.54 (s, 2H), 1.71 (m, 2H), 1.84-2.05 (m, 2H), 3.04 (m, 2H), 3.72 (s, 3H), 4.23 (s, 1H), 4.44 (s, 1H), 5.65 (s, 1H); MS m/z 283 (M+H)+.

Step 3: Trans-5-(2-isobutylpiperidin-4-yl)isoxazol-3(2H)-one

Racemic trans-methyl 2-isobutyl-4-(3-oxo-2,3-dihydroisoxazol-5-yl)piperidine-1-carboxylate (0.39 g, 1.3 mmol) was stirred in HBr (33% in HOAc) for 16 h. The volatiles were concentrated and the residue purified by preparative HPLC on a XBridge C18 column (10 µm 250×50 ID mm) using a gradient of 0-25% acetonitrile in $H_2O$/MeCN/$NH_3$ 95/5/0.2 buffer over 10 minutes with a flow of 100 mL/minutes. The title compound (0.26 g) was isolated. $^1$H NMR (600 MHz, d$_2$o) δ 0.76 (d, 3H), 0.79 (d, 3H), 1.14 (m, 1H), 1.33-1.41 (m, 1H), 1.45 (m, 1H), 1.59 (m, 1H), 1.76 (m, 1H), 1.98 (m, 1H), 2.06 (m, 1H), 2.21 (m, 1H), 3.04 (m, 2H), 3.14-3.31 (m, 4H), 5.67 (s, 1H).

Step 4: 5-((2R,4S)-2-Isobutylpiperidin-4-yl)isoxazol-3(2H)-one

A racemic mixture of trans-5-(2-isobutylpiperidin-4-yl)isoxazol-3(2H)-one was subjected to chiral separation using Chiralcel IC, mobile phase heptane/EtOH/FA/TEA 60/40/0.4/0.2 which resulted in the title compound (117 mg, 40%). $[α]^{20}_D$ +21.1 ($H_2O$, c=1); HRMS Calculated for $[C_{12}H_{21}N_2O_2]$+: 225.1603. found: 225.1599.

Example 6

5-((2S,4R)-2-Isobutylpiperidin-4-yl)isoxazol-3(2H)-one

The titled compound was obtained from Example 5, Step 4 (113 mg, 39%). HRMS Calculated for $[C_{12}H_{21}N_2O_2]$+: 225.1603. found: 225.1596.

Example 7

5-((2S,4S)-2-Isobutylpiperidin-4-yl)isoxazol-3(2H)-one

Step 1: Cis-methyl 2-isobutyl-4-(3-oxo-2,3-dihydroisoxazol-5-yl)piperidine-1-carboxylate The compound was prepared as described in Example 5, Step 2 starting from cis-methyl 2-isobutyl-4-(3-ethoxy-3-oxopropanoyl)piperidine-1-carboxylate obtained in Example 5, Step 1 (0.59 g, 1.9 mmol) which resulted in the title compound (0.29 g, 51%). $^1$H NMR (600 MHz, cdcl$_3$) δ 0.85 (2 d, 6H), 1.15 (m, 1H), 1.29-1.40 (m, 1H), 1.50 (m, 1H), 1.82-1.93 (m, 2H), 2.04 (m, 2H), 2.91-3.05 (m, 1H), 3.06-3.20 (m, 1H), 3.69 (s, 3H), 3.93 (m, 1H), 4.17 (m, 1H), 5.70 (s, 1H). MS m/z 283 (M+H)+.

Step 2: Cis-5-(2-isobutylpiperidin-4-yl)isoxazol-3(2H)-one

Racemic cis-methyl 2-isobutyl-4-(3-oxo-2,3-dihydroisoxazol-5-yl)piperidine-1-carboxylate (0.29 g, 1.03 mmol) was stirred in HBr (12 mL, 33% in HOAc) for 24 h. The volatiles were concentrated and the residue purified by preparative HPLC on a XBridge C18 column (10 μm 250×50 ID mm) using a gradient of 0-25% acetonitrile in H$_2$O/MeCN/NH$_3$ 95/5/0.2 buffer over 10 minutes with a flow of 100 mL/min. The title compound (160 mg) was isolated. $^1$H NMR (600 MHz, d$_2$o) δ 0.79 (2 d, 6H), 1.34-1.51 (m, 3H), 1.54-1.72 (m, 2H), 2.13 (m, 1H), 2.25 (m, 1H), 2.99 (m, 2H), 3.21 (m, 1H), 3.38 (m, 1H), 5.61 (s, 1H).

Step 3: 5-((2S,4S)-2-Isobutylpiperidin-4-yl)isoxazol-3(2H)-one

A racemic mixture of cis-5-(2-isobutylpiperidin-4-yl)isoxazol-3(2H)-one was subjected to chiral separation using Chiralpak IC, mobile phase heptane/EtOH/FA/TEA 60/40/0.4/0.2 which resulted in the title compound (85 mg, 37%). [α]$^{20}_D$ +19.5 (H$_2$O, c=1); HRMS Calculated for [C$_{12}$H$_{21}$N$_2$O$_2$]+: 225.1603. found: 225.1593

Example 8

5-((2R,4S)-2-Phenethylpiperidin-4-yl)isoxazol-3(2H)-one

Step 1: Trans-methyl 4-(3-ethoxy-3-oxopropanoyl)-2-phenethylpiperidine-1-carboxylate and cis-methyl 4-(3-ethoxy-3-oxopropanoyl)-2-phenethylpiperidine-1-carboxylate The compounds were prepared as described in Example 1, Step 1 starting from crude 1-(methoxycarbonyl)-2-phenethylpiperidine-4-carboxylic acid (5.7 g, 19.6 mmol) (Reference Compound 3), magnesium chloride (1.86 g, 19.6 mmol), ethyl potassium malonate (4.99 g, 29.3 mmol) and carbonyldiimidazole (3.81 g, 23.5 mmol) which resulted in trans-methyl 4-(3-ethoxy-3-oxopropanoyl)-2-phenethylpiperidine-1-carboxylate (2.56 g, 36%) and cis-methyl 4-(3-ethoxy-3-oxopropanoyl)-2-phenethylpiperidine-1-carboxylate (0.29 g, 4%). Trans isomer: $^1$H NMR (600 MHz, cdcl$_3$) δ 1.28 (m, 3H), 1.49 (m, 1H), 1.60-1.93 (m, 4H), 2.01 (m, 1H), 2.57 (m, 2H), 2.84 (m, 2H), 3.42 (m, 2H), 3.69 (s, 3H), 4.00-4.63 (m, 4H), 7.08-7.41 (m, 5H). MS m/z 362 (M+H)$^+$. Cis isomer: $^1$H NMR (600 MHz, cdcl$_3$) δ 1.25 (t, 3H), 1.63-1.82 (m, 3H), 1.91 (m, 3H), 2.00-2.12 (m, 1H), 2.53-2.66 (m, 2H), 2.71 (m, 1H), 3.09 (m, 1H), 3.49 (s, 2H), 3.69 (s, 3H), 3.89 (m, 1H), 4.08 (m, 1H), 4.17 (q, 2H), 7.15-7.31 (m, 5H). MS m/z 362 (M+H)$^+$.

Step 2: Trans-methyl 4-(3-oxo-2,3-dihydroisoxazol-5-yl)-2-phenethylpiperidine-1-carboxylate The compounds were prepared as described in Example 1, Step 2 starting from trans-methyl 4-(3-ethoxy-3-oxopropanoyl)-2-phenethylpiperidine-1-carboxylate (2.53 g, 7.0 mmol) which resulted in the title compound (1.35 g, 58%). $^1$H NMR (600 MHz, cdcl$_3$) δ 1.55 (m, 1H), 1.79 (m, 2H), 2.03 (m, 3H), 2.58 (m, 2H), 3.01 (m, 2H), 3.70 (s, 3H), 4.01-4.60 (m 2H), 5.62 (s, 1H), 7.05-7.40 (m, 5H). MS m/z 331 (M+H)$^+$.

Step 3: (2R,4S)-Methyl 4-(3-oxo-2,3-dihydroisoxazol-5-yl)-2-phenethylpiperidine-1-carboxylate As described in Example 1, Step 3, racemic trans-methyl 4-(3-oxo-2,3-dihydroisoxazol-5-yl)-2-phenethylpiperidine-1-carboxylate (1.35 g, 4.09 mmol) was subjected to chiral separation using Chiralpak AD, mobile phase heptane/EtOH/TEA 80/20 at 30° C. which resulted in (2R,4S)-methyl 4-(3-oxo-2,3-dihydroisoxazol-5-yl)-2-phenethylpiperidine-1-carboxylate (0.53 g, 1.6 mmol)

Step 4: 5-((2R,4S)-2-Phenethylpiperidin-4-yl)isoxazol-3(2H)-one

Starting from (2R,4S)-methyl 4-(3-oxo-2,3-dihydroisoxazol-5-yl)-2-phenethylpiperidine-1-carboxylate (0.53 g) and following the procedure in Example 1, Step 4 the title compound was obtained (0.30 g, 28%). $^1$H NMR (600 MHz, dmso) δ 1.47 (m, 1H), 1.55 (m, 1H), 1.62 (m, 1H), 1.70 (m, 2H), 1.86 (m, 1H), 2.58 (m, 4H), 2.76 (m, 1H), 3.06 (m, 1H), 5.70 (s, 1H), 7.15-7.32 (m, 5H). [α]$^{20}_D$ +24.6 (MeOH/H$_2$O 1:1, c=1); HRMS calculated for [C$_{16}$H$_{21}$N$_2$O$_2$]+: 273.1603. found: 273.1598.

Example 9

5-((2S,4R)-2-Phenethylpiperidin-4-yl)isoxazol-3(2H)-one

Step 1: (2S,4R)-Methyl 4-(3-oxo-2,3-dihydroisoxazol-5-yl)-2-phenethylpiperidine-1-carboxylate The title compound was obtained from the preparation in Example 8, Step 3 (0.62 g, 1.87 mmol).

Step 2: 5-((2S,4R)-2-Phenethylpiperidin-4-yl)isoxazol-3(2H)-one

Following the same procedure as described in Example 8, step 4 and starting from (2S,4R)-methyl 4-(3-oxo-2,3-dihydroisoxazol-5-yl)-2-phenethylpiperidine-1-carboxylate yielded the title compound (0.62 g, 24%): [α]$^{20}_D$ −23.0 (MeOH/H$_2$O 1:1, c=1); HRMS calculated for [C$_{16}$H$_{21}$N$_2$O$_2$]+: 273.1603. found: 273.1592.

Example 10

5-((2S,4S)-2-Phenethylpiperidin-4-yl)isoxazol-3(2H)-one

Step 1: Cis-methyl 4-(3-oxo-2,3-dihydroisoxazol-5-yl)-2-phenethylpiperidine-1-carboxylate The compound was prepared as described in Example 1, Step 2 starting from cis-methyl 4-(3-ethoxy-3-oxopropanoyl)-2-phenethylpiperidine-1-carboxylate from Example 8, Step 1 (0.29 g, 0.82 mmol) resulting in the title compound (0.07 g, 26%). $^1$H NMR (600 MHz, cdcl$_3$) δ 1.65 (m, 1H), 1.79-2.14 (m, 5H), 2.60 (m, 2H), 3.00 (m, 1H), 3.20 (m, 1H), 3.70 (s, 3H), 3.92 (m, 1H), 4.10 (m, 1H), 5.71 (s, 1H), 7.10-7.29 (m, 5H); MS m/z 331 (M+H)$^+$.

Step 2: (2S,4S)-Methyl 4-(3-oxo-2,3-dihydroisoxazol-5-yl)-2-phenethylpiperidine-1-carboxylate Following the procedure described in Example 1, Step 3, racemic cis-methyl 4-(3-oxo-2,3-dihydroisoxazol-5-yl)-2-phenethylpiperidine-1-carboxylate (0.07 g, 0.22 mmol) was subjected to chiral separation using Chiralcel IC, mobile phase heptane/IPA 80/20 at 40° C. which resulted in (2S,4S)-methyl 4-(3-oxo-2,3-dihydroisoxazol-5-yl)-2-phenethylpiperidine-1-carboxylate (0.032 g, 0.1 mmol) and (2R,4R)-methyl 4-(3-oxo-2,3-dihydroisoxazol-5-yl)-2-phenethylpiperidine-1-carboxylate (0.03 g, 0.09 mmol).

Step 3: 5-((2S,4S)-2-Phenethylpiperidin-4-yl)isoxazol-3(2H)-one

Starting from (2S,4S)-methyl 4-(3-oxo-2,3-dihydroisoxazol-5-yl)-2-phenethylpiperidine-1-carboxylate (0.032 g) and following the procedure described in Example 1, Step 4 could the title compound be obtained (12.6 mg, 21%): $^1$H NMR (400 MHz, dmso) δ 1.15 (m, 1H), 1.38 (m, 1H), 1.60 (m, 2H), 1.79 (m, 1H), 1.95 (m, 1H), 2.45-2.75 (m, 5H), 3.05 (m, 1H), 5.77 (s, 1H), 7.15-7.30 (m, 5H). $[\alpha]^{20}_D$ +54.1 (MeOH/H$_2$O 1:1, c=1); HRMS calculated for $[C_{16}H_{21}N_2O_2]$+: 273.1603. found: 273.1601.

Example 11

5-((2S,4S)-2-(4-tert-Butylbenzyl)piperidin-4-yl)isoxazol-3(2H)-one

Step 1: Trans-methyl 2-(4-tert-butylbenzyl)-4-(3-ethoxy-3-oxopropanoyl)piperidine-1-carboxylate and cis-methyl 2-(4-tert-butylbenzyl)-4-(3-ethoxy-3-oxopropanoyl)piperidine-1-carboxylate The compounds were prepared as described in Example 1, Step 1 starting from crude 2-(4-tert-butylbenzyl)-1-(methoxycarbonyl)piperidine-4-carboxylic acid (3.07 g, 9.2 mmol) (Reference Compound 4), magnesium chloride (0.88 g, 9.2 mmol) and ethyl potassium malonate (2.35 g, 13.8 mmol) and subsequently carbonyldiimidazole (1.98 g, 12.2 mmol) which resulted in trans-methyl 2-(4-tert-butylbenzyl)-4-(3-ethoxy-3-oxopropanoyl)piperidine-1-carboxylate (0.55 g, 15%) and cis-methyl 2-(4-tert-butylbenzyl)-4-(3-ethoxy-3-oxopropanoyl)piperidine-1-carboxylate (1.65 g, 44%). Trans isomer: $^1$H NMR (600 MHz, cdcl$_3$) δ 1.08-1.32 (m, 12H), 1.32-1.78 (m, 4H), 2.53-3.06 (m, 4H), 3.30-3.62 (m, 5H), 3.93-4.61 (m, 4H), 7.03-7.36 (m, 4H); MS m/z 404 (M+H)+. Cis isomer: $^1$H NMR (600 MHz, cdcl$_3$) δ 1.21-1.35 (m, 12H), 1.59-1.79 (m, 1H), 1.79-1.99 (m, 3H), 2.69 (m, 2H), 2.84-2.94 (m, 1H), 2.94-3.07 (m, 1H), 3.45 (s, 2H), 3.61 (m, 3H), 3.92 (m, 1H), 4.08-4.22 (m, 3H), 7.09 (m, 2H), 7.25-7.32 (m, 2H); MS m/z 404 (M+H)+.

Step 2: Trans-methyl 2-(4-tert-butylbenzyl)-4-(3-oxo-2,3-dihydroisoxazol-5-yl)piperidine-1-carboxylate The compound was prepared as described in Example 1, Step 2 starting from trans-methyl 2-(4-tert-butylbenzyl)-4-(3-ethoxy-3-oxopropanoyl)piperidine-1-carboxylate (0.54 g, 1.34 mmol) which resulted in trans-methyl 2-(4-tert-butylbenzyl)-4-(3-oxo-2,3-dihydroisoxazol-5-yl)piperidine-1-carboxylate (0.24 g, 48%); $^1$H NMR (600 MHz, cdcl$_3$) δ 1.29 (s, 9H), 1.41-1.60 (m, 2H), 1.89-2.09 (m, 2H), 2.87 (m, 2H), 3.03-3.20 (m, 2H), 3.42-3.73 (m, 3H), 4.06-4.32 (m, 1H), 4.45-4.77 (m, 1H), 5.63 (s, 1H), 7.02-7.17 (m, 2H), 7.31 (m, 2H); MS m/z 373 (M+H)+.

Step 3: (2S,4S)-Methyl 2-(4-tert-butylbenzyl)-4-(3-oxo-2,3-dihydroisoxazol-5-yl)piperidine-1-carboxylate Following the procedure described in Example 1, Step 3, racemic trans-methyl 2-(4-tert-butylbenzyl)-4-(3-oxo-2,3-dihydroisoxazol-5-yl)piperidine-1-carboxylate (0.24 g, 0.64 mmol) was subjected to chiral separation using Chiralcel AD, mobile phase heptane/EtOH/FA 80/20/0.1 which resulted in (2S,4S)-methyl 2-(4-tert-butylbenzyl)-4-(3-oxo-2,3-dihydroisoxazol-5-yl)piperidine-1-carboxylate (0.106 g, 0.28 mmol).

Step 4: 5-((2S,4S)-2-(4-tert-Butylbenzyl)piperidin-4-yl)isoxazol-3(2H)-one

Starting from (2S,4S)-methyl 2-(4-tert-butylbenzyl)-4-(3-oxo-2,3-dihydroisoxazol-5-yl)piperidine-1-carboxylate (0.106 g, 0.28 mmol) and following the procedure described in Example 1, Step 4 the title compound (50.3 mg, 25%) was obtained: $^1$H NMR (600 MHz, cdcl$_3$) δ 1.29 (s, 9H), 1.43-1.74 (m, 1H), 1.81-2.07 (m, 3H), 2.60 (m, 3H), 2.82 (m, 2H), 3.11 (m, 1H), 5.71 (s, 1H), 7.08 (d, 2H), 7.27 (d, 2H); $[\alpha]^{20}_D$ +56.7 (MeOH/H$_2$O 1:1, c=1); HRMS calculated for $[C_{19}H_{27}N_2O_2]$+: 315.2072. found: 315.2069.

Example 12

5-((2R,4S)-2-(4-tert-Butylbenzyl)piperidin-4-yl)isoxazol-3(2H)-one

Step 1: Cis-methyl 2-(4-tert-butylbenzyl)-4-(3-oxo-2,3-dihydroisoxazol-5-yl)piperidine-1-carboxylate The compounds were prepared as described in Example 1, Step 2 by starting from cis-methyl 2-(4-tert-butylbenzyl)-4-(3-ethoxy-3-oxopropanoyl)piperidine-1-carboxylate (1.64 g, 4.06 mmol) that resulted in cis-methyl 2-(4-tert-butylbenzyl)-4-(3-oxo-2,3-dihydroisoxazol-5-yl)-piperidine-1-carboxylate (0.69 g, 47%). $^1$H NMR (500 MHz, cdcl$_3$) δ 1.31 (s, 9H), 1.84-1.93 (m, 2H), 1.96 (m, 1H), 2.10 (m, 1H), 2.62 (m, 1H), 2.82 (m, 2H), 2.97 (m, 1H), 3.08-3.24 (m, 1H), 3.62 (s, 3H), 4.02 (m, 1H), 4.18-4.34 (m, 1H), 5.73 (s, 1H), 7.06 (m, 2H), 7.23-7.38 (m, 2H). MS m/z 373 (M+H)+.

Step 2: (2R,4S)-Methyl 2-(4-tert-butylbenzyl)-4-(3-oxo-2,3-dihydroisoxazol-5-yl)piperidine-1-carboxylate Following the procedure described in Example 1, Step 3, racemic cis-methyl 2-(4-tert-butylbenzyl)-4-(3-oxo-2,3-dihydroisoxazol-5-yl)piperidine-1-carboxylate (0.69 g, 1.85 mmol) was subjected to chiral separation using Chiralcel AD, mobile phase heptane/EtOH/FA 80/20/0.1 which resulted in (2R,4S)-methyl 2-(4-tert-butylbenzyl)-4-(3-oxo-2,3-dihydroisoxazol-5-yl)piperidine-1-carboxylate (0.32 g, 0.86 mmol).

Step 3: 5-((2R,4S)-2-(4-tert-Butylbenzyl)piperidin-4-yl)isoxazol-3(2H)-one

Using (2R,4S)-methyl 2-(4-tert-butylbenzyl)-4-(3-oxo-2,3-dihydroisoxazol-5-yl)piperidine-1-carboxylate (0.32 g, 0.86 mmol) and following the procedure described in Example 1, Step 4 the title compound could be obtained (0.125 g, 22%). $^1$H NMR (600 MHz, dmso) δ 1.05 (m, 1H), 1.23 (m, 9H), 1.34 (m, 1H), 1.74 (m, 2H), 2.50-2.80 (m, 5H), 2.96 (m, 1H), 5.63 (s, 1H), 7.08 (m, 2H), 7.27 (m, 2H). $[\alpha]^{20}_D$ −7.5 (CHCl$_3$ c=0.2). HRMS calculated for $[C_{19}H_{27}N_2O_2]$+: 315.2072. found: 315.2058.

Example 13

5-((2S,4S)-2-Neopentylpiperidin-4-yl)isoxazol-3(2H)-one

Step 1: Trans-methyl 4-(3-ethoxy-3-oxopropanoyl)-2-neopentylpiperidine-1-carboxylate The compound was prepared as described in Example 1, Step 1 starting from crude 1-(methoxycarbonyl)-2-neopentylpiperidine-4-carboxylic acid (4.95 g, 19.2 mmol) (Reference Compound 5), magnesium chloride (2.381 g, 25.01 mmol), ethyl potassium malonate (5.57 g, 32.70 mmol) and carbonyldiimidazole (3.74 g, 23.08 mmol) which resulted in cis-methyl 4-(3-ethoxy-3-oxopropanoyl)-2-neopentylpiperidine-1-carboxylate (2.40 g, 38%) and trans-methyl 4-(3-ethoxy-3-oxopropanoyl)-2-neopentylpiperidine-1-carboxylate (1.2 g, 19%). Cis-isomer: $^1$H NMR (400 MHz, cdcl$_3$) δ 0.93 (m, 9H), 1.18 (m, 1H), 1.28 (t, 3H), 1.52-1.65 (m, 1H), 1.65-1.83 (m, 2H), 1.89 (m, 1H), 2.12 (m, 1H), 2.69 (m, 1H), 3.11 (m, 1H), 3.52 (s, 2H), 3.69 (s, 3H), 3.87 (m, 1H), 4.15-4.24 (m, 2H), 4.27 (m, 1H); MS m/z 328 (M+H)$^+$.

Step 2: Trans-methyl 2-neopentyl-4-(3-oxo-2,3-dihydroisoxazol-5-yl)piperidine-1-carboxylate The compounds were prepared as described in Example 1, Step 2 starting from trans-methyl 4-(3-ethoxy-3-oxopropanoyl)-2-neopentylpiperidine-1-carboxylate (4.49 g, 13.7 mmol) that resulted in trans-methyl 2-neopentyl-4-(3-oxo-2,3-dihydroisoxazol-5-yl)piperidine-1-carboxylate (1.26 g, 31%). $^1$H NMR (600 MHz, cdcl$_3$) δ 0.94 (s, 9H), 1.34 (m, 1H), 1.40-1.62 (m, 1H), 1.71 (m, 2H), 1.83 (m, 1H), 1.97 (m, 1H), 3.05 (m, 2H), 3.70 (s, 3H), 4.01-4.31 (m, 1H), 4.44-4.74 (m, 1H), 5.62 (s, 1H). MS m/z 297 (M+H)$^+$.

Step 3: (2S,4S)-Methyl 2-neopentyl-4-(3-oxo-2,3-dihydroisoxazol-5-yl)piperidine-1-carboxylate Following the procedure described in Example 1, Step 3, racemic trans-methyl 2-neopentyl-4-(3-oxo-2,3-dihydroisoxazol-5-yl)piperidine-1-carboxylate (1.26 g, 4.26 mmol) was subjected to chiral separation using Chiralcel OD, mobile phase heptane/IPA/FA 80/20/0.1 which resulted in (2S,4S)-methyl 2-neopentyl-4-(3-oxo-2,3-dihydroisoxazol-5-yl)piperidine-1-carboxylate (0.64 g, 2.16 mmol)

Step-4: (2S,4S)-5-(2-Neopentylpiperidin-4-yl)isoxazol-3(2H)-one

Starting from (2S,4S)-methyl 2-neopentyl-4-(3-oxo-2,3-dihydroisoxazol-5-yl)piperidine-1-carboxylate (0.64 g, 2.16 mmol) and following the procedure described in Example 1, Step 4 the title compound (0.44 g, 85%) was obtained: $^1$H NMR (600 MHz, dmso) δ 0.86 (s, 9H), 1.17 (dd, 1H), 1.27 (dd, 1H), 1.45 (m, 1H), 1.68 (m, 2H), 1.81 (m, 1H), 2.59 (m, 1H), 2.67 (m, 1H), 2.73 (m, 1H), 3.04 (m, 2H), 5.71 (s, 1H); [α]$^{20}_D$ +18.4 (MeOH/H$_2$O 1:1, c=1); HRMS calculated for [C$_{13}$H$_{23}$N$_2$O$_2$]+: 239.1759. found: 239.1742.

Example 14

5-((2R,4S)-2-Neopentylpiperidin-4-yl)isoxazol-3(2H)-one

Step 1: Cis-methyl 2-neopentyl-4-(3-oxo-2,3-dihydroisoxazol-5-yl)piperidine-1-carboxylate The compound was prepared as described in Example 1, Step 2 starting from cis-methyl 4-(3-ethoxy-3-oxopropanoyl)-2-neopentylpiperidine-1-carboxylate (2.68 g, 8.19 mmol) which resulted in cis-methyl 2-neopentyl-4-(3-oxo-2,3-dihydroisoxazol-5-yl)piperidine-1-carboxylate (1.60 g, 66%): 1H NMR (400 MHz, cdcl3) δ 0.89 (s, 9H), 1.18 (dd, 1H), 1.45 (dd, 1H), 1.80-1.92 (m, 2H), 1.97-2.17 (m, 2H), 2.94-3.02 (m, 1H), 3.11-3.23 (m, 1H), 3.71 (s, 3H), 3.88-3.99 (m, 1H), 4.22-4.32 (m, 1H), 5.72 (s, 1H); m/z (MH$^+$) 297.

Step 2: (2R,4S)-Methyl 2-neopentyl-4-(3-oxo-2,3-dihydroisoxazol-5-yl)piperidine-1-carboxylate Following the procedure described in Example 1, Step 3, racemic cis-methyl 2-neopentyl-4-(3-oxo-2,3-dihydroisoxazol-5-yl)piperidine-1-carboxylate (1.60 g, 5.4 mmol) was subjected to chiral separation using Chiralcel IC mobile phase heptane/IPA/FA 60/40/0.1 which resulted in (2R,4S)-methyl 2-neopentyl-4-(3-oxo-2,3-dihydroisoxazol-5-yl)piperidine-1-carboxylate (0.8 g, 2.7 mmol).

Step 3: 5-((2R,4S)-2-Neopentylpiperidin-4-yl)isoxazol-3(2H)-one

Starting from (2R,4S)-methyl 2-neopentyl-4-(3-oxo-2,3-dihydroisoxazol-5-yl)piperidine-1-carboxylate (0.8 g, 2.7 mmol) and following the procedure described in Example 1, Step 4 the title compound was obtained (0.44 g, 69%): $^1$H NMR (600 MHz, DMSO-d6) δ 0.89 (s, 9H), 1.18 (m, 2H), 1.50 (m, 2H), 1.82-1.90 (m, 2H), 2.70-2.85 (m, 3H), 3.08 (m, 1H), 5.71 (s, 1H). [α]$^{20}_D$ +43.8 (MeOH/H$_2$O 1:1, c=1); HRMS calculated for [C$_{13}$H$_{23}$N$_2$O$_2$]+: 239.1759. found: 239.1753.

Example 15

5-((2R,4S)-2-Methylpiperidin-4-yl)isoxazol-3(2H)-one

Step 1: Trans-methyl 4-(3-ethoxy-3-oxopropanoyl)-2-methylpiperidine-1-carboxylate and cis-methyl 4-(3-ethoxy-3-oxopropanoyl)-2-methylpiperidine-1-carboxylate The compounds were prepared as described in Example 1, Step 1 starting from crude 1-(methoxycarbonyl)-2-methylpiperidine-4-carboxylic acid (0.90 g, 4.47 mmol) (Reference Compound 6), magnesium chloride (0.42 g, 4.47 mmol) and ethyl potassium malonate (1.14 g, 6.71 mmol) and subsequently carbonyldiimidazole (0.87 g, 5.47 mmol) which resulted in trans-methyl 4-(3-ethoxy-3-oxopropanoyl)-2-methylpiperidine-1-carboxylate (0.31 g, 26%) and cis-methyl 4-(3-ethoxy-3-oxopropanoyl)-2-methylpiperidine-1-carboxylate (0.50 g, 41%). Trans isomer: $^1$H NMR (600 MHz, cdcl$_3$) δ 1.18 (dd, 3H), 1.23-1.31 (m, 3H), 1.47 (m, 1H), 1.65-1.78 (m, 2H), 1.85 (m, 1H), 2.82 (m, 1H), 2.91 (m, 1H), 3.48 (s, 2H), 3.68 (s, 3H), 3.99-4.14 (m, 1H), 4.15-4.23 (m, 2H), 4.57 (m, 1H). Cis isomer: $^1$H NMR (600 MHz, cdcl$_3$) δ 1.13 (d, 3H), 1.22-1.32 (m, 3H), 1.63-1.73 (m, 1H), 1.78-1.94 (m, 2H), 1.95-2.07 (m, 1H), 2.67-2.76 (m, 1H), 3.04-3.16 (m, 1H), 3.50 (s, 2H), 3.68 (s, 3H), 3.79-3.91 (m, 1H), 4.12 (m, 1H), 4.15 (m, 2H).

Step 2: Trans-methyl 2-methyl-4-(3-oxo-2,3-dihydroisoxazol-5-yl)piperidine-1-carboxylate The compound was prepared as described in Example 1, Step 2 starting from trans-methyl 4-(3-ethoxy-3-oxopropanoyl)-2-methylpiperidine-1-carboxylate (0.31 g, 1.15 mmol) which resulted in trans methyl 2-methyl-4-(3-oxo-2,3-dihydroisoxazol-5-yl)piperidine-1-carboxylate (0.149 g, 54%); $^1$H NMR (600 MHz, cdcl$_3$) δ 1.21 (m, 3H), 1.49-1.59 (m, 1H), 1.76 (m, 1H), 1.86 (m, 1H), 1.99 (m, 1H), 3.02 (m, 2H), 3.69 (m, 3H), 4.13 (m, 1H), 4.59 (m, 1H), 5.64 (s, 1H). MS m/z 241 (M+H)$^+$.

Step 3: (2R,4S)-Methyl 2-methyl-4-(3-oxo-2,3-dihydroisoxazol-5-yl)piperidine-1-carboxylate Following the procedure described in Example 1, Step 3, racemic trans methyl 2-methyl-4-(3-oxo-2,3-dihydroisoxazol-5-yl)piperidine-1-carboxylate (0.149 g, 0.62 mmol) was subjected to chiral separation using Chiralcel OJ, mobile phase heptane/EtOH 80/20 at 22° C. which resulted in (2R,4S)-methyl 2-methyl-4-(3-oxo-2,3-dihydroisoxazol-5-yl)piperidine-1-carboxylate (0.051 g, 0.21 mmol).

Step 4: 5-((2R,4S)-2-Methylpiperidin-4-yl)isoxazol-3(2H)-one

Starting from (2R,4S)-methyl 2-methyl-4-(3-oxo-2,3-dihydroisoxazol-5-yl)piperidine-1-carboxylate (0.051 g, 0.21 mmol) and following the procedure described in Example 1, Step 4 the title compound was obtained (32 mg, 84%). $^1$H NMR (600 MHz, cd3od) δ 1.31 (d, 3H), 1.79-1.89 (m, 1H), 2.02-2.25 (m, 3H), 3.04-3.13 (m, 1H), 3.26 (d, 2H), 3.38 (m, 1H), 5.66 (s, 1H); [α]$^{20}_D$ +8.4 (MeOH/H$_2$O 1:1, c=1)

Example 16

5-((2S,4R)-2-Methylpiperidin-4-yl)isoxazol-3(2H)-one

Step-1: (2S,4R)-Methyl 2-methyl-4-(3-oxo-2,3-dihydroisoxazol-5-yl)piperidine-1-carboxylate The title compound was obtained from Example 15, Step 3 (62 mg, 0.26 mmol).

Step 2: 5-((2S,4R)-2-Methylpiperidin-4-yl)isoxazol-3(2H)-one

Using the same procedure as described in Example 1, Step 4 and starting from (2S,4R)-methyl 2-methyl-4-(3-oxo-2,3-dihydroisoxazol-5-yl)piperidine-1-carboxylate (62 mg, 0.26 mmol) the title compound was obtained (30 mg, 64%).

Example 17

5-((2S,4S)-2-Methylpiperidin-4-yl)isoxazol-3(2H)-one

Step 1: Cis-methyl 2-methyl-4-(3-oxo-2,3-dihydroisoxazol-5-yl)piperidine-1-carboxylate The compound was prepared as described in Example 1, Step 2 starting from cis-methyl 4-(3-ethoxy-3-oxopropanoyl)-2-methylpiperidine-1-carboxylate (0.49 g, 1.83 mmol), which resulted in cis-methyl 2-methyl-4-(3-oxo-2,3-dihydroisoxazol-5-yl)piperidine-1-carboxylate (0.23 g, 52%); $^1$H NMR (600 MHz, cdcl$_3$) δ 1.08 (d, 3H), 1.86 (m, 2H), 2.05 (m, 2H), 2.96-3.02 (m, 1H), 3.12-3.30 (m, 1H), 3.69 (s, 3H), 3.83-3.99 (m, 1H), 4.19 (m, 1H), 5.70 (s, 1H); MS m/z 241 (M+H)$^+$.

Step 2: (2S,4S)-Methyl 2-methyl-4-(3-oxo-2,3-dihydroisoxazol-5-yl)piperidine-1-carboxylate Following the procedure described in Example 1, Step 3, racemic cis-methyl 2-methyl-4-(3-oxo-2,3-dihydroisoxazol-5-yl)piperidine-1-carboxylate (0.23 g, 0.96 mmol) was subjected to chiral separation using Chiralcel IC, mobile phase heptane/IPA 70/30 which resulted in (2S,4S)-methyl 2-methyl-4-(3-oxo-2,3-dihydroisoxazol-5-yl)piperidine-1-carboxylate (0.101 g, 0.42 mmol).

Step 3: 5-((2S,4S)-2-Methylpiperidin-4-yl)isoxazol-3(2H)-one

Starting from (2S,4S)-methyl 2-methyl-4-(3-oxo-2,3-dihydroisoxazol-5-yl)piperidine-1-carboxylate (0.101 g, 0.42 mmol) and following the procedure described in Example 1, Step 4 the title compound was obtained (0.046 g, 60%) $^1$H NMR (600 MHz, cd3od) δ 1.32-1.44 (d, 3H), 1.65 (m, 1H), 1.84 (m, 1H), 2.24 (m, 2H), 3.08-3.23 (m, 2H), 3.34-3.52 (m, 2H), 5.82 (s, 1H); [α]$^{20}_D$ +0 (MeOH/H$_2$O 1:1, c=1).

Example 18

5-((2S,4S)-2-(2-Methyl-2-phenylpropyl)piperidin-4-yl)isoxazol-3(2H)-one

Step 1: Trans-methyl 4-(3-ethoxy-3-oxopropanoyl)-2-(2-methyl-2-phenylpropyl)piperidine-1-carboxylate and cis-methyl 4-(3-ethoxy-3-oxopropanoyl)-2-(2-methyl-2-phenylpropyl)-piperidine-1-carboxylate The compounds were prepared as described in Example 1, Step 1 starting from crude 1-(methoxycarbonyl)-2-(2-methyl-2-phenylpropyl)piperidine-4-carboxylic acid (7.24 g, 22.7 mmol) (Reference compound 7), magnesium chloride (2.16 g, 22.7 mmol) and ethyl potassium malonate (5.79 g, 34 mmol) and subsequently carbonyldiimidazole (4.41 g, 27.2 mmol) which gave trans-methyl 4-(3-ethoxy-3-oxopropanoyl)-2-(2-methyl-2-phenylpropyl)piperidine-1-carboxylate (1.59 g, 18%) and cis-methyl 4-(3-ethoxy-3-oxopropanoyl)-2-(2-methyl-2-phenylpropyl)piperidine-1-carboxylate (2.38 g, 27%). Trans isomer: $^1$H NMR (600 MHz, cdcl$_3$) δ 1.20-1.50 (m, 10H), 1.59-1.84 (m, 2H), 1.90 (m, 2H), 2.50-2.89 (m, 2H), 3.16 (m, 2H), 3.58 (m, 4H), 4.17 (m, 4H), 7.06-7.51 (m, 5H). Cis isomer: $^1$H NMR (600 MHz, cdcl$_3$) δ 1.20-1.41 (m, 10H), 1.57-1.74 (m, 3H), 1.79 (d, 1H), 2.03 (m, 1H), 2.53 (m, 1H), 2.83-3.02 (m, 1H), 3.40 (m, 2H), 3.48-3.68 (m, 4H), 4.03 (m, 1H), 4.12-4.22 (m, 2H), 7.18-7.44 (m, 5H).

Step 2: Trans-methyl 2-(2-methyl-2-phenylpropyl)-4-(3-oxo-2,3-dihydroisoxazol-5-yl)-piperidine-1-carboxylate The compound was prepared as described in Example 1, Step 2 starting from trans-methyl 4-(3-ethoxy-3-oxopropanoyl)-2-(2-methyl-2-phenylpropyl)piperidine-1-carboxylate (1.58 g, 4.06 mmol) which resulted in trans-methyl 2-(2-methyl-2-phenylpropyl)-4-(3-oxo-2,3-dihydroisoxazol-5-yl)piperidine-1-carboxylate (0.82 g, 56%); $^1$H NMR (600 MHz, cdcl3) δ 1.29-1.65 (m, 6H), 1.67-1.98 (m, 4H), 2.10 (m, 2H), 2.88 (m, 2H), 3.57 (s, 3H), 3.70-4.18 (m, 1H), 4.18-4.67 (m, 1H), 5.45 (s, 1H), 7.17-7.31 (m, 5H); MS m/z 359 (M+H)$^+$.

Step 3: (2S,4S)-methyl 2-(2-methyl-2-phenylpropyl)-4-(3-oxo-2,3-dihydroisoxazol-5-yl)-piperidine-1-carboxylate Racemic trans-methyl 2-(2-methyl-2-phenylpropyl)-4-(3-oxo-2,3-dihydroisoxazol-5-yl)-piperidine-1-carboxylate (0.82 g, 2.28 mmol) was subjected to chiral separation using Chiralcel IC, mobile phase heptane/IPA 80/20 at 40° C. which resulted in (2S,4S)-methyl 2-(2-methyl-2-phenylpropyl)-4-(3-oxo-2,3-dihydroisoxazol-5-yl)piperidine-1-carboxylate (0.361 g, 1.01 mmol).

Step 4: 5-((2S,4S)-2-(2-methyl-2-phenylpropyl)piperidin-4-yl)isoxazol-3(2H)-one Starting from (2S,4S)-methyl 2-(2-methyl-2-phenylpropyl)-4-(3-oxo-2,3-dihydroisoxazol-5-yl)piperidine-1-carboxylate (0.361 g, 1.01 mmol) and following the procedure described in Example 1, Step 4 the title compound was obtained (0.21 g, 69%) $^1$H NMR (600 MHz, dmso) δ 1.24 (m, 7H), 1.45 (m, 1H), 1.59 (m, 2H), 1.69 (m, 2H), 2.42 (m, 1H), 2.59 (m, 2H), 2.87 (m, 1H), 5.36 (s, 1H), 7.12 (m, 1H), 7.21-7.36 (m, 4H); $[α]^{20}_D$ +66.7 (MeOH/H$_2$O 1:1, c=1); HRMS Calculated for $[C_{18}H_{25}N_2O_2]$+: 301.1916. found: 301.1888.

Example 19

5-((2R,4S)-2-(2-Methyl-2-phenylpropyl)piperidin-4-yl)isoxazol-3(2H)-one

Step 1: Cis-methyl 2-(2-methyl-2-phenylpropyl)-4-(3-oxo-2,3-dihydroisoxazol-5-yl)-piperidine-1-carboxylate The compound was prepared as described in Example 1, Step 2 starting from cis-methyl 4-(3-ethoxy-3-oxopropanoyl)-2-(2-methyl-2-phenylpropyl)piperidine-1-carboxylate (2.38 g, 6.11 mmol) which resulted in cis-methyl 2-(2-methyl-2-phenylpropyl)-4-(3-oxo-2,3-dihydroisoxazol-5-yl)piperidine-1-carboxylate (0.93 g, 42%); $^1$H NMR (500 MHz, cdcl3) δ 1.31 (s, 3H), 1.37 (s, 3H), 1.53-1.67 (m, 2H), 1.77 (m, 2H), 1.90-2.01 (m, 2H), 2.80-2.91 (m, 1H), 2.95-3.06 (m, 1H), 3.60 (s, 3H), 3.69 (m, 1H), 4.01-4.15 (m, 1H), 5.63 (s, 1H), 7.17 (m, 1H), 7.30 (m, 4H); MS m/z 359 (M+H)+.

Step 2: (2R,4S)-Methyl 2-(2-methyl-2-phenylpropyl)-4-(3-oxo-2,3-dihydroisoxazol-5-yl)piperidine-1-carboxylate Racemic cis-methyl 2-(2-methyl-2-phenylpropyl)-4-(3-oxo-2,3-dihydroisoxazol-5-yl)-piperidine-1-carboxylate (0.93 g, 2.59 mmol) was subjected to chiral separation using Chiralcel IC, mobile phase heptane/IPA 80/20 at the temperature 40° C. which resulted in (2R,4S)-methyl 2-(2-methyl-2-phenylpropyl)-4-(3-oxo-2,3-dihydroisoxazol-5-yl)piperidine-1-carboxylate (0.432 g, 1.21 mmol).

Step 3: 5-((2R,4S)-2-(2-Methyl-2-phenylpropyl)piperidin-4-yl)isoxazol-3(2H)-one Starting from (2R,4S)-methyl 2-(2-methyl-2-phenylpropyl)-4-(3-oxo-2,3-dihydroisoxazol-5-yl)-piperidine-1-carboxylate (0.432 g, 1.21 mmol) and following the procedure described in Example 1, Step 4 the title compound was obtained (0.16 g, 43%); $^1$H NMR (600 MHz, dmso) δ 1.08 (m, 1H), 1.28 (s, 3H), 1.34 (m, 4H), 1.46 (m, 1H), 1.76-1.83 (m, 1H), 1.83-1.97 (m, 2H), 2.73 (m, 1H), 2.86 (m, 1H), 2.97 (m, 1H), 3.17 (m, 1H), 5.46 (s, 1H), 7.16 (m, 1H), 7.28 (m, 2H), 7.35 (m, 2H); $[α]^{20}_D$ +57.9 (MeOH/H$_2$O 1:1, c=1); HRMS Calculated for $[C_{18}H_{25}N_2O_2]$+: 301.1916. found: 301.1892.

Example 20

5-((2R,4S)-2-(Cyclohexylmethyl)piperidin-4-yl)isoxazol-3(2H)-one

Step 1: Methyl 2-(cyclohexylmethyl)-4-(3-ethoxy-3-oxopropanoyl)piperidine-1-carboxylate Ethyl potassium malonate (1.75 g, 10.3 mmol) and MgCl$_2$ (0.665 g, 6.88 mmol) were added to dry THF (50 mL). The reaction flask was stirred vigorously 4 h at 50° C. (flask 1). 2-(Cyclohexylmethyl)-1-(methoxycarbonyl)piperidine-4-carboxylic acid (1.95 g, 6.88 mmol) (Reference Compound 8) and carbonyldiimidazole (1.34 g, 8.26 mmol) were added to dry THF (50 mL) at 5° C. (flask 2). The contents of flask 2 was added to flask 1 at room temperature. The reaction mixture was evaporated to remove most of the THF. The crude was partitioned between water and diethyl ether. The organic phase was isolated, dried with MgSO$_4$, filtered through Celite® and the solvent was evaporated. The residue was purified by automated column chromatography using the Biotage equipment. Gradient eluation using ethylacetate-heptane, started 15-85 and ended 40-60 which gave trans-methyl 2-(cyclohexylmethyl)-4-(3-ethoxy-3-oxopropanoyl)piperidine-1-carboxylate (0.38 g, 16%) and cis-methyl 2-(cyclohexylmethyl)-4-(3-ethoxy-3-oxopropanoyl)piperidine-1-carboxylate (1.28 g, 53%). Trans-isomer: $^1$H NMR (600 MHz, cdcl$_3$) δ 0.88 (d, 2H), 0.99-1.32 (m, 8H), 1.38-1.56 (m, 2H), 1.68 (dd, 8H), 2.80 (t, 2H), 3.45 (s, 2H), 3.66 (s, 3H), 3.93-4.21 (m, 3H), 4.47 (d, 1H). Cis-isomer $^1$H NMR (600 MHz, cdcl$_3$) δ 0.72-0.95 (m, 2H), 1.04-1.31 (m, 8H), 1.38-1.49 (m, 1H), 1.53-1.69 (m, 6H), 1.70-1.92 (m, 3H), 2.02 (dt, 1H), 2.61-2.71 (m, 1H), 2.95-3.07 (m, 1H), 3.48 (s, 2H), 3.66 (s, 3H), 3.85 (dd, 1H), 4.09-4.21 (m, 3H).

Step 2: (2R,4S)-Methyl 2-(cyclohexylmethyl)-4-(3-oxo-2,3-dihydroisoxazol-5-yl)piperidine-1-carboxylate A solution of methyl 2-(cyclohexylmethyl)-4-(3-ethoxy-3-oxopropanoyl)piperidine-1-carboxylate (1.5 g, 4.2 mmol) in MeOH (4 mL) was added to a solution of NaOH (221 mg, 5.5 mmol) in MeOH/H$_2$O (4 mL/0.25 mL) at −30° C. After 10 minutes was added hydroxylamine-HCl (0.59 g, 8.5 mmol) and NaOH (0.339 g, 8.5 mmol) in MeOH (5 mL) and H$_2$O (5 mL). Stirring was continued at −30° C. for 30 minutes. The reaction solution was poured into 6M HCl (6 mL) at 80° C. and heated for 30 minutes. The reaction mixture was partitioned between water and ethyl acetate. The organic phase was isolated, dried with Na$_2$SO$_4$, filtered through Celite® and the solvent was evaporated. Crude 1.7 g. Purification using reversed phase chromatography, which gave 0.3 g, yield 22%. Chiral separation using Chiralcel OJ, mobile phase heptane/ethanol 80/20 at 40° C. gave of (2R,4S)-methyl 2-(cyclohexylmethyl)-4-(3-oxo-2,3-dihydroisoxazol-5-yl)piperidine-1-carboxylate (0.11 g). $^1$H NMR (600 MHz, cdcl$_3$) δ 0.91 (d, 2H), 1.06-1.39 (m, 5H), 1.68 (dt, 7H), 1.85 (s, 2H), 1.94 (s, 1H), 2.99 (t, 2H), 3.68 (s, 3H), 4.11 (d, 1H), 4.50 (d, 1H), 5.60 (s, 1H). $[α]^{20}_D$ +3.2 (MeCN, c=1).

Step 3: 5-((2R,4S)-2-(Cyclohexylmethyl)piperidin-4-yl)isoxazol-3(2H)-one

HBr (33% in acetic acid) (7 mL) was added to a reaction flask containing (2R,4S)-methyl 2-(cyclohexylmethyl)-4-(3-oxo-2,3-dihydroisoxazol-5-yl)piperidine-1-carboxylate (0.11 g, 0.34 mmol). The reaction was stirred vigorously overnight. The solvent was evaporated. Purification using preparative HPLC (pH=11, small column, sample dissolved in methanol/water (50/50), gradient 0-40, 20 minutes) gave the title compound (62 mg, yield 69%). $^1$H NMR (600 MHz, cd$_3$od) δ 0.94 (s, 2H), 1.18 (s, 1H), 1.27 (s, 2H), 1.35-1.55 (m, 3H), 1.57-1.80 (m, 6H), 2.01 (s, 1H), 2.13 (s, 1H), 2.24 (s, 1H), 3.09 (s, 1H), 3.22 (s, 3H), 5.53 (s, 1H).

Example 21

5-((2R,4R)-2-(Cyclohexylmethyl)piperidin-4-yl)isoxazol-3(2H)-one

Step 1: (2R,4R)-Methyl 2-(cyclohexylmethyl)-4-(3-oxo-2,3-dihydroisoxazol-5-yl)piperidine-1-carboxylate and (2S,4S)-Methyl 2-(cyclohexylmethyl)-4-(3-oxo-2,3-dihydroisoxazol-5-yl)-piperidine-1-carboxylate A solution of cis-methyl 2-(cyclohexylmethyl)-4-(3-ethoxy-3-oxopropanoyl)piperidine-1-carboxylate, from a preparation of Example 20, Step 1 (1.28 g, 3.62 mmol) in MeOH (3 mL) was added dropwise to a solution of NaOH (0.159 g) in MeOH/H$_2$O (3 mL/0.2 mL) at −30° C. After stirring for 10 minutes a solution of hydroxylamine hydrochloride (0.50 g, 7.24 mmol) and NaOH (0.29 g, 7.24 mmol) in methanol/water (5 mL/5 mL) was added at −30° C. Stirring was continued for 30 minutes at −30° C. The solution was added dropwise to HCl (6M) at 80° C. Stirred 30 minutes at 80° C. The reaction mixture was partitioned between water and ethyl acetate. The organic phase was isolated, dried with Na$_2$SO$_4$, filtered through Celite® and the solvent was evaporated. Acidic reversed phase chromatography, gradient 35% to 75% acetonitrile gave cis-methyl 2-(cyclohexylmethyl)-4-(3-oxo-2,3-dihydroisoxazol-5-yl)piperidine-1-carboxylate (0.62 g, 53.1%). Chiral separation using Chiralpac IC, mobile phase heptane/isopropyl alcohol 80/20 at the temperature 40° C. gave (2R,4R)-methyl 2-(cyclohexylmethyl)-4-(3-oxo-2,3-dihydroisoxazol-5-yl)piperidine-1-carboxylate (0.28 g), e.e. 98.5% and (2S,4S)-methyl 2-(cyclohexylmethyl)-4-(3-oxo-2,3-dihydroisoxazol-5-yl)piperidine-1-carboxylate (0.27 g), e.e 98.5%. $^1$H NMR (600 MHz, cdcl$_3$, RR) δ 0.67-0.88 (m, 2H), 0.98-1.20 (m, 5H), 1.28 (dd, 1H), 1.56 (dd, 5H), 1.75-1.86 (m, 2H), 1.92-2.06 (m, 2H), 2.87-2.99 (m, 1H), 3.02-3.15 (m, 1H), 3.65 (s, 3H), 3.88 (dd, 1H), 4.15 (p, 1H), 5.65 (d, 1H). [α]$^{20}_D$ −30.7 (MeCN, c=1); $^1$H NMR (600 MHz, cdcl$_3$, SS) δ 0.70-0.87 (m, 2H), 0.97-1.20 (m, 5H), 1.28 (dd, 1H), 1.51-1.65 (m, 5H), 1.77-1.85 (m, 2H), 1.96-2.05 (m, 2H), 2.87-2.96 (m, 1H), 3.03-3.14 (m, 1H), 3.65 (s, 3H), 3.88 (dd, 1H), 4.15 (p, 1H), 5.65 (d, 1H) [α]$^{20}_D$ +29.9 (MeCN, c=1).

Step 2: 5-((2R,4R)-2-(Cyclohexylmethyl)piperidin-4-yl)isoxazol-3(2H)-one

HBr (33% in acetic acid) (5 mL) was added to (2R,4R)-methyl 2-(cyclohexylmethyl)-4-(3-oxo-2,3-dihydroisoxazol-5-yl)piperidine-1-carboxylate (0.28 g, 0.87 mmol). The reaction was stirred vigorously overnight. The solvent was evaporated. Purification using PrepLC (pH=11, small column, no sandwitching, sample dissolved in methanol/water (50/50), gradient 15-55, 20 minutes). The title compound (57 mg, 25%) was obtained. $^1$H NMR (400 MHz, cd$_3$od) δ 0.78-0.95 (m, 2H), 1.17 (dd, 3H), 1.28-1.48 (m, 4H), 1.63 (dd, 6H), 2.04 (d, 1H), 2.12 (d, 1H), 2.85 (t, 1H), 2.96 (dd, 1H), 3.13 (s, 1H), 3.31 (d, 1H), 5.40 (s, 1H).

Example 22

5-((2S,4S)-2-(Cyclohexylmethyl)piperidin-4-yl)isoxazol-3(2H)-one

HBr (33% in acetic acid) (5 mL) was added to (2S,4S)-methyl 2-(cyclohexylmethyl)-4-(3-oxo-2,3-dihydroisoxazol-5-yl)piperidine-1-carboxylate, from a preparation of example 21, step 1 (0.27 g, 0.85 mmol). The reaction was stirred vigorously overnight. The solvent was evaporated. Purification using PrepLC (pH=11, small column, sample dissolved in acetonitrile/water (40/60), gradient 15-55, 20 minutes) gave the title compound (75 mg, 33%). $^1$H NMR (600 MHz, cd$_3$od) δ 0.80-0.95 (m, 2H), 1.03-1.27 (m, 3H), 1.29-1.47 (m, 4H), 1.53-1.72 (m, 6H), 2.05 (d, 1H), 2.13 (d, 1H), 2.82-2.90 (m, 1H), 2.97 (td, 1H), 3.13 (s, 1H), 3.31 (d, 1H), 5.40 (s, 1H).

Example 23

5-((2R,4S)-2-(3,4-Difluorophenyl)piperidin-4-yl)isoxazol-3(2H)-one

Step 1: Trans-methyl 2-(3,4-difluorophenyl)-4-(3-ethoxy-3-oxopropanoyl)piperidine-1-carboxylate and cis-methyl 2-(3,4-difluorophenyl)-4-(3-ethoxy-3-oxopropanoyl)piperidine-1-carboxylate 2-(3,4-Difluorophenyl)-1-(methoxycarbonyl)piperidine-4-carboxylic acid (5.655 g, 18.90 mmol) (reference compound 9) was dissolved in THF (60 mL) and di(1H-imidazol-1-yl)methanone (4.60 g, 28.34 mmol) added. The suspension was stirred at room temperature under nitrogen for 5 h (flask 1). In a separate flask 3-ethoxy-3-oxopropanoic acid, potassium salt (6.47 g, 37.79 mmol) and magnesium chloride (3.60 g, 37.79 mmol) were suspended in THF (60 mL) and stirred with an oversized stirring bar at 50° C. under nitrogen for 5 h. The white suspension in flask 2 was then added to flask 1. The thick white suspension was stirred at room temperature for 18 h. The reaction mixture was acidified by addition of 3 M HCl to pH 1. The solvent was evaporated in vacuo. EtOAc (250 mL) and water were added, shaken and the phases separated. The organic phase was washed with water (200 mL), satd NaHCO$_3$ (200 mL), brine (200 mL), dried with a phase separator and evaporated in vacuo. The residue was purified by automated flash chromatography on a Biotage® KP-SIL 100 g column. A gradient from 10% EtOAc in heptane over 2 CV followed by 10% to 40% of EtOAc in heptane over 9 CV was used as mobile phase. Cis-methyl 2-(3,4-difluorophenyl)-4-(3-ethoxy-3-oxopropanoyl)piperidine-1-carboxylate (5.23 g, 74.9%) and trans-methyl 2-(3,4-difluorophenyl)-4-(3-ethoxy-3-oxopropanoyl)piperidine-1-carboxylate (0.502 g, 7.19%) were obtained. Cis-isomer: $^1$H NMR (400 MHz, cdcl$_3$) δ 1.23-1.30 (m, 3H), 1.74-2.18 (m, 3H), 2.22-2.30 (m, 1H), 2.82-2.91 (m, 1H), 3.24-3.37 (m, 1H), 3.44 (d, 2H), 3.65 (s, 3H), 4.05-4.22 (m, 1H), 4.18 (q, 2H), 4.85-4.98 (m, 1H), 6.90-6.97 (m, 1H), 6.98-7.05 (m, 1H), 7.05-7.14 (m, 1H). MS m/z 370 (M+H)$^+$. Trans-isomer: $^1$H NMR (400 MHz, cdcl$_3$) δ 1.23-1.32 (m, 3H), 1.51-2.02 (m, 3H), 2.42-2.53 (m, 1H), 2.59-2.71 (m, 1H), 2.77-2.88 (m, 1H), 3.47 (d, 2H), 3.76 (s, 3H), 4.19 (q, 2H), 4.14-4.33 (m, 1H), 5.47-5.66 (m, 1H), 6.90-6.97 (m, 1H), 6.99-7.07 (m, 1H), 7.11-7.20 (m, 1H). MS m/z 370 (M+H)$^+$ Step 2: Cis-methyl 2-(3,4-difluorophenyl)-4-(3-oxo-2,3-dihydroisoxazol-5-yl)piperidine-1-carboxylate Cis-methyl 2-(3,4-difluorophenyl)-4-(3-ethoxy-3-oxopropanoyl)piperidine-1-carboxylate (5.23 g, 14.16 mmol) was dissolved in MeOH (50 mL) and cooled to −40° C. Sodium hydroxide (3.73 mL, 14.16 mmol) dissolved in water (5.00 mL) was added and the reaction stirred at −40° C. for 40 min. Hydroxylamine (0.868 mL, 14.16 mmol) was added and stirring continued for 3.5 h at −40° C. The reaction mixture was then added to a prewarmed 80° C. solution of 6 M hydrogen chloride (73.2 mL, 438.95 mmol) and stirred for 20 min. The solvent was concentrated in vacuo. DCM (200 mL) and water (150 mL) were added, shaken and the phases separated. The aqueous phase was extracted with DCM (150 mL). The combined organic phases were dried with a phase separator and evaporated in vacuo. The compound was purified by preparative HPLC on a Kromasil C8 column (10 µm 250×50 ID mm) using a gradient of 20-60% Acetonitrile in H2O/MeCN/AcOH 95/5/0.2 buffer over 25 minutes with a flow of 100 mL/min. Cis-methyl 2-(3,4-difluorophenyl)-4-(3-oxo-2,3-dihydroisoxazol-5-yl)piperidine-1-carboxylate (3.41 g, 71.2%) was isolated as a white solid. $^1$H NMR (600 MHz, CDCl$_3$) δ 1.81-1.88 (m, 1H), 2.08-2.18 (m, 1H), 2.19-2.28 (m, 1H), 2.30-2.38 (m, 1H), 3.02-3.11 (m, 1H), 3.32-3.40 (m, 1H), 3.67 (s, 3H), 4.09-4.18 (m, 1H), 5.02-5.08 (m, 1H), 5.56 (s, 1H), 6.86-6.92 (m, 1H), 6.95-7.01 (m, 1H), 7.03-7.10 (m, 1H). MS m/z 339 (M+H)$^+$.

Step 3: (2R,4S)-Methyl 2-(3,4-difluorophenyl)-4-(3-oxo-2,3-dihydroisoxazol-5-yl)piperidine-1-carboxylate Cis-methyl 2-(3,4-difluorophenyl)-4-(3-oxo-2,3-dihydroisoxazol-5-yl)piperidine-1-carboxylate (3.41 g, 10 mmol) was subjected to chiral preparative HPLC (Column: Lux Cell2 (250×30), 5 µm particle size, mobile phase: 15% MeOH in CO$_2$ (175 bar), flow rate 130 mL/min, temperature 40° C.) to yield (2R,4S)-Methyl 2-(3,4-difluorophenyl)-4-(3-oxo-2,3-dihydroisoxazol-5-yl)piperidine-1-carboxylate (1.70 g, 50%), Chiral purity 99.0% ee, Optical rotation [α]$_D^{20}$=+49.9 (acetonitrile, c=1). $^1$H NMR (600 MHz, cdcl$_3$) δ 1.81-1.87 (m, 1H), 2.09-2.17 (m, 1H), 2.20-2.28 (m, 1H), 2.31-2.37 (m, 1H), 3.02-3.09 (m, 1H), 3.32-3.41 (m, 1H), 3.67 (s, 3H), 4.10-4.16 (m, 1H), 5.03-5.08 (m, 1H), 5.56 (s, 1H), 6.87-6.92 (m, 1H), 6.95-7.01 (m, 1H), 7.03-7.09 (m, 1H).

Step 4: 5-((2R,4S)-2-(3,4-Difluorophenyl)piperidin-4-yl)isoxazol-3(2H)-one (2R,4S)-methyl 2-(3,4-difluorophenyl)-4-(3-oxo-2,3-dihydroisoxazol-5-yl)piperidine-1-carboxylate (1.7 g, 5.03 mmol) was dissolved in hydrobromic acid (33% in AcOH, 25 mL, 151.92 mmol) and stirred at room temperature for 20 h. The solvent was evaporated in vacuo. The compound was purified by preparative HPLC on a XBridge C18 column (10 µm 250×50 ID mm) using a gradient of 5-30% Acetonitrile in H2O/MeCN/NH3 95/5/0.2 buffer over 25 minutes with a flow of 100 mL/min. The compound was repurified by preparative HPLC on a XBridge C18 column (10 µm 250×50 ID mm) using a gradient of 0-30% Acetonitrile in H2O/MeCN/NH3 95/5/0.2 buffer over 25 minutes with a flow of 100 mL/min. 5-((2R,4S)-2-(3,4-difluorophenyl)piperidin-4-yl)isoxazol-3(2H)-one (0.923 g, 65.5%) was isolated as a white solid. $^1$H NMR (600 MHz, cd$_3$od) δ 1.66-1.76 (m, 2H), 2.09 (d, 1H), 2.19 (d, 1H), 2.96-3.07 (m, 2H), 3.28-3.35 (omitted signals), 3.90-3.95 (m, 1H), 5.65 (s, 1H), 7.20-7.29 (m, 2H), 7.34-7.39 (m, 1H). HRMS Calcd for [C$_{14}$H$_{14}$F$_2$N$_2$O$_2$+H]$^+$: 281.1101. Found: 281.1106.

Example 24

5-(Trans-2-(3,4-difluorophenyl)piperidin-4-yl)isoxazol-3(2H)-one

Step 1: Trans-methyl 2-(3,4-difluorophenyl)-4-(3-oxo-2,3-dihydroisoxazol-5-yl)piperidine-1-carboxylate Trans-methyl 2-(3,4-difluorophenyl)-4-(3-ethoxy-3-oxopropanoyl)piperidine-1-carboxylate (502 mg, 1.36 mmol) (from example 23, step 1) was dissolved in MeOH (5 mL) and cooled to −40° C. Sodium hydroxide (0.358 mL, 1.36 mmol) dissolved in water (0.500 mL) was added and the reaction stirred at −40° C. for 20 min. Hydroxylamine (0.083 mL, 1.36 mmol) was added and stirring continued for 3.5 h at −40° C. The reaction mixture was then added to a prewarmed 80° C. solution of hydrogen chloride (7.02 mL, 42.13 mmol) and stirred for 20 min. The solvent was evaporated in vacuo. DCM (50 mL) and water (50 mL) were added, shaken and the phases separated. The aqueous phase was extracted with DCM (50 mL). The combined organic phase were dried with a phase separator and evaporated in vacuo. The compound was purified by preparative HPLC on a Kromasil C8 column (10 µm 250×50 ID mm) using a gradient of 20-60% Acetonitrile in H2O/MeCN/AcOH 95/5/0.2 buffer over 25 minutes with a flow of 100 mL/min. Trans-methyl 2-(3,4-difluorophenyl)-4-(3-oxo-2,3-dihydroisoxazol-5-yl)piperidine-1-carboxylate (242 mg, 52.6%) was isolated as a white solid. $^1$H NMR (600 MHz, CDCl$_3$) δ 1.60-1.72 (m, 1H), 1.94 (d, 1H), 1.98-2.07 (m, 1H), 2.60 (d, 1H), 2.78-2.94 (m, 2H), 3.77 (s, 3H), 4.25 (s, 1H), 5.51-5.71 (m, 2H), 6.94-6.99 (m, 1H), 7.02-7.09 (m, 1H), 7.17 (dd, 1H). MS m/z 337 (M−H)$^−$.

Step 2: 5-(Trans-2-(3,4-difluorophenyl)piperidin-4-yl)isoxazol-3(2H)-one

Trans-methyl 2-(3,4-difluorophenyl)-4-(3-oxo-2,3-dihydroisoxazol-5-yl)piperidine-1-carboxylate (242 mg, 0.72 mmol) was dissolved in hydrobromic acid (33% in AcOH, 4 mL, 24.31 mmol) and stirred at room temperature for 20 h. The solvent was evaporated in vacuo. The residue was purified by preparative HPLC (Instrument: Agilent, Mobilphase: gradient 5-95% MeCN in 0.2% NH$_3$, pH10, Column: Xbridge Prep C18 5 µm OBD 19*150 mm) to yield 5-(trans-2-(3,4-difluorophenyl)piperidin-4-yl)isoxazol-3(2H)-one (137 mg, 68%). $^1$H NMR (600 MHz, dmso) δ 1.74-1.81 (m, 2H), 1.84-1.89 (m, 1H), 1.98-2.03 (m, 1H), 2.65-2.71 (m, 1H), 2.81 (dt, 1H), 3.09-3.13 (m, 1H), 3.70 (dd, 1H), 5.96 (s, 1H), 7.18-7.22 (m, 1H), 7.30-7.36 (m, 1H), 7.39-7.44 (m, 1H). HRMS Calcd for [C$_{14}$H$_{14}$F$_2$N$_2$O$_2$+H]$^+$: 281.1101. Found: 281.1114.

Example 25

5-((2R,4S)-2-(4-Fluorophenyl)piperidin-4-yl)isoxazol-3(2H)-one

Step 1: Trans-methyl 4-(3-ethoxy-3-oxopropanoyl)-2-(4-fluorophenyl)piperidine-1-carboxylate and cis-methyl 4-(3-ethoxy-3-oxopropanoyl)-2-(4-fluorophenyl)piperidine-1-carboxylate 2-(4-fluorophenyl)-1-(methoxycarbonyl)piperidine-4-carboxylic acid (8.4 g, 29.86 mmol) (reference compound 10) was dissolved in methyl THF (120 mL) and di(1H-imidazol-1-yl)methanone (7.26 g, 44.80 mmol) added. The suspension was stirred at room temperature under nitrogen for 2 h (flask 1). In a separate flask potassium 3-ethoxy-3-oxopropanoate (9.15 g, 53.75 mmol) was suspended in methyl THF (120 mL) and magnesium chloride (5.12 g, 53.75 mmol) added. The suspension was stirred at 50° C. under nitrogen for 3 h using an oversized stirring bar (flask 2). The beige suspension in flask 1 was now added to the white suspension in flask 2. The resulting beige suspension was stirred under nitrogen at room temperature for 23 h. The mixture was acidified to pH 1 with 3 M HCl (50 mL) and MTBE (200 mL) and water (70 mL) were added. The phases were separated and the organic phase extracted with water (30 mL), satd NaHCO$_3$ (30 mL) and water (30 mL), dried over anhydrous Na$_2$SO$_4$ and evaporated. The diastereoisomers were separated on Biotage (20%=>55% EtOAc in heptane, 8 CV; Biotage® KP-SIL 340 g column) to yield trans-methyl 4-(3-ethoxy-3-oxopropanoyl)-2-(4-fluorophenyl)piperidine-1-carboxylate (1.26 g, 12%) and cis-methyl 4-(3-ethoxy-3-oxopropanoyl)-2-(4-fluorophenyl)piperidine-1-carboxylate (6.58 g, 62%) as colorless oils. Cis-isomer: $^1$H NMR (400 MHz, cdcl$_3$) δ 1.27 (t, 3H), 1.83-2.14 (m, 3H), 2.27 (ddd, 1H), 2.80-2.93 (m, 1H), 3.26-3.50 (m, 3H), 3.64 (s, 3H), 4.10-4.22 (m, 3H), 4.93-5.01 (m, 1H), 6.95-7.05 (m, 2H), 7.14-7.22 (m, 2H). MS m/z 352 (M+H)$^+$. Trans-isomer: $^1$H NMR (400 MHz, cdcl$_3$) δ 1.18-1.33 (m, 3H), 1.50-1.89 (m, 2H), 1.90-2.02 (m, 1H), 2.47-2.59 (m, 1H), 2.59-2.72 (m, 1H), 2.79-2.91 (m, 1H), 3.47 (s, 2H), 3.76 (s, 3H), 4.08-4.30 (m, 3H), 5.50-5.69 (s, br., 1H), 6.98-7.10 (m, 2H), 7.10-7.23 (m, 2H). MS m/z 350 (M−H)$^-$

Step 2: Cis-methyl 2-(4-fluorophenyl)-4-(3-oxo-2,3-dihydroisoxazol-5-yl)piperidine-1-carboxylate Cis-methyl 4-(3-ethoxy-3-oxopropanoyl)-2-(4-fluorophenyl)piperidine-1-carboxylate (6.58 g, 18.7 mmol) was dissolved in MeOH (50 mL) and cooled to −40° C. under nitrogen. Sodium hydroxide (0.749 g, 18.73 mmol) dissolved in water (5.00 mL) was added during 10 min and the colourless solution continued to stir at −40° C. for 20 min. Hydroxylamine (50% by weight in water, 1.148 mL, 18.73 mmol) was added during 8 min. The resulting solution was stirred at −40° C. for 3 h 20 min. The mixture was transferred into a prewarmed (80° C.) solution of 6 M hydrogen chloride (94 mL, 561.80 mmol) and the mixture continued to stir at 80° C. for 20 min. The solvent was evaporated and DCM/water added. The phases were separated and the organic phase passed through a phase separator and evaporated to yield 5.8 g of a yellow solid. 2.9 g of this solid was purified by preparative HPLC in 3 injections on a XBridge C18 column (10 μm 250×50 ID mm) using a gradient of 30-75% Acetonitrile in H2O/MeCN/HOAc 95/5/0.2 buffer over 15 minutes with a flow of 100 mL/min. Cis-methyl 2-(4-fluorophenyl)-4-(3-oxo-2,3-dihydroisoxazol-5-yl)piperidine-1-carboxylate (1.7 g, 28%) was obtained. $^1$H NMR (400 MHz, cdcl$_3$) δ 1.79-1.90 (m, 1H), 2.08-2.40 (m, 3H), 3.01-3.12 (m, 1H), 3.32-3.44 (m, 1H), 3.67 (s, 3H), 4.15 (ddd, 1H), 5.05-5.14 (m, 1H), 5.54 (s, 1H), 6.92-7.02 (m, 2H), 7.10-7.18 (m, 2H). MS m/z 321 (M+H)$^+$.

Step 3: (2R,4S)-Methyl 2-(4-fluorophenyl)-4-(3-oxo-2,3-dihydroisoxazol-5-yl)piperidine-1-carboxylate Cis-methyl 2-(4-fluorophenyl)-4-(3-oxo-2,3-dihydroisoxazol-5-yl)piperidine-1-carboxylate (1.7 g, 5.3 mmol) was subjected to chiral preparative HPLC (Column: Chiralcel OJ (250×50), 20 μm particle size, mobile phase: EtOH, flow rate 118 mL/min) to yield (2R,4S)-methyl 2-(4-fluorophenyl)-4-(3-oxo-2,3-dihydroisoxazol-5-yl)piperidine-1-carboxylate (860 mg, 50%), Chiral purity 99.9% ee, Optical rotation $[\alpha]_D^{20}$=+57.0 (acetonitrile, c=1).

Step 4: 5-((2R,4S)-2-(4-Fluorophenyl)piperidin-4-yl)isoxazol-3(2H)-one (2R,4S)-Methyl 2-(4-fluorophenyl)-4-(3-oxo-2,3-dihydroisoxazol-5-yl)piperidine-1-carboxylate (0.86 g, 2.68 mmol) was dissolved in hydrogen bromide (33% in acetic acid, 15.52 mL, 88.60 mmol) and the solution stirred at room temperature overnight. The solvent was evaporated and the residue was purified by preparative HPLC (Instrument: Agilent, Mobilphase: gradient 5-95% MeCN in 0.2% NH$_3$, pH10, Column: Xbridge Prep C18 5 μm OBD 19*150 mm) and on a XBridge C18 column (10 μm 250×19 ID mm) using a gradient of 0-30% Acetonitrile in H2O/MeCN/NH3 95/5/0.2 buffer over 20 minutes with a flow of 19 mL/min. 5-((2R, 4S)-2-(4-Fluorophenyl)piperidin-4-yl)isoxazol-3(2H)-one (167 mg, 23%) was isolated. $^1$H NMR (400 MHz, dmso) δ 1.27-1.53 (m, 2H), 1.81-1.98 (m, 2H), 2.67-2.77 (m, 1H), 2.78-2.91 (m, 1H), 3.10 (d, 1H), 3.63 (d, 1H), 5.67-5.77 (m, 1H), 7.04-7.16 (m, 2H), 7.34-7.45 (m, 2H). HRMS Calculated for [C$_{14}$H$_{15}$FN$_2$O$_2$+H]$^+$: 263.1196. Found: 263.1201

Example 26

5-(Trans-2-(4-fluorophenyl)piperidin-4-yl)isoxazol-3(2H)-one

Step 1: Trans-methyl 2-(4-fluorophenyl)-4-(3-oxo-2,3-dihydroisoxazol-5-yl)piperidine-1-carboxylate Trans-methyl 4-(3-ethoxy-3-oxopropanoyl)-2-(4-fluorophenyl)piperidine-1-carboxylate (1.26 g, 3.59 mmol) (from example 25, step 1) was dissolved in MeOH (50 mL) and cooled to −40° C. under nitrogen. Sodium hydroxide (0.143 g, 3.59 mmol) dissolved in water (5.00 mL) was added during 5 min and the colourless solution continued to stir at −40° C. for 20 min. Hydroxylamine (50% by weight in water, 0.220 mL, 3.59 mmol) was added during 8 min. The resulting solution was stirred at −40° C. for 3 h 20 min. The mixture was transferred into a prewarmed (80° C.) solution of 6 M hydrogen chloride (17.93 mL, 107.58 mmol) and the mixture continued to stir at 80° C. for 20 min. The solvent was evaporated and DCM/water added. The phases were separated and the organic phase passed through a phase separator and evaporated to yield trans-methyl 2-(4-fluorophenyl)-4-(3-oxo-2,3-dihydroisoxazol-5-yl)piperidine-1-carboxylate (1.1 g, 95%) as a brown solid, 1.1 g. MS m/z 321 (M+H)$^+$.

Step 2: 5-(Trans-2-(4-fluorophenyl)piperidin-4-yl)isoxazol-3(2H)-one

Trans-methyl 2-(4-fluorophenyl)-4-(3-oxo-2,3-dihydroisoxazol-5-yl)piperidine-1-carboxylate (0.3 g, 0.94 mmol) was dissolved in hydrogen bromide (33% in acetic acid, 6 mL, 34.26 mmol) and the solution stirred at room temperature overnight. The solvent was evaporated and the residue was purified by preparative HPLC (Instrument: Agilent, Mobilphase: gradient 5-95% MeCN in 0.2% $NH_3$, pH10, Column: Xbridge Prep C18 5 μm OBD 19*150 mm) 5-(Trans-2-(4-fluorophenyl)piperidin-4-yl)isoxazol-3(2H)-one (54 mg, 22%) was isolated. $^1$H NMR (400 MHz, dmso) δ 1.75-2.10 (m, 4H), 2.67-2.77 (m, 1H), 2.80-2.89 (m, 1H), 3.11-3.18 (m, 1H), 3.70 (d, 1H), 5.94 (s, 1H), 7.07-7.15 (m, 2H), 7.36-7.43 (m, 2H). HRMS Calculated for $[C_{14}H_{15}FN_2O_2+H]^+$: 263.1196. Found: 263.1201

Example 27

5-((2R,4S)-2-(4-Chlorophenyl)piperidin-4-yl)isoxazol-3(2H)-one

Step 1: Trans-methyl 2-(4-chlorophenyl)-4-(3-ethoxy-3-oxopropanoyl)piperidine-1-carboxylate and cis-methyl 2-(4-chlorophenyl)-4-(3-ethoxy-3-oxopropanoyl)piperidine-1-carboxylate 2-(4-Chlorophenyl)-1-(methoxycarbonyl)piperidine-4-carboxylic acid (3.49 g, 11.72 mmol) (reference compound 11) was dissolved in methyl THF (120 mL), then di(1H-imidazol-1-yl)methanone (2.85 g, 17.58 mmol) was added. The mixture was stirred at room temperature under nitrogen for 3 h (flask 1). In a separate flask potassium 3-ethoxy-3-oxopropanoate (3.59 g, 21.10 mmol) was suspended in methyl THF (120 mL), then magnesium chloride (2.009 g, 21.10 mmol) was added. The suspension was stirred at 50° C. under nitrogen for 3 h using a large magnetic stirring bar (flask 2). The contents of flask 1 was transferred to flask 2. The resulting white suspension was stirred under nitrogen at room temperature overnight. The mixture was acidified to pH 1 with 3.8 M HCl, then MTBE (50 mL) and water (50 mL) was added. The phases were separated and the organic layer was washed with water, satd $NaHCO_3$ and brine. The organic layer was dried over $Na_2SO_4$, filtered and evaporated giving a slightly yellow oil. The residue was purified by automated column chromatography on Biotage (340 g) with a gradient of 20-60% EtOAc in n-heptane (8 CV) to yield trans-methyl 2-(4-chlorophenyl)-4-(3-ethoxy-3-oxopropanoyl)piperidine-1-carboxylate (205 mg, 5%) and cis-methyl 2-(4-chlorophenyl)-4-(3-ethoxy-3-oxopropanoyl)piperidine-1-carboxylate (2.27 g, 53%). Cis-isomer: $^1$H NMR (400 MHz, cdcl$_3$) δ 1.21-1.32 (m, 3H), 1.82-2.15 (m, 3H), 2.22-2.31 (m, 1H), 2.81-2.92 (m, 1H), 3.26-3.49 (m, 3H), 3.63 (s, 3H), 4.06-4.22 (m, 3H), 4.91-4.99 (m, 1H), 7.11-7.18 (m, 2H), 7.24-7.31 (m, 2H). MS m/z 366 (M−H)$^-$. Trans-isomer: $^1$H NMR (400 MHz, cdcl$_3$) δ 1.16-1.33 (m, 3H), 1.47-2.02 (m, 3H), 2.43-2.70 (m, 2H), 2.75-2.91 (m, 1H), 3.42-3.48 (m, 2H), 3.74 (s, 3H), 4.00-4.39 (m, 3H), 5.45-5.71 (s, br., 1H), 7.14 (d, 2H), 7.29-7.35 (m, 2H). MS m/z 368 (M+H)$^+$.

Step 2: Cis-methyl 2-(4-chlorophenyl)-4-(3-oxo-2,3-dihydroisoxazol-5-yl)piperidine-1-carboxylate Cis-methyl 2-(4-chlorophenyl)-4-(3-ethoxy-3-oxopropanoyl)piperidine-1-carboxylate (2.11 g, 5.74 mmol) was dissolved in MeOH (24 mL) and cooled to −40° C. under nitrogen. Sodium hydroxide (1.687 mL, 5.74 mmol) was added during 10 min and the yellow solution continued to stir at −40° C. for 20 min. Hydroxylamine (50% by weight in water, 0.352 mL, 5.74 mmol) was added during 8 min. The resulting solution was stirred at −40° C. for 3 h. The mixture was then rapidly poured into a prewarmed (80° C.) solution of 6 M hydrogen chloride (29.5 mL, 177.26 mmol) and the mixture continued to stir at 80° C. for 20 min. The solvent was evaporated and DCM/water added. The phases were separated and the organic phase passed through a phase separator and evaporated to yield a white solid. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 2-(4-chlorophenyl)-4-(3-oxo-2,3-dihydroisoxazol-5-yl)piperidine-1-carboxylate (923 mg, 47%) was isolated. MS m/z 337 (M+H)$^+$ Step 3: (2R,4S)-Methyl 2-(4-chlorophenyl)-4-(3-oxo-2,3-dihydroisoxazol-5-yl)piperidine-1-carboxylate and (2S,4R)-methyl 2-(4-chlorophenyl)-4-(3-oxo-2,3-dihydroisoxazol-5-yl)-piperidine-1-carboxylate Cis-methyl 2-(4-chlorophenyl)-4-(3-oxo-2,3-dihydroisoxazol-5-yl)piperidine-1-carboxylate (923 mg, 2.75 mmol) was subjected to chiral preparative HPLC (Column: ReproSil (250×50), 8 μm particle size, mobile phase: EtOH, flow rate 100 mL/min) to yield (2R,4S)-methyl 2-(4-chlorophenyl)-4-(3-oxo-2,3-dihydroisoxazol-5-yl)piperidine-1-carboxylate (447 mg, 48%), Chiral purity 99.9% ee, Optical rotation $[\alpha]_D^{20}$=+67.7 (acetonitrile, c=1), $^1$H NMR (400 MHz, cdcl$_3$) δ 1.79-1.89 (m, 1H), 2.07-2.40 (m, 3H), 3.01-3.11 (m, 1H), 3.33-3.43 (m, 1H), 3.66 (s, 3H), 4.10-4.19 (m, 1H), 5.07 (dd, 1H), 5.55 (s, 1H), 7.08-7.14 (m, 2H), 7.23-7.28 (m, 2H) and (2S,4R)-methyl 2-(4-chlorophenyl)-4-(3-oxo-2,3-dihydroisoxazol-5-yl)-piperidine-1-carboxylate (458 mg, 49%), Chiral purity 99.6% ee, Optical rotation $[\alpha]_D^{20}$=−67.6 (acetonitrile, c=1), $^1$H NMR (400 MHz, cdcl$_3$) δ 1.79-1.88 (m, 1H), 2.07-2.38 (m, 3H), 3.02-3.10 (m, 1H), 3.33-3.43 (m, 1H), 3.66 (s, 3H), 4.11-4.18 (m, 1H), 5.04-5.09 (m, 1H), 5.54 (s, 1H), 7.09-7.13 (m, 2H), 7.23-7.28 (m, 2H).

Step 4: 5-((2R,4S)-2-(4-Chlorophenyl)piperidin-4-yl)isoxazol-3(2H)-one (2R,4S)-Methyl 2-(4-chlorophenyl)-4-(3-oxo-2,3-dihydroisoxazol-5-yl)piperidine-1-carboxylate (0.447 g, 1.33 mmol) was dissolved in hydrogen bromide (33% in acetic acid, 10.46 mL, 59.73 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4S)-2-(4-chlorophenyl)piperidin-4-yl)isoxazol-3(2H)-one (233 mg, 63%). $^1$H NMR (600 MHz, dmso) δ 1.32 (q, 1H), 1.44 (dq, 1H), 1.82-1.88 (m, 1H), 1.90-1.97 (m, 1H), 2.71 (dt, 1H), 2.80-2.88 (m, 1H), 3.06-3.12 (m, 1H), 3.63 (dd, 1H), 5.70 (s, 1H), 7.31-7.35 (m, 2H), 7.35-7.40 (m, 2H). HRMS Calculated for $[C_{14}H_{15}ClN_2O_2+H]^+$: 279.0900. Found: 279.0905

Example 28

5-((2S,4R)-2-(4-Chlorophenyl)piperidin-4-yl)isoxazol-3(2H)-one (2S,4R)-Methyl 2-(4-chlorophenyl)-4-(3-oxo-2,3-dihydroisoxazol-5-yl)piperidine-1-carboxylate (0.458 g, 1.36 mmol) (from example 27, step 3) was dissolved in hydrogen bromide (33% in acetic acid, 10.72 mL, 61.20 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-(4-chlorophenyl)piperidin-4-yl)isoxazol-3(2H)-one (198 mg, 52%). $^1$H NMR (600 MHz, dmso) δ 1.32 (q, 1H), 1.44 (dq, 1H), 1.83-1.88 (m, 1H), 1.91-1.96 (m, 1H), 2.71 (dt, 1H), 2.84 (tt, 1H), 3.07-3.11 (m, 1H), 3.63 (dd, 1H), 5.70 (s, 1H), 7.31-7.40 (m, 4H). HRMS Calculated for [C$_{14}$H$_{15}$ClN$_2$O$_2$+H]$^+$: 279.0900. Found: 279.0887

Example 29

5-(Trans-2-(4-chlorophenyl)piperidin-4-yl)isoxazol-3(2H)-one

Step 1: Trans-methyl 2-(4-chlorophenyl)-4-(3-oxo-2,3-dihydroisoxazol-5-yl)piperidine-1-carboxylate Trans-methyl 2-(4-chlorophenyl)-4-(3-ethoxy-3-oxopropanoyl)piperidine-1-carboxylate (184 mg, 0.50 mmol) (from example 27, step 1) was dissolved in MeOH (2 mL) and cooled to −40° C. under nitrogen. Sodium hydroxide (0.147 mL, 0.50 mmol) was added during 10 min and the yellow solution continued to stir at −40° C. for 20 min. Hydroxylamine (50% by weight in water, 0.031 mL, 0.50 mmol) was added during 8 min. The resulting solution was stirred at −40° C. for 3 h. The mixture was then rapidly poured into a prewarmed (80° C.) solution of 6 M hydrogen chloride (2.58 mL, 15.46 mmol) and the mixture continued to stir at 80° C. for 20 min. The solvent was evaporated and DCM/water added. The phases were separated and the organic phase passed through a phase separator and evaporated to yield crude trans-methyl 2-(4-chlorophenyl)-4-(3-oxo-2,3-dihydroisoxazol-5-yl)piperidine-1-carboxylate (155 mg, 92%) as a slightly yellow oil. MS m/z 337 (M+H)$^+$ Step 2: 5-(Trans-2-(4-chlorophenyl)piperidin-4-yl)isoxazol-3(2H)-one Trans-methyl 2-(4-chlorophenyl)-4-(3-oxo-2,3-dihydroisoxazol-5-yl)piperidine-1-carboxylate (155 mg, 0.46 mmol) was dissolved in hydrogen bromide (33% in acetic acid, 3.63 mL, 20.71 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(4-chlorophenyl)piperidin-4-yl)isoxazol-3(2H)-one (23.5 mg, 18%). $^1$H NMR (600 MHz, dmso) δ 1.74-1.83 (m, 2H), 1.84-1.91 (m, 1H), 1.96-2.03 (m, 1H), 2.70 (dt, 1H), 2.79-2.86 (m, 1H), 3.09-3.15 (m, 1H), 3.69 (dd, 1H), 5.89-5.98 (m, 1H), 7.32-7.36 (m, 2H), 7.36-7.41 (m, 2H). HRMS Calculated for [C$_{14}$H$_{15}$ClN$_2$O$_2$+H]$^+$: 279.0900. Found: 279.0889

Example 30

5-((2R,4S)-2-(3-(Trifluoromethyl)phenyl)piperidin-4-yl)isoxazol-3(2H)-one

Step 1: Trans-methyl 4-(3-ethoxy-3-oxopropanoyl)-2-(3-(trifluoromethyl)phenyl)piperidine-1-carboxylate and cis-methyl 4-(3-ethoxy-3-oxopropanoyl)-2-(3-(trifluoromethyl)phenyl)-piperidine-1-carboxylate 1-(Methoxycarbonyl)-2-(3-(trifluoromethyl)phenyl)piperidine-4-carboxylic acid (1.479 g, 4.46 mmol) (reference compound 12) was dissolved into methyl THF (50 mL), then di(1H-imidazol-1-yl)methanone (1.086 g, 6.70 mmol) was added. The mixture was stirred at room temperature under nitrogen for 3 h (flask 1). In a separate flask potassium 3-ethoxy-3-oxopropanoate (1.368 g, 8.04 mmol) was suspended in methyl THF (50.0 mL), then magnesium chloride (0.765 g, 8.04 mmol) was added. The suspension was stirred at 50° C. under nitrogen for 3 h using a large magnetic stirring bar (flask 2). The contents of flask 1 was transferred to flask 2. The resulting white suspension was stirred under nitrogen at room temperature overnight. The mixture was acidified to pH 1 with 3.8 M HCl, then MTBE (50 mL) and water (50 mL) were added. The phases were separated and the organic layer was washed with water, satd NaHCO$_3$ and brine. The organic layer was dried over Na$_2$SO$_4$, filtered and evaporated leaving a slightly yellow oil. The residue was purified by automated column chromatography on Biotage (340 g) with a gradient of 20-55% EtOAc in n-heptane (8 CV) to yield trans-methyl 4-(3-ethoxy-3-oxopropanoyl)-2-(3-(trifluoromethyl)phenyl)-piperidine-1-carboxylate (157 mg, 9%) and cis-methyl 4-(3-ethoxy-3-oxopropanoyl)-2-(3-(trifluoromethyl)phenyl)piperidine-1-carboxylate (679 mg, 38%). Cis-isomer: $^1$H NMR (400 MHz, cdcl$_3$) δ 1.19-1.27 (m, 3H), 1.75-2.20 (m, 3H), 2.23-2.32 (m, 1H), 2.82-2.94 (m, 1H), 3.26-3.48 (m, 3H), 3.61 (s, 3H), 4.05-4.21 (m, 3H), 4.91-5.04 (m, 1H), 7.35-7.50 (m, 4H). MS m/z 402 (M+H)$^+$. Trans-isomer: $^1$H NMR (400 MHz, cdcl$_3$) δ 1.16-1.32 (m, 3H), 1.46-2.09 (m, 4H), 2.48-2.90 (m, 2H), 3.40-3.50 (m, 2H), 3.75 (s, 3H), 4.02-4.42 (m, 3H), 5.65 (s, br., 1H), 7.36-7.56 (m, 4H). MS m/z 402 (M+H)$^+$ Step 2: Cis-methyl 4-(3-oxo-2,3-dihydroisoxazol-5-yl)-2-(3-(trifluoromethyl)phenyl)-piperidine-1-carboxylate Cis-methyl 4-(3-ethoxy-3-oxopropanoyl)-2-(3-(trifluoromethyl)phenyl)piperidine-1-carboxylate (679 mg, 1.69 mmol) was dissolved in MeOH (8 mL) and cooled to −40° C. under nitrogen. Sodium hydroxide (0.498 mL, 1.69 mmol) dissolved in water (0.800 mL) was added during 10 min and the yellow solution continued to stir at −40° C. for 20 min. Hydroxylamine (50% by weight in water, 0.104 mL, 1.69 mmol) was added during 8 min. The resulting solution was stirred at −40° C. for 3 h. The mixture was then rapidly poured into a prewarmed (80° C.) solution of 6 M hydrogen chloride (8.71 mL, 52.27 mmol) and the mixture continued to stir at 80° C. for 20 min. The solvent was evaporated and DCM/water added. The phases were separated and the organic phase passed through a phase separator and evaporated to yield a white solid. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 4-(3-oxo-2,3-dihydroisoxazol-5-yl)-2-(3-(trifluoromethyl)phenyl)piperidine-1-carboxylate (311 mg, 50%) was isolated. MS m/z 371 (M+H)$^+$ Step 3: (2R,4S)-Methyl 4-(3-oxo-2,3-dihydroisoxazol-5-yl)-2-(3-(trifluoromethyl)phenyl)-piperidine-1-carboxylate and (2S,4R)-methyl 4-(3-oxo-2,3-dihydroisoxazol-5-yl)-2-(3-(trifluoromethyl)phenyl)piperidine-1-carboxylate Cis-methyl 4-(3-oxo-2,3-dihydroisoxazol-5-yl)-2-(3-(trifluoromethyl)phenyl)piperidine-1-carboxylate (311 mg, 0.84 mmol) was subjected to chiral preparative HPLC (Column: Chiralpak IC (250×20), 5 μm particle size, mobile phase:

Heptane/IPA 40/60, flow rate 12 mL/min) to yield (2R,4S)-methyl 4-(3-oxo-2,3-dihydroisoxazol-5-yl)-2-(3-(trifluoromethyl)-phenyl)piperidine-1-carboxylate (155 mg, 50%), Chiral purity 99.9% ee, Optical rotation $[\alpha]_D^{20}$=−54.4 (acetonitrile, c=1), $^1$H NMR (400 MHz, cdcl$_3$) δ 1.78-1.90 (m, 1H), 2.08-2.42 (m, 3H), 3.01-3.13 (m, 1H), 3.34-3.48 (m, 1H), 3.65 (s, 3H), 4.09-4.22 (m, 1H), 5.08-5.19 (m, 1H), 5.53 (s, 1H), 7.31-7.50 (m, 4H) and (2S,4R)-methyl 4-(3-oxo-2,3-dihydroisoxazol-5-yl)-2-(3-(trifluoromethyl)phenyl)piperidine-1-carboxylate (152 mg, 49%), Chiral purity 99.9% ee. Optical rotation $[\alpha]_D^{20}$=−55.7 (acetonitrile, c=1), $^1$H NMR (400 MHz, cdcl$_3$) δ 1.80-1.90 (m, 1H), 2.11-2.32 (m, 2H), 2.33-2.42 (m, 1H), 3.02-3.12 (m, 1H), 3.36-3.47 (m, 1H), 3.66 (s, 3H), 4.12-4.21 (m, 1H), 5.11-5.17 (m, 1H), 5.53 (s, 1H), 7.33-7.48 (m, 4H).

Step 4: 5-((2R,4S)-2-(3-(Trifluoromethyl)phenyl)piperidin-4-yl)isoxazol-3(2H)-one (2R,4S)-Methyl 4-(3-oxo-2,3-dihydroisoxazol-5-yl)-2-(3-(trifluoromethyl)phenyl)piperidine-1-carboxylate (0.155 g, 0.42 mmol) was dissolved in hydrogen bromide (33% in acetic acid, 3.30 mL, 18.83 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(3-(trifluoromethyl)phenyl)piperidin-4-yl)isoxazol-3(2H)-one (43 mg, 33%). $^1$H NMR (600 MHz, dmso) δ 1.35 (q, 1H), 1.47 (dq, 1H), 1.87 (d, 1H), 2.00 (d, 1H), 2.69-2.77 (m, 1H), 2.83-2.91 (m, 1H), 3.08-3.14 (m, 1H), 3.75 (d, 1H), 5.74 (s, 1H), 7.50-7.55 (m, 1H), 7.55-7.59 (m, 1H), 7.64-7.68 (m, 1H), 7.71 (s, 1H). HRMS Calculated for $[C_{15}H_{15}F_3N_2O_2+H]^+$: 313.1164. Found: 313.1144

Example 31

5-((2S,4R)-2-(3-(Trifluoromethyl)phenyl)piperidin-4-yl)isoxazol-3(2H)-one (2S,4R)-Methyl 4-(3-oxo-2,3-dihydroisoxazol-5-yl)-2-(3-(trifluoromethyl)phenyl)piperidine-1-carboxylate (0.152 g, 0.42 mmol) (from example 30, step 3) was dissolved in hydrogen bromide (33% in acetic acid, 3.30 mL, 18.83 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-(3-(trifluoromethyl)phenyl)piperidin-4-yl)isoxazol-3(2H)-one (28 mg, 22%). $^1$H NMR (600 MHz, dmso) δ 1.35 (q, 1H), 1.47 (qd, 1H), 1.87 (d, 1H), 2.00 (d, 1H), 2.73 (dt, 1H), 2.84-2.91 (m, 1H), 3.09-3.14 (m, 1H), 3.75 (d, 1H), 5.74 (s, 1H), 7.50-7.54 (m, 1H), 7.55-7.58 (m, 1H), 7.66 (d, 1H), 7.71 (s, 1H). HRMS Calculated for $[C_{15}H_{15}F_3N_2O_2+H]^+$: 313.1164. Found: 313.1158

Example 32

5-(Trans-2-(3-(trifluoromethyl)phenyl)piperidin-4-yl)isoxazol-3(2H)-one

Step 1: Trans-methyl 4-(3-oxo-2,3-dihydroisoxazol-5-yl)-2-(3-(trifluoromethyl)phenyl)-piperidine-1-carboxylate Trans-methyl 4-(3-ethoxy-3-oxopropanoyl)-2-(3-(trifluoromethyl)phenyl)piperidine-1-carboxylate (157 mg, 0.39 mmol) (from example 30, step 1) was dissolved in MeOH (2 mL) and cooled to −40° C. under nitrogen. Sodium hydroxide (0.115 mL, 0.39 mmol) dissolved in water (0.200 mL) was added during 10 min and the yellow solution continued to stir at −40° C. for 20 min. Hydroxylamine (50% by weight in water, 0.024 mL, 0.39 mmol) was added during 8 min. The resulting solution was stirred at −40° C. for 3 h 15 min. The mixture was then rapidly poured into a prewarmed (80° C.) solution of 6 M hydrogen chloride (2.014 mL, 12.09 mmol) and the mixture continued to stir at 80° C. for 20 min. The solvent was evaporated and DCM/water added. The phases were separated and the organic phase passed through a phase separator and evaporated to yield crude trans-methyl 4-(3-oxo-2,3-dihydroisoxazol-5-yl)-2-(3-(trifluoromethyl)phenyl)piperidine-1-carboxylate (128 mg, 88%) as a white solid. MS m/z 371 (M+H)$^+$ Step 2: 5-(Trans-2-(3-(trifluoromethyl)phenyl)piperidin-4-yl)isoxazol-3(2H)-one Trans-methyl 4-(3-oxo-2,3-dihydroisoxazol-5-yl)-2-(3-(trifluoromethyl)phenyl)piperidine-1-carboxylate (0.128 g, 0.35 mmol) was dissolved in hydrogen bromide (33% in acetic acid, 2.72 mL, 15.55 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(3-(trifluoromethyl)phenyl)piperidin-4-yl)isoxazol-3(2H)-one (31 mg, 28%). $^1$H NMR (600 MHz, dmso) δ 1.77-1.86 (m, 2H), 1.86-1.93 (m, 1H), 2.01-2.08 (m, 1H), 2.71 (dt, 1H), 2.81-2.87 (m, 1H), 3.11-3.16 (m, 1H), 3.76-3.83 (m, 1H), 5.99 (s, 1H), 7.50-7.55 (m, 1H), 7.55-7.59 (m, 1H), 7.64-7.68 (m, 1H), 7.72 (s, 1H). HRMS Calculated for $[C_{15}H_{15}F_3N_2O_2+H]^+$: 313.1164. Found: 313.1153

Example 33

5-((2R,4S)-2-(4-(Trifluoromethyl)phenyl)piperidin-4-yl)isoxazol-3(2H)-one

Step 1: Trans-methyl 4-(3-ethoxy-3-oxopropanoyl)-2-(4-(trifluoromethyl)phenyl)piperidine-1-carboxylate and cis-methyl 4-(3-ethoxy-3-oxopropanoyl)-2-(4-(trifluoromethyl)phenyl)-piperidine-1-carboxylate 1-(Methoxycarbonyl)-2-(4-(trifluoromethyl)phenyl)piperidine-4-carboxylic acid (5.629 g, 16.99 mmol) (reference compound 13) was dissolved in methyl THF (120 mL) and di(1H-imidazol-1-yl)methanone (4.13 g, 25.49 mmol) added. The suspension was stirred at room temperature under nitrogen for 3 h 45 min (flask 1). In a separate flask potassium 3-ethoxy-3-oxopropanoate (5.21 g, 30.58 mmol) was suspended in methyl THF (120 mL) and magnesium chloride (2.91 g, 30.58 mmol) added. The suspension was stirred at 50° C. under nitrogen for 3.5 h using an oversized stirring bar (flask 2). The beige suspension in flask 1 was now added to the white suspension in flask 2. The resulting beige suspension was stirred under nitrogen at room temperature for 23 h. The mixture was acidified to pH 1 with 3.8 M HCl and MTBE and water added. The phases were separated and the organic phase extracted with water, satd NaHCO$_3$ and water. The organic layer was evaporated and traces of water were azeotropically removed by MeCN to yield a brown oil. The diastereoisomers were separated in 2 runs on Biotage (20%=>55% EtOAc in heptane, 8 CV; Biotage® KP-SIL 340 g column). Trans-methyl 4-(3-ethoxy-3-oxopropanoyl)-2-(4-(trifluoromethyl)phenyl)piperidine-1-carboxylate (0.474 g, 7%) and cis-methyl 4-(3-ethoxy-3-oxopropanoyl)-2-(4-(trifluoromethyl)phenyl)-piperidine-1-carboxylate (3.532 g, 52%) were isolated as colorless oils. Cis-isomer: $^1$H NMR (400 MHz, cdcl$_3$) δ 1.26 (t, 3H), 1.72-2.22 (m, 3H), 2.29 (ddd, 1H), 2.83-2.96 (m, 1H), 3.29-3.49 (m, 3H), 3.64 (s, 3H), 4.07-4.23 (m, 3H), 4.92-5.06 (m, 1H), 7.32 (d, 2H), 7.58 (d, 2H). MS m/z 402 (M+H)$^+$. Trans-isomer: $^1$H NMR (400 MHz, cdcl$_3$) δ 1.13-1.26 (m, 3H), 1.43-1.60 (m, 1H), 1.64-1.85 (m, 1H), 1.95 (dt, 1H), 2.44-2.61 (m, 2H), 2.73-2.85 (m, 1H), 3.39 (s, 2H), 3.70 (s, 3H), 3.99-4.36 (m, 3H), 5.59 (br. s, 1H), 7.28 (d, 2H), 7.56 (d, 2H). MS m/z 402 (M+H)$^+$ Step 2: Cis-methyl 4-(3-oxo-2,3-dihydroisoxazol-5-yl)-2-(4-(trifluoromethyl)phenyl)-piperidine-1-carboxylate Cis-methyl 4-(3-ethoxy-3-oxopropanoyl)-2-(4-(trifluoromethyl)phenyl)piperidine-1-carboxylate (2.307 g, 5.75 mmol) was dissolved in MeOH (20 mL) and cooled to −40° C. under nitrogen. Sodium hydroxide (0.230 g, 5.75 mmol) dissolved in water (2 mL) was added during 10 min and the colourless solution continued to stir at −40° C. for 20 min. Hydroxylamine (50% by weight in water, 0.352 mL, 5.75 mmol) was added during 8 min. The resulting solution was stirred at −40° C. for 3 h 20 min. The mixture was then transferred into a prewarmed (80° C.) solution of 6 M hydrogen chloride (30 mL, 180.00 mmol) and the mixture continued to stir at 80° C. for 20 min. The solvent was evaporated and DCM/water added. The phases were separated and the organic phase passed through a phase separator and evaporated to yield a yellow solid. The compound was purified by preparative HPLC in 3 injections on a XBridge C18 column (10 μm 250×50 ID mm) using a gradient of 0-25% Acetonitrile in H2O/MeCN/NH3 95/5/0.2 buffer over 20 minutes with a flow of 100 mL/min. Cis-methyl 4-(3-oxo-2,3-dihydroisoxazol-5-yl)-2-(4-(trifluoromethyl)phenyl)piperidine-1-carboxylate (1.682 g, 79%) was isolated as a white solid. $^1$H NMR (400 MHz, cd$_3$od) δ 1.83-1.94 (m, 1H), 2.16-2.29 (m, 2H), 2.34-2.43 (m, 1H), 3.06-3.18 (m, 1H), 3.51 (ddd, 1H), 3.64 (s, 3H), 4.12 (ddd, 1H), 5.10-5.22 (m, 1H), 5.57 (s, 1H), 7.40 (d, 2H), 7.58 (d, 2H). MS m/z 371 (M+H)$^+$ Step 3: (2R,4S)-Methyl 4-(3-oxo-2,3-dihydroisoxazol-5-yl)-2-(4-(trifluoromethyl)phenyl)-piperidine-1-carboxylate and (2R,4S)-methyl 4-(3-oxo-2,3-dihydroisoxazol-5-yl)-2-(4-(trifluoromethyl)phenyl) piperidine-1-carboxylate Cis-methyl 4-(3-oxo-2,3-dihydroisoxazol-5-yl)-2-(4-(trifluoromethyl)phenyl)piperidine-1-carboxylate (1.682 g, 4.54 mmol) was subjected to chiral preparative HPLC (Column: Chiralpak IA (250×30), 5 μm particle size, mobile phase: 15% MeOH in CO$_2$ (175 bar), flow rate 130 mL/min, temperature 40° C.) to yield (2R,4S)-methyl 4-(3-oxo-2,3-dihydroisoxazol-5-yl)-2-(4-(trifluoromethyl)phenyl)piperidine-1-carboxylate (580 mg, 34%), Chiral purity 99.9% ee, Optical rotation $[α]_D^{20}$=+53.3 (acetonitrile, c=1) and (2S,4R)-methyl 4-(3-oxo-2,3-dihydroisoxazol-5-yl)-2-(4-(trifluoromethyl)phenyl)piperidine-1-carboxylate (591 mg, 35%), Chiral purity 98.8% ee, Optical rotation $[α]_D^{20}$=−74.2 (acetonitrile, c=1)

Step 4: 5-((2R,4S)-2-(4-(Trifluoromethyl)phenyl) piperidin-4-yl)isoxazol-3(2H)-one (2R,4S)-Methyl 4-(3-oxo-2,3-dihydroisoxazol-5-yl)-2-(4-(trifluoromethyl)phenyl)piperidine-1-carboxylate (580 mg, 1.57 mmol) was dissolved in hydrogen bromide (33% in acetic acid, 12 mL, 68.52 mmol) and the mixture stirred at room temperature for 17 h. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(4-(trifluoromethyl)phenyl)piperidin-4-yl)isoxazol-3(2H)-one (341 mg, 70%). $^1$H NMR (600 MHz, cd$_3$od) δ 1.68-1.79 (m, 2H), 2.10 (d, 1H), 2.21 (d, 1H), 2.98-3.10 (m, 2H), 3.35 (d, 1H), 3.99-4.07 (m, 1H), 5.64 (s, 1H), 7.60 (d, 2H), 7.66 (d, 2H). HRMS Calculated for $[C_{15}H_{15}F_3N_2O_2+H]^+$: 313.1164. Found: 313.1150

Example 34

5-((2S,4R)-2-(4-(Trifluoromethyl)phenyl)piperidin-4-yl)isoxazol-3(2H)-one (2S,4R)-Methyl 4-(3-oxo-2,3-dihydroisoxazol-5-yl)-2-(4-(trifluoromethyl)phenyl)piperidine-1-carboxylate (591 mg, 1.60 mmol) (from example 33, step 3) was dissolved in hydrogen bromide (33% in acetic acid, 12 mL, 68.52 mmol) and the mixture stirred at room temperature. After 24 h more hydrogen bromide (33% in acetic acid, 5 mL, 28.55 mmol) was added and the reaction continued at room temperature for a total of 1.5 days. The solvent was evaporated and the residue purified by preparative HPLC (Instrument: FractionLynx III, Mobilphase: gradient 5-95% MeCN in 0.2% NH$_3$, pH10, Column: Xbridge Prep C18 5 μm OBD 19*150 mm) to yield 5-((2S,4R)-2-(4-(trifluoromethyl)phenyl)piperidin-4-yl) isoxazol-3(2H)-one (337 mg, 67%). $^1$H NMR (600 MHz, cd$_3$od) δ 1.69-1.78 (m, 2H), 2.09 (d, 1H), 2.21 (d, 1H), 2.99-3.09 (m, 2H), 3.32-3.38 (m, 1H), 4.01-4.04 (m, 1H), 5.63 (s, 1H), 7.59 (d, 2H), 7.66 (d, 2H). HRMS Calculated for $[C_{15}H_{15}F_3N_2O_2+H]^+$: 313.1164. Found: 313.1156

Example 35

5-(Trans-2-(4-(trifluoromethyl)phenyl)piperidin-4-yl)isoxazol-3(2H)-one

Step 1: Trans-methyl 4-(3-oxo-2,3-dihydroisoxazol-5-yl)-2-(4-(trifluoromethyl)phenyl)-piperidine-1-carboxylate Trans-methyl 4-(3-ethoxy-3-oxopropanoyl)-2-(4-(trifluoromethyl)phenyl)piperidine-1-carboxylate (0.467 g, 1.16 mmol) (from example 33, step 1) was dissolved in MeOH (4 mL) and cooled to −40° C. under nitrogen. Sodium hydroxide (0.047 g, 1.16 mmol) dissolved in water (0.4 mL) was added during 10 min and the colourless solution continued to stir at −40° C. for 20 min. Hydroxylamine (50% by weight in water, 0.071 mL, 1.16 mmol) was added during 8 min. The resulting solution was stirred at −40° C. for 3.5 h. The mixture was then transferred into a prewarmed (80° C.) solution of 6 M hydrogen chloride (6 mL, 36.00 mmol) and the mixture continued to stir at 80° C. for 20 min. The solvent was evaporated and DCM/water added. The phases were separated and the organic phase passed through a phase separator and evaporated to yield crude trans-methyl 4-(3-oxo-2,3-dihydroisoxazol-5-yl)-2-(4-(trifluoromethyl)phenyl)piperidine-1-carboxylate (0.432 g, quant.) as a yellow oil. MS m/z 371 (M+H)$^+$ Step 2: 5-(Trans-2-(4-(trifluoromethyl)phenyl)piperidin-4-yl)isoxazol-3(2H)-one Trans-methyl 4-(3-oxo-2,3-dihydroisoxazol-5-yl)-2-(4-(trifluoromethyl)phenyl)piperidine-1-carboxylate (148 mg, 0.40 mmol) was dissolved in hydrogen bromide (33% in acetic acid, 3 mL, 17.13 mmol) and the solution stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 µm OBD 19*150 mm) to yield 5-(trans-2-(4-(trifluoromethyl)phenyl)piperidin-4-yl)isoxazol-3(2H)-one (50 mg, 40%). $^1$H NMR (600 MHz, dmso) δ 1.75-1.83 (m, 2H), 1.84-1.92 (m, 1H), 2.00-2.06 (m, 1H), 2.70 (dt, 1H), 2.79-2.86 (m, 1H), 3.09-3.15 (m, 1H), 3.77 (d, 1H), 5.95 (s, 1H), 7.59 (d, 2H), 7.64 (d, 2H). HRMS Calculated for $[C_{15}H_{15}F_3N_2O_2+H]^+$: 313.1164. Found: 313.1166

Example 36

5-((2R,4S)-2-(3-tert-Butylphenyl)piperidin-4-yl)isoxazol-3(2H)-one

Step 1: Methyl 2-(3-tert-butylphenyl)-4-(3-ethoxy-3-oxopropanoyl)piperidine-1-carboxylate 2-(3-tert-Butylphenyl)-1-(methoxycarbonyl)piperidine-4-carboxylic acid (2.73 g, 8.55 mmol) (reference compound 14) was dissolved in methyl THF (40 mL) and di(1H-imidazol-1-yl)methanone (2.079 g, 12.82 mmol) added. The suspension was stirred at room temperature under nitrogen for 2 h (flask 1). In a separate flask potassium 3-ethoxy-3-oxopropanoate (2.62 g, 15.39 mmol) was suspended in methyl THF (60 mL) and magnesium chloride (1.465 g, 15.39 mmol) added. The suspension was stirred at 50° C. under nitrogen for 3 h using an oversized stirring bar (flask 2). The beige suspension in flask 1 was now added to the white suspension in flask 2. The resulting beige suspension was stirred under nitrogen at room temperature for 23 h. The mixture was acidified to pH 1 with 0.5 M HCl (100 mL) and MTBE (200 mL) was added. The phases were separated and the organic phase extracted with water (30 mL), satd NaHCO$_3$ (30 mL) and water (30 mL), dried over anhydrous Na$_2$SO$_4$, and evaporated to yield crude methyl 2-(3-tert-butylphenyl)-4-(3-ethoxy-3-oxopropanoyl)-piperidine-1-carboxylate (3.14 g, 95%) as a brown oil.

Step 2: Cis-methyl 2-(3-tert-butylphenyl)-4-(3-oxo-2,3-dihydroisoxazol-5-yl)piperidine-1-carboxylate Methyl 2-(3-tert-butylphenyl)-4-(3-ethoxy-3-oxopropanoyl)piperidine-1-carboxylate (3.14 g, 8.06 mmol) was dissolved in MeOH (50 mL) and cooled to −40° C. under nitrogen. Sodium hydroxide (0.322 g, 8.06 mmol) dissolved in water (5.00 mL) was added during 5 min and the colourless mixture continued to stir at −40° C. for 20 min. Hydroxylamine (50% by weight in water, 0.494 mL, 8.06 mmol) was added during 8 min. The resulting solution was stirred at −55° C. for 6 h 30 min. The mixture was then transferred into a prewarmed (80° C.) solution of 6 M hydrogen chloride (60 mL, 360.00 mmol) and the mixture continued to stir at 80° C. for 20 min. The solvent was evaporated and DCM/water added. The phases were separated and the organic phase passed through a phase separator and evaporated to yield a brown oil. The crude was purified by preparative HPLC in 3 injections on a XBridge C18 column (10 µm 250×50 ID mm) using a gradient of 40-85% Acetonitrile in H2O/MeCN/HOAc 95/5/0.2 buffer over 25 minutes with a flow of 100 mL/min. Cis-methyl 2-(3-tert-butylphenyl)-4-(3-oxo-2,3-dihydroisoxazol-5-yl)piperidine-1-carboxylate (690 mg, 24%) was isolated. $^1$H NMR (600 MHz, cdcl$_3$) δ 1.29 (s, 9H), 1.81-1.88 (m, 1H), 2.14-2.21 (m, 1H), 2.22-2.31 (m, 1H), 2.35-2.42 (m, 1H), 3.03-3.10 (m, 1H), 3.37-3.44 (m, 1H), 3.66 (s, 3H), 4.16-4.22 (m, 1H), 5.12-5.16 (m, 1H), 5.48 (s, 1H), 6.97-7.01 (m, 1H), 7.17 (s, 1H), 7.21-7.25 (m, 2H). MS m/z 359 (M+H)$^+$ Step 3: (2R,4S)-Methyl 2-(3-tert-butylphenyl)-4-(3-oxo-2,3-dihydroisoxazol-5-yl)piperidine-1-carboxylate Cis-methyl 2-(3-tert-butylphenyl)-4-(3-oxo-2,3-dihydroisoxazol-5-yl)piperidine-1-carboxylate (690 mg, 1.93 mmol) was subjected to chiral preparative HPLC (Column: ReproSil (250×50), 8 µm particle size, mobile phase: Heptane/EtOH 40/60, flow rate 118 mL/min) to yield (2R,4S)-methyl 2-(3-tert-butylphenyl)-4-(3-oxo-2,3-dihydroisoxazol-5-yl)-piperidine-1-carboxylate (340 mg, 49%), Chiral purity 99.9% ee, Optical rotation $[\alpha]_D^{20}$=+55.8 (acetonitrile, c=1).

Step 4: 5-((2R,4S)-2-(3-tert-Butylphenyl)piperidin-4-yl)isoxazol-3(2H)-one (2R,4S)-Methyl 2-(3-tert-butylphenyl)-4-(3-oxo-2,3-dihydroisoxazol-5-yl)piperidine-1-carboxylate (0.340 g, 0.95 mmol) was dissolved in hydrogen bromide (33% in acetic acid, 5.49 mL, 31.35 mmol) and the solution stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 µm OBD 19*150 mm) to yield 5-((2R,4S)-2-(3-tert-butylphenyl)piperidin-4-yl)isoxazol-3(2H)-one (107 mg, 37%). $^1$H NMR (400 MHz, dmso) δ 1.26 (s, 9H), 1.32-1.43 (m, 1H), 1.43-1.54 (m, 1H), 1.81-1.90 (m, 1H), 1.90-1.99 (m, 1H), 2.68-2.78 (m, 1H), 2.80-2.91 (m, 1H), 3.08-3.16 (m, 1H), 3.59-3.66 (m, 1H), 5.72 (s, 1H), 7.13-7.29 (m, 3H), 7.37 (s, 1H). HRMS Calcd for $[C_{18}H_{24}N_2O_2+H]^+$: 301.1916. Found: 301.1909.

Example 37

5-(Trans-2-(4-tert-butylphenyl)piperidin-4-yl)isoxazol-3(2H)-one

Step 1: Trans-methyl 2-(4-tert-butylphenyl)-4-(3-ethoxy-3-oxopropanoyl)piperidine-1-carboxylate Magnesium chloride (5.38 g, 56.51 mmol) and potassium 3-ethoxy-3-oxopropanoate (9.62 g, 56.51 mmol) were suspended in methyl THF (100 mL) and heated to 50° C. under nitrogen for 18 h using an oversized stirring bar, then cooled to room temperature (flask 1). In a separate flask was to a suspension of 2-(4-tert-butylphenyl)-1-(methoxycarbonyl)piperidine-4-carboxylic acid (9.5 g, 29.74 mmol) (reference compound 15) in methyl THF (100 mL) added di(1H-imidazol-1-yl)methanone (7.23 g, 44.62 mmol) under nitrogen. The resulting mixture was stirred at room temperature for 4 h (flask 2). Then, the contents of flask 2 is transferred into flask 1 by transfer needle. Wash with methyl THF (30 mL). Resulting suspension stirred at room temperature for 18 h. 3.8 M HCl was added (ca. 150 mL) and the resulting biphasic mixture stirred vigorously for 2 h. The phases were separated. The organic phase was washed with water, satd NaHCO$_3$ and brine, then dried over MgSO4 and evaporated. The residue was purified via Biotage in two equal portions (Biotage® KP-SIL 340 g column, 1 CV 20% EtOAc in heptanes, then 20%=>60% over 7 CV). Trans-methyl 2-(4-tert-butylphenyl)-4-(3-ethoxy-3-oxopropanoyl)piperidine-1-carboxylate (1.09 g, 9.4%) was isolated as a pale yellow oil. $^1$H NMR (400 MHz, cdcl$_3$) δ 1.22-1.31 (m, 3H), 1.31 (s, 9H), 1.50-1.99 (m, 4H), 2.50-2.96 (m, 2H), 3.47 (s, 2H), 3.74 (s, 3H), 4.08-4.23 (m, 3H), 5.46-5.71 (m, 1H), 7.09-7.16 (m, 2H), 7.34-7.40 (m, 2H).

Step 2: Trans-methyl 2-(4-tert-butylphenyl)-4-(3-oxo-2,3-dihydroisoxazol-5-yl)piperidine-1-carboxylate Trans-methyl 2-(4-tert-butylphenyl)-4-(3-ethoxy-3-oxopropanoyl)piperidine-1-carboxylate (1.09 g, 2.80 mmol) was dissolved in MeOH (10 mL) and cooled to −40° C. Sodium hydroxide (0.112 g, 2.80 mmol) dissolved in water (1.2 mL) was added over 1 min and the resulting solution was stirred at −40° C. for 20 min. Then, hydroxylamine (50% in water, 0.178 mL, 2.91 mmol) was added over 1 min and stirring continued at −40° C. for 3 h. The reaction mixture was then transferred into a prewarmed (80° C.) solution of 6M hydrogen chloride (30 mL, 180.00 mmol) and the mixture was continued to be stirred at 80° C. for 1 h. Then cooled to room temperature. Methanol was evaporated, then water was added. Extracted three times with DCM. Combined organic layers dried over MgSO$_4$ and evaporated. Crude trans-methyl 2-(4-tert-butylphenyl)-4-(3-oxo-2,3-dihydroisoxazol-5-yl)piperidine-1-carboxylate (910 mg, 90%) was isolated as off-white foam. $^1$H NMR (400 MHz, cdcl$_3$) δ 1.32 (s, 9H), 1.46-2.23 (m, 3H), 2.46-3.05 (m, 3H), 3.74 (s, 3H), 3.98-4.43 (m, 1H), 5.48-5.72 (m, 2H), 7.10-7.22 (m, 2H), 7.35-7.45 (m, 2H). MS m/z 359 (M+H)$^+$ Step 3: 5-(Trans-2-(4-tert-butylphenyl)piperidin-4-yl)isoxazol-3(2H)-one Trans-methyl 2-(4-tert-butylphenyl)-4-(3-oxo-2,3-dihydroisoxazol-5-yl)piperidine-1-carboxylate (0.26 g, 0.73 mmol) was dissolved in hydrogen bromide (33% in acetic acid, 5 mL, 71.37 mmol) and stirred at room temperature for 18 h. Solvents were evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(4-tert-butylphenyl)piperidin-4-yl)isoxazol-3(2H)-one (182 mg, 84%). $^1$H NMR (600 MHz, dmso) δ 1.23 (s, 9H), 1.76-1.85 (m, 2H), 1.86-1.93 (m, 1H), 1.96-2.03 (m, 1H), 2.71 (td, 1H), 2.81-2.88 (m, 1H), 3.10-3.15 (m, 1H), 3.65 (dd, 1H), 5.90 (s, 1H), 7.24-7.33 (m, 4H). HRMS Calculated for [C$_{18}$H$_{24}$N$_2$O$_2$+H]$^+$: 301.1916. Found: 301.1919

Example 38

5-((2R,4S)-2-(4-(Methylsulfonyl)phenyl)piperidin-4-yl)isoxazol-3(2H)-one

Step 1: Trans-methyl 4-(3-ethoxy-3-oxopropanoyl)-2-(4-(methylsulfonyl)phenyl)piperidine-1-carboxylate and cis-methyl 4-(3-ethoxy-3-oxopropanoyl)-2-(4-(methylsulfonyl)phenyl)-piperidine-1-carboxylate 1-(Methoxycarbonyl)-2-(4-(methylsulfonyl)phenyl)piperidine-4-carboxylic acid (4.756 g, 13.93 mmol) was dissolved in methyl THF (70 mL) and di(1H-imidazol-1-yl) methanone (3.39 g, 20.90 mmol) added. A thick white precipitate was formed. methyl THF (70.0 mL) was added and the suspension stirred under nitrogen at room temperature for 6 h (flask 1). In a separate flask potassium 3-ethoxy-3-oxopropanoate (4.74 g, 27.86 mmol) was suspended in methyl THF (70.0 mL) and magnesium chloride (2.65 g, 27.86 mmol) added. Heated at 50° C. under nitrogen for 6 h (flask 2). The white suspension in flask 2 was then added to the thick white suspension in flask 1. The suspension was stirred at room temperature for 16 h. The temperature was increased to 50° C. for 6 h. More of potassium 3-ethoxy-3-oxopropanoate (4.74 g, 27.86 mmol) and magnesium chloride (2.65 g, 27.86 mmol) in MeTHF (15 mL) was added along with dioxane (60 mL). The reaction was stirred at 50° C. for 18 h. The reaction mixture was acidified to pH 1 with 3 M HCl. The organic phase was washed with water (2×400 mL), satd NaHCO$_3$ (400 mL), brine (400 mL), dried with Na$_2$SO$_4$, filtered and evaporated in vacuo. The residue was purified by automated flash chromatography on a Biotage® KP-SIL 100 g column. A gradient from 50% EtOAc in heptane over 2 CV followed by 50% to 80% of EtOAc in heptane over 10 CV was used as mobile phase. Cis-methyl 4-(3-ethoxy-3-oxopropanoyl)-2-(4-(methylsulfonyl)phenyl)piperidine-1-carboxylate (2.70 g, 47.1%) and trans-methyl 4-(3-ethoxy-3-oxopropanoyl)-2-(4-(methylsulfonyl)phenyl)-piperidine-1-carboxylate (0.505 g, 8.81%) were isolated. Cis-isomer: NMR: $^1$H NMR (600 MHz, CDCl3) δ 1.25 (t, 3H), 1.80-1.95 (m, 2H), 2.04-2.16 (m, 1H), 2.23-2.32 (m, 1H), 2.84-2.95 (m, 1H), 3.02 (s, 3H), 3.29-3.38 (m, 1H), 3.38-3.48 (m, 2H), 3.63 (s, 3H), 4.10-4.21 (m, 3H), 4.95-5.04 (m, 1H), 7.40 (d, 2H), 7.88 (d, 2H). MS m/z 410 (M−H)$^-$. Trans-isomer: $^1$H NMR (600 MHz, cdcl$_3$) δ 1.23 (t, 3H), 1.12-2.26 (m, 3H), 2.51-2.62 (m, 2H), 2.83 (td, 1H), 3.04 (s, 3H), 3.40-3.48 (s, 2H), 3.75 (s, 3H), 4.07-4.38 (m, 1H), 4.15 (q, 2H), 5.49-5.77 (m, 1H), 7.41 (d, 2H), 7.93 (d, 2H). MS m/z 412 (M+H)$^+$ Step 2: Cis-methyl 2-(4-(methylsulfonyl)phenyl)-4-(3-oxo-2,3-dihydroisoxazol-5-yl)piperidine-1-carboxylate Cis-methyl 4-(3-ethoxy-3-oxopropanoyl)-2-(4-(methylsulfonyl)phenyl)piperidine-1-carboxylate (2.6 g, 6.32 mmol) was suspended in MeOH (100 mL). DCM (40 mL) was added and the reaction cooled to −40° C. 3.8 M sodium hydroxide (1.663 mL, 6.32 mmol) in water (10.00 mL) was added and the reaction stirred at −40° C. for 20 min. Hydroxylamine (50% in water, 0.387 mL, 6.32 mmol) was added and the reaction stirred at −40° C. for 3 h. The reaction mixture was then added to a prewarmed 80° C. solution of 6 M hydrogen chloride (63.2 mL, 379.13 mmol) and the reaction stirred for 30 min. The solvent was evaporated in vacuo. DCM (250 mL) and water (250 mL) were added, shaken and the phases separated. The organic phase was dried with a phase separator and evaporated in vacuo. The compound was purified by preparative HPLC on a Kromasil C8 column (10 μm 250×50 ID mm) using a gradient of 15-45% Acetonitrile in H2O/MeCN/AcOH 95/5/0.2 buffer over 30 minutes with a flow of 100 mL/min. Cis-methyl 2-(4-(methylsulfonyl)phenyl)-4-(3-oxo-2,3-dihydroisoxazol-5-yl)piperidine-1-carboxylate (1.200 g, 49.9%) was isolated as a white solid. $^1$H NMR (600 MHz, cdcl$_3$) δ 1.85-1.91 (m, 1H), 2.18-2.29 (m, 2H), 2.35-2.41 (m, 1H), 2.98 (s, 3H), 3.00-3.13 (m, 1H), 3.38-3.44 (m, 1H), 3.67 (s, 3H), 4.13-4.19 (m, 1H), 5.20 (t, 1H), 5.47 (s, 1H), 7.34 (d, 2H), 7.83 (d, 2H). MS m/z 381 (M+H)$^+$ Step 3: (2R,4S)-Methyl 2-(4-(methylsulfonyl)phenyl)-4-(3-oxo-2,3-dihydroisoxazol-5-yl)piperidine-1-carboxylate Cis-methyl 2-(4-(methylsulfonyl)phenyl)-4-(3-oxo-2,3-dihydroisoxazol-5-yl)piperidine-1-carboxylate (1.200 g, 3.16 mmol) was subjected to chiral preparative HPLC (Column: ReproSil (250×50), 8 μm particle size, mobile phase: EtOH, flow rate 120 mL/min) to yield (2R,4S)-methyl 2-(4-(methylsulfonyl)phenyl)-4-(3-oxo-2,3-dihydroisoxazol-5-yl)piperidine-1-carboxylate (536 mg, 45%), Chiral purity 99.9% ee, Optical rotation $[\alpha]_D^{20}=+59.5$ (acetonitrile, c=1), $^1$H NMR (600 MHz, cdcl$_3$) δ 1.78-1.85 (m, 1H), 2.12-2.23 (m, 2H), 2.29-2.37 (m, 1H), 2.93 (s, 3H), 3.02-3.08 (m, 1H), 3.33-3.41 (m, 1H), 3.61 (s, 3H), 4.07-4.13 (m, 1H), 5.14 (t, 1H), 5.44 (s, 1H), 7.31 (d, 2H), 7.77 (d, 2H).

Step 4: 5-((2R,4S)-2-(4-(Methylsulfonyl)phenyl) piperidin-4-yl)isoxazol-3(2H)-one (2R,4S)-Methyl 2-(4-(methylsulfonyl)phenyl)-4-(3-oxo-2,3-dihydroisoxazol-5-yl)piperidine-1-carboxylate (536 mg, 1.41 mmol) was dissolved in hydrogen bromide (33% in AcOH, 5 mL, 71.37 mmol) and stirred at room temperature for 20 h. The reaction mixture was evaporated and the residue purified by preparative HPLC (Instrument: FractionLynx III, Mobilphase: gradient 5-95% MeCN in 0.2% NH$_3$, pH10, Column: Xbridge Prep C18 5 μm OBD 19*150 mm) to yield 5-((2R,4S)-2-(4-(methylsulfonyl)phenyl)piperidin-4-yl) isoxazol-3(2H)-one (309 mg, 68%), $^1$H NMR (600 MHz, dmso) δ 1.39 (q, 1H), 1.49 (dq, 1H), 1.87-1.93 (m, 1H), 2.01 (d, 1H), 2.76 (t, 1H), 2.87-2.94 (m, 1H), 3.11-3.19 (m, 1H), 3.17 (s, 3H), 3.80 (d, 1H), 5.74 (s, 1H), 7.64 (d, 2H), 7.85 (d, 2H). HRMS Calcd for $[C_{15}H_{18}N_2O_4S+H]^+$: 323.1065. Found: 323.1042.

Example 39

5-((Trans-2-(4-(methylsulfonyl)phenyl)piperidin-4-yl)isoxazol-3(2H)-one

Step 1: Trans-methyl 2-(4-(methylsulfonyl)phenyl)-4-(3-oxo-2,3-dihydroisoxazol-5-yl)-piperidine-1-carboxylate Trans-methyl 4-(3-ethoxy-3-oxopropanoyl)-2-(4-(methylsulfonyl)phenyl)piperidine-1-carboxylate (505 mg, 1.23 mmol) (from example 38, step 1) was suspended in MeOH (5 mL) and cooled to −40° C. 3.8 M sodium hydroxide (0.323 mL, 1.23 mmol) in water was added. After 20 min, hydroxylamine (50% in water, 0.075 mL, 1.23 mmol) was added and stirring continued at −40° C. for 3 h. The reaction mixture was then added to a prewarmed 80° C. solution of 6 M hydrogen chloride (6.14 mL, 36.82 mmol) and stirred for 20 min. The solvent was evaporated in vacuo. DCM (50 mL) and water (50 mL) were added, shaken and the phases separated. The organic phase was dried with a phase separator and evaporated in vacuo. The residue was purified by preparative HPLC on a Kromasil C8 column (10 μm 250×20 ID mm) using a gradient of 15-40% Acetonitrile in H2O/MeCN/AcOH 95/5/0.2 buffer, over 25 minutes with a flow of 19 mL/min. Trans-methyl 2-(4-(methylsulfonyl)phenyl)-4-(3-oxo-2,3-dihydroisoxazol-5-yl)piperidine-1-carboxylate (301 mg, 64.5%) was isolated. $^1$H NMR (600 MHz, cdcl$_3$) δ 1.61-1.73 (m, 1H), 1.91-1.99 (m, 1H), 2.05-2.14 (m, 1H), 2.66-2.82 (m, 2H), 2.91 (t, 1H), 3.05 (s, 3H), 3.77 (s, 3H), 4.12-4.46 (m, 1H), 5.60-5.80 (m, 2H), 7.44 (d, 2H), 7.95 (d, 2H). MS m/z 381 (M+H)$^+$ Step 2: 5-(Trans-2-(4-(methylsulfonyl)phenyl)piperidin-4-yl)isoxazol-3(2H)-one Trans-methyl 2-(4-(methylsulfonyl)phenyl)-4-(3-oxo-2,3-dihydroisoxazol-5-yl)piperidine-1-carboxylate (301 mg, 0.79 mmol) was dissolved in hydrogen bromide (33% in acetic acid, 2 mL, 28.55 mmol) and stirred at room temperature for 20 h. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(4-(methylsulfonyl)phenyl)piperidin-4-yl)isoxazol-3(2H)-one (119 mg, 47%), HRMS Calcd for $[C_{15}H_{18}N_2O_4S+H]^+$: 323.1065. Found: 323.1054.

Example 40

5-((2R,4S)-2-(6-(Trifluoromethyl)pyridin-3-yl)piperidin-4-yl)isoxazol-3(2H)-one

Step 1: Trans-methyl 4-(3-ethoxy-3-oxopropanoyl)-2-(6-(trifluoromethyl)pyridin-3-yl)piperidine-1-carboxylate and cis-methyl 4-(3-ethoxy-3-oxopropanoyl)-2-(6-(trifluoro-methyl)pyridin-3-yl) piperidine-1-carboxylate 1-(Methoxycarbonyl)-2-(6-(trifluoromethyl)pyridin-3-yl) piperidine-4-carboxylic acid (2.5 g, 3.76 mmol) (reference compound 17) was dissolved in methyl THF (80 mL) then di(1H-imidazol-1-yl)methanone (1.098 g, 6.77 mmol) was added. The mixture was stirred at room temperature under nitrogen for 3 h (flask 1). In a separate flask potassium 3-ethoxy-3-oxopropanoate (1.153 g, 6.77 mmol) was suspended in methyl THF (80 mL), then magnesium chloride (0.645 g, 6.77 mmol) was added. The suspension was stirred at 50° C. under nitrogen for 3 h using a large magnetic stirring bar (flask 2). After 3 h, the contents of flask 1 was transferred into flask 2. The resulting white suspension was stirred under nitrogen at room temperature overnight. The mixture was acidified to pH 1 with 3.8 M HCl, then MTBE (50 mL) and water (50 mL) was added. The phases were separated and the organic layer was washed with water, satd NaHCO$_3$ and brine. The organic layer was dried over Na$_2$SO$_4$, filtered and evaporated leaving a slightly yellow oil. The product was flashed on Biotage (340 g) with 1 CV at 20% followed by a gradient of 20-60% EtOAc in n-heptane (8 CV). Trans-methyl 4-(3-ethoxy-3-oxopropanoyl)-2-(6-(trifluoromethyl)pyridin-3-yl)piperidine-1-carboxylate (70 mg, 5%) and cis-methyl 4-(3-ethoxy-3-oxopropanoyl)-2-(6-(trifluoro-methyl) pyridin-3-yl)piperidine-1-carboxylate (1.085 g, 72%) were isolated. Cis-isomer: MS m/z 403 (M+H)$^+$. Trans-isomer: $^1$H NMR (400 MHz, cdcl$_3$) δ 1.18-1.31 (m, 3H), 1.53-1.72 (m, 1H), 1.82-1.93 (m, 1H), 2.00-2.13 (m, 1H), 2.49-2.69 (m, 2H), 2.82 (dt, 1H), 3.46 (d, 2H), 3.76 (s, 3H), 4.10-4.40 (m, 3H), 5.72 (s, br., 1H), 7.64-7.77 (m, 2H), 8.63 (s, 1H). MS m/z 403 (M+H)$^+$ Step 2: Cis-methyl 4-(3-oxo-2,3-dihydroisoxazol-5-yl)-2-(6-(trifluoromethyl)pyridin-3-yl)-piperidine-1-carboxylate Cis-methyl 4-(3-ethoxy-3-oxopropanoyl)-2-(6-(trifluoromethyl)pyridin-3-yl)piperidine-1-carboxylate (1.085 g, 2.70 mmol) was dissolved in MeOH (12 mL) and cooled to −45° C. under nitrogen. Sodium hydroxide (0.793 mL, 2.70 mmol) was added during 10 min and the yellow solution continued to stir at −45° C. for 20 min. Hydroxylamine (50% by weight in water, 0.165 mL, 2.70 mmol) was added during 8 min. The resulting solution was stirred at −45° C. for 3 h. The mixture was then rapidly poured into a prewarmed (80° C.) solution of 6 M hydrogen chloride (13.89 mL, 83.32 mmol) and the mixture continued to stir at 80° C. for 20 min.

The solvent was evaporated and DCM/water added. The phases were separated and the organic phase passed through a phase separator and evaporated to yield a white solid. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 4-(3-oxo-2,3-dihydroisoxazol-5-yl)-2-(6-(trifluoromethyl)pyridin-3-yl)piperidine-1-carboxylate (160 mg, 16%) was isolated. MS m/z 372 (M+H)$^+$ Step 3: (2R,4S)-Methyl 4-(3-oxo-2,3-dihydroisoxazol-5-yl)-2-(6-(trifluoromethyl)pyridin-3-yl)piperidine-1-carboxylate Cis-methyl 4-(3-oxo-2,3-dihydroisoxazol-5-yl)-2-(6-(trifluoromethyl)pyridin-3-yl)piperidine-1-carboxylate (160 mg, 0.43 mmol) was subjected to chiral preparative HPLC (Column: CelluCoat (250×50 mm), 10 μm particle size, mobile phase: Heptane/EtOH 50/50, flow rate 120 mL/min) to yield (2R,4S)-methyl 4-(3-oxo-2,3-dihydroisoxazol-5-yl)-2-(6-(trifluoro-methyl)pyridin-3-yl)piperidine-1-carboxylate (74.5 mg, 47%), Chiral purity 99.9% ee, Optical rotation $[\alpha]_D^{20}$=+32.0 (acetonitrile, c=0.1)

Step 4: 5-((2R,4S)-2-(6-(Trifluoromethyl)pyridin-3-yl)piperidin-4-yl)isoxazol-3(2H)-one (2R,4S)-Methyl 4-(3-oxo-2,3-dihydroisoxazol-5-yl)-2-(6-(trifluoromethyl)pyridin-3-yl)-piperidine-1-carboxylate (74.5 mg, 0.20 mmol) was dissolved in hydrogen bromide (33% in acetic acid, 1.58 mL, 9.03 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(6-(trifluoromethyl)pyridin-3-yl)piperidin-4-yl)isoxazol-3(2H)-one (43 mg, 68%), $^1$H NMR (600 MHz, dmso) δ 1.36-1.53 (m, 2H), 1.89 (d, 1H), 2.04 (d, 1H), 2.70-2.78 (m, 1H), 2.90 (tt, 1H), 3.09-3.16 (m, 1H), 3.83 (d, 1H), 5.75 (s, 1H), 7.84 (d, 1H), 8.04 (dd, 1H), 8.75 (d, 1H). HRMS Calculated for [C$_{14}$H$_{14}$F$_3$N$_3$O$_2$+H]$^+$: 314.1116. Found: 314.1134

Example 41

5-(Trans-2-(6-(trifluoromethyl)pyridin-3-yl)piperidin-4-yl)isoxazol-3(2H)-one

Step 1: Trans-methyl 4-(3-oxo-2,3-dihydroisoxazol-5-yl)-2-(6-(trifluoromethyl)pyridin-3-yl)piperidine-1-carboxylate Trans-methyl 4-(3-ethoxy-3-oxopropanoyl)-2-(6-(trifluoromethyl)pyridin-3-yl)piperidine-1-carboxylate (70 mg, 0.17 mmol) (from example 40, step 1) was dissolved in MeOH (1 mL) and cooled to −45° C. under nitrogen. Sodium hydroxide (0.051 mL, 0.17 mmol) was added during 10 min and the yellow solution continued to stir at −45° C. for 20 min. Hydroxylamine (50% by weight in water, 10.66 μL, 0.17 mmol) was added during 8 min. The resulting solution was stirred at −45° C. for 3 h. The mixture was then rapidly poured into a prewarmed (80° C.) solution of 6 M hydrogen chloride (0.896 mL, 5.38 mmol) and the mixture continued to stir at 80° C. for 20 min. The solvent was evaporated and DCM/water added. The phases were separated and the organic phase passed through a phase separator and evaporated to yield crude trans-methyl 4-(3-oxo-2,3-dihydroisoxazol-5-yl)-2-(6-(trifluoromethyl)pyridin-3-yl)piperidine-1-carboxylate (60 mg, quant.) as a slightly yellow oil. MS m/z 372 (M+H)$^+$ Step 2: 5-(Trans-2-(6-(trifluoromethyl)pyridin-3-yl)piperidin-4-yl)isoxazol-3(2H)-one Trans-methyl 4-(3-oxo-2,3-dihydroisoxazol-5-yl)-2-(6-(trifluoromethyl)pyridin-3-yl)-piperidine-1-carboxylate (60 mg, 0.16 mmol) was dissolved in hydrogen bromide (33% in acetic acid, 1.27 mL, 7.27 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(6-(trifluoromethyl)pyridin-3-yl)piperidin-4-yl)isoxazol-3(2H)-one (11.4 mg, 23%), $^1$H NMR (400 MHz, dmso) δ 1.77-1.99 (m, 3H), 2.06-2.16 (m, 1H), 2.69-2.80 (m, 1H), 2.83-2.94 (m, 1H), 3.07-3.59 (m, 1H), 3.94 (d, 1H), 6.03 (s, 1H), 7.86 (d, 1H), 8.08 (d, 1H), 8.78 (s, 1H). HRMS Calculated for [C$_{14}$H$_{14}$F$_3$N$_3$O$_2$+H]$^+$: 314.1116. Found: 314.1122

Example 42

5-((2R,4S)-2-(5-tert-Butylthiophen-2-yl)piperidin-4-yl)isoxazol-3(2H)-one

Step 1: Cis-methyl 2-(5-tert-butylthiophen-2-yl)-4-(3-ethoxy-3-oxopropanoyl)piperidine-1-carboxylate 2-(5-tert-Butylthiophen-2-yl)-1-(methoxycarbonyl)piperidine-4-carboxylic acid (1.125 g, 3.46 mmol) (reference compound 18) was dissolved in THF (30 mL) and di(1H-imidazol-1-yl)methanone (0.911 g, 5.62 mmol) added. The suspension was stirred at room temperature under nitrogen for 6 h (flask 1). In a separate flask 3-ethoxy-3-oxopropanoic acid, potassium salt (1.509 g, 8.82 mmol) and magnesium chloride (0.84 g, 8.82 mmol) were suspended in THF (30 mL) and stirred with an oversized stirring bar at 50° C. under nitrogen for 20 h (flask 2). The white suspension in flask 2 was then added to flask 1. The thick white suspension was stirred at room temperature for 18 h. The reaction mixture was acidified by addition of 3 M HCl to pH 1. The solvent was evaporated in vacuo. MTBE (250 mL) and water were added, shaken and the phases separated. The organic phase was washed with water (200 mL), satd NaHCO$_3$ (200 mL), brine (200 mL), dried with a phase separator and evaporated in vacuo. The residue was purified by automated flash chromatography on a Biotage® KP-SIL 100 g column. A gradient from 10% EtOAc in heptane over 2 CV followed by 10% to 40% of EtOAc in heptane over 9 CV was used as mobile phase. Cis-methyl 2-(5-tert-butylthiophen-2-yl)-4-(3-ethoxy-3-oxopropanoyl)piperidine-1-carboxylate (0.963 g, 70.4%) was isolated. Cis-isomer: MS m/z 396 (M+H)$^+$ Step 2: Cis-methyl 245-tert-butylthiophen-2-yl)-4-(3-oxo-2,3-dihydroisoxazol-5-yl)-piperidine-1-carboxylate Cis-methyl 2-(5-tert-butylthiophen-2-yl)-4-(3-ethoxy-3-oxopropanoyl)piperidine-1-carboxylate (963 mg, 2.43 mmol) was dissolved in methanol (15 mL) and cooled to −40° C. NaOH (0.641 mL, 2.43 mmol) dissolved in water (1 mL) was added and stirred for 20 min. Hydroxylamine (50% by weight in water, 0.149 mL, 2.43 mmol) was added and the reaction stirred at −40° C. for 3 h. The reaction mixture was then added to a prewarmed 80° C. solution of 6 M HCl (12.58 mL, 75.48 mmol) and stirred for 20 min. The solvent was evaporated in vacuo. DCM (150 mL) and water (150 mL) were added, shaken and the phases separated. The aqueous phase was extracted with DCM (150 mL). The combined organic phase were dried with a phase separator and evaporated in vacuo. The compound was purified by preparative HPLC on a Kromasil C8 column (10 μm 250×50 ID mm) using a gradient of 35-75% Acetonitrile in H2O/MeCN/AcOH 95/5/0.2 buffer over 25 minutes with a flow of 100 mL/min. Cis-methyl 2-(5-tert-butylthiophen-2-yl)-4-(3-oxo-2,3-dihydroisoxazol-5-yl)piperidine-1-carboxylate (436 mg, 49.1%) was isolated as a white solid. MS m/z 363 (M−H)−

Step 3: (2R,4S)-Methyl 2-(5-tert-butylthiophen-2-yl)-4-(3-oxo-2,3-dihydroisoxazol-5-yl)piperidine-1-carboxylate and (2S,4R)-methyl 2-(5-tert-butylthiophen-2-yl)-4-(3-oxo-2,3-dihydroisoxazol-5-yl)piperidine-1-carboxylate Cis-methyl 2-(5-tert-butylthiophen-2-yl)-4-(3-oxo-2,3-dihydroisoxazol-5-yl)piperidine-1-carboxylate (436 mg, 1.2 mmol) was subjected to chiral preparative HPLC (Column: CelluCoat (250×20 mm), 5 μm particle size, mobile phase: Heptane/EtOH 80/20, flow rate 18 mL/min) to yield (2R,4S)-methyl 2-(5-tert-butylthiophen-2-yl)-4-(3-oxo-2,3-dihydroisoxazol-5-yl)piperidine-1-carboxylate (212 mg, 49%), Chiral purity 98.7% ee, Optical rotation $[\alpha]_D^{20}$=+3.0 (acetonitrile, c=1.0), $^1$H NMR (600 MHz, cdcl$_3$) δ 1.34 (s, 9H), 1.55-1.68 (m, 1H), 1.90-2.04 (m, 2H), 2.49 (d, 1H), 3.12 (s, br., 2H), 3.76 (s, 3H), 4.19 (d, br., 1H), 5.60-5.87 (m, 2H), 6.59-6.69 (m, 2H) and (2S,4R)-methyl 2-(5-tert-butylthiophen-2-yl)-4-(3-oxo-2,3-dihydroisoxazol-5-yl)piperidine-1-carboxylate (210 mg, 48%), Chiral purity 99.3% ee, Optical rotation $[\alpha]_D^{20}$=−1.1 (acetonitrile, c=1.0), $^1$H NMR (600 MHz, cdcl$_3$) δ 1.33 (s, 9H), 1.54-1.66 (m, 1H), 1.88-2.03 (m, 2H), 2.48 (d, 1H), 3.11 (s, br., 2H), 3.74 (s, 3H), 4.17 (d, br., 1H), 5.58-5.85 (m, 2H), 6.58-6.67 (m, 2H).

Step 4: 5-((2R,4S)-2-(5-tert-butylthiophen-2-yl)piperidin-4-yl)isoxazol-3(2H)-one (2R,4S)-Methyl 245-tert-butylthiophen-2-yl)-4-(3-oxo-2,3-dihydroisoxazol-5-yl)piperidine-1-carboxylate (50 mg, 0.14 mmol) was dissolved in hydrobromic acid (33% in acetic acid, 1 mL, 6.08 mmol) and stirred at room temperature for 24 h. The solvent was evaporated in vacuo and the residue was purified by preparative HPLC on a XBridge C18 column (10 μm 250×19 ID mm) using a gradient of 10-50% Acetonitrile in H2O/MeCN/NH3 95/5/0.2 buffer over 25 minutes with a flow of 19 mL/min. 5-((2R,4S)-2-(5-tert-Butylthiophen-2-yl)piperidin-4-yl)isoxazol-3(2H)-one (4.00 mg, 9.52%) was isolated as a white solid. $^1$H NMR (400 MHz, cd$_3$od) δ 1.36 (s, 9H), 1.99-2.17 (m, 2H), 2.20-2.31 (m, 1H), 2.36-2.44 (m, 1H), 3.05-3.21 (m, 2H), 3.28-3.37 (m, 1H), 4.37 (dd, 1H), 5.70 (d, 1H), 6.77 (d, 1H), 6.93 (d, 1H). HRMS Calculated for $[C_{16}H_{22}N_2O_2S+H]^+$: 307.1480. Found: 307.1502

Example 43

5-((2S,4R)-2-(5-tert-Butylthiophen-2-yl)piperidin-4-yl)isoxazol-3(2H)-one (2S,4R)-Methyl 2-(5-tert-butylthiophen-2-yl)-4-(3-oxo-2,3-dihydroisoxazol-5-yl)piperidine-1-carboxylate (50 mg, 0.14 mmol) (from example 42, step 3) was dissolved in hydrobromic acid (33% in AcOH, 1 mL, 6.08 mmol) and stirred at room temperature for 20 h. The solvent was evaporated in vacuo. The compound was purified by preparative HPLC on a XBridge C18 column (10 μm 250×19 ID mm) using a gradient of 10-50% Acetonitrile in H2O/MeCN/NH3 95/5/0.2 buffer over 25 minutes with a flow of 19 mL/min. 5-((2S,4R)-2-(5-tert-Butylthiophen-2-yl)piperidin-4-yl) isoxazol-3(2H)-one (7.00 mg, 16.65%) was isolated as a white solid. $^1$H NMR (600 MHz, cd$_3$od) δ 1.36 (s, 9H), 2.03-2.12 (m, 1H), 2.12-2.19 (m, 1H), 2.26-2.33 (m, 1H), 2.40-2.46 (m, 1H), 3.09-3.17 (m, 1H), 3.18-3.24 (m, 1H), 3.34-3.40 (m, 1H), 4.38-4.44 (m, 1H), 5.75 (s, 1H), 6.78 (d, 1H), 6.96 (d, 1H).

Example 44

5-((2R,4S)-2-(2,4-Difluorophenyl)piperidin-4-yl)isoxazol-3(2H)-one

Step 1: Cis-methyl 2-(2,4-difluorophenyl)-4-(3-ethoxy-3-oxopropanoyl)piperidine-1-carboxylate 2-(2,4-Difluorophenyl)-1-(methoxycarbonyl)piperidine-4-carboxylic acid (2.20 g, 7.35 mmol) (reference compound 19) was dissolved in methyl THF (70 mL), then di(1H-imidazol-1-yl)methanone (2.146 g, 13.23 mmol) was added. The mixture was stirred at room temperature under nitrogen for 5 h (flask 1). In a separate flask potassium 3-ethoxy-3-oxopropanoate (2.252 g, 13.23 mmol) was suspended in methyl THF (70.0 mL), then magnesium chloride (1.260 g, 13.23 mmol) was added. The suspension was stirred at 50° C. under nitrogen for 5 h using a large magnetic stirring bar (flask 2). After the 3 h, the contents of flask 1 was transferred into flask 2. The resulting white suspension was stirred under nitrogen at room temperature overnight. The mixture was acidified to pH 1 with 3.8 M HCl, then MTBE (50 mL) and water (50 mL) was added. The phases were separated and the organic layer was washed with water, satd NaHCO3 and brine. The organic layer was dried over Na2SO4, filtered and evaporated leaving a slightly yellow oil. The product was flashed on Biotage (340 g) with 1 CV EtOAc in heptane (20%) followed by a gradient of 20-60% EtOAc in n-heptane (8 CV). The column was conditioned at 20% EtOAc in -n-heptane (1 CV). Cis-methyl 2-(2,4-difluorophenyl)-4-(3-ethoxy-3-oxopropanoyl)piperidine-1-carboxylate (870 mg, 32%) was isolated. MS m/z 370 (M+H)+

Step 2: Cis-methyl 2-(2,4-difluorophenyl)-4-(3-oxo-2,3-dihydroisoxazol-5-yl)piperidine-1-carboxylate Cis-methyl 2-(2,4-difluorophenyl)-4-(3-ethoxy-3-oxopropanoyl)piperidine-1-carboxylate (870 mg, 2.36 mmol) was dissolved in MeOH (9 mL) and cooled to −45° C. under nitrogen. Sodium hydroxide (0.693 mL, 2.36 mmol) was added during 10 min and the yellow solution continued to stir at −45° C. for 20 min. Hydroxylamine (50% by weight in water, 0.144 mL, 2.36 mmol) was added during 8 min. The resulting solution was stirred at −45° C. for 3 h. The mixture was then rapidly poured into a prewarmed (80° C.) solution of 6 M hydrogen chloride (12.13 mL, 72.78 mmol) and the mixture continued to stir at 80° C. for 20 min. The solvent was evaporated and DCM/water added. The phases were separated and the organic phase passed through a phase separator and evaporated to yield a white solid. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 2-(2,4-difluorophenyl)-4-(3-oxo-2,3-dihydroisoxazol-5-yl)piperidine-1-carboxylate (397 mg, 49%) was isolated. MS m/z 339 (M+H)$^+$ Step 3: (2R,4S)-Methyl 2-(2,4-difluorophenyl)-4-(3-oxo-2,3-dihydroisoxazol-5-yl)piperidine-1-carboxylate Cis-methyl 2-(2,4-difluorophenyl)-4-(3-oxo-2,3-dihydroisoxazol-5-yl)piperidine-1-carboxylate (397 mg, 1.17 mmol) was subjected to chiral preparative HPLC (Column: CelluCoat (250×50 mm), 10 μm particle size, mobile phase: Heptane/EtOH 60/40, flow rate 120 mL/min) to yield (2R,4S)-methyl 2-(2,4-difluorophenyl)-4-(3-oxo-2,3-dihydroisoxazol-5-yl)piperidine-1-carboxylate (187 mg, 47%), Chiral purity 99.1% ee, Optical rotation [α]$_D^{20}$=+65.0 (acetonitrile, c=0.5), $^1$H NMR (400 MHz, cdcl$_3$) δ 1.82-1.92 (m, 1H), 2.02-2.14 (m, 1H), 2.23-2.40 (m, 2H), 3.01-3.13 (m, 1H), 3.44-3.55 (m, 1H), 3.63 (s, 3H), 4.11-4.21 (m, 1H), 5.16 (dd, 1H), 5.61 (s, 1H), 6.74-6.83 (m, 2H), 7.06-7.15 (m, 1H).

Step 4: 5-((2R,4S)-2-(2,4-difluorophenyl)piperidin-4-yl)isoxazol-3(2H)-one (2R,4S)-methyl 2-(2,4-difluorophenyl)-4-(3-oxo-2,3-dihydroisoxazol-5-yl)piperidine-1-carboxylate (187 mg, 0.55 mmol) was dissolved in hydrogen bromide (33% in acetic acid, 4.36 mL, 24.87 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(2,4-difluorophenyl)piperidin-4-yl)isoxazol-3(2H)-one (93 mg, 60%). $^1$H NMR (600 MHz, dmso) δ 1.36 (q, 1H), 1.46 (dq, 1H), 1.83-1.89 (m, 1H), 1.90-1.95 (m, 1H), 2.72 (dt, 1H), 2.89 (tt, 1H), 3.06-3.12 (m, 1H), 3.89 (dd, 1H), 5.73 (s, 1H), 7.03 (dt, 1H), 7.11-7.17 (m, 1H), 7.52-7.59 (m, 1H). HRMS Calculated for [C$_{14}$H$_{14}$F$_2$N$_2$O$_2$+H]$^+$: 281.1101. Found: 281.1106

Example 45

5-((2R,4S)-2-(4-Chloro-2-fluorophenyl)piperidin-4-yl)isoxazol-3(2H)-one

Step 1: Trans-methyl 2-(4-chloro-2-fluorophenyl)-4-(3-ethoxy-3-oxopropanoyl)piperidine-1-carboxylate and cis-methyl 2-(4-chloro-2-fluorophenyl)-4-(3-ethoxy-3-oxopropanoyl)-piperidine-1-carboxylate 2-(4-Chloro-2-fluorophenyl)-1-(methoxycarbonyl)piperidine-4-carboxylic acid (6.49 g, 20.56 mmol) (reference compound 20) was dissolved in methyl THF (250 mL), then di(1H-imidazol-1-yl)methanone (5.00 g, 30.83 mmol) was added. The mixture was stirred at room temperature under nitrogen for 3 h (flask 1). In a separate flask potassium 3-ethoxy-3-oxopropanoate (6.30 g, 37.00 mmol) was suspended in methyl THF (250 mL), then magnesium chloride (3.52 g, 37.00 mmol) was added. The suspension was stirred at 50° C. under nitrogen for 3 h using a large magnetic stirring bar (flask 2). After the 3 h, the contents of flask 1 was transferred into flask 2. The resulting white suspension was stirred under nitrogen at room temperature overnight. The mixture was acidified to pH 1 with 3.8 M HCl, then MTBE (50 mL) and water (50 mL) was added. The phases were separated and the organic layer was washed with water, satd NaHCO$_3$ and brine. The organic layer was dried over Na$_2$SO$_4$, filtered and evaporated leaving a slightly yellow oil. The product was flashed on Biotage (340 g) with 1 CV 20% EtOAc in heptane followed by a gradient of 20-60% EtOAc in n-heptane (8 CV). The column was conditioned at 20% EtOAc in -n-heptane (1 CV). Trans-methyl 2-(4-chloro-2-fluorophenyl)-4-(3-ethoxy-3-oxopropanoyl)piperidine-1-carboxylate (0.5 g, 6%) and cis-methyl 2-(4-chloro-2-fluorophenyl)-4-(3-ethoxy-3-oxopropanoyl)piperidine-1-carboxylate (2.31 g, 29%) were isolated. Cis-isomer: $^1$H NMR (400 MHz, cdcl$_3$) δ 1.27 (t, 3H), 1.79-1.99 (m, 2H), 2.03-2.21 (m, 1H), 2.23-2.32 (m, 1H), 2.84-2.95 (m, 1H), 3.33-3.51 (m, 3H), 3.62 (s, 3H), 4.12-4.23 (m, 3H), 4.98-5.21 (m, 1H), 6.98-7.24 (m, 3H). MS m/z 386 (M+H)$^+$. Trans-isomer: $^1$H NMR (400 MHz, cdcl$_3$) δ 1.22 (t, 3H), 1.57-1.69 (m, 1H), 1.86-2.01 (m, 2H), 2.36-2.62 (m, 2H), 3.07-3.18 (m, 1H), 3.44 (s, 2H), 3.70 (s, 3H), 4.10-4.21 (m, 2H), 4.32 (br, 1H), 5.67 (br, 1H), 7.02-7.14 (m, 3H). MS m/z 386 (M+H)$^+$ Step 2: Cis-methyl 2-(4-chloro-2-fluorophenyl)-4-(3-oxo-2,3-dihydroisoxazol-5-yl)-piperidine-1-carboxylate Cis-methyl 2-(4-chloro-2-fluorophenyl)-4-(3-ethoxy-3-oxopropanoyl)piperidine-1-carboxylate (2.31 g, 5.99 mmol) was dissolved in MeOH (24 mL) and cooled to −40° C. under nitrogen. Sodium hydroxide (1.761 mL, 5.99 mmol) was added during 10 min and the yellow solution continued to stir at −40° C. for 20 min. Hydroxylamine (50% by weight in water, 0.367 mL, 5.99 mmol) was added during 8 min. The resulting solution was stirred at −40° C. for 3 h. The mixture was then rapidly poured into a prewarmed (80° C.) solution of 6 M hydrogen chloride (30.8 mL, 185.01 mmol) and the mixture continued to stir at 80° C. for 20 min. The solvent was evaporated and DCM/water added. The phases were separated and the organic phase passed through a phase separator and evaporated to yield a slightly yellow solid. The compound was purified by preparative HPLC on a XBridge C18 column (10 μm 250×50 ID mm) using a gradient of 10-55% Acetonitrile in H2O/MeCN/NH3 95/5/0.2 buffer over 30 minutes with a flow of 100 mL/min. Cis-methyl 2-(4-chloro-2-fluorophenyl)-4-(3-oxo-2,3-dihydroisoxazol-5-yl)piperidine-1-carboxylate (1 g, 47%) was isolated after. MS m/z 355 (M+H)$^+$ Step 3: (2R,4S)-methyl 2-(4-chloro-2-fluorophenyl)-4-(3-oxo-2,3-dihydroisoxazol-5-yl)-piperidine-1-carboxylate Cis-methyl 2-(4-chloro-2-fluorophenyl)-4-(3-oxo-2,3-dihydroisoxazol-5-yl)piperidine-1-carboxylate (1 g, 2.82 mmol) was subjected to chiral preparative HPLC (Column: CelluCoat (250×50), 10 μm particle size, mobile phase: Heptane/IPA 50/50, flow rate 120 mL/min) to yield (2R,4S)-methyl 2-(4-chloro-2-fluorophenyl)-4-(3-oxo-2,3-dihydroisoxazol-5-yl)-piperidine-1-carboxylate (504 mg, 50%), Chiral purity 99.7% ee. Optical rotation [α]$_D^{20}$=+65.5 (acetonitrile, c=1)

Step 4: 5-((2R,4S)-2-(4-chloro-2-fluorophenyl)piperidin-4-yl)isoxazol-3(2H)-one (2R,4S)-Methyl 2-(4-chloro-2-fluorophenyl)-4-(3-oxo-2,3-dihydroisoxazol-5-yl)piperidine-1-carboxylate (0.504 g, 1.42 mmol) was dissolved in hydrogen bromide (33% in acetic acid, 11.20 mL, 63.93 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(4-chloro-2-fluorophenyl)piperidin-4-yl)isoxazol-3(2H)-one (313 mg, 74%). $^1$H NMR (600 MHz, dmso) δ 1.35 (q, 1H), 1.46 (dq, 1H), 1.86 (d, 1H), 1.94 (d, 1H), 2.73 (dt, 1H), 2.90 (tt, 1H), 3.10 (td, 1H), 3.91 (d, 1H), 5.73 (s, 1H), 7.25 (dd, 1H), 7.34 (dd, 1H), 7.55 (t, 1H). HRMS Calcd for [C$_{14}$H$_{14}$ClFN$_2$O$_2$+H]+: 297.0806. Found: 297.0786.

Example 46

5-(Trans-2-(4-chloro-2-fluorophenyl)piperidin-4-yl)isoxazol-3(2H)-one

Step 1: Trans-methyl 2-(4-chloro-2-fluorophenyl)-4-(3-oxo-2,3-dihydroisoxazol-5-yl)-piperidine-1-carboxylate Trans-methyl 2-(4-chloro-2-fluorophenyl)-4-(3-ethoxy-3-oxopropanoyl)piperidine-1-carboxylate (500 mg, 1.30 mmol) (from example 45, step 1) was dissolved in MeOH (6 mL) and cooled to −40° C. under nitrogen. Sodium hydroxide (0.381 mL, 1.30 mmol) was added during 10 min and the yellow solution continued to stir at −40° C. for 20 min. Hydroxylamine (50% by weight in water, 0.079 mL, 1.30 mmol) was added during 8 min. The resulting solution was stirred at −40° C. for 3 h. The mixture was then rapidly poured into a prewarmed (80° C.) solution of 6 M hydrogen chloride (6.67 mL, 40.05 mmol) and the mixture continued to stir at 80° C. for 20 min. The solvent was evaporated and DCM/water added. The phases were separated and the organic phase passed through a phase separator and evaporated to yield crude trans-methyl 2-(4-chloro-2-fluorophenyl)-4-(3-oxo-2,3-dihydroisoxazol-5-yl)piperidine-1-carboxylate (0.45 g, 98%) as a slightly yellow dry film. MS m/z 355 (M+H)$^+$ Step 2: 5-(Trans-2-(4-chloro-2-fluorophenyl)piperidin-4-yl)isoxazol-3(2H)-one (2S,4S)-methyl 2-(4-chloro-2-fluorophenyl)-4-(3-oxo-2,3-dihydroisoxazol-5-yl)piperidine-1-carboxylate (0.45 g, 1.27 mmol) was dissolved in hydrogen bromide (33% in acetic acid, 10.00 mL, 57.08 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(4-chloro-2-fluorophenyl)piperidin-4-yl)isoxazol-3(2H)-one (82 mg, 22%). $^1$H NMR (400 MHz, dmso) δ 1.66-1.77 (m, 1H), 1.77-1.90 (m, 1H), 1.92-2.00 (m, 1H), 2.02-2.10 (m, 1H), 2.63-2.79 (m, 1H), 2.88-2.97 (m, 1H), 3.03-3.86 (omitted signals), 3.95 (d, 1H), 5.88 (s, 1H), 7.27 (dd, 1H), 7.35 (dd, 1H), 7.56 (t, 1H). HRMS Calcd for [C$_{14}$H$_{14}$ClFN$_2$O$_2$+H]+: 297.0806. Found: 297.0806.

Example 47

5-((2R,4S)-2-(2-Chloro-4-fluorophenyl)piperidin-4-yl)isoxazol-3(2H)-one

Step 1: Methyl 2-(2-chloro-4-fluorophenyl)-4-(3-ethoxy-3-oxopropanoyl)piperidine-1-carboxylate 2-(2-Chloro-4-fluorophenyl)-1-(methoxycarbonyl)piperidine-4-carboxylic acid (2.13 g, 6.75 mmol) (reference compound 21) was dissolved in methyl THF (50 mL) under nitrogen atmosphere and di(1H-imidazol-1-yl)methanone (1.641 g, 10.12 mmol) was added. The suspension was stirred at room temperature for 3 h (flask 1). In a separate flask was potassium 3-ethoxy-3-oxopropanoate (2.067 g, 12.14 mmol) suspended in methyl THF (25 mL) and magnesium chloride (1.156 g, 12.14 mmol) was added. The suspension was stirred at 50° C. under nitrogen for 15 h using an oversized stirring bar. The contents of flask 1 was added to flask 2 and the resulting white suspension was stirred at room temperature for 20 h. In a separate flask was potassium 3-ethoxy-3-oxopropanoate (1.033 g, 6.07 mmol) suspended in methyl THF (25 mL) and magnesium chloride (0.578 g, 6.07 mmol) was added. The suspension was stirred at 50° C. for 15 h and then added to the reaction mixture. The mixture was stirred at room temperature for 15 h. 0.1 M HCl and DCM were added and the phases separated. The aqueous phase was extracted with DCM, the combined organic layers filtered through a phase separator and evaporated. The residue was purified via Biotage (gradient 2:1->1:1 heptane:EtOAc, Biotage® KP-SIL 340 g column, 10 CV). Methyl 2-(2-chloro-4-fluorophenyl)-4-(3-ethoxy-3-oxopropanoyl)piperidine-1-carboxylate (1.655 g, 63.6%) was isolated as a colorless oil. MS m/z 386 (M+H)$^+$ Step 2: Methyl 2-(2-chloro-4-fluorophenyl)-4-(3-oxo-2,3-dihydroisoxazol-5-yl)piperidine-1-carboxylate Methyl 2-(2-chloro-4-fluorophenyl)-4-(3-ethoxy-3-oxopropanoyl)piperidine-1-carboxylate (1.655 g, 4.29 mmol) was dissolved in MeOH (22 mL) and cooled to −40° C. under nitrogen. Sodium hydroxide (0.180 g, 4.50 mmol) dissolved in water (2.200 mL) was added and the mixture was stirred at −40° C. for 15 min. Hydroxylamine (50% by weight in water, 0.276 mL, 4.50 mmol) was added. The resulting solution was stirred at −40° C. for 1 h. The mixture was then transferred with a pipette into a prewarmed (80° C.) solution of 6 M hydrogen chloride (22.16 mL, 132.98 mmol) and the mixture was stirred at 80° C. for 15 min. Water and DCM were added and the phases separated. The aqueous phase was extracted with DCM and the combined organic layers were filtered through a phase separator and evaporated. The compound was purified by preparative HPLC on a Kromasil C8 column (10 μm 250×50 ID mm) using a gradient of 15-55% Acetonitrile in H2O/MeCN/FA 95/5/0.2 buffer over 25 minutes with a flow of 100 mL/min (3 runs). Methyl 2-(2-chloro-4-fluorophenyl)-4-(3-oxo-2,3-dihydroisoxazol-5-yl)piperidine-1-carboxylate (0.995 g, 65.4%) was yielded as a white solid. MS m/z 355 (M+H)$^+$ Step 3: (2R,4S)-Methyl 2-(2-chloro-4-fluorophenyl)-4-(3-oxo-2,3-dihydroisoxazol-5-yl)piperidine-1-carboxylate and trans-methyl 2-(2-chloro-4-fluorophenyl)-4-(3-oxo-2,3-dihydroisoxazol-5-yl)piperidine-1-carboxylate Methyl 2-(2-chloro-4-fluorophenyl)-4-(3-oxo-2,3-dihydroisoxazol-5-yl)piperidine-1-carboxylate (0.995 g, 2.81 mmol) was subjected to chiral chromatography: Separation 1: Chiral preparative HPLC (Column: Chiralpak IA (250×50 mm), 20 μm particle size, mobile phase: Heptane/EtOH 70/30, flow rate 120 mL/min). Separation 2: Chiral preparative HPLC (Column: CelluCoat (250×50 mm), 10 μm particle size, mobile phase: Heptane/EtOH 90/10, flow rate 120 mL/min). (2R,4S)-Methyl 2-(2-chloro-4-fluorophenyl)-4-(3-oxo-2,3-dihydroisoxazol-5-yl)piperidine-1-carboxylate was isolated (382 mg, 38%), Chiral purity: 98.9% ee. Optical rotation $[\alpha]_D^{20}$=+71.2 (acetonitrile, c=0.5). Trans-methyl 2-(2-chloro-4-fluorophenyl)-4-(3-oxo-2,3-dihydroisoxazol-5-yl)piperidine-1-carboxylate was isolated (130 mg, 13%).

Step 4: 5-((2R,4S)-2-(2-Chloro-4-fluorophenyl)piperidin-4-yl)isoxazol-3(2H)-one (2R,4S)-methyl 2-(2-chloro-4-fluorophenyl)-4-(3-oxo-2,3-dihydroisoxazol-5-yl)piperidine-1-carboxylate (382 mg, 1.08 mmol) was dissolved in hydrogen bromide (33% in acetic acid (8.5 mL, 48.46 mmol) and stirred at room temperature for 16 h. The solvent was removed in vacuo and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4S)-2-(2-chloro-4-fluorophenyl)piperidin-4-yl)isoxazol-3(2H)-one (304 mg, 95%). $^1$H NMR (600 MHz, dmso) δ 1.24 (q, 1H), 1.47 (dq, 1H), 1.85-1.91 (m, 1H), 1.97-2.02 (m, 1H), 2.75 (dt, 1H), 2.87 (tt, 1H), 3.09-3.14 (m, 1H), 3.97 (d, 1H), 5.73 (d, 1H), 7.19 (dt, 1H), 7.37 (dd, 1H), 7.66 (dd, 1H). HRMS Calculated for $[C_{14}H_{14}ClFN_2O_2+H]^+$: 297.0806. Found: 297.0834

Example 48

5-(Trans-2-(2-chloro-4-fluorophenyl)piperidin-4-yl)isoxazol-3(2H)-one

Trans-methyl 2-(2-chloro-4-fluorophenyl)-4-(3-oxo-2,3-dihydroisoxazol-5-yl)piperidine-1-carboxylate (130 mg, 0.37 mmol) (from example 47, step 3) was dissolved in hydrogen bromide (33% in acetic acid, 2.9 mL, 16.49 mmol) and stirred at room temperature for 16 h. The solvent was removed and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(Trans-2-(2-chloro-4-fluorophenyl)piperidin-4-yl)isoxazol-3(2H)-one (94 mg, 86%). $^1$H NMR (600 MHz, dmso) δ 1.50-1.60 (m, 1H), 1.79-1.88 (m, 1H), 1.95-2.01 (m, 1H), 2.06-2.12 (m, 1H), 2.70 (t, 1H), 2.88-2.96 (m, 1H), 3.20-3.24 (m, 1H), 4.01 (d, 1H), 5.95 (d, 1H), 7.21 (dt, 1H), 7.37 (dd, 1H), 7.68 (dd, 1H). HRMS Calculated for $[C_{14}H_{14}ClFN_2O_2+H]^+$: 297.0806. Found: 297.0823

Example 49

5-((2R,4S)-2-(4-Chloro-3-fluorophenyl)piperidin-4-yl)isoxazol-3(2H)-one

Step 1: Trans-methyl 2-(4-chloro-3-fluorophenyl)-4-(3-ethoxy-3-oxopropanoyl)piperidine-1-carboxylate and cis-methyl 2-(4-chloro-3-fluorophenyl)-4-(3-ethoxy-3-oxopropanoyl)-piperidine-1-carboxylate 2-(4-Chloro-3-fluorophenyl)-1-(methoxycarbonyl)piperidine-4-carboxylic acid (1.430 g, 4.53 mmol) (reference compound 22) was dissolved in methyl THF (20 mL) and di(1H-imidazol-1-yl)methanone (1.102 g, 6.79 mmol) added. The reaction was stirred at room temperature for 6 h (flask 1). In a separate flask potassium 3-ethoxy-3-oxopropanoate (1.388 g, 8.15 mmol) was suspended in methyl THF (20.00 mL) and magnesium chloride (0.776 g, 8.15 mmol) added. The suspension was stirred at 50° C. for 6 h (flask 2). The white suspension from flask 2 was added to flask 1. A white suspension was formed. The suspension was stirred at room temperature for 18 h. The suspension was acidified to pH 1 with 3 M HCl. MTBE (100 mL) and water (150 mL) were added, shaken and the phases separated. The organic phase was washed with water (150 mL), satd $NaHCO_3$ (150 mL) and brine (150 mL), dried with $Na_2SO_4$, filtered and evaporated in vacuo. The residue was purified by automated flash chromatography on a Biotage® KP-SIL 100 g column. A gradient of 20% EtOAc in heptane over 2 CV followed by 20-60% of EtOAc in heptane over 10 CV was used as mobile phase. Cis-methyl 2-(4-chloro-3-fluorophenyl)-4-(3-ethoxy-3-oxopropanoyl)piperidine-1-carboxylate (1.153 g, 66.0%) and trans-methyl 2-(4-chloro-3-fluorophenyl)-4-(3-ethoxy-3-oxopropanoyl)piperidine-1-carboxylate (0.107 g, 6.12%) were isolated as colorless oils. Cis-isomer: $^1$H NMR (600 MHz, cdcl$_3$) δ 1.19-1.30 (m, 3H), 1.73-1.97 (m, 2H), 2.00-2.16 (m, 1H), 2.20-2.27 (m, 1H), 2.81-2.89 (m, 1H), 3.24-3.48 (m, 3H), 3.60-3.65 (m, 3H), 4.04-4.20 (m, 3H), 4.84-4.98 (m, 1H), 6.86-7.01 (m, 2H), 7.28-7.34 (m, 1H). MS m/z 386 (M+H)$^+$. Trans-isomer: $^1$H NMR (600 MHz, cdcl$_3$) δ 1.19-1.29 (m, 3H), 1.38-2.98 (m, 6H), 3.39-3.49 (m, 2H), 3.63-3.82 (m, 3H), 4.00-4.37 (m, 3H), 5.56 (s, br., 1H), 6.86-7.02 (m, 2H), 7.33-7.39 (m, 1H). MS m/z 386 (M+H)$^+$

Step 2: Cis-methyl 2-(4-chloro-3-fluorophenyl)-4-(3-oxo-2,3-dihydroisoxazol-5-yl)piperidine-1-carboxylate Cis-methyl 2-(4-chloro-3-fluorophenyl)-4-(3-ethoxy-3-oxopropanoyl)piperidine-1-carboxylate (1.731 g, 4.49 mmol) was dissolved in MeOH (20 mL) and cooled to –40° C. under nitrogen. Sodium hydroxide (1.181 mL, 4.49 mmol) dissolved in water (2 mL) was added and the reaction stirred at –40° C. for 20 min. Hydroxylamine (50% by weight in water, 0.247 mL, 4.49 mmol) was added dropwise and stirring continued for 3 h. The mixture was then transferred to a prewarmed 80° C. solution of 6 M hydrogen chloride (23.18 mL, 139.09 mmol) and stirring was continued at 80° C. for 20 min. The solvent was evaporated and DCM (200 mL) and water (200 mL) were added. The phases were shaken, separated and the organic phase dried with a phase separator and evaporated in vacuo. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 2-(4-chloro-3-fluorophenyl)-4-(3-oxo-2,3-dihydroisoxazol-5-yl)-piperidine-1-carboxylate (0.921 g, 57.9%) was isolated as a white solid. $^1$H NMR (600 MHz, cdcl$_3$) δ 1.79-1.87 (m, 1H), 2.06-2.15 (m, 1H), 2.19-2.28 (m, 1H), 2.30-2.37 (m, 1H), 3.00-3.09 (m, 1H), 3.31-3.40 (m, 1H), 3.66 (s, 3H), 4.07-4.16 (m, 1H), 5.00-5.07 (m, 1H), 5.56 (s, 1H), 6.87-6.91 (m, 1H), 6.95 (dd, 1H), 7.29 (t, 1H). MS m/z 355 (M+H)$^+$

Step 3: (2R,4S)-Methyl 2-(4-chloro-3-fluorophenyl)-4-(3-oxo-2,3-dihydroisoxazol-5-yl)piperidine-1-carboxylate Cis-methyl 2-(4-chloro-3-fluorophenyl)-4-(3-oxo-2,3-dihydroisoxazol-5-yl)piperidine-1-carboxylate (0.921 g, 2.6 mmol) was subjected to chiral preparative HPLC (Column: CelluCoat (250×50 mm), 10 μm particle size, mobile phase: Heptane/EtOH 1/1, flow rate 120 mL/min) to yield (2R,4S)-methyl 2-(4-chloro-3-fluorophenyl)-4-(3-oxo-2,3-dihydroisoxazol-5-yl)piperidine-1-carboxylate (446 mg, 48%), Chiral purity 99.9% ee, Optical rotation $[\alpha]_D^{20}$=+61.8 (acetonitrile, c=0.5)

Step 4: 5-((2R,4S)-2-(4-chloro-3-fluorophenyl)piperidin-4-yl)isoxazol-3(2H)-one (2R,4S)-Methyl 2-(4-chloro-3-fluorophenyl)-4-(3-oxo-2,3-dihydroisoxazol-5-yl)piperidine-1-carboxylate (446 mg, 1.26 mmol) was dissolved in hydrogen bromide (33% in AcOH, 6.8 mL, 38.97 mmol) and stirred at room temperature for 20 h. The solvent was then evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4S)-2-(4-chloro-3-fluorophenyl)piperidin-4-yl)isoxazol-3(2H)-one (266 mg, 71%). $^1$H NMR (600 MHz, dmso) δ 1.31 (q, 1H), 1.44 (dq, 1H), 1.82-1.89 (m, 1H), 1.94-2.00 (m, 1H), 2.70 (dt, 1H), 2.84 (tt, 1H), 3.06-3.12 (m, 1H), 3.66 (dd, 1H), 5.72 (s, 1H), 7.23 (dd, 1H), 7.38 (dd, 1H), 7.49 (t, 1H). HRMS Calculated for $[C_{14}H_{14}ClFN_2O_2+H]^+$: 297.0806. Found: 297.0795

Example 50

5-(Trans-2-(4-chloro-3-fluorophenyl)piperidin-4-yl)isoxazol-3(2H)-one

Step 1: Trans-methyl 2-(4-chloro-3-fluorophenyl)-4-(3-oxo-2,3-dihydroisoxazol-5-yl)piperidine-1-carboxylate Trans-methyl 2-(4-chloro-3-fluorophenyl)-4-(3-ethoxy-3-oxopropanoyl)piperidine-1-carboxylate (171 mg, 0.44 mmol) (from example 49, step 1) was dissolved in MeOH (2 mL) and cooled to −40° C. Sodium hydroxide (0.117 mL, 0.44 mmol) dissolved in water (0.200 mL) was added dropwise and the solution stirred for 20 min. Hydroxylamine (50% by weight in water, 0.024 mL, 0.44 mmol) was then added and stirring was continued for 3.5 h. The mixture was then transferred to a prewarmed 80° C. solution of 6 M hydrogen chloride (2.290 mL, 13.74 mmol) and stirring was continued at 80° C. for 20 min. The solvent was evaporated in vacuo and DCM (50 mL) and water (50 mL) were added. The phases were shaken, separated and the organic phase dried with a phase separator and evaporated in vacuo. The compound was purified by preparative HPLC on a Kromasil C8 column (10 μm 250×20 ID mm) using a gradient of 10-60% Acetonitrile in H2O/MeCN/AcOH 95/5/0.2 buffer over 30 minutes with a flow of 19 mL/min. (2S,4S)-Methyl 2-(4-chloro-3-fluorophenyl)-4-(3-oxo-2,3-dihydroisoxazol-5-yl)piperidine-1-carboxylate (49.0 mg, 31.2%) was isolated as a white solid. $^1$H NMR (600 MHz, cdcl$_3$) δ 1.58-1.70 (m, 1H), 1.85-2.06 (m, 2H), 2.60 (d, 1H), 2.73-2.96 (m, 2H), 3.73 (s, 3H), 4.04-4.44 (m, 1H), 5.42-5.78 (m, 2H), 6.92-7.05 (m, 2H), 7.38 (t, 1H). MS m/z 355 (M+H)$^+$

Step 2: 5-(Trans-2-(4-chloro-3-fluorophenyl)piperidin-4-yl)isoxazol-3(2H)-one Trans-methyl 2-(4-chloro-3-fluorophenyl)-4-(3-oxo-2,3-dihydroisoxazol-5-yl)piperidine-1-carboxylate (49 mg, 0.14 mmol) was dissolved in hydrogen bromide (33% in AcOH, 2 mL, 11.42 mmol) and stirred at room temperature for 5 h. The reaction was heated to 50° C. for 3 h. The reaction mixture was evaporated in vacuo and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(trans-2-(4-chloro-3-fluorophenyl)piperidin-4-yl)isoxazol-3(2H)-one (23 mg, 56%). $^1$H NMR (600 MHz, dmso) δ 1.72-1.81 (m, 2H), 1.82-1.89 (m, 1H), 1.97-2.04 (m, 1H), 2.64-2.71 (m, 1H), 2.77-2.83 (m, 1H), 3.06-3.12 (m, 1H), 3.72 (dd, 1H), 5.96 (s, 1H), 7.23 (dd, 1H), 7.40 (dd, 1H), 7.49 (t, 1H). HRMS Calculated for $[C_{14}H_{14}ClFN_2O_2+H]^+$: 297.0806. Found: 297.0807

Example 51

5-((2R,4S)-2-(2,4-Dichlorophenyl)piperidin-4-yl)isoxazol-3(2H)-one

Step 1: Methyl 2-(2,4-dichlorophenyl)-4-(3-ethoxy-3-oxopropanoyl)piperidine-1-carboxylate 2-(2,4-Dichlorophenyl)-1-(methoxycarbonyl)piperidine-4-carboxylic acid (2.44 g, 7.35 mmol) (reference compound 23) was dissolved in methyl THF (36.7 mL) and di(1H-imidazol-1-yl)methanone (1.787 g, 11.02 mmol) added. The suspension was stirred at room temperature under nitrogen for 6 h (flask 1). In a separate flask potassium 3-ethoxy-3-oxopropanoate (2.250 g, 13.22 mmol) was suspended in methyl THF (36.7 mL) and magnesium chloride (1.259 g, 13.22 mmol) added. The suspension was stirred under nitrogen for 6 h (flask 2). The white suspension in flask 2 was then added to the brown suspension in flask 1. The resulting suspension was stirred at room temperature for 40 h. The mixture was acidified to pH 1 with 3 M HCl. Water and methyl THF were added, the phases separated. The organic layer was washed with water, satd $NaHCO_3$, brine, dried over $MgSO_4$, filtered and evaporated. Purified by flash chromatography using 20% EtOAc in heptane ->50% EtOAc over 10 CV, 3CV at 50%. Repurified by flash chromatography using 20% EtOAc in EtOAc ->30% EtOAc over 12 CV. Methyl 2-(2,4-dichlorophenyl)-4-(3-ethoxy-3-oxopropanoyl)piperidine-1-carboxylate (1.55 g, 52%) was isolated.

Step 2: Methyl 2-(2,4-dichlorophenyl)-4-(3-oxo-2,3-dihydroisoxazol-5-yl)piperidine-1-carboxylate Methyl 2-(2,4-dichlorophenyl)-4-(3-ethoxy-3-oxopropanoyl)piperidine-1-carboxylate (1.55 g, 3.85 mmol) was dissolved in MeOH (15.79 mL) and cooled to −40° C. under nitrogen. Sodium hydroxide (1.014 mL, 3.85 mmol) in water (1.579 mL) was added and the mixture stirred at −40° C. for 20 min. Hydroxylamine (50% by weight in water, 0.236 mL, 3.85 mmol) was added and stirring continued at −40° C. for 3.5 h. The reaction mixture was then transferred to a preheated 80° C. solution of 6 M hydrogen chloride (19.91 mL, 119.45 mmol) and heating was continued for 20 min. The solvent was then evaporated. DCM and water were added, shaken and the phases separated. The organic phase was dried with a phase separator and evaporated in vacuo. The compound was purified by preparative HPLC on a Kromasil C8 column (10 μm 250×50 ID mm) using a gradient of 25-65% Acetonitrile in H2O/MeCN/AcOH 95/5/0.2 buffer over 30 minutes with a flow of 100 mL/min. Methyl 2-(2,4-dichlorophenyl)-4-(3-oxo-2,3-dihydroisoxazol-5-yl)piperidine-1-carboxylate (0.870 g, 60.8%) was isolated as a white solid. MS m/z 371 (M+H)$^+$

Step 3: (2R,4S)-Methyl 2-(2,4-dichlorophenyl)-4-(3-oxo-2,3-dihydroisoxazol-5-yl)piperidine-1-carboxylate, (2S,4R)-methyl 2-(2,4-dichlorophenyl)-4-(3-oxo-2,3-dihydroisoxazol-5-yl)piperidine-1-carboxylate, (2S,4S)-methyl 2-(2,4-dichlorophenyl)-4-(3-oxo-2,3-dihydro-isoxazol-5-yl)piperidine-1-carboxylate and (2R,4R)-methyl 2-(2,4-dichlorophenyl)-4-(3-oxo-2,3-dihydroisoxazol-5-yl)piperidine-1-carboxylate Methyl 2-(2,4-dichlorophenyl)-4-(3-oxo-2,3-dihydroisoxazol-5-yl)piperidine-1-carboxylate (0.870 g, 2.34 mmol) was subjected to chiral preparative HPLC: Separation 1: The enantiomers were separated using chiral preparative HPLC (Column: ReproSil (250×50 mm), 8 μm particle size, mobile phase: Heptane/EtOH/FA 60/40/0.1, flow rate 120 mL/min) to yield a mixture of one cis- and one trans-enantiomer. Separation 2: The enantiomers were separated using chiral preparative HPLC (Column: CelluCoat (250×20 mm), 5 μm particle size, mobile phase: Heptane/IPA/FA 80/20/0.1, flow rate 18 mL/min) (2R,4S)-Methyl 2-(2,4-dichlorophenyl)-4-(3-oxo-2,3-dihydroisoxazol-5-yl)piperidine-1-carboxylate (334 mg, 38%) was isolated. Chiral purity 99.7% de, Optical rotation $[\alpha]_D^{20}$=+64.0 (acetonitrile, c=1.0), $^1$H NMR (400 MHz, cdcl$_3$) δ 1.79-1.92 (m, 2H), 2.25-2.48 (m, 2H), 3.02-3.13 (m, 1H), 3.53-3.64 (m, 4H), 4.12-4.21 (m, 1H), 5.16 (dd, 1H), 5.64 (s, 1H), 7.12-7.22 (m, 2H), 7.36 (d, 1H). (2S,4R)-methyl 2-(2,4-dichlorophenyl)-4-(3-oxo-2,3-dihydroisoxazol-5-yl)piperidine-1-carboxylate (340 mg, 39%) was isolated. Chiral purity 99.9% de, Optical rotation $[\alpha]_D^{20}$=−65.1 (acetonitrile, c=1.0), $^1$H NMR (400 MHz, cdcl$_3$) δ 1.79-1.92 (m, 2H), 2.26-2.38 (m, 1H), 2.39-2.48 (m, 1H), 3.03-3.13 (m, 1H), 3.53-3.64 (m, 4H), 4.12-4.22 (m, 1H), 5.16 (dd, 1H), 5.64 (s, 1H), 7.13-7.22 (m, 2H), 7.36 (d, 1H). (2S,4S)-Methyl 2-(2,4-dichlorophenyl)-4-(3-oxo-2,3-dihydroisoxazol-5-yl)piperidine-1-carboxylate (67 mg, 8%) was isolated. Chiral purity 98.7% de, Optical rotation $[\alpha]_D^{20}$=+11.5 (acetonitrile, c=1.0), $^1$H NMR (400 MHz, cdcl$_3$) δ 1.72 (dq, 1H), 2.01-2.19 (m, 2H), 2.40-2.49 (m, 1H), 2.74 (tt, 1H), 3.43 (dt, 1H), 3.66 (s, 3H), 4.40 (d, br., 1H), 5.61-5.71 (m, 2H), 7.14-7.24 (m, 2H), 7.40 (d, 1H). (2R,4R)-Methyl 2-(2,4-dichlorophenyl)-4-(3-oxo-2,3-dihydroisoxazol-5-yl)piperidine-1-carboxylate (75 mg, 9%) was isolated. Chiral purity 98.5% de, Optical rotation $[\alpha]_D^{20}$=−10.9 (acetonitrile, c=1.0), $^1$H NMR (400 MHz, cdcl$_3$) δ 1.72 (dq, 1H), 2.01-2.19 (m, 2H), 2.40-2.49 (m, 1H), 2.74 (tt, 1H), 3.43 (dt, 1H), 3.68 (s, 3H), 4.40 (d, br., 1H), 5.61-5.71 (m, 2H), 7.14-7.24 (m, 2H), 7.41 (d, 1H).

Step 4: 5-((2R,4S)-2-(2,4-Dichlorophenyl)piperidin-4-yl)isoxazol-3(2H)-one (2R,4S)-Methyl 2-(2,4-dichlorophenyl)-4-(3-oxo-2,3-dihydroisoxazol-5-yl)piperidine-1-carboxylate (334 mg, 0.90 mmol) was diluted with hydrogen bromide (33% in AcOH, 4.7 mL, 26.99 mmol) and stirred at ambient temperature for 24 h. Evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(2,4-dichlorophenyl)piperidin-4-yl)isoxazol-3(2H)-one (173 mg, 61%). $^1$H NMR (600 MHz, dmso) δ 1.22 (q, 1H), 1.47 (dq, 1H), 1.85-1.90 (m, 1H), 1.97-2.02 (m, 1H), 2.74 (dt, 1H), 2.87 (tt, 1H), 3.09-3.14 (m, 1H), 3.96 (dd, 1H), 5.73 (d, 1H), 7.40 (dd, 1H), 7.54 (d, 1H), 7.64 (d, 1H). HRMS Calculated for [C$_{14}$H$_{14}$Cl$_2$N$_2$O$_2$+H]$^+$: 313.0511. Found: 313.0493

Example 52

5-((2S,4R)-2-(2,4-Dichlorophenyl)piperidin-4-yl)isoxazol-3(2H)-one (2S,4R)-Methyl 2-(2,4-dichlorophenyl)-4-(3-oxo-2,3-dihydroisoxazol-5-yl)piperidine-1-carboxylate (340 mg, 0.92 mmol) (from example 51, step 3) was diluted with hydrogen bromide (33% in AcOH, 4812 μl, 27.48 mmol) and stirred at ambient temperature for 24 h. Evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-(2,4-dichlorophenyl)piperidin-4-yl)isoxazol-3(2H)-one ( ). $^1$H NMR (600 MHz, dmso) δ 1.22 (q, 1H), 1.47 (dq, 1H), 1.84-1.90 (m, 1H), 1.96-2.03 (m, 1H), 2.74 (dt, 1H), 2.87 (tt, 1H), 3.07-3.15 (m, 1H), 3.96 (dd, 1H), 5.73 (s, 1H), 7.40 (dd, 1H), 7.54 (d, 1H), 7.64 (d, 1H). HRMS Calculated for [C$_{14}$H$_{14}$Cl$_2$N$_2$O$_2$+H]$^+$: 313.0511. Found: 313.0490

Example 53

5-((2S,4S)-2-(2,4-Dichlorophenyl)piperidin-4-yl)isoxazol-3(2H)-one (2S,4S)-Methyl 2-(2,4-dichlorophenyl)-4-(3-oxo-2,3-dihydroisoxazol-5-yl)piperidine-1-carboxylate (67 mg, 0.18 mmol) (from example 51, step 3) was diluted with hydrogen bromide (33% in AcOH, 948 μl, 5.41 mmol) and stirred at ambient temperature for 24 h. Evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4S)-2-(2,4-dichlorophenyl)piperidin-4-yl)isoxazol-3(2H)-one (36 mg, 64%). $^1$H NMR (600 MHz, dmso) δ 1.46-1.54 (m, 1H), 1.77-1.85 (m, 1H), 1.93-1.99 (m, 1H), 2.05-2.11 (m, 1H), 2.67 (dt, 1H), 2.86-2.92 (m, 1H), 3.18-3.22 (m, 1H), 3.98 (dd, 1H), 5.93 (d, 1H), 7.40 (dd, 1H), 7.53 (d, 1H), 7.66 (d, 1H). HRMS Calculated for [C$_{14}$H$_{14}$Cl$_2$N$_2$O$_2$+H]$^+$: 313.0511. Found: 313.0499

Example 54

5-((2R,4R)-2-(2,4-Dichlorophenyl)piperidin-4-yl)isoxazol-3(2H)-one (2R,4R)-Methyl 2-(2,4-dichlorophenyl)-4-(3-oxo-2,3-dihydroisoxazol-5-yl)piperidine-1-carboxylate (75 mg, 0.20 mmol) (from example 51, step 3) was diluted with hydrogen bromide (33% in AcOH, 1062 μl, 6.06 mmol) and stirred at ambient temperature for 24 h. Evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4R)-2-(2,4-dichlorophenyl)piperidin-4-yl)isoxazol-3(2H)-one (38 mg, 60%). $^1$H NMR (600 MHz, dmso) δ 1.47-1.54 (m, 1H), 1.78-1.85 (m, 1H), 1.93-1.99 (m, 1H), 2.05-2.11 (m, 1H), 2.67 (dt, 1H), 2.86-2.92 (m, 1H), 3.18-3.22 (m, 1H), 3.98 (dd, 1H), 5.93 (d, 1H), 7.41 (dd, 1H), 7.53 (d, 1H), 7.66 (d, 1H). HRMS Calculated for [C$_{14}$H$_{14}$Cl$_2$N$_2$O$_2$+H]$^+$: 313.0511. Found: 313.0494

Example 55

5-((2R,4S)-2-(3,5-Dichlorophenyl)piperidin-4-yl)isoxazol-3(2H)-one

Step 1: Trans-methyl 2-(3,5-dichlorophenyl)-4-(3-ethoxy-3-oxopropanoyl)piperidine-1-carboxylate and cis-methyl 2-(3,5-dichlorophenyl)-4-(3-ethoxy-3-oxopropanoyl)piperidine-1-carboxylate 2-(3,5-Dichlorophenyl)-1-(methoxycarbonyl)piperidine-4-carboxylic acid (4.6 g, 13.85 mmol) (reference compound 24) was dissolved in methyl THF (69.2 mL) and di(1H-imidazol-1-yl)methanone (3.37 g, 20.77 mmol) added. The suspension was stirred at room temperature overnight under nitrogen (flask 1). In a separate flask potassium 3-ethoxy-3-oxopropanoate (4.24 g, 24.93 mmol) was suspended in methyl THF (69.2 mL) and magnesium chloride (2.373 g, 24.93 mmol) added. The suspension was stirred at 50° C. overnight under nitrogen (flask 2). The white suspension in flask 2 was then added to the brown suspension in flask 1. The resulting suspension was stirred at room temperature for 40 h. The mixture was acidified to pH 1 with 3 M HCl. Water and methyl THF were added. The phases were separated, the organic layer washed with water, satd NaHCO$_3$, brine, dried over MgSO4, filtered and evaporated. Purified by flash chromatography using 20% EtOAc in heptane ->50% EtOAc over 10 CV, 3 CV at 50%. Trans-methyl 2-(3,5-dichlorophenyl)-4-(3-ethoxy-3-oxopropanoyl)piperidine-1-carboxylate (0.6 g, 11%) and cis-methyl 2-(3,5-dichlorophenyl)-4-(3-ethoxy-3-oxopropanoyl)piperidine-1-carboxylate (3.57 g, 64%) were isolated. Cis-isomer: $^1$H NMR (400 MHz, cdcl$_3$) δ 1.22-1.32 (m, 3H), 1.79-1.94 (m, 2H), 2.03-2.17 (m, 1H), 2.20-2.29 (m, 1H), 2.82-2.93 (m, 1H), 3.24-3.34 (m, 1H), 3.46 (d, 2H), 3.64-3.68 (m, 3H), 4.10-4.23 (m, 3H), 4.83-4.92 (m, 1H), 7.06-7.09 (m, 2H), 7.22-7.25 (m, 1H). MS m/z 402 (M+H)$^+$. Trans-isomer: MS m/z 402 (M+H)$^+$ Step 2: Cis-methyl 2-(3,5-dichlorophenyl)-4-(3-oxo-2,3-dihydroisoxazol-5-yl)piperidine-1-carboxylate Cis-methyl 2-(3,5-dichlorophenyl)-4-(3-ethoxy-3-oxopropanoyl)piperidine-1-carboxylate (3.57 g, 8.87 mmol) was dissolved in MeOH (36.4 mL) and cooled to −40° C. under nitrogen. Sodium hydroxide (2.335 mL, 8.87 mmol) in water (3.64 mL) was added and the mixture stirred at −40° C. for 20 min. Hydroxylamine (50% by weight in water, 0.544 mL, 8.87 mmol) was added and stirring continued at −40° C. for 3.5 h. The reaction mixture was then transferred to a preheated 80° C. solution of 6 M hydrogen chloride (45.9 mL, 275.11 mmol) and heating was continued for 20 min. The solvent was then evaporated. DCM and water were added, shaken and the phases separated. The organic phase was dried with a phase separator and evaporated in vacuo. The compound was purified by preparative HPLC on a Kromasil C8 column (10 μm 250×50 ID mm) using a gradient of 25-65% Acetonitrile in H2O/MeCN/AcOH 95/5/0.2 buffer over 30 minutes with a flow of 100 mL/min. Cis-methyl 2-(3,5-dichlorophenyl)-4-(3-oxo-2,3-dihydroisoxazol-5-yl)piperidine-1-carboxylate (2.000 g, 60.7%) was isolated as a white solid. $^1$H NMR (400 MHz, cd$_3$od) δ 1.82-1.93 (m, 1H), 2.13-2.27 (m, 2H), 2.30-2.39 (m, 1H), 3.06-3.16 (m, 1H), 3.42-3.53 (m, 1H), 3.66 (s, 3H), 4.04-4.12 (m, 1H), 5.06 (dd, 1H), 5.64 (d, 1H), 7.14-7.18 (m, 2H), 7.27 (t, 1H). MS m/z 371 (M+H)$^+$ Step 3: (2R,4S)-Methyl 2-(3,5-dichlorophenyl)-4-(3-oxo-2,3-dihydroisoxazol-5-yl)piperidine-1-carboxylate and (2S,4R)-Methyl 2-(3,5-dichlorophenyl)-4-(3-oxo-2,3-dihydroisoxazol-5-yl)piperidine-1-carboxylate Cis-methyl 2-(3,5-dichlorophenyl)-4-(3-oxo-2,3-dihydroisoxazol-5-yl)piperidine-1-carboxylate (2.000 g, 5.4 mmol) was subjected to chiral preparative HPLC (Column: CelluCoat (250×50 mm), 10 μm particle size, mobile phase: Heptane/EtOH 70/30, flow rate 120 mL/min) to yield (2R,4S)-methyl 2-(3,5-dichlorophenyl)-4-(3-oxo-2,3-dihydroisoxazol-5-yl)piperidine-1-carboxylate (1.05 g, 50%), Chiral purity 99.6% ee, Optical rotation $[\alpha]_D^{20}$=+67.1 (acetonitrile, c=1.0), and (2S,4R)-methyl 2-(3,5-dichlorophenyl)-4-(3-oxo-2,3-dihydroisoxazol-5-yl)piperidine-1-carboxylate (1.06 g, 50%), Chiral purity 97.6% ee, Optical rotation $[\alpha]_D^{20}$=−58.4 (acetonitrile, c=1.0).

Step 4: 5-((2R,4S)-2-(3,5-Dichlorophenyl)piperidin-4-yl)isoxazol-3(2H)-one (2R,4S)-Methyl 2-(3,5-dichlorophenyl)-4-(3-oxo-2,3-dihydroisoxazol-5-yl)piperidine-1-carboxylate (1 g, 2.69 mmol) was dissolved in hydrogen bromide (33% in AcOH, 4.67 mL, 80.82 mmol). Stirred overnight and evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(3,5-dichlorophenyl)piperidin-4-yl)isoxazol-3(2H)-one (607 mg, 72%). $^1$H NMR (600 MHz, dmso) δ 1.32 (q, 1H), 1.44 (dq, 1H), 1.84-1.89 (m, 1H), 1.97-2.03 (m, 1H), 2.70 (dt, 1H), 2.80-2.87 (m, 1H), 3.06-3.12 (m, 1H), 3.67 (dd, 1H), 5.75 (s, 1H), 7.42 (d, 2H), 7.44 (t, 1H). HRMS Calculated for $[C_{14}H_{14}Cl_2N_2O_2+H]^+$: 313.0511. Found: 313.0513

Example 56

5-((2S,4R)-2-(3,5-Dichlorophenyl)piperidin-4-yl)isoxazol-3(2H)-one (2S,4R)-Methyl 2-(3,5-dichlorophenyl)-4-(3-oxo-2,3-dihydroisoxazol-5-yl)piperidine-1-carboxylate (1 g, 2.69 mmol) (from example 55, step 3) was dissolved in hydrogen bromide (33% in AcOH, 4.67 mL, 80.82 mmol) and stirred overnight. Evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-(3,5-dichlorophenyl)piperidin-4-yl)isoxazol-3(2H)-one (509 mg, 60%). $^1$H NMR (600 MHz, dmso) δ 1.32 (q, 1H), 1.44 (dq, 1H), 1.84-1.89 (m, 1H), 1.97-2.02 (m, 1H), 2.70 (dt, 1H), 2.84 (tt, 1H), 3.07-3.12 (m, 1H), 3.67 (dd, 1H), 5.75 (s, 1H), 7.42 (d, 2H), 7.44 (t, 1H). HRMS Calculated for $[C_{14}H_{14}Cl_2N_2O_2+H]^+$: 313.0511. Found: 313.0516

Example 57

5-(Trans-2-(3,5-dichlorophenyl)piperidin-4-yl)isoxazol-3(2H)-one

Step 1: Trans-methyl 2-(3,5-dichlorophenyl)-4-(3-oxo-2,3-dihydroisoxazol-5-yl)piperidine-1-carboxylate Trans-methyl 2-(3,5-dichlorophenyl)-4-(3-ethoxy-3-oxopropanoyl)piperidine-1-carboxylate (0.6 g, 1.49 mmol) (from example 55, step 1) was dissolved in MeOH (6.11 mL) and cooled to −40° C. under nitrogen. Sodium hydroxide (0.393 mL, 1.49 mmol) in water (0.611 mL) was added and the mixture stirred at −40° C. for 20 min. Hydroxylamine (50% by weight in water, 0.091 mL, 1.49 mmol) was added and stirring continued at −40° C. for 3.5 h. The reaction mixture was then transferred to a preheated 80° C. solution of 6 M hydrogen chloride (7.71 mL, 46.24 mmol) and heating was continued for 20 min. The solvent was then evaporated. DCM and water were added, shaken and the phases separated. The organic phase was dried with a phase separator and evaporated to yield crude trans-methyl 2-(3,5-dichlorophenyl)-4-(3-oxo-2,3-dihydroisoxazol-5-yl)piperidine-1-carboxylate (300 mg, 54%). MS m/z 371 (M+H)$^+$

5-(Trans-2-(3,5-dichlorophenyl)piperidin-4-yl)isoxazol-3(2H)-one

Trans-methyl 2-(3,5-dichlorophenyl)-4-(3-oxo-2,3-dihydroisoxazol-5-yl)piperidine-1-carboxylate (300 mg, 0.81 mmol) was diluted with hydrogen bromide (33% in AcOH, 4.3 mL, 24.24 mmol) and stirred at ambient temperature for 48 h. Evaporated and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-(trans-2-(3,5-dichlorophenyl)piperidin-4-yl)isoxazol-3(2H)-one (162 mg, 64%). $^1$H NMR (600 MHz, $CDCl_3$) δ 1.77-2.17 (m, 4H), 2.66-2.74 (m, 1H), 2.82-2.89 (m, 1H), 3.12-3.18 (m, 1H), 3.79 (d, 1H), 6.06 (s, 1H), 7.44-7.51 (m, 3H). HRMS Calculated for $[C_{14}H_{14}Cl_2N_2O_2+H]^+$: 313.0511. Found: 313.0513

Example 58

5-((2R,4S)-2-(2-Fluoro-4-(trifluoromethoxy)phenyl)piperidin-4-yl)isoxazol-3(2H)-one

Step 1: Trans-methyl 4-(3-ethoxy-3-oxopropanoyl)-2-(2-fluoro-4-(trifluoromethoxy)phenyl)-piperidine-1-carboxylate and cis-methyl 4-(3-ethoxy-3-oxopropanoyl)-2-(2-fluoro-4-(trifluoromethoxy)phenyl)piperidine-1-carboxylate 2-(2-Fluoro-4-(trifluoromethoxy)phenyl)-1-(methoxycarbonyl)piperidine-4-carboxylic acid (4.07 g, 11.14 mmol) (reference compound 25) was dissolved in methyl THF (100 mL) under nitrogen atmosphere and di(1H-imidazol-1-yl)methanone (2.71 g, 16.71 mmol) was added. The suspension was stirred at room temperature for 5 h (flask 1). In a separate flask was potassium 3-ethoxy-3-oxopropanoate (3.41 g, 20.06 mmol) suspended in methyl THF (50 mL) and magnesium chloride (1.910 g, 20.06 mmol) was added. The suspension was stirred at 50° C. under nitrogen for 15 h using an oversized stirring bar (flask 2). The contents of flask 1 was added to flask 2 and the resulting white suspension was stirred at room temperature for 20 h. 0.1 M HCl and DCM were added and the phases separated. The aqueous phase was extracted with DCM, the combined organic layers filtered through a phase separator and evaporated. The residue was purified via Biotage (gradient 3:1->1:1 heptane:EtOAc, Biotage® KP-SIL 340 g column, 10 CV). Cis-methyl 4-(3-ethoxy-3-oxopropanoyl)-2-(2-fluoro-4-(trifluoromethoxy)phenyl)piperidine-1-carboxylate (3.44 g, 70.9%) and trans-methyl 4-(3-ethoxy-3-oxopropanoyl)-2-(2-fluoro-4-(trifluoromethoxy)phenyl)piperidine-1-carboxylate (0.420 g, 8.66%) were isolated as colorless oils. Cis-isomer: $^1$H NMR (600 MHz, $cdcl_3$) δ 1.23-1.28 (m, 3H), 1.77-1.96 (m, 2H), 2.03-2.14 (m, 1H), 2.24-2.31 (m, 1H), 2.84-2.93 (m, 1H), 3.32-3.48 (m, 3H), 3.57-3.65 (m, 3H), 4.08-4.20 (m, 3H), 5.03-5.12 (m, 1H), 6.89-6.98 (m, 2H), 7.13-7.21 (m, 1H). MS m/z 436 $(M+H)^+$. Trans-isomer: $^1$H NMR (600 MHz, $cdcl_3$) δ 1.16-1.28 (m, 3H), 1.62 (dq, 1H), 1.85-2.00 (m, 2H), 2.37-2.60 (m, 2H), 3.12 (dt, 1H), 3.43 (s, 2H), 3.68 (s, br., 3H), 4.08-4.20 (m, 2H), 4.25 (s, br., 1H), 5.68 (s, br., 1H), 6.92-7.01 (m, 2H), 7.13 (t, 1H). MS m/z 436 $(M+H)^+$

Step 2: Cis-methyl 2-(2-fluoro-4-(trifluoromethoxy)phenyl)-4-(3-oxo-2,3-dihydroisoxazol-5-yl)piperidine-1-carboxylate Cis-methyl 4-(3-ethoxy-3-oxopropanoyl)-2-(2-fluoro-4-(trifluoromethoxy)phenyl)piperidine-1-carboxylate (3.22 g, 7.40 mmol) was dissolved in MeOH (30 mL) and cooled to −40° C. under nitrogen. Sodium hydroxide (0.311 g, 7.77 mmol) dissolved in water (3.00 mL) was added and the mixture was stirred at −40° C. for 15 min. Hydroxylamine (50% by weight in water, 0.476 mL, 7.77 mmol) was added. The resulting solution was stirred at −40° C. for 1 h. The mixture was then transferred into a prewarmed (80° C.) solution of 6 M hydrogen chloride (38.2 mL, 229.28 mmol) and the mixture was stirred at 80° C. for 15 min. Water and DCM were added and the phases separated. The aqueous phase was extracted with DCM and the combined organic layers were filtered through a phase separator and evaporated. The compound was purified by preparative HPLC on a Kromasil C8 column (4 runs) (10 µm 250×50 ID mm) using a gradient of 25-65% Acetonitrile in H2O/MeCN/HOAc 95/5/0.2 buffer over 25 minutes with a flow of 100 mL/min. Cis-methyl 2-(2-fluoro-4-(trifluoromethoxy)phenyl)-4-(3-oxo-2,3-dihydroisoxazol-5-yl)piperidine-1-carboxylate (1.82 g, 61%) was isolated. $^1$H NMR (600 MHz, $cdcl_3$) δ 1.82-1.91 (m, 1H), 2.03-2.13 (m, 1H), 2.22-2.41 (m, 2H), 3.01-3.10 (m, 1H), 3.43-3.53 (m, 1H), 3.63 (s, 3H), 4.11-4.21 (m, 1H), 5.19 (dd, 1H), 5.59 (s, 1H), 6.89-6.95 (m, 2H), 7.14 (t, 1H). MS m/z 405 $(M+H)^+$

Step 3: (2R,4S)-Methyl 2-(2-fluoro-4-(trifluoromethoxy)phenyl)-4-(3-oxo-2,3-dihydro-isoxazol-5-yl)piperidine-1-carboxylate Cis-methyl 2-(2-fluoro-4-(trifluoromethoxy)phenyl)-4-(3-oxo-2,3-dihydroisoxazol-5-yl)-piperidine-1-carboxylate (1.82 g, 4.5 mmol) was subjected to chiral preparative HPLC (Column: CelluCoat (250×50 mm), 10 µm particle size, mobile phase: Heptane/EtOH 1/1, flow rate 120 mL/min) to yield (2R,4S)-methyl 2-(2-fluoro-4-(trifluoromethoxy)phenyl)-4-(3-oxo-2,3-dihydroisoxazol-5-yl)piperidine-1-carboxylate (917 mg, 50%), Chiral purity 99.9% ee, Optical rotation $[\alpha]_D^{20}$=+49.7 (acetonitrile, c=1.0)

Step 4: 5-(2R,4S)-2-(2-Fluoro-4-(trifluoromethoxy)phenyl)piperidin-4-yl)isoxazol-3(2H)-one (2R,4S)-Methyl 2-(2-fluoro-4-(trifluoromethoxy)phenyl)-4-(3-oxo-2,3-dihydroisoxazol-5-yl)-piperidine-1-carboxylate (458 mg, 1.13 mmol) was dissolved in hydrogen bromide (33% in acetic acid, 8.93 mL, 50.98 mmol) and stirred at room temperature for 16 h. The solvent was removed in vacuo and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-((2R,4S)-2-(2-fluoro-4-(trifluoromethoxy)phenyl)piperidin-4-yl)isoxazol-3(2H)-one (246 mg, 63%). $^1$H NMR (600 MHz, dmso) δ 1.37 (q, 1H), 1.47 (dq, 1H), 1.84-1.90 (m, 1H), 1.93-1.99 (m, 1H), 2.74 (dt, 1H), 2.87-2.94 (m, 1H), 3.07-3.13 (m, 1H), 3.94 (dd, 1H), 5.74 (s, 1H), 7.18-7.22 (m, 1H), 7.28-7.33 (m, 1H), 7.66 (t, 1H); HRMS Calculated for $[C_{15}H_{14}F_4N_2O_3+H]^+$: 347.1019. Found: 347.0995

Example 59

5-(Trans-2-(2-fluoro-4-(trifluoromethoxy)phenyl)piperidin-4-yl)isoxazol-3(2H)-one

Step 1: Trans-methyl 2-(2-fluoro-4-(trifluoromethoxy)phenyl)-4-(3-oxo-2,3-dihydroisoxazol-5-yl)piperidine-1-carboxylate Trans-methyl 4-(3-ethoxy-3-oxopropanoyl)-2-(2-fluoro-4-(trifluoromethoxy)phenyl)-piperidine-1-carboxylate (420 mg, 0.96 mmol) (from example 58, step 1) was dissolved in MeOH (4 mL) and cooled to −40° C. under nitrogen. Sodium hydroxide (40.5 mg, 1.01 mmol) dissolved in water (0.400 mL) was added and the mixture was stirred at −40° C. for 15 min. Hydroxylamine (50% by weight in water, 62 μL, 1.01 mmol) was added. The resulting solution was stirred at −40° C. for 1 h. The mixture was then transferred into a prewarmed (80° C.) solution of 6 M hydrogen chloride (4.98 mL, 29.91 mmol) and the mixture was stirred at 80° C. for 15 min. Water and DCM were added and the phases separated. The aqueous phase was extracted with DCM and the combined organic layers were filtered through a phase separator and evaporated. Crude trans-methyl 2-(2-fluoro-4-(trifluoromethoxy)phenyl)-4-(3-oxo-2,3-dihydroisoxazol-5-yl)piperidine-1-carboxylate (365 mg, 94%) was yielded as a colorless oil. MS m/z 405 (M+H)$^+$ Step 2: 5-(Trans-2-(2-fluoro-4-(trifluoromethoxy) phenyl)piperidin-4-yl)isoxazol-3(2H)-one Trans-methyl 2-(2-fluoro-4-(trifluoromethoxy)phenyl)-4-(3-oxo-2,3-dihydroisoxazol-5-yl)piperidine-1-carboxylate (365 mg, 0.90 mmol) was dissolved in hydrogen bromide (33% in acetic acid, 7.115 mL, 40.62 mmol) and stirred at room temperature for 16 h. The solvent was removed in vacuo and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(2-fluoro-4-(trifluoromethoxy)phenyl)-piperidin-4-yl)isoxazol-3(2H)-one (185 mg, 59%). $^1$H NMR (600 MHz, dmso) δ 1.64-1.72 (m, 1H), 1.77-1.85 (m, 1H), 1.91-1.97 (m, 1H), 2.02-2.08 (m, 1H), 2.69 (dt, 1H), 2.86-2.92 (m, 1H), 3.17-3.22 (m, 1H), 3.95 (dd, 1H), 5.87 (d, 1H), 7.19-7.23 (m, 1H), 7.28-7.32 (m, 1H), 7.66 (t, 1H); HRMS Calculated for [C$_{15}$H$_{14}$F$_4$N$_2$O$_3$+H]$^+$: 347.1019. Found: 347.1002

Example 60

5-((2R,4S)-2-(3,4,5-Trifluorophenyl)piperidin-4-yl) isoxazol-3(2H)-one

Step 1: Trans-methyl 4-(3-ethoxy-3-oxopropanoyl)-2-(3,4,5-trifluorophenyl)piperidine-1-carboxylate and cis-methyl 4-(3-ethoxy-3-oxopropanoyl)-2-(3,4,5-trifluorophenyl)piperidine-1-carboxylate 1-(Methoxycarbonyl)-2-(3,4,5-trifluorophenyl)piperidine-4-carboxylic acid (1.94 g, 6.11 mmol) (reference compound 26) was dissolved in methyl THF (70 mL), then di(1H-imidazol-1-yl)methanone (1.487 g, 9.17 mmol) was added. The mixture was stirred at room temperature under nitrogen for 3 h (flask 1). In a separate flask potassium 3-ethoxy-3-oxopropanoate (1.873 g, 11.01 mmol) was suspended in methyl THF (70.0 mL), then magnesium chloride (1.048 g, 11.01 mmol) was added. The suspension was stirred at 50° C. under nitrogen for 3 h using a large magnetic stirring bar (flask 2). Then the contents of flask 1 was transferred into flask 2. The resulting white suspension was stirred under nitrogen at room temperature overnight. The mixture was acidified to pH 1 with 3.8 M HCl, then MTBE (50 mL) and water (50 mL) was added. The phases were separated and the organic layer was washed with water, satd NaHCO$_3$ and brine. The organic layer was dried over Na$_2$SO$_4$, filtered and evaporated leaving a slightly yellow oil. The product was flashed on Biotage (340 g) with a gradient of 20-60% EtOAc in n-heptane (8 CV). The column was conditioned at 20% EtOAc in n-heptane (1 CV). Trans-methyl 4-(3-ethoxy-3-oxopropanoyl)-2-(3,4,5-trifluorophenyl)piperidine-1-carboxylate (59 mg, 2.5%) and cis-methyl 4-(3-ethoxy-3-oxopropanoyl)-2-(3,4,5-trifluorophenyl)piperidine-1-carboxylate (810 mg, 34%) were isolated. Cis-isomer: $^1$H NMR (400 MHz, cdcl$_3$) δ 1.07-1.18 (m, 3H), 1.60-2.43 (m, 4H), 2.71-2.83 (m, 1H), 3.12-3.27 (m, 1H), 3.36 (s, 2H), 3.52 (s, 3H), 3.91-4.09 (m, 3H), 4.72-4.83 (m, 1H), 6.71-6.81 (m, 2H). MS m/z 388 (M+H)$^+$. Trans-isomer: $^1$H NMR (400 MHz, cdcl$_3$) δ 1.20-1.30 (m, 3H), 1.47-2.01 (m, 3H), 2.35-2.47 (m, 1H), 2.55-2.68 (m, 1H), 2.79 (dt, 1H), 3.42-3.49 (m, 2H), 3.75 (s, 3H), 4.09-4.37 (m, 3H), 5.52 (s, br., 1H), 6.78-6.89 (m, 2H). MS m/z 388 (M+H)$^+$ Step 2: Cis-methyl 4-(3-oxo-2,3-dihydroisoxazol-5-yl)-2-(3,4,5-trifluorophenyl)piperidine-1-carboxylate Cis-methyl 4-(3-ethoxy-3-oxopropanoyl)-2-(3,4,5-trifluorophenyl)piperidine-1-carboxylate (810 mg, 2.09 mmol) was dissolved in MeOH (8 mL) and cooled to −40° C. under nitrogen. Sodium hydroxide (0.615 mL, 2.09 mmol) was added during 10 min and the yellow solution continued to stir at −40° C. for 20 min. Hydroxylamine (50% by weight in water, 0.128 mL, 2.09 mmol) was added during 8 min. The resulting solution was stirred at −40° C. for 3 h. The mixture was then rapidly poured into a prewarmed (80° C.) solution of 6 M hydrogen chloride (10.77 mL, 64.62 mmol) and the mixture continued to stir at 80° C. for 20 min. The solvent was evaporated and DCM/water added. The phases were separated and the organic phase passed through a phase separator and evaporated to yield a white solid. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 4-(3-oxo-2,3-dihydroisoxazol-5-yl)-2-(3,4,5-trifluoro-phenyl)piperidine-1-carboxylate (355 mg, 48%) was isolated. MS m/z 357 (M+H)$^+$ Step 3: (2R,4S)-methyl 4-(3-oxo-2,3-dihydroisoxazol-5-yl)-2-(3,4,5-trifluorophenyl)-piperidine-1-carboxylate and (2S,4R)-methyl 4-(3-oxo-2,3-dihydroisoxazol-5-yl)-2-(3,4,5-trifluorophenyl) piperidine-1-carboxylate Cis-methyl 4-(3-oxo-2,3-dihydroisoxazol-5-yl)-2-(3,4,5-trifluorophenyl)piperidine-1-carboxylate (355 mg, 1 mmol) was subjected to chiral preparative HPLC (Column: Cellu-Coat (250×20), 5 μm particle size, mobile phase: Heptane/EtOH 60/40, flow rate 18 mL/min) to yield (2R,4S)-methyl 4-(3-oxo-2,3-dihydroisoxazol-5-yl)-2-(3,4,5-trifluorophenyl)piperidine-1-carboxylate (164 mg, 46%), Chiral purity 98.7% ee, Optical rotation [α]$_D^{20}$=+60.6 (acetonitrile, c=0.5), $^1$H NMR (400 MHz, cdcl$_3$) δ 1.80-1.90 (m, 1H), 1.99-2.40 (m, 3H), 3.00-3.13 (m, 1H), 3.29-3.42 (m, 1H), 3.69 (s, 3H), 4.07-4.19 (m, 1H), 4.97-5.07 (m, 1H), 5.60 (s, 1H), 6.75-6.85 (m, 2H), and (2S,4R)-methyl 4-(3-oxo-2,3-dihydroisoxazol-5-yl)-2-(3,4,5-trifluorophenyl)piperidine-1-carboxylate (160 mg, 45%), Chiral purity 99.9% ee, Optical rotation [α]$_D^{20}$=−52.9 (acetonitrile, c=1), $^1$H NMR (400 MHz, cdcl$_3$) δ 1.81-1.90 (m, 1H), 2.05-2.15 (m, 1H), 2.19-2.38 (m, 2H), 3.02-3.11 (m, 1H), 3.30-3.40 (m, 1H), 3.69 (s, 3H), 4.09-4.18 (m, 1H), 4.99-5.05 (m, 1H), 5.60 (s, 1H), 6.76-6.84 (m, 2H).

Step 4: 5-((2R,4S)-2-(3,4,5-Trifluorophenyl)piperidin-4-yl)isoxazol-3(2H)-one (2R,4S)-Methyl 4-(3-oxo-2,3-dihydroisoxazol-5-yl)-2-(3, 4,5-trifluorophenyl)piperidine-1-carboxylate (164 mg, 0.46 mmol) was dissolved in hydrogen bromide (33% in acetic acid (3.63 mL, 20.71 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(3,4,5-trifluorophenyl)piperidin-4-yl)isoxazol-3(2H)-one (93 mg, 67%). $^1$H NMR (600 MHz, dmso) δ 1.29 (q, 1H), 1.43 (dq, 1H), 1.82-1.89 (m, 1H), 1.96-2.02 (m, 1H), 2.70 (dt, 1H), 2.79-2.87 (m, 1H), 3.05-3.12 (m, 1H), 3.64 (dd, 1H), 5.72 (s, 1H), 7.26-7.34 (m, 2H). HRMS Calculated for [C$_{14}$H$_{13}$F$_3$N$_2$O$_2$+H]$^+$: 299.1007. Found: 299.1002

Example 61

5-((2S,4R)-2-(3,4,5-Trifluorophenyl)piperidin-4-yl)isoxazol-3(2H)-one (2S,4R)-methyl 4-(3-oxo-2,3-dihydroisoxazol-5-yl)-2-(3,4,5-trifluorophenyl)piperidine-1-carboxylate (160 mg, 0.45 mmol) (from example 60, step 3) was dissolved in hydrogen bromide (33% in acetic acid, 3.54 mL, 20.21 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-(3,4,5-trifluorophenyl)piperidin-4-yl)isoxazol-3(2H)-one (85 mg, 63%) $^1$H NMR (600 MHz, dmso) δ 1.29 (q, 1H), 1.43 (qd, 1H), 1.83-1.88 (m, 1H), 1.97-2.02 (m, 1H), 2.70 (td, 1H), 2.80-2.87 (m, 1H), 3.06-3.12 (m, 1H), 3.64 (dd, 1H), 5.73 (s, 1H), 7.27-7.34 (m, 2H). HRMS Calculated for [C$_{14}$H$_{13}$F$_3$N$_2$O$_2$+H]$^+$: 299.1007. Found: 299.1037

Example 62

5-(Trans-2-(3,4,5-trifluorophenyl)piperidin-4-yl)isoxazol-3(2H)-one

Step 1: Trans-methyl 4-(3-oxo-2,3-dihydroisoxazol-5-yl)-2-(3,4,5-trifluorophenyl)piperidine-1-carboxylate Trans-methyl 4-(3-ethoxy-3-oxopropanoyl)-2-(3,4,5-trifluorophenyl)piperidine-1-carboxylate (59 mg, 0.15 mmol) (from example 60, step 1) was dissolved in MeOH (1 mL) and cooled to −40° C. under nitrogen. Sodium hydroxide (0.045 mL, 0.15 mmol) was added during 10 min and the yellow solution continued to stir at −40° C. for 20 min. Hydroxylamine (50% by weight in water, 9.33 μL, 0.15 mmol) was added during 8 min. The resulting solution was stirred at −40° C. for 3 h 15 min. The mixture was then rapidly poured into a prewarmed (80° C.) solution of 6 M hydrogen chloride (0.784 mL, 4.71 mmol) and the mixture continued to stir at 80° C. for 20 min. The solvent was evaporated and DCM/water added. The phases were separated, the organic phase passed through a phase separator and evaporated to yield crude trans-methyl 4-(3-oxo-2,3-dihydroisoxazol-5-yl)-2-(3,4,5-trifluorophenyl)piperidine-1-carboxylate (53 mg, quant.) as a slightly yellow oil. MS m/z 357 (M+H)$^+$ Step 2: 5-(Trans-2-(3,4,5-trifluorophenyl)piperidin-4-yl)isoxazol-3(2H)-one Trans-methyl 4-(3-oxo-2,3-dihydroisoxazol-5-yl)-2-(3,4,5-trifluorophenyl)piperidine-1-carboxylate (53.4 mg, 0.15 mmol) was dissolved in hydrogen bromide (33% in acetic acid, 1.18 mL, 6.75 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(3,4,5-trifluorophenyl)piperidin-4-yl)isoxazol-3(2H)-one (11 mg, 25%). $^1$H NMR (600 MHz, dmso) δ 1.72-1.88 (m, 3H), 1.97-2.04 (m, 1H), 2.61-2.69 (m, 1H), 2.76-2.83 (m, 1H), 3.06-3.11 (m, 1H), 3.69-3.75 (m, 1H), 5.98 (s, 1H), 7.28-7.36 (m, 2H). HRMS Calculated for [C$_{14}$H$_{13}$F$_3$N$_2$O$_2$+H]$^+$: 299.1007. Found: 299.1031

Example 63

5-((2R,4S)-2-(2,4,5-Trifluorophenyl)piperidin-4-yl)isoxazol-3(2H)-one

Step 1: Cis-methyl 4-(3-ethoxy-3-oxopropanoyl)-2-(2,4,5-trifluorophenyl)piperidine-1-carboxylate 1-(Methoxycarbonyl)-2-(2,4,5-trifluorophenyl)piperidine-4-carboxylic acid (2.388 g, 7.53 mmol) (reference compound 27) was dissolved in methyl THF (50 mL) and di(1H-imidazol-1-yl)methanone (1.831 g, 11.29 mmol) added. The suspension was stirred at room temperature under nitrogen for 6 h (flask 1). In a separate flask potassium 3-ethoxy-3-oxopropanoate (2.306 g, 13.55 mmol) was suspended in methyl THF (50.0 mL) and magnesium chloride (1.290 g, 13.55 mmol) added. The suspension was stirred at 50° C. under nitrogen for 5.5 h using an oversized stirring bar (flask 2). The suspension in flask 1 was now added to the white suspension in flask 2. The resulting beige suspension was stirred under nitrogen at room temperature overnight. The mixture was acidified to pH 1 with 3.8 M HCl and MTBE and water added. The phases were separated and the organic phase washed with water, satd NaHCO$_3$ and water and was evaporated. Traces of water were azeotropically removed by MeCN to yield a yellow oil. The residue was purified on Biotage (20%=>50% EtOAc in heptane, 8 CV; Biotage® KP-SIL 340 g column). Cis-methyl 4-(3-ethoxy-3-oxopropanoyl)-2-(2,4,5-trifluorophenyl)piperidine-1-carboxylate (1.877 g, 64%) was isolated as colorless oil. $^1$H NMR (600 MHz, cdcl$_3$) δ 1.19-1.29 (m, 3H), 1.49-2.19 (m, 3H), 2.22-2.29 (m, 1H), 2.82-2.91 (m, 1H), 3.34 (ddd, 1H), 3.39-3.48 (m, 2H), 3.62 (s, 3H), 4.05-4.20 (m, 3H), 5.00-5.06 (m, 1H), 6.85-7.00 (m, 2H). MS m/z 388 (M+H)$^+$.

Step 2: Cis-methyl 4-(3-oxo-2,3-dihydroisoxazol-5-yl)-2-(2,4,5-trifluorophenyl)piperidine-1-carboxylate and trans-methyl 4-(3-oxo-2,3-dihydroisoxazol-5-yl)-2-(2,4,5-trifluorophenyl)-piperidine-1-carboxylate Cis-methyl 4-(3-ethoxy-3-oxopropanoyl)-2-(2,4,5-trifluorophenyl)piperidine-1-carboxylate (1.888 g, 4.87 mmol) was dissolved in MeOH (18 mL) and cooled to −40° C. under nitrogen. Sodium hydroxide (0.195 g, 4.87 mmol) dissolved in water (1.800 mL) was added during 10 min and the colourless solution continued to stir at −40° C. for 20 min. Hydroxylamine (50% by weight in water, 0.299 mL, 4.87 mmol) was added during 8 min. The resulting solution was stirred at −40° C. for 3 h 20 min. The mixture was then transferred into a prewarmed (80° C.) solution of 6 M hydrogen chloride (24 mL, 144.00 mmol) and the mixture continued to stir at 80° C. for 20 min. The solvent was evaporated and DCM/water added. The phases were separated and the organic phase passed through a phase separator and evaporated to yield a yellow oil. The compound was purified by preparative HPLC in 3 injections on a XBridge C18 column (10 µm 250×50 ID mm) using a gradient of 5-30% Acetonitrile in H2O/MeCN/NH3 95/5/0.2 buffer over 20 minutes with a flow of 100 mL/min. A mixture of cis-methyl 4-(3-oxo-2,3-dihydroisoxazol-5-yl)-2-(2,4,5-trifluorophenyl)piperidine-1-carboxylate and trans-methyl 4-(3-oxo-2,3-dihydroisoxazol-5-yl)-2-(2,4,5-trifluorophenyl)-piperidine-1-carboxylate (1.027 g, 59%) was obtained as white solid after freeze drying. MS m/z 357 (M+H)$^+$ Step 3: (2R,4S)-Methyl 4-(3-oxo-2,3-dihydroisoxazol-5-yl)-2-(2,4,5-trifluorophenyl)-piperidine-1-carboxylate and (2S,4S)-methyl 4-(3-oxo-2,3-dihydroisoxazol-5-yl)-2-(2,4,5-trifluorophenyl)piperidine-1-carboxylate The mixture of cis-methyl 4-(3-oxo-2,3-dihydroisoxazol-5-yl)-2-(2,4,5-trifluorophenyl)-piperidine-1-carboxylate and trans-methyl 4-(3-oxo-2,3-dihydroisoxazol-5-yl)-2-(2,4,5-trifluorophenyl)piperidine-1-carboxylate (1.027 g, 2.88 mmol) was subjected to chiral preparative HPLC (Column: CelluCoat (250×20), 5 µm particle size, mobile phase: Heptane/IPA 80/20, flow rate 18 mL/min) to yield (2R,4S)-methyl 4-(3-oxo-2,3-dihydroisoxazol-5-yl)-2-(2,4,5-trifluorophenyl)piperidine-1-carboxylate (259 mg, 25%), Chiral purity A % 99.9, Optical rotation $[\alpha]_D^{20}$=+50.3 (acetonitrile, c=1), and (2S,4S)-methyl 4-(3-oxo-2,3-dihydroisoxazol-5-yl)-2-(2,4,5-trifluorophenyl)piperidine-1-carboxylate (203 mg, 20%), Chiral purity A %: 99.9, Optical rotation $[\alpha]_D^{20}$=+4.5 (acetonitrile, c=1)

Step 4: 5-((2R,4S)-2-(2,4,5-Trifluorophenyl)piperidin-4-yl)isoxazol-3(2H)-one (2R,4S)-methyl 4-(3-oxo-2,3-dihydroisoxazol-5-yl)-2-(2,4,5-trifluorophenyl)piperidine-1-carboxylate (259 mg, 0.73 mmol) was dissolved in hydrogen bromide (33% in acetic acid, 4 mL, 22.84 mmol) and the mixture stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 µm OBD 19*150 mm) to yield 5-((2R,4S)-2-(2,4,5-trifluorophenyl)piperidin-4-yl)isoxazol-3(2H)-one (161 mg, 74%). $^1$H NMR (600 MHz, dmso) δ 1.36 (q, 1H), 1.45 (dq, 1H), 1.83-1.90 (m, 1H), 1.91-1.97 (m, 1H), 2.74 (dt, 1H), 2.90 (tt, 1H), 3.06-3.13 (m, 1H), 3.91 (d, 1H), 5.74 (d, 1H), 7.44-7.57 (m, 2H). HRMS Calculated for $[C_{14}H_{13}F_3N_2O_2+H]^+$: 299.1007. Found: 299.1021

Example 64

5-((2S,4S)-2-(2,4,5-Trifluorophenyl)piperidin-4-yl)isoxazol-3(2H)-one (2S,4S)-Methyl 4-(3-oxo-2,3-dihydroisoxazol-5-yl)-2-(2,4,5-trifluorophenyl)piperidine-1-carboxylate (203 mg, 0.57 mmol) (from example 63, step 4) was dissolved in hydrogen bromide (33% in acetic acid, 4 mL, 22.84 mmol) and the mixture stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 µm OBD 19*150 mm) to yield 5-((2S,4S)-2-(2,4,5-trifluorophenyl)piperidin-4-yl)isoxazol-3(2H)-one (138 mg, 81%). $^1$H NMR (600 MHz, dmso) δ 1.62-1.70 (m, 1H), 1.80 (tt, 1H), 1.90-1.96 (m, 1H), 2.00-2.06 (m, 1H), 2.68 (dt, 1H), 2.85-2.91 (m, 1H), 3.20 (s, br., 1H), 3.90 (d, 1H), 5.86 (d, 1H), 7.43-7.56 (m, 2H). HRMS Calculated for $[C_{14}H_{13}F_3N_2O_2+H]^+$: 299.1007. Found: 299.1023

Example 65

5-((2R,4S)-2-(4-Chloro-3,5-difluorophenyl)piperidin-4-yl)isoxazol-3(2H)-one

Step 1: Trans-methyl 2-(4-chloro-3,5-difluorophenyl)-4-(3-ethoxy-3-oxopropanoyl)-piperidine-1-carboxylate and cis-methyl 2-(4-chloro-3,5-difluorophenyl)-4-(3-ethoxy-3-oxopropanoyl)piperidine-1-carboxylate 2-(4-Chloro-3,5-difluorophenyl)-1-(methoxycarbonyl)piperidine-4-carboxylic acid (1.6 g, 4.79 mmol) (reference compound 28) was dissolved in methyl THF (30 mL) under nitrogen atmosphere and di(1H-imidazol-1-yl)methanone (1.166 g, 7.19 mmol) was added. The suspension was stirred at room temperature for 3 h (flask 1). In a separate flask was potassium 3-ethoxy-3-oxopropanoate (1.469 g, 8.63 mmol) suspended in methyl THF (15 mL) and magnesium chloride (0.822 g, 8.63 mmol) was added. The suspension was stirred at 50° C. under nitrogen for 7 h using an oversized stirring bar (flask 2). To flask 2 the contents of flask 1 was added and the resulting white suspension was stirred at room temperature for 20 h. In a separate flask was potassium 3-ethoxy-3-oxopropanoate (0.734 g, 4.32 mmol) suspended in methyl THF (15 mL) and magnesium chloride (0.411 g, 4.32 mmol) was added. The suspension was stirred at 50° C. for 5 h and then added to the reaction mixture. The mixture was stirred at room temperature for 15 h. 0.1 M HCl and DCM were added and the phases separated. The aqueous phase was extracted with DCM, the combined organic layers filtered through a phase separator and evaporated. The residue was purified by column chromatography on silica (2:1 heptane:EtOAc, Biotage® KP-SIL 340 g column, 10 CV). Cis-methyl 2-(4-chloro-3,5-difluorophenyl)-4-(3-ethoxy-3-oxopropanoyl)piperidine-1-carboxylate (1.448 g, 74.8%) and trans-methyl 2-(4-chloro-3,5-difluorophenyl)-4-(3-ethoxy-3-oxopropanoyl)piperidine-1-carboxylate (0.178 g, 9.19%) were isolated as colorless oils. Cis-isomer: $^1$H NMR (400 MHz, cdcl$_3$) δ 1.23-1.32 (m, 3H), 1.74-2.19 (m, 3H), 2.20-2.30 (m, 1H), 2.82-2.92 (m, 1H), 3.23-3.34 (m, 1H), 3.46 (s, 2H), 3.63-3.69 (m, 3H), 4.04-4.23 (m, 3H), 4.84-4.95 (m, 1H), 6.81-6.90 (m, 2H). MS m/z 404 (M+H)$^+$. Trans-isomer: $^1$H NMR (400 MHz, cdcl$_3$) δ 1.20-1.33 (m, 3H), 1.48-1.92 (m, 2H), 1.92-2.04 (m, 1H), 2.36-2.51 (m, 1H), 2.54-2.70 (m, 1H), 2.82 (dt, 1H), 3.47 (d, 2H), 3.73 (s, 3H), 4.08-4.45 (m, 3H), 5.56 (s, br., 1H), 6.86 (d, 2H). MS m/z 404 (M+H)$^+$ Step 2: Cis-methyl 2-(4-chloro-3,5-difluorophenyl)-4-(3-oxo-2,3-dihydroisoxazol-5-yl)piperidine-1-carboxylate Cis-methyl 2-(4-chloro-3,5-difluorophenyl)-4-(3-ethoxy-3-oxopropanoyl)piperidine-1-carboxylate (1.445 g, 3.58 mmol) was dissolved in MeOH (14 mL) and cooled to −40° C. under nitrogen. Sodium hydroxide (0.150 g, 3.76 mmol) dissolved in water (1.4 mL) was added and the mixture was stirred at −40° C. for 15 min. Hydroxylamine (50% by weight in water, 0.230 mL, 3.76 mmol) was added. The resulting solution was stirred at −40° C. for 1 h. The mixture was then transferred into a prewarmed (80° C.) solution of 6 M hydrogen chloride (18.49 mL, 110.93 mmol) and the mixture was stirred at 80° C. for 20 min. Water and DCM were added and the phases separated. The aqueous phase was extracted with DCM and the combined organic layers were filtered through a phase separator and evaporated. The compound was purified by preparative HPLC on a Kromasil C8 column (10 μm 250×50 ID mm) using a gradient of 15-55% Acetonitrile in H2O/MeCN/FA 95/5/0.2 buffer over 30 minutes with a flow of 100 mL/min. The compounds were detected by UV at 220 nm. Cis-methyl 2-(4-chloro-3,5-difluorophenyl)-4-(3-oxo-2,3-dihydroisoxazol-5-yl)piperidine-1-carboxylate (0.831 g, 62.3%) was yielded as colorless solid. $^1$H NMR (600 MHz, cdcl$_3$) δ 1.80-1.87 (m, 1H), 2.04-2.15 (m, 1H), 2.19-2.28 (m, 1H), 2.30-2.36 (m, 1H), 3.00-3.09 (m, 1H), 3.30-3.39 (m, 1H), 3.66 (s, 3H), 4.07-4.16 (m, 1H), 4.98-5.05 (m, 1H), 5.59 (s, br., 1H), 6.80 (d, 2H). MS m/z 273 (M+H)$^+$

Step 3: (2R,4S)-Methyl 2-(4-chloro-3,5-difluorophenyl)-4-(3-oxo-2,3-dihydroisoxazol-5-yl)piperidine-1-carboxylate Cis-methyl 2-(4-chloro-3,5-difluorophenyl)-4-(3-oxo-2,3-dihydroisoxazol-5-yl)piperidine-1-carboxylate (830 mg, 2.23 mmol) was subjected to chiral preparative HPLC (Column: CelluCoat (250×50 mm), 10 μm particle size, mobile phase: Heptane/EtOH 1/1, flow rate 120 mL/min) to yield (2R,4S)-methyl 2-(4-chloro-3,5-difluorophenyl)-4-(3-oxo-2,3-dihydroisoxazol-5-yl)piperidine-1-carboxylate (390 mg, 47%), Chiral purity 99.7% ee, Optical rotation $[\alpha]_D^{20}$=+55.9 (acetonitrile, c=1.0)

Step 4: 5-((2R,4S)-2-(4-Chloro-3,5-difluorophenyl)piperidin-4-yl)isoxazol-3(2H)-one (2R,4S)-Methyl 2-(4-chloro-3,5-difluorophenyl)-4-(3-oxo-2,3-dihydroisoxazol-5-yl)piperidine-1-carboxylate (0.39 g, 1.05 mmol) was dissolved in hydrogen bromide (33% in acetic acid, 10 mL, 142.75 mmol) and stirred at room temperature for 18 h. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(4-chloro-3,5-difluorophenyl)piperidin-4-yl)isoxazol-3(2H)-one (272 mg, 83%). $^1$H NMR (600 MHz, dmso) δ 1.29 (q, 1H), 1.43 (dq, 1H), 1.82-1.89 (m, 1H), 1.97-2.04 (m, 1H), 2.70 (dt, 1H), 2.84 (tt, 1H), 3.06-3.12 (m, 1H), 3.68 (dd, 1H), 5.73 (s, 1H), 7.31 (d, 2H). HRMS Calculated for [C$_{14}$H$_{13}$ClF$_2$N$_2$O$_2$+H]$^+$: 315.0712. Found: 315.0707

Example 66

5-(Trans-2-(4-chloro-3,5-difluorophenyl)piperidin-4-yl)isoxazol-3(2H)-one

Step 1: Trans-methyl 2-(4-chloro-3,5-difluorophenyl)-4-(3-oxo-2,3-dihydroisoxazol-5-yl)-piperidine-1-carboxylate Trans-methyl 2-(4-chloro-3,5-difluorophenyl)-4-(3-ethoxy-3-oxopropanoyl)piperidine-1-carboxylate (178 mg, 0.44 mmol) (from example 65, step 1) was dissolved in MeOH (2 mL) and cooled to −40° C. under nitrogen. Sodium hydroxide (18.51 mg, 0.46 mmol) dissolved in water (0.200 mL) was added and the mixture was stirred at −40° C. for 15 min. Hydroxylamine (50% by weight in water, 0.028 mL, 0.46 mmol) was added. The resulting solution was stirred at −40° C. for 1 h. The mixture was transferred into a prewarmed (80° C.) solution of 6 M hydrogen chloride (2.278 mL, 13.67 mmol) and the mixture was stirred at 80° C. for 20 min. Water and DCM were added and the phases separated. The aqueous phase was extracted with DCM and the combined organic layers were filtered through a phase separator and evaporated. Crude trans-methyl 2-(4-chloro-3,5-difluorophenyl)-4-(3-oxo-2,3-dihydro-isoxazol-5-yl)piperidine-1-carboxylate (158 mg, 96%) was isolated as a light yellow oil. MS m/z 273 (M+H)$^+$

Step 2: 5-(Trans-2-(4-chloro-3,5-difluorophenyl)piperidin-4-yl)isoxazol-3(2H)-one Trans-methyl 2-(4-chloro-3,5-difluorophenyl)-4-(3-oxo-2,3-dihydroisoxazol-5-yl)piperidine-1-carboxylate (157 mg, 0.42 mmol) was dissolved in hydrogen bromide (33% in acetic acid, 3.32 mL, 18.95 mmol) and stirred at room temperature for 16 h. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(4-chloro-3,5-difluorophenyl)piperidin-4-yl)isoxazol-3(2H)-one (26 mg, 19%). $^1$H NMR (600 MHz, dmso) δ 1.75-2.11 (m, 4H), 2.66-2.77 (m, 1H), 2.81-2.95 (m, 1H), 3.14 (s, br., 1H), 3.86 (s, br., 1H), 6.03 (s, 1H), 7.32-7.42 (m, 2H). HRMS Calculated for [C$_{14}$H$_{13}$ClF$_2$N$_2$O$_2$+H]$^+$: 315.0712. Found: 315.0715

Example 67

5-((2R,4S)-2-(3-Methyl-4-(trifluoromethyl)phenyl)piperidin-4-yl)isoxazol-3(2H)-one

Step 1: Trans-methyl 4-(3-ethoxy-3-oxopropanoyl)-2-(3-methyl-4-(trifluoromethyl)phenyl)-piperidine-1-carboxylate and cis-methyl 4-(3-ethoxy-3-oxopropanoyl)-2-(3-methyl-4-(trifluoromethyl)phenyl)piperidine-1-carboxylate Ethyl potassium malonate (1.567 g, 9.21 mmol) and MgCl$_2$ (0.731 g, 7.67 mmol) were added to dry THF (50 mL). The reaction flask was stirred vigorously for 4 h at 50° C. (flask 1). 1-(Methoxycarbonyl)-2-(3-methyl-4-(trifluoromethyl)phenyl)piperidine-4-carboxylic acid (2.65 g, 7.67 mmol) (reference compound 29) and carbonyldiimidazole (1.867 g, 11.51 mmol) were added to dry THF (50 mL) at room temperature (flask 2). The contents of flask 2 was added to flask 1 and the resulting mixture stirred at room temperature overnight. The reaction mixture was dissolved between water and diethyl ether. The organic phase was isolated, dried with Na$_2$SO$_4$, filtered through celite and the solvent was evaporated. Chromatography using the Biotage equipment. Gradient elution using ethylacetate-heptane, started 0-100 and ended 100-0. Trans-methyl 4-(3-ethoxy-3-oxopropanoyl)-2-(3-methyl-4-(trifluoromethyl)phenyl)-piperidine-1-carboxylate (0.69 g, 22%) and cis-methyl 4-(3-ethoxy-3-oxopropanoyl)-2-(3-methyl-4-(trifluoromethyl)phenyl)piperidine-1-carboxylate (1.40 g, 44%) were isolated. Cis-isomer: $^1$H NMR (600 MHz, cdcl$_3$) δ 1.25 (t, 3H), 1.00-2.29 (m, 4H), 2.44 (s, 3H), 2.47-2.95 (m, 1H), 3.27-3.34 (m, 1H), 3.37-3.48 (m, 2H), 3.62 (s, 3H), 3.66-4.20 (m, 3H), 4.88-4.96 (m, 1H), 7.05-7.11 (m, 2H), 7.50-7.54 (m, 1H). Trans-isomer: $^1$H NMR (600 MHz, cdcl$_3$) δ 1.22 (t, 3H), 1.47-2.03 (m, 4H), 2.47 (s, 3H), 2.49-2.89 (m, 2H), 3.40-3.47 (m, 2H), 3.74 (s, 3H), 4.15 (q, 2H), 4.11-4.36 (m, 1H), 5.37-5.75 (m, 1H), 7.06-7.13 (m, 2H), 7.57 (d, 1H).

Step 2: Cis-methyl 2-(3-methyl-4-(trifluoromethyl)phenyl)-4-(3-oxo-2,3-dihydroisoxazol-5-yl)piperidine-1-carboxylate Cis-methyl 4-(3-ethoxy-3-oxopropanoyl)-2-(3-methyl-4-(trifluoromethyl)phenyl)piperidine-1-carboxylate (1.4 g, 3.37 mmol) was dissolved in MeOH (20 mL) and cooled to −40° C. NaOH (0.135 g, 3.37 mmol) dissolved in water (2 mL) was added during 10 min and the resulting colourless solution continued to stir at −40° C. for 20 min. Hydroxylamine (50% by weight in water, 0.223 g, 3.37 mmol) was added dropwise. The resulting solution was stirred at −40° C. for 30 min. The mixture was then transferred into a pre-warmed (80° C.) solution of 6 M HCl and the mixture continued to stir at 80° C. for 20 min. The mixture was dissolved between diethyl ether and water. The phases were separated and the organic phase was dried over $Na_2SO_4$, filtered through celite and the solvent removed. Purified by preparative HPLC. Gradient elution using acetonitrile-acidic buffer, started 40-60 and ended 55-45. Cis-methyl 2-(3-methyl-4-(trifluoromethyl)phenyl)-4-(3-oxo-2,3-dihydroisoxazol-5-yl)piperidine-1-carboxylate (0.37 g, 29%) was isolated. $^1$H NMR (600 MHz, cdcl$_3$) δ 1.80-1.87 (m, 1H), 2.07-2.28 (m, 2H), 2.31-2.38 (m, 1H), 2.41 (s, 3H), 3.03-3.10 (m, 1H), 3.35-3.43 (m, 1H), 3.66 (s, 3H), 4.13-4.19 (m, 1H), 5.09 (t, 1H), 5.52 (s, 1H), 7.02-7.06 (m, 2H), 7.49 (d, 1H). MS m/z 385 (M+H)$^+$

Step 3: (2R,4S)-Methyl 2-(3-methyl-4-(trifluoromethyl)phenyl)-4-(3-oxo-2,3-dihydro-isoxazol-5-yl)piperidine-1-carboxylate and (2S,4R)-methyl 2-(3-methyl-4-(trifluoromethyl)-phenyl)-4-(3-oxo-2,3-dihydroisoxazol-5-yl)piperidine-1-carboxylate Cis-methyl 2-(3-methyl-4-(trifluoromethyl)phenyl)-4-(3-oxo-2,3-dihydroisoxazol-5-yl)-piperidine-1-carboxylate (0.37 g, 0.96 mmol) was subjected to chiral preparative HPLC (Column: CelluCoat OJ (250×50), 10 μm particle size, mobile phase: Heptane/EtOH 50/50, flow rate 120 mL/min) to yield (2R,4S)-methyl 2-(3-methyl-4-(trifluoromethyl)phenyl)-4-(3-oxo-2,3-dihydroisoxazol-5-yl)piperidine-1-carboxylate (177 mg, 48%), Chiral purity 99.2% ee, Optical rotation $[\alpha]_D^{20}$=+57.1 (acetonitrile, c=1), $^1$H NMR (600 MHz, cdcl$_3$) δ 1.78-1.85 (m, 1H), 2.08-2.16 (m, 1H), 2.17-2.26 (m, 1H), 2.29-2.36 (m, 1H), 2.39 (s, 3H), 3.01-3.09 (m, 1H), 3.34-3.42 (m, 1H), 3.64 (s, 3H), 4.09-4.17 (m, 1H), 5.07 (t, 1H), 5.50 (s, 1H), 7.01-7.07 (m, 2H), 7.47 (d, 1H), 10.63 (br, 1H), and (2S,4R)-methyl 2-(3-methyl-4-(trifluoromethyl)phenyl)-4-(3-oxo-2,3-dihydroisoxazol-5-yl)piperidine-1-carboxylate (168 mg, 45%), Chiral purity 99.9% ee, Optical rotation $[\alpha]_D^{20}$=−57.1 (acetonitrile, c=1), $^1$H NMR (600 MHz, cdcl$_3$) δ 1.79-1.86 (m, 1H), 2.10-2.18 (m, 1H), 2.19-2.27 (m, 1H), 2.31-2.37 (m, 1H), 2.41 (s, 3H), 3.02-3.09 (m, 1H), 3.35-3.42 (m, 1H), 3.65 (s, 3H), 4.11-4.18 (m, 1H), 5.08 (t, 1H), 5.51 (s, 1H), 7.02-7.07 (m, 2H), 7.48 (d, 1H).

Step 4: 5-((2R,4S)-2-(3-Methyl-4-(trifluoromethyl)phenyl)piperidin-4-yl)isoxazol-3(2H)-one (2R,4S)-Methyl 2-(3-methyl-4-(trifluoromethyl)phenyl)-4-(3-oxo-2,3-dihydroisoxazol-5-yl)-piperidine-1-carboxylate (0.177 g, 0.46 mmol) was dissolved in HBr (33% in acetic acid, 5.6 g, 22.84 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(3-methyl-4-(trifluoromethyl)phenyl)piperidin-4-yl)isoxazol-3(2H)-one (0.082 g, 55%). $^1$H NMR (600 MHz, dmso) δ 1.31-1.39 (m, 1H), 1.41-1.50 (m, 1H), 1.84-1.90 (m, 1H), 1.95-2.00 (m, 1H), 2.40 (d, 3H), 2.57-2.59 (m, 1H), 2.83-2.90 (m, 1H), 3.08-3.13 (m, 1H), 3.68 (d, 1H), 5.72 (s, 1H), 7.35 (d, 1H), 7.43 (s, 1H), 7.57 (d, 1H). HRMS Calcd for $[C_{16}H_{17}F_3N_2O_2+H]^+$: 327.1320. Found: 327.1311.

Example 68

5-((2S,4R)-2-(3-Methyl-4-(trifluoromethyl)phenyl)piperidin-4-yl)isoxazol-3(2H)-one (2S,4R)-Methyl 2-(3-methyl-4-(trifluoromethyl)phenyl)-4-(3-oxo-2,3-dihydroisoxazol-5-yl)-piperidine-1-carboxylate (0.168 g, 0.44 mmol) (from example 67, step 3) was dissolved in HBr (33% in acetic acid, 5.6 g, 22.84 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-(3-methyl-4-(trifluoromethyl)phenyl)piperidin-4-yl)isoxazol-3(2H)-one (0.068 g, 48%). $^1$H NMR (600 MHz, dmso) δ 1.31-1.40 (m, 1H), 1.41-1.50 (m, 1H), 1.85-1.90 (m, 1H), 1.95-2.00 (m, 1H), 2.40 (s, 3H), 2.69-2.76 (m, 1H), 2.83-2.90 (m, 1H), 3.08-3.13 (m, 1H), 3.68 (d, 1H), 5.73 (s, 1H), 7.36 (d, 1H), 7.43 (s, 1H), 7.57 (d, 1H). HRMS Calcd for $[C_{16}H_{17}F_3N_2O_2+H]^+$: 327.1320. Found: 327.1318.

Example 69

5-(Trans-2-(3-methyl-4-(trifluoromethyl)phenyl)piperidin-4-yl)isoxazol-3(2H)-one

Step 1: Trans-methyl 2-(3-methyl-4-(trifluoromethyl)phenyl)-4-(3-oxo-2,3-dihydroisoxazol-5-yl)piperidine-1-carboxylate Trans-methyl 4-(3-ethoxy-3-oxopropanoyl)-2-(3-methyl-4-(trifluoromethyl)phenyl)-piperidine-1-carboxylate (0.69 g, 1.66 mmol) (from example 67, step 1) was dissolved in MeOH (8 mL) and cooled to −40° C. under nitrogen. NaOH (0.066 g, 1.66 mmol) dissolved in water (0.7 mL) was added during 10 min and the resulting colourless solution continued to stir at −40° C. for 20 min. Hydroxylamine (50% by weight in water, 0.110 g, 1.66 mmol) was added dropwise. The resulting solution was stirred at −40° C. for 30 min. The mixture was then transferred into a prewarmed (80° C.) solution of 6 M HCl and the mixture continued to stir at 80° C. for 20 min. The mixture was dissolved between diethyl ether and water. The phases were separated and the organic phase was dried over $Na_2SO_4$, filtered through celite and evaporated to yield crude trans-methyl 2-(3-methyl-4-(trifluoromethyl)phenyl)-4-(3-oxo-2,3-dihydroisoxazol-5-yl)piperidine-1-carboxylate (0.54 g, 85%). $^1$H NMR (600 MHz, cdcl$_3$) δ 1.60-1.72 (m, 1H), 1.89-1.97 (m, 1H), 1.99-2.07 (m, 1H), 2.48 (s, 3H), 2.58-2.71 (m, 1H), 2.80 (s, 1H), 2.93 (t, 1H), 3.73 (s, 3H), 4.23 (s, 1H), 5.49-5.73 (m, 2H), 7.06-7.16 (m, 2H), 7.60 (d, 1H).

Step 2: 5-(Trans-2-(3-methyl-4-(trifluoromethyl)phenyl)piperidin-4-yl)isoxazol-3(2H)-one Trans-methyl 2-(3-methyl-4-(trifluoromethyl)phenyl)-4-(3-oxo-2,3-dihydroisoxazol-5-yl)piperidine-1-carboxylate (0.139 g, 0.36 mmol) was dissolved in HBr (33% in acetic acid, 5.60 g, 22.84 mmol) and the mixture was stirred at room temperature overnight. The solvent was evaporated and the residue purified by preparative HPLC (Instrument: FractionLynx II, Mobilphase: gradient 5-95% MeCN in 0.2% NH₃, pH 10, Column: Xbridge Prep C18 5 µm OBD 19*150 mm) to yield 5-(trans-2-(3-methyl-4-(trifluoromethyl)phenyl)piperidin-4-yl)isoxazol-3(2H)-one (0.075 g, 64%). $^1$H NMR (600 MHz, dmso) δ 1.76-1.85 (m, 2H), 1.85-1.93 (m, 1H), 1.99-2.07 (m, 1H), 2.40 (d, 2H), 2.67-2.75 (m, 1H), 2.80-2.89 (m, 1H), 3.10-3.17 (m, 1H), 3.68-3.78 (m, 1H), 5.96 (s, 1H), 7.36 (d, 1H), 7.43 (s, 1H), 7.57 (d, 1H). HRMS Calcd for $[C_{16}H_{17}F_3N_2O_2+H]^+$: 327.1320. Found: 327.1298.

Example 70

5-((2R,4S)-2-(3,5-Difluoro-4-(trifluoromethyl)phenyl)piperidin-4-yl)isoxazol-3(2H)-one Step 1: Trans-methyl 2-(3,5-difluoro-4-(trifluoromethyl)phenyl)-4-(3-ethoxy-3-oxopropanoyl)piperidine-1-carboxylate and cis-methyl 2-(3,5-difluoro-4-(trifluoromethyl)-phenyl)-4-(3-ethoxy-3-oxopropanoyl)piperidine-1-carboxylate 2-(3,5-Difluoro-4-(trifluoromethyl)phenyl)-1-(methoxycarbonyl)piperidine-4-carboxylic acid (2.363 g, 6.43 mmol) (reference compound 30) was dissolved in methyl THF (30 mL) and di(1H-imidazol-1-yl)methanone (1.565 g, 9.65 mmol) added. The suspension was stirred at room temperature under nitrogen for 20 h (flask 1). In a separate flask potassium 3-ethoxy-3-oxopropanoate (2.190 g, 12.87 mmol) and magnesium chloride (1.225 g, 12.87 mmol) were suspended in methyl THF (30.0 mL) and stirred with an oversized stirring bar at 50° C. under nitrogen for 20 h (flask 2). The white suspension in flask 2 was then added to flask 1. The thick white suspension was stirred at room temperature for 24 h. The reaction mixture was acidified by addition of 3 M HCl to pH 1. MTBE (250 mL) and water were added, shaken and the phases separated. The organic phase was washed with water (200 mL), satd NaHCO₃ (200 mL), brine (200 mL), dried with a phase separator and evaporated in vacuo. The residue was purified by automated flash chromatography on a Biotage® KP-SIL 100 g column. A gradient from 40% EtOAc in heptane over 2 CV followed by 40% to 80% of EtOAc in heptane over 10 CV was used as mobile phase. Cis-methyl 2-(3,5-difluoro-4-(trifluoromethyl)phenyl)-4-(3-ethoxy-3-oxopropanoyl)piperidine-1-carboxylate (1.489 g, 52.9%) and trans-methyl 2-(3,5-difluoro-4-(trifluoromethyl)phenyl)-4-(3-ethoxy-3-oxopropanoyl)piperidine-1-carboxylate (0.110 g, 3.91%) were isolated. Cis-isomer: $^1$H NMR (600 MHz, cdcl₃) δ 1.25 (t, 3H), 1.49-2.28 (m, 4H), 2.80-2.91 (m, 1H), 3.23-3.31 (m, 1H), 3.44 (s, 2H), 3.65 (s, 3H), 4.07-4.14 (m, 1H), 4.17 (q, 2H), 4.86-4.95 (m, 1H), 6.83 (d, 2H). Trans-isomer: $^1$H NMR (600 MHz, cdcl₃) δ 1.24 (t, 3H), 1.54-1.60 (m, 1H), 1.73-1.89 (m, 1H), 1.96-2.03 (m, 1H), 2.38-2.47 (m, 1H), 2.53-2.62 (m, 1H), 2.76-2.84 (m, 1H), 3.40-3.49 (m, 2H), 3.75 (s, 3H), 4.17 (q, 2H), 4.15-4.42 (m, 1H), 5.40-5.71 (m, 1H), 6.87 (d, 2H).

Step 2: Cis-methyl 2-(3,5-difluoro-4-(trifluoromethyl)phenyl)-4-(3-oxo-2,3-dihydroisoxazol-5-yl)piperidine-1-carboxylate Cis-methyl 2-(3,5-difluoro-4-(trifluoromethyl)phenyl)-4-(3-ethoxy-3-oxopropanoyl)-piperidine-1-carboxylate (1.489 g, 3.40 mmol) was dissolved in MeOH (15 mL) and cooled to −40° C. Sodium hydroxide (0.896 mL, 3.40 mmol) dissolved in water (1.500 mL) was added and the reaction stirred at −40° C. for 20 min. Hydroxylamine (50% by weight in water, 0.209 mL, 3.40 mmol) was added and stirring continued for 3.5 h at −40° C. The reaction mixture was then added to a prewarmed 80° C. solution of hydrogen chloride (17.59 mL, 105.54 mmol) and stirred for 20 min. The solvent was evaporated in vacuo. DCM (100 mL) and water (100 mL) were added, shaken and the phases separated. The organic phase was dried with a phase separator and evaporated in vacuo. The compound was purified by preparative HPLC on a Kromasil C8 column (10 µm 250×50 ID mm) using a gradient of 20-65% Acetonitrile in H2O/MeCN/AcOH 95/5/0.2 buffer over 30 minutes with a flow of 100 mL/min. Cis-methyl 2-(3,5-difluoro-4-(trifluoromethyl)phenyl)-4-(3-oxo-2,3-dihydroisoxazol-5-yl)piperidine-1-carboxylate (0.594 g, 42.9%) was isolated as a white solid. $^1$H NMR (600 MHz, cdcl₃) δ 1.82-1.89 (m, 1H), 2.08-2.16 (m, 1H), 2.19-2.27 (m, 1H), 2.32-2.38 (m, 1H), 3.04-3.11 (m, 1H), 3.34-3.41 (m, 1H), 3.68 (s, 3H), 4.09-4.15 (m, 1H), 5.04-5.08 (m, 1H), 5.57 (s, 1H), 6.80 (d, 2H).

Step 3: (2R,4S)-methyl 2-(3,5-difluoro-4-(trifluoromethyl)phenyl)-4-(3-oxo-2,3-dihydro-isoxazol-5-yl)piperidine-1-carboxylate Cis-methyl 2-(3,5-difluoro-4-(trifluoromethyl)phenyl)-4-(3-oxo-2,3-dihydroisoxazol-5-yl)-piperidine-1-carboxylate (465 mg, 1.14 mmol) was subjected to chiral preparative HPLC (Column: CelluCoat (250×50), 10 µm particle size, mobile phase: Heptane/EtOH 60/40, flow rate 120 mL/min) to yield (2R,4S)-methyl 2-(3,5-difluoro-4-(trifluoromethyl)phenyl)-4-(3-oxo-2,3-dihydroisoxazol-5-yl)piperidine-1-carboxylate (226 mg, 48%), Chiral purity 99.8% ee, Optical rotation $[\alpha]_D^{20}$=+48.2 (acetonitrile, c=1), $^1$H NMR (600 MHz, cdcl₃) δ 1.82-1.88 (m, 1H), 2.07-2.14 (m, 1H), 2.19-2.27 (m, 1H), 2.32-2.38 (m, 1H), 3.04-3.10 (m, 1H), 3.34-3.41 (m, 1H), 3.68 (s, 3H), 4.09-4.15 (m, 1H), 5.04-5.08 (m, 1H), 5.58 (s, 1H), 6.80 (d, 2H).

Step 4: 5-((2R,4S)-2-(3,5-Difluoro-4-(trifluoromethyl)phenyl)piperidin-4-yl)isoxazol-3(2H)-one (2R,4S)-Methyl 2-(3,5-difluoro-4-(trifluoromethyl)phenyl)-4-(3-oxo-2,3-dihydroisoxazol-5-yl)piperidine-1-carboxylate (226 mg, 0.56 mmol) was dissolved in hydrobromic acid (33% in AcOH, 5 mL, 30.38 mmol) and stirred at room temperature for 20 h. The solvent was evaporated and the residue purified by preparative HPLC (Instrument: FractionLynx II, Mobilphase: gradient 5-95% MeCN in 0.2% NH₃, pH 10, Column: Xbridge Prep C18 5 µm OBD 19*150 mm) to yield 5-((2R,4S)-2-(3,5-difluoro-4-(trifluoromethyl)phenyl)piperidin-4-yl)isoxazol-3(2H)-one (133 mg, 68%). $^1$H NMR (600 MHz, dmso) δ 1.30 (q, 1H), 1.43 (dq, 1H), 1.84-1.89 (m, 1H), 2.02-2.07 (m, 1H), 2.70 (dt, 1H), 2.86 (tt, 1H), 3.07-3.13 (m, 1H), 3.75 (dd, 1H), 5.73 (s, 1H), 7.37 (d, 2H). HRMS Calcd for $[C_{15}H_{13}F_5N_2O_2+H]^+$: 349.0975. Found: 349.0972.

Example 71

5-(Trans-2-(3,5-difluoro-4-(trifluoromethyl)phenyl)piperidin-4-yl)isoxazol-3(2H)-one Step 1: Trans-methyl 2-(3,5-difluoro-4-(trifluoromethyl)phenyl)-4-(3-oxo-2,3-dihydro-isoxazol-5-yl)piperidine-1-carboxylate Trans-methyl 2-(3,5-difluoro-4-(trifluoromethyl)phenyl)-4-(3-ethoxy-3-oxopropanoyl)-piperidine-1-carboxylate (110 mg, 0.25 mmol) (from example 70, step 1) was dissolved in MeOH (5 mL) and cooled to −40° C. Sodium hydroxide (0.066 mL, 0.25 mmol) dissolved in water (0.500 mL) was added. After 20 min at −40° C., hydroxylamine (50% by weight in water, 7.71 μL, 0.25 mmol) was added and stirring continued for 4 h. The reaction mixture was then added to a prewarmed 80° C. solution of 6 M hydrogen chloride (1.299 mL, 7.80 mmol) and stirred for 1 h. The solvent was evaporated in vacuo. DCM (50 mL) and water (50 mL) were added, shaken and the phases separated. The organic phase was dried with a phase separator and evaporated in vacuo. The compound was purified by preparative HPLC on a Kromasil C8 column (10 μm 250×20 ID mm) using a gradient of 20-65% Acetonitrile in H2O/MeCN/AcOH 95/5/0.2 buffer, over 30 minutes with a flow of 19 mL/min. Trans-methyl 2-(3,5-difluoro-4-(trifluoromethyl)phenyl)-4-(3-oxo-2,3-dihydroisoxazol-5-yl)piperidine-1-carboxylate (7.00 mg, 6.85%) was isolated as a white solid. $^1$H NMR (600 MHz, cdcl$_3$) δ 1.61-1.73 (m, 1H), 1.90-2.01 (m, 1H), 2.06 (dt, 1H), 2.56 (d, 1H), 2.76 (t, 1H), 2.89 (t, 1H), 3.78 (s, 3H), 4.13-4.47 (m, 1H), 5.46-5.74 (m, 1H), 5.68 (s, 1H), 6.89 (d, 2H). MS m/z 407 (M+H)$^+$ Step 2: 5-(Trans-2-(3,5-difluoro-4-(trifluoromethyl) phenyl)piperidin-4-yl)isoxazol-3(2H)-one Trans-methyl 2-(3,5-difluoro-4-(trifluoromethyl)phenyl)-4-(3-oxo-2,3-dihydroisoxazol-5-yl)piperidine-1-carboxylate (26 mg, 0.06 mmol) was dissolved in hydrogen bromide (33% in AcOH, 2 mL, 0.06 mmol) and stirred at room temperature for 20 h. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(3,5-difluoro-4-(trifluoromethyl)phenyl)piperidin-4-yl)isoxazol-3(2H)-one (7.00 mg, 31%). $^1$H NMR (600 MHz, dmso) δ 1.73-1.88 (m, 3H), 2.02-2.08 (m, 1H), 2.64-2.70 (m, 1H), 2.77-2.83 (m, 1H), 3.06-3.11 (m, 1H), 3.83-3.86 (m, 1H), 6.02 (s, 1H), 7.42 (d, 2H). HRMS Calcd for [C$_{15}$H$_{13}$F$_5$N$_2$O$_2$+H]$^+$: 349.0975. Found: 349.0983.

Example 72

5-((2R,4S)-2-(2-Methyl-4-(trifluoromethyl)phenyl) piperidin-4-yl)isoxazol-3(2H)-one Step 1: Cis-methyl 4-(3-ethoxy-3-oxopropanoyl)-2-(2-methyl-4-(trifluoromethyl)phenyl) piperidine-1-carboxylate 1-(Methoxycarbonyl)-2-(2-methyl-4-(trifluoromethyl) phenyl)piperidine-4-carboxylic acid (7.79 g, 22.56 mmol) (reference compound 31) was dissolved in THF (60 mL) and then di(1H-imidazol-1-yl)methanone (5.49 g, 33.84 mmol) was added. The reaction was stirred overnight at room temperature (flask 1). In a separate flask potassium 3-ethoxy-3-oxopropanoate (7.68 g, 45.12 mmol) and anhydrous magnesium chloride (4.30 g, 45.12 mmol) were suspended in THF (60.0 mL) and stirred at 50° C. under nitrogen overnight and then allowed to cool to room temperature (flask 2). The content of flask 1 was added to flask 2 and stirred under nitrogen for 48 h. The reaction was quenched by addition of 2 M HCl. The mixture was extracted three times with EtOAc, the combined organic phases were evaporated and purified by column chromatography on silica (100 g Biotage column with heptane/EtOAc 88/12-33/67 over 9 column volumes) to give cis-methyl 4-(3-ethoxy-3-oxopropanoyl)-2-(2-methyl-4-(trifluoromethyl)phenyl)piperidine-1-carboxylate (6.28 g, 67%). $^1$H NMR (400 MHz, cdcl$_3$) δ 1.23-1.33 (m, 3H), 1.68-1.97 (m, 2H), 2.08-2.21 (m, 2H), 2.44 (s, 3H), 2.87-2.98 (m, 1H), 3.46 (s, 2H), 3.44-3.66 (m, 1H), 3.58 (s, 3H), 4.15-4.29 (m, 3H), 4.91-5.01 (m, 1H), 7.24-7.32 (m, 1H), 7.36-7.43 (m, 2H). MS m/z 416 (M+H)$^+$ Step 2: Cis-methyl 2-(2-methyl-4-(trifluoromethyl) phenyl)-4-(3-oxo-2,3-dihydroisoxazol-5-yl)piperidine-1-carboxylate Cis-methyl 4-(3-ethoxy-3-oxopropanoyl)-2-(2-methyl-4-(trifluoromethyl)phenyl)piperidine-1-carboxylate (6.28 g, 15.12 mmol) was dissolved in MeOH (60 mL) and cooled to −40° C. 3.8 M NaOH (3.98 mL, 15.12 mmol) was dissolved in water (6 mL) and added to the mixture and the reaction stirred at −40° C. for 40 min. Hydroxylamine (50% by weight in water, 0.926 mL, 15.12 mmol) was added and stirring continued for 3.5 h at −40° C. The reaction mixture was then added to a preheated 80° C. warm solution of 6 M HCl (76 mL, 453.53 mmol) and stirred for 20 min. The reaction mixture was partitioned between water and DCM. The aqueous phase was extracted twice with DCM and the combined organic phase was dried and evaporated. The compound was purified in two runs by preparative HPLC on a Kromasil C8 column (10 μm 250×50 ID mm) using a gradient of 35-75% acetonitrile in H2O/MeCN/AcOH 95/5/0.2 buffer over 30 minutes with a flow of 100 mL/min. Cis-methyl 2-(2-methyl-4-(trifluoromethyl)phenyl)-4-(3-oxo-2,3-dihydroisoxazol-5-yl)piperidine-1-carboxylate (3.2 g, 55%) was isolated. $^1$H NMR (400 MHz, cdcl$_3$) δ 1.81-1.93 (m, 2H), 2.21-2.42 (m, 2H), 2.44 (s, 3H), 3.03-3.13 (m, 1H), 3.59 (s, 3H), 3.63-3.75 (m, 1H), 4.12-4.20 (m, 1H), 5.02 (dd, 1H), 5.65 (s, 1H), 7.30 (d, 1H), 7.37-7.44 (m, 2H). MS m/z 383 (M−H)$^−$ Step 3: (2R,4S)-Methyl 2-(2-methyl-4-(trifluoromethyl)phenyl)-4-(3-oxo-2,3-dihydroisoxazol-5-yl) piperidine-1-carboxylate Cis-methyl 2-(2-methyl-4-(trifluoromethyl)phenyl)-4-(3-oxo-2,3-dihydroisoxazol-5-yl)-piperidine-1-carboxylate (3.2 g, 8.33 mmol) was subjected to chiral preparative HPLC (Column: CelluCoat (250×50), 10 μm particle size, mobile phase: Heptane/EtOH 75/25, flow rate 120 mL/min) to yield (2R,4S)-Methyl 2-(2-methyl-4-(trifluoromethyl)phenyl)-4-(3-oxo-2,3-dihydroisoxazol-5-yl)piperidine-1-carboxylate (1.45 g, 45%), Chiral purity 99.3% ee, Optical rotation $[α]_D^{20}$=+49.0 (acetonitrile, c=1), $^1$H NMR (400 MHz, cdcl$_3$) δ 1.79-1.95 (m, 2H), 2.20-2.40 (m, 2H), 2.44 (s, 3H), 3.02-3.15 (m, 1H), 3.59 (s, 3H), 3.63-3.76 (m, 1H), 4.11-4.22 (m, 1H), 5.02 (dd, 1H), 5.65 (s, 1H), 7.24-7.32 (m, 1H), 7.36-7.43 (m, 2H).

Step 4: 5-((2R,4S)-2-(2-Methyl-4-(trifluoromethyl) phenyl)piperidin-4-yl)isoxazol-3(2H)-one (2R,4S)-Methyl 2-(2-methyl-4-(trifluoromethyl)phenyl)-4-(3-oxo-2,3-dihydroisoxazol-5-yl)-piperidine-1-carboxylate (1.45 g, 3.77 mmol) was dissolved in hydrogen bromide (33% in HOAc, 19.82 mL, 113.18 mmol) and stirred overnight. The mixture was evaporated and purified on a Kromasil C8 column (10 μm 250×50 ID mm) using a gradient of 15-55% acetonitrile in H$_2$O/MeCN/NH$_3$ 95/5/0.2 buffer over 20 minutes with a flow of 100 mL/min. 5-((2R,4S)-2-(2-Methyl-4-(trifluoromethyl)phenyl)piperidin-4-yl)isoxazol-3 (2H)-one (810 mg, 65%) was isolated as a white powder. $^1$H NMR (400 MHz, cdcl$_3$) δ 1.35 (q, 1H), 1.52 (dq, 1H), 1.88-

2.01 (m, 2H), 2.42 (s, 3H), 2.75-2.85 (m, 1H), 2.89-3.00 (m, 1H), 3.12-3.18 (m, 1H), 3.93 (d, 1H), 5.76 (s, 1H), 7.49-7.54 (m, 2H), 7.73 (d, 1H). HRMS Calculated for $[C_{16}H_{17}F_3N_2O_2+H]^+$: 327.1320. Found: 327.1312.

Example 73

5-((2R,4S)-2-(2-Fluoro-4-(trifluoromethyl)phenyl)piperidin-4-yl)isoxazol-3(2H)-one Step 1: Trans-methyl 4-(3-ethoxy-3-oxopropanoyl)-2-(2-fluoro-4-(trifluoromethyl)phenyl)piperidine-1-carboxylate and cis-methyl 4-(3-ethoxy-3-oxopropanoyl)-2-(2-fluoro-4-(trifluoromethyl)phenyl)piperidine-1-carboxylate 2-(2-fluoro-4-(trifluoromethyl)phenyl)-1-(methoxycarbonyl)piperidine-4-carboxylic acid (4.82 g, 13.80 mmol) was dissolved in methyl THF (120 mL), then di(1H-imidazol-1-yl)methanone (4.03 g, 24.84 mmol) was added. The mixture was stirred at room temperature under nitrogen for 5 h (flask 1). In a separate flask potassium 3-ethoxy-3-oxopropanoate (4.23 g, 24.84 mmol) was suspended in methyl THF (120 mL), then magnesium chloride (2.365 g, 24.84 mmol) was added. The suspension was stirred at 50° C. under nitrogen for 5 h using a large magnetic stirring bar (flask 2). The contents of flask 1 was transferred into flask 2. The resulting white suspension was stirred under nitrogen at room temperature overnight. The mixture was acidified to pH 1 with 3.8 M HCl, then MTBE (50 mL) and water (50 mL) was added. The phases were separated and the organic layer was washed with water, satd NaHCO$_3$ and brine. The organic layer was dried over Na$_2$SO$_4$, filtered and evaporated leaving a slightly yellow oil. The residue was purified by chromatography on silica (Biotage (340 g) with a 1 CV EtOAc in heptane (20%) followed by a gradient of 20-60% EtOAc in n-heptane (8 CV). The column was conditioned at 20% EtOAc in -n-heptane (1 CV)). Trans-methyl 4-(3-ethoxy-3-oxopropanoyl)-2-(2-fluoro-4-(trifluoromethyl)phenyl) piperidine-1-carboxylate (413 mg, 7%) and cis-methyl 4-(3-ethoxy-3-oxopropanoyl)-2-(2-fluoro-4-(trifluoromethyl)-phenyl)piperidine-1-carboxylate (2.83 g, 49%) were isolated. Cis-isomer: $^1$H NMR (400 MHz, cdcl$_3$) δ 1.22-1.32 (m, 3H), 1.81-1.96 (m, 2H), 2.06-2.18 (m, 1H), 2.27-2.36 (m, 1H), 2.87-2.97 (m, 1H), 3.34-3.51 (m, 3H), 3.58-3.66 (m, 3H), 4.14-4.23 (m, 3H), 5.15 (dd, 1H), 7.25-7.40 (m, 3H). MS m/z 420 (M+H)$^+$. Trans-isomer: $^1$H NMR (400 MHz, cdcl$_3$) δ 1.18-1.31 (m, 3H), 1.58-1.72 (m, 1H), 1.87-2.06 (m, 2H), 2.40-2.60 (m, 2H), 3.17 (dt, 1H), 3.45 (s, 2H), 3.73 (s, br., 3H), 4.08-4.23 (m, 2H), 4.34 (s, br., 1H), 5.75 (s, br., 1H), 7.22-7.43 (m, 3H). MS m/z 420 (M+H)$^+$ Step 2: Cis-methyl 2-(2-fluoro-4-(trifluoromethyl)phenyl)-4-(3-oxo-2,3-dihydroisoxazol-5-yl)piperidine-1-carboxylate Cis-methyl 4-(3-ethoxy-3-oxopropanoyl)-2-(2-fluoro-4-(trifluoromethyl)phenyl)piperidine-1-carboxylate (3 g, 7.15 mmol) was dissolved in MeOH (25 mL) and cooled to −45° C. under nitrogen. Sodium hydroxide (2.104 mL, 7.15 mmol) was added during 10 min and the yellow solution continued to stir at −45° C. for 20 min. Hydroxylamine (50% by weight in water, 0.438 mL, 7.15 mmol) was added during 8 min. The resulting solution was stirred at −45° C. for 3 h. The mixture was then rapidly poured into a prewarmed (80° C.) solution of 6 M hydrogen chloride (36.8 mL, 221.05 mmol) and the mixture continued to stir at 80° C. for 20 min. The solvent was evaporated and DCM/water added. The phases were separated and the organic phase passed through a phase separator and evaporated to yield a slightly yellow solid. The compound was purified by preparative HPLC on a XBridge C18 column (10 μm 250×50 ID mm) using a gradient of 10-60% Acetonitrile in H2O/MeCN/NH3 95/5/0.2 buffer over 20 minutes with a flow of 100 mL/min. Cis-methyl 2-(2-fluoro-4-(trifluoromethyl)phenyl)-4-(3-oxo-2,3-dihydroisoxazol-5-yl)piperidine-1-carboxylate (2.12 g, 76%) was isolated as a colourless oil. MS m/z 389 (M+H)$^+$ Step 3: (2R,4S)-Methyl 2-(2-fluoro-4-(trifluoromethyl)phenyl)-4-(3-oxo-2,3-dihydroisoxazol-5-yl)piperidine-1-carboxylate Cis-methyl 2-(2-fluoro-4-(trifluoromethyl)phenyl)-4-(3-oxo-2,3-dihydroisoxazol-5-yl)piperidine-1-carboxylate (2.12 g, 5.46 mmol) was subjected to chiral preparative HPLC (Column: CelluCoat (250×50 mm), 10 μm particle size, mobile phase: Heptane/EtOH 50/50, flow rate 120 mL/min) to yield (2R,4S)-methyl 2-(2-fluoro-4-(trifluoromethyl)phenyl)-4-(3-oxo-2,3-dihydroisoxazol-5-yl)piperidine-1-carboxylate (958 mg, 45%), Chiral purity 99.9% ee, Optical rotation $[α]_D^{20}$=+48.0 (acetonitrile, c=1.0), $^1$H NMR (400 MHz, cdcl$_3$) δ 1.84-1.95 (m, 1H), 2.04-2.15 (m, 1H), 2.24-2.45 (m, 2H), 3.04-3.15 (m, 1H), 3.47-3.58 (m, 1H), 3.65 (s, 3H), 4.14-4.23 (m, 1H), 5.25 (dd, 1H), 5.61 (s, 1H), 7.23-7.37 (m, 3H).

Step 4: 5-((2R,4S)-2-(2-Fluoro-4-(trifluoromethyl)phenyl)piperidin-4-yl)isoxazol-3(2H)-one (2R,4S)-Methyl 2-(2-fluoro-4-(trifluoromethyl)phenyl)-4-(3-oxo-2,3-dihydroisoxazol-5-yl)piperidine-1-carboxylate (0.96 g, 2.47 mmol) was dissolved in hydrogen bromide (33% in acetic acid, 19.48 mL, 111.25 mmol) and the mixture was stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-(2-fluoro-4-(trifluoromethyl)phenyl)piperidin-4-yl)isoxazol-3(2H)-one (687 mg, 84%). $^1$H NMR (600 MHz, dmso) δ 1.36 (q, 1H), 1.48 (dq, 1H), 1.84-1.92 (m, 1H), 1.94-2.02 (m, 1H), 2.75 (dt, 1H), 2.92 (tt, 1H), 3.08-3.15 (m, 1H), 4.00 (d, 1H), 5.73 (s, 1H), 7.53-7.62 (m, 2H), 7.78 (t, 1H). HRMS Calculated for $[C_{15}H_{14}F_4N_2O_2+H]^+$: 331.1070. Found: 331.1086

Example 74

5-(Trans-2-(2-fluoro-4-(trifluoromethyl)phenyl)piperidin-4-yl)isoxazol-3(2H)-one Step 1: Trans-methyl 2-(2-fluoro-4-(trifluoromethyl)phenyl)-4-(3-oxo-2,3-dihydroisoxazol-5-yl)piperidine-1-carboxylate Trans-methyl 4-(3-ethoxy-3-oxopropanoyl)-2-(2-fluoro-4-(trifluoromethyl)phenyl)piperidine-1-carboxylate (430 mg, 1.03 mmol) (from example 73, step 1) was dissolved in MeOH (3 mL) and cooled to −45° C. under nitrogen. Sodium hydroxide (0.302 mL, 1.03 mmol) was added during 10 min and the yellow solution continued to stir at −45° C. for 20 min. Hydroxylamine (50% by weight in water, 0.063 mL, 1.03 mmol) was added during 8 min. The resulting solution was stirred at −45° C. for 3 h. The mixture was then rapidly poured into a prewarmed (80° C.) solution of 6 M hydrogen chloride (5.28 mL, 31.68 mmol) and the mixture continued to stir at 80° C. for 20 min. The solvent was evaporated and DCM/water added. The phases were separated and the organic phase passed through a phase separator and evaporated to yield a slightly yellow oil. Crude trans-methyl 2-(2-fluoro-4-(trifluoromethyl)phenyl)-4-(3-oxo-2,3-dihydroisoxazol-5-yl)piperidine-1-carboxylate (398 mg, quant.) was isolated. MS m/z 387 (M−H)$^-$ Step 2: 5-(Trans-2-(2-fluoro-4-(trifluoromethyl)phenyl)piperidin-4-yl)isoxazol-3(2H)-one Trans-methyl 2-(2-fluoro-4-(trifluoromethyl)phenyl)-4-(3-oxo-2,3-dihydroisoxazol-5-yl)-piperidine-1-carboxylate (400 mg, 1.03 mmol) was dissolved in hydrogen bromide (33% in acetic acid, 8.12 mL, 46.35 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-(trans-2-(2-fluoro-4-(trifluoromethyl)phenyl)-piperidin-4-yl)isoxazol-3(2H)-one (146 mg, 43%). $^1$H NMR (600 MHz, dmso) δ 1.63-1.71 (m, 1H), 1.78-1.86 (m, 1H), 1.91-1.99 (m, 1H), 2.04-2.11 (m, 1H), 2.69 (dt, 1H), 2.87-2.93 (m, 1H), 3.19-3.23 (m, 1H), 4.00 (d, 1H), 5.88 (d, 1H), 7.53-7.61 (m, 2H), 7.77 (t, 1H). HRMS Calculated for $[C_{15}H_{14}F_4N_2O_2+H]^+$: 331.1070. Found: 331.1074

Example 75

5-((2R,4S)-2-(3-Fluoro-4-(trifluoromethyl)phenyl)piperidin-4-yl)isoxazol-3(2H)-one Step 1: Methyl 4-(3-ethoxy-3-oxopropanoyl)-2-(3-fluoro-4-(trifluoromethyl)phenyl)piperidine-1-carboxylate 2-(3-Fluoro-4-(trifluoromethyl)phenyl)-1-(methoxycarbonyl)piperidine-4-carboxylic acid (3.07 g, 8.8 mmol) (reference compound 33) was dissolved in methyl THF (60 mL) under nitrogen atmosphere and di(1H-imidazol-1-yl)methanone (2.140 g, 13.20 mmol) was added. The suspension was stirred at room temperature for 3 h (flask 1). In a separate flask was potassium 3-ethoxy-3-oxopropanoate (2.70 g, 15.84 mmol) suspended in methyl THF (30 mL) and magnesium chloride (1.508 g, 15.84 mmol) was added. The suspension was stirred at 50° C. under nitrogen for 22 h using an oversized stirring bar (flask 2). The contents of flask 1 was transferred into flask 2 and the resulting white suspension was stirred at room temperature for 20 h. In a separate flask was potassium 3-ethoxy-3-oxopropanoate (1.348 g, 7.92 mmol) suspended in methyl THF (30 mL) and magnesium chloride (0.754 g, 7.92 mmol) was added. The suspension was stirred at 50° C. for 5 h and then added to the reaction mixture. The mixture was stirred at room temperature for 15 h. 0.1 M HCl and DCM were added and the phases separated. The aqueous phase was extracted with DCM, the combined organic layers filtered through a phase separator and evaporated. The residue was purified via Biotage (5:1 heptane:EtOAc, Biotage® KP-SIL 340 g column, 10 CV). The product methyl 4-(3-ethoxy-3-oxopropanoyl)-2-(3-fluoro-4-(trifluoromethyl)phenyl)piperidine-1-carboxylate (2.190 g, 59.3%) was isolated as a colorless oil. MS m/z 420 (M+H)$^+$ Step 2: Methyl 2-(3-fluoro-4-(trifluoromethyl)phenyl)-4-(3-oxo-2,3-dihydroisoxazol-5-yl)piperidine-1-carboxylate Methyl 4-(3-ethoxy-3-oxopropanoyl)-2-(3-fluoro-4-(trifluoromethyl)phenyl)piperidine-1-carboxylate (2.19 g, 5.22 mmol) was dissolved in MeOH (20 mL) and cooled to −40° C. under nitrogen. Sodium hydroxide (0.219 g, 5.48 mmol) dissolved in water (2.000 mL) was added and the mixture was stirred at −40° C. for 15 min. Hydroxylamine (50% by weight in water, 0.336 mL, 5.48 mmol) was added. The resulting solution was stirred at −40° C. for 1 h. The mixture was then transferred into a prewarmed (80° C.) solution of 6 M hydrogen chloride (27.0 mL, 161.89 mmol) and the mixture was stirred at 80° C. for 20 min. Water and DCM were added and the phases separated. The aqueous phase was extracted with DCM and the combined organic layers were filtered through a phase separator and evaporated. The compound was purified by preparative HPLC on a Kromasil C8 column (10 µm 250×50 ID mm) using a gradient of 15-55% Acetonitrile in H2O/MeCN/FA 95/5/0.2 buffer over 25 minutes with a flow of 100 mL/min. Methyl 2-(3-fluoro-4-(trifluoromethyl)phenyl)-4-(3-oxo-2,3-dihydroisoxazol-5-yl)piperidine-1-carboxylate (0.670 g, 33.0%) was yielded as a colorless solid. $^1$H NMR (400 MHz, cdcl$_3$) δ 1.82-1.93 (m, 1H), 2.12-2.44 (m, 3H), 3.04-3.16 (m, 1H), 3.35-3.46 (m, 1H), 3.69 (s, 3H), 4.11-4.21 (m, 1H), 5.09-5.18 (m, 1H), 5.56 (s, 1H), 6.97-7.09 (m, 2H), 7.52 (t, 1H). MS m/z 387 (M−H)$^-$ Step 3: (2R,4S)-Methyl 2-(3-fluoro-4-(trifluoromethyl)phenyl)-4-(3-oxo-2,3-dihydroisoxazol-5-yl)piperidine-1-carboxylate and (2S,4R)-methyl 2-(3-fluoro-4-(trifluoromethyl)phenyl)-4-(3-oxo-2,3-dihydroisoxazol-5-yl)piperidine-1-carboxylate Methyl 2-(3-fluoro-4-(trifluoromethyl)phenyl)-4-(3-oxo-2,3-dihydroisoxazol-5-yl)piperidine-1-carboxylate (670 mg, 1.73 mmol) was subjected to chiral preparative HPLC (Column: CelluCoat (250×50), 10 µm particle size, mobile phase: Heptane/EtOH 50/50, flow rate 120 mL/min) to yield (2R,4S)-methyl 2-(3-fluoro-4-(trifluoromethyl)phenyl)-4-(3-oxo-2,3-dihydroisoxazol-5-yl)piperidine-1-carboxylate (319 mg, 47%), Chiral purity 99.9% ee, optical rotation $[α]_D^{20}$=+53.4 (acetonitrile, c=0.5) and (2S,4R)-methyl 2-(3-fluoro-4-(trifluoromethyl)phenyl)-4-(3-oxo-2,3-dihydroisoxazol-5-yl)piperidine-1-carboxylate (332 mg, 49%), Chiral purity 99.3% ee, Optical rotation $[α]_D^{20}$=−47.6 (acetonitrile, c=0.5).

Step 4: 5-((2R,4S)-2-(3-Fluoro-4-(trifluoromethyl)phenyl)piperidin-4-yl)isoxazol-3(2H)-one (2R,4S)-Methyl 2-(3-fluoro-4-(trifluoromethyl)phenyl)-4-(3-oxo-2,3-dihydroisoxazol-5-yl)piperidine-1-carboxylate (319 mg, 0.82 mmol) was dissolved in hydrogen bromide (33% in acetic acid, 6.5 mL, 36.97 mmol) and stirred at room temperature for 16 h. The solvent was removed in vacuo and the residue was purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-((2R,4S)-2-(3-fluoro-4-(trifluoromethyl)phenyl)-piperidin-4-yl)isoxazol-3(2H)-one (150 mg, 55%). $^1$H NMR (600 MHz, dmso) δ 1.33 (q, 1H), 1.45 (dq, 1H), 1.84-1.90 (m, 1H), 1.99-2.05 (m, 1H), 2.72 (dt, 1H), 2.83-2.91 (m, 1H), 3.07-3.14 (m, 1H), 3.72-3.79 (m, 1H), 5.73 (s, 1H), 7.41 (d, 1H), 7.48 (d, 1H), 7.70 (t, 1H). HRMS Calculated for $[C_{15}H_{14}F_4N_2O_2+H]^+$: 331.1070. Found: 331.1058.

Example 76

5-((2S,4R)-2-(3-Fluoro-4-(trifluoromethyl)phenyl)piperidin-4-yl)isoxazol-3(2H)-one (2S,4R)-Methyl 2-(3-fluoro-4-(trifluoromethyl)phenyl)-4-(3-oxo-2,3-dihydroisoxazol-5-yl)piperidine-1-carboxylate (332 mg, 0.85 mmol) was dissolved in hydrogen bromide (33% in acetic acid (6.74 mL, 38.47 mmol) and stirred at room temperature for 16 h. The solvent was removed in vacuo and the residue was purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2S,4R)-2-(3-fluoro-4-(trifluoromethyl)phenyl)-piperidin-4-yl)isoxazol-3(2H)-one (174 mg, 62%). $^1$H NMR (600 MHz, dmso) δ 1.32 (q, 1H), 1.45 (dq, 1H), 1.85-1.90 (m, 1H), 2.00-2.04 (m, 1H), 2.72 (dt, 1H), 2.87 (tt, 1H), 3.08-3.13 (m, 1H), 3.73-3.77 (m, 1H), 5.73 (s, 1H), 7.41 (d, 1H), 7.48 (d, 1H), 7.70 (t, 1H). HRMS Calculated for $[C_{15}H_{14}F_4N_2O_2+H]^+$: 331.1070. Found: 331.1067.

Example 77

5-((2R,4S)-2-Phenylpiperidin-4-yl)isoxazol-3(2H)-one

Step 1: Trans-methyl 4-(3-ethoxy-3-oxopropanoyl)-2-phenylpiperidine-1-carboxylate and cis-methyl 4-(3-ethoxy-3-oxopropanoyl)-2-phenylpiperidine-1-carboxylate 1-(Methoxycarbonyl)-2-phenylpiperidine-4-carboxylic acid (5.133 g, 19.50 mmol) (reference compound 34) was dissolved in methyl THF (90 mL) and di(1H-imidazol-1-yl)methanone (4.74 g, 29.24 mmol) was added. The suspension was stirred at room temperature under nitrogen overnight (flask 1). In a separate flask potassium 3-ethoxy-3-oxopropanoate (5.97 g, 35.09 mmol) was suspended in methyl THF (90 mL) and magnesium chloride (3.34 g, 35.09 mmol) was added. The suspension was stirred at room temperature under nitrogen overnight (flask 2). Then, the slightly yellow suspension in flask 1 was added to the white suspension in flask 2. The resulting white suspension was stirred under nitrogen at room temperature for 6 h 30 min. In the meantime, potassium 3-ethoxy-3-oxopropanoate (5.97 g, 35.09 mmol) was suspended in methyl THF (90 mL) and magnesium chloride (3.34 g, 35.09 mmol) was added. The suspension was stirred at 50° C. under nitrogen for 2 h and then added to the reaction mixture. The resulting white suspension was stirred at room temperature under nitrogen for 3 days. The mixture was acidified to pH 1 with 1 M HCl and MTBE was added. The phases were separated and the organic phase washed with water, satd $NaHCO_3$ and water. The solvents were evaporated to yield a yellow oil. The diastereoisomers were separated by column chromatography on silica (Biotage, gradient 0%=>50% EtOAc in heptane; Biotage® KP-SIL 340 g column) to yield trans-methyl 4-(3-ethoxy-3-oxopropanoyl)-2-phenylpiperidine-1-carboxylate (1.14 g, 19%) and cis-methyl 4-(3-ethoxy-3-oxopropanoyl)-2-phenylpiperidine-1-carboxylate (3.77 g, 62%). Cis-isomer: $^1$H NMR (400 MHz, cdcl$_3$) δ 1.22-1.31 (m, 3H), 1.84-2.11 (m, 3H), 2.26-2.35 (m, 1H), 2.82-2.92 (m, 1H), 3.28-3.48 (m, 3H), 3.63 (s, 3H), 4.12-4.21 (m, 3H), 4.96-5.04 (m, 1H), 7.17-7.35 (m, 5H). MS m/z 334 $(M+H)^+$. Trans-isomer: $^1$H NMR (400 MHz, cdcl$_3$) δ 1.13-1.25 (m, 3H), 1.44-1.95 (m, 3H), 2.45-2.66 (m, 2H), 2.78-2.88 (m, 1H), 3.39 (s, 2H), 3.68 (s, 3H), 3.98-4.34 (m, 3H), 5.55 (s, br., 1H), 7.10-7.23 (m, 3H), 7.26-7.34 (m, 2H). MS m/z 334 $(M+H)^+$.

Step 2: Cis-methyl 4-(3-oxo-2,3-dihydroisoxazol-5-yl)-2-phenylpiperidine-1-carboxylate Cis-methyl 4-(3-ethoxy-3-oxopropanoyl)-2-phenylpiperidine-1-carboxylate (1.913 g, 5.74 mmol) was dissolved in MeOH (15 mL) and cooled to −40° C. under nitrogen. Sodium hydroxide (0.230 g, 5.74 mmol) dissolved in water (1.500 mL) was added during 5 min and the colourless solution continued to stir at −40° C. for 20 min. Hydroxylamine (50% by weight in water, 0.352 mL, 5.74 mmol) was added during 8 min. The resulting solution was stirred at −40° C. for 2 h 15 min. The mixture was then rapidly poured into a prewarmed (80° C.) solution of 6 M hydrogen chloride (24 mL, 144.00 mmol) and the mixture continued to stir at 80° C. for 20 min. The solvent was evaporated and MTBE/water added. The phases were separated and the organic phase evaporated to yield a slightly yellow oil. The compound was purified by preparative HPLC in 2 injections on a XBridge C18 column (10 μm 250×50 ID mm) using a gradient of 0-30% Acetonitrile in H2O/MeCN/NH3 95/5/0.2 buffer over 20 minutes with a flow of 100 mL/min. Cis-methyl 4-(3-oxo-2,3-dihydroisoxazol-5-yl)-2-phenylpiperidine-1-carboxylate (1.344 g, 77%) was isolated as a white solid. $^1$H NMR (600 MHz, cdcl$_3$) δ 1.77-1.85 (m, 1H), 2.10-2.18 (m, 1H), 2.19-2.28 (m, 1H), 2.32-2.39 (m, 1H), 3.01-3.08 (m, 1H), 3.37 (ddd, 1H), 3.64 (s, 3H), 4.15 (ddd, 1H), 5.08-5.13 (m, 1H), 5.48 (s, 1H), 7.13-7.20 (m, 3H), 7.27 (t, 2H). MS m/z 303 $(M+H)^+$

Step 3: (2R,4S)-Methyl 4-(3-oxo-2,3-dihydroisoxazol-5-yl)-2-phenylpiperidine-1-carboxylate Racemic cis-methyl 4-(3-oxo-2,3-dihydroisoxazol-5-yl)-2-phenylpiperidine-1-carboxylate (1.34 g, 4.42 mmol) was subjected to chiral preparative HPLC (Column: ReproSil (250×20), 8 μm particle size, mobile phase: EtOH, flow rate 100 mL/min) to yield (2R,4S)-methyl 4-(3-oxo-2,3-dihydroisoxazol-5-yl)-2-phenylpiperidine-1-carboxylate (621 mg, 46%). Chiral purity 99.9% ee. Optical rotation $[\alpha]_D^{20}$=+65.8 (acetonitrile, c=1).

Step 4: 5-((2R,4S)-2-phenylpiperidin-4-yl)isoxazol-3(2H)-one (2R,4S)-methyl 4-(3-oxo-2,3-dihydroisoxazol-5-yl)-2-phenylpiperidine-1-carboxylate (621 mg, 2.05 mmol) was dissolved in hydrogen bromide (33% in acetic acid, 7 mL, 99.92 mmol) and the mixture stirred at room temperature for 24 h. The solvent was evaporated and the residue was purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4S)-2-phenylpiperidin-4-yl)isoxazol-3(2H)-one (306 mg, 61%) (the isolated sample contained DMSO). $^1$H NMR (400 MHz, cd$_3$od) δ 1.76-2.02 (m, 2H), 2.11-2.30 (m, 2H), 3.05-3.21 (m, 2H), 3.41-3.49 (m, 1H), 4.14 (dd, 1H), 5.56 (s, 1H), 7.27-7.48 (m, 5H). HRMS Calculated for $[C_{14}H_{16}N_2O_2+H]^+$: 245.1290. Found: 245.1270

Example 78

5-(2S,4S)-2-Phenylpiperidin-4-yl)isoxazol-3(2H)-one

Step 1: Trans-methyl 4-(3-oxo-2,3-dihydroisoxazol-5-yl)-2-phenylpiperidine-1-carboxylate Trans-methyl 4-(3-ethoxy-3-oxopropanoyl)-2-phenylpiperidine-1-carboxylate (1.104 g, 3.31 mmol) (from example 77, step 1) was dissolved in MeOH (10 mL) and cooled to −40° C. under nitrogen. Sodium hydroxide (0.132 g, 3.31 mmol) dissolved in water (1.000 mL) was added during 10 min and the colourless solution continued to stir at −40° C. for 30 min. Hydroxylamine (50% by weight in water, 0.203 mL, 3.31 mmol) was added during 6 min. The resulting solution was stirred at −40° C. for 2 h 30 min. The mixture was then rapidly poured into a prewarmed (80° C.) solution of 6 M hydrogen chloride (14 mL, 84.00 mmol) and the mixture continued to stir at 80° C. for 20 min. The solvent was evaporated and MTBE/water was added. The phases were separated and the organic phase evaporated to yield a brown oil. The residue was purified by preparative HPLC on a XBridge C18 column (10 μm 250×50 ID mm) using a gradient of 0-30% Acetonitrile in $H_2O$/MeCN/$NH_3$ 95/5/0.2 buffer over 20 minutes with a flow of 100 mL/min. Trans-methyl 4-(3-oxo-2,3-dihydroisoxazol-5-yl)-2-phenylpiperidine-1-carboxylate (722 mg, 72%) was isolated. $^1$H NMR (400 MHz, cdcl$_3$) δ 1.66 (dq, 1H), 1.86-2.09 (m, 2H), 2.72 (d, 1H), 2.79-3.03 (m, 2H), 3.78 (s, 3H), 4.26 (br. s, 1H), 5.68 (br. s, 2H), 7.20-7.32 (m, 3H), 7.34-7.43 (m, 2H). MS m/z 303 $(M+H)^+$

Step 2: (2S,4S)-methyl 4-(3-oxo-2,3-dihydroisoxazol-5-yl)-2-phenylpiperidine-1-carboxylate Racemic trans-methyl 4-(3-oxo-2,3-dihydroisoxazol-5-yl)-2-phenylpiperidine-1-carboxylate (772 mg, 2.55 mmol) was subjected to chiral preparative HPLC (Column: Chiralpak AD (250×20), 5 μm particle size, mobile phase: Heptane/EtOH 75/25, flow rate 15 mL/min) to yield (2S,4S)-methyl 4-(3-oxo-2,3-dihydroisoxazol-5-yl)-2-phenylpiperidine-1-carboxylate (249 mg, 32%). Optical rotation $[\alpha]_D^{20}$=+23.0 (acetonitrile, c=1), Chiral purity 99.7% ee.

Step 3: 5-((2S,4S)-2-phenylpiperidin-4-yl)isoxazol-3(2H)-one (2S,4S)-Methyl 4-(3-oxo-2,3-dihydroisoxazol-5-yl)-2-phenylpiperidine-1-carboxylate (249 mg, 0.82 mmol) was dissolved in hydrogen bromide (33% in acetic acid, 3 mL, 42.82 mmol) and the mixture was stirred at room temperature for 16 h. The solvent was evaporated and the residue was purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2S,4S)-2-phenylpiperidin-4-yl)isoxazol-3(2H)-one (255 mg, 127%) (the isolated sample contained DMSO). $^1$H NMR (400 MHz, cdcl$_3$) δ 2.10-2.43 (m, 4H), 3.21 (dt, 1H), 3.26-3.35 (m, 1H), 3.35-3.43 (m, 1H), 4.17 (dd, 1H), 5.73 (s, 1H), 7.34-7.48 (m, 5H). HRMS Calculated for $[C_{14}H_{16}N_2O_2+H]^+$: 245.1290. Found: 245.1271.

Example 79

5-((2R,4S)-2-Cyclohexylpiperidin-4-yl)isoxazol-3(2H)-one

Step 1: Trans-methyl 2-cyclohexyl-4-(3-ethoxy-3-oxopropanoyl)piperidine-1-carboxylate and cis-methyl 2-cyclohexyl-4-(3-ethoxy-3-oxopropanoyl)piperidine-1-carboxylate A suspension of magnesium chloride (2.085 g, 21.89 mmol) and ethyl potassium malonate (3.73 g, 21.89 mmol) in dry THF (80 mL) was stirred under nitrogen atmosphere at 50° C. for 2.5 h (flask 1). In another flask di(1H-imidazol-1-yl)methanone (2.96 g, 18.24 mmol) was added portionwise to a solution of 2-cyclohexyl-1-(methoxycarbonyl)piperidine-4-carboxylic acid (3.28 g, 12.16 mmol) (reference compound 35) in dry THF (20 mL) at 0° C. and put under nitrogen atmosphere. The ice bath was removed and the solution was stirred for 2 h at room temperature (flask 2). Then the contents of flask 1 was added to flask 2 and the resulting mixture was stirred overnight (20 h). The reaction mixture was concentrated and the residue was taken up in EtOAc and $H_2O$. The aqueous phase was extracted once with EtOAc and the combined organic phase was washed with water, 10% $Na_2CO_3$ and then dried over $Na_2SO_4$. The organic phase was washed with 0.1 M NaOH and dried again and evaporated to give a yellow oil. The compound was purified further via Biotage, 2 runs, SNAP 340 g KP-SIL, linear gradient heptanes/ethyl acetate 9:1 to 1:1 over 7CV. Trans-methyl 2-cyclohexyl-4-(3-ethoxy-3-oxopropanoyl)piperidine-1-carboxylate (349 mg, 6.9%) and cis-methyl 2-cyclohexyl-4-(3-ethoxy-3-oxopropanoyl)piperidine-1-carboxylate (2.501, 49%) were isolated. Cis-isomer: $^1$H NMR (400 MHz, cdcl$_3$) δ 0.90-1.29 (m, 5H), 1.26 (t, 3H), 1.37-2.05 (m, 10H), 2.57-2.70 (m, 1H), 2.85-3.02 (m, 1H), 3.48 (s, 2H), 3.67 (s, 3H), 3.71-3.84 (m, 1H), 3.86-3.99 (m, 1H), 4.18 (q, 2H). MS m/z 340 $(M+H)^+$. Trans-isomer: $^1$H NMR (400 MHz, cdcl$_3$) δ 0.80-1.30 (m, 5H), 1.26 (t, 3H), 1.33-1.90 (m, 9H), 1.96-2.12 (m, 1H), 2.69-2.86 (m, 2H), 3.46 (s, 2H), 3.67 (s, 3H), 3.84-4.33 (m, 2H), 4.21 (q, 2H). MS m/z 340 $(M+H)^+$

Step 2: Cis-methyl 2-cyclohexyl-4-(3-oxo-2,3-dihydroisoxazol-5-yl)piperidine-1-carboxylate Cis-methyl 2-cyclohexyl-4-(3-ethoxy-3-oxopropanoyl)piperidine-1-carboxylate (1.644 g, 4.84 mmol) was dissolved in MeOH (15 mL) and cooled to −40° C. Sodium hydroxide (0.194 g, 4.84 mmol) dissolved in water (1.500 mL) was added dropwise and the colourless solution continued to stir at −40° C. for 30 min. Hydroxylamine (50% by weight in water, 0.297 mL, 4.84 mmol) was added dropwise. The resulting solution was stirred at −40° C. for 3 h. The mixture was then rapidly poured into a prewarmed (80° C.) solution of 6 M hydrogen chloride (21 mL, 126.00 mmol) and the mixture continued to stir at 80° C. for 20 min. The solvent was evaporated and MTBE/water added. The phases were separated and the organic phase dried over $Na_2SO_4$ and evaporated to yield a slightly yellow foam. The compound was purified by preparative HPLC on a Kromasil C8 column (10 μm 250×50 ID mm) using two injections with a gradient of 15-75% Acetonitrile in H2O/MeCN/AcOH 95/5/0.2 buffer over 30 minutes with a flow of 100 mL/min. Cis-methyl 2-cyclohexyl-4-(3-oxo-2,3-dihydroisoxazol-5-yl)piperidine-1-carboxylate (814 mg, 55%) was isolated. $^1$H NMR (400 MHz, cdcl$_3$) δ 0.83-0.98 (m, 2H), 1.01-1.16 (m, 3H), 1.25-1.40 (m, 1H), 1.50-1.88 (m, 6H), 1.95-2.13 (m, 3H), 2.88-3.07 (m, 2H), 3.70 (s, 3H), 3.79-3.89 (m, 1H), 3.95-4.07 (m, 1H), 5.70 (s, 1H). MS m/z 309 (M+H)$^+$ Step 3: (2R,4S)-Methyl 2-cyclohexyl-4-(3-oxo-2,3-dihydroisoxazol-5-yl)piperidine-1-carboxylate Cis-methyl 2-cyclohexyl-4-(3-oxo-2,3-dihydroisoxazol-5-yl)piperidine-1-carboxylate (814 mg, 2.66 mmol) was subjected to chiral preparative HPLC (Column: Chiralpak IC (250×20), 5 µm particle size, mobile phase: Heptane/IPA 60/40, flow rate 15 mL/min) to yield (2R,4S)-methyl 2-cyclohexyl-4-(3-oxo-2,3-dihydroisoxazol-5-yl)piperidine-1-carboxylate (427 mg, 50%), Chiral purity 99.9% ee. Optical rotation $[\alpha]_D^{20}$=+38.5 (acetonitrile, c=1)

Step 4: 5-((2R,4S)-2-Cyclohexylpiperidin-4-yl)isoxazol-3(2H)-one (2R,4S)-Methyl 2-cyclohexyl-4-(3-oxo-2,3-dihydroisoxazol-5-yl)piperidine-1-carboxylate (0.427 g, 1.38 mmol) was stirred in HBr (33% in AcOH) overnight (19 hours). Evaporation of solvents and the residue purified by preparative HPLC (Instrument: FractionLynx I, Mobilphase: gradient 5-95% MeCN in 0.2% NH$_3$, pH 10, Column: Xbridge Prep C18 5 µm OBD 19*150 mm) to yield 5-((2R,4S)-2-cyclohexylpiperidin-4-yl)isoxazol-3(2H)-one (228 mg, 66%). $^1$H NMR (400 MHz, cd$_3$od) δ 1.05-1.42 (m, 5H), 1.49-1.66 (m, 2H), 1.67-1.91 (m, 6H), 2.17-2.26 (m, 1H), 2.26-2.35 (m, 1H), 2.97-3.19 (m, 3H), 3.43-3.52 (m, 1H), 5.70 (s, 1H), 8.51 (s, 1H). HRMS Calcd for [C$_{14}$H$_{22}$N$_2$O$_2$+H]+: 251.1760. Found: 251.1750.

Example 80

5-((2S,4S)-2-Cyclohexylpiperidin-4-yl)isoxazol-3(2H)-one

Step 1: Trans-methyl 2-cyclohexyl-4-(3-oxo-2,3-dihydroisoxazol-5-yl)piperidine-1-carboxylate Trans-methyl 2-cyclohexyl-4-(3-ethoxy-3-oxopropanoyl)piperidine-1-carboxylate (349 mg, 1.03 mmol) (from example 79, step 1) was dissolved in MeOH (5 mL) and cooled to −40° C. Sodium hydroxide (41.1 mg, 1.03 mmol) dissolved in water (0.500 mL) was added dropwise and the colourless solution continued to stir at −40° C. for 30 min. Hydroxylamine (50% by weight in water, 0.063 mL, 1.03 mmol) was added dropwise. The resulting solution was stirred at −40° C. for 2 h 20 min. The mixture was then rapidly poured into a prewarmed (80° C.) solution of 6 M hydrogen chloride (5 mL, 30.00 mmol) and the mixture continued to stir at 80° C. for 20 min. The solvent was evaporated and MTBE/water added. The phases were separated and the organic phase was dried over Na$_2$SO$_4$ and evaporated to yield a yellow oil. The compound was purified by preparative HPLC on a Kromasil C8 column (10 µm 250×50 ID mm) using a gradient of 15-75% Acetonitrile in H2O/MeCN/AcOH 95/5/0.2 buffer over 30 minutes with a flow of 100 mL/min. Trans-methyl 2-cyclohexyl-4-(3-oxo-2,3-dihydroisoxazol-5-yl)piperidine-1-carboxylate (170 mg, 53%) was isolated. $^1$H NMR (400 MHz, cdcl$_3$) δ 0.82-1.08 (m, 2H), 1.08-1.32 (m, 3H), 1.45-1.83 (m, 8H), 1.89-2.02 (m, 1H), 2.12-2.23 (m, 1H), 2.79-3.04 (m, 2H), 3.70 (s, 3H), 3.87-4.83 (m, 2H), 5.64 (s, 1H). MS m/z 309 (M+H)$^+$ Step 2: (2S,4S)-Methyl 2-cyclohexyl-4-(3-oxo-2,3-dihydroisoxazol-5-yl)piperidine-1-carboxylate Trans-methyl 2-cyclohexyl-4-(3-oxo-2,3-dihydroisoxazol-5-yl)piperidine-1-carboxylate (212 mg, 0.69 mmol) was subjected to chiral preparative HPLC (Column: Chiralcel OJ (250×20), 5 µm particle size, mobile phase: EtOH, flow rate 12 mL/min) to yield (2S,4S)-methyl 2-cyclohexyl-4-(3-oxo-2,3-dihydroisoxazol-5-yl)piperidine-1-carboxylate (79 mg, 37%), Chiral purity 99.3% ee. Optical rotation $[\alpha]_D^{20}$=+5.1 (acetonitrile, c=1)

Step 3: 5-((2S,4S)-2-Cyclohexylpiperidin-4-yl)isoxazol-3(2H)-one (2S,4S)-Methyl 2-cyclohexyl-4-(3-oxo-2,3-dihydroisoxazol-5-yl)piperidine-1-carboxylate (79 mg, 0.26 mmol) was stirred in HBr (33% in AcOH) overnight. Evaporation of solvents and the residue purified by preparative HPLC (Instrument: FractionLynx I, Mobilphase: gradient 5-95% MeCN in 0.2% NH$_3$, pH10, Column: Xbridge Prep C18 5 µm OBD 19*150 mm.) to yield 5-((2S,4S)-2-cyclohexylpiperidin-4-yl)isoxazol-3(2H)-one 22 mg (35%). $^1$H NMR (400 MHz, cd$_3$od) δ 1.00-1.39 (m, 5H), 1.51-1.64 (m, 1H), 1.64-1.93 (m, 6H), 1.96-2.11 (m, 1H), 2.15-2.25 (m, 1H), 2.26-2.35 (m, 1H), 2.92-3.02 (m, 1H), 3.03-3.16 (m, 1H), 3.22-3.33 (m, 2H), 5.57 (s, 1H). HRMS Calcd for [C$_{14}$H$_{22}$N$_2$O$_2$+H]+: 251.1760. Found: 251.1754.

Example 81

5-((2R,4S)-2-(2-Methyl-2H-tetrazol-5-yl)piperidin-4-yl)isoxazol-3(2H)-one

Step 1: Benzyl 4-(3-ethoxy-3-oxopropanoyl)-2-(2-methyl-2H-tetrazol-5-yl)piperidine-1-carboxylate 1-(Benzyloxycarbonyl)-2-(2-methyl-2H-tetrazol-5-yl)piperidine-4-carboxylic acid (0.828 g, 2.40 mmol) (reference compound 36) was dissolved in THF (7 mL) and then di(1H-imidazol-1-yl)methanone (0.583 g, 3.60 mmol) was added. The reaction was stirred overnight at room temperature (flask 1). In a separate flask potassium 3-ethoxy-3-oxopropanoate (0.816 g, 4.80 mmol) and anhydrous magnesium chloride (0.457 g, 4.80 mmol) were suspended in THF (7.00 mL) and stirred at 50° C. under nitrogen overnight and then allowed to cool to room temperature (flask 2). The content of flask 1 was added to flask 2 and stirred under nitrogen over the weekend (72 h). The reaction was quenched by addition of 2 M HCl. The mixture was extracted three times with EtOAc, the combined organic phase was evaporated and purified on a 50 g Biotage column with heptane/EtOAc 88/12-100/0 over 12 CV. Benzyl 4-(3-ethoxy-3-oxopropanoyl)-2-(2-methyl-2H-tetrazol-5-yl)piperidine-1-carboxylate (499 mg, 59%) was isolated. $^1$H NMR (400 MHz, cdcl$_3$) δ 1.22-1.31 (m, 3H), 1.72-1.83 (m, 1H), 2.00-2.08 (m, 1H), 2.41 (dt, 1H), 2.70-2.78 (m, 1H), 2.88-2.95 (m, 1H), 3.35-3.63 (m, 3H), 3.99-4.07 (m, 1H), 4.12-4.20 (m, 2H), 4.28 (s, 3H), 5.11-5.21 (m, 2H), 5.59 (t, 1H), 7.27-7.40 (m, 5H). MS m/z 416 (M+H)$^+$ Step 2: Benzyl 2-(2-methyl-2H-tetrazol-5-yl)-4-(3-oxo-2,3-dihydroisoxazol-5-yl)piperidine-1-carboxylate Benzyl 4-(3-ethoxy-3-oxopropanoyl)-2-(2-methyl-2H-tetrazol-5-yl)piperidine-1-carboxylate (0.499 g, 1.20 mmol) was dissolved in MeOH (6 mL) and cooled to −40° C. 3.8 M NaOH (0.316 mL, 1.20 mmol) dissolved in water (0.6 mL) was added and the reaction stirred at −40° C. for 40 min. Hydroxylamine (50% by weight in water, 0.074 mL, 1.20 mmol) was added and stirring continued for 3.5 h at −40° C. The reaction mixture was then added to a preheated 80° C.

solution of 6 M HCl (6.01 mL, 36.03 mmol) and stirred for 20 min. The reaction mixture was partitioned between water and DCM. The aqueous phase was extracted twice with DCM and the combined organic phase was dried and evaporated. The compound was purified by preparative HPLC on a Kromasil C8 column (10 µm 250×50 ID mm) using a gradient of 15-55% Acetonitrile in H₂O/MeCN/NH₃ 95/5/0.2 buffer over 20 minutes with a flow of 100 mL/min. Benzyl 2-(2-methyl-2H-tetrazol-5-yl)-4-(3-oxo-2,3-dihydroisoxazol-5-yl)piperidine-1-carboxylate (327 mg, 71%) was isolated. $^1$H NMR (400 MHz, cdcl₃) δ 1.96-2.15 (m, 2H), 2.41 (dt, 1H), 2.64-2.74 (m, 1H), 3.12-3.19 (m, 1H), 3.61-3.72 (m, 1H), 4.07-4.20 (m, 4H), 5.13 (s, 2H), 5.43 (s, 1H), 5.58-5.64 (m, 1H), 7.25-7.41 (m, 5H). MS m/z 385 (M+H)⁺

Step 3: (2R,4S)-Benzyl 2-(2-methyl-2H-tetrazol-5-yl)-4-(3-oxo-2,3-dihydroisoxazol-5-yl)-piperidine-1-carboxylate and trans-benzyl 2-(2-methyl-2H-tetrazol-5-yl)-4-(3-oxo-2,3-dihydroisoxazol-5-yl)piperidine-1-carboxylate Benzyl 2-(2-methyl-2H-tetrazol-5-yl)-4-(3-oxo-2,3-dihydroisoxazol-5-yl)piperidine-1-carboxylate (866 mg, 2.25 mmol) was subjected to chiral preparative HPLC: The cis isomers were separated from the trans isomers using preparative HPLC (Column: Chiralcel OJ (250×20), 5 µm particle size, mobile phase: Heptane/EtOH/DEA 65/45/0.1, flow rate 18 mL/min). The cis-enantiomers were separated using chiral preparative HPLC (Column: Chiralpak AD (250×20), 5 µm particle size, mobile phase: Heptane/IPA/DEA 50/50/0.1, flow rate 15 mL/min) to yield (2R,4S)-benzyl 2-(2-methyl-2H-tetrazol-5-yl)-4-(3-oxo-2,3-dihydroisoxazol-5-yl)piperidine-1-carboxylate (301 mg, 35%), chiral purity 99.1% ee, Optical rotation $[\alpha]_D^{20}$=+28.9 (acetonitrile, c=1), $^1$H NMR (400 MHz, cdcl₃) δ 1.96-2.13 (m, 2H), 2.39 (dt, 1H), 2.61-2.71 (m, 1H), 3.10 (p, 1H), 3.62-3.72 (m, 1H), 4.09 (dt, 1H), 4.18 (s, 3H), 5.12 (d, 2H), 5.33 (s, 1H), 5.56 (t, 1H), 7.21-7.36 (m, 5H). and trans-benzyl 2-(2-methyl-2H-tetrazol-5-yl)-4-(3-oxo-2,3-dihydroisoxazol-5-yl)piperidine-1-carboxylate (99 mg, 11%) were isolated.

Step 4: 5-((2R,4S)-2-(2-Methyl-2H-tetrazol-5-yl)piperidin-4-yl)isoxazol-3(2H)-one (2R,4S)-Benzyl 2-(2-methyl-2H-tetrazol-5-yl)-4-(3-oxo-2,3-dihydroisoxazol-5-yl)piperidine-1-carboxylate (301 mg, 0.78 mmol) was dissolved in hydrogen bromide (33% in AcOH) (4.1 mL, 23.49 mmol) and reacted for 1 h. The mixture was evaporated and the residue was partitioned between water and EtOAc. The aqueous phase was purified by preparative HPLC on a Kromasil C8 column (10 µm 250×50 ID mm) using a gradient of 0-15% Acetonitrile in H2O/MeCN/NH3 95/5/0.2 buffer over 20 minutes with a flow of 100 mL/min. 5-((2R,4S)-2-(2-Methyl-2H-tetrazol-5-yl)piperidin-4-yl)isoxazol-3(2H)-one (143 mg, 73%) was isolated. $^1$H NMR (400 MHz, cdcl₃) δ 1.70 (qd, 1H), 1.85 (q, 1H), 2.04-2.12 (m, 1H), 2.43-2.50 (m, 1H), 2.91-3.02 (m, 2H), 3.33-3.41 (m, 1H), 4.18 (dd, 1H), 4.32 (s, 3H), 5.68 (s, 1H). HRMS Calcd for [C₁₀H₁₄N₆O₂+H]⁺: 251.1256. Found: 251.1233.

Example 82

5-(Trans-2-(2-methyl-2H-tetrazol-5-yl)piperidin-4-yl)isoxazol-3(2H)-one

Trans-benzyl 2-(2-methyl-2H-tetrazol-5-yl)-4-(3-oxo-2,3-dihydroisoxazol-5-yl)piperidine-1-carboxylate (99 mg, 0.26 mmol) (from example 81, step 3) was dissolved in hydrogen bromide (33% in HOAc, 1.35 mL, 7.73 mmol) and reacted for 1 h. The mixture was evaporated and the residue was partitioned between water and EtOAc. The aqueous phase was purified by preparative HPLC on a Kromasil C8 column (10 µm 250×50 ID mm) using a gradient of 0-15% Acetonitrile in H2O/MeCN/NH3 95/5/0.2 buffer over 20 minutes with a flow of 100 mL/min. 5-(Trans-2-(2-methyl-2H-tetrazol-5-yl)piperidin-4-yl)isoxazol-3(2H)-one (45 mg, 70%). $^1$H NMR (400 MHz, cd₃od) δ 1.83-2.05 (m, 2H), 2.21-2.31 (m, 1H), 2.36-2.44 (m, 1H), 2.93-3.06 (m, 2H), 3.17-3.25 (m, 1H), 4.37 (s, 3H), 4.49 (t, 1H), 5.77 (s, 1H). HRMS Calcd for [C₁₀H₁₄N₆O₂+H]⁺: 251.1256. Found: 251.1262.

Example 83

5-((2R,4S)-2-(1-Methyl-1H-tetrazol-5-yl)piperidin-4-yl)isoxazol-3(2H)-one

Step 1: Cis-benzyl 4-(3-ethoxy-3-oxopropanoyl)-2-(1-methyl-1H-tetrazol-5-yl)piperidine-1-carboxylate 1-(Benzyloxycarbonyl)-2-(1-methyl-1H-tetrazol-5-yl)piperidine-4-carboxylic acid (0.495 g, 1.43 mmol) (reference compound 37) was dissolved in THF (4 mL) and then di(1H-imidazol-1-yl)methanone (0.349 g, 2.15 mmol) was added. The reaction was stirred overnight at room temperature (flask 1). In a separate flask potassium 3-ethoxy-3-oxopropanoate (0.488 g, 2.87 mmol) and anhydrous magnesium chloride (0.273 g, 2.87 mmol) were suspended in THF (4.00 mL) and stirred at 50° C. under nitrogen overnight and then allowed to cool to room temperature (flask 2). The contents of flask 1 was added to flask 2 and stirred under nitrogen over the weekend (72 h). The reaction was quenched by addition of 2 M HCl. The mixture was extracted three times with EtOAc, the combined organic phase was evaporated and purified on a 50 g Biotage column with heptane/EtOAc 88/12-100/0 over 12 CV. Cis-benzyl 4-(3-ethoxy-3-oxopropanoyl)-2-(1-methyl-1H-tetrazol-5-yl)piperidine-1-carboxylate (482 mg, 81%) was isolated. $^1$H NMR (600 MHz, cdcl₃) δ 1.25 (t, 3H), 1.89-1.97 (m, 1H), 2.05-2.12 (m, 1H), 2.28-2.34 (m, 1H), 2.59-2.66 (m, 1H), 2.93 (p, 1H), 3.35-3.41 (m, 1H), 3.62 (dd, 2H), 3.85-3.98 (m, 4H), 4.16 (q, 2H), 5.09 (q, 2H), 5.36-5.42 (m, 1H), 7.21-7.37 (m, 5H). MS m/z 416 (M+H)⁺

Step 2: Benzyl 2-(1-methyl-1H-tetrazol-5-yl)-4-(3-oxo-2,3-dihydroisoxazol-5-yl)piperidine-1-carboxylate Benzyl 4-(3-ethoxy-3-oxopropanoyl)-2-(1-methyl-1H-tetrazol-5-yl)piperidine-1-carboxylate (0.947 g, 2.28 mmol) was dissolved in MeOH (10 mL) and cooled to −40° C. 3.8 M NaOH (0.600 mL, 2.28 mmol) dissolved in water (1 mL) was added and the reaction stirred at −40° C. for 40 min. Hydroxylamine (50% by weight in water, 0.140 mL, 2.28 mmol) was added and stirring continued for 3.5 h at −40° C. The reaction mixture was then added to a preheated 80° C. warm solution of 6 M HCl (11.40 mL, 68.38 mmol) and stirred for 20 min. The reaction mixture was partitioned between water and DCM. The aqueous phase was extracted twice with DCM and the combined organic phase was dried and evaporated. The compound was purified by preparative HPLC on a Kromasil C8 column (10 µm 250×50 ID mm) using a gradient of 15-55% Acetonitrile in H2O/MeCN/NH3 95/5/0.2 buffer over 20 minutes with a flow of 100 mL/min. Benzyl 2-(1-methyl-1H-tetrazol-5-yl)-4-(3-oxo-2,3-dihydroisoxazol-5-yl)piperidine-1-carboxylate (488 mg, 56%) was isolated. $^1$H NMR (400 MHz, cdcl₃) δ 1.86-1.99 (m, 1H), 2.18-2.30 (m, 1H), 2.33-2.54 (m, 2H), 3.01-3.12 (m, 1H), 3.78-4.09 (m, 5H), 5.05 (s, 2H), 5.20-5.30 (m, 1H), 5.67 (s, 1H), 7.20-7.27 (m, 2H), 7.27-7.39 (m, 3H). MS m/z 385 (M+H)$^+$ Step 3: (2R,4S)-Benzyl 2-(1-methyl-1H-tetrazol-5-yl)-4-(3-oxo-2,3-dihydroisoxazol-5-yl)piperidine-1-carboxylate Benzyl 2-(1-methyl-1H-tetrazol-5-yl)-4-(3-oxo-2,3-dihydroisoxazol-5-yl)piperidine-1-carboxylate (488 mg, 1.27 mmol) was subjected to chiral preparative HPLC (Column: Chiralpak AS (250×20), 5 μm particle size, mobile phase: Heptane/EtOH/DEA 60/40/0.1, flow rate 18 mL/min) to yield (2R,4S)-benzyl 2-(1-methyl-1H-tetrazol-5-yl)-4-(3-oxo-2,3-dihydroisoxazol-5-yl)piperidine-1-carboxylate (231 mg, 47%), chiral purity 98% ee, Optical rotation $[\alpha]_D^{20}$=+14.5 (acetonitrile, c=1)

Step 4: 5-((2R,4S)-2-(1-Methyl-1H-tetrazol-5-yl)piperidin-4-yl)isoxazol-3(2H)-one (2R,4S)-Benzyl 2-(1-methyl-1H-tetrazol-5-yl)-4-(3-oxo-2,3-dihydroisoxazol-5-yl)piperidine-1-carboxylate (0.231 g, 0.60 mmol) was dissolved in hydrogen bromide (33% in HOAc, 5.26 mL, 30.05 mmol) and allowed to react for 1 h. The mixture was evaporated and the residue was partitioned between water and EtOAc. The aqueous phase was purified by preparative HPLC on a Kromasil C8 column (10 μm 250×50 ID mm) using a gradient of 0-10% Acetonitrile in H$_2$O/MeCN/NH$_3$ 95/5/0.2 buffer over 20 minutes with a flow of 100 mL/min. The compounds were detected by UV at 220 nm. Product fractions (which contained DMSO) were collected and the acetonitrile was evaporated. The aqueous phase was freeze dried. Most of the DMSO was left so the residue was dissolved in 2 mL of MeOH and loaded onto a 2 g SCX-2 column and the column washed with MeOH. The amine was liberated by running 10 mL of 10% triethylamine in MeOH through it. The solvent was evaporated and the residue was freeze dried from water to yield 5-((2R,4S)-2-(1-methyl-1H-tetrazol-5-yl)piperidin-4-yl)isoxazol-3(2H)-one (100 mg, 67%). $^1$H NMR (400 MHz, dmso) δ 1.47 (dq, 1H), 1.70-1.81 (m, 1H), 1.87 (d, 1H), 2.12 (d, 1H), 2.74 (dt, 1H), 2.92-3.02 (m, 1H), 3.04-3.13 (m, 1H), 4.09 (s, 3H), 4.18 (dd, 1H), 5.78 (s, 1H). HRMS Calcd for [(2×C$_{10}$H$_{14}$N$_6$O$_2$)+H]$^+$: 501.2435. Found: 501.2418.

Example 84

5-((2R,4S)-2-(Cyclohexyloxymethyl)piperidin-4-yl)isoxazol-3(2H)-one

Step 1: Trans-methyl 2-(cyclohexyloxymethyl)-4-(3-ethoxy-3-oxopropanoyl)piperidine-1-carboxylate and cis-methyl 2-(cyclohexyloxymethyl)-4-(3-ethoxy-3-oxopropanoyl)piperidine-1-carboxylate 2-(Cyclohexyloxymethyl)-1-(methoxycarbonyl)piperidine-4-carboxylic acid (2.425 g, 8.1 mmol) (reference compound 38) was dissolved in methyl THF (60 mL) under nitrogen atmosphere and di(1H-imidazol-1-yl)methanone (1.970 g, 12.15 mmol) was added. The suspension was stirred at room temperature for 3 h (flask 1). In a separate flask was potassium 3-ethoxy-3-oxopropanoate (2.482 g, 14.58 mmol) suspended in methyl THF (30 mL) and magnesium chloride (1.388 g, 14.58 mmol) was added. The suspension was stirred at 50° C. under nitrogen for 22 h using an oversized stirring bar (flask 2). The contents of flask 1 was added to flask 2 and the resulting white suspension was stirred at room temperature for 20 h. In a separate flask was potassium 3-ethoxy-3-oxopropanoate (1.241 g, 7.29 mmol) suspended in methyl THF (30 mL) and magnesium chloride (0.694 g, 7.29 mmol) was added. The suspension was stirred at 50° C. for 5 h and then added to the reaction mixture. The mixture was stirred at room temperature for 15 h. 0.1 M HCl and DCM were added and the phases separated. The aqueous phase was extracted with DCM, the combined organic layers filtered through a phase separator and evaporated. The residue was purified via Biotage (5:1 heptane:EtOAc, Biotage® KP-SIL 340 g column, 10 CV). Trans-methyl 2-(cyclohexyloxymethyl)-4-(3-ethoxy-3-oxopropanoyl)piperidine-1-carboxylate (210 mg, 7%) and cis-methyl 2-(cyclohexyloxymethyl)-4-(3-ethoxy-3-oxopropanoyl)piperidine-1-carboxylate (1.13 g, 38%) were isolated. Cis-isomer: $^1$H NMR (400 MHz, cdcl$_3$) δ 1.14-2.14 (m, 17H), 2.70-2.79 (m, 1H), 3.11-3.30 (m, 2H), 3.34-3.62 (m, 4H), 3.69 (s, 3H), 3.82-3.91 (m, 1H), 4.07-4.24 (m, 3H). MS m/z 370 (M+H)$^+$. Trans-isomer: $^1$H NMR (400 MHz, cdcl$_3$) δ 1.16-2.19 (m, 17H), 2.80-3.10 (m, 2H), 3.16-3.32 (m, 1H), 3.44-3.64 (m, 4H), 3.66-3.74 (m, 3H), 3.97-4.27 (m, 3H), 4.33-4.57 (m, 1H). MS m/z 370 (M+H)$^+$ Step 2: Cis-methyl 2-(cyclohexyloxymethyl)-4-(3-oxo-2,3-dihydroisoxazol-5-yl)piperidine-1-carboxylate Cis-methyl 2-(cyclohexyloxymethyl)-4-(3-ethoxy-3-oxopropanoyl)piperidine-1-carboxylate (1.13 g, 3.06 mmol) was dissolved in MeOH (14 mL) and cooled to −40° C. under nitrogen. Sodium hydroxide (0.128 g, 3.21 mmol) dissolved in water (1.400 mL) was added and the mixture was stirred at −40° C. for 15 min. Hydroxylamine (50% by weight in water, 0.197 mL, 3.21 mmol) was added. The resulting solution was stirred at −40° C. for 1 h. The mixture was transferred into a prewarmed (80° C.) solution of 6 M hydrogen chloride (15.80 mL, 94.82 mmol) and the mixture was stirred at 80° C. for 20 min. Water and DCM were added and the phases separated. The aqueous phase was extracted with DCM and the combined organic layers were filtered through a phase separator and evaporated. The compound was purified by preparative HPLC on a Kromasil C8 column (10 μm 250×50 ID mm) using a gradient of 15-55% Acetonitrile in H2O/MeCN/AcOH 95/5/0.2 buffer over 25 minutes with a flow of 100 mL/min. Cis-methyl 2-(cyclohexyloxymethyl)-4-(3-oxo-2,3-dihydroisoxazol-5-yl)piperidine-1-carboxylate (423 mg, 41%) was isolated. $^1$H NMR (400 MHz, cdcl$_3$) δ 1.12-2.15 (m, 14H), 2.93-3.04 (m, 1H), 3.10-3.31 (m, 2H), 3.35-3.50 (m, 2H), 3.70 (s, 3H), 3.83-3.94 (m, 1H), 4.05-4.15 (m, 1H), 5.75 (s, 1H). MS m/z 339 (M+H)$^+$ Step 3: (2R,4S)-Methyl 2-(cyclohexyloxymethyl)-4-(3-oxo-2,3-dihydroisoxazol-5-yl)-piperidine-1-carboxylate and (2S,4R)-methyl 2-(cyclohexyloxymethyl)-4-(3-oxo-2,3-dihydro-isoxazol-5-yl)piperidine-1-carboxylate Cis-Methyl 2-(cyclohexyloxymethyl)-4-(3-oxo-2,3-dihydroisoxazol-5-yl)piperidine-1-carboxylate (423 mg, 1.25 mmol) was subjected to chiral preparative HPLC (Column: Chiralpak IC (250×20), 5 μm particle size, mobile phase: Heptane/EtOH 70/30, flow rate 18 mL/min) to yield (2R,4S)-methyl 2-(cyclohexyloxymethyl)-4-(3-oxo-2,3-dihydroisoxazol-5-yl)piperidine-1-carboxylate (190 mg, 45%), Chiral purity 98.3% ee, Optical rotation $[\alpha]_D^{20}$=+55.9 (acetonitrile, c=1) and (2S,4R)-methyl 2-(cyclohexyloxymethyl)-4-(3- oxo-2,3-dihydroisoxazol-5-yl)piperidine-1-carboxylate (194 mg, 46%), Chiral purity 98.6% ee, Optical rotation $[\alpha]_D^{20}=-55.4$ (acetonitrile, c=1)

Step 4: 5-((2R,4S)-2-(Cyclohexyloxymethyl)piperidin-4-yl)isoxazol-3(2H)-one (2R,4S)-Methyl 2-(cyclohexyloxymethyl)-4-(3-oxo-2,3-dihydroisoxazol-5-yl)piperidine-1-carboxylate (190 mg, 0.56 mmol) was dissolved in hydrogen bromide (33% in acetic acid, 4.43 mL, 25.27 mmol) and stirred at room temperature for 16 h. The solvent was removed in vacuo and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-((2R,4S)-2-(cyclohexyloxymethyl)piperidin-4-yl)isoxazol-3(2H)-one (5 mg, 3%). $^1$H NMR (600 MHz, dmso) δ 1.03-1.25 (m, 6H), 1.32-1.48 (m, 2H), 1.55-1.68 (m, 2H), 1.70-1.90 (m, 4H), 2.56-2.66 (m, 1H), 2.68-2.79 (m, 2H), 2.99-3.06 (m, 1H), 3.06-3.83 (m, 3H), 5.70 (s, 1H). HRMS Calculated for $[C_{15}H_{24}N_2O_3+H]^+$: 281.1865. Found: 281.1860

Example 85

5-((2S,4R)-2-(Cyclohexyloxymethyl)piperidin-4-yl)isoxazol-3(2H)-one (2S,4R)-Methyl 2-(cyclohexyloxymethyl)-4-(3-oxo-2,3-dihydroisoxazol-5-yl)piperidine-1-carboxylate (194 mg, 0.57 mmol) (from example 84, step 3) was dissolved in hydrogen bromide (33% in acetic acid, 4.52 mL, 25.80 mmol) and stirred at room temperature for 16 h. The solvent was removed in vacuo and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-((2S,4R)-2-(Cyclohexyloxymethyl)piperidin-4-yl)isoxazol-3(2H)-one (4.5 mg, 3%). $^1$H NMR (600 MHz, dmso) δ 1.04-1.24 (m, 6H), 1.33-1.46 (m, 2H), 1.57-1.66 (m, 2H), 1.73-1.88 (m, 4H), 2.56-2.67 (m, 1H), 2.68-2.80 (m, 2H), 2.99-3.06 (m, 1H), 3.07-3.84 (m, 3H), 5.70 (s, 1H). HRMS Calculated for $[C_{15}H_{24}N_2O_3+H]^+$: 281.1865. Found: 281.1893

Example 86

5-(Trans-2-(cyclohexyloxymethyl)piperidin-4-yl)isoxazol-3(2H)-one

Step 1: Trans-methyl 2-(cyclohexyloxymethyl)-4-(3-oxo-2,3-dihydroisoxazol-5-yl)piperidine-1-carboxylate Trans-methyl 2-(cyclohexyloxymethyl)-4-(3-ethoxy-3-oxopropanoyl)piperidine-1-carboxylate (210 mg, 0.57 mmol) (from example 84, step 1) was dissolved in MeOH (3 mL) and cooled to −40° C. under nitrogen. Sodium hydroxide (23.87 mg, 0.60 mmol) dissolved in water (0.300 mL) was added and the mixture was stirred at −40° C. for 15 min. Hydroxylamine (50% by weight in water, 0.037 mL, 0.60 mmol) was added. The resulting solution was stirred at −40° C. for 1 h. The mixture was transferred into a prewarmed (80° C.) solution of 6 M hydrogen chloride (2.94 mL, 17.62 mmol) and the mixture was stirred at 80° C. for 20 min. Water and DCM were added and the phases separated. The aqueous phase was extracted with DCM and the combined organic layers were filtered through a phase separator and evaporated. The compound was purified by preparative HPLC on a Kromasil C8 column (10 µm 250×50 ID mm) using a gradient of 15-55% Acetonitrile in H2O/MeCN/AcOH 95/5/0.2 buffer over 20 minutes with a flow of 100 mL/min. Trans-methyl 2-(cyclohexyloxymethyl)-4-(3-oxo-2,3-dihydroisoxazol-5-yl)piperidine-1-carboxylate (121 mg, 63%) was isolated. MS m/z 339 (M+H)$^+$

Step 2: 5-(Trans-2-(cyclohexyloxymethyl)piperidin-4-yl)isoxazol-3(2H)-one

Trans-methyl 2-(cyclohexyloxymethyl)-4-(3-oxo-2,3-dihydroisoxazol-5-yl)piperidine-1-carboxylate (121 mg, 0.36 mmol) was dissolved in hydrogen bromide (33% in acetic acid, (2.75 mL, 15.69 mmol) and stirred at room temperature for 16 h. The solvent was removed in vacuo and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-(trans-2-(cyclohexyloxymethyl)piperidin-4-yl)isoxazol-3(2H)-one (15 mg, 15%). $^1$H NMR (600 MHz, dmso) δ 1.09-1.25 (m, 5H), 1.38-1.53 (m, 2H), 1.55-1.65 (m, 2H), 1.65-1.83 (m, 5H), 2.55-2.63 (m, 1H), 2.69-2.80 (m, 2H), 3.02-3.88 (m, 4H), 5.76 (s, 1H). HRMS Calculated for $[C_{15}H_{24}N_2O_3+H]^+$: 281.1865. Found: 281.1879

Example 87

5-((2R,4S)-2-(Difluoromethyl)piperidin-4-yl)isoxazol-3(2H)-one

Step 1: Trans-methyl 2-(difluoromethyl)-4-(3-ethoxy-3-oxopropanoyl)piperidine-1-carboxylate and cis-methyl 2-(difluoromethyl)-4-(3-ethoxy-3-oxopropanoyl)piperidine-1-carboxylate 2-(Difluoromethyl)-1-(methoxycarbonyl)piperidine-4-carboxylic acid (2.2 g, 9.27 mmol) (reference compound 39) was dissolved in methyl THF (60 mL) under nitrogen atmosphere and di(1H-imidazol-1-yl)methanone (2.256 g, 13.91 mmol) was added. The suspension was stirred at room temperature for 3 h (flask 1). In a separate flask was potassium 3-ethoxy-3-oxopropanoate (2.84 g, 16.69 mmol) suspended in methyl THF (60 mL) and magnesium chloride (1.590 g, 16.69 mmol) was added. The suspension was stirred at 50° C. under nitrogen for 22 h using an oversized stirring bar (flask 2). The contents of flask 1 was added to flask 2 and the resulting white suspension was stirred at room temperature for 20 h. In a separate flask potassium 3-ethoxy-3-oxopropanoate (0.71 g, 4.17 mmol) was suspended in methyl THF (30 mL) under nitrogen atmosphere and magnesium chloride (0.41 g, 4.31 mmol) was added. The suspension was stirred vigorously at 50° C. for 6 h. The suspension was added to the reaction mixture and stirring was continued at room temperature for 17 h. Satd $NH_4Cl$ and DCM were added and the phases were separated. The aqueous phase was extracted with DCM and the combined organic layers were filtered through a phase separator and evaporated. The residue was purified by automated flash chromatography on a Biotage® KP-SIL 340 g column. A gradient of 5:1 to 1:1 of EtOAc in heptane over 15 CV was used as mobile phase. Trans-methyl 2-(difluoromethyl)-4-(3-ethoxy-3-oxopropanoyl)piperidine-1-carboxylate (203 mg, 7%) and cis-methyl 2-(difluoromethyl)-4-(3-ethoxy-3-oxopropanoyl)-piperidine-1-carboxylate (1.38 g, 48%) were isolated. Cis-isomer: $^1$H NMR (400 MHz, cdcl$_3$) δ 1.29 (t, 3H), 1.47-2.09 (m, 4H), 2.70-2.83 (m, 1H), 3.05-3.18 (m, 1H), 3.51 (d, 2H), 3.73 (s, 3H), 3.91-4.02 (m, 1H), 4.20 (q, 2H), 4.11-4.30 (m, 1H), 5.91 (dt, 1H). MS m/z 308 (M+H)$^+$. Trans-isomer: $^1$H NMR (400 MHz, cdcl$_3$) δ 1.28 (t, 3H), 1.39-2.32 (m, 4H), 2.88-3.23 (m, 2H), 3.51 (s, 2H), 3.73 (s, 3H), 4.20 (q, 2H), 4.11-4.70 (m, 2H), 5.88 (t, 1H). MS m/z 308 (M+H)$^+$

Step 2: Cis-methyl 2-(difluoromethyl)-4-(3-oxo-2,3-dihydroisoxazol-5-yl)piperidine-1-carboxylate Cis-methyl 2-(difluoromethyl)-4-(3-ethoxy-3-oxopropanoyl)piperidine-1-carboxylate (1.38 g, 4.49 mmol) was dissolved in MeOH (20 mL) and cooled to −40° C. under nitrogen. Sodium hydroxide (0.180 g, 4.49 mmol) dissolved in water (2.000 mL) was added and the mixture was stirred at −40° C. for 15 min. Hydroxylamine (50% by weight in water, 0.275 mL, 4.49 mmol) was added. The resulting solution was stirred at −40° C. for 1 h. The mixture was then transferred into a prewarmed (80° C.) solution of 6 M hydrogen chloride (23.20 mL, 139.22 mmol) and the mixture was stirred at 80° C. for 20 min. Water and DCM were added and the phases separated. The aqueous phase was extracted with DCM and the combined organic layers were filtered through a phase separator and evaporated. The compound was purified by preparative HPLC on a Kromasil C8 column (10 μm 250×50 ID mm) using a gradient of 5-55% Acetonitrile in H2O/MeCN/AcOH 95/5/0.2 buffer over 20 minutes with a flow of 100 mL/min. Cis-methyl 2-(difluoromethyl)-4-(3-oxo-2,3-dihydroisoxazol-5-yl)piperidine-1-carboxylate (650 mg, 52%) was isolated. $^1$H NMR (400 MHz, cdcl$_3$) δ 1.77-1.88 (m, 1H), 2.03-2.24 (m, 3H), 2.93-3.03 (m, 1H), 3.22-3.33 (m, 1H), 3.75 (s, 3H), 3.92-4.02 (m, 1H), 4.21-4.34 (m, 1H), 5.73 (s, 1H), 5.92 (dt, 1H). MS m/z 275 (M−H)$^-$

Step 3: (2R,4S)-Methyl 2-(difluoromethyl)-4-(3-oxo-2,3-dihydroisoxazol-5-yl)piperidine-1-carboxylate Cis-methyl 2-(difluoromethyl)-4-(3-oxo-2,3-dihydroisoxazol-5-yl)piperidine-1-carboxylate (650 mg, 2.35 mmol) was subjected to chiral preparative HPLC (Column: Chiralpak AD (250×20), 5 μm particle size, mobile phase: Heptane/EtOH 70/30, flow rate 18 mL/min) to yield (2R,4S)-methyl 2-(difluoromethyl)-4-(3-oxo-2,3-dihydroisoxazol-5-yl)piperidine-1-carboxylate (278 mg, 43%), Chiral purity 99.5% ee, Optical rotation [α]$_D^{20}$=+73.7 (acetonitrile, c=1), $^1$H NMR (400 MHz, cdcl$_3$) δ 1.75-1.86 (m, 1H), 2.01-2.21 (m, 3H), 2.91-3.01 (m, 1H), 3.20-3.30 (m, 1H), 3.72 (s, 3H), 3.89-4.01 (m, 1H), 4.18-4.33 (m, 1H), 5.72 (s, 1H), 5.88 (dt, 1H), 9.00 (br, 1H).

Step 4: 5-((2R,4S)-2-(Difluoromethyl)piperidin-4-yl)isoxazol-3(2H)-one (2R,4S)-Methyl 2-(difluoromethyl)-4-(3-oxo-2,3-dihydroisoxazol-5-yl)piperidine-1-carboxylate (278 mg, 1.01 mmol) was dissolved in hydrogen bromide (33% in acetic acid, 7.93 mL, 45.29 mmol) and stirred at room temperature for 16 h. The solvent was removed in vacuo and the compound was purified by preparative HPLC on a XBridge C18 column (10 μm 250×19 ID mm) using a gradient of 0-10% Acetonitrile in H2O/MeCN/NH3 95/5/0.2 buffer over 20 minutes with a flow of 19 mL/min. 5-((2R,4S)-2-(Difluoromethyl)piperidin-4-yl)isoxazol-3(2H)-one (224 mg) was isolated. $^1$H NMR (400 MHz, cd$_3$od) δ 1.66-1.77 (m, 1H), 1.77-1.89 (m, 1H), 2.24-2.31 (m, 1H), 2.36-2.43 (m, 1H), 3.12-3.27 (m, 2H), 3.51-3.58 (m, 1H), 3.73-3.86 (m, 1H), 5.84 (s, 1H), 6.14 (dt, 1H). HRMS Calcd for [C$_9$H$_{12}$F$_2$N$_2$O$_2$+H]+: 219.0945. Found: 219.0950.

Example 88

5-(Trans-2-(difluoromethyl)piperidin-4-yl)isoxazol-3(2H)-one

Step 1: Trans-methyl 2-(difluoromethyl)-4-(3-oxo-2,3-dihydroisoxazol-5-yl)piperidine-1-carboxylate Trans-methyl 2-(difluoromethyl)-4-(3-ethoxy-3-oxopropanoyl)piperidine-1-carboxylate (203 mg, 0.66 mmol) (from example 87, step 1) was dissolved in MeOH (3 mL) and cooled to −40° C. under nitrogen. Sodium hydroxide (26.4 mg, 0.66 mmol) dissolved in water (0.300 mL) was added and the mixture was stirred at −40° C. for 15 min. Hydroxylamine (50% by weight in water, 0.040 mL, 0.66 mmol) was added. The resulting solution was stirred at −40° C. for 2 h. The mixture was then transferred into a prewarmed (80° C.) solution of 6 M hydrogen chloride (3.41 mL, 20.48 mmol) and the mixture was stirred at 80° C. for 20 min. Water and DCM were added and the phases separated. The aqueous phase was extracted with DCM and the combined organic layers were filtered through a phase separator and evaporated. The compound was purified by preparative HPLC on a Kromasil C8 column (10 μm 250×20 ID mm) using a gradient of 5-55% Acetonitrile in H2O/MeCN/AcOH 95/5/0.2 buffer, over 15 minutes with a flow of 19 mL/min. Trans-methyl 2-(difluoromethyl)-4-(3-oxo-2,3-dihydroisoxazol-5-yl)piperidine-1-carboxylate (122 mg, 67%) was isolated. $^1$H NMR (400 MHz, cdcl$_3$) δ 1.35-1.65 (m, 1H), 1.68-1.82 (m, 1H), 1.87-2.12 (m, 1H), 2.30-2.45 (m, 1H), 2.70-3.22 (m, 2H), 3.74 (s, 3H), 4.10-4.74 (m, 2H), 5.69 (s, 1H), 5.75-6.09 (m, 1H). MS m/z 275 (M−H)−

Step 2: 5-(Trans-2-(difluoromethyl)piperidin-4-yl)isoxazol-3(2H)-one

Trans-methyl 2-(difluoromethyl)-4-(3-oxo-2,3-dihydroisoxazol-5-yl)piperidine-1-carboxylate (122 mg, 0.44 mmol) was dissolved in hydrogen bromide (33% in acetic acid, 8.21 mL, 46.87 mmol) and stirred at room temperature for 16 h. The solvent was removed in vacuo and the compound was purified by preparative HPLC on a XBridge C18 column (10 μm 250×19 ID mm) using a gradient of 0-10% Acetonitrile in H2O/MeCN/NH3 95/5/0.2 buffer over 20 minutes with a flow of 19 mL/min. 5-(Trans-2-(difluoromethyl)piperidin-4-yl)isoxazol-3(2H)-one (86 mg, 89%) was isolated. $^1$H NMR (400 MHz, cd$_3$od) δ 1.80-2.00 (m, 3H), 2.03-2.12 (m, 1H), 2.76-2.86 (m, 1H), 2.93-3.13 (m, 2H), 3.22-3.28 (m, 1H), 5.78 (s, 1H), 5.81 (dt, 1H). MS m/z 219 (M+H)$^+$

Example 89

5-((2S,4S)-2-((4,4-Difluorocyclohexyl)methyl)piperidin-4-yl)isoxazol-3(2H)-one

Step 1: Trans-methyl 2-((4,4-difluorocyclohexyl)methyl)-4-(3-ethoxy-3-oxopropanoyl)-piperidine-1-carboxylate and cis-methyl 2-((4,4-difluorocyclohexyl)methyl)-4-(3-ethoxy-3-oxopropanoyl)piperidine-1-carboxylate 2-((4,4-Difluorocyclohexyl)methyl)-1-(methoxycarbonyl)piperidine-4-carboxylic acid (4.82 g, 15.09 mmol) (reference compound 40) was dissolved in methyl THF (150 mL), then di(1H-imidazol-1-yl)methanone (3.67 g, 22.64 mmol) was added. The mixture was stirred at room temperature under nitrogen for 3 h (flask 1). In a separate flask potassium 3-ethoxy-3-oxopropanoate (4.62 g, 27.17 mmol) was suspended in methyl THF (150 mL), then magnesium chloride (2.59 g, 27.17 mmol) was added. The suspension was stirred at 50° C. under nitrogen for 3 h using a large magnetic stirring bar (flask 2). The contents of flask 1 was transferred into flask 2. The resulting yellow suspension was stirred under nitrogen at room temperature overnight. The mixture was acidified to pH 1 with 3.8 M HCl, then MTBE (100 mL) and water (100 mL) was added. The phases were separated and the organic layer was washed with water, satd $NaHCO_3$ and brine. The organic layer was dried over $Na_2SO_4$, filtered and evaporated leaving a colourless oil. The residue was purified by automated flash chromatography on Biotage (340 g) with a gradient of 20-50% (8 CV). The column was conditioned at 20% (1 CV). Trans-methyl 2-((4,4-difluorocyclohexyl)methyl)-4-(3-ethoxy-3-oxopropanoyl)piperidine-1-carboxylate (300 mg, 5%) and cis-methyl 2-((4,4-difluoro-cyclohexyl)methyl)-4-(3-ethoxy-3-oxopropanoyl)piperidine-1-carboxylate (2.66 g, 45%) were isolated. Cis-isomer: $^1$H NMR (400 MHz, cdcl$_3$) δ 1.15-2.11 (m, 18H), 2.66-2.76 (m, 1H), 2.98-3.09 (m, 1H), 3.50 (s, 2H), 3.70 (s, 3H), 3.83-3.93 (m, 1H), 4.11-4.24 (m, 3H). MS m/z 390 (M+H)$^+$. Trans-isomer: $^1$H NMR (400 MHz, cdcl$_3$) δ 1.15-2.13 (m, 18H), 2.77-2.94 (m, 2H), 3.49 (s, 2H), 3.70 (s, 3H), 3.97-4.33 (m, 3H), 4.34-4.65 (m, 1H).

Step 2: Cis-methyl 2-((4,4-difluorocyclohexyl)methyl)-4-(3-oxo-2,3-dihydroisoxazol-5-yl)piperidine-1-carboxylate Cis-methyl 2-((4,4-difluorocyclohexyl)methyl)-4-(3-ethoxy-3-oxopropanoyl)piperidine-1-carboxylate (2.66 g, 6.83 mmol) was dissolved in MeOH (20 mL) and cooled to −40° C. under nitrogen. Sodium hydroxide (2.009 mL, 6.83 mmol) dissolved in water (2.000 mL) was added during 10 min and the yellow solution continued to stir at −40° C. for 20 min. Hydroxylamine (50% by weight in water, 0.419 mL, 6.83 mmol) was added during 8 min. The resulting solution was stirred at −40° C. for 3 h. The mixture was then rapidly poured into a prewarmed (80° C.) solution of 6 M hydrogen chloride (30 mL, 180.00 mmol) and the mixture continued to stir at 80° C. for 20 min. The solvent was evaporated and DCM/water added. The phases were separated and the organic phase passed through a phase separator and evaporated to yield a white solid. The compound was purified by preparative HPLC on a Kromasil C8 column (10 µm 250×50 ID mm) using a gradient of 5-55% Acetonitrile in H2O/MeCN/FA 95/5/0.2 buffer over 30 minutes with a flow of 100 mL/min. Cis-methyl 2-((4,4-difluorocyclohexyl)methyl)-4-(3-oxo-2,3-dihydroisoxazol-5-yl)piperidine-1-carboxylate (1.6 g, 65%) was isolated. $^1$H NMR (400 MHz, cdcl$_3$) δ 1.10-2.12 (m, 15H), 2.96-3.05 (m, 1H), 3.08-3.19 (m, 1H), 3.71 (s, 3H), 3.87-4.00 (m, 1H), 4.14-4.24 (m, 1H), 5.72 (s, 1H). MS m/z 357 (M−H)$^−$ Step 3: 2 S,4S)-Methyl 2-((4,4-difluorocyclohexyl)methyl)-4-(3-oxo-2,3-dihydroisoxazol-5-yl)piperidine-1-carboxylate and (2R,4R)-methyl 2-((4,4-difluorocyclohexyl)methyl)-4-(3-oxo-2,3-dihydroisoxazol-5-yl)piperidine-1-carboxylate Cis-methyl 2-((4,4-difluorocyclohexyl)methyl)-4-(3-oxo-2,3-dihydroisoxazol-5-yl)piperidine-1-carboxylate (1.6 g, 4.46 mmol) was subjected to chiral preparative HPLC (Column: CelluCoat (250×20), 5 µm particle size, mobile phase: Heptane/IPA 80/20, flow rate 18 mL/min) to yield (2S,4S)-methyl 2-((4,4-difluorocyclohexyl)methyl)-4-(3-oxo-2,3-dihydro-isoxazol-5-yl)piperidine-1-carboxylate (787 mg, 49%), Chiral purity 99.8% ee, Optical rotation $[α]_D^{20}$=+28.8 (acetonitrile, c=1) and (2R,4R)-methyl 2-((4,4-difluorocyclohexyl)-methyl)-4-(3-oxo-2,3-dihydroisoxazol-5-yl)piperidine-1-carboxylate (752 mg, 47%) Chiral purity 99.9% ee, Optical rotation $[α]_D^{20}$=−30.2 (acetonitrile, c=1).

Step 4: 5-((2S,4S)-2-((4,4-Difluorocyclohexyl)methyl)piperidin-4-yl)isoxazol-3(2H)-one (2S,4S)-Methyl 2-((4,4-difluorocyclohexyl)methyl)-4-(3-oxo-2,3-dihydroisoxazol-5-yl)-piperidine-1-carboxylate (0.787 g, 2.20 mmol) was dissolved in hydrogen bromide (33% in acetic acid, 17.31 mL, 98.82 mmol) and the mixture stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 µm OBD 19*150 mm) to yield 5-((2S,4S)-2-((4,4-difluorocyclohexyl)methyl)-piperidin-4-yl)isoxazol-3(2H)-one (424 mg, 64%). $^1$H NMR (600 MHz, DMSO) δ 0.98-1.41 (m, 5H), 1.51-2.61 (m, 12H), 2.66-2.75 (m, 1H), 2.95-3.04 (m, 1H), 5.59-5.67 (m, 1H). HRMS Calculated for $[C_{15}H_{22}F_2N_2O_2+H]^+$: 301.1728. Found: 301.1713

Example 90

5-((2R,4R)-2-((4,4-Difluorocyclohexyl)methyl)piperidin-4-yl)isoxazol-3(2H)-one (2R,4R)-Methyl 2-((4,4-difluorocyclohexyl)methyl)-4-(3-oxo-2,3-dihydroisoxazol-5-yl)-piperidine-1-carboxylate (0.752 g, 2.10 mmol) (from example 89, step 3) was dissolved in hydrogen bromide (33% in acetic acid, 16.54 mL, 94.42 mmol) and the mixture stirred at room temperature overnight. The solvent was evaporated and the residue purified by preparative HPLC (Instrument: FractionLynx II, Mobilphase: gradient 5-95% MeCN in 0.2% NH$_3$, pH 10, Column: Xbridge Prep C18 5 µm OBD 19*150 mm) to yield 5-((2R,4R)-2-((4,4-difluorocyclohexyl)methyl)piperidin-4-yl)isoxazol-3(2H)-one (415 mg, 66%). HRMS Calculated for $[C_{15}H_{22}F_2N_2O_2+H]^+$: 301.1728. Found: 301.1741

Example 91

5-(Trans-2-((4,4-difluorocyclohexyl)methyl)piperidin-4-yl)isoxazol-3(2H)-one

Step 1: Trans-methyl 2-((4,4-difluorocyclohexyl)methyl)-4-(3-oxo-2,3-dihydroisoxazol-5-yl)-piperidine-1-carboxylate Trans-methyl 2-((4,4-difluorocyclohexyl)methyl)-4-(3-ethoxy-3-oxopropanoyl)piperidine-1-carboxylate (300 mg, 0.77 mmol) (from example 89, step 1) was dissolved in MeOH (3 mL) and cooled to −40° C. under nitrogen. Sodium hydroxide (0.227 mL, 0.77 mmol) dissolved in water (0.300 mL) was added during 10 min and the yellow solution continued to stir at −40° C. for 20 min. Hydroxylamine (50% by weight in water, 0.047 mL, 0.77 mmol) was added during 8 min. The resulting solution was stirred at −40° C. for 3 h 15 min. The mixture was then rapidly poured into a prewarmed (80° C.) solution of 6 M hydrogen chloride (4 mL, 24.00 mmol) and the mixture continued to stir at 80° C. for 20 min. The solvent was evaporated and DCM/water added. The phases were separated and the organic phase passed through a phase separator and evaporated to yield crude trans-methyl 2-((4,4-difluorocyclohexyl)methyl)-4-(3-oxo-2,3-dihydroisoxazol-5-yl)piperidine-1-carboxylate (267 mg, 97%) as a slightly yellow solid. MS m/z 357 (M−H)⁻

Step 2: 5-(Trans-2-((4,4-difluorocyclohexyl)methyl)piperidin-4-yl)isoxazol-3(2H)-one Trans-methyl 2-((4,4-difluorocyclohexyl)methyl)-4-(3-oxo-2,3-dihydroisoxazol-5-yl)-piperidine-1-carboxylate (0.267 g, 0.75 mmol) was dissolved in hydrogen bromide (33% in acetic acid, 5.87 mL, 33.53 mmol) and the mixture stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(trans-2-((4,4-difluorocyclohexyl)methyl)-piperidin-4-yl)isoxazol-3(2H)-one (63 mg, 28%). $^1$H NMR (600 MHz, dmso) δ 0.99-1.19 (m, 3H), 1.27-1.35 (m, 1H), 1.38-1.46 (m, 1H), 1.46-1.55 (m, 1H), 1.61-1.87 (m, 7H), 1.87-1.98 (m, 2H), 2.54-2.61 (m, 1H), 2.61-2.70 (m, 1H), 2.72-2.79 (m, 1H), 3.03-3.09 (m, 1H), 5.75 (s, 1H). HRMS Calculated for $[C_{15}H_{22}F_2N_2O_2+H]^+$: 301.1728. Found: 301.1751

Example 92

5-((2S,4S)-2-(4-Fluorophenethyl)piperidin-4-yl)isoxazol-3(2H)-one

Step 1: Trans-methyl 4-(3-ethoxy-3-oxopropanoyl)-2-(4-fluorophenethyl)piperidine-1-carboxylate and cis-methyl 4-(3-ethoxy-3-oxopropanoyl)-2-(4-fluorophenethyl)piperidine-1-carboxylate 2-(4-Fluorophenethyl)-1-(methoxycarbonyl)piperidine-4-carboxylic acid (4.34 g, 14.03 mmol) (reference compound 41) was dissolved in methyl THF (100 mL) under nitrogen atmosphere and di(1H-imidazol-1-yl)methanone (3.41 g, 21.05 mmol) added. The suspension was stirred at room temperature for 4 h (flask 1). In a separate flask was potassium 3-ethoxy-3-oxopropanoate (4.30 g, 25.25 mmol) suspended in methyl THF (100 mL) and magnesium chloride (2.404 g, 25.25 mmol) was added. The suspension was stirred at 50° C. under nitrogen for 4 h using an oversized stirring bar (flask 2). The contents of flask 1 was added to flask 2 and the mixture (white suspension) was stirred at room temperature for 19 h. In a new flask was potassium 3-ethoxy-3-oxopropanoate (4.30 g, 25.25 mmol) suspended in methyl THF (100 mL) and magnesium chloride (2.404 g, 25.25 mmol) was added. The suspension was stirred at 50° C. under nitrogen for 4 h using an oversized stirring bar and subsequently added to the reaction mixture. The mixture was stirred at room temperature for another 16 h at room temperature. 0.1 M HCl and DCM was added, the phases separated and the aqueous phase was extracted with DCM. The combined organic layers were washed with satd $NaHCO_3$, filtered through a phase separator and evaporated. The residue was purified by automated flash chromatography on 2 Biotage® KP-SIL 340 g columns. Mobile phase 2:1 heptane:EtOAc over 4 CV, then gradient from 2:1->1:1 heptane:EtOAc over 6 CV. Trans-methyl 4-(3-ethoxy-3-oxopropanoyl)-2-(4-fluorophenethyl)piperidine-1-carboxylate (0.74 g, 14%) and cis-methyl 4-(3-ethoxy-3-oxopropanoyl)-2-(4-fluorophenethyl)piperidine-1-carboxylate (3.17 g, 60%) were isolated. Cis-isomer: $^1$H NMR (400 MHz, cdcl₃) δ 1.24 (t, 3H), 1.50-2.11 (m, 6H), 2.48-2.65 (m, 2H), 2.67-7.77 (m, 1H), 3.03-3.14 (m, 1H), 3.50 (s, 2H), 3.69 (s, 3H), 3.84-3.93 (m, 1H), 4.07 (p, 1H), 4.12-4.22 (m, 2H), 6.95 (t, 2H), 7.08-7.16 (m, 2H). MS m/z 380 (M+H)⁺. Trans-isomer: $^1$H NMR (400 MHz, cdcl₃) δ 1.23-1.32 (m, 3H), 1.41-2.11 (m, 6H), 2.42-2.66 (m, 2H), 2.76-2.96 (m, 2H), 3.45 (s, 2H), 3.69 (s, 3H), 4.01-4.65 (m, 4H), 6.97 (t, 2H), 7.13 (s, br., 2H). MS m/z 380 (M+H)⁺

Step 2: Cis-methyl 2-(4-fluorophenethyl)-4-(3-oxo-2,3-dihydroisoxazol-5-yl)piperidine-1-carboxylate Cis-methyl 4-(3-ethoxy-3-oxopropanoyl)-2-(4-fluorophenethyl)piperidine-1-carboxylate (3.15 g, 8.30 mmol) was dissolved in MeOH (30 mL) and cooled to −40° C. under nitrogen. Sodium hydroxide (0.332 g, 8.30 mmol) dissolved in water (3.00 mL) was added and the mixture was stirred at −40° C. for 15 min. Hydroxylamine (50% by weight in water, 0.509 mL, 8.30 mmol) was added. The resulting solution was stirred at −40° C. for 3 h. The mixture was then transferred into a prewarmed (80° C.) solution of 6 M hydrogen chloride (42.9 mL, 257.36 mmol) and the mixture was stirred at 80° C. for 20 min. DCM and water were added. The phases were separated and the organic phase passed through a phase separator and evaporated. The compound (split into 4 runs) was purified by preparative HPLC on a XBridge C18 column (10 μm 250×50 ID mm) using a gradient of 0-25% Acetonitrile in $H_2O$/MeCN/$NH_3$ 95/5/0.2 buffer over 20 minutes with a flow of 100 mL/min. Cis-methyl 2-(4-fluorophenethyl)-4-(3-oxo-2,3-dihydroisoxazol-5-yl)piperidine-1-carboxylate (1.9 g, 66%) was isolated. $^1$H NMR (400 MHz, cdcl₃) δ 1.53-2.14 (m, 6H), 2.46-2.64 (m, 2H), 2.98-3.07 (m, 1H), 3.12-3.24 (m, 1H), 3.70 (s, 3H), 3.87-3.99 (m, 1H), 4.05-4.16 (m, 1H), 5.72 (s, 1H), 6.85-6.94 (m, 2H), 7.04-7.11 (m, 2H). MS m/z 349 (M+H)⁺

Step 3: (2S,4S)-Methyl 2-(4-fluorophenethyl)-4-(3-oxo-2,3-dihydroisoxazol-5-yl)piperidine-1-carboxylate and (2R,4R)-methyl 2-(4-fluorophenethyl)-4-(3-oxo-2,3-dihydroisoxazol-5-yl)-piperidine-1-carboxylate Cis-methyl 2-(4-fluorophenethyl)-4-(3-oxo-2,3-dihydroisoxazol-5-yl)piperidine-1-carboxylate (1.4 g, 4 mmol) was subjected to chiral preparative HPLC (Column: Chiralpak AD (250×20), 5 μm particle size, mobile phase: Heptane/EtOH 80/20, flow rate 18 mL/min) to yield (2S,4S)-methyl 2-(4-fluorophenethyl)-4-(3-oxo-2,3-dihydroisoxazol-5-yl)piperidine-1-carboxylate (582 mg, 42%), Chiral purity 99.9% ee, Optical rotation $[\alpha]_D^{20}$=+51.6 (acetonitrile, c=1) and (2R,4R)-methyl 2-(4-fluorophenethyl)-4-(3-oxo-2,3-dihydroisoxazol-5-yl)piperidine-1-carboxylate (676 mg, 48%), Chiral purity 99.4% ee, Optical rotation $[\alpha]_D^{20}$=−45.0 (acetonitrile, c=1)

Step 4: 5-((2S,4S)-2-(4-Fluorophenethyl)piperidin-4-yl)isoxazol-3(2H)-one (2S,4S)-Methyl 2-(4-fluorophenethyl)-4-(3-oxo-2,3-dihydroisoxazol-5-yl)piperidine-1-carboxylate (435 mg, 1.25 mmol) was dissolved in hydrogen bromide (33% in acetic acid, 9.84 mL, 56.19 mmol) to give a yellow solution. The mixture was stirred at room temperature for 16 h, the solvent was removed and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2S,4S)-2-(4-fluorophenethyl)piperidin-4-yl)isoxazol-3(2H)-one (228 mg, 63%). $^1$H NMR (400 MHz, cd₃od) δ 1.48 (dd, 1H), 1.64-1.97 (m, 3H), 2.13 (d, 1H), 2.30 (d, 1H), 2.66-2.80 (m, 2H), 2.84-3.10 (m, 3H), 3.34-3.43 (m, 1H), 5.51 (s, 1H), 6.97-7.05 (m, 2H), 7.19-7.28 (m, 2H). HRMS Calculated for $[C_{16}H_{19}FN_2O_2+H]^+$: 291.1509. Found: 291.1497

Example 93

5-((2R,4R)-2-(4-Fluorophenethyl)piperidin-4-yl)isoxazol-3(2H)-one (2R,4R)-Methyl 2-(4-fluorophenethyl)-4-(3-oxo-2,3-dihydroisoxazol-5-yl)piperidine-1-carboxylate (507 mg, 1.46 mmol) (from example 92, step 3) was dissolved in hydrogen bromide (33% in acetic acid (11.5 mL, 65.49 mmol) to give a yellow solution. The mixture was stirred at room temperature for 16 h, the solvent was removed and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4R)-2-(4-fluorophenethyl)piperidin-4-yl)isoxazol-3(2H)-one (278 mg, 65%). $^1$H NMR (400 MHz, $cd_3od$) δ 1.48 (q, 1H), 1.70 (dq, 1H), 1.78-1.96 (m, 2H), 2.09-2.17 (m, 1H), 2.26-2.34 (m, 1H), 2.66-2.80 (m, 2H), 2.86-3.09 (m, 3H), 3.35-3.43 (m, 1H), 5.52 (s, 1H), 6.98-7.05 (m, 2H), 7.21-7.26 (m, 2H). HRMS Calculated for $[C_{16}H_{19}FN_2O_2+H]^+$: 291.1509. Found: 291.1483

Example 94

5-(Trans-2-(4-fluorophenethyl)piperidin-4-yl)isoxazol-3(2H)-one

Step 1: Trans-methyl 2-(4-fluorophenethyl)-4-(3-oxo-2,3-dihydroisoxazol-5-yl)piperidine-1-carboxylate Trans-methyl 4-(3-ethoxy-3-oxopropanoyl)-2-(4-fluorophenethyl)piperidine-1-carboxylate (730 mg, 1.92 mmol) (from example 92, step 1) was dissolved in MeOH (7 mL) and cooled to −40° C. under nitrogen. Sodium hydroxide (77 mg, 1.92 mmol) dissolved in water (0.700 mL) was added and the mixture was stirred at −40° C. for 15 min. Hydroxylamine (50% by weight in water, 0.118 mL, 1.92 mmol) was added. The resulting solution was stirred at −40° C. for 3 h. The mixture was then transferred into a prewarmed (80° C.) solution of 6 M hydrogen chloride (9.94 mL, 59.64 mmol) and the mixture was stirred at 80° C. for 20 min. DCM and water were added. The phases were separated, the aqueous phase extracted with DCM and the combined organic layers passed through a phase separator and evaporated. The residue was purified by automated flash chromatography on a Biotage® KP-SIL 100 g column. DCM:MeOH:HCOOH=50:1:0.1 over 10 CV was used as mobile phase. Trans-methyl 2-(4-fluorophenethyl)-4-(3-oxo-2,3-dihydroisoxazol-5-yl)piperidine-1-carboxylate (550 mg, 82%) was isolated. $^1$H NMR (400 MHz, $cdcl_3$) δ 1.01-2.13 (m, 6H), 2.48-2.70 (m, 2H), 2.88-3.08 (m, 2H), 3.70 (s, 3H), 3.98-4.69 (m, 2H), 5.64 (s, 1H), 6.91-7.02 (m, 2H), 7.06-7.21 (m, 2H). MS m/z 349 $(M+H)^+$ Step 2: 5-(Trans-2-(4-fluorophenethyl)piperidin-4-yl)isoxazol-3(2H)-one Trans-methyl 2-(4-fluorophenethyl)-4-(3-oxo-2,3-dihydroisoxazol-5-yl)piperidine-1-carboxylate (137 mg, 0.39 mmol) dissolved in hydrogen bromide (33% in acetic acid, 3.1 mL, 17.70 mmol) to give a yellow solution. The mixture was stirred at room temperature for 16 h, the solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(trans-2-(4-fluorophenethyl)piperidin-4-yl)isoxazol-3(2H)-one (80 mg, 70%). $^1$H NMR (400 MHz, dmso) δ 1.42-1.78 (m, 5H), 1.82-1.95 (m, 1H), 2.52-2.68 (m, 4H), 2.74-2.84 (m, 1H), 3.05-3.13 (m, 1H), 5.73 (s, 1H), 7.01-7.10 (m, 2H), 7.15-7.25 (m, 2H). HRMS Calculated for $[C_{16}H_{19}FN_2O_2+H]^+$: 291.1509. Found: 291.1522

Example 95

5-((2S,4S)-2-(3,3-Dimethylbutyl)piperidin-4-yl)isoxazol-3(2H)-one

Step 1: Trans-methyl 2-(3,3-dimethylbutyl)-4-(3-ethoxy-3-oxopropanoyl)piperidine-1-carboxylate and cis-methyl 2-(3,3-dimethylbutyl)-4-(3-ethoxy-3-oxopropanoyl)piperidine-1-carboxylate A suspension of magnesium chloride (0.852 g, 8.94 mmol) and ethyl potassium malonate (2.283 g, 13.42 mmol) in dry THF (40 mL) was stirred under nitrogen atmosphere at 50° C. for 3.5 h (flask 1). In another flask was added carbonyldiimidazole (1.740 g, 10.73 mmol) portionwise to a solution of 2-(3,3-dimethylbutyl)-1-(methoxycarbonyl)piperidine-4-carboxylic acid (2.427 g, 8.94 mmol) (reference compound 42) in dry THF (40 mL) at 0° C. under nitrogen atmosphere. This solution was stirred for 1.5 h (flask 2). The contents of flask 1 was added over 10 min to flask 2 and the resulting mixture was stirred at room temperature for 20 h. The reaction mixture was concentrated and the residue was taken up in EtOAc and H2O. The aqueous phase was extracted once with EtOAc and the combined organic phase was washed with $H_2O$, satd $NaHCO_3$ and then dried over $Na_2SO_4$, filtered and evaporated to give a black oil. Separation using Biotage (340 g column, grad 20-30% EtOAc in heptane 7 CV) yielded trans-methyl 2-(3,3-dimethylbutyl)-4-(3-ethoxy-3-oxopropanoyl)piperidine-1-carboxylate (574 mg, 24%) and cis-methyl 2-(3,3-dimethylbutyl)-4-(3-ethoxy-3-oxopropanoyl)piperidine-1-carboxylate (1.74 g, 72%) as yellow oils. Cis-isomer: $^1$H NMR (400 MHz, $cdcl_3$) δ 0.85 (s, 9H), 1.03-1.95 (m, 10H), 2.01-2.10 (m, 1H), 2.65-2.75 (m, 1H), 2.98-3.08 (m, 1H), 3.51 (s, 2H), 3.69 (s, 3H), 3.83-4.02 (m, 2H), 4.19 (q, 2H). MS m/z 342 $(M+H)^+$. Trans-isomer: MS m/z 342 $(M+H)^+$ Step 2: Cis-methyl 2-(3,3-dimethylbutyl)-4-(3-oxo-2,3-dihydroisoxazol-5-yl)piperidine-1-carboxylate A solution of cis-methyl 2-(3,3-dimethylbutyl)-4-(3-ethoxy-3-oxopropanoyl)piperidine-1-carboxylate (1.78 g, 5.22 mmol) in MeOH (3.9 mL) was added to a solution of NaOH (288 mg, 7.2 mmol) in MeOH/H2O (4.4 mL/0.3 mL) at −30° C. After 10 min was added hydroxylamine hydrochloride (726 mg, 10.45 mmol) and NaOH (418 mg, 10.45 mmol) in MeOH (5.2 mL) and H2O (5.2 mL). Stirring was continued at −30° C. for 30 min. The reaction solution was poured into 6 M HCl (7.7 mL) at 80° C. and heated at 80° C. for 1 h. Concentration of the organic solvent and extraction with DCM (×2), drying using a phase separator and evaporation gave an orange oil. The compound was purified by preparative HPLC on a Kromasil C8 column (10 μm 250×50 ID mm) using a gradient of 30-60% Acetonitrile in H2O/MeCN/FA 95/5/0.2 buffer over 30 minutes with a flow of 100 mL/min. Cis-methyl 2-(3,3-dimethylbutyl)-4-(3-oxo-2,3-dihydroisoxazol-5-yl)piperidine-1-carboxylate (717 mg, 44%) was isolated. ¹H NMR (400 MHz, cdcl₃) δ 0.79 (s, 9H), 1.01-1.19 (m, 2H), 1.23-1.48 (m, 2H), 1.83-1.96 (m, 2H), 1.98-2.11 (m, 2H), 2.94-3.04 (m, 1H), 3.09-3.19 (m, 1H), 3.70 (s, 3H), 3.91-4.06 (m, 2H), 5.71 (d, 1H). MS m/z 311 (M+H)⁺

Step 3: 2 S,4S)-Methyl 2-(3,3-dimethylbutyl)-4-(3-oxo-2,3-dihydroisoxazol-5-yl)piperidine-1-carboxylate Cis-methyl 2-(3,3-dimethylbutyl)-4-(3-oxo-2,3-dihydroisoxazol-5-yl)piperidine-1-carboxylate (717 mg, 2.31 mmol) was subjected to chiral preparative HPLC (Column: Chiralpak IC (250×20), 5 μm particle size, mobile phase: Heptane/IPA 80/20, flow rate 18 mL/min) to yield (2S,4S)-methyl 2-(3,3-dimethylbutyl)-4-(3-oxo-2,3-dihydroisoxazol-5-yl)-piperidine-1-carboxylate (341 mg, 48%), Chiral purity 99.9% ee, Optical rotation $[\alpha]_D^{20}$=+36.5 (acetonitrile, c=1)

Step 4: 5-((2S,4S)-2-(3,3-Dimethylbutyl)piperidin-4-yl)isoxazol-3(2H)-one (2S,4S)-Methyl 2-(3,3-dimethylbutyl)-4-(3-oxo-2,3-dihydroisoxazol-5-yl)piperidine-1-carboxylate (341 mg, 1.1 mmol) was dissolved in hydrogen bromide (33% in acetic acid, 20 mL) and the mixture was stirred at room temperature for 24 h. The solvent was evaporated and the compound was purified by preparative HPLC on a XBridge C18 column (10 μm 250×50 ID mm) using a gradient of 5-30% Acetonitrile in H2O/MeCN/NH3 95/5/0.2 buffer over 15 minutes with a flow of 100 mL/min. 5-((2S,4S)-2-(3,3-Dimethylbutyl)piperidin-4-yl)-isoxazol-3(2H)-one (235 mg, 85%) was isolated. ¹H NMR (600 MHz, cd₃od) δ 0.90 (s, 9H), 1.22-1.34 (m, 2H), 1.43-1.78 (m, 4H), 2.10 (d, 1H), 2.22 (d, 1H), 2.85-2.94 (m, 1H), 2.98-3.07 (m, 2H), 3.40 (d, 1H), 5.46 (s, 1H). HRMS Calculated for $[C_{14}H_{24}N_2O_2+H]^+$: 253.1916. Found: 253.1898

Example 96

5-((2R,4S)-2-(3,3-Dimethylbutyl)piperidin-4-yl)isoxazol-3(2H)-one

Step 1: Trans-methyl 2-(3,3-dimethylbutyl)-4-(3-oxo-2,3-dihydroisoxazol-5-yl)piperidine-1-carboxylate A solution of cis-methyl 2-(3,3-dimethylbutyl)-4-(3-ethoxy-3-oxopropanoyl)piperidine-1-carboxylate (549 mg, 1.61 mmol) (from example 95, step 1) in MeOH (1.2 mL) was added to a solution of NaOH (70 mg, 1.75 mmol) in MeOH/H2O (1.3 mL/0.08 mL) at −30° C. After 10 min was added hydroxylaminehydrochloride (223 mg, 3.22 mmol) and NaOH (129 mg, 3.22 mmol) in MeOH (1.6 mL) and H₂O (1.6 mL). Stirring was continued at −30° C. for 30 min. The reaction solution was poured into 6 M HCl (2.4 mL) at 80° C. and heated at 80° C. for 1 h. Concentration of the organic solvent and extraction with DCM (×2), drying using a phase separator and evaporation gave an orange oil. The compound was purified by preparative HPLC on a Kromasil C8 column (10 μm 250×50 ID mm) using a gradient of 30-60% Acetonitrile in H2O/MeCN/FA 95/5/0.2 buffer over 30 minutes with a flow of 100 mL/min. Trans-methyl 2-(3,3-dimethylbutyl)-4-(3-oxo-2,3-dihydroisoxazol-5-yl)piperidine-1-carboxylate (194 mg, 39%) was isolated as a white solid. ¹H NMR (400 MHz, cdcl₃) δ 0.89 (s, 9H), 1.02-1.78 (m, 6H), 1.89-2.03 (m, 2H), 2.83-3.09 (m, 2H), 3.71 (s, 3H), 3.99-4.51 (m, 2H), 5.65 (s, 1H). MS m/z 311 (M+H)⁺

Step 2: (2R,4S)-Methyl 2-(3,3-dimethylbutyl)-4-(3-oxo-2,3-dihydroisoxazol-5-yl)piperidine-1-carboxylate Trans-methyl 2-(3,3-dimethylbutyl)-4-(3-oxo-2,3-dihydroisoxazol-5-yl)piperidine-1-carboxylate (194 mg, 0.63 mmol) was subjected to chiral preparative HPLC (Column: Chiralpak IC (250×20), 5 μm particle size, mobile phase: Heptane/IPA 85/15, flow rate 18 mL/min) to yield (2R,4S)-methyl 2-(3,3-dimethylbutyl)-4-(3-oxo-2,3-dihydroisoxazol-5-yl)-piperidine-1-carboxylate (83 mg, 43%), Chiral purity 99.3% ee, Optical rotation $[\alpha]_D^{20}$=−12.3 (acetonitrile, c=1)

Step 3: 5-((2R,4S)-2-(3,3-Dimethylbutyl)piperidin-4-yl)isoxazol-3(2H)-one (2R,4S)-Methyl 2-(3,3-dimethylbutyl)-4-(3-oxo-2,3-dihydroisoxazol-5-yl)piperidine-1-carboxylate (62 mg, 0.2 mmol) was dissolved in hydrogen bromide (33% in acetic acid, 4 mL) and the mixture was stirred at room temperature for 18 h. The solvent was evaporated and the compound was purified by preparative HPLC on a XBridge C18 column (10 μm 250×19 ID mm) using a gradient of 5-30% Acetonitrile in H2O/MeCN/NH3 95/5/0.2 buffer over 15 minutes with a flow of 19 mL/min. 5-((2R,4S)-2-(3,3-Dimethylbutyl)piperidin-4-yl)isoxazol-3(2H)-one (39.8 mg, 79%) was isolated as a white solid. ¹H NMR (600 MHz, cd₃od) δ 0.92 (s, 9H), 1.20-1.34 (m, 2H), 1.56-1.69 (m, 2H), 1.83-1.90 (m, 1H), 2.05-2.13 (m, 1H), 2.14-2.21 (m, 1H), 2.26-2.34 (m, 1H), 3.05-3.19 (m, 2H), 3.25-3.34 (m, 2H), 5.75 (s, 1H). HRMS Calculated for $[C_{14}H_{24}N_2O_2+H]^+$: 253.1916. Found: 253.1925

Example 97

5-((2R,4S)-2-(4-Fluorobenzyl)piperidin-4-yl)isoxazol-3(2H)-one

Step 1: Trans-methyl 4-(3-ethoxy-3-oxopropanoyl)-2-(4-fluorobenzyl)piperidine-1-carboxylate and cis-methyl 4-(3-ethoxy-3-oxopropanoyl)-2-(4-fluorobenzyl)piperidine-1-carboxylate 2-(4-Fluorobenzyl)-1-(methoxycarbonyl)piperidine-4-carboxylic acid (4.428 g, 14.99 mmol) (reference compound 43) was dissolved in methyl THF (100 mL) and di(1H-imidazol-1-yl)methanone (3.65 g, 22.49 mmol) added. The suspension was stirred at room temperature overnight under nitrogen (flask 1). In a separate flask potassium 3-ethoxy-3-oxopropanoate (4.59 g, 26.99 mmol) was suspended in methyl THF (100 mL) and magnesium chloride (2.57 g, 26.99 mmol) added. The suspension was stirred at 50° C. under nitrogen for 3 h (flask 2). The slightly yellow suspension in flask 1 was now added to the white suspension in flask 2. The resulting white suspension was stirred under nitrogen at room temperature overnight. The mixture was acidified to pH 1 with 3.8 M HCl and MTBE added. The phases were separated and the organic phase extracted with water, sat NaHCO₃ and water. Evaporated the solvents to yield a yellow oil. The diastereoisomers were separated on Biotage (0%=>70% EtOAc in heptane, 7 CV; Biotage® KP-SIL 340 g column). Mixed fractions were repurified on Biotage (30%=>65%

EtOAc in heptane, 10 CV; Biotage® KP-SIL 50 g column). Trans-methyl 4-(3-ethoxy-3-oxopropanoyl)-2-(4-fluorobenzyl)piperidine-1-carboxylate (0.458 g, 10.36%) and cis-methyl 4-(3-ethoxy-3-oxopropanoyl)-2-(4-fluorobenzyl)piperidine-1-carboxylate (2.531 g, 57.3%) were isolated. Cis-isomer: $^1$H NMR (600 MHz, cdcl$_3$) δ 1.20-1.25 (m, 3H), 1.61-1.68 (m, 1H), 1.77-1.91 (m, 3H), 2.64-2.73 (m, 2H), 2.82-2.87 (m, 1H), 2.94-3.00 (m, 1H), 3.43 (s, 2H), 3.60 (s, 3H), 3.90 (dd, 1H), 4.11-4.17 (m, 3H), 6.91-6.96 (m, 2H), 7.08-7.13 (m, 2H). MS m/z 366 (M+H)$^+$. Trans-isomer: $^1$H NMR (600 MHz, cdcl$_3$) δ 1.15-1.26 (m, 3H), 1.39-1.94 (m, 4H), 2.59-3.00 (m, 4H), 3.32-3.66 (m, 5H), 3.96-4.28 (m, 3H), 4.50 (d, br., 1H), 6.88-6.95 (m, 2H), 6.99-7.18 (m, 2H). MS m/z 366 (M+H)$^+$ Step 2: Cis-methyl 2-(4-fluorobenzyl)-4-(3-oxo-2,3-dihydroisoxazol-5-yl)piperidine-1-carboxylate Cis-methyl 4-(3-ethoxy-3-oxopropanoyl)-2-(4-fluorobenzyl)piperidine-1-carboxylate (2.53 g, 6.92 mmol) was dissolved in MeOH (20 mL) and cooled to −40° C. under nitrogen. Sodium hydroxide (0.277 g, 6.92 mmol) dissolved in water (2.000 mL) was added during 10 min and the colourless solution continued to stir at −40° C. for 20 min. Hydroxylamine (50% by weight in water, 0.424 mL, 6.92 mmol) was added during 8 min. The resulting solution was stirred at −40° C. for 2 h. The mixture was then rapidly poured into a prewarmed (80° C.) solution of 6 M hydrogen chloride (30 mL, 180.00 mmol) and the mixture continued to stir at 80° C. for 20 min. The solvent was evaporated and DCM/water added. The phases were separated and the organic phase passed through a phase separator and evaporated to yield a yellow solid. The compound was purified by preparative HPLC in 3 injections on a XBridge C18 column (10 µm 250×50 ID mm) using a gradient of 0-35% Acetonitrile in H2O/MeCN/NH3 95/5/0.2 buffer over 20 minutes with a flow of 100 mL/min. Cis-methyl 2-(4-fluorobenzyl)-4-(3-oxo-2,3-dihydroisoxazol-5-yl)piperidine-1-carboxylate (1.516 g, 65.5%) was isolated as a white solid. $^1$H NMR (400 MHz, cdcl$_3$) δ 1.83-2.14 (m, 4H), 2.55-2.65 (m, 1H), 2.72-2.81 (m, 1H), 2.93-3.03 (m, 1H), 3.08-3.19 (m, 1H), 3.61 (s, 3H), 3.95-4.05 (m, 1H), 4.20-4.30 (m, 1H), 5.73 (s, 1H), 6.91-6.99 (m, 2H), 7.02-7.09 (m, 2H). MS m/z 335 (M+H)$^+$ Step 3: (2R,4S)-Methyl 2-(4-fluorobenzyl)-4-(3-oxo-2,3-dihydroisoxazol-5-yl)piperidine-1-carboxylate Cis-methyl 2-(4-fluorobenzyl)-4-(3-oxo-2,3-dihydroisoxazol-5-yl)piperidine-1-carboxylate (1.516 g, 4.53 mmol) was subjected to chiral preparative HPLC (Column: Chiralpak IC (250×20), 5 µm particle size, mobile phase: Heptane/(MTBE/MeOH 95/5) 50/50, flow rate 18 mL/min) to yield (2R,4S)-methyl 2-(4-fluorobenzyl)-4-(3-oxo-2,3-dihydroisoxazol-5-yl)piperidine-1-carboxylate 647 mg (43%), Chiral purity 99.9% ee, Optical rotation $[α]_D^{20}$=+17.8 (acetonitrile, c=1)

Step 4: 5-((2R,4S)-2-(4-Fluorobenzyl)piperidin-4-yl)isoxazol-3(2H)-one (2R,4S)-Methyl 2-(4-fluorobenzyl)-4-(3-oxo-2,3-dihydroisoxazol-5-yl)piperidine-1-carboxylate (647 mg, 1.94 mmol) was dissolved in hydrogen bromide (33% in acetic acid, 15 mL, 85.65 mmol) and the mixture stirred at room temperature overnight. The solvent was evaporated and the residue purified by preparative HPLC (Instrument: Fraction-Lynx II, Mobilphase: gradient 5-95% MeCN in 0.2% NH$_3$, pH 10, Column: Xbridge Prep C18 5 µm OBD 19*150 mm) to yield 5-((2R,4S)-2-(4-fluorobenzyl)piperidin-4-yl)isoxazol-3(2H)-one (360 mg, 67%). $^1$H NMR (600 MHz, DMSO) δ 1.08 (q, 1H), 1.37 (dq, 1H), 1.73-1.81 (m, 2H), 2.44-2.73 (m, 5H), 2.96-3.03 (m, 1H), 5.70 (s, 1H), 7.07-7.14 (m, 2H), 7.21-7.27 (m, 2H). HRMS Calculated for [C$_{15}$H$_{17}$FN$_2$O$_2$+H]$^+$: 277.1352. Found: 277.1333

Example 98

5-((2S,4S)-2-(4-Fluorobenzyl)piperidin-4-yl)isoxazol-3(2H)-one

Step 1: Trans-methyl 2-(4-fluorobenzyl)-4-(3-oxo-2,3-dihydroisoxazol-5-yl)piperidine-1-carboxylate Trans-methyl 4-(3-ethoxy-3-oxopropanoyl)-2-(4-fluorobenzyl)piperidine-1-carboxylate (0.454 g, 1.24 mmol) (from example 97, step 1) was dissolved in MeOH (5 mL) and cooled to −40° C. under nitrogen. Sodium hydroxide (0.050 g, 1.24 mmol) dissolved in water (1 mL) was added during 10 min and the colourless solution continued to stir at −40° C. for 20 min. Hydroxylamine (50% by weight in water, 0.076 mL, 1.24 mmol) was added during 5 min. The resulting solution was stirred at −40° C. for 2 h. The mixture was then rapidly poured into a prewarmed (80° C.) solution of 6 M hydrogen chloride (6 mL, 36.00 mmol) and the mixture continued to stir at 80° C. for 20 min. The solvent was evaporated and DCM/water added. The phases were separated and the organic phase passed through a phase separator and evaporated to yield a slightly yellow oil. The compound was purified by preparative HPLC on a XBridge C18 column (10 µm 250×50 ID mm) using a gradient of 0-30% Acetonitrile in H2O/MeCN/NH3 95/5/0.2 buffer over 20 minutes with a flow of 100 mL/min. Trans-methyl 2-(4-fluorobenzyl)-4-(3-oxo-2,3-dihydroisoxazol-5-yl)piperidine-1-carboxylate (0.268 g, 64.5%) was isolated as a white solid. $^1$H NMR (400 MHz, cdcl$_3$) δ 1.47-1.75 (m, 2H), 1.85-2.14 (m, 2H), 2.71-3.00 (m, 2H), 3.02-3.16 (m, 2H), 3.40-3.76 (m, 3H), 4.22 (d, br., 1H), 4.59 (d, br., 1H), 5.64 (s, 1H), 6.95-7.03 (m, 2H), 7.15 (s, br., 2H). MS m/z 335 (M+H)$^+$ Step 2: (2S,4S)-Methyl 2-(4-fluorobenzyl)-4-(3-oxo-2,3-dihydroisoxazol-5-yl)piperidine-1-carboxylate Trans-methyl 2-(4-fluorobenzyl)-4-(3-oxo-2,3-dihydroisoxazol-5-yl)piperidine-1-carboxylate (0.268 g, 0.8 mmol) was subjected to chiral preparative HPLC (Column: Chiralcel OJ (250×30), 5 µm particle size, mobile phase: 10% EtOH in CO2 (175 bar), flow rate 150 mL/min) to yield (2S,4S)-methyl 2-(4-fluorobenzyl)-4-(3-oxo-2,3-dihydroisoxazol-5-yl)-piperidine-1-carboxylate (81 mg, 30%), Chiral purity 99.8% ee, Optical rotation $[α]_D^{20}$=+29.3 (acetonitrile, c=1)

Step 3: 5-((2S,4S)-2-(4-Fluorobenzyl)piperidin-4-yl)isoxazol-3(2H)-one (2S,4S)-Methyl 2-(4-fluorobenzyl)-4-(3-oxo-2,3-dihydroisoxazol-5-yl)piperidine-1-carboxylate (81 mg, 0.24 mmol) was dissolved in hydrogen bromide (33% in acetic acid, 2 mL, 11.42 mmol) and the mixture stirred at room temperature for 24 h, then more hydrogen bromide (33% in acetic acid, 0.5 mL) was added and stirring continued overnight, then more hydrogen bromide (33% in acetic acid, 1 mL) was added and stirring continued overnight. The solvent was evaporated and the residue purified by preparative HPLC (Instrument: Agilent, Mobilphase: gradient 5-95% MeCN in 0.2% NH$_3$, pH 10, Column: Xbridge Prep C18 5 µm OBD 19*150 mm) to yield 5-((2S,4S)-2-(4-fluorobenzyl)piperidin-4-yl)isoxazol-3(2H)-one (46.9 g, 70%). $^1$H NMR (400 MHz, cd$_3$od) δ 1.73-1.83 (m, 1H), 1.98-2.17 (m, 3H), 2.81-3.10 (m, 3H), 3.20-3.28 (m, 2H), 3.32-3.41 (m, 1H), 5.48 (d, 1H), 7.01-7.09 (m, 2H), 7.20-7.27 (m, 2H). HRMS Calculated for [C$_{15}$H$_{17}$FN$_2$O$_2$+H]$^+$: 277.1352. Found: 277.1346

Example 99

5-((2R,4S)-2-(3-Fluorobenzyl)piperidin-4-yl)isoxazol-3(2H)-one

Step 1: Trans-methyl 4-(3-ethoxy-3-oxopropanoyl)-2-(3-fluorobenzyl)piperidine-1-carboxylate and cis-methyl 4-(3-ethoxy-3-oxopropanoyl)-2-(3-fluorobenzyl)piperidine-1-carboxylate 2-(3-Fluorobenzyl)-1-(methoxycarbonyl)piperidine-4-carboxylic acid (7.112 g, 24.08 mmol) (reference compound 44) was dissolved in methyl THF (150 mL) and di(1H-imidazol-1-yl)methanone (5.86 g, 36.13 mmol) added. The suspension was stirred at room temperature under nitrogen for 3.5 h (flask 1). In a separate flask potassium 3-ethoxy-3-oxopropanoate (7.38 g, 43.35 mmol) was suspended in methyl THF (150 mL) and magnesium chloride (4.13 g, 43.35 mmol) added. The suspension was stirred at 50° C. under nitrogen for 3 h (flask 2). The orange suspension in flask 1 was now added to the white suspension in flask 2. The resulting yellow suspension was stirred under nitrogen at room temperature for 3 days. The mixture was acidified to pH 1 with 3.8 M HCl and MTBE added. The phases were separated and the organic phase extracted with water, satd NaHCO$_3$ and water. Evaporated the solvents to yield an orange oil. 42% of the oil was purified on Biotage (20%=>50% EtOAc in heptane, 6 CV+50%, 4 CV; Biotage® KP-SIL 340 g column) to yield trans-methyl 4-(3-ethoxy-3-oxopropanoyl)-2-(3-fluorobenzyl)piperidine-1-carboxylate (664 mg, 18%) and cis-methyl 4-(3-ethoxy-3-oxopropanoyl)-2-(3-fluorobenzyl)piperidine-1-carboxylate (1.8 g, 49%). Cis-isomer: $^1$H NMR (400 MHz, cdcl$_3$) δ 1.20 (t, 3H), 1.56-1.93 (m, 4H), 2.62-2.73 (m, 2H), 2.83-3.03 (m, 2H), 3.41 (s, 2H), 3.59 (s, 3H), 3.83-3.93 (m, 1H), 4.07-4.20 (m, 3H), 6.82-6.93 (m, 3H), 7.15-7.22 (m, 1H). MS m/z 366 (M+H)$^+$. Trans-isomer: MS m/z 366 (M+H)$^+$ Step 2: Cis-methyl 2-(3-fluorobenzyl)-4-(3-oxo-2,3-dihydroisoxazol-5-yl)piperidine-1-carboxylate Cis-methyl 4-(3-ethoxy-3-oxopropanoyl)-2-(3-fluorobenzyl)piperidine-1-carboxylate (1.826 g, 5.00 mmol) was dissolved in MeOH (20 mL) and cooled to −40° C. under nitrogen. Sodium hydroxide (0.200 g, 5.00 mmol) dissolved in water (2.000 mL) was added during 20 min and the yellow solution continued to stir at −40° C. for 20 min. Hydroxylamine (50% by weight in water, 0.306 mL, 5.00 mmol) was added during 8 min. The resulting solution was stirred at −40° C. for 3.5 h. The mixture was then rapidly poured into a prewarmed (80° C.) solution of 6 M hydrogen chloride (25 mL, 150.00 mmol) and the mixture continued to stir at 80° C. for 20 min. The solvent was evaporated and DCM/water added. The phases were separated and the organic phase passed through a phase separator and evaporated to yield a brown semi-solid. The compound was purified by preparative HPLC in 2 injections on a XBridge C18 column (10 µm 250×50 ID mm) using a gradient of 0-25% Acetonitrile in H2O/MeCN/NH3 95/5/0.2 buffer over 20 minutes with a flow of 100 mL/min. Cis-methyl 2-(3-fluorobenzyl)-4-(3-oxo-2,3-dihydroisoxazol-5-yl)piperidine-1-carboxylate (1.141 g, 68%) was isolated as a white solid. $^1$H NMR (400 MHz, cdcl$_3$) δ 1.83-2.15 (m, 4H), 2.58-2.67 (m, 1H), 2.77-2.86 (m, 1H), 2.93-3.03 (m, 1H), 3.10-3.21 (m, 1H), 3.63 (s, 3H), 3.96-4.05 (m, 1H), 4.22-4.32 (m, 1H), 5.73 (s, 1H), 6.81-6.95 (m, 3H), 7.18-7.27 (m, 1H). MS m/z 335 (M+H)$^+$ Step 3: (2R,4S)-Methyl 2-(3-fluorobenzyl)-4-(3-oxo-2,3-dihydroisoxazol-5-yl)piperidine-1-carboxylate Cis-methyl 2-(3-fluorobenzyl)-4-(3-oxo-2,3-dihydroisoxazol-5-yl)piperidine-1-carboxylate (1.141 g, 3.42 mmol) was subjected to chiral preparative HPLC (Column: Chiralpak IC (250×20), 5 µm particle size, mobile phase: Heptane/THF 80/20, flow rate 18 mL/min) to yield (2R,4S)-methyl 2-(3-fluorobenzyl)-4-(3-oxo-2,3-dihydroisoxazol-5-yl)piperidine-1-carboxylate (545 mg, 48%), Chiral purity 99.7% ee, Optical rotation [α]$_D^{20}$=+17.8 (acetonitrile, c=1)

Step 4: 5-((2R,4S)-2-(3-Fluorobenzyl)piperidin-4-yl)isoxazol-3(2H)-one (2R,4S)-Methyl 2-(3-fluorobenzyl)-4-(3-oxo-2,3-dihydroisoxazol-5-yl)piperidine-1-carboxylate (545 mg, 1.63 mmol) was dissolved in hydrogen bromide (33% in acetic acid, 10 mL, 57.10 mmol) and the mixture stirred at room temperature for 23 h. The solvent was evaporated and the residue purified by preparative HPLC (Instrument: FractionLynx I, Mobilphase: gradient 5-95% MeCN in 0.2% NH$_3$, pH 10, Column: Xbridge Prep C18 5 µm OBD 19*150 mm) to yield 5-((2R,4S)-2-(3-fluorobenzyl)piperidin-4-yl)isoxazol-3(2H)-one (286 mg, 63.5%). $^1$H NMR (400 MHz, dmso) δ 1.09 (q, 1H), 1.36 (dq, 1H), 1.71-1.81 (m, 2H), 2.50-2.79 (m, 5H), 2.95-3.03 (m, 1H), 5.66 (s, 1H), 6.95-7.07 (m, 3H), 7.26-7.34 (m, 1H). HRMS Calculated for [C$_{15}$H$_{17}$FN$_2$O$_2$+H]$^+$: 277.1352. Found: 277.1343

Example 100

5-((2S,4S)-2-(3-Fluorobenzyl)piperidin-4-yl)isoxazol-3(2H)-one

Step 1: Trans-methyl 2-(3-fluorobenzyl)-4-(3-oxo-2,3-dihydroisoxazol-5-yl)piperidine-1-carboxylate Trans-methyl 4-(3-ethoxy-3-oxopropanoyl)-2-(3-fluorobenzyl)piperidine-1-carboxylate (0.663 g, 1.81 mmol) (from example 99, step 1) was dissolved in MeOH (8 mL) and cooled to −40° C. under nitrogen. Sodium hydroxide (0.073 g, 1.81 mmol) dissolved in water (1 mL) was added during 20 min and the yellow solution continued to stir at −40° C. for 20 min. Hydroxylamine (50% by weight in water, 0.111 mL, 1.81 mmol) was added during 5 min. The resulting solution was stirred at −40° C. for 4 h. The mixture was then rapidly poured into a prewarmed (80° C.) solution of 6 M hydrogen chloride (9 mL, 54.00 mmol) and the mixture continued to stir at 80° C. for 20 min. The solvent was evaporated and DCM/water added. The phases were separated and the organic phase passed through a phase separator and evaporated to yield a brown semi-solid. The compound was purified by preparative HPLC on a XBridge C18 column (10 µm 250×50 ID mm) using a gradient of 0-25% Acetonitrile in H2O/MeCN/NH3 95/5/0.2 buffer over 20 minutes with a flow of 100 mL/min. Trans-methyl 2-(3-fluorobenzyl)-4-(3-oxo-2,3-dihydroisoxazol-5-yl)piperidine-1-carboxylate (214 mg, 35%) was isolated. $^1$H NMR (400 MHz, cdcl$_3$) δ 1.47-1.77

(m, 2H), 1.82-2.15 (m, 2H), 2.75-3.00 (m, 2H), 3.00-3.15 (m, 2H), 3.40-3.80 (m, 3H), 4.00-4.42 (m, 1H), 4.42-4.80 (m, 1H), 5.64 (s, 1H), 6.83-7.05 (m, 3H), 7.22-7.31 (m, 1H). MS m/z 335 (M+H)$^+$

Step 2: (2S,4S)-Methyl 2-(3-fluorobenzyl)-4-(3-oxo-2,3-dihydroisoxazol-5-yl)piperidine-1-carboxylate Trans-methyl 2-(3-fluorobenzyl)-4-(3-oxo-2,3-dihydroisoxazol-5-yl)piperidine-1-carboxylate (214 mg, 0.64 mmol) was subjected to chiral preparative HPLC (Column: Chiralcel OJ (250×30), 5 μm particle size, mobile phase: 10% EtOH in CO2 (175 bar), flow rate 150 mL/min) to yield (2S,4S)-methyl 2-(3-fluorobenzyl)-4-(3-oxo-2,3-dihydroisoxazol-5-yl)piperidine-1-carboxylate 77 mg (38.5%), Chiral purity 99.6% ee, Optical rotation $[\alpha]_D^{20}$=+64.9 (acetonitrile, c=1)

Step 3: 5-((2S,4S)-2-(3-Fluorobenzyl)piperidin-4-yl)isoxazol-3(2H)-one (2S,4S)-methyl 2-(3-fluorobenzyl)-4-(3-oxo-2,3-dihydroisoxazol-5-yl)piperidine-1-carboxylate (77 mg, 0.23 mmol) was dissolved in hydrogen bromide (33% in acetic acid, 2 mL, 11.42 mmol) and the mixture stirred at room temperature overnight. The solvent was evaporated and the residue purified by preparative HPLC (Instrument: Agilent, Mobilphase: gradient 5-95% MeCN in 0.2% $NH_3$, pH 10, Column: Xbridge Prep C18 5 μm OBD 19*150 mm) to yield 5-((2S,4S)-2-(3-fluorobenzyl)piperidin-4-yl)isoxazol-3(2H)-one (51.4 mg, 81%). $^1$H NMR (400 MHz, cd$_3$od) δ 1.74-1.84 (m, 1H), 1.98-2.16 (m, 3H), 2.84-3.10 (m, 3H), 3.19-3.29 (m, 2H), 3.35-3.44 (m, 1H), 5.50 (s, 1H), 6.96-7.07 (m, 3H), 7.29-7.37 (m, 1H). HRMS Calculated for $[C_{15}H_{17}FN_2O_2+H]^+$: 277.1352. Found: 277.1357

Example 101

5-((2R,4S)-2-(2-Fluorobenzyl)piperidin-4-yl)isoxazol-3(2H)-one

Step 1: Trans-methyl 4-(3-ethoxy-3-oxopropanoyl)-2-(2-fluorobenzyl)piperidine-1-carboxylate and cis-methyl 4-(3-ethoxy-3-oxopropanoyl)-2-(2-fluorobenzyl)piperidine-1-carboxylate A suspension of magnesium chloride (2.60 g, 27.33 mmol) and ethyl potassium malonate (4.65 g, 27.33 mmol) in dry THF (80 mL) was stirred under nitrogen atmosphere at 50° C. for 2.5 h (flask 1). In another flask di(1H-imidazol-1-yl)methanone (3.69 g, 22.77 mmol) was added portionwise to a solution of 2-(2-fluorobenzyl)-1-(methoxycarbonyl)piperidine-4-carboxylic acid (4.483 g, 15.18 mmol) (reference compound 45) in dry THF (20 mL) at 0° C. under nitrogen atmosphere. The ice bath was removed and the solution was stirred for 2 h at room temperature (flask 2). The contents of flask 1 was added slowly to flask 2 and the resulting mixture was stirred for 19 h under nitrogen. The reaction mixture was concentrated and the residue was taken up in EtOAc and $H_2O$. The aqueous phase was extracted once with EtOAc and the combined organic phases were washed with $H_2O$, 10% $Na_2CO_3$ and then dried over $Na_2SO_4$. The compound was purified further via Biotage, 2 runs, SNAP 340 g KP-SIL, first 8:2 for 2 CV then linear gradient heptanes/ethyl acetate 8:2 to 3:7 over 7CV. Trans-methyl 4-(3-ethoxy-3-oxopropanoyl)-2-(2-fluorobenzyl)piperidine-1-carboxylate (1.145 g, 14%) and cis-methyl 4-(3-ethoxy-3-oxopropanoyl)-2-(2-fluorobenzyl)piperidine-1-carboxylate (3.19 g, 58%) were isolated. Cis-isomer: $^1$H NMR (400 MHz, cdcl$_3$) δ 1.20-1.30 (m, 3H), 1.63-1.99 (m, 4H), 2.63-2.76 (m, 1H), 2.77-3.13 (m, 3H), 3.46 (s, 2H), 3.53 (s, 3H), 3.85-3.99 (m, 1H), 4.17 (q, 2H), 4.22-4.32 (m, 1H), 6.93-7.08 (m, 2H), 7.09-7.22 (m, 2H). MS m/z 366 (M+H)$^+$. Trans-isomer: $^1$H NMR (400 MHz, cdcl$_3$) δ 1.19-1.32 (m, 3H), 1.39-1.99 (m, 4H), 2.52-3.12 (m, 4H), 3.37-3.71 (m, 5H), 4.18 (q, 2H), 4.02-4.32 (m, 1H), 4.48-4.71 (m, 1H), 6.94-7.24 (m, 4H). MS m/z 366 (M+H)$^+$ Step 2: Cis-methyl 2-(2-fluorobenzyl)-4-(3-oxo-2,3-dihydroisoxazol-5-yl)piperidine-1-carboxylate Cis-methyl 4-(3-ethoxy-3-oxopropanoyl)-2-(2-fluorobenzyl)piperidine-1-carboxylate (1.95 g, 5.34 mmol) was dissolved in MeOH (20 mL) and cooled to −40° C. Sodium hydroxide (0.213 g, 5.34 mmol) dissolved in water (2.000 mL) was added dropwise and the colourless solution continued to stir at −40° C. for 30 min. Hydroxylamine (50% by weight in water, 0.327 mL, 5.34 mmol) was added dropwise. The resulting solution was stirred at −40° C. for 3 h. The mixture was then rapidly poured into a prewarmed (80° C.) solution of 6 M hydrogen chloride (25 mL, 150.00 mmol) and the mixture continued to stir at 80° C. for 20 min. The solvent was evaporated and MTBE/water added. The phases were separated and the organic phase dried over $Na_2SO_4$ and evaporated to yield a slightly yellow foam. The compound was purified by preparative HPLC on a Kromasil C8 column (10 μm 250×50 ID mm) using two injections with a gradient of 15-75% Acetonitrile in H2O/MeCN/AcOH 95/5/0.2 buffer over 30 minutes with a flow of 100 mL/min. Cis-methyl 2-(2-fluorobenzyl)-4-(3-oxo-2,3-dihydroisoxazol-5-yl)piperidine-1-carboxylate (1.09 g, 61%) was isolated. $^1$H NMR (400 MHz, cdcl$_3$) δ 1.80-2.17 (m, 4H), 2.72-2.87 (m, 2H), 2.91-3.02 (m, 1H), 3.12-3.24 (m, 1H), 3.52 (s, 3H), 3.95-4.05 (m, 1H), 4.29-4.40 (m, 1H), 5.72 (s, 1H), 6.94-7.12 (m, 3H), 7.12-7.20 (m, 1H). MS m/z 335 (M+H)$^+$ Step 3: (2R,4S)-Methyl 2-(2-fluorobenzyl)-4-(3-oxo-2,3-dihydroisoxazol-5-yl)piperidine-1-carboxylate Cis-methyl 2-(2-fluorobenzyl)-4-(3-oxo-2,3-dihydroisoxazol-5-yl)piperidine-1-carboxylate (1.09 g, 3.26 mmol) was subjected to chiral preparative HPLC (Column: Chiralpak AS (250×20), 5 μm particle size, mobile phase: Heptane/EtOH 80/20, flow rate 18 mL/min) to yield (2R,4S)-methyl 2-(2-fluorobenzyl)-4-(3-oxo-2,3-dihydroisoxazol-5-yl)piperidine-1-carboxylate (492 mg, 45%), Chiral purity 98.2% ee. Optical rotation $[\alpha]_D^{20}$=−3 (acetonitrile, c=1)

Step 4: 5-((2R,4S)-2-(2-Fluorobenzyl)piperidin-4-yl)isoxazol-3(2H)-one (2R,4S)-Methyl 2-(2-fluorobenzyl)-4-(3-oxo-2,3-dihydroisoxazol-5-yl)piperidine-1-carboxylate (492 mg, 1.47 mmol) was stirred in hydrogen bromide (33% in AcOH) overnight (19 h). Evaporation of solvents and purification by preparative HPLC (Instrument: FractionLynx I, Mobilphase: gradient 5-95% MeCN in 0.2% $NH_3$, pH 10, Column: Xbridge Prep C18 5 μm OBD 19*150 mm) yielded 5-((2R,4S)-2-(2-fluorobenzyl)piperidin-4-yl)isoxazol-3(2H)-one (504 mg, 124%). The sample contained DMSO and acetic acid. $^1$H NMR (400 MHz, cd$_3$od) δ 1.50-1.65 (m, 1H), 1.69-1.84 (m, 1H), 2.08-2.22 (m, 2H), 2.89-3.18 (m, 4H), 3.38-3.51 (m, 2H), 5.66 (s, 1H), 7.11-7.23 (m, 2H), 7.28-7.41 (m, 2H). HRMS Calcd for $[C_{15}H_{17}FN_2O_2+H]+$: 277.1352. Found: 277.1344.

Example 102

5-((2S,4S)-2-(2-Fluorobenzyl)piperidin-4-yl)isoxazol-3(2H)-one

Step 1: Trans-methyl 2-(2-fluorobenzyl)-4-(3-oxo-2,3-dihydroisoxazol-5-yl)piperidine-1-carboxylate Trans-methyl 4-(3-ethoxy-3-oxopropanoyl)-2-(2-fluorobenzyl)piperidine-1-carboxylate (1.145 g, 3.13 mmol) (from example 101, step 1) was dissolved in methanol (10 mL) and cooled to −40° C. Sodium hydroxide (0.194 g, 4.84 mmol) dissolved in water (1.000 mL) was added dropwise and continued to stir at −40° C. for 30 min. Hydroxylamine (50% by weight in water, 0.192 mL, 3.13 mmol) was added dropwise. The resulting solution was stirred at −40° C. for 2 h. The mixture was then rapidly poured into a prewarmed (80° C.) solution of 6 M hydrogen chloride (15 mL, 90.00 mmol) and the mixture continued to stir at 80° C. for 55 min. The solvent was evaporated and MTBE/water added. The phases were separated and the organic phase dried over $Na_2SO_4$ and evaporated to a yellow foam. The compound was purified by preparative HPLC on a Kromasil C8 column (10 μm 250×50 ID mm) with a gradient of 15-75% Acetonitrile in H2O/MeCN/AcOH 95/5/0.2 buffer over 30 minutes with a flow of 100 mL/min. Trans-methyl 2-(2-fluorobenzyl)-4-(3-oxo-2,3-dihydroisoxazol-5-yl)-piperidine-1-carboxylate (468 mg, 45%) was isolated. $^1$H NMR (400 MHz, cdcl$_3$) δ 1.46-1.77 (m, 2H), 1.80-2.13 (m, 2H), 2.28-3.23 (m, 4H), 3.38-3.80 (m, 3H), 4.04-4.34 (m, 1H), 4.50-4.80 (m, 1H), 5.65 (s, 1H), 6.99-7.12 (m, 2H), 7.12-7.30 (m, 2H). MS m/z 335 (M+H)$^+$

Step 2: (2S,4S)-Methyl 2-(2-fluorobenzyl)-4-(3-oxo-2,3-dihydroisoxazol-5-yl)piperidine-1-carboxylate and (2R,4R)-methyl 2-(2-fluorobenzyl)-4-(3-oxo-2,3-dihydroisoxazol-5-yl)piperidine-1-carboxylate Trans-methyl 2-(2-fluorobenzyl)-4-(3-oxo-2,3-dihydroisoxazol-5-yl)piperidine-1-carboxylate (468 mg, 1.4 mmol) was subjected to chiral preparative HPLC (Column: Chiralcel OJ (250×30), 5 μm particle size, mobile phase: 20% EtOH in $CO_2$ (175 bar), flow rate 130 mL/min, temperature 40° C.) to yield (2S,4S)-methyl 2-(2-fluorobenzyl)-4-(3-oxo-2,3-dihydroisoxazol-5-yl)piperidine-1-carboxylate (199 mg, 43%), Chiral purity 98.5% ee, Optical rotation $[\alpha]_D^{20}$=+28.8 (acetonitrile, c=1) and (2R,4R)-methyl 2-(2-fluorobenzyl)-4-(3-oxo-2,3-dihydroisoxazol-5-yl)piperidine-1-carboxylate (185 mg, 40%), Chiral purity 99.7% ee, Optical rotation $[\alpha]_D^{20}$=−28.9 (acetonitrile, c=1)

Step 3: 5-((2S,4S)-2-(2-Fluorobenzyl)piperidin-4-yl)isoxazol-3(2H)-one (2S,4S)-Methyl 2-(2-fluorobenzyl)-4-(3-oxo-2,3-dihydroisoxazol-5-yl)piperidine-1-carboxylate (199 mg, 0.60 mmol) was stirred in hydrogen bromide (33% in AcOH) overnight (17 h). Evaporation of solvents and purification by preparative HPLC (Instrument: FractionLynx I, Mobilphase: gradient 5-95% MeCN in 0.2% NH$_3$, pH 10, Column: Xbridge Prep C18 5 μm OBD 19*150 mm) yielded 5-((2S,4S)-2-(2-fluorobenzyl)piperidin-4-yl)isoxazol-3(2H)-one (115 mg, 70%). $^1$H NMR (600 MHz, DMSO) δ 1.47-1.56 (m, 1H), 1.67-1.81 (m, 3H), 2.57-2.64 (m, 1H), 2.72 (d, 2H), 2.81-2.87 (m, 1H), 2.87-2.95 (m, 1H), 3.12-3.18 (m, 1H), 5.70 (s, 1H), 7.09-7.18 (m, 2H), 7.22-7.33 (m, 2H). HRMS Calcd for $[C_{15}H_{17}FN_2O_2+H]+$: 277.1352. Found: 277.1352.

Example 103

5-((2R,4R)-2-(2-Fluorobenzyl)piperidin-4-yl)isoxazol-3(2H)-one (2R,4R)-Methyl 2-(2-fluorobenzyl)-4-(3-oxo-2,3-dihydroisoxazol-5-yl)piperidine-1-carboxylate (185 mg, 0.55 mmol) (from example 102, step 2) was stirred in hydrogen bromide (33% in AcOH) overnight (17 h). Evaporation of solvents and purification by preparative HPLC (Instrument: FractionLynx I, Mobilphase: gradient 5-95% MeCN in 0.2% NH3, pH10, Column: Xbridge Prep C18 5 μm OBD 19*150 mm) yielded 5-((2R,4R)-2-(2-fluorobenzyl)-piperidin-4-yl)isoxazol-3(2H)-one (75 mg, 49%). $^1$H NMR (600 MHz, DMSO) δ 1.48-1.55 (m, 1H), 1.68-1.80 (m, 3H), 2.58-2.64 (m, 1H), 2.72 (d, 2H), 2.81-2.87 (m, 1H), 2.87-2.94 (m, 1H), 3.12-3.17 (m, 1H), 5.70 (s, 1H), 7.11-7.17 (m, 2H), 7.24-7.31 (m, 2H). HRMS Calcd for $[C_{15}H_{17}FN_2O_2+H]+$: 277.1352. Found: 277.1357.

Example 104

5-((2R,4S)-2-(4-(Trifluoromethyl)benzyl)piperidin-4-yl)isoxazol-3(2H)-one

Step 1: Cis-methyl 4-(3-ethoxy-3-oxopropanoyl)-2-(4-(trifluoromethyl)benzyl)piperidine-1-carboxylate Magnesium chloride (7.39 g, 77.58 mmol) and potassium 3-ethoxy-3-oxopropanoate (13.20 g, 77.58 mmol) were suspended in methyl THF (100 mL) under nitrogen and the resulting suspension heated to 50° C. while stirring with an oversized stirring bar for 4 h, then cooled to room temperature (flask 1). In a separate flask was added to cis-1-(methoxycarbonyl)-2-(4-(trifluoromethyl)benzyl)piperidine-4-carboxylic acid (14.1 g, 40.83 mmol) (reference compound 46) in methyl THF (100 mL) di(1H-imidazol-1-yl)methanone (10 g, 61.67 mmol) under nitrogen. The resulting mixture was stirred at room temperature for 4 h 30 min (flask 2). Then, the contents of flask 2 is transferred into flask 1 by transfer needle, washed with methyl THF (40 mL). The resulting suspension was stirred at room temperature for 19 h 30 min. Additional magnesium chloride (3.7 g, 38.86 mmol) and potassium 3-ethoxy-3-oxopropanoate (6.6 g, 38.78 mmol) in methyl THF (50 mL) were sonicated at 50° C. for 2 h 30 min, then added to the reaction mixture. Stirred at room temperature for 21 h. The reaction mixture was partitioned between 2 M HCl (ca. 150 mL) and MTBE. The phases were separated. The organic phase was washed with brine and satd NaHCO$_3$, then dried over MgSO$_4$ and evaporated. Crude cis-methyl 4-(3-ethoxy-3-oxopropanoyl)-2-(4-(trifluoromethyl)benzyl)piperidine-1-carboxylate (14.9 g, 88%) was isolated. $^1$H NMR (400 MHz, cdcl$_3$) δ 1.21-1.30 (m, 3H), 1.63-2.04 (m, 4H), 2.67-2.86 (m, 2H), 2.93-3.09 (m, 2H), 3.46 (s, 2H), 3.60 (s, 3H), 3.85-3.98 (m, 1H), 4.11-4.26 (m, 3H), 7.30 (d, 2H), 7.53 (d, 2H). MS m/z 416 (M+H)$^+$

Step 2: Cis-methyl 4-(3-oxo-2,3-dihydroisoxazol-5-yl)-2-(4-(trifluoromethyl)benzyl)-piperidine-1-carboxylate Cis-methyl 4-(3-ethoxy-3-oxopropanoyl)-2-(4-(trifluoromethyl)benzyl)piperidine-1-carboxylate (14.9 g, 35.87 mmol) was dissolved in MeOH (120 mL) and cooled to −40° C. Sodium hydroxide (1.495 g, 37.38 mmol) dissolved in water (14.4 mL) was added over 2 min and the resulting solution stirred at −40° C. for 20 min. Then hydroxylamine (50% by weight in water, 2.2 mL, 35.90 mmol) was added over 1 min and stirring continued between −40° C. and −45° C. for 80 min. The reaction mixture was then poured into a prewarmed (80° C.) solution of 6 M hydrogen chloride (400 mL, 2400.00 mmol) and the mixture was continued to be stirred at 80° C. for 1 h. Then cooled to room temperature. Methanol was evaporated, then water was added. Extracted three times with DCM. Combined organic layers dried over $Na_2SO_4$ and evaporated. Crude cis-methyl 4-(3-oxo-2,3-dihydroisoxazol-5-yl)-2-(4-(trifluoromethyl)benzyl)piperidine-1-carboxylate (12.88 g, 94%) was isolated. MS m/z 385 (M+H)$^+$ Step 3: (2R,4S)-Methyl 4-(3-oxo-2,3-dihydroisoxazol-5-yl)-2-(4-(trifluoromethyl)benzyl)-piperidine-1-carboxylate Crude cis-methyl 4-(3-oxo-2,3-dihydroisoxazol-5-yl)-2-(4-(trifluoromethyl)benzyl)-piperidine-1-carboxylate (12.88 g, 33.54 mmol) was purified by preparative HPLC (Column: Kromasil-C18 (250×20), 10 µm particle size, mobile phase: MeCN/H2O/FA 50/50/0.1, flow rate 120 mL/min) to yield pure cis-methyl 4-(3-oxo-2,3-dihydroisoxazol-5-yl)-2-(4-(trifluoromethyl)benzyl)piperidine-1-carboxylate (8.7 g) which was then separated using chiral preparative HPLC (Column: Chiralpak AD (250×20), 5 µm particle size, mobile phase: Heptane/EtOH/DEA 85/15, flow rate 18 mL/min) to yield (2R,4S)-methyl 4-(3-oxo-2,3-dihydroisoxazol-5-yl)-2-(4-(trifluoromethyl)benzyl)piperidine-1-carboxylate (3.90 g, 30%), chiral purity 98.5% ee, Optical rotation $[\alpha]_D^{20}$=+11.9 (acetonitrile, c=1), $^1$H NMR (400 MHz, cdcl$_3$) δ 1.86-2.01 (m, 3H), 2.03-2.15 (m, 1H), 2.67 (dd, 1H), 2.85 (dd, 1H), 2.96-3.05 (m, 1H), 3.12-3.22 (m, 1H), 3.59 (s, 3H), 3.97-4.07 (m, 1H), 4.26-4.34 (m, 1H), 5.75 (s, 1H), 7.22 (d, 2H), 7.52 (d, 2H).

Step 4: 5-((2R,4S)-2-(4-(Trifluoromethyl)benzyl) piperidin-4-yl)isoxazol-3(2H)-one (2R,4S)-Methyl 4-(3-oxo-2,3-dihydroisoxazol-5-yl)-2-(4-(trifluoromethyl)benzyl)piperidine-1-carboxylate (4.889 g, 12.72 mmol) was dissolved in hydrogen bromide (33% in AcOH, 30 mL, 428.24 mmol) and stirred at room temperature for 18 h. The compound was purified by preparative HPLC (2 equal injections) on a XBridge C18 column (10 µm 250×50 ID mm) using a gradient of 05-40% Acetonitrile in H2O/MeCN/NH3 95/5/0.2 buffer over 20 minutes with a flow of 100 mL/min. The product containing fractions were freeze dried and again treated with hydrogen bromide as described above. The compound was purified by preparative HPLC (3 equal injections) on a XBridge C18 column (10 µm 250×50 ID mm) using a gradient of 05-40% Acetonitrile in H2O/MeCN/NH3 95/5/0.2 buffer over 20 minutes with a flow of 100 mL/min. 5-((2R,4S)-2-(4-(Trifluoromethyl)benzyl)piperidin-4-yl)isoxazol-3(2H)-one (3.34 g, 80%) was isolated as a colorless solid. $^1$H NMR (400 MHz, dmso) δ 1.04-1.15 (m, 1H), 1.35 (qd, 1H), 1.72-1.80 (m, 2H), 2.49-2.58 (m, 1H), 2.61-2.81 (m, 4H), 2.94-3.02 (m, 1H), 5.66 (s, 1H), 7.42 (d, 2H), 7.62 (d, 2H). HRMS Calcd for $[C_{16}H_{17}F_3N_2O_2+H]^+$: 327.1320. Found: 327.1305.

Example 105

5-((2S,4S)-2-(4-(Trifluoromethyl)benzyl)piperidin-4-yl)isoxazol-3(2H)-one

Step 1: Trans-methyl 4-(3-ethoxy-3-oxopropanoyl)-2-(4-(trifluoromethyl)benzyl)piperidine-1-carboxylate Ethyl potassium malonate (1.065 g, 6.26 mmol) and MgCl$_2$ (0.496 g, 5.21 mmol) were added to dry THF (50 mL). The reaction mixture was stirred vigorously for 4 h at 50° C. (flask 1). 1-(Methoxycarbonyl)-2-(4-(trifluoromethyl)benzyl)piperidine-4-carboxylic acid (1.8 g, 5.21 mmol) (reference compound 47) and carbonyldiimidazole (1.268 g, 7.82 mmol) were added to dry THF (50 ml) at 5° C. (flask 2). The contents of flask 2 was added to flask 1 and the resulting suspension was stirred at room temperature overnight. THF was evaporated and the reaction mixture was partitioned between water and diethyl ether. The organic phase was isolated, dried with $Na_2SO_4$, filtered through celite and the solvent was evaporated. Chromatography using the Biotage equipment. Gradient eluation using ethylacetate-heptane, started 15-85 and ended 40-60. Trans-methyl 4-(3-ethoxy-3-oxopropanoyl)-2-(4-(trifluoromethyl)benzyl)piperidine-1-carboxylate (0.93 g, 42.9%) was isolated. $^1$H NMR (600 MHz, cdcl$_3$) δ 1.20-1.29 (m, 3H), 1.46-1.99 (m, 4H), 2.74-3.04 (m, 4H), 3.34-3.70 (m, 5H), 4.01-4.32 (m, 3H), 4.60 (d, 1H), 7.22-7.38 (m, 2H), 7.51-7.56 (m, 2H). MS m/z 416 (M+H)$^+$ Step 2: Trans-methyl 4-(3-oxo-2,3-dihydroisoxazol-5-yl)-2-(4-(trifluoromethyl)benzyl)-piperidine-1-carboxylate A solution of trans-methyl 4-(3-ethoxy-3-oxopropanoyl)-2-(4-(trifluoromethyl)benzyl)-piperidine-1-carboxylate (0.4 g, 0.96 mmol) in methanol (3 mL) was added dropwise to a solution of NaOH (0.042 g, 1.06 mmol) in methanol/water (3 mL/0.2 mL) at −30° C. After stirring for 10 min a solution of hydroxylamine hydrochloride (0.134 g, 1.93 mmol) and NaOH (0.077 g, 1.93 mmol) in methanol/water (5 mL/5 mL) was added at −30° C. Stirring was continued for 30 min at −30° C. The solution was added dropwise to 6 M HCl at 80° C. Stirred 30 min at 80° C. The reaction mixture was dissolved between water and ethyl acetate. The organic phase was isolated, dried with $Na_2SO_4$, filtered through celite and the solvent was evaporated. Acidic reversed phase chromatography, gradient 35% to 75% acetonitrile. Trans-methyl 4-(3-oxo-2,3-dihydroisoxazol-5-yl)-2-(4-(trifluoromethyl) benzyl)piperidine-1-carboxylate (205 mg, 55.4%) was isolated. $^1$H NMR (600 MHz, cdcl$_3$) δ 1.63 (d, 2H), 1.98 (d, 2H), 2.81-3.14 (m, 4H), 3.55 (d, 3H), 4.21 (d, 1H), 4.63 (d, 1H), 5.63 (s, 1H), 7.22-7.37 (m, 2H), 7.54 (d, 2H). MS m/z 385 (M+H)$^+$ Step 3: (2S,4S)-Methyl 4-(3-oxo-2,3-dihydroisoxazol-5-yl)-2-(4-(trifluoromethyl)benzyl)-piperidine-1-carboxylate and (2R,4R)-methyl 4-(3-oxo-2,3-dihydroisoxazol-5-yl)-2-(4-(trifluoromethyl)benzyl) piperidine-1-carboxylate Trans-methyl 4-(3-oxo-2,3-dihydroisoxazol-5-yl)-2-(4-(trifluoromethyl)benzyl)piperidine-1-carboxylate (205 mg, 0.53 mmol) was subjected to chiral preparative HPLC (Column: Chiralpak IC (250×20), 5 µm particle size, mobile phase: Heptane/EtOH/FA 90/10/0.1, flow rate 18 mL/min) to yield (2S,4S)-methyl 4-(3-oxo-2,3-dihydroisoxazol-5-yl)-2-(4-(trifluoromethyl)benzyl)piperidine-1-carboxylate (77 mg, 38.5%), chiral purity 99.3% ee, Optical rotation $[\alpha]_D^{20}$=+34.6 (acetonitrile, c=1) and (2R,4R)-methyl 4-(3-oxo-2,3-dihydroisoxazol-5-yl)-2-(4-(trifluoromethyl)benzyl)piperidine-1-carboxylate (87 mg, 43.5%), chiral purity 99.9% ee, Optical rotation $[\alpha]_D^{20}$−30.2 (acetonitrile, c=1)

Step 4: 5-((2S,4S)-2-(4-(Trifluoromethyl)benzyl) piperidin-4-yl)isoxazol-3(2H)-one Hydrogen bromide (33% in acetic acid, 5 mL) was added to a reaction flask containing (2S,4S)-methyl 4-(3-oxo-2,3-dihydroisoxazol-5-yl)-2-(4-(trifluoromethyl)benzyl)piperidine-1-carboxylate (77 mg, 0.20 mmol). The reaction was stirred vigorously overnight. The solvent was evaporated. Purification using PrepLC (pH=11, small column, sample dissolved in MeOH, gradient 5-45, 20 min) yielded 5-((2S,4S)-2-(4-(trifluoromethyl)benzyl)piperidin-4-yl)isoxazol-3(2H)-one (50 mg, 76%). $^1$H NMR (600 MHz, cd$_3$od) δ 1.73-1.79 (m, 1H), 1.98-2.12 (m, 3H), 2.93 (dd, 1H), 2.97-3.04 (m, 2H), 3.17-3.25 (m, 2H), 3.35-3.41 (m, 1H), 5.48 (s, 1H), 7.41 (d, 2H), 7.61 (d, 2H). HRMS Calcd for [C$_{16}$H$_{17}$F$_3$N$_2$O$_2$+H]$^+$: 327.1320. Found: 327.1289.

Example 106

5-((2R,4R)-2-(4-(Trifluoromethyl)benzyl)piperidin-4-yl)isoxazol-3(2H)-one

Hydrogen bromide (33% in acetic acid, 5 mL) was added to a reaction flask containing (2R,4R)-methyl 4-(3-oxo-2,3-dihydroisoxazol-5-yl)-2-(4-(trifluoromethyl)benzyl)piperidine-1-carboxylate (87 mg, 0.23 mmol). The reaction was stirred vigorously overnight. The solvent was evaporated. Purification using PrepLC (pH=11, small column, sample dissolved in MeOH, gradient 5-45, 20 min) yielded 5-((2R,4R)-2-(4-(trifluoromethyl)benzyl)piperidin-4-yl)isoxazol-3(2H)-one (48 mg, 65%). $^1$H NMR (600 MHz, cd$_3$od) δ 1.74-1.80 (m, 1H), 1.99-2.13 (m, 3H), 2.94 (dd, 1H), 2.98-3.05 (m, 2H), 3.19-3.26 (m, 2H), 3.36-3.42 (m, 1H), 5.50 (s, 1H), 7.42 (d, 2H), 7.62 (d, 2H). HRMS Calcd for [C$_{16}$H$_{17}$F$_3$N$_2$O$_2$+H]$^+$: 327.1320. Found: 327.1289.

Example 107

5-((2R,4S)-2-(3-(Trifluoromethyl)benzyl)piperidin-4-yl)isoxazol-3(2H)-one

Step 1: Trans-methyl 4-(3-ethoxy-3-oxopropanoyl)-2-(3-(trifluoromethyl)benzyl)piperidine-1-carboxylate and cis-methyl 4-(3-ethoxy-3-oxopropanoyl)-2-(3-(trifluoromethyl)benzyl)-piperidine-1-carboxylate Ethyl potassium malonate (3.42 g, 20.16 mmol) and MgCl$_2$ (1.599 g, 16.80 mmol) were added to dry THF (50 ml). The reaction flask was stirred vigorously overnight at 50° C. (flask 1). 1-(Methoxycarbonyl)-2-(3-(trifluoromethyl)benzyl)piperidine-4-carboxylic acid (5.8 g, 16.80 mmol) (reference compound 48) and carbonyldiimidazole (4.09 g, 25.19 mmol) were added to dry THF (50 mL) at 5° C. and was stirred overnight at room temperature (flask 2). The contents of flask 2 was added to flask 1 at room temperature and stirred for 3 days. The reaction mixture was dissolved between water and diethyl ether. The organic phase was evaporated to remove most of the THF. Dissolved the crude between water and diethyl ether again. The organic phase was isolated, dried with Na$_2$SO$_4$, filtered through celite and the solvent was evaporated. Chromatography using the Biotage equipment. Gradient elution using ethyl acetate-heptane, started 0-100 and ended 100-0. Trans-methyl 4-(3-ethoxy-3-oxopropanoyl)-2-(3-(trifluoromethyl)benzyl)piperidine-1-carboxylate (1.8 g, 26%) and cis-methyl 4-(3-ethoxy-3-oxopropanoyl)-2-(3-(trifluoromethyl)benzyl)piperidine-1-carboxylate (2.45 g, 35%) were isolated. Cis-isomer: $^1$H NMR (400 MHz, cdcl$_3$) δ 1.20-1.32 (m, 3H), 1.63-1.99 (m, 4H), 2.67-2.86 (m, 2H), 2.92-3.12 (m, 2H), 3.47 (s, 2H), 3.59 (s, 3H), 3.89-4.00 (m, 1H), 4.09-4.29 (m, 1H), 7.32-7.51 (m, 4H). MS m/z 416 (M+H)$^+$. Trans-isomer: $^1$H NMR (400 MHz, cdcl$_3$) δ 1.19-1.35 (m, 3H), 1.42-2.08 (m, 4H), 2.51-3.09 (m, 4H), 3.35-3.78 (m, 5H), 4.04-4.38 (m, 3H), 4.47-4.79 (m, 1H), 7.23-7.56 (m, 4H). MS m/z 416 (M+H)$^+$ Step 2: Cis-methyl 4-(3-oxo-2,3-dihydroisoxazol-5-yl)-2-(3-(trifluoromethyl)benzyl)-piperidine-1-carboxylate A solution of Cis-methyl 4-(3-ethoxy-3-oxopropanoyl)-2-(3-(trifluoromethyl)benzyl)-piperidine-1-carboxylate (2.45 g, 5.90 mmol) in MeOH (7 mL) was added to a solution of NaOH (307 mg, 7.67 mmol) in MeOH/H2O (8 ml/0.5 mL) at −30° C. After 10 min hydroxylamine hydrochloride (0.82 g, 11.80 mmol) and NaOH (472 mg, 11.80 mmol) were added in MeOH (8 mL) and H$_2$O (8 mL). Stirring was continued at −30° C. for 30 min. The reaction solution was poured into 6 M HCl 60 mL) at 80° C. and heated for 30 min. The reaction mixture was dissolved between water and ethyl acetate. The organic phase was isolated, dried with Na$_2$SO$_4$, filtered through celite and the solvent was evaporated. Purification using prepLC (pH=3, large column 40-55% MeCN over 20 min) Cis-methyl 4-(3-oxo-2,3-dihydroisoxazol-5-yl)-2-(3-(trifluoromethyl)benzyl)piperidine-1-carboxylate (1.27 g, 56%) was isolated. $^1$H NMR (400 MHz, cdcl$_3$) δ 1.86-2.15 (m, 4H), 2.68 (dd, 1H), 2.86 (dd, 1H), 2.96-3.06 (m, 1H), 3.12-3.25 (m, 1H), 3.58 (s, 3H), 3.95-4.08 (m, 1H), 4.25-4.37 (m, 1H), 5.75 (s, 1H), 7.23-7.32 (m, 1H), 7.35-7.41 (m, 2H), 7.43-4.49 (m, 1H). MS m/z 385 (M+H)$^+$ Step 3: (2R,4S)-Methyl 4-(3-oxo-2,3-dihydroisoxazol-5-yl)-2-(3-(trifluoromethyl)benzyl)-piperidine-1-carboxylate and (2S,4R)-Methyl 4-(3-oxo-2,3-dihydroisoxazol-5-yl)-2-(3-(trifluoromethyl)benzyl)piperidine-1-carboxylate Cis-methyl 4-(3-oxo-2,3-dihydroisoxazol-5-yl)-2-(3-(trifluoromethyl)benzyl)piperidine-1-carboxylate (1.27 g, 3.31 mmol) was subjected to chiral preparative HPLC (Column: Chiralpak AD (250×20), 5 µm particle size, mobile phase: Heptane/IPA/FA 90/10/0.1, flow rate 18 mL/min) to yield (2R,4S)-methyl 4-(3-oxo-2,3-dihydroisoxazol-5-yl)-2-(3-(trifluoromethyl)benzyl)piperidine-1-carboxylate (620 mg, 49%), Chiral purity 99.7% ee, Optical rotation [α]$_D^{20}$=+7.3 (acetonitrile, c=1) and (2S,4R)-methyl 4-(3-oxo-2,3-dihydroisoxazol-5-yl)-2-(3-(trifluoromethyl)benzyl)piperidine-1-carboxylate (640 mg, 50%), Chiral purity 99.3% ee, Optical rotation [α]$_D^{20}$=−6.3 (acetonitrile, c=1)

Step 4: 5-((2R,4S)-2-(3-(Trifluoromethyl)benzyl)piperidin-4-yl)isoxazol-3(2H)-one (2R,4S)-Methyl 4-(3-oxo-2,3-dihydroisoxazol-5-yl)-2-(3-(trifluoromethyl)benzyl)piperidine-1-carboxylate (0.62 g, 1.61 mmol) was dissolved in hydrogen bromide (33% in acetic acid, 5 mL, 71.37 mmol) and stirred at room temperature for 41 h. Reaction mixture was evaporated and restarted under the same conditions. After 28 h solvents evaporated and the residue purified by preparative HPLC. (Instrument: FractionLynx I, Mobilphase: gradient 5-95% MeCN in 0.2% NH$_3$, pH10, Column: Xbridge Prep C18 5 µm OBD 19*150 mm) to yield 5-((2R,4S)-2-(3-(trifluoromethyl)benzyl)piperidin-4-yl)isoxazol-3(2H)-one (366 mg, 69%). $^1$H NMR (600 MHz, DMSO) δ 1.07-1.17 (m, 1H), 1.32-1.41 (m, 1H), 1.73-1.81 (m, 2H), 2.48-2.58 (m, 1H), 2.63-2.79 (m, 4H), 2.96-3.02 (m, 1H), 5.67 (s, 1H), 7.50-7.60 (m, 4H). HRMS Calculated for [C$_{16}$H$_{17}$F$_3$N$_2$O$_2$+H]$^+$: 327.1320. Found: 327.1328

Example 108

5-((2S,4R)-2-(3-(Trifluoromethyl)benzyl)piperidin-4-yl)isoxazol-3(2H)-one (2S,4R)-Methyl 4-(3-oxo-2,3-dihydroisoxazol-5-yl)-2-(3-(trifluoromethyl)benzyl)piperidine-1-carboxylate (0.64 g, 1.67 mmol) (from example 107, step 3) was dissolved in hydrogen bromide (33% in acetic acid, 5 mL, 71.37 mmol) and stirred at room temperature for 41 h. Reaction mixture was evaporated and restarted under the same conditions. After 28 h solvents evaporated and the residue purified by preparative HPLC (Instrument: FractionLynx I, Mobilphase: gradient 5-95% MeCN in 0.2% $NH_3$, pH10, Column: Xbridge Prep C18 5 μm OBD 19*150 mm) to yield 5-((2S,4R)-2-(3-(trifluoromethyl)benzyl)piperidin-4-yl)isoxazol-3(2H)-one (368 mg, 68%). $^1$H NMR (600 MHz, DMSO) δ 1.07-1.15 (m, 1H), 1.36 (dq, 1H), 1.74-1.80 (m, 2H), 2.54-2.58 (m, 1H), 2.64-2.79 (m, 4H), 2.96-3.01 (m, 1H), 5.66 (s, 1H), 7.50-7.59 (m, 4H). HRMS Calculated for $[C_{16}H_{17}F_3N_2O_2+H]^+$: 327.1320. Found: 327.1333

Example 109

5-(Trans-2-(3-(trifluoromethyl)benzyl)piperidin-4-yl)isoxazol-3(2H)-one

Step 1: Trans-methyl 4-(3-oxo-2,3-dihydroisoxazol-5-yl)-2-(3-(trifluoromethyl)benzyl)-piperidine-1-carboxylate A solution of trans-methyl 4-(3-ethoxy-3-oxopropanoyl)-2-(3-(trifluoromethyl)benzyl)-piperidine-1-carboxylate (1.8 g, 4.33 mmol) (from example 107, step 1) in MeOH (7 mL) was added to a solution of NaOH (225 mg, 5.63 mmol) in MeOH/H2O (8 mL/0.5 mL) at −30° C. After 10 min hydroxylamine hydrochloride (0.602 g, 8.67 mmol) and NaOH (347 mg, 8.67 mmol) were added in MeOH (7 mL) and $H_2O$ (7 mL). Stirring was continued at −30° C. for 30 min. The reaction solution was poured into 6 M HCl (60 mL) at 80° C. and heated for 30 min. The reaction mixture was dissolved between water and ethyl acetate. The organic phase was isolated, dried with $Na_2SO_4$, filtered through celite and the solvent was evaporated. Purification using prepLC (pH=3, large column 25-55% MeCN over 20 min) Trans-methyl 4-(3-oxo-2,3-dihydroisoxazol-5-yl)-2-(3-(trifluoromethyl)benzyl)piperidine-1-carboxylate (1.06 g, 63.6%) was isolated. $^1$H NMR (400 MHz, cdcl₃) δ 1.49-2.17 (m, 4H), 2.80-3.22 (m, 4H), 3.34-3.76 (m, 3H), 4.07-4.40 (m, 1H), 4.52-4.84 (m, 1H), 5.65 (s, 1H), 7.28-7.54 (m, 4H). MS m/z 385 (M+H)$^+$

Step 2: 5-(Trans-2-(3-(trifluoromethyl)benzyl)piperidin-4-yl)isoxazol-3(2H)-one Hydrogen bromide (33% in acetic acid, 10 mL) was added to a reaction flask containing trans-methyl 4-(3-oxo-2,3-dihydroisoxazol-5-yl)-2-(3-(trifluoromethyl)benzyl)piperidine-1-carboxylate (0.25 g, 0.65 mmol). The reaction was stirred vigorously overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(trans-2-(3-(trifluoromethyl)benzyl)piperidin-4-yl)isoxazol-3(2H)-one (91 mg, 43%). $^1$H NMR (600 MHz, cd₃od) δ 1.94-2.05 (m, 1H), 2.11-2.30 (m, 3H), 3.09-3.26 (m, 3H), 3.37-3.47 (m, 2H), 3.58-3.66 (m, 1H), 5.83 (s, 1H), 7.53-7.67 (m, 4H). HRMS Calculated for $[C_{16}H_{17}F_3N_2O_2+H]^+$: 327.1320. Found: 327.1322

Example 110

5-((2R,4S)-2-(2-(Trifluoromethyl)benzyl)piperidin-4-yl)isoxazol-3(2H)-one

Step 1: Trans-methyl 4-(3-ethoxy-3-oxopropanoyl)-2-(2-(trifluoromethyl)benzyl)piperidine-1-carboxylate and cis-methyl 4-(3-ethoxy-3-oxopropanoyl)-2-(2-(trifluoromethyl)benzyl)-piperidine-1-carboxylate 1-(Methoxycarbonyl)-2-(2-(trifluoromethyl)benzyl)piperidine-4-carboxylic acid (4.718 g, 13.66 mmol) (reference compound 49) was dissolved in methyl THF (100 mL) and di(1H-imidazol-1-yl)methanone (3.32 g, 20.49 mmol) added. The suspension was stirred at room temperature under nitrogen overnight (flask 1). In a separate flask potassium 3-ethoxy-3-oxopropanoate (4.19 g, 24.59 mmol) was suspended in methyl THF (100 mL) and magnesium chloride (2.342 g, 24.59 mmol) added. The suspension was stirred at 50° C. under nitrogen overnight using an oversized stirring bar (flask 2). The yellow suspension in flask 1 was now added to the white suspension in flask 2. The resulting white suspension was stirred under nitrogen at room temperature for 3 days. The mixture was acidified to pH 1 with 3.8 M HCl and MTBE and water added. The phases were separated and the organic phase washed with water and satd $NaHCO_3$. Evaporated the solvents to yield a yellow oil. The diastereomers were separated in 2 runs on Biotage (20%=>50% EtOAc in heptane, 8 CV; Biotage® KP-SIL 340 g column). Trans-methyl 4-(3-ethoxy-3-oxopropanoyl)-2-(2-(trifluoromethyl)-benzyl)piperidine-1-carboxylate (0.67 g, 12%) and cis-methyl 4-(3-ethoxy-3-oxopropanoyl)-2-(2-(trifluoromethyl)benzyl)piperidine-1-carboxylate (2.11 g, 37%) were isolated as yellow oils. Cis-isomer: $^1$H NMR (600 MHz, cdcl₃) δ 1.22 (t, 3H), 1.65-1.99 (m, 4H), 2.65-2.73 (m, 1H), 2.85-2.91 (m, 1H), 2.95-3.02 (m, 1H), 3.15 (ddd, 1H), 3.35 (s, 3H), 3.46 (s, 2H), 4.01 (dd, 1H), 4.12-4.19 (m, 2H), 4.23-4.33 (m, 1H), 7.20 (d, 1H), 7.27 (t, 1H), 7.41 (t, 1H), 7.60 (d, 1H). MS m/z 416 (M+H)$^+$. Trans-isomer: $^1$H NMR (600 MHz, cdcl₃) δ 1.13-1.27 (m, 3H), 1.41-1.97 (m, 5H), 2.79-3.67 (m, 8H), 4.01-4.33 (m, 3H), 4.64 (br. d, 1H), 7.07-7.50 (m, 3H), 7.53-7.62 (m, 1H). MS m/z 416 (M+H)$^+$

Step 2: Cis-methyl 4-(3-oxo-2,3-dihydroisoxazol-5-yl)-2-(2-(trifluoromethyl)benzyl)-piperidine-1-carboxylate Cis-methyl 4-(3-ethoxy-3-oxopropanoyl)-2-(2-(trifluoromethyl)benzyl)piperidine-1-carboxylate (2.062 g, 4.96 mmol) was dissolved in MeOH (16 mL) and cooled to −40° C. under nitrogen. Sodium hydroxide (0.199 g, 4.96 mmol) dissolved in water (1.600 mL) was added during 10 min and the colourless solution continued to stir at −40° C. for 20 min. Hydroxylamine (50% by weight in water, 0.304 mL, 4.96 mmol) was added during 8 min. The resulting solution was stirred at −40° C. for 3.5 h. The mixture was then transferred into a prewarmed (80° C.) solution of 6 M hydrogen chloride (25 mL, 150.00 mmol) and the mixture continued to stir at 80° C. for 20 min. DCM and water were added. The phases were separated and the organic phase passed through a phase separator and evaporated to yield a yellow semi-solid. The compound was purified by preparative HPLC in 3 injections on a XBridge C18 column (10 μm 250×50 ID mm) using a gradient of 5-30% Acetonitrile in H2O/MeCN/NH3 95/5/0.2 buffer over 20 minutes with a flow of 100 mL/min. Cis-methyl 4-(3-oxo-2,3-dihydroisoxazol-5-yl)-2-(2-(trifluoromethyl)benzyl)piperidine-1-carboxylate (1.30 g, 68%) was isolated as a white solid. $^1$H NMR (600 MHz, cdcl$_3$) δ 1.79-1.95 (m, 2H), 1.95-2.14 (m, 2H), 2.79-2.98 (m, 3H), 3.17-3.27 (m, 1H), 3.34 (s, 3H), 4.04 (dd, 1H), 4.30-4.41 (m, 1H), 5.68 (s, 1H), 7.14 (d, 1H), 7.19-7.28 (m, 1H), 7.39 (t, 1H), 7.57 (d, 1H). MS m/z 385 (M+H)$^+$

Step 3: (2R,4S)-Methyl 4-(3-oxo-2,3-dihydroisoxazol-5-yl)-2-(2-(trifluoromethyl)benzyl)-piperidine-1-carboxylate and (2S,4R)-methyl 4-(3-oxo-2,3-dihydroisoxazol-5-yl)-2-(2-(trifluoromethyl)benzyl)piperidine-1-carboxylate Cis-methyl 4-(3-oxo-2,3-dihydroisoxazol-5-yl)-2-(2-(trifluoromethyl)benzyl)piperidine-1-carboxylate (1.30 g, 3.39 mmol) was subjected to chiral preparative HPLC (Column: Chiralcel OJ (250×20), 5 μm particle size, mobile phase: Heptane/EtOH/FA 80/20/0.1, flow rate 18 mL/min) to yield (2R,4S)-methyl 4-(3-oxo-2,3-dihydroisoxazol-5-yl)-2-(2-(trifluoromethyl)benzyl)piperidine-1-carboxylate (597 mg, 46%), Chiral purity 99.6% ee, Optical rotation $[α]_D^{20}$=−4.0 (acetonitrile, c=1) and (2S,4R)-methyl 4-(3-oxo-2,3-dihydroisoxazol-5-yl)-2-(2-(trifluoromethyl)benzyl)piperidine-1-carboxylate (624 mg, 48%), Chiral purity 99.8% ee, Optical rotation $[α]_D^{20}$=+6.1 (acetonitrile, c=1).

Step 4: 5-((2R,4S)-2-(2-(Trifluoromethyl)benzyl)piperidin-4-yl)isoxazol-3(2H)-one (2R,4S)-Methyl 4-(3-oxo-2,3-dihydroisoxazol-5-yl)-2-(2-(trifluoromethyl)benzyl)piperidine-1-carboxylate (597 mg, 1.55 mmol) was dissolved in hydrogen bromide (33% in acetic acid, 10 mL, 57.10 mmol) and the mixture stirred at room temperature overnight. The solvent was evaporated and the residue purified by preparative HPLC (Instrument: FractionLynx III, Mobilphase: gradient 5-95% MeCN in 0.2% NH3, pH 10, Column: Xbridge Prep C18 5 μm OBD 19*150 mm) to yield 5-((2R,4S)-2-(2-(trifluoromethyl)benzyl)piperidin-4-yl)isoxazol-3(2H)-one (358 mg, 71%). $^1$H NMR (600 MHz, cd$_3$od) δ 1.68 (q, 1H), 1.84 (qd, 1H), 2.11 (d, 1H), 2.22 (d, 1H), 3.02-3.20 (m, 3H), 3.21-3.32 (m, 1H), 3.51 (d, 1H), 3.57-3.67 (m, 1H), 5.74 (s, 1H), 7.44-7.56 (m, 2H), 7.64 (t, 1H), 7.74 (d, 1H). HRMS Calculated for $[C_{16}H_{17}F_3N_2O_2+H]^+$: 327.1320. Found: 327.1328

Example 111

5-((2S,4R)-2-(2-(trifluoromethyl)benzyl)piperidin-4-yl)isoxazol-3(2H)-one (2S,4R)-Methyl 4-(3-oxo-2,3-dihydroisoxazol-5-yl)-2-(2-(trifluoromethyl)benzyl)piperidine-1-carboxylate (624 mg, 1.62 mmol) was dissolved in hydrogen bromide (33% in acetic acid, 10 mL, 57.10 mmol) and the mixture stirred at room temperature overnight. The solvent was evaporated and the residue purified by preparative HPLC (Instrument: FractionLynx III, Mobilphase: gradient 5-95% MeCN in 0.2% NH$_3$, pH 10, Column: Xbridge Prep C18 5 μm OBD 19*150 mm) to yield 5-((2S,4R)-2-(2-(trifluoromethyl)benzyl)piperidin-4-yl)isoxazol-3(2H)-one (359 mg, 68%). $^1$H NMR (600 MHz, cd$_3$od) δ 1.68 (q, 1H), 1.84 (dq, 1H), 2.11 (d, 1H), 2.22 (d, 1H), 3.04-3.19 (m, 3H), 3.23-3.30 (m, 4H), 3.49-3.54 (m, 1H), 3.59-3.66 (m, 1H), 5.74 (s, 1H), 7.48 (t, 1H), 7.52 (d, 1H), 7.64 (t, 1H), 7.74 (d, 1H). HRMS Calculated for $[C_{16}H_{17}F_3N_2O_2+H]^+$: 327.1320. Found: 327.1321

Example 112

5-(Trans-2-(2-(trifluoromethyl)benzyl)piperidin-4-yl)isoxazol-3(2H)-one

Step 1: Trans-methyl 4-(3-oxo-2,3-dihydroisoxazol-5-yl)-2-(2-(trifluoromethyl)benzyl)-piperidine-1-carboxylate Trans-methyl 4-(3-ethoxy-3-oxopropanoyl)-2-(2-(trifluoromethyl)benzyl)piperidine-1-carboxylate (0.661 g, 1.59 mmol) was dissolved in MeOH (5 mL) and cooled to −40° C. under nitrogen. Sodium hydroxide (0.064 g, 1.59 mmol) dissolved in water (0.500 mL) was added during 10 min and the colourless solution continued to stir at −40° C. for 20 min. Hydroxylamine (50% by weight in water, 0.098 mL, 1.59 mmol) was added during 8 min. The resulting solution was stirred at −40° C. for 3.5 h. The mixture was then transferred into a prewarmed (80° C.) solution of 6 M hydrogen chloride (8 mL, 48.00 mmol) and the mixture continued to stir at 80° C. for 20 min. DCM and water were added. The phases were separated and the organic phase passed through a phase separator and evaporated to yield crude trans-methyl 4-(3-oxo-2,3-dihydroisoxazol-5-yl)-2-(2-(trifluoromethyl)benzyl)piperidine-1-carboxylate (0.748 g, 122%) as a yellow semisolid. MS m/z 385 (M+H)$^+$

Step 2: 5-(Trans-2-(2-(trifluoromethyl)benzyl)piperidin-4-yl)isoxazol-3(2H)-one Trans-methyl 4-(3-oxo-2,3-dihydroisoxazol-5-yl)-2-(2-(trifluoromethyl)benzyl)piperidine-1-carboxylate (157 mg, 0.41 mmol) was dissolved in hydrogen bromide (33% in acetic acid (3 mL, 17.13 mmol) and the mixture stirred at room temperature overnight. The solvent was evaporated and the residue purified by preparative HPLC (Instrument: FractionLynx III, Mobilphase: gradient 5-95% MeCN in 0.2% NH$_3$, pH 10, Column: Xbridge Prep C18 5 μm OBD 19*150 mm) to yield 5-(trans-2-(2-(trifluoromethyl)benzyl)piperidin-4-yl)isoxazol-3(2H)-one (53 mg, 40%). $^1$H NMR (600 MHz, cd$_3$od) δ 1.95 (ddd, 1H), 2.08-2.19 (m, 2H), 2.19-2.28 (m, 1H), 3.07-3.18 (m, 2H), 3.18-3.25 (m, 1H), 3.33-3.43 (m, 2H), 3.51-3.62 (m, 1H), 5.75 (d, 1H), 7.43-7.51 (m, 2H), 7.63 (t, 1H), 7.73 (d, 1H). HRMS Calculated for $[C_{16}H_{17}F_3N_2O_2+H]^+$: 327.1320. Found: 327.1297

Example 113

5-((2R,4S)-2-(4-(Trifluoromethoxy)benzyl)piperidin-4-yl)isoxazol-3(2H)-one

Step 1: Trans-methyl 4-(3-ethoxy-3-oxopropanoyl)-2-(4-(trifluoromethoxy)benzyl)piperidine-1-carboxylate and cis-methyl 4-(3-ethoxy-3-oxopropanoyl)-2-(4-(trifluoromethoxy)benzyl)-piperidine-1-carboxylate 1-(Methoxycarbonyl)-2-(4-(trifluoromethoxy)benzyl)piperidine-4-carboxylic acid (4.7 g, 13.01 mmol) (reference compound 50) was dissolved into methyl THF (150 mL), then di(1H-imidazol-1-yl)methanone (3.16 g, 19.51 mmol) was added in one portion. The mixture was stirred at room temperature under nitrogen for 3 h (flask 1). In a separate flask potassium 3-ethoxy-3-oxopropanoate (3.99 g, 23.41 mmol)

was suspended in methyl THF (150 mL) then magnesium chloride (2.229 g, 23.41 mmol) was added. The suspension was stirred at 50° C. under nitrogen for 3 h using a large magnetic stirring bar (flask 2). After 3 h, the contents of flask 1 was transferred into flask 2. The resulting yellow suspension was stirred under nitrogen at room temperature overnight. The mixture was acidified to pH 1 with 3.8 M HCl, then MTBE (100 mL) and water (100 mL) was added. The phases were separated and the organic layer was washed with water, satd NaHCO₃ and brine. The organic layer was dried over Na₂SO₄, filtered and evaporated leaving a slightly yellow oil. The product was flashed on Biotage (340 g) with a gradient of 20-60% EtOAc in n-heptane (8 CV). The column was conditioned at 20% EtOAc in -n-heptane (1 CV). Trans-methyl 4-(3-ethoxy-3-oxopropanoyl)-2-(4-(trifluoromethoxy)benzyl)piperidine-1-carboxylate (679 mg, 12.1%) and cis-methyl 4-(3-ethoxy-3-oxopropanoyl)-2-(4-(trifluoromethoxy)benzyl)piperidine-1-carboxylate (2.457 g, 43.8%) were isolated. Cis-isomer: $^1$H NMR (400 MHz, cdcl₃) δ 1.19-1.32 (m, 3H), 1.64-1.98 (m, 4H), 2.67-2.78 (m, 2H), 2.86-3.11 (m, 2H), 3.47 (s, 2H), 3.59 (s, 3H), 3.87-3.98 (m, 1H), 4.07-4.23 (m, 3H), 7.09-7.16 (m, 2H), 7.16-7.23 (m, 2H). MS m/z 432 (M+H)⁺. Trans-isomer: $^1$H NMR (400 MHz, cdcl₃) δ 1.20-1.31 (m, 3H), 1.38-2.03 (m, 4H), 2.66-3.08 (m, 4H), 3.32-3.75 (m, 5H), 3.97-4.36 (m, 3H), 4.40-4.77 (m, 1H), 7.10-7.32 (m, 4H). MS m/z 432 (M+H)⁺

Step 2: Cis-methyl 4-(3-oxo-2,3-dihydroisoxazol-5-yl)-2-(4-(trifluoromethoxy)benzyl)-piperidine-1-carboxylate Cis-methyl 4-(3-ethoxy-3-oxopropanoyl)-2-(4-(trifluoromethoxy)benzyl)piperidine-1-carboxylate (2.475 g, 5.74 mmol) was dissolved in MeOH (20 mL) and cooled to −40° C. under nitrogen. Sodium hydroxide (1.687 mL, 5.74 mmol) dissolved in water (2.000 mL) was added during 10 min and the yellow solution continued to stir at −40° C. for 20 min. Hydroxylamine (50% by weight in water, 0.352 mL, 5.74 mmol) was added during 8 min. The resulting solution was stirred at −40° C. for 3 h. The mixture was then rapidly poured into a prewarmed (80° C.) solution of 6 M hydrogen chloride (29.5 mL, 177.28 mmol) and the mixture continued to stir at 80° C. for 20 min. The solvent was evaporated and DCM/water added. The phases were separated and the organic phase passed through a phase separator and evaporated to yield a white solid. The compound was purified by preparative HPLC on a Kromasil C8 column (10 μm 250×50 ID mm) using a gradient of 10-60% Acetonitrile in H2O/MeCN/AcOH 95/5/0.2 buffer over 30 minutes with a flow of 100 mL/min. Cis-methyl 4-(3-oxo-2,3-dihydroisoxazol-5-yl)-2-(4-(trifluoromethoxy)benzyl)piperidine-1-carboxylate (1.41 g, 61.4%) was isolated. MS m/z 401 (M+H)⁺

Step 3: (2R,4S)-Methyl 4-(3-oxo-2,3-dihydroisoxazol-5-yl)-2-(4-(trifluoromethoxy)benzyl)-piperidine-1-carboxylate Cis-methyl 4-(3-oxo-2,3-dihydroisoxazol-5-yl)-2-(4-(trifluoromethoxy)benzyl)piperidine-1-carboxylate (1.41 g, 3.53 mmol) was subjected to chiral preparative HPLC (Column: Chiralpak AD (250×20), 5 μm particle size, mobile phase: Heptane/EtOH 90/10, flow rate 18 mL/min) to yield (2R,4S)-methyl 4-(3-oxo-2,3-dihydroisoxazol-5-yl)-2-(4-(trifluoromethoxy)benzyl)piperidine-1-carboxylate (691 mg, 49%), Chiral purity 99.0% ee, Optical rotation $[\alpha]_D^{20}$=+9.4 (acetonitrile, c=1), $^1$H NMR (400 MHz, cdcl₃) δ 1.84-2.14 (m, 4H), 2.56-2.66 (m, 1H), 2.72-2.82 (m, 1H), 2.94-3.04 (m, 1H), 3.09-3.21 (m, 1H), 3.57 (s, 3H), 3.96-4.06 (m, 1H), 4.21-4.32 (m, 1H), 5.74 (s, 1H), 7.06-7.15 (m, 4H).

Step 4: 5-((2R,4S)-2-(4-(Trifluoromethoxy)benzyl)piperidin-4-yl)isoxazol-3(2H)-one (2R,4S)-methyl 4-(3-oxo-2,3-dihydroisoxazol-5-yl)-2-(4-(trifluoromethoxy)benzyl)-piperidine-1-carboxylate (0.690 g, 1.72 mmol) was dissolved in hydrogen bromide (33% in acetic acid, 13.58 mL, 77.56 mmol) and the mixture stirred at room temperature overnight. The solvent was evaporated and the residue purified by preparative HPLC (Instrument: FractionLynx III, Mobilphase: gradient 5-95% MeCN in 0.2% NH₃, pH 10, Column: Xbridge Prep C18 5 μm OBD 19*150 mm) to yield 5-((2R,4S)-2-(4-(trifluoromethoxy)benzyl)-piperidin-4-yl)isoxazol-3(2H)-one (55 mg, 9.4%). $^1$H NMR (600 MHz, dmso) δ 1.07 (q, 1H), 1.34 (dq, 1H), 1.69-1.78 (m, 2H), 2.45-2.74 (m, 5H), 2.93-2.99 (m, 1H), 5.64 (s, 1H), 7.20-7.25 (m, 2H), 7.26-7.32 (m, 2H). HRMS Calculated for [C₁₆H₁₇F₃N₂O₃+H]⁺: 343.1270. Found: 343.1241

Example 114

5-(Trans-2-(4-(trifluoromethoxy)benzyl)piperidin-4-yl)isoxazol-3(2H)-one

Step 1: Trans-methyl 4-(3-oxo-2,3-dihydroisoxazol-5-yl)-2-(4-(trifluoromethoxy)benzyl)-piperidine-1-carboxylate Trans-methyl 4-(3-ethoxy-3-oxopropanoyl)-2-(4-(trifluoromethoxy)benzyl)piperidine-1-carboxylate (679 mg, 1.57 mmol) (from example 113, step 1) was dissolved in MeOH (10 mL) and cooled to −40° C. under nitrogen. Sodium hydroxide (0.463 mL, 1.57 mmol) dissolved in water (1.000 mL) was added during 10 min and the yellow solution continued to stir at −40° C. for 20 min. Hydroxylamine (50% by weight in water, 0.096 mL, 1.57 mmol) was added during 8 min. The resulting solution was stirred at −40° C. for 3 h 15 min. The mixture was then rapidly poured into a prewarmed (80° C.) solution of 6 M hydrogen chloride (8.11 mL, 48.63 mmol) and the mixture continued to stir at 80° C. for 20 min. The solvent was evaporated and DCM/water added. The phases were separated and the organic phase passed through a phase separator and evaporated to yield a white solid. Crude trans-methyl 4-(3-oxo-2,3-dihydroisoxazol-5-yl)-2-(4-(trifluoromethoxy)benzyl)piperidine-1-carboxylate (603 mg, 96%) was isolated. MS m/z 401 (M+H)⁺

Step 2: 5-(Trans-2-(4-(trifluoromethoxy)benzyl)piperidin-4-yl)isoxazol-3(2H)-one Trans-methyl 4-(3-oxo-2,3-dihydroisoxazol-5-yl)-2-(4-(trifluoromethoxy)benzyl)piperidine-1-carboxylate (0.603 g, 1.51 mmol) was dissolved in hydrogen bromide (33% in acetic acid, 11.87 mL, 67.78 mmol) and the mixture was stirred at room temperature overnight. The solvent was evaporated and the compound was purified by preparative HPLC on a XBridge C18 column (10 μm 250×50 ID mm) using a gradient of 10-50% Acetonitrile in H2O/AcN/NH3 95/5/0.2 buffer over 20 minutes with a flow of 100 mL/min. 5-(Trans-2-(4-(trifluoromethoxy)benzyl)piperidin-4-yl)isoxazol-3(2H)-one (200 mg, 38.8%) was isolated as a white solid. $^1$H NMR (400 MHz, dmso) δ 1.47-1.60 (m, 1H), 1.68-1.87 (m, 3H), 2.43-4.01 (m, 6H), 5.73 (s, 1H), 7.20-7.40 (m, 4H). HRMS Calculated for [C₁₆H₁₇F₃N₂O₃+H]⁺: 343.1270. Found: 343.1260

Example 115

5-((2R,4S)-2-(4-Chlorobenzyl)piperidin-4-yl)isoxazol-3(2H)-one

Step 1: Methyl 2-(4-chlorobenzyl)-4-((2,2-dimethyl-4,6-dioxo-1,3-dioxan-5-ylidene)-(hydroxy)methyl)piperidine-1-carboxylate Dichloromethane (200 mL) was added to 2-(4-chlorobenzyl)-1-(methoxycarbonyl)piperidine-4-carboxylic acid (4.27 g, 13.7 mmol) (reference compound 51). The mixture was cooled with an ice bath. DMAP (2.008 g, 16.44 mmol), 2,2-dimethyl-1,3-dioxane-4,6-dione (2.96 g, 20.54 mmol) and DIPEA (5.25 mL, 30.13 mmol) were added and then N1-((ethylimino)methylene)-N3,N3-dimethylpropane-1,3-diamine hydrochloride (5.25 g, 27.39 mmol) was added. The mixture was stirred at 0° C. for 15 min, then the mixture was warmed to room temperature and stirred overnight. The organic phase was washed with 1 M HCl and once with water. The organic layer was filtered through a phase separator and evaporated to yield crude methyl 2-(4-chlorobenzyl)-4-((2,2-dimethyl-4,6-dioxo-1,3-dioxan-5-ylidene)(hydroxy)methyl)-piperidine-1-carboxylate (7.00 g, 117%). MS m/z 438, 440 (M+H)$^+$

Step 2: Trans-methyl 2-(4-chlorobenzyl)-4-(3-ethoxy-3-oxopropanoyl)piperidine-1-carboxylate and cis-methyl 2-(4-chlorobenzyl)-4-(3-ethoxy-3-oxopropanoyl)piperidine-1-carboxylate Methyl 2-(4-chlorobenzyl)-4-((2,2-dimethyl-4,6-dioxo-1,3-dioxan-5-ylidene)(hydroxy)-methyl)piperidine-1-carboxylate (7.00 g, 16 mmol) was dissolved in EtOH (100 mL) to give a yellow solution. The mixture was warmed up to almost reflux and stirred for 90 min. The solvent was evaporated and the residue was purified via Biotage (heptane:ethyl acetate, gradient 20%->70% ethyl acetate, 7 CV, 340 g column, two runs) to yield trans-methyl 2-(4-chlorobenzyl)-4-(3-ethoxy-3-oxopropanoyl)piperidine-1-carboxylate (780 mg, 13%) and cis-methyl 2-(4-chlorobenzyl)-4-(3-ethoxy-3-oxopropanoyl)piperidine-1-carboxylate (1.45 g, 24%) Cis-isomer: $^1$H NMR (400 MHz, cdcl$_3$) δ 1.14-1.31 (m, 3H), 1.56-1.95 (m, 4H), 2.59-3.08 (m, 4H), 3.43 (d, 2H), 3.59 (d, 3H), 3.80-3.95 (m, 1H), 4.00-4.22 (m, 3H), 7.05-7.11 (m, 2H), 7.18-7.24 (m, 2H). MS m/z 382, 384 (M+H)$^+$. Trans-isomer: $^1$H NMR (400 MHz, cdcl$_3$) δ 1.26 (t, 3H), 1.39-1.99 (m, 4H), 2.46-3.06 (m, 4H), 3.35-3.72 (m, 5H), 3.95-4.32 (m, 3H), 4.40-4.72 (m, 1H), 6.99-7.37 (m, 4H). MS m/z 382, 384 (M+H)$^+$

Step 3: Cis-methyl 2-(4-chlorobenzyl)-4-(3-oxo-2,3-dihydroisoxazol-5-yl)piperidine-1-carboxylate A solution of cis-methyl 2-(4-chlorobenzyl)-4-(3-ethoxy-3-oxopropanoyl)piperidine-1-carboxylate (1.45 g, 3.80 mmol) in MeOH (10 mL) was added to a solution of sodium hydroxide (3.16 mL, 3.80 mmol) in MeOH/H2O (2.981 mL/0.179 mL) at −30° C. After 10 min a solution of hydroxylamine hydrochloride (0.528 g, 7.59 mmol) and sodium hydroxide (0.304 g, 7.59 mmol) in MeOH (10 mL) and H2O (10 mL) was added. Stirring was continued at −30° C. for 30 min. The reaction solution was poured into 6 M HCl (6.33 mL, 37.97 mmol) at 80° C. and heated at 80° C. for 1 hour. Concentration of the organic solvent and extraction with diethyl ether (×3), drying over Na$_2$SO$_4$ and evaporation gave a yellow foam. Purification using prepLC (2 injections, pH=3, large column 20-80% MeCN over 30 min) yielded cis-methyl 2-(4-chlorobenzyl)-4-(3-oxo-2,3-dihydroisoxazol-5-yl)piperidine-1-carboxylate (557 mg, 41%). $^1$H NMR (400 MHz, cdcl$_3$) δ 1.83-2.00 (m, 3H), 2.02-2.12 (m, 1H), 2.59 (dd, 1H), 2.77 (dd, 1H), 2.97-3.02 (m, 1H), 3.08-3.20 (m, 1H), 3.62 (s, 3H), 4.00 (dd, 1H), 4.21-4.29 (m, 1H), 5.73 (s, 1H), 7.04 (d, 2H), 7.21-7.25 (m, 2H). MS m/z 351, 353 (M+H)$^+$

Step 4: (2R,4S)-Methyl 2-(4-chlorobenzyl)-4-(3-oxo-2,3-dihydroisoxazol-5-yl)piperidine-1-carboxylate Cis-methyl 2-(4-chlorobenzyl)-4-(3-oxo-2,3-dihydroisoxazol-5-yl)piperidine-1-carboxylate (557 mg, 1.58 mmol) was subjected to chiral preparative HPLC (Column: Chiralpak IC (250×20), 5 μm particle size, mobile phase: Heptane/IPA/FA 50/50/0.1, flow rate 15 mL/min) to yield (2R,4S)-methyl 2-(4-chlorobenzyl)-4-(3-oxo-2,3-dihydroisoxazol-5-yl)piperidine-1-carboxylate (253 mg, 45%), Chiral purity 99.3% ee, Optical rotation $[\alpha]_D^{20}$=+16.2 (acetonitrile, c=1)

Step 5: 5-((2R,4S)-2-(4-Chlorobenzyl)piperidin-4-yl)isoxazol-3(2H)-one (2R,4S)-Methyl 2-(4-chlorobenzyl)-4-(3-oxo-2,3-dihydroisoxazol-5-yl)piperidine-1-carboxylate (253 mg, 0.72 mmol) was stirred in HBr (33% in AcOH) overnight (24 hours). Evaporation of solvents and the residue was purified by preparative HPLC on a XBridge C18 column (10 μm 250×50 ID mm) using a gradient of 5% to 45% Acetonitrile in H2O/MeCN/NH3 95/5/0.2 buffer over 20 minutes with a flow of 100 mL/min. 5-((2R,4S)-2-(4-chlorobenzyl)piperidin-4-yl)isoxazol-3(2H)-one (150 mg, 71%) was isolated. $^1$H NMR (400 MHz, cd$_3$od) δ 1.37-1.50 (m, 1H), 1.61-1.77 (m, 1H), 2.01-2.13 (m, 2H), 2.78-2.98 (m, 4H), 3.18-3.28 (m, 1H), 3.28-3.36 (m, 1H), 5.51 (s, 1H), 7.24 (d, 2H), 7.34 (d, 2H). HRMS Calcd for [C$_{15}$H$_{17}$ClN$_2$O$_2$+H]+: 293.1057. Found: 293.1043.

Example 116

5-(Trans-2-(4-chlorobenzyl)piperidin-4-yl)isoxazol-3(2H)-one

Step 1: Trans-methyl 2-(4-chlorobenzyl)-4-(3-oxo-2,3-dihydroisoxazol-5-yl)piperidine-1-carboxylate A solution of methyl 2-(4-chlorobenzyl)-4-(3-ethoxy-3-oxopropanoyl)piperidine-1-carboxylate (780 mg, 2.04 mmol) (from example 115, step 2) in MeOH (5 mL) was added to a solution of sodium hydroxide (1.705 mL, 2.05 mmol) in MeOH/H2O (1.608 mL/0.097 mL) at −30° C. After 10 min a solution of hydroxylamine hydrochloride (284 mg, 4.09 mmol) and sodium hydroxide (163 mg, 4.09 mmol) in MeOH (5 mL) and H2O (5 mL) was added. Stirring was continued at −30° C. for 30 min. The reaction solution was poured into 6 M HCl (3.40 mL, 20.43 mmol) at 80° C. and heated at 80° C. for 30 min. Concentration of the organic solvent and extraction with diethyl ether (×3), drying over Na$_2$SO$_4$ and evaporation gave a yellow foam. Purification using prepLC (pH=3, large column 20-80% MeCN over 30 min) yielded trans-methyl 2-(4-chlorobenzyl)-4-(3-oxo-2,3-dihydroisoxazol-5-yl)piperidine-1-carboxylate (272.5 mg, 38%). $^1$H NMR (400 MHz, cdcl$_3$) δ 1.44-2.18 (m, 4H), 2.70-3.01 (m, 2H), 3.02-3.14 (m, 2H), 3.42-3.76 (m, 3H), 4.04-

4.37 (m, 1H), 4.39-4.79 (m, 1H), 5.64 (s, 1H), 7.05-7.31 (m, 4H). MS m/z 351, 353 (M+H)+

Step 2: 5-(Trans-2-(4-chlorobenzyl)piperidin-4-yl)isoxazol-3(2H)-one

Methyl 2-(4-chlorobenzyl)-4-(3-oxo-2,3-dihydroisoxazol-5-yl)piperidine-1-carboxylate (347 mg, 0.99 mmol) was stirred in HBr (33% in AcOH) overnight (19 hours). Evaporation of solvents and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) yielded 5-(trans-2-(4-chlorobenzyl)piperidin-4-yl)isoxazol-3(2H)-one (151 mg, 52%). $^1$H NMR (400 MHz, tfa) δ 2.25-2.60 (m, 4H), 3.06-3.20 (m, 2H), 3.35-3.52 (m, 1H), 3.55-3.75 (s, 2H), 3.77-3.96 (m, 1H), 6.59 (s, 1H), 7.15-7.22 (m, 2H), 7.22-7.41 (m, 2H). HRMS Calcd for $[C_{15}H_{17}ClN_2O_2+H]$+: 293.1057. Found: 293.1031.

Example 117

5-((2R,4S)-2-(4-(Methylsulfonyl)benzyl)piperidin-4-yl)isoxazol-3(2H)-one

Step 1: Methyl 4-(3-ethoxy-3-oxopropanoyl)-2-(4-(methylsulfonyl)benzyl)piperidine-1-carboxylate Ethyl potassium malonate (2.414 g, 14.18 mmol) and $MgCl_2$ (1.125 g, 11.82 mmol) were added to dry THF (75 mL). The reaction flask was stirred vigorously for 4 h at 50° C. (flask 1). 1-(Methoxycarbonyl)-2-(4-(methylsulfonyl)benzyl)piperidine-4-carboxylic acid (4.2 g, 11.82 mmol) (reference compound 51) and carbonyldiimidazole (2.87 g, 17.73 mmol) were added to dry THF (75 mL) at room temperature (flask 2). More di(1H-imidazol-1-yl)methanone (0.5 g) was added and after 2 h the contents of flask 2 was added to flask 1 at room temperature and stirred overnight. The reaction mixture was dissolved between water and diethyl ether. The organic phase was isolated, dried with $Na_2SO_4$, filtered through celite and the solvent was evaporated. Chromatography using the Biotage equipment. Gradient elution using ethylacetate-heptane, started 10-90 and ended 100-0. Methyl 4-(3-ethoxy-3-oxopropanoyl)-2-(4-(methylsulfonyl)benzyl)piperidine-1-carboxylate (3.99 g, 79%) was isolated.

Step 2: Methyl 2-(4-(methylsulfonyl)benzyl)-4-(3-oxo-2,3-dihydroisoxazol-5-yl)piperidine-1-carboxylate Methyl 4-(3-ethoxy-3-oxopropanoyl)-2-(4-(methylsulfonyl)benzyl)piperidine-1-carboxylate (3.99 g, 9.38 mmol) was dissolved in MeOH (70 mL) and cooled to −30° C. NaOH (0.375 g, 9.38 mmol) dissolved in water (7 mL) was added during 10 min and the resulting colourless solution continued to stir at −30° C. for 20 min. Hydroxylamine (50% by weight in water, 0.575 mL, 9.38 mmol) was added dropwise. The resulting solution was stirred at −30° C. for 30 min. The mixture was then transferred into a prewarmed (80° C.) solution of 6 M HCl (30 mL, 180 mmol) and the mixture continued to stir at 80° C. for 20 min. The mixture was dissolved between ethyl acetate and water. The aqueous layer was extracted three more times with ethyl acetate. The combined organic layers were dried over $Na_2SO_4$, filtered through celite and the solvent was evaporated. The residue was purified using reversed phase chromatography, gradient acid buffer and acetonitril, started 35% and ended 40%. Methyl 2-(4-(methylsulfonyl)benzyl)-4-(3-oxo-2,3-dihydroisoxazol-5-yl)piperidine-1-carboxylate (1.05 g, 28.4%) was isolated.

Step 3: (2R,4S)-Methyl 2-(4-(methylsulfonyl)benzyl)-4-(3-oxo-2,3-dihydroisoxazol-5-yl)piperidine-1-carboxylate, (2S,4R)-methyl 2-(4-(methylsulfonyl)benzyl)-4-(3-oxo-2,3-dihydroisoxazol-5-yl)piperidine-1-carboxylate and trans-methyl 2-(4-(methylsulfonyl)-benzyl)-4-(3-oxo-2,3-dihydroisoxazol-5-yl)piperidine-1-carboxylate Methyl 2-(4-(methylsulfonyl)benzyl)-4-(3-oxo-2,3-dihydroisoxazol-5-yl)piperidine-1-carboxylate (1 g, 2.54 mmol) was subjected to chiral preparative HPLC in two steps (first using Column: Chiralcel OJ (250×50), 20 μm particle size, mobile phase: Heptane/IPA/FA 30/70/0.1, flow rate 120 mL/min and then using Column: Chiralpak AD (250×50), 20 μm particle size, mobile phase: Heptane/EtOH/FA 40/60/0.1, flow rate 120 mL/min) to yield (2R,4S)-Methyl 2-(4-(methylsulfonyl)benzyl)-4-(3-oxo-2,3-dihydroisoxazol-5-yl)piperidine-1-carboxylate (231 mg, 23%), Chiral purity 99.5% ee, Optical rotation $[α]_D^{20}$=+10.1 (acetonitrile, c=1), $^1$H NMR (600 MHz, cdcl$_3$) δ 1.87-1.97 (m, 3H), 2.02-2.11 (m, 1H), 2.68 (dd, 1H), 2.88 (dd, 1H), 2.96-3.06 (m, 4H), 3.12-3.22 (m, 1H), 3.60 (s, 3H), 3.96-4.02 (m, 1H), 4.27-4.35 (m, 1H), 5.74 (s, 1H), 7.30 (d, 2H), 7.82 (d, 2H); (2S,4R)-methyl 2-(4-(methylsulfonyl)benzyl)-4-(3-oxo-2,3-dihydroisoxazol-5-yl)piperidine-1-carboxylate (225 mg, 22.5%), Chiral purity 98.4% ee, Optical rotation $[α]_D^{20}$=−11.4 (acetonitrile, c=1), $^1$H NMR (600 MHz, cdcl$_3$) δ 1.86-1.97 (m, 3H), 2.02-2.10 (m, 1H), 2.67 (dd, 1H), 2.87 (dd, 1H), 2.96-3.05 (m, 4H), 3.12-3.20 (m, 1H), 3.59 (s, 3H), 3.95-4.02 (m, 1H), 4.27-4.34 (m, 1H), 5.74 (s, 1H), 7.29 (d, 2H), 7.81 (d, 2H) and trans-methyl 2-(4-(methylsulfonyl)benzyl)-4-(3-oxo-2,3-dihydroisoxazol-5-yl)piperidine-1-carboxylate (185 mg, 18.5%)

Step 4: 5-((2R,4S)-2-(4-(Methylsulfonyl)benzyl)piperidin-4-yl)isoxazol-3(2H)-one (2R,4S)-Methyl 2-(4-(methylsulfonyl)benzyl)-4-(3-oxo-2,3-dihydroisoxazol-5-yl)piperidine-1-carboxylate (231 mg, 0.59 mmol) was dissolved in HBr (33% in acetic acid, 5 mL, 28.55 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4S)-2-(4-(methylsulfonyl)benzyl)piperidin-4-yl)isoxazol-3(2H)-one (171 mg, 87%). $^1$H NMR (600 MHz, dmso) δ 1.06-1.15 (m, 1H), 1.30-1.39 (m, 1H), 1.76 (d, 2H), 2.43-2.56 (omitted signals), 2.62-2.81 (m, 4H), 2.95-3.00 (m, 1H), 3.16 (s, 3H), 5.68 (s, 1H), 7.46 (d, 2H), 7.80 (d, 2H). HRMS Calcd for $[C_{16}H_{20}N_2O_4S+H]$+: 337.1222. Found: 337.1198

Example 118

5-((2S,4R)-2-(4-(Methylsulfonyl)benzyl)piperidin-4-yl)isoxazol-3(2H)-one (2S,4R)-Methyl 2-(4-(methylsulfonyl)benzyl)-4-(3-oxo-2,3-dihydroisoxazol-5-yl)piperidine-1-carboxylate (225 mg, 0.57 mmol) was dissolved in HBr (33% in acetic acid, 5 mL, 28.55 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2S,4R)-2-(4-(methylsulfonyl)benzyl)piperidin-4-yl) isoxazol-3(2H)-one (91 mg, 47.4%). ¹H NMR (600 MHz, dmso) δ 1.05-1.14 (m, 1H), 1.30-1.38 (m, 1H), 1.72-1.79 (m, 2H), 2.39-2.56 (omitted signals), 2.62-2.80 (m, 4H), 2.94-3.00 (m, 1H), 3.16 (s, 3H), 5.68 (s, 1H), 7.46 (d, 2H), 7.80 (d, 2H). HRMS Calcd for [$C_{16}H_{20}N_2O_4S$+H]+: 337.1222. Found: 337.1198

Example 119

5-(Trans-2-(4-(methylsulfonyl)benzyl)piperidin-4-yl) isoxazol-3(2H)-one

Trans-methyl 2-(4-(methylsulfonyl)benzyl)-4-(3-oxo-2,3-dihydroisoxazol-5-yl)piperidine-1-carboxylate (185 mg, 0.47 mmol) was dissolved in HBr (33% in acetic acid, 4 mL, 22.84 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(trans-2-(4-(methylsulfonyl)benzyl)piperidin-4-yl)isoxazol-3(2H)-one (161 mg, 102%). ¹H NMR (600 MHz, dmso) δ 1.65-1.97 (m, 4H), 2.34-2.63 (omitted signals), 2.80-3.15 (m, 5H), 3.18 (s, 3H), 5.84 (s, 1H), 7.51 (d, 2H), 7.87 (d, 2H). HRMS Calcd for [$C_{16}H_{20}N_2O_4S$+H]+: 337.1222. Found: 337.1236

Example 120

5-((2R,4S)-2-(3,4-Difluorobenzyl)piperidin-4-yl) isoxazol-3(2H)-one

Step 1: Trans-methyl 2-(3,4-difluorobenzyl)-4-(3-ethoxy-3-oxopropanoyl)piperidine-1-carboxylate and cis-methyl 2-(3,4-difluorobenzyl)-4-(3-ethoxy-3-oxopropanoyl)piperidine-1-carboxylate 2-(3,4-Difluorobenzyl)-1-(methoxycarbonyl)piperidine-4-carboxylic acid (6.62 g, 21.13 mmol) (reference compound 53) was dissolved in methyl THF (150 mL) and di(1H-imidazol-1-yl)methanone (5.14 g, 31.70 mmol) added. The suspension was stirred at room temperature under nitrogen for 3.5 h (flask 1). In a separate flask potassium 3-ethoxy-3-oxopropanoate (6.47 g, 38.03 mmol) was suspended in methyl THF (150 mL) and magnesium chloride (3.62 g, 38.03 mmol) added. The suspension was stirred at 50° C. under nitrogen for 3 h using an oversized stirring bar (flask 2). The yellow suspension in flask 1 was now added to the white suspension in flask 2. The resulting yellow suspension was stirred under nitrogen at room temperature for 4 h. The mixture was acidified to pH 1 with 3.8 M HCl and MTBE and water added. The phases were separated and the organic phase extracted with water, satd $NaHCO_3$ and water. Evaporated the solvents to yield an orange oil. The diastereomers were separated in 2 runs on Biotage (20%=>50% EtOAc in heptane, 8 CV; Biotage® KP-SIL 340 g column). Trans-methyl 2-(3,4-difluorobenzyl)-4-(3-ethoxy-3-oxopropanoyl) piperidine-1-carboxylate (0.278 g, 3.4%) and cis-methyl 2-(3,4-difluorobenzyl)-4-(3-ethoxy-3-oxopropanoyl)piperidine-1-carboxylate (2.233 g, 27.6%) were isolated as yellow oils. Cis-isomer: ¹H NMR (400 MHz, cdcl₃) δ 1.21-1.29 (m, 3H), 1.61-1.98 (m, 4H), 2.63-2.78 (m, 2H), 2.82-3.11 (m, 2H), 3.47 (s, 2H), 3.64 (s, 3H), 3.86-3.97 (m, 1H), 4.12-4.23 (m, 3H), 6.85-6.92 (m, 1H), 6.95-7.13 (m, 2H). MS m/z 384 (M+H)+. Trans-isomer: ¹H NMR (400 MHz, cdcl₃) δ 1.22-1.29 (m, 3H), 1.40-2.00 (m, 4H), 2.63-3.03 (m, 4H), 3.37-3.75 (m, 5H), 4.00-4.31 (m, 3H), 4.55 (d, br., 1H), 6.77-7.12 (m, 3H). MS m/z 384 (M+H)+

Step 2: Cis-methyl 2-(3,4-difluorobenzyl)-4-(3-oxo-2,3-dihydroisoxazol-5-yl)piperidine-1-carboxylate Cis-methyl 2-(3,4-difluorobenzyl)-4-(3-ethoxy-3-oxopropanoyl)piperidine-1-carboxylate (2.233 g, 5.82 mmol) was dissolved in MeOH (20 mL) and cooled to −40° C. under nitrogen. Sodium hydroxide (0.233 g, 5.82 mmol) dissolved in water (2.000 mL) was added during 10 min and the yellow solution continued to stir at −40° C. for 20 min. Hydroxylamine (50% by weight in water, 0.357 mL, 5.82 mmol) was added during 8 min. The resulting solution was stirred at −40° C. for 3 h. The mixture was then rapidly poured into a prewarmed (80° C.) solution of 6 M hydrogen chloride (30 mL, 180.00 mmol) and the mixture continued to stir at 80° C. for 20 min. The solvent was evaporated and DCM/water added. The phases were separated and the organic phase passed through a phase separator and evaporated to yield a yellow semi-solid. The compound was purified by preparative HPLC in 3 injections on a XBridge C18 column (10 μm 250×50 ID mm) using a gradient of 0-25% Acetonitrile in H2O/MeCN/NH3 95/5/0.2 buffer over 20 minutes with a flow of 100 mL/min. Cis-methyl 2-(3,4-difluorobenzyl)-4-(3-oxo-2,3-dihydroisoxazol-5-yl)piperidine-1-carboxylate (1.361 g, 66%) was isolated as a white solid. ¹H NMR (400 MHz, cdcl₃) δ 1.84-2.14 (m, 4H), 2.52-2.62 (m, 1H), 2.71-2.80 (m, 1H), 2.95-3.05 (m, 1H), 3.09-3.20 (m, 1H), 3.64 (s, 3H), 3.95-4.06 (m, 1H), 4.20-4.30 (m, 1H), 5.74 (s, 1H), 6.77-6.83 (m, 1H), 6.90-6.98 (m, 1H), 6.98-7.09 (m, 1H). MS m/z 353 (M+H)+

Step 3: (2R,4S)-Methyl 2-(3,4-difluorobenzyl)-4-(3-oxo-2,3-dihydroisoxazol-5-yl)piperidine-1-carboxylate and (2S,4R)-methyl 2-(3,4-difluorobenzyl)-4-(3-oxo-2,3-dihydroisoxazol-5-yl)-piperidine-1-carboxylate Cis-methyl 2-(3,4-difluorobenzyl)-4-(3-oxo-2,3-dihydroisoxazol-5-yl)piperidine-1-carboxylate (1.36 g, 3.87 mmol) was subjected to chiral preparative HPLC (Column: Chiralpak AD (250×20), 5 μm particle size, mobile phase: Heptane/EtOH/FA 90/10/0.2, flow rate 18 mL/min) to yield (2R,4S)-methyl 2-(3,4-difluorobenzyl)-4-(3-oxo-2,3-dihydroisoxazol-5-yl)piperidine-1-carboxylate (550 mg (40%), Chiral purity 98.2% ee, Optical rotation $[α]_D^{20}$=+15.0 (acetonitrile, c=1) and (2S,4R)-methyl 2-(3,4-difluorobenzyl)-4-(3-oxo-2,3-dihydroisoxazol-5-yl)piperidine-1-carboxylate (596 mg, 44%), Chiral purity 99.4% ee, Optical rotation $[α]_D^{20}$=−13.2 (acetonitrile, c=1)

Step 4: 5-((2R,4S)-2-(3,4-Difluorobenzyl)piperidin-4-yl)isoxazol-3(2H)-one (2R,4S)-Methyl 2-(3,4-difluorobenzyl)-4-(3-oxo-2,3-dihydroisoxazol-5-yl)piperidine-1-carboxylate (550 mg, 1.56 mmol) was dissolved in hydrogen bromide (33% in acetic acid, 15 mL, 85.65 mmol) and the mixture stirred at room temperature overnight. The solvent was evaporated and the residue purified by preparative HPLC (Instrument: FractionLynx I, Mobilphase: gradient 5-95% MeCN in 0.2% $NH_3$, pH 10, Column: Xbridge Prep C18 5 μm OBD 19*150 mm) to yield 5-((2R,4S)-2-(3,4-difluorobenzyl)piperidin-4-yl)isoxazol-3(2H)-one (183 mg, 40%). ¹H NMR (600 MHz, cd₃od) δ 1.41 (q, 1H), 1.67 (dq, 1H), 1.99-2.08 (m, 2H), 2.77-2.95

(m, 4H), 3.17-3.24 (m, 1H), 3.26-3.34 (m, 1H), 5.49 (s, 1H), 7.00-7.05 (m, 1H), 7.14-7.22 (m, 2H). HRMS Calculated for [C$_{15}$H$_{16}$F$_{2}$N$_{2}$O$_{2}$+H]$^+$: 295.1258. Found: 295.1253

Example 121

5-((2S,4R)-2-(3,4-Difluorobenzyl)piperidin-4-yl)isoxazol-3(2H)-one (2S,4R)-Methyl 2-(3,4-difluorobenzyl)-4-(3-oxo-2,3-dihydroisoxazol-5-yl)piperidine-1-carboxylate (596 mg, 1.69 mmol) (from example 120, step 3) was dissolved in hydrogen bromide (33% in acetic acid, 15 mL, 85.65 mmol) and the mixture stirred at room temperature overnight. The solvent was evaporated and the residue purified by preparative HPLC (Instrument: FractionLynx I, Mobilphase: gradient 5-95% MeCN in 0.2% NH$_3$, pH 10, Column: Xbridge Prep C18 5 μm OBD 19*150 mm) to yield 5-((2S,4R)-2-(3,4-difluorobenzyl)piperidin-4-yl)isoxazol-3(2H)-one (136 mg, 27%). $^1$H NMR (600 MHz, cd$_3$od) δ 1.42 (q, 1H), 1.68 (dq, 1H), 2.04 (t, 2H), 2.78-2.95 (m, 4H), 3.19-3.25 (m, 1H), 3.29-3.35 (m, 1H), 5.49 (s, 1H), 7.00-7.05 (m, 1H), 7.14-7.22 (m, 2H). HRMS Calculated for [C$_{15}$H$_{16}$F$_{2}$N$_{2}$O$_{2}$+H]$^+$: 295.1258. Found: 295.1264

Example 122

5-((2S,4S)-2-(3,4-Difluorobenzyl)piperidin-4-yl)isoxazol-3(2H)-one

Step 1: Trans-methyl 2-(3,4-difluorobenzyl)-4-(3-oxo-2,3-dihydroisoxazol-5-yl)piperidine-1-carboxylate Trans-methyl 2-(3,4-difluorobenzyl)-4-(3-ethoxy-3-oxopropanoyl)piperidine-1-carboxylate (0.278 g, 0.73 mmol) (from example 120, step 1) was dissolved in MeOH (3 mL) and cooled to −40° C. under nitrogen. Sodium hydroxide (0.029 g, 0.73 mmol) dissolved in water (0.300 mL) was added during 10 min and the yellow solution continued to stir at −40° C. for 20 min. Hydroxylamine (50% by weight in water, 0.044 mL, 0.73 mmol) was added during 8 min. The resulting solution was stirred at −40° C. for 3 h 15 min. The mixture was then rapidly poured into a prewarmed (80° C.) solution of 6 M hydrogen chloride (4 mL, 24.00 mmol) and the mixture continued to stir at 80° C. for 20 min. The solvent was evaporated and DCM/water added. The phases were separated and the organic phase passed through a phase separator and evaporated to yield a yellow semi-solid. The compound was purified by preparative HPLC on a XBridge C18 column (10 μm 250×50 ID mm) using a gradient of 0-25% Acetonitrile in H2O/MeCN/NH3 95/5/0.2 buffer over 20 minutes with a flow of 100 mL/min. Trans-methyl 2-(3,4-difluorobenzyl)-4-(3-oxo-2,3-dihydroisoxazol-5-yl)piperidine-1-carboxylate (83 mg, 34%) was isolated. $^1$H NMR (400 MHz, cdcl$_3$) δ 1.47-2.14 (m, 4H), 2.71-3.14 (m, 4H), 3.43-3.75 (m, 3H), 4.01-4.78 (m, 2H), 5.65 (s, 1H), 6.78-7.14 (m, 3H). MS m/z 353 (M+H)$^+$ Step 2: (2S,4S)-Methyl 2-(3,4-difluorobenzyl)-4-(3-oxo-2,3-dihydroisoxazol-5-yl)piperidine-1-carboxylate and (2R,4R)-methyl 2-(3,4-difluorobenzyl)-4-(3-oxo-2,3-dihydroisoxazol-5-yl)piperidine-1-carboxylate Trans-methyl 2-(3,4-difluorobenzyl)-4-(3-oxo-2,3-dihydroisoxazol-5-yl)piperidine-1-carboxylate (83 mg, 0.24 mmol) was subjected to chiral preparative HPLC (Column: ReproSil (250×20), 8 μm particle size, mobile phase: Heptane/(MTBE/MeOH 95/5) 70/30, flow rate 18 mL/min) to yield (2S,4S)-methyl 2-(3,4-difluorobenzyl)-4-(3-oxo-2,3-dihydroisoxazol-5-yl)piperidine-1-carboxylate (45 mg, 54%), Chiral purity 99.6% ee and (2R,4R)-methyl 2-(3,4-difluorobenzyl)-4-(3-oxo-2,3-dihydroisoxazol-5-yl)piperidine-1-carboxylate (32 mg, 38%), Chiral purity 99.9% ee.

Step 3: 5-((2S,4S)-2-(3,4-Difluorobenzyl)piperidin-4-yl)isoxazol-3(2H)-one (2S,4S)-Methyl 2-(3,4-difluorobenzyl)-4-(3-oxo-2,3-dihydroisoxazol-5-yl)piperidine-1-carboxylate (45 mg, 0.13 mmol) was dissolved in hydrogen bromide (33% in acetic acid, 1 mL, 5.71 mmol) and the mixture stirred at room temperature. After 17 h more hydrogen bromide (33% in acetic acid, 0.5 mL, 2.85 mmol) was added and the reaction continued at room temperature for a total of 24 h. The solvent was evaporated and the residue purified by preparative HPLC (Instrument: FractionLynx III, Mobilphase: gradient 5-95% MeCN in 0.2% NH3, pH 10, Column: Xbridge Prep C18 5 μm OBD 19*150 mm) to yield 5-((2S,4S)-2-(3,4-difluorobenzyl)piperidin-4-yl)isoxazol-3(2H)-one (8.5 mg, 22%). $^1$H NMR (600 MHz, cd$_3$od) δ 1.71-1.79 (m, 1H), 1.96-2.04 (m, 1H), 2.04-2.12 (m, 2H), 2.79-2.92 (m, 2H), 2.95-3.03 (m, 1H), 3.14-3.36 (m, 3H), 5.51 (s, 1H), 7.00-7.04 (m, 1H), 7.13-7.24 (m, 2H). HRMS Calculated for [C$_{15}$H$_{16}$F$_{2}$N$_{2}$O$_{2}$+H]$^+$: 295.1258. Found: 295.1276

Example 123

5-((2R,4R)-2-(3,4-Difluorobenzyl)piperidin-4-yl)isoxazol-3(2H)-one (2R,4R)-Methyl 2-(3,4-difluorobenzyl)-4-(3-oxo-2,3-dihydroisoxazol-5-yl)piperidine-1-carboxylate (32.5 mg, 0.09 mmol) was dissolved in hydrogen bromide (33% in acetic acid, 0.8 mL, 4.57 mmol) and the mixture stirred at room temperature overnight. The solvent was evaporated and the residue purified by preparative HPLC (Instrument: FractionLynx III, Mobilphase: gradient 5-95% MeCN in 0.2% NH$_3$, pH 10, Column: Xbridge Prep C18 5 μm OBD 19*150 mm) to yield 5-((2R,4R)-2-(3,4-difluorobenzyl)piperidin-4-yl)isoxazol-3(2H)-one (10.4 mg, 38%). $^1$H NMR (600 MHz, cd$_3$od) δ 1.71-1.78 (m, 1H), 1.96-2.04 (m, 1H), 2.05-2.12 (m, 2H), 2.80-2.92 (m, 2H), 2.96-3.03 (m, 1H), 3.15-3.25 (m, 2H), 3.26-3.35 (m, 1H), 5.50 (s, 1H), 6.99-7.05 (m, 1H), 7.13-7.23 (m, 2H). HRMS Calculated for [C$_{15}$H$_{16}$F$_{2}$N$_{2}$O$_{2}$+H]$^+$: 295.1258. Found: 295.1267

Example 124

5-((2R,4S)-2-(2,5-Difluorobenzyl)piperidin-4-yl)isoxazol-3(2H)-one

Step 1: Trans-methyl 2-(2,5-difluorobenzyl)-4-(3-ethoxy-3-oxopropanoyl)piperidine-1-carboxylate and cis-methyl 2-(2,5-difluorobenzyl)-4-(3-ethoxy-3-oxopropanoyl)piperidine-1-carboxylate To a mixture of 2-(2,5-difluorobenzyl)-1-(methoxycarbonyl)piperidine-4-carboxylic acid (7.4 g, 23.62 mmol) (reference compound 54) in anhydrous methyl-THF (150 mL) was added di(1H-imidazol-1-yl)methanone (5.74 g, 35.43 mmol) at room temperature under nitrogen. The suspension was stirred at room temperature for 4 h (flask 1). To a mixture of potassium 3-ethoxy-3-oxopropanoate (7.24 g, 42.52 mmol) in anhydrous methyl-THF (150 mL) was added magnesium chloride (4.05 g, 42.52 mmol) at room temperature under nitrogen. The mixture was heated at 50° C. for 4 h, and then allowed to cool to room temperature (flask 2). The suspension in flask 1 was added to the suspension in flask 2. The reaction mixture was stirred at room temperature for 48 h. The mixture was acidified to pH 1 with 4 M HCl and then water and MTBE was added. The organic phase was separated, washed with water, satd NaHCO$_3$, dried and evaporated. The diastereomers were separated by flash chromatography on silica gel using iso-hexane/EtOAc (100:15 and 100:50) as eluent. Trans-methyl 2-(2,5-difluorobenzyl)-4-(3-ethoxy-3-oxopropanoyl)piperidine-1-carboxylate (1.6 g, 18%) and cis-methyl 2-(2,5-difluorobenzyl)-4-(3-ethoxy-3-oxopropanoyl)piperidine-1-carboxylate (6.2 g, 69%) were isolated as oils. Cis-isomer: $^1$H NMR (400 MHz, cdcl$_3$) δ 1.20-1.32 (m, 3H), 1.64-2.00 (m, 4H), 2.67-3.15 (m, 4H), 3.48 (s, 2H), 3.58 (s, 3H), 3.87-3.99 (m, 1H), 4.07-4.32 (m, 3H), 6.82-7.01 (m, 3H). Trans-isomer: $^1$H NMR (400 MHz, cdcl$_3$) δ 1.22-1.32 (m, 3H), 1.45-2.01 (m, 4H), 2.52-3.12 (m, 4H), 3.41-3.74 (m, 5H), 4.04-4.34 (m, 3H), 4.48-4.74 (m, 1H), 6.82-7.06 (m, 3H). MS m/z 384 (M+H)$^+$ Step 2: Cis-methyl 2-(2,5-difluorobenzyl)-4-(3-oxo-2,3-dihydroisoxazol-5-yl)piperidine-1-carboxylate Cis-methyl 2-(2,5-difluorobenzyl)-4-(3-ethoxy-3-oxopropanoyl)piperidine-1-carboxylate (2.241 g, 5.85 mmol) was dissolved in MeOH (20 mL) and cooled to −40° C. under nitrogen. Sodium hydroxide (0.234 g, 5.85 mmol) dissolved in water (2.000 mL) was added during 10 min and the colourless solution continued to stir at −40° C. for 20 min. Hydroxylamine (50% by weight in water, 0.358 mL, 5.85 mmol) was added during 8 min. The resulting solution was stirred at −40° C. for 3 h. The mixture was then transferred into a prewarmed (80° C.) solution of 6 M hydrogen chloride (30 mL, 180.00 mmol) and the mixture continued to stir at 80° C. for 20 min. The solvent was evaporated and DCM/water added. The phases were separated and the organic phase passed through a phase separator and evaporated to yield a yellow semi-solid. The compound was purified by preparative HPLC in 3 injections on a XBridge C18 column (10 μm 250×50 ID mm) using a gradient of 0-20% Acetonitrile in H2O/MeCN/NH3 95/5/0.2 buffer over 20 minutes with a flow of 100 mL/min. Cis-methyl 2-(2,5-difluorobenzyl)-4-(3-oxo-2,3-dihydroisoxazol-5-yl)piperidine-1-carboxylate (1.259 g, 61%) was isolated as a white solid. $^1$H NMR (400 MHz, cd$_3$od) δ 1.88-2.13 (m, 4H), 2.63-2.83 (m, 2H), 2.99-3.10 (m, 1H), 3.23-3.34 (m, 1H), 3.45 (s, 3H), 3.88-4.00 (m, 1H), 4.35-4.46 (m, 1H), 5.85 (d, 1H), 6.88-7.06 (m, 3H). MS m/z 353 (M+H)$^+$ Step 3: (2R,4S)-Methyl 2-(2,5-difluorobenzyl)-4-(3-oxo-2,3-dihydroisoxazol-5-yl)piperidine-1-carboxylate and (2S,4R)-methyl 2-(2,5-difluorobenzyl)-4-(3-oxo-2,3-dihydroisoxazol-5-yl)-piperidine-1-carboxylate Cis-methyl 2-(2,5-difluorobenzyl)-4-(3-oxo-2,3-dihydroisoxazol-5-yl)piperidine-1-carboxylate (1.259 g, 3.58 mmol) was subjected to chiral preparative HPLC (Column: Chiralpak AD (250×20), 5 μm particle size, mobile phase: Heptane/EtOH/FA 90/10/0.2, flow rate 18 mL/min) to yield (2R,4S)-methyl 2-(2,5-difluorobenzyl)-4-(3-oxo-2,3-dihydroisoxazol-5-yl)piperidine-1-carboxylate (505 mg, 40%), Chiral purity 98.8% ee, Optical rotation $[\alpha]_D^{20}$=−5.7 (acetonitrile, c=1) and (2S,4R)-methyl 2-(2,5-difluorobenzyl)-4-(3-oxo-2,3-dihydroisoxazol-5-yl)piperidine-1-carboxylate (499 mg, 39.6%), Chiral purity 98.8% ee, Optical rotation $[\alpha]_D^{20}$ +3.5 (acetonitrile, c=1).

Step 4: 5-((2R,4S)-2-(2,5-Difluorobenzyl)piperidin-4-yl)isoxazol-3(2H)-one (2R,4S)-methyl 2-(2,5-difluorobenzyl)-4-(3-oxo-2,3-dihydroisoxazol-5-yl)piperidine-1-carboxylate (505 mg, 1.43 mmol) was dissolved in hydrogen bromide (33% in acetic acid, 10 mL, 57.10 mmol) and the mixture stirred at room temperature for 22 h. The solvent was evaporated and the residue purified by preparative HPLC (Instrument: FractionLynx III, Mobilphase: gradient 5-95% MeCN in 0.2% NH$_3$, pH 10, Column: Xbridge Prep C18 5 μm OBD 19*150 mm) to yield 5-((2R,4S)-2-(2,5-difluorobenzyl)piperidin-4-yl)isoxazol-3(2H)-one 299 mg (71%). $^1$H NMR (600 MHz, cd$_3$od) δ 1.49 (q, 1H), 1.71 (dq, 1H), 1.99-2.08 (m, 2H), 2.82-3.00 (m, 4H), 3.24-3.31 (m, 1H), 3.31-3.37 (m, 1H), 5.50 (s, 1H), 6.99-7.13 (m, 3H). HRMS Calculated for [C$_{15}$H$_{16}$F$_2$N$_2$O$_2$+H]$^+$: 295.1258. Found: 295.1244

Example 125

5-((2S,4R)-2-(2,5-Difluorobenzyl)piperidin-4-yl)isoxazol-3(2H)-one (2S,4R)-Methyl 2-(2,5-difluorobenzyl)-4-(3-oxo-2,3-dihydroisoxazol-5-yl)piperidine-1-carboxylate (499 mg, 1.42 mmol) (from example 124, step 3) was dissolved in hydrogen bromide (33% in acetic acid, 10 mL, 57.10 mmol) and the mixture stirred at room temperature for 22 h. The solvent was evaporated and the residue purified by preparative HPLC (Instrument: FractionLynx III, Mobilphase: gradient 5-95% MeCN in 0.2% NH$_3$, pH 10, Column: Xbridge Prep C18 5 μm OBD 19*150 mm) to yield 5-((2S,4R)-2-(2,5-difluorobenzyl)piperidin-4-yl)isoxazol-3(2H)-one (292 mg, 70%). $^1$H NMR (600 MHz, cd$_3$od) δ 1.49 (q, 1H), 1.71 (dq, 1H), 2.00-2.08 (m, 2H), 2.83-2.91 (m, 2H), 2.93-3.00 (m, 2H), 3.25-3.31 (m, 1H), 3.33-3.37 (m, 1H), 5.50 (s, 1H), 6.99-7.12 (m, 3H). HRMS Calculated for [C$_{15}$H$_{16}$F$_2$N$_2$O$_2$+H]$^+$: 295.1258. Found: 295.1254

Example 126

5-(Trans-2-(2,5-difluorobenzyl)piperidin-4-yl)isoxazol-3(2H)-one

Step 1: Trans-methyl 2-(2,5-difluorobenzyl)-4-(3-oxo-2,3-dihydroisoxazol-5-yl)piperidine-1-carboxylate Trans-methyl 2-(2,5-difluorobenzyl)-4-(3-ethoxy-3-oxopropanoyl)piperidine-1-carboxylate (0.611 g, 1.59 mmol) (from example 124, step 1) was dissolved in MeOH (5 mL) and cooled to −40° C. under nitrogen. Sodium hydroxide (0.064 g, 1.59 mmol) dissolved in water (0.500 mL) was added during 10 min and the colourless solution continued to stir at −40° C. for 20 min. Hydroxylamine (50% by weight in water, 0.098 mL, 1.59 mmol) was added during 8 min. The resulting solution was stirred at −40° C. for 3 h. The mixture was then transferred into a prewarmed (80° C.) solution of 6 M hydrogen chloride (8 mL, 48.00 mmol) and the mixture continued to stir at 80° C. for 20 min. The solvent was evaporated and DCM/water added. The phases were separated and the organic phase passed through a phase separator and evaporated to yield crude trans-methyl 2-(2,5-difluorobenzyl)-4-(3-oxo-2,3-dihydroisoxazol-5-yl)piperidine-1-carboxylate (0.552 g, 98%) as a yellow semi-solid. MS m/z 353 (M+H)+

Step 2: 5-(Trans-2-(2,5-difluorobenzyl)piperidin-4-yl)isoxazol-3(2H)-one

Trans-methyl 2-(2,5-difluorobenzyl)-4-(3-oxo-2,3-dihydroisoxazol-5-yl)piperidine-1-carboxylate (148 mg, 0.42 mmol) was dissolved in hydrogen bromide (33% in acetic acid, 3 mL, 17.13 mmol) and the solution stirred at room temperature overnight. The solvent was evaporated and the residue was purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-(2,5-difluorobenzyl)piperidin-4-yl) isoxazol-3(2H)-one (54.7 mg, 44%). $^1$H NMR (400 MHz, cd$_3$od) δ 1.90-2.00 (m, 1H), 2.10-2.25 (m, 3H), 3.05 (d, 2H), 3.09-3.19 (m, 1H), 3.34-3.45 (m, 2H), 3.51-3.61 (m, 1H), 5.81 (d, 1H), 7.02-7.21 (m, 3H). HRMS Calculated for [C$_{15}$H$_{16}$F$_2$N$_2$O$_2$+H]+: 295.1258. Found: 295.1278

Example 127

5-((2R,4S)-2-(2,6-Difluorobenzyl)piperidin-4-yl) isoxazol-3(2H)-one

Step 1: Trans-methyl 2-(2,6-difluorobenzyl)-4-(3-ethoxy-3-oxopropanoyl)piperidine-1-carboxylate and cis-methyl 2-(2,6-difluorobenzyl)-4-(3-ethoxy-3-oxopropanoyl)piperidine-1-carboxylate 2-(2,6-Difluorobenzyl)-1-(methoxycarbonyl)piperidine-4-carboxylic acid (4.72 g, 15.07 mmol) (reference compound 55) was dissolved in methyl THF (108 mL) and di(1H-imidazol-1-yl)methanone (3.66 g, 22.60 mmol) was added. The suspension was stirred at room temperature for 3 h 45 min under nitrogen (flask 1). In a separate flask was to a suspension of potassium 3-ethoxy-3-oxopropanoate (4.62 g, 27.12 mmol) in methyl THF (108 mL) magnesium chloride (2.58 g, 27.12 mmol) added. The suspension was stirred with a large stirring bar for 3.5 h at 50° C. under nitrogen (flask 2). The suspension in flask 1 was added to the suspension in flask 2 and the reaction mixture was then stirred at room temperature overnight. The reaction mixture was acidified to pH 1 with 2 M HCl. MTBE and water were added and the phases were separated. The organic phase was washed with water, satd NaHCO$_3$ and water before it was dried and concentrated. The residue was purified in 2 runs by automated flash chromatography on a Biotage® KP-SIL 340 g column. A gradient from 15% to 50% of EtOAc in heptane over 8 CV (3 CV initial waste+5 CV collected) was used as mobile phase. Trans-methyl 2-(2,6-difluorobenzyl)-4-(3-ethoxy-3-oxopropanoyl) piperidine-1-carboxylate (0.405 g, 7%) and cis-methyl 2-(2, 6-difluorobenzyl)-4-(3-ethoxy-3-oxopropanoyl)piperidine-1-carboxylate (2.404 g, 41%) were isolated. Cis-isomer: $^1$H NMR (400 MHz, cdcl$_3$) δ 1.20-1.33 (m, 3H), 1.68-2.05 (m, 4H), 2.65-2.89 (m, 2H), 2.93-3.16 (m, 2H), 3.49 (s, 5H), 3.96 (dd, 1H), 4.14-4.22 (m, 2H), 4.27-4.40 (m, 1H), 6.77-6.89 (m, 2H), 7.09-7.20 (m, 1H). MS m/z 384 (M+H)+. Trans-isomer: $^1$H NMR (400 MHz, cdcl$_3$) δ 1.22-1.34 (m, 3H), 1.41-2.01 (m, 4H), 2.75-3.20 (m, 4H), 3.37-3.70 (m, 5H), 4.02-4.32 (m, 3H), 4.55-4.85 (m, 1H), 6.81-6.92 (m, 2H), 7.11-7.23 (m, 1H). MS m/z 384 (M+H)+

Step 2: Cis-methyl 2-(2,6-difluorobenzyl)-4-(3-oxo-2,3-dihydroisoxazol-5-yl)piperidine-1-carboxylate Cis-methyl 2-(2,6-difluorobenzyl)-4-(3-ethoxy-3-oxopropanoyl)piperidine-1-carboxylate (2.404 g, 6.27 mmol) was dissolved in MeOH (21 mL) and cooled to −40° C. under nitrogen atmosphere. Sodium hydroxide (0.251 g, 6.27 mmol) dissolved in water (2.100 mL) was added over 8 min. After 20 min with stirring, hydroxylamine (50% by weight in water, 0.384 mL, 6.27 mmol) was added over 6 minutes and the solution was stirred for 3.5 hours at −40° C. The reaction mixture was then rapidly poured into a prewarmed (80° C.) solution of 6 M hydrogen chloride (32.3 mL, 193.76 mmol) and the mixture continued to stir at 80° C. for 25 min. The solvent was evaporated and the crude mixture was redissolved in DCM/water. The organic phase was dried and concentrated. The compound was purified by preparative HPLC on a XBridge C18 column (10 μm 250×50 ID mm) using a gradient of 0-20% Acetonitrile in H2O/MeCN/NH3 95/5/0.2 buffer over 20 minutes with a flow of 100 mL/min. Cis-methyl 2-(2,6-difluorobenzyl)-4-(3-oxo-2,3-dihydroisoxazol-5-yl)piperidine-1-carboxylate (1.232 g, 55.8%) was isolated as a white solid. $^1$H NMR (400 MHz, cd$_3$od) δ 1.94-2.04 (m, 2H), 2.08-2.16 (m, 2H), 2.63-2.73 (m, 1H), 2.81-2.91 (m, 1H), 2.98-3.09 (m, 1H), 3.24-3.37 (m, 4H), 3.88-3.99 (m, 1H), 4.41-4.54 (m, 1H), 5.81 (s, 1H), 6.82-6.92 (m, 2H), 7.16-7.26 (m, 1H). MS m/z 353 (M+H)+

Step 3: (2R,4S)-Methyl 2-(2,6-difluorobenzyl)-4-(3-oxo-2,3-dihydroisoxazol-5-yl)piperidine-1-carboxylate and (2S,4R)-methyl 2-(2,6-difluorobenzyl)-4-(3-oxo-2,3-dihydroisoxazol-5-yl)-piperidine-1-carboxylate Cis-methyl 2-(2,6-difluorobenzyl)-4-(3-oxo-2,3-dihydroisoxazol-5-yl)piperidine-1-carboxylate (1.232 g, 3.5 mmol) was subjected to chiral preparative HPLC (Column: Chiralpak AD (250×20), 5 μm particle size, mobile phase: Heptane/EtOH/FA 90/10/0.2, flow rate 18 mL/min) to yield (2R,4S)-methyl 2-(2,6-difluorobenzyl)-4-(3-oxo-2,3-dihydro-isoxazol-5-yl)piperidine-1-carboxylate (370 mg, 30%), Chiral purity 99.2% ee, Optical rotation [α]$_D^{20}$=−24.4 (acetonitrile, c=1) and (2S,4R)-methyl 2-(2,6-difluorobenzyl)-4-(3-oxo-2,3-dihydroisoxazol-5-yl)piperidine-1-carboxylate yield (344 mg, 28%), Chiral purity 97.6% ee. Optical rotation [α]$_D^{20}$=+22.9 (acetonitrile, c=1)

Step 4: 5-((2R,4S)-2-(2,6-Difluorobenzyl)piperidin-4-yl)isoxazol-3(2H)-one (2R,4S)-methyl 2-(2,6-difluorobenzyl)-4-(3-oxo-2,3-dihydroisoxazol-5-yl)piperidine-1-carboxylate (370 mg, 1.05 mmol) was dissolved in hydrogen bromide (33% in acetic acid, 8 mL, 45.68 mmol) and the mixture stirred at room temperature for 24 h. The solvent was evaporated and the residue purified by preparative HPLC (Instrument: FractionLynx III, Mobilphase: gradient 5-95% MeCN in 0.2% NH$_3$, pH 10, Column: Xbridge Prep C18 5 μm OBD 19*150 mm) to yield 5-((2R,4S)-2-(2,6-difluorobenzyl)piperidin-4-yl) isoxazol-3(2H)-one (254 mg, 82%). $^1$H NMR (600 MHz, cd$_3$od) δ 1.47 (q, 1H), 1.67 (qd, 1H), 2.02 (dd, 2H), 2.78-3.02 (m, 4H), 3.16-3.24 (m, 1H), 3.27-3.33 (m, 1H), 5.49 (s, 1H), 6.98 (t, 2H), 7.27-7.37 (m, 1H). HRMS Calculated for [C$_{15}$H$_{16}$F$_2$N$_2$O$_2$+H]+: 295.1258. Found: 295.1248

Example 128

5-((2S,4R)-2-(2,6-Difluorobenzyl)piperidin-4-yl) isoxazol-3(2H)-one (2S,4R)-Methyl 2-(2,6-difluorobenzyl)-4-(3-oxo-2,3-dihydroisoxazol-5-yl)piperidine-1-carboxylate (344 mg, 0.98 mmol) (from example 127, step 3) was dissolved in hydrogen bromide (33% in acetic acid, 8 mL, 45.68 mmol) and the mixture stirred at room temperature for 24 h. The solvent was evaporated and the residue purified by preparative HPLC (Instrument: FractionLynx III, Mobilphase: gradient 5-95% MeCN in 0.2% $NH_3$, pH 10, Column: Xbridge Prep C18 5 µm OBD 19*150 mm) to yield 5-((2S,4R)-2-(2,6-difluorobenzyl)piperidin-4-yl)isoxazol-3(2H)-one (222 mg, 77%). $^1$H NMR (600 MHz, $cd_3od$) δ 1.47 (q, 1H), 1.68 (dq, 1H), 1.96-2.07 (m, 2H), 2.79-3.02 (m, 4H), 3.18-3.25 (m, 1H), 3.27-3.34 (m, 1H), 5.49 (s, 1H), 6.95-7.01 (m, 2H), 7.28-7.36 (m, 1H). HRMS Calculated for $[C_{15}H_{16}F_2N_2O_2+H]^+$: 295.1258. Found: 295.1240

Example 129

5-(Trans-2-(2,6-difluorobenzyl)piperidin-4-yl)isoxazol-3(2H)-one

Step 1: Trans-methyl 2-(2,6-difluorobenzyl)-4-(3-oxo-2,3-dihydroisoxazol-5-yl)piperidine-1-carboxylate Trans-methyl 2-(2,6-difluorobenzyl)-4-(3-ethoxy-3-oxopropanoyl)piperidine-1-carboxylate (0.399 g, 1.04 mmol) (from example 127, step 1) was dissolved in MeOH (3.5 mL) and cooled to −40° C. under nitrogen atmosphere. Sodium hydroxide (0.306 mL, 1.04 mmol) was added over 5 min. After 45 min with stirring, hydroxylamine (50% by weight in water, 0.064 mL, 1.04 mmol) was added over one minute and the solution was stirred for 3.5 hours at −40° C. The reaction mixture was then rapidly poured into a prewarmed (80° C.) solution of 6 M hydrogen chloride (5.36 mL, 32.16 mmol) and the mixture continued to stir at 80° C. for 20 min. The solvent was evaporated and the crude mixture redissolved in DCM and washed with water. The organic phase was dried and concentrated to give crude trans-methyl 2-(2,6-difluorobenzyl)-4-(3-oxo-2,3-dihydroisoxazol-5-yl)piperidine-1-carboxylate (0.331 g, 90%). MS m/z 353 $(M+H)^+$ Step 2: 5-(Trans-2-(2,6-difluorobenzyl)piperidin-4-yl)isoxazol-3(2H)-one Trans-methyl 2-(2,6-difluorobenzyl)-4-(3-oxo-2,3-dihydroisoxazol-5-yl)piperidine-1-carboxylate (0.329 g, 0.93 mmol) was dissolved in hydrogen bromide (33% in acetic acid, 7.5 mL, 42.82 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 µm OBD 19*150 mm) to yield 5-(trans-2-(2,6-difluorobenzyl)piperidin-4-yl)isoxazol-3(2H)-one (4.6 mg, 1.7%). HRMS Calculated for $[C_{15}H_{16}F_2N_2O_2+H]^+$: 295.1258. Found: 295.1257

Example 130

5-((2R,4S)-2-(3,5-Difluorobenzyl)piperidin-4-yl)isoxazol-3(2H)-one

Step 1: Trans-methyl 2-(3,5-difluorobenzyl)-4-(3-ethoxy-3-oxopropanoyl)piperidine-1-carboxylate and cis-methyl 2-(3,5-difluorobenzyl)-4-(3-ethoxy-3-oxopropanoyl)piperidine-1-carboxylate 2-(3,5-Difluorobenzyl)-1-(methoxycarbonyl)piperidine-4-carboxylic acid (6.87 g, 21.93 mmol) (reference compound 56) was dissolved in methyl THF (150 mL) and di(1H-imidazol-1-yl)methanone (5.33 g, 32.89 mmol) was added. The suspension was stirred at room temperature for 3 hours under nitrogen (flask 1). In a separate flask was to potassium 3-ethoxy-3-oxopropanoate (6.72 g, 39.47 mmol) in methyl THF (150 mL) magnesium chloride (3.76 g, 39.47 mmol) added. The suspension was stirred with a large stirring bar for 3 h at 50° C. (flask 2). The suspension in flask 1 was added to the suspension in flask 2 and the reaction mixture was then stirred at room temperature for 3 days. The reaction mixture was acidified to pH 1 with 2 M HCl. MTBE and water were added and the phases were separated. The organic phase was washed with water, satd NaHCO3 and water before it was dried and concentrated. 60% of the residue was purified in 2 runs by automated flash chromatography on a Biotage® KP-SIL 340 g column. A gradient from 20% to 60% of EtOAc in heptane over 8 CV (3 CV initial waste+5 CV collected) was used as mobile phase. Trans-methyl 2-(3,5-difluorobenzyl)-4-(3-ethoxy-3-oxopropanoyl)piperidine-1-carboxylate (0.92 g, 20%) and cis-methyl 2-(3,5-difluorobenzyl)-4-(3-ethoxy-3-oxopropanoyl)piperidine-1-carboxylate (2.66 g, 57%). Cis-isomer: $^1$H NMR (400 MHz, $cdcl_3$) δ 1.19-1.33 (m, 3H), 1.62-2.00 (m, 4H), 2.65-2.78 (m, 2H), 2.86-3.14 (m, 2H), 3.47 (s, 2H), 3.66 (s, 3H), 3.86-3.98 (m, 1H), 4.13-4.24 (m, 3H), 6.60-6.77 (m, 3H). MS m/z 384 $(M+H)^+$. Trans-isomer: $^1$H NMR (400 MHz, $cdcl_3$) δ 1.21-1.34 (m, 3H), 1.43-2.02 (m, 4H), 2.68-3.06 (m, 4H), 3.46 (s, 2H), 3.51-3.75 (m, 3H), 4.03-4.34 (m, 3H), 4.45-4.73 (m, 1H), 6.61-6.83 (m, 3H). MS m/z 384 $(M+H)^+$ Step 2: Cis-methyl 2-(3,5-difluorobenzyl)-4-(3-oxo-2,3-dihydroisoxazol-5-yl)piperidine-1-carboxylate Cis-methyl 2-(3,5-difluorobenzyl)-4-(3-ethoxy-3-oxopropanoyl)piperidine-1-carboxylate (2.662 g, 6.94 mmol) was dissolved in MeOH (24 mL) and cooled to −40° C. under nitrogen atmosphere. Sodium hydroxide (0.278 g, 6.94 mmol) dissolved in water (2.400 mL) was added over 13 min. After 20 min with stirring, hydroxylamine (50% by weight in water, 0.425 mL, 6.94 mmol) was added over 9 minutes and the solution was stirred for 3.5 hours at −40° C. The reaction mixture was then rapidly poured into a prewarmed (80° C.) solution of 6 M hydrogen chloride (35.8 mL, 214.55 mmol) and the mixture continued to stir at 80° C. for 25 min. The solvent was evaporated and the crude mixture was redissolved in DCM/water. The organic phase was dried and concentrated. The compound was purified by preparative HPLC in 2 injections on a XBridge C18 column (10 µm 250×50 ID mm) using a gradient of 0-25% Acetonitrile in H2O/MeCN/NH3 95/5/0.2 buffer over 20 minutes with a flow of 100 mL/min. Cis-methyl 2-(3,5-difluorobenzyl)-4-(3-oxo-2,3-dihydroisoxazol-5-yl)piperidine-1-carboxylate (1.604 g, 65.6%) was isolated as a white solid. $^1$H NMR (400 MHz, $cd_3od$) δ 1.91-2.07 (m, 4H), 2.62-2.80 (m, 2H), 2.97-3.04 (m, 1H), 3.23-3.34 (m, 1H), 3.54 (s, 3H), 3.89-3.99 (m, 1H), 4.26-4.36 (m, 1H), 5.73 (s, 1H), 6.69-6.79 (m, 3H). MS m/z 353 $(M+H)^+$ Step 3: (2R,4S)-Methyl 2-(3,5-difluorobenzyl)-4-(3-oxo-2,3-dihydroisoxazol-5-yl)piperidine-1-carboxylate and (2S,4R)-methyl 2-(3,5-difluorobenzyl)-4-(3-oxo-2,3-dihydroisoxazol-5-yl)-piperidine-1-carboxylate Cis-methyl 2-(3,5-difluorobenzyl)-4-(3-oxo-2,3-dihydroisoxazol-5-yl)piperidine-1-carboxylate (1.604 g, 4.56 mmol) was subjected to chiral preparative HPLC (Column:

Chiralpak AD (250×20), 5 μm particle size, mobile phase: Heptane/EtOH 90/10, flow rate 18 mL/min) to yield (2R,4S)-methyl 2-(3,5-difluorobenzyl)-4-(3-oxo-2,3-dihydroisoxazol-5-yl)piperidine-1-carboxylate (645 mg, 40%), Chiral purity 99.2% ee, Optical rotation $[\alpha]_D^{20}$=+13.1 (MeOH, c=1) and (2S,4R)-methyl 2-(3,5-difluorobenzyl)-4-(3-oxo-2,3-dihydroisoxazol-5-yl)piperidine-1-carboxylate (789 mg, 49%), Chiral purity 99.6% ee, Optical rotation $[\alpha]_D^{20}$=−10.1 (MeOH, c=1)

Step 4: 5-((2R,4S)-2-(3,5-Difluorobenzyl)piperidin-4-yl)isoxazol-3(2H)-one (2R,4S)-Methyl 2-(3,5-difluorobenzyl)-4-(3-oxo-2,3-dihydroisoxazol-5-yl)piperidine-1-carboxylate (0.645 g, 1.83 mmol) was dissolved in hydrogen bromide (33% in acetic acid, 14.43 mL, 82.38 mmol) and the mixture was stirred at room temperature overnight. The solvent was evaporated and the residue purified by preparative HPLC (Instrument: FractionLynx III, Mobilphase: gradient 5-95% MeCN in 0.2% $NH_3$, pH 10, Column: Xbridge Prep C18 5 μm OBD 19*150 mm) to yield 5-((2R,4S)-2-(3,5-difluorobenzyl)piperidin-4-yl)isoxazol-3(2H)-one (153 mg, 28%). $^1$H NMR (600 MHz, dmso) δ 1.01-1.11 (m, 1H), 1.26-1.38 (m, 1H), 1.68-1.78 (m, 2H), 2.41-2.77 (m, 5H), 2.91-2.99 (m, 1H), 5.67 (s, 1H), 6.92 (d, 2H), 6.99 (s, 1H). HRMS Calculated for $[C_{15}H_{16}F_2N_2O_2+H]^+$: 295.1258. Found: 295.1249

Example 131

5-((2S,4R)-2-(3,5-Difluorobenzyl)piperidin-4-yl)isoxazol-3(2H)-one (2S,4R)-Methyl 2-(3,5-difluorobenzyl)-4-(3-oxo-2,3-dihydroisoxazol-5-yl)piperidine-1-carboxylate (0.789 g, 2.24 mmol) (from example 130, step 3) was dissolved in hydrogen bromide (33% in acetic acid, 17.65 mL, 100.77 mmol) and the mixture was stirred at room temperature overnight. The solvent was evaporated and the residue purified by preparative HPLC (Instrument: FractionLynx III, Mobilphase: gradient 5-95% MeCN in 0.2% $NH_3$, pH 10, Column: Xbridge Prep C18 5 μm OBD 19*150 mm) to yield 5-((2S,4R)-2-(3,5-difluorobenzyl)piperidin-4-yl)isoxazol-3(2H)-one (123 mg, 19%). $^1$H NMR (600 MHz, dmso) δ 1.07 (q, 1H), 1.33 (dq, 1H), 1.71-1.78 (m, 2H), 2.49-2.56 (m, 1H), 2.57-2.71 (m, 3H), 2.72-2.78 (m, 1H), 2.94-2.99 (m, 1H), 5.67 (s, 1H), 6.89-6.94 (m, 2H), 7.00 (tt, 1H). HRMS Calculated for $[C_{15}H_{16}F_2N_2O_2+H]^+$: 295.1258. Found: 295.1248

Example 132

5-((2S,4S)-2-(3,5-Difluorobenzyl)piperidin-4-yl)isoxazol-3(2H)-one

Step 1: Trans-methyl 2-(3,5-difluorobenzyl)-4-(3-oxo-2,3-dihydroisoxazol-5-yl)piperidine-1-carboxylate Trans-methyl 2-(3,5-difluorobenzyl)-4-(3-ethoxy-3-oxopropanoyl)piperidine-1-carboxylate (0.927 g, 2.42 mmol) (from example 130, step 1) was dissolved in MeOH (8 mL) and cooled to −40° C. under nitrogen atmosphere. Sodium hydroxide (0.097 g, 2.42 mmol) dissolved in water (0.800 mL) was added over 7 min. After 20 min with stirring, hydroxylamine (50% by weight in water, 0.148 mL, 2.42 mmol) was added over 4.5 minutes and the solution was stirred for 3.5 hours at −40° C. The reaction mixture was then rapidly poured into a prewarmed (80° C.) solution of 6 M hydrogen chloride (12.45 mL, 74.71 mmol) and the mixture continued to stir at 80° C. for 20 min. The solvent was evaporated and the crude mixture redissolved in DCM and washed with water. The organic phase was dried and concentrated. The compound was purified by preparative HPLC on a XBridge C18 column (10 μm 250×50 ID mm) using a gradient of 0-25% Acetonitrile in H2O/MeCN/NH3 95/5/0.2 buffer over 20 minutes with a flow of 100 mL/min. Trans-methyl 2-(3,5-difluorobenzyl)-4-(3-oxo-2,3-dihydroisoxazol-5-yl)piperidine-1-carboxylate (0.648 g, 76%) was isolated as a white solid. $^1$H NMR (400 MHz, $cd_3od$) δ 1.45-2.12 (m, 4H), 2.80-3.35 (m, 4H), 3.35-3.70 (m, 3H), 4.12 (s, br., 1H), 4.62 (s, br., 1H), 5.71 (s, 1H), 6.77 (t, 1H), 6.87 (s, br., 2H). MS m/z 353 (M+H)$^+$ Step 2: (2S,4S)-Methyl 2-(3,5-difluorobenzyl)-4-(3-oxo-2,3-dihydroisoxazol-5-yl)piperidine-1-carboxylate and (2R,4R)-methyl 2-(3,5-difluorobenzyl)-4-(3-oxo-2,3-dihydroisoxazol-5-yl)piperidine-1-carboxylate Trans-methyl 2-(3,5-difluorobenzyl)-4-(3-oxo-2,3-dihydroisoxazol-5-yl)piperidine-1-carboxylate (0.648 g, 1.84 mmol) was subjected to chiral preparative HPLC (Column: Chiralpak AD (250×20), 5 μm particle size, mobile phase: Heptane/EtOH 70/30, flow rate 18 mL/min) to yield (2S,4S)-methyl 2-(3,5-difluorobenzyl)-4-(3-oxo-2,3-dihydroisoxazol-5-yl)piperidine-1-carboxylate 249 mg (38%), Chiral purity 99.9% ee, Optical rotation $[\alpha]_D^{20}$=+27.1 (acetonitrile, c=1) and (2R,4R)-methyl 2-(3,5-difluorobenzyl)-4-(3-oxo-2,3-dihydroisoxazol-5-yl)piperidine-1-carboxylate (244 mg, 37%), Chiral purity 99.9% ee, Optical rotation $[\alpha]_D^{20}$=−26.4 (acetonitrile, c=1)

Step 3: 5-((2S,4S)-2-(3,5-Difluorobenzyl)piperidin-4-yl)isoxazol-3(2H)-one (2S,4S)-Methyl 2-(3,5-difluorobenzyl)-4-(3-oxo-2,3-dihydroisoxazol-5-yl)piperidine-1-carboxylate (0.249 g, 0.71 mmol) was dissolved in hydrogen bromide (33% in acetic acid, 5.57 mL, 31.80 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2S,4S)-2-(3,5-difluorobenzyl)piperidin-4-yl)isoxazol-3(2H)-one (34 mg, 16%). $^1$H NMR (400 MHz, $cd_3od$) δ 1.70-2.16 (m, 4H), 2.84-3.43 (m, 6H), 5.57 (s, 1H), 6.81-7.02 (m, 3H). HRMS Calculated for $[C_{15}H_{16}F_2N_2O_2+H]^+$: 295.1258. Found: 295.1254

Example 133

5-((2R,4R)-2-(3,5-Difluorobenzyl)piperidin-4-yl)isoxazol-3(2H)-one (2R,4R)-Methyl 2-(3,5-difluorobenzyl)-4-(3-oxo-2,3-dihydroisoxazol-5-yl)piperidine-1-carboxylate (0.244 g, 0.69 mmol) was dissolved in hydrogen bromide (33% in acetic acid, 5.46 mL, 31.16 mmol) and the mixture was stirred at room temperature overnight. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4R)-2-(3,5-difluorobenzyl)piperidin-4-yl)isoxazol-3(2H)-one (51 mg, 25%). $^1$H NMR (600 MHz, dmso) δ 1.44-1.51 (m, 1H), 1.65-1.80 (m, 3H), 2.52-2.60 (m, 1H), 2.65-2.70 (m, 2H), 2.76-2.83 (m, 1H), 2.86-2.94 (m, 1H), 3.09-3.14 (m, 1H), 5.74 (s, 1H), 6.90-6.95 (m, 2H), 7.00 (tt, 1H). HRMS Calculated for $[C_{15}H_{16}F_2N_2O_2+H]^+$: 295.1258. Found: 295.1276

Example 134

5-((2R,4S)-2-(2,4-Difluorobenzyl)piperidin-4-yl)isoxazol-3(2H)-one

Step 1: Trans-methyl 2-(2,4-difluorobenzyl)-4-(3-ethoxy-3-oxopropanoyl)piperidine-1-carboxylate and cis-methyl 2-(2,4-difluorobenzyl)-4-(3-ethoxy-3-oxopropanoyl)piperidine-1-carboxylate Magnesium chloride (4.55 g, 47.75 mmol) and potassium 3-ethoxy-3-oxopropanoate (8 g, 47.00 mmol) were dissolved in methyl THF (100 mL) under nitrogen and the resulting suspension was stirred at 50° C. with an oversized stirring bar for 6 h 30 min, then cooled to room temperature (flask 1). To a suspension of 2-(2,4-difluorobenzyl)-1-(methoxycarbonyl)piperidine-4-carboxylic acid (7.48 g, 23.88 mmol) (reference compound 57) in methyl THF (100 mL) was added di(1H-imidazol-1-yl)methanone (5.81 g, 35.81 mmol) under nitrogen. The resulting mixture was stirred at room temperature for 1 h 20 min (flask 2). The contents of flask 2 is transferred into flask 1 by transfer needle. Wash with methyl THF (30 mL). The resulting suspension was stirred at room temperature for 16 h. 3.8 M HCl was added (ca. 200 mL) and the resulting biphasic mixture stirred vigorously for 30 min. Water and MTBE were added and the phases separated. The organic phase was washed with water, satd NaHCO$_3$ and water, then dried over MgSO$_4$ and evaporated. The residue was purified via Biotage (Biotage® KP-SIL 340 g column, 1 CV 20% EtOAc in heptanes, then 20%=>60% over 7 CV). Trans-methyl 2-(2,4-difluorobenzyl)-4-(3-ethoxy-3-oxopropanoyl)piperidine-1-carboxylate (1.18 g, 13%) and cis-methyl 2-(2,4-difluorobenzyl)-4-(3-ethoxy-3-oxopropanoyl)piperidine-1-carboxylate (4.17 g, 45%) were isolated as yellow oils. Cis-isomer: $^1$H NMR (400 MHz, cdcl$_3$) δ 1.20-1.32 (m, 3H), 1.59-1.99 (m, 4H), 2.66-3.12 (m, 4H), 3.48 (s, 2H), 3.55 (s, 3H), 3.89-3.98 (m, 1H), 4.07-4.29 (m, 3H), 6.71-6.83 (m, 2H), 7.05-7.17 (m, 1H). MS m/z 384 (M+H)$^+$. Trans-isomer: $^1$H NMR (400 MHz, cdcl$_3$) δ 1.19-1.35 (m, 3H), 1.42-2.02 (m, 4H), 2.65-3.11 (m, 4H), 3.38-3.75 (m, 5H), 4.02-4.34 (m, 3H), 4.45-4.70 (m, 1H), 6.73-6.89 (m, 2H), 7.03-7.34 (m, 1H). MS m/z 384 (M+H)$^+$ Step 2: Cis-methyl 2-(2,4-difluorobenzyl)-4-(3-oxo-2,3-dihydroisoxazol-5-yl)piperidine-1-carboxylate Cis-methyl 2-(2,4-difluorobenzyl)-4-(3-ethoxy-3-oxopropanoyl)piperidine-1-carboxylate (2.46 g, 6.42 mmol) was dissolved in MeOH (20 mL) and cooled to −40° C. Sodium hydroxide (0.257 g, 6.42 mmol) dissolved in water (2 mL) was added over 5 min and the resulting solution was stirred at −40° C. for 20 min. Then hydroxylamine (50% by weight in water, 0.4 mL, 6.53 mmol) was added over 1 min and stirring continued at −40° C. for 1 h 15 min. The reaction mixture was then transferred into a prewarmed (80° C.) solution of 6 M hydrogen chloride (30 mL, 180.00 mmol) and the mixture was continued to be stirred at 80° C. for 35 min. Then cooled to room temperature. Methanol was evaporated, then water was added. Extracted three times with DCM. Combined organic layers dried over MgSO$_4$ and evaporated. The residue was purified by preparative HPLC on a Kromasil C8 column (10 µm 250×50 ID mm) using a gradient of 15-60% Acetonitrile in H2O/MeCN/Acetic Acid 95/5/0.2 buffer over 30 minutes with a flow of 100 mL/min. Cis-methyl 2-(2,4-difluorobenzyl)-4-(3-oxo-2,3-dihydroisoxazol-5-yl)piperidine-1-carboxylate (1.62 g, 72%) was isolated as a colorless foam. $^1$H NMR (400 MHz, cd$_3$od) δ 1.90-2.10 (m, 4H), 2.65-2.80 (m, 2H), 3.04 (p, 1H), 3.19-3.34 (m, 1H), 3.44 (s, 3H), 3.94 (ddd, 1H), 4.32-4.44 (m, 1H), 5.85 (s, 1H), 6.78-6.90 (m, 2H), 7.09-7.20 (m, 1H). MS m/z 353 (M+H)$^+$ Step 3: (2R,4S)-Methyl 2-(2,4-difluorobenzyl)-4-(3-oxo-2,3-dihydroisoxazol-5-yl)piperidine-1-carboxylate and (2S,4R)-methyl 2-(2,4-difluorobenzyl)-4-(3-oxo-2,3-dihydroisoxazol-5-yl)-piperidine-1-carboxylate Cis-methyl 2-(2,4-difluorobenzyl)-4-(3-oxo-2,3-dihydroisoxazol-5-yl)piperidine-1-carboxylate (1.62 g, 4.6 mmol) was subjected to chiral preparative HPLC (Column: Chiralpak AD (250×20), 5 µm particle size, mobile phase: Heptane/EtOH/FA 90/10/0.2, flow rate 18 mL/min) to yield (2R,4S)-methyl 2-(2,4-difluorobenzyl)-4-(3-oxo-2,3-dihydroisoxazol-5-yl)piperidine-1-carboxylate (799 mg, 49%), Chiral purity 99.9% ee, Optical rotation $[\alpha]_D^{20}$=−4.0 (acetonitrile, c=1) and (2S,4R)-methyl 2-(2,4-difluorobenzyl)-4-(3-oxo-2,3-dihydroisoxazol-5-yl)piperidine-1-carboxylate (734 mg, 45%), Chiral purity 99.5% ee, Optical rotation $[\alpha]_D^{20}$=+4.5 (acetonitrile, c=1).

Step 4: 5-((2R,4S)-2-(2,4-Difluorobenzyl)piperidin-4-yl)isoxazol-3(2H)-one (2R,4S)-Methyl 2-(2,4-difluorobenzyl)-4-(3-oxo-2,3-dihydroisoxazol-5-yl)piperidine-1-carboxylate (399 mg, 1.13 mmol) was dissolved in hydrogen bromide (33% in acetic acid (8.2 mL, 46.87 mmol) and stirred at room temperature for 16 h. The solvent was removed in vacuo and the residue purified by preparative HPLC (Instrument: FractionLynx III, Mobilphase: gradient 5-95% MeCN in 0.2% NH$_3$, pH 10, Column: Xbridge Prep C18 5 µm OBD 19*150 mm) to yield 5-((2R,4S)-2-(2,4-difluorobenzyl)piperidin-4-yl)isoxazol-3(2H)-one (146 mg, 44%). $^1$H NMR (400 MHz, cd$_3$od) δ 1.43 (q, 1H), 1.67 (dq, 1H), 1.99-2.12 (m, 2H), 2.79-2.97 (m, 4H), 3.14-3.24 (m, 1H), 3.27-3.35 (m, 1H), 5.52 (s, 1H), 6.91-7.02 (m, 2H), 7.27-7.36 (m, 1H). HRMS Calculated for $[C_{15}H_{16}F_2N_2O_2+H]^+$: 295.1258. Found: 295.1252

Example 135

5-((2S,4R)-2-(2,4-Difluorobenzyl)piperidin-4-yl)isoxazol-3(2H)-one (2S,4R)-Methyl 2-(2,4-difluorobenzyl)-4-(3-oxo-2,3-dihydroisoxazol-5-yl)piperidine-1-carboxylate 367 mg, 1.04 mmol) (from example 134, step 3) was dissolved in hydrogen bromide (33% in acetic acid, 8.2 mL, 46.87 mmol) and stirred at room temperature for 16 h. The solvent was removed in vacuo and the residue purified by preparative HPLC (Instrument: FractionLynx III, Mobilphase: gradient 5-95% MeCN in 0.2% NH$_3$, pH 10, Column: Xbridge Prep C18 5 µm OBD 19*150 mm) to yield 5-((2S,4R)-2-(2,4-difluorobenzyl)piperidin-4-yl)isoxazol-3(2H)-one (144 mg, 47%). $^1$H NMR (400 MHz, cd$_3$od) δ 1.43 (q, 1H), 1.67 (dq, 1H), 2.01-2.11 (m, 2H), 2.79-2.96 (m, 4H), 3.14-3.23 (m, 1H), 3.27-3.35 (m, 1H), 5.52 (s, 1H), 6.92-7.01 (m, 2H), 7.28-7.35 (m, 1H). HRMS Calculated for $[C_{15}H_{16}F_2N_2O_2+H]^+$: 295.1258. Found: 295.1259

Example 136

Step 1: Trans-methyl 2-(2,4-difluorobenzyl)-4-(3-oxo-2,3-dihydroisoxazol-5-yl)piperidine-1-carboxylate Trans-methyl 2-(2,4-difluorobenzyl)-4-(3-ethoxy-3-oxopropanoyl)piperidine-1-carboxylate (1.18 g, 3.08 mmol) (from example 134, step 1) was dissolved in MeOH (15 mL) and cooled to −40° C. Sodium hydroxide (0.123 g, 3.08 mmol) dissolved in water (1.7 mL) was added over 1 min and the resulting solution was stirred at −40° C. for 20 min. Then hydroxylamine (50% by weight in water, 0.2 mL, 3.26 mmol) was added over 1 min and stirring continued at −40° C. for 2 h. The reaction mixture was then transferred into a prewarmed (80° C.) solution of 6 M hydrogen chloride (30 mL, 180.00 mmol) and the mixture was continued to be stirred at 80° C. for 1 h. Then cooled to room temperature. Methanol was evaporated, then water was added. Extracted three times with DCM. Combined organic layers dried over $MgSO_4$ and evaporated. Crude trans-methyl 2-(2,4-difluorobenzyl)-4-(3-oxo-2,3-dihydroisoxazol-5-yl)piperidine-1-carboxylate (1.1 g, 101%) was isolated as a pale orange foam. $^1$H NMR (500 MHz, $cdcl_3$) δ 1.43-2.15 (m, 4H), 2.66-3.23 (m, 4H), 3.39-3.79 (m, 3H), 4.04-4.41 (m, 1H), 4.45-4.78 (m, 1H), 5.67 (s, 1H), 6.73-6.90 (m, 2H), 7.03-7.37 (m, 1H). MS m/z 353 $(M+H)^+$

Step 2: 5-(Trans-2-(2,4-difluorobenzyl)piperidin-4-yl)isoxazol-3(2H)-one

Trans-methyl 2-(2,4-difluorobenzyl)-4-(3-oxo-2,3-dihydroisoxazol-5-yl)piperidine-1-carboxylate (0.25 g, 0.71 mmol) was dissolved in hydrogen bromide (33% in acetic acid, 6.21 mL, 35.48 mmol) and stirred at room temperature for 16 h. The solvents were evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-(trans-2-(2,4-difluorobenzyl)piperidin-4-yl)isoxazol-3 (2H)-one (94.6 mg, 45%). $^1$H NMR (600 MHz, dmso) δ 1.43-1.51 (m, 1H), 1.63-1.78 (m, 3H), 2.52-2.60 (m, 1H), 2.65 (d, 2H), 2.76-2.87 (m, 2H), 3.08-3.13 (m, 1H), 5.67 (s, 1H), 6.98 (td, 1H), 7.12 (td, 1H), 7.27-7.34 (m, 1H). HRMS Calculated for $[C_{15}H_{16}F_2N_2O_2+H]^+$: 295.1258. Found: 295.1265

Example 137

5-((2R,4S)-2-(3-Fluoro-5-(trifluoromethyl)benzyl)piperidin-4-yl)isoxazol-3(2H)-one

Step 1: Trans-methyl 4-(3-ethoxy-3-oxopropanoyl)-2-(3-fluoro-5-(trifluoromethyl)benzyl)-piperidine-1-carboxylate and cis-methyl 4-(3-ethoxy-3-oxopropanoyl)-2-(3-fluoro-5-(trifluoromethyl)benzyl)piperidine-1-carboxylate Magnesium chloride (2.3 g, 24.16 mmol) and potassium 3-ethoxy-3-oxopropanoate (4 g, 23.50 mmol) were suspended in methyl THF (70 mL) under nitrogen and the resulting suspension was stirred at 50° C. with an oversized stirring bar for 18 h, then cooled to room temperature (flask 1). To a suspension of 2-(3-fluoro-5-(trifluoromethyl)benzyl)-1-(methoxycarbonyl)piperidine-4-carboxylic acid (4.58 g, 12.61 mmol) (reference compound 58) in methyl THF (70.0 mL) was added di(1H-imidazol-1-yl)methanone (3.36 g, 20.72 mmol) under nitrogen. The resulting mixture was stirred at room temperature for 2 h (flask 2). The contents of flask 2 is transferred into flask 1 by transfer needle. Wash with methyl THF (30 mL). Resulting suspension stirred at room temperature for 72 h. 3.8 M HCl was added (ca. 200 mL) and the resulting biphasic mixture stirred vigorously for 30 min. MTBE was added and the phases separated. The organic phase was washed with water, satd $NaHCO_3$ and water, then dried over $MgSO_4$ and evaporated. The residue was purified via Biotage (Biotage® KP-SIL 340 g column, 1 CV 20% EtOAc in heptanes, then 20%=>60% over 7 CV). Trans-methyl 4-(3-ethoxy-3-oxopropanoyl)-2-(3-fluoro-5-(trifluoromethyl)benzyl)-piperidine-1-carboxylate (758 mg, 14%) and cis-methyl 4-(3-ethoxy-3-oxopropanoyl)-2-(3-fluoro-5-(trifluoromethyl)benzyl)piperidine-1-carboxylate (2.52 g, 46%) were isolated. Cis-isomer: $^1$H NMR (600 MHz, $cdcl_3$) δ 1.20-1.28 (m, 3H), 1.64-1.95 (m, 4H), 2.68-2.81 (m, 2H), 2.95 (dd, 1H), 3.02 (ddd, 1H), 3.45 (s, 2H), 3.59 (s, 3H), 3.84-3.96 (m, 1H), 4.06-4.23 (m, 3H), 7.04-7.11 (m, 1H), 7.15 (d, 1H), 7.19-7.24 (m, 1H). MS m/z 434 $(M+H)^+$. Trans-isomer: $^1$H NMR (600 MHz, $cdcl_3$) δ 1.20-1.29 (m, 3H), 1.43-1.99 (m, 4H), 2.75-2.89 (m, 1H), 2.89-3.04 (m, 3H), 3.36-3.72 (m, 5H), 4.03-4.33 (m, 3H), 4.49-4.72 (m, 1H), 6.98-7.20 (m, 2H), 7.20-7.28 (m, 1H).

Step 2: Cis-methyl 2-(3-fluoro-5-(trifluoromethyl)benzyl)-4-(3-oxo-2,3-dihydroisoxazol-5-yl)piperidine-1-carboxylate Cis-methyl 4-(3-ethoxy-3-oxopropanoyl)-2-(3-fluoro-5-(trifluoromethyl)benzyl)piperidine-1-carboxylate (2.52 g, 5.81 mmol) was dissolved in MeOH (20 mL) and cooled to −40° C. Sodium hydroxide (0.246 g, 6.15 mmol) dissolved in water (2.2 mL) was added over 1 min and the resulting solution was stirred at −40° C. for 20 min. Then hydroxylamine (50% by weight in water, 0.38 mL, 6.20 mmol) was added over 1 min and stirring continued at −40° C. for 2 h 20 min. The reaction mixture was then transferred into a prewarmed (80° C.) solution of 6 M hydrogen chloride (40 mL, 240.00 mmol) and the mixture was continued to be stirred at 80° C. for 1 h. Then cooled to room temperature. Methanol was evaporated, then water was added. Extracted three times with DCM. Combined organic layers dried over $MgSO_4$ and evaporated. The compound was purified by preparative HPLC in 3 injections on a XBridge C18 column (10 μm 250×50 ID mm) using a gradient of 0-35% Acetonitrile in H2O/MeCN/NH3 95/5/0.2 buffer over 25 minutes with a flow of 100 mL/min. Cis-methyl 2-(3-fluoro-5-(trifluoromethyl)benzyl)-4-(3-oxo-2,3-dihydroisoxazol-5-yl)piperidine-1-carboxylate (1.52 g, 65%) was isolated as a colorless foam. $^1$H NMR (600 MHz, $cdcl_3$) δ 1.87-2.10 (m, 4H), 2.61-2.67 (m, 1H), 2.80-2.87 (m, 1H), 2.97-3.04 (m, 1H), 3.13-3.21 (m, 1H), 3.60 (s, 3H), 3.96-4.04 (m, 1H), 4.26-4.32 (m, 1H), 5.74 (s, 1H), 7.00 (d, 1H), 7.11-7.16 (m, 2H). MS m/z 403 $(M+H)^+$

Step 3: (2R,4S)-Methyl 2-(3-fluoro-5-(trifluoromethyl)benzyl)-4-(3-oxo-2,3-dihydroisoxazol-5-yl)piperidine-1-carboxylate and (2S,4R)-methyl 2-(3-fluoro-5-(trifluoromethyl)benzyl)-4-(3-oxo-2,3-dihydroisoxazol-5-yl)piperidine-1-carboxylate Cis-Methyl 2-(3-fluoro-5-(trifluoromethyl)benzyl)-4-(3-oxo-2,3-dihydroisoxazol-5-yl)-piperidine-1-carboxylate (1.47 g, 3.66 mmol) was subjected to chiral preparative HPLC (Column: Chiralcel OJ (250×20), 5 μm particle size, mobile phase: Heptane/EtOH 90/10, flow rate 18 mL/min) to yield (2R,4S)-methyl 2-(3-fluoro-5-(trifluoromethyl)benzyl)-4-

(3-oxo-2,3-dihydroisoxazol-5-yl)piperidine-1-carboxylate (703 mg, 47.8%), Chiral purity 99.3% ee, Optical rotation $[\alpha]_D^{20}$=+5.5 (acetonitrile, c=1) and (2S,4R)-methyl 2-(3-fluoro-5-(trifluoromethyl)benzyl)-4-(3-oxo-2,3-dihydroisoxazol-5-yl)piperidine-1-carboxylate (675 mg, 45.9%), Chiral purity 99.7% ee, Optical rotation $[\alpha]_D^{20}$=−5.1 (acetonitrile, c=1)

Step 4: 5-((2R,4S)-2-(3-Fluoro-5-(trifluoromethyl) benzyl)piperidin-4-yl)isoxazol-3(2H)-one (2R,4S)-Methyl 2-(3-fluoro-5-(trifluoromethyl)benzyl)-4-(3-oxo-2,3-dihydroisoxazol-5-yl)piperidine-1-carboxylate (0.703 g, 1.75 mmol) was dissolved in hydrogen bromide (33% in AcOH, 5 mL, 71.37 mmol) and stirred at room temperature overnight. The solvents were evaporated and the residue purified by preparative HPLC (Instrument: FractionLynx II, Mobilphase: gradient 5-95% MeCN, pH 10, Column: Xbridge Prep C18 5 µm OBD 19*150 mm) to yield 5-((2R,4S)-2-(3-fluoro-5-(trifluoromethyl)benzyl)piperidin-4-yl)isoxazol-3(2H)-one (375 mg, 62%). $^1$H NMR (600 MHz, dmso) δ 1.08 (q, 1H), 1.31 (dq, 1H), 1.71-1.80 (m, 2H), 2.48-2.54 (m, 1H), 2.63-2.80 (m, 4H), 2.92-2.99 (m, 1H), 5.65 (s, 1H), 7.37-7.46 (m, 3H). HRMS Calculated for $[C_{16}H_{16}F_4N_2O_2+H]^+$: 345.1226. Found: 345.1228

Example 138

5-((2S,4R)-2-(3-Fluoro-5-(trifluoromethyl)benzyl) piperidin-4-yl)isoxazol-3(2H)-one (2S,4R)-Methyl 2-(3-fluoro-5-(trifluoromethyl)benzyl)-4-(3-oxo-2,3-dihydroisoxazol-5-yl)piperidine-1-carboxylate (0.675 g, 1.68 mmol) (from example 137, step 3) was dissolved in hydrogen bromide (33% in AcOH, 5 mL, 71.37 mmol) and stirred at room temperature overnight. The solvents were evaporated and the residue purified by preparative HPLC (Instrument: FractionLynx II, Mobilphase: gradient 5-95% MeCN, pH 10, Column: Xbridge Prep C18 5 µm OBD 19*150 mm) to yield 5-((2S,4R)-2-(3-fluoro-5-(trifluoromethyl)benzyl)-piperidin-4-yl)isoxazol-3(2H)-one (443 mg, 77%). $^1$H NMR (600 MHz, dmso) δ 1.08 (q, 1H), 1.31 (dq, 1H), 1.75 (t, 2H), 2.48-2.54 (m, 1H), 2.64-2.79 (m, 4H), 2.96 (d, 1H), 5.65 (s, 1H), 7.38-7.46 (m, 3H). HRMS Calculated for $[C_{16}H_{16}F_4N_2O_2+H]^+$: 345.1226. Found: 345.1212.

Example 139

5-(Trans-2-(3-fluoro-5-(trifluoromethyl)benzyl)piperidin-4-yl)isoxazol-3(2H)-one Step 1: Trans-methyl 2-(3-fluoro-5-(trifluoromethyl) benzyl)-4-(3-oxo-2,3-dihydroisoxazol-5-yl)piperidine-1-carboxylate Trans-methyl 4-(3-ethoxy-3-oxopropanoyl)-2-(3-fluoro-5-(trifluoromethyl)benzyl)piperidine-1-carboxylate (0.75 g, 1.73 mmol) (from example 137, step 1) was dissolved in MeOH (15 mL) and cooled to −40° C. Sodium hydroxide (0.073 g, 1.82 mmol) dissolved in water (1 mL) was added over 1 min and the resulting solution was stirred at −40° C. for 20 min. Then hydroxylamine (50% by weight in water, 0.115 mL, 1.88 mmol) was added over 1 min and stirring continued at −40° C. for 2 h 20 min. The reaction mixture was then transferred into a prewarmed (80° C.) solution of 6 M hydrogen chloride (30 mL, 180.00 mmol) and the mixture was continued to be stirred at 80° C. for 1 h. Then cooled to room temperature. Methanol was evaporated, then water was added. Extracted three times with DCM. Combined organic layers dried over MgSO$_4$ and evaporated. Trans-methyl 2-(3-fluoro-5-(trifluoromethyl)benzyl)-4-(3-oxo-2,3-dihydroisoxazol-5-yl)piperidine-1-carboxylate (658 mg, 95%) was isolated as an off-white solid. MS m/z 403 (M+H)$^+$ Step 2: 5-(Trans-2-(3-fluoro-5-(trifluoromethyl)benzyl)piperidin-4-yl)isoxazol-3(2H)-one Trans-methyl 2-(3-fluoro-5-(trifluoromethyl)benzyl)-4-(3-oxo-2,3-dihydroisoxazol-5-yl)piperidine-1-carboxylate (0.255 g, 0.63 mmol) was dissolved in hydrogen bromide (33% in acetic acid, 5 mL, 71.37 mmol) and stirred at room temperature for 1 week. The solvents were evaporated and the residue purified by preparative HPLC (Instrument: FractionLynx III, Mobilphase: gradient 5-95% MeCN in 0.2% NH$_3$, pH 10, Column: Xbridge Prep C18 5 µm OBD 19*150 mm) to yield 5-(trans-2-(3-fluoro-5-(trifluoromethyl)benzyl)piperidin-4-yl)isoxazol-3(2H)-one (172 mg, 79%). $^1$H NMR (600 MHz, dmso) δ 1.43-1.51 (m, 1H), 1.62-1.80 (m, 3H), 2.51-2.58 (m, 1H), 2.71-2.82 (m, 3H), 2.86-2.94 (m, 1H), 3.07-3.14 (m, 1H), 5.72 (s, 1H), 7.37-7.46 (m, 3H). HRMS Calculated for $[C_{16}H_{16}F_4N_2O_2+H]^+$: 345.1226. Found: 345.1241

Example 140

5-((2R,4S)-2-(3-Fluoro-4-(trifluoromethyl)benzyl) piperidin-4-yl)isoxazol-3(2H)-one Step 1: Trans-methyl 4-(3-ethoxy-3-oxopropanoyl)-2-(3-fluoro-4-(trifluoromethyl)benzyl)-piperidine-1-carboxylate and cis-methyl 4-(3-ethoxy-3-oxopropanoyl)-2-(3-fluoro-4-(trifluoromethyl)benzyl) piperidine-1-carboxylate Magnesium chloride (3.25 g, 34.13 mmol) and potassium 3-ethoxy-3-oxopropanoate (5.82 g, 34.19 mmol) were suspended under a nitrogen atmosphere in methyl THF (100 mL) and stirred with an oversized stirring bar at 50° C. for 18 h, then cooled to room temperature (flask 1). To a suspension of 2-(3-fluoro-4-(trifluoromethyl)benzyl)-1-(methoxycarbonyl)piperidine-4-carboxylic acid (6.56 g, 18.06 mmol) (reference compound 59) in methyl THF (100 mL) was added di(1H-imidazol-1-yl)methanone (4.77 g, 29.42 mmol) under nitrogen. The resulting mixture was stirred at room temperature for 2 h (flask 2). The contents of flask 2 is transferred into flask 1 by transfer needle. Wash with methyl THF (30 mL). Resulting suspension stirred at room temperature for 18 h. 3.8 M HCl was added (ca. 200 mL) and the resulting biphasic mixture stirred vigorously for 30 min. MTBE was added and the phases separated. The organic phase was washed with water, satd NaHCO$_3$ and water, then dried over MgSO$_4$ and evaporated. The residue was purified via Biotage (Biotage® KP-SIL 340 g column, 1 CV 20% EtOAc in heptanes, then 20%=>60% over 7 CV). Trans-methyl 4-(3-ethoxy-3-oxopropanoyl)-2-(3-fluoro-4-(trifluoromethyl)benzyl)piperidine-1-carboxylate (0.794 g, 10%) and cis-methyl 4-(3-ethoxy-3-oxopropanoyl)-2-(3-fluoro-4-(trifluoromethyl)-benzyl)piperidine-1-carboxylate (3.57 g, 45%) were isolated as pale yellow oils. Cis-isomer: MS m/z 434 (M+H)$^+$. Trans-isomer: MS m/z 434 (M+H)$^+$ Step 2: Cis-methyl 2-(3-fluoro-4-(trifluoromethyl) benzyl)-4-(3-oxo-2,3-dihydroisoxazol-5-yl)piperidine-1-carboxylate Cis-methyl 4-(3-ethoxy-3-oxopropanoyl)-2-(3-fluoro-4-(trifluoromethyl)benzyl)piperidine-1-carboxylate (2.033 g, 4.69 mmol) was dissolved in MeOH (20 mL) and cooled to −40° C. Sodium hydroxide (0.188 g, 4.69 mmol) dissolved in water (2.4 mL) was added over 1 min and the resulting solution was stirred at −40° C. for 20 min. Then hydroxylamine (50% by weight in water, 0.3 mL, 4.90 mmol) was added over 1 min and stirring continued at −40° C. for 2 h 20 min. The reaction mixture was then transferred into a prewarmed (80° C.) solution of 6 M hydrogen chloride (40 mL, 240.00 mmol) and the mixture was continued to be stirred at 80° C. for 1 h. Then cooled to room temperature. Methanol was evaporated, then water was added. Extracted three times with DCM. Combined organic layers dried over $MgSO_4$ and evaporated. Product was pale yellow oil. The compound was purified by preparative HPLC in 3 injections on a XBridge C18 column (10 μm 250×50 ID mm) using a gradient of 0-35% Acetonitrile in H2O/MeCN/NH3 95/5/0.2 buffer over 25 minutes with a flow of 100 mL/min. Cis-methyl 2-(3-fluoro-4-(trifluoromethyl)benzyl)-4-(3-oxo-2,3-dihydroisoxazol-5-yl)-piperidine-1-carboxylate (1.32 g, 70%) was isolated as a colorless foam. $^1$H NMR (600 MHz, $cdcl_3$) δ 1.84-1.99 (m, 3H), 1.99-2.10 (m, 1H), 2.62 (dd, 1H), 2.82 (dd, 1H), 2.92-3.06 (m, 1H), 3.10-3.19 (m, 1H), 3.59 (s, 3H), 3.93-4.03 (m, 1H), 4.19-4.34 (m, 1H), 5.73 (s, 1H), 6.91-6.99 (m, 2H), 7.46 (t, 1H). MS m/z 403 (M+H)$^+$ Step 3: (2R,4S)-Methyl 2-(3-fluoro-4-(trifluoromethyl)benzyl)-4-(3-oxo-2,3-dihydroisoxazol-5-yl)piperidine-1-carboxylate and (2S,4R)-methyl 2-(3-fluoro-4-(trifluoromethyl)benzyl)-4-(3-oxo-2,3-dihydroisoxazol-5-yl)piperidine-1-carboxylate Cis-methyl 2-(3-fluoro-4-(trifluoromethyl)benzyl)-4-(3-oxo-2,3-dihydroisoxazol-5-yl)-piperidine-1-carboxylate (1.32 g, 3.28 mmol) was subjected to chiral preparative HPLC (Column: Chiralpak AD (250×20), 5 μm particle size, mobile phase: Heptane/EtOH 85/15, flow rate 18 mL/min) to yield (2R,4S)-methyl 2-(3-fluoro-4-(trifluoromethyl)benzyl)-4-(3-oxo-2,3-dihydroisoxazol-5-yl)piperidine-1-carboxylate (594 mg, 46%), Chiral purity 99.5% ee, Optical rotation $[α]_D^{20}$=+9.1 (acetonitrile, c=1) and (2S,4R)-methyl 2-(3-fluoro-4-(trifluoromethyl)benzyl)-4-(3-oxo-2,3-dihydroisoxazol-5-yl)piperidine-1-carboxylate (589 mg, 45%), Chiral purity 99.2% ee, Optical rotation $[α]_D^{20}$=−8.8 (acetonitrile, c=1)

Step 4: 5-((2R,4S)-2-(3-Fluoro-4-(trifluoromethyl)benzyl)piperidin-4-yl)isoxazol-3(2H)-one (2R,4S)-Methyl 2-(3-fluoro-4-(trifluoromethyl)benzyl)-4-(3-oxo-2,3-dihydroisoxazol-5-yl)piperidine-1-carboxylate (594 mg, 1.48 mmol) was dissolved in hydrogen bromide (33% in acetic acid, 10 mL, 57.10 mmol) and the mixture stirred at room temperature overnight. The solvent was evaporated and the residue purified by preparative HPLC (Instrument: FractionLynx III, Mobilphase: gradient 5-95% MeCN in 0.2% NH3, pH10, Column: Xbridge Prep C18 5 μm OBD 19*150 mm) to yield 5-((2R,4S)-2-(3-fluoro-4-(trifluoromethyl)benzyl)-piperidin-4-yl)isoxazol-3(2H)-one (338 mg, 66%). $^1$H NMR (600 MHz, dmso) δ 1.08 (q, 1H), 1.32 (qd, 1H), 1.71-1.79 (m, 2H), 2.45-2.72 (m, 4H), 2.72-2.80 (m, 1H), 2.96 (d, 1H), 5.68 (s, 1H), 7.23 (d, 1H), 7.35 (d, 1H), 7.65 (t, 1H). HRMS Calculated for $[C_{16}H_{16}F_4N_2O_2+H]^+$: 345.1226. Found: 345.1232

Example 141

5-((2S,4R)-2-(3-Fluoro-4-(trifluoromethyl)benzyl)piperidin-4-yl)isoxazol-3(2H)-one (2S,4R)-Methyl 2-(3-fluoro-4-(trifluoromethyl)benzyl)-4-(3-oxo-2,3-dihydroisoxazol-5-yl)piperidine-1-carboxylate (589 mg, 1.46 mmol) (from example 140, step 3) was dissolved in hydrogen bromide (33% in acetic acid, 10 mL, 57.10 mmol) and the mixture stirred at room temperature overnight. The solvent was evaporated and the residue purified by preparative HPLC (Instrument: FractionLynx III, Mobilphase: gradient 5-95% MeCN in 0.2% NH3, pH 10, Column: Xbridge Prep C18 5 μm OBD 19*150 mm) to yield 5-((2S,4R)-2-(3-fluoro-4-(trifluoromethyl)benzyl)piperidin-4-yl)isoxazol-3(2H)-one (329 mg, 65%). $^1$H NMR (600 MHz, $cd_3od$) δ 1.66 (q, 1H), 1.81 (dq, 1H), 2.17-2.25 (m, 2H), 3.00-3.15 (m, 4H), 3.47-3.52 (m, 1H), 3.56-3.62 (m, 1H), 5.76 (s, 1H), 7.28 (dd, 2H), 7.67 (t, 1H). HRMS Calculated for $[C_{16}H_{16}F_4N_2O_2+H]^+$: 345.1226. Found: 345.1225

Example 142

5-(Trans-2-(3-fluoro-4-(trifluoromethyl)benzyl)piperidin-4-yl)isoxazol-3(2H)-one Step 1: Trans-methyl 2-(3-fluoro-4-(trifluoromethyl)benzyl)-4-(3-oxo-2,3-dihydroisoxazol-5-yl)piperidine-1-carboxylate Trans-methyl 4-(3-ethoxy-3-oxopropanoyl)-2-(3-fluoro-4-(trifluoromethyl)benzyl)piperidine-1-carboxylate (0.781 g, 1.80 mmol) (from example 140, step 1) was dissolved in MeOH (15 mL) and cooled to −40° C. Sodium hydroxide (0.072 g, 1.80 mmol) dissolved in water (1 mL) was added over 1 min and the resulting solution was stirred at −40° C. for 20 min. Then hydroxylamine (50% by weight in water, 0.12 mL, 1.96 mmol) was added over 1 min and stirring continued at −40° C. for 2 h 15 min. The reaction mixture was then transferred into a prewarmed (80° C.) solution of 6 M hydrogen chloride (30 mL, 180.00 mmol) and the mixture was continued to be stirred at 80° C. for 1 h. Then cooled to room temperature. Methanol was evaporated, then water was added. Extracted three times with DCM. Combined organic layers dried over $MgSO_4$ and evaporated. Crude trans-methyl 2-(3-fluoro-4-(trifluoromethyl)-benzyl)-4-(3-oxo-2,3-dihydroisoxazol-5-yl)piperidine-1-carboxylate (678 mg, 94%) was isolated as an off-white foam. MS m/z 403 (M+H)$^+$ Step 2: 5-(Trans-2-(3-fluoro-4-(trifluoromethyl)benzyl)piperidin-4-yl)isoxazol-3(2H)-one Trans-methyl 2-(3-fluoro-4-(trifluoromethyl)benzyl)-4-(3-oxo-2,3-dihydroisoxazol-5-yl)-piperidine-1-carboxylate (0.224 g, 0.56 mmol) was dissolved in hydrogen bromide (33% in acetic acid, 5 mL, 71.37 mmol) and stirred at room temperature for 1 week. The solvents were evaporated and the residue purified by preparative HPLC (Instrument: FractionLynx III, Mobilphase: gradient 5-95% MeCN in 0.2% NH3, pH 10, Column: Xbridge Prep C18 5 μm OBD 19*150 mm) to yield 5-(trans-2-(3-fluoro-4-(trifluoromethyl)benzyl)piperidin-4-yl)isoxazol-3(2H)-one (160 mg, 83%). $^1$H NMR (600 MHz, dmso) δ 1.48 (ddd, 1H), 1.63-1.81 (m, 3H), 2.51-2.59 (m, 1H), 2.70-2.82 (m, 3H), 2.88-2.95 (m, 1H), 3.07-3.14 (m, 1H), 5.72 (s, 1H), 7.21 (d, 1H), 7.33 (d, 1H), 7.63 (t, 1H). HRMS Calculated for $[C_{16}H_{16}F_4N_2O_2+H]^+$: 345.1226. Found: 345.1241

Example 143

5-((2R,4S)-2-(3,4,5-Trifluorobenzyl)piperidin-4-yl)isoxazol-3(2H)-one

Step 1: Trans-methyl 4-(3-ethoxy-3-oxopropanoyl)-2-(3,4,5-trifluorobenzyl)piperidine-1-carboxylate and cis-methyl 4-(3-ethoxy-3-oxopropanoyl)-2-(3,4,5-trifluorobenzyl)piperidine-1-carboxylate 1-(Methoxycarbonyl)-2-(3,4,5-trifluorobenzyl)piperidine-4-carboxylic acid (3.42 g, 10.32 mmol) (reference compound 60) was dissolved in methyl THF (60 mL) and di(1H-imidazol-1-yl)methanone (2.51 g, 15.49 mmol) added. The suspension was stirred at room temperature under nitrogen for 6 h (flask 1). In a separate flask potassium 3-ethoxy-3-oxopropanoate (3.16 g, 18.58 mmol) was suspended in methyl THF (60.0 mL) and magnesium chloride (1.769 g, 18.58 mmol) added. The suspension was stirred under nitrogen for 6 h (flask 2). The white suspension in flask 2 was then added to the brown suspension in flask 1. The resulting suspension was stirred at room temperature for 18 h. The mixture was acidified to pH 1 with 3 M HCl. MTBE (250 mL) and water (250 mL) were added, shaken and the phases separated. The organic phase was washed with water (250 mL), satd $NaHCO_3$ (250 mL) and brine (250 mL), dried with $Na_2SO_4$, filtered and evaporated in vacuo. The residue was purified by automated flash chromatography on a Biotage® KP-SIL 100 g column. A gradient 20% EtOAc in heptane over 2 CV followed by 20% to 60% of EtOAc in heptane over 8 CV was used as mobile phase. Trans-methyl 4-(3-ethoxy-3-oxopropanoyl)-2-(3,4,5-trifluorobenzyl)-piperidine-1-carboxylate (0.309 g, 7.46%) and cis-methyl 4-(3-ethoxy-3-oxopropanoyl)-2-(3,4,5-trifluorobenzyl)piperidine-1-carboxylate (1.967 g, 47.5%) were isolated. Cis-isomer: $^1$H NMR (600 MHz, $cdcl_3$) δ 1.19-1.30 (m, 3H), 1.62-1.96 (m, 4H), 2.61-2.68 (m, 1H), 2.68-2.76 (m, 1H), 2.80-2.87 (m, 1H), 2.96-3.04 (m, 1H), 3.46 (s, 2H), 3.65 (s, 3H), 3.83-3.94 (m, 1H), 4.09-4.20 (m, 3H), 6.76-6.84 (m, 2H). MS m/z 402 $(M+H)^+$. Trans-isomer: MS m/z 402 $(M+H)^+$

Step 2: Cis-methyl 4-(3-oxo-2,3-dihydroisoxazol-5-yl)-2-(3,4,5-trifluorophenyl)piperidine-1-carboxylate Cis-methyl 4-(3-ethoxy-3-oxopropanoyl)-2-(3,4,5-trifluorobenzyl)piperidine-1-carboxylate (1.967 g, 4.90 mmol) was dissolved in MeOH (20 mL) and cooled to −40° C. under nitrogen. Sodium hydroxide (1.290 mL, 4.90 mmol) in water (2.000 mL) was added and the mixture stirred at −40° C. for 20 min. Hydroxylamine (50% by weight in water, 0.300 mL, 4.90 mmol) was added and stirring continued at −40° C. for 3.5 h. The reaction mixture was then transferred to a preheated 80° C. solution of 6 M hydrogen chloride (25.3 mL, 151.92 mmol) and heating was continued for 20 min. The solvent was then evaporated. DCM (150 mL) and water (150 mL) were added, shaken and the phases separated. The organic phase was dried with a phase separator and evaporated in vacuo. The compound was purified by preparative HPLC on a Kromasil C8 column (10 μm 250×50 ID mm) using a gradient of 10-55% Acetonitrile in H2O/MeCN/AcOH 95/5/0.2 buffer over 30 minutes with a flow of 100 mL/min. Cis-methyl 4-(3-oxo-2,3-dihydroisoxazol-5-yl)-2-(3,4,5-trifluorobenzyl)piperidine-1-carboxylate (1.354 g, 74.6%) was isolated as a white solid. $^1$H NMR (600 MHz, $cdcl_3$) δ 1.84-2.10 (m, 4H), 2.48-2.54 (m, 1H), 2.69-2.76 (m, 1H), 2.96-3.03 (m, 1H), 3.10-3.18 (m, 1H), 3.64 (s, 3H), 3.94-4.01 (m, 1H), 4.18-4.25 (m, 1H), 5.73 (s, 1H), 6.69-6.75 (m, 2H). MS m/z 369 $(M-H)^-$

Step 3: (2R,4S)-Methyl 4-(3-oxo-2,3-dihydroisoxazol-5-yl)-2-(3,4,5-trifluorobenzyl)-piperidine-1-carboxylate and (2S,4R)-methyl 4-(3-oxo-2,3-dihydroisoxazol-5-yl)-2-(3,4,5-trifluorobenzyl)piperidine-1-carboxylate Cis-methyl 4-(3-oxo-2,3-dihydroisoxazol-5-yl)-2-(3,4,5-trifluorobenzyl)piperidine-1-carboxylate (1.354 g, 3.68 mmol) was subjected to chiral preparative HPLC (Column: Chiralpak AD (250×20 mm), 5 μm particle size, mobile phase: Heptane/EtOH/FA 80/20/0.1, flow rate 18 mL/min) to yield (2R,4S)-methyl 4-(3-oxo-2,3-dihydroisoxazol-5-yl)-2-(3,4,5-trifluorobenzyl)piperidine-1-carboxylate (584 mg, 43%), Chiral purity 99.3% ee, Optical rotation $[α]_D^{20}$=+13.0 (acetonitrile, c=1.0) and (2S,4R)-methyl 4-(3-oxo-2,3-dihydroisoxazol-5-yl)-2-(3,4,5-trifluorobenzyl)piperidine-1-carboxylate (598 mg, 44%), Chiral purity 99.2% ee, Optical rotation $[α]_D^{20}$=−12.5 (acetonitrile, c=1.0)

Step 4: 5-((2R,4S)-2-(3,4,5-Trifluorobenzyl)piperidin-4-yl)isoxazol-3(2H)-one (2R,4S)-Methyl 4-(3-oxo-2,3-dihydroisoxazol-5-yl)-2-(3,4,5-trifluorobenzyl)piperidine-1-carboxylate (584 mg, 1.58 mmol) was dissolved in hydrogen bromide (33% in AcOH, 7 mL, 302.80 mmol) and stirred at room temperature for 20 h. The solvent was evaporated and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2R,4S)-2-(3,4,5-trifluorobenzyl)piperidin-4-yl)isoxazol-3(2H)-one (325 mg, 66%). $^1$H NMR (600 MHz, dmso) δ 1.05 (q, 1H), 1.31 (dq, 1H), 1.71-1.78 (m, 2H), 2.34-3.78 (m, 6H), 5.68 (s, 1H), 7.12-7.20 (m, 2H). HRMS Calculated for $[C_{15}H_{15}F_3N_2O_2+H]^+$: 313.1164. Found: 313.1172

Example 144

5-((2S,4R)-2-(3,4,5-Trifluorobenzyl)piperidin-4-yl)isoxazol-3(2H)-one (2S,4R)-Methyl 4-(3-oxo-2,3-dihydroisoxazol-5-yl)-2-(3,4,5-trifluorobenzyl)piperidine-1-carboxylate (598 mg, 1.61 mmol) (from example 143, step 3) was dissolved in hydrogen bromide (33% in AcOH, 7 mL, 99.92 mmol) and stirred at room temperature for 20 h. The solvent was evaporated in vacuo and the residue purified by preparative HPLC (Instrument: FractionLynx II, Mobilphase: gradient 5-95% MeCN in 0.2% $NH_3$, pH 10, Column: Xbridge Prep C18 5 μm OBD 19*150 mm) to yield 5-((2S,4R)-2-(3,4,5-trifluorobenzyl)piperidin-4-yl)isoxazol-3(2H)-one (357 mg, 70.8%). $^1$H NMR (600 MHz, dmso) δ 1.05 (q, 1H), 1.32 (dq, 1H), 1.70-1.78 (m, 2H), 2.33-3.58 (m, 6H), 5.68 (s, 1H), 7.12-7.19 (m, 2H). HRMS Calculated for $[C_{15}H_{15}F_3N_2O_2+H]^+$: 313.1164. Found: 313.1158

Example 145

5-(Trans-2-(3,4,5-trifluorobenzyl)piperidin-4-yl)isoxazol-3(2H)-one

Step 1: Trans-methyl 4-(3-oxo-2,3-dihydroisoxazol-5-yl)-2-(3,4,5-trifluorophenyl)piperidine-1-carboxylate Trans-methyl 4-(3-ethoxy-3-oxopropanoyl)-2-(3,4,5-trifluorobenzyl)piperidine-1-carboxylate (309 mg, 0.77 mmol)

(from example 143, step 1) was dissolved in MeOH (5 mL) and cooled to −40° C. under nitrogen. Sodium hydroxide (0.203 mL, 0.77 mmol) in water (0.500 mL) was added and the mixture was stirred at −40° C. for 20 min. Hydroxylamine (50% in water, 0.047 mL, 0.77 mmol) was added and stirring continued at −40° C. for 3 h. The reaction mixture was then transferred to a preheated 80° C. solution of 6 M hydrogen chloride (3.98 mL, 23.87 mmol) and heating was continued for 20 min. The solvent was then evaporated. DCM (50 mL) and water (50 mL) were added, shaken and the phases separated. The organic phase was dried with a phase separator and evaporated in vacuo. The compound was purified by preparative HPLC on a Kromasil C8 column (10 µm 250×20 ID mm) using a gradient of 10-55% Acetonitrile in H2O/MeCN/AcOH 95/5/0.2 buffer, over 30 minutes with a flow of 19 mL/min. Trans-methyl 4-(3-oxo-2,3-dihydroisoxazol-5-yl)-2-(3,4,5-trifluorobenzyl)-piperidine-1-carboxylate (111 mg, 38.9%) was isolated. MS m/z 371 (M+H)$^+$ Step 2: 5-(Trans-2-(3,4,5-trifluorobenzyl)piperidin-4-yl)isoxazol-3(2H)-one Trans-methyl 4-(3-oxo-2,3-dihydroisoxazol-5-yl)-2-(3,4,5-trifluorobenzyl)piperidine-1-carboxylate (111 mg, 0.3 mmol) was stirred in hydrogen bromide (33% in AcOH, 2 mL, 86.51 mmol) for 18 h. The reaction mixture was evaporated in vacuo and the residue purified by preparative HPLC (Instrument: FractionLynx II, Mobilphase: gradient 5-95% MeCN in 0.2% NH$_3$, pH10, Column: Xbridge Prep C18 5 µm OBD 19*150 mm) to yield 5-(trans-2-(3,4,5-trifluorobenzyl)piperidin-4-yl)isoxazol-3(2H)-one (20.17 mg, 21.5%). $^1$H NMR (600 MHz, dmso) δ 1.43-1.49 (m, 1H), 1.65-1.79 (m, 3H), 2.33-3.75 (m, 6H), 5.75 (s, 1H), 7.12-7.19 (m, 2H). HRMS Calculated for $[C_{15}H_{15}F_3N_2O_2+H]^+$: 313.1164. Found: 313.1147

Example 146

5-((2R,4S)-2-(3,5-Di-tert-butylbenzyl)piperidin-4-yl)isoxazol-3(2H)-one

Step 1: Trans-methyl 2-(3,5-di-tert-butylbenzyl)-4-(3-ethoxy-3-oxopropanoyl)piperidine-1-carboxylate and cis-methyl 2-(3,5-di-tert-butylbenzyl)-4-(3-ethoxy-3-oxopropanoyl)-piperidine-1-carboxylate 2-(3,5-Di-tert-butylbenzyl)-1-(methoxycarbonyl)piperidine-4-carboxylic acid (3.723 g, 9.56 mmol) (reference compound 61) was dissolved in methyl THF (70 mL) and di(1H-imidazol-1-yl)methanone (2.325 g, 14.34 mmol) added. The suspension was stirred at room temperature under nitrogen overnight (flask 1). In a separate flask potassium 3-ethoxy-3-oxopropanoate (2.93 g, 17.20 mmol) was suspended in methyl THF (70.0 mL) and magnesium chloride (1.638 g, 17.20 mmol) added. The suspension was stirred at 50° C. under nitrogen overnight using an oversized stirring bar (flask 2). The yellow suspension in flask 1 was now added to the white suspension in flask 2. The resulting white suspension was stirred under nitrogen at room temperature for 2 days. The mixture was acidified to pH 1 with 3.8 M HCl and MTBE and water added. The phases were separated and the organic phase washed with water, satd NaHCO$_3$ and water. Evaporated the solvents to yield a yellow oil. The diastereomers were separated in 2 runs on Biotage (0%=>40% EtOAc in heptane, 8 CV; Biotage® KP-SIL 340 g column). Trans-methyl 2-(3,5-di-tert-butylbenzyl)-4-(3-ethoxy-3-oxopropanoyl)piperidine-1-carboxylate (0.734 g, 17%) and cis-methyl 2-(3,5-di-tert-butylbenzyl)-4-(3-ethoxy-3-oxopropanoyl)piperidine-1-carboxylate (2.027 g, 46%) were isolated as colorless oils. Cis-isomer: $^1$H NMR (400 MHz, cdcl$_3$) δ 1.19-1.35 (m, 21H), 1.63-1.99 (m, 4H), 2.62-3.05 (m, 4H), 3.46 (s, 2H), 3.57-3.64 (m, 3H), 3.88-3.97 (m, 1H), 4.07-4.26 (m, 3H), 6.97-7.01 (m, 2H), 7.24-7.28 (m, 1H). MS m/z 460 (M+H)$^+$. Trans-isomer: $^1$H NMR (400 MHz, cdcl$_3$) δ 1.11-1.39 (m, 21H), 1.40-2.02 (m, 4H), 2.52-3.14 (m, 4H), 3.33-3.55 (m, 3H), 3.64 (s, br., 2H), 3.98-4.35 (m, 3H), 4.37-4.80 (m, 1H), 6.91-7.12 (m, 2H), 7.24-7.30 (m, 1H). MS m/z 460 (M+H)$^+$ Step 2: Cis-methyl 2-(3,5-di-tert-butylbenzyl)-4-(3-oxo-2,3-dihydroisoxazol-5-yl)piperidine-1-carboxylate Cis-methyl 2-(3,5-di-tert-butylbenzyl)-4-(3-ethoxy-3-oxopropanoyl)piperidine-1-carboxylate (2.03 g, 4.42 mmol) was dissolved in MeOH (16 mL) and cooled to −40° C. under nitrogen. Sodium hydroxide (0.177 g, 4.42 mmol) dissolved in water (1.600 mL) was added during 10 min and the colourless solution continued to stir at −40° C. for 20 min. Hydroxylamine (50% by weight in water, 0.271 mL, 4.42 mmol) was added during 8 min. The resulting solution was stirred at −40° C. for 3.5 h. The mixture was then transferred into a pre-warmed (80° C.) solution of 6 M hydrogen chloride (20 mL, 120.00 mmol) and the mixture continued to stir at 80° C. for 20 min. DCM and water were added. The phases were separated and the organic phase passed through a phase separator and evaporated to yield a yellow semi-solid. The compound was purified by preparative HPLC in 3 injections on a XBridge C18 column (10 µm 250×50 ID mm) using a gradient of 10-50% Acetonitrile in H2O/MeCN/NH3 95/5/0.2 buffer over 20 minutes with a flow of 100 mL/min. Cis-methyl 2-(3,5-di-tert-butylbenzyl)-4-(3-oxo-2,3-dihydroisoxazol-5-yl)piperidine-1-carboxylate (1.358 g, 72%) was isolated as a white solid. $^1$H NMR (600 MHz, cdcl$_3$) δ 1.22-1.33 (m, 18H), 1.80-2.10 (m, 4H), 2.59-2.67 (m, 1H), 2.71-2.78 (m, 1H), 2.92-2.98 (m, 1H), 3.07-3.15 (m, 1H), 3.55 (s, 3H), 3.97 (dd, 1H), 4.18-4.27 (m, 1H), 5.68 (s, 1H), 6.92 (d, 2H), 7.22 (s, 1H). MS m/z 429 (M+H)$^+$ Step 3: (2R,4S)-Methyl 2-(3,5-di-tert-butylbenzyl)-4-(3-oxo-2,3-dihydroisoxazol-5-yl)-piperidine-1-carboxylate and (2S,4R)-methyl 2-(3,5-di-tert-butylbenzyl)-4-(3-oxo-2,3-dihydroisoxazol-5-yl) piperidine-1-carboxylate Cis-methyl 2-(3,5-di-tert-butylbenzyl)-4-(3-oxo-2,3-dihydroisoxazol-5-yl)piperidine-1-carboxylate (1.358 g, 3.16 mmol) was subjected to chiral preparative HPLC (Column: Chiralcel OJ (250×20), 5 µm particle size, mobile phase: Heptane/EtOH/FA 90/10/0.1, flow rate 18 mL/min) to yield (2R,4S)-methyl 2-(3,5-di-tert-butylbenzyl)-4-(3-oxo-2,3-dihydroisoxazol-5-yl)piperidine-1-carboxylate (550 mg, 40%), Chiral purity 99.6% ee, Optical rotation $[α]_D^{20}$=+14.7 (acetonitrile, c=1) and (2S,4R)-methyl 2-(3,5-di-tert-butylbenzyl)-4-(3-oxo-2,3-dihydroisoxazol-5-yl)piperidine-1-carboxylate (619 mg, 45%), Chiral purity 99.7% ee, Optical rotation $[α]_D^{20}$=−11.2 (acetonitrile, c=1)

Step 4: 5-((2R,4S)-2-(3,5-Di-tert-butylbenzyl)piperidin-4-yl)isoxazol-3(2H)-one (2R,4S)-Methyl 2-(3,5-di-tert-butylbenzyl)-4-(3-oxo-2,3-dihydroisoxazol-5-yl)piperidine-1-carboxylate (550 mg, 1.28 mmol) was dissolved in hydrogen bromide (33% in acetic acid (10 mL, 57.10 mmol) and the mixture stirred at room temperature overnight. The solvent was evaporated and the residue purified by preparative HPLC (Instrument: FractionLynx III, Mobilphase: gradient 5-95% MeCN in 0.2% $NH_3$, pH 10, Column: Xbridge Prep C18 5 μm OBD 19*150 mm) to yield 5-((2R,4S)-2-(3,5-di-tert-butylbenzyl)piperidin-4-yl)isoxazol-3(2H)-one (315 mg, 66%). $^1$H NMR (600 MHz, $cd_3od$) δ 1.30 (s, 18H), 1.58-1.67 (m, 1H), 1.80 (dq, 1H), 2.17-2.27 (m, 2H), 2.85-3.14 (m, 4H), 3.41-3.51 (m, 2H), 5.73 (s, 1H), 7.07-7.13 (m, 2H), 7.36-7.40 (m, 1H). HRMS Calculated for $[C_{23}H_{34}N_2O_2+H]^+$: 371.2698. Found: 371.2714

Example 147

5-((2S,4R)-2-(3,5-Di-tert-butylbenzyl)piperidin-4-yl)isoxazol-3(2H)-one (2S,4R)-Methyl 2-(3,5-di-tert-butylbenzyl)-4-(3-oxo-2,3-dihydroisoxazol-5-yl)piperidine-1-carboxylate (619 mg, 1.44 mmol) (from example 146, step 3) was dissolved in hydrogen bromide (33% in acetic acid, 10 mL, 57.10 mmol) and the mixture stirred at room temperature overnight. The solvent was evaporated and the residue purified by preparative HPLC (Instrument: FractionLynx III, Mobilphase: gradient 5-95% MeCN in 0.2% $NH_3$, pH 10, Column: Xbridge Prep C18 5 μm OBD 19*150 mm) to yield 5-((2S,4R)-2-(3,5-di-tert-butylbenzyl)piperidin-4-yl)isoxazol-3(2H)-one (330 mg, 61%). $^1$H NMR (600 MHz, $cd_3od$) δ 1.30 (s, 18H), 1.63 (q, 1H), 1.80 (dq, 1H), 2.19-2.27 (m, 2H), 2.86-3.18 (m, 4H), 3.43-3.56 (m, 2H), 5.73 (s, 1H), 7.10 (d, 2H), 7.37-7.40 (m, 1H). HRMS Calculated for $[C_{23}H_{34}N_2O_2+H]^+$: 371.2698. Found: 371.2693

Example 148

5-(Trans-2-(3,5-di-tert-butylbenzyl)piperidin-4-yl)isoxazol-3(2H)-one

Step 1: Trans-methyl 2-(3,5-di-tert-butylbenzyl)-4-(3-oxo-2,3-dihydroisoxazol-5-yl)piperidine-1-carboxylate Trans-methyl 2-(3,5-di-tert-butylbenzyl)-4-(3-ethoxy-3-oxopropanoyl)piperidine-1-carboxylate (0.734 g, 1.60 mmol) was dissolved in MeOH (5 mL) and cooled to −40° C. under nitrogen. Sodium hydroxide (0.064 g, 1.60 mmol) dissolved in water (0.500 mL) was added during 10 min and the colourless solution continued to stir at −40° C. for 20 min. Hydroxylamine (50% by weight in water, 0.098 mL, 1.60 mmol) was added during 8 min. The resulting solution was stirred at −40° C. for 4 h. The mixture was then transferred into a prewarmed (80° C.) solution of 6 M hydrogen chloride (8 mL, 48.00 mmol) and the mixture continued to stir at 80° C. for 20 min. DCM and water were added. The phases were separated and the organic phase passed through a phase separator and evaporated to yield crude trans-methyl 2-(3,5-di-tert-butylbenzyl)-4-(3-oxo-2,3-dihydroisoxazol-5-yl)piperidine-1-carboxylate (0.723 g, 106%) as a yellow semi-solid. MS m/z 429 (M+H)$^+$ Step 2: 5-(Trans-2-(3,5-di-tert-butylbenzyl)piperidin-4-yl)isoxazol-3(2H)-one Trans-Methyl 2-(3,5-di-tert-butylbenzyl)-4-(3-oxo-2,3-dihydroisoxazol-5-yl)piperidine-1-carboxylate (155 mg, 0.36 mmol) was dissolved in hydrogen bromide (33% in acetic acid, 3 mL, 17.13 mmol) and the mixture stirred at room temperature overnight. The solvent was evaporated and the residue purified by preparative HPLC (Instrument: FractionLynx III, Mobilphase: gradient 5-95% MeCN in 0.2% $NH_3$, pH 10, Column: Xbridge Prep C18 5 μm OBD 19*150 mm) to yield 5-(trans-2-(3,5-di-tert-butylbenzyl)piperidin-4-yl)isoxazol-3(2H)-one (69 mg, 51%). $^1$H NMR (600 MHz, DMSO) δ 1.26 (s, 18H), 1.45-1.53 (m, 1H), 1.69-1.87 (m, 3H), 2.58-2.72 (m, 3H), 2.83-2.93 (m, 2H), 3.09-3.16 (m, 1H), 5.64 (s, 1H), 6.99 (d, 2H), 7.18-7.23 (m, 1H). HRMS Calculated for $[C_{23}H_{34}N_2O_2+H]^+$: 371.2698. Found: 371.2688

Example 149

5-((2R,4S)-2-Benzyl-2,3,4,5,6-$d_5$-piperidin-4-yl)isoxazol-3(2H)-one

Step 1: Trans-methyl 2-benzyl-2,3,4,5,6-$d_5$-4-(3-ethoxy-3-oxopropanoyl)piperidine-1-carboxylate and cis-methyl 2-benzyl-2,3,4,5,6-$d_5$-4-(3-ethoxy-3-oxopropanoyl)piperidine-1-carboxylate Magnesium chloride (3.13 g, 32.90 mmol) and potassium 3-ethoxy-3-oxopropanoate (5.60 g, 32.90 mmol) suspended in THF (100 mL) were stirred with an oversized stirring bar at 50° C. under nitrogen for 18 h, then cooled to room temperature (flask 1). To a suspension of 2-benzyl-2,3,4,5,6-$d_5$-1-(methoxycarbonyl)piperidine-4-carboxylic acid (5.16 g, 18.28 mmol) (reference compound 62) in methyl THF (100 mL) was added di(1H-imidazol-1-yl)methanone (4.77 g, 29.42 mmol) under nitrogen. The resulting mixture was stirred at room temperature for 19 h (flask 2). The contents of flask 2 is transferred into flask 1 by transfer needle. Wash with THF (35 mL). Resulting suspension stirred at room temperature for 24 h. 3.8 M HCl was added (ca. 200 mL) and the resulting biphasic mixture stirred vigorously for 30 min. MTBE was added and the phases separated. The aqueous phase extracted once more with MTBE. The combined organic layers dried over $MgSO_4$ and evaporated. The residue was purified via Biotage (Biotage® KP-SIL 340 g column, 1 CV 20% EtOAc in heptanes, then 20%=>60% over 7 CV). Trans-methyl 2-benzyl-2,3,4,5,6-$d_5$-4-(3-ethoxy-3-oxopropanoyl)piperidine-1-carboxylate (1.15 g, 18%) and cis-methyl 2-benzyl-2,3,4,5,6-$d_5$-4-(3-ethoxy-3-oxopropanoyl)piperidine-1-carboxylate (2.27 g, 35%) were isolated as pale yellow oils. Cis-isomer: $^1$H NMR (600 MHz, $cdcl_3$) δ 1.19-1.28 (m, 3H), 1.60-1.92 (m, 4H), 2.63-2.77 (m, 2H), 2.85-3.04 (m, 2H), 3.42 (s, 2H), 3.61 (s, 3H), 3.85-3.94 (m, 1H), 4.05-4.22 (m, 3H). MS m/z 353 (M+H)$^+$. Trans-isomer: $^1$H NMR (600 MHz, $cdcl_3$) δ 1.19-1.31 (m, 3H), 1.39-1.66 (m, 2H), 1.67-1.98 (m, 2H), 2.71-3.07 (m, 4H), 3.33-3.73 (m, 5H), 3.99-4.33 (m, 3H), 4.57 (d, br., 1H). MS m/z 353 (M+H)$^+$ Step 2: Cis-methyl 2-benzyl-2,3,4,5,6-$d_5$-4-(3-oxo-2,3-dihydroisoxazol-5-yl)piperidine-1-carboxylate Cis-methyl 2-benzyl-2,3,4,5,6-$d_5$-4-(3-ethoxy-3-oxopropanoyl)piperidine-1-carboxylate (2.27 g, 6.44 mmol) was dissolved in MeOH (20 mL) and cooled to −40° C. Sodium hydroxide (0.258 g, 6.44 mmol) dissolved in water (2 mL) was added over 2 min and the resulting solution was stirred at −40° C. for 25 min. Then hydroxylamine (50% by weight in water, 0.41 mL, 6.69 mmol) was added over 1 min and stirring continued at −50 to −40° C. for 1 h 40 min. The reaction mixture was then transferred into a prewarmed (80° C.) solution of 6 M hydrogen chloride (30 mL, 180.00 mmol) and the mixture was continued to be stirred at 80° C. for 30 min. Then cooled to room temperature. Methanol was evaporated, then water was added. Extracted three times with DCM. Combined organic layers dried over MgSO$_4$ and evaporated. The compound was purified in 3 injections by preparative HPLC on a XBridge C18 column (10 μm 250×50 ID mm) using a gradient of 0-25% Acetonitrile in H2O/MeCN/NH3 95/5/0.2 buffer over 23 minutes with a flow of 100 mL/min. Cis-methyl 2-benzyl-2,3,4,5,6-d$_5$-4-(3-oxo-2,3-dihydroisoxazol-5-yl)piperidine-1-carboxylate (1.458 g, 70%) was isolated as a colorless solid. $^1$H NMR (600 MHz, cdcl$_3$) δ 1.79-1.97 (m, 3H), 1.99-2.12 (m, 1H), 2.62 (dd, 1H), 2.81 (dd, 1H), 2.89-2.99 (m, 1H), 3.07-3.17 (m, 1H), 3.59 (s, 3H), 3.98 (dd, 1H), 4.20-4.30 (m, 1H), 5.69 (s, 1H). MS m/z 322 (M+H)$^+$ Step 3: (2R,4S)-Methyl 2-benzyl-2,3,4,5,6-d$_5$-4-(3-oxo-2,3-dihydroisoxazol-5-yl)piperidine-1-carboxylate and (2S,4R)-methyl 2-benzyl-2,3,4,5,6-d$_5$-4-(3-oxo-2,3-dihydroisoxazol-5-yl)piperidine-1-carboxylate Cis-methyl 2-benzyl-2,3,4,5,6-d$_5$-4-(3-oxo-2,3-dihydroisoxazol-5-yl)piperidine-1-carboxylate (1.25 g, 3.89 mmol) was subjected to chiral preparative HPLC (Column: Chiralcel OD (250×20), 5 μm particle size, mobile phase: Heptane/EtOH/FA 90/10/0.1, flow rate 18 mL/min) to yield (2R,4S)-methyl 2-benzyl-2,3,4,5,6-d$_5$-4-(3-oxo-2,3-dihydroisoxazol-5-yl)piperidine-1-carboxylate (502 mg, 40%), Chiral purity 98.9% ee, Optical rotation $[\alpha]_D^{20}$=+23.7 (acetonitrile, c=1) and (2S,4R)-methyl 2-benzyl-2,3,4,5,6-d$_5$-4-(3-oxo-2,3-dihydroisoxazol-5-yl)piperidine-1-carboxylate (512 mg, 41%), Chiral purity 99.1% ee, Optical rotation $[\alpha]_D^{20}$=−22.2 (acetonitrile, c=1).

Step 4: 5-((2R,4S)-2-Benzyl-2,3,4,5,6-d$_5$-piperidin-4-yl)isoxazol-3(2H)-one (2R,4S)-Methyl 2-benzyl-2,3,4,5,6-d$_5$-4-(3-oxo-2,3-dihydroisoxazol-5-yl)piperidine-1-carboxylate (0.502 g, 1.56 mmol) was dissolved in hydrogen bromide (33% in AcOH, 10 mL, 142.75 mmol) and stirred at room temperature for 20 h, then solvents evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2R,4S)-2-benzyl-2,3,4,5,6-d$_5$-piperidin-4-yl)isoxazol-3(2H)-one. HRMS Calculated for [C$_{15}$H$_{13}$D5N$_2$O$_2$+H]$^+$: 264.1760. Found: 264.1751

Example 150

5-((2S,4R)-2-Benzyl-2,3,4,5,6-d$_5$-piperidin-4-yl)isoxazol-3(2H)-one (2S,4R)-Methyl 2-benzyl-2,3,4,5,6-d$_5$-4-(3-oxo-2,3-dihydroisoxazol-5-yl)piperidine-1-carboxylate (0.512 g, 1.59 mmol) (from example 149, step 3) was dissolved in hydrogen bromide (33% in acetic acid, 10 mL, 142.75 mmol) and stirred at room temperature for 20 h, then solvents evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-((2S,4R)-2-benzyl-2,3,4,5,6-d$_5$-piperidin-4-yl)isoxazol-3(2H)-one. HRMS Calculated for [C$_{15}$H$_{13}$D$_5$N$_2$O$_2$+H]$^+$: 264.1760. Found: 264.1749

Example 151

5-Trans-2-benzyl-2,3,4,5,6-d$_5$-1 isoxazol-3(2H)-one

Step 1: Trans-methyl 2-benzyl-2,3,4,5,6-d$_5$-4-(3-oxo-2,3-dihydroisoxazol-5-yl)piperidine-1-carboxylate Trans-methyl 2-benzyl-2,3,4,5,6-d$_5$-4-(3-ethoxy-3-oxopropanoyl)piperidine-1-carboxylate (1.15 g, 3.26 mmol) (from example 149, step 1) was dissolved in MeOH (20 mL) and cooled to −40 C. Sodium hydroxide (0.131 g, 3.26 mmol) dissolved in water (2 mL) was added over 1 min and the resulting solution was stirred at −40° C. for 20 min. Hydroxylamine (50% by weight in water, 0.208 mL, 3.39 mmol) was added over 1 min and stirring continued at −50 to −40° C. for 1 h. The reaction mixture was then transferred into a prewarmed (80° C.) solution of 6 M hydrogen chloride (30 mL, 180.00 mmol) and the mixture was continued to be stirred at 80° C. for 40 min. Then cooled to room temperature. Methanol was evaporated, then water was added. Extracted three times with DCM. Combined organic layers dried over MgSO$_4$ and evaporated to yield crude cis-methyl 2-benzyl-2,3,4,5,6-d$_5$-4-(3-oxo-2,3-dihydroisoxazol-5-yl)piperidine-1-carboxylate (1.06 g, 101%) as an orange foam. MS m/z 322 (M+H)$^+$ Step 2: 5-(Trans-2-benzyl-2,3,4,5,6-d$_5$-piperidin-4-yl)isoxazol-3(2H)-one Cis-methyl 2-benzyl-2,3,4,5,6-d$_5$-4-(3-oxo-2,3-dihydroisoxazol-5-yl)piperidine-1-carboxylate (0.204 g, 0.63 mmol) was dissolved in hydrogen bromide (33% in acetic acid, 6 mL, 34.26 mmol) and stirred at room temperature for 20 h, then solvents evaporated and the residue purified by preparative HPLC (Instrument: FractionLynx II, Mobilphase: gradient 5-95% MeCN in 0.2% NH$_3$, pH 10, Column: Xbridge Prep C18 5 μm OBD 19*150 mm) to yield 5-(trans-2-benzyl-2,3,4,5,6-d$_5$-piperidin-4-yl)isoxazol-3(2H)-one (29 mg, 23%). HRMS Calculated for [C$_{15}$H$_{13}$D$_5$N$_2$O$_2$+H]$^+$: 264.1760. Found: 264.1747

General Procedures for the Preparation of Crystalline Forms of the Examples

Method A—Neutral Form

The substance is slurried in water at room temperature over a prolonged period, then collected by filtration.

Method B—Neutral Form

The substance is slurried in a mixture of methanol and dichloromethane. The solvents are allowed to evaporate slowly.

Method C—HCl Salt

The substance is dissolved in 1 M HCl at room temperature. The formed HCl salt is collected by filtration.

Method D—HCl Salt

The substance is dissolved in 1.25 M HCl in methanol. The solvent is allowed to evaporate slowly.

Crystal forms of examples 14 and 104 were prepared according to method A. Crystal forms of examples 55, 65, 115 and 143 were prepared according to method B. Crystal forms of HCl salts of examples 14 and 104 were prepared according to method C. Crystal forms of HCl salts of examples 10, 18, 55, 65 and 143 were prepared according to method D.

The invention claimed is:

1. A compound, or a pharmaceutically acceptable salt thereof, selected from:

5-((2S,4S)-2-Benzylpiperidin-4-yl)isoxazol-3(2H)-one;
5-((2R,4R)-2-Benzylpiperidin-4-yl)isoxazol-3(2H)-one;
5-((2R,4S)-2-Benzylpiperidin-4-yl)isoxazol-3(2H)-one;
5-((2S,4R)-2-Benzylpiperidin-4-yl)isoxazol-3(2H)-one;
5-((2S,4S)-2-Isobutylpiperidin-4-yl)isoxazol-3(2H)-one;
5-((2R,4R)-2-Isobutylpiperidin-4-yl)isoxazol-3(2H)-one;
5-((2S,4S)-2-Isobutylpiperidin-4-yl)isoxazol-3(2H)-one;
5-((2R,4S)-2-Phenethylpiperidin-4-yl)isoxazol-3(2H)-one;
5-((2S,4R)-2-Phenethylpiperidin-4-yl)isoxazol-3(2H)-one;
5-((2S,4S)-2-Phenethylpiperidin-4-yl)isoxazol-3(2H)-one;
5-((2S,4S)-2-(4-tert-Butylbenzyl)piperidin-4-yl)isoxazol-3(2H)-one;
5-((2R,4S)-2-(4-tert-Butylbenzyl)piperidin-4-yl)isoxazol-3(2H)-one;
5-((2S,4S)-2-Neopentylpiperidin-4-yl)isoxazol-3(2H)-one;
5-((2R,4S)-2-Neopentylpiperidin-4-yl)isoxazol-3(2H)-one;
5-((2S,4S)-2-(2-Methyl-2-phenylpropyl)piperidin-4-yl)isoxazol-3(2H)-one;
5-((2R,4S)-2-(2-Methyl-2-phenylpropyl)piperidin-4-yl)isoxazol-3(2H)-one;
5-((2R,4S)-2-(Cyclohexylmethyl)piperidin-4-yl)isoxazol-3(2H)-one;
5-((2R,4R)-2-(Cyclohexylmethyl)piperidin-4-yl)isoxazol-3(2H)-one;
5-((2S,4S)-2-(Cyclohexylmethyl)piperidin-4-yl)isoxazol-3(2H)-one;
5-((2R,4S)-2-(3,4-Difluorophenyl)piperidin-4-yl)isoxazol-3(2H)-one;
5-(Trans-2-(3,4-difluorophenyl)piperidin-4-yl)isoxazol-3(2H)-one;
5-((2R,4S)-2-(4-Fluorophenyl)piperidin-4-yl)isoxazol-3(2H)-one;
5-(Trans-2-(4-fluorophenyl)piperidin-4-yl)isoxazol-3(2H)-one;
5-((2R,4S)-2-(4-Chlorophenyl)piperidin-4-yl)isoxazol-3(2H)-one;
5-((2S,4R)-2-(4-Chlorophenyl)piperidin-4-yl)isoxazol-3(2H)-one;
5-(Trans-2-(4-chlorophenyl)piperidin-4-yl)isoxazol-3(2H)-one;
5-((2R,4S)-2-(3-(Trifluoromethyl)phenyl)piperidin-4-yl)isoxazol-3(2H)-one;
5-((2S,4R)-2-(3-(Trifluoromethyl)phenyl)piperidin-4-yl)isoxazol-3(2H)-one;
5-(Trans-2-(3-(trifluoromethyl)phenyl)piperidin-4-yl)isoxazol-3(2H)-one;
5-((2R,4S)-2-(4-(Trifluoromethyl)phenyl)piperidin-4-yl)isoxazol-3(2H)-one;
5-((2S,4R)-2-(4-(Trifluoromethyl)phenyl)piperidin-4-yl)isoxazol-3(2H)-one;
5-(Trans-2-(4-(trifluoromethyl)phenyl)piperidin-4-yl)isoxazol-3(2H)-one;
5-((2R,4S)-2-(3-tert-Butylphenyl)piperidin-4-yl)isoxazol-3(2H)-one;
5-(Trans-2-(4-tert-butylphenyl)piperidin-4-yl)isoxazol-3(2H)-one;
5-((2R,4S)-2-(4-(Methylsulfonyl)phenyl)piperidin-4-yl)isoxazol-3(2H)-one;
5-((Trans-2-(4-(methylsulfonyl)phenyl)piperidin-4-yl)isoxazol-3(2H)-one;
5-((2R,4S)-2-(6-(Trifluoromethyl)pyridin-3-yl)piperidin-4-yl)isoxazol-3(2H)-one;
5-(Trans-2-(6-(trifluoromethyl)pyridin-3-yl)piperidin-4-yl)isoxazol-3(2H)-one;
5-((2R,4S)-2-(5-tert-Butylthiophen-2-yl)piperidin-4-yl)isoxazol-3(2H)-one;
5-((2S,4R)-2-(5-tert-Butylthiophen-2-yl)piperidin-4-yl)isoxazol-3(2H)-one;
5-((2R,4S)-2-(2,4-Difluorophenyl)piperidin-4-yl)isoxazol-3(2H)-one;
5-((2R,4S)-2-(4-Chloro-2-fluorophenyl)piperidin-4-yl)isoxazol-3(2H)-one;
5-(Trans-2-(4-chloro-2-fluorophenyl)piperidin-4-yl)isoxazol-3(2H)-one;
5-((2R,4S)-2-(2-Chloro-4-fluorophenyl)piperidin-4-yl)isoxazol-3(2H)-one;
5-(Trans-2-(2-chloro-4-fluorophenyl)piperidin-4-yl)isoxazol-3(2H)-one;
5-((2R,4S)-2-(4-Chloro-3-fluorophenyl)piperidin-4-yl)isoxazol-3(2H)-one;
5-(Trans-2-(4-chloro-3-fluorophenyl)piperidin-4-yl)isoxazol-3(2H)-one;
5-((2R,4S)-2-(2,4-Dichlorophenyl)piperidin-4-yl)isoxazol-3(2H)-one;
5-((2S,4R)-2-(2,4-Dichlorophenyl)piperidin-4-yl)isoxazol-3(2H)-one;
5-((2S,4S)-2-(2,4-Dichlorophenyl)piperidin-4-yl)isoxazol-3(2H)-one;
5-((2R,4R)-2-(2,4-Dichlorophenyl)piperidin-4-yl)isoxazol-3(2H)-one;
5-((2R,4S)-2-(3,5-Dichlorophenyl)piperidin-4-yl)isoxazol-3(2H)-one;
5-((2S,4R)-2-(3,5-Dichlorophenyl)piperidin-4-yl)isoxazol-3(2H)-one;
5-(Trans-2-(3,5-dichlorophenyl)piperidin-4-yl)isoxazol-3(2H)-one;
5-((2R,4S)-2-(2-Fluoro-4-(trifluoromethoxy)phenyl)piperidin-4-yl)isoxazol-3(2H)-one;
5-(Trans-2-(2-fluoro-4-(trifluoromethoxy)phenyl)piperidin-4-yl)isoxazol-3(2H)-one;
5-((2R,4S)-2-(3,4,5-Trifluorophenyl)piperidin-4-yl)isoxazol-3(2H)-one;
5-((2S,4R)-2-(3,4,5-Trifluorophenyl)piperidin-4-yl)isoxazol-3(2H)-one;
5-(Trans-2-(3,4,5-trifluorophenyl)piperidin-4-yl)isoxazol-3(2H)-one;
5-((2R,4S)-2-(2,4,5-Trifluorophenyl)piperidin-4-yl)isoxazol-3(2H)-one;
5-((2S,4S)-2-(2,4,5-Trifluorophenyl)piperidin-4-yl)isoxazol-3(2H)-one;
5-((2R,4S)-2-(4-Chloro-3,5-difluorophenyl)piperidin-4-yl)isoxazol-3(2H)-one;
5-(Trans-2-(4-chloro-3,5-difluorophenyl)piperidin-4-yl)isoxazol-3(2H)-one;
5-((2R,4S)-2-(3-Methyl-4-(trifluoromethyl)phenyl)piperidin-4-yl)isoxazol-3(2H)-one;
5-((2S,4R)-2-(3-Methyl-4-(trifluoromethyl)phenyl)piperidin-4-yl)isoxazol-3(2H)-one;
5-(Trans-2-(3-methyl-4-(trifluoromethyl)phenyl)piperidin-4-yl)isoxazol-3(2H)-one;
5-((2R,4S)-2-(3,5-Difluoro-4-(trifluoromethyl)phenyl)piperidin-4-yl)isoxazol-3(2H)-one;
5-(Trans-2-(3,5-difluoro-4-(trifluoromethyl)phenyl)piperidin-4-yl)isoxazol-3(2H)-one;

5-((2R,4S)-2-(2-Methyl-4-(trifluoromethyl)phenyl)piperidin-4-yl)isoxazol-3(2H)-one;
5-((2R,4S)-2-(2-Fluoro-4-(trifluoromethyl)phenyl)piperidin-4-yl)isoxazol-3(2H)-one;
5-(Trans-2-(2-fluoro-4-(trifluoromethyl)phenyl)piperidin-4-yl)isoxazol-3(2H)-one;
5-((2R,4S)-2-(3-fluoro-4-(trifluoromethyl)phenyl)piperidin-4-yl)isoxazol-3(2H)-one;
5-((2S,4R)-2-(3-Fluoro-4-(trifluoromethyl)phenyl)piperidin-4-yl)isoxazol-3(2H)-one;
5-((2R,4S)-2-phenylpiperidin-4-yl)isoxazol-3(2H)-one;
5-((2S,4S)-2-phenylpiperidin-4-yl)isoxazol-3(2H)-one;
5-((2R,4S)-2-Cyclohexylpiperidin-4-yl)isoxazol-3(2H)-one;
5-((2S,4S)-2-Cyclohexylpiperidin-4-yl)isoxazol-3(2H)-one;
5-((2R,4S)-2-(2-Methyl-2H-tetrazol-5-yl)piperidin-4-yl)isoxazol-3(2H)-one;
5-(Trans-2-(2-methyl-2H-tetrazol-5-yl)piperidin-4-yl)isoxazol-3(2H)-one;
5-((2R,4S)-2-(1-Methyl-1H-tetrazol-5-yl)piperidin-4-yl)isoxazol-3(2H)-one;
5-((2R,4S)-2-(Cyclohexyloxymethyl)piperidin-4-yl)isoxazol-3(2H)-one;
5-((2S,4R)-2-(Cyclohexyloxymethyl)piperidin-4-yl)isoxazol-3(2H)-one;
5-(Trans-2-(cyclohexyloxymethyl)piperidin-4-yl)isoxazol-3(2H)-one;
5-((2R,4S)-2-(Difluoromethyl)piperidin-4-yl)isoxazol-3(2H)-one;
5-(Trans-2-(difluoromethyl)piperidin-4-yl)isoxazol-3(2H)-one;
5-((2S,4S)-2-((4,4-Difluorocyclohexyl)methyl)piperidin-4-yl)isoxazol-3(2H)-one;
5-((2R,4R)-2-((4,4-Difluorocyclohexyl)methyl)piperidin-4-yl)isoxazol-3(2H)-one;
5-(Trans-2-((4,4-difluorocyclohexyl)methyl)piperidin-4-yl)isoxazol-3(2H)-one;
5-((2S,4S)-2-(4-Fluorophenethyl)piperidin-4-yl)isoxazol-3(2H)-one;
5-((2R,4R)-2-(4-Fluorophenethyl)piperidin-4-yl)isoxazol-3(2H)-one;
5-(Trans-2-(4-fluorophenethyl)piperidin-4-yl)isoxazol-3(2H)-one;
5-((2S,4S)-2-(3,3-Dimethylbutyl)piperidin-4-yl)isoxazol-3(2H)-one;
5-((2R,4S)-2-(3,3-Dimethylbutyl)piperidin-4-yl)isoxazol-3(2H)-one;
5-((2R,4S)-2-(4-Fluorobenzyl)piperidin-4-yl)isoxazol-3(2H)-one;
5-((2S,4S)-2-(4-Fluorobenzyl)piperidin-4-yl)isoxazol-3(2H)-one;
5-((2R,4S)-2-(3-Fluorobenzyl)piperidin-4-yl)isoxazol-3(2H)-one;
5-((2S,4S)-2-(3-Fluorobenzyl)piperidin-4-yl)isoxazol-3(2H)-one;
5-((2R,4S)-2-(2-Fluorobenzyl)piperidin-4-yl)isoxazol-3(2H)-one;
5-((2S,4S)-2-(2-Fluorobenzyl)piperidin-4-yl)isoxazol-3(2H)-one;
5-((42R,4R)-2-(2-Fluorobenzyl)piperidin-4-yl)isoxazol-3(2H)-one;
5-((2R,4S)-2-(4-(Trifluoromethyl)benzyl)piperidin-4-yl)isoxazol-3(2H)-one;
5-((2S,4S)-2-(4-(Trifluoromethyl)benzyl)piperidin-4-yl)isoxazol-3(2H)-one;
5-((2R,4R)-2-(4-(Trifluoromethyl)benzyl)piperidin-4-yl)isoxazol-3(2H)-one;
5-((2R,4S)-2-(3-(Trifluoromethyl)benzyl)piperidin-4-yl)isoxazol-3(2H)-one;
5-((2S,4R)-2-(3-(Trifluoromethyl)benzyl)piperidin-4-yl)isoxazol-3(2H)-one;
5-(Trans-2-(3-(trifluoromethyl)benzyl)piperidin-4-yl)isoxazol-3(2H)-one;
5-((2R,4S)-2-(2-(Trifluoromethyl)benzyl)piperidin-4-yl)isoxazol-3(2H)-one;
5-((2S,4R)-2-(2-(trifluoromethyl)benzyl)piperidin-4-yl)isoxazol-3(2H)-one;
5-(Trans-2-(2-(trifluoromethyl)benzyl)piperidin-4-yl)isoxazol-3(2H)-one;
5-((2R,4S)-2-(4-(Trifluoromethoxy)benzyl)piperidin-4-yl)isoxazol-3(2H)-one;
5-(Trans-2-(4-(trifluoromethoxy)benzyl)piperidin-4-yl)isoxazol-3(2H)-one;
5-((2R,4S)-2-(4-Chlorobenzyl)piperidin-4-yl)isoxazol-3(2H)-one;
5-(Trans-2-(4-chlorobenzyl)piperidin-4-yl)isoxazol-3(2H)-one;
5-((2R,4S)-2-(4-(Methylsulfonyl)benzyl)piperidin-4-yl)isoxazol-3(2H)-one;
5-((2S,4R)-2-(4-(Methylsulfonyl)benzyl)piperidin-4-yl)isoxazol-3(2H)-one;
5-(Trans-2-(4-(methylsulfonyl)benzyl)piperidin-4-yl)isoxazol-3(2H)-one;
5-((2R,4S)-2-(3,4-Difluorobenzyl)piperidin-4-yl)isoxazol-3(2H)-one;
5-((2S,4R)-2-(3,4-Difluorobenzyl)piperidin-4-yl)isoxazol-3(2H)-one;
5-((2S,4S)-2-(3,4-Difluorobenzyl)piperidin-4-yl)isoxazol-3(2H)-one;
5-((2R,4R)-2-(3,4-Difluorobenzyl)piperidin-4-yl)isoxazol-3(2H)-one;
5-((2R,4S)-2-(2,5-Difluorobenzyl)piperidin-4-yl)isoxazol-3(2H)-one;
5-((2S,4R)-2-(2,5-Difluorobenzyl)piperidin-4-yl)isoxazol-3(2H)-one;
5-(Trans-2-(2,5-difluorobenzyl)piperidin-4-yl)isoxazol-3(2H)-one;
5-((2R,4S)-2-(2,6-Difluorobenzyl)piperidin-4-yl)isoxazol-3(2H)-one;
5-((2S,4R)-2-(2,6-Difluorobenzyl)piperidin-4-yl)isoxazol-3(2H)-one;
5-(Trans-2-(2,6-difluorobenzyl)piperidin-4-yl)isoxazol-3(2H)-one;
5-((2R,4S)-2-(3,5-Difluorobenzyl)piperidin-4-yl)isoxazol-3(2H)-one;
5-((2S,4R)-2-(3,5-Difluorobenzyl)piperidin-4-yl)isoxazol-3(2H)-one;
5-((2S,4S)-2-(3,5-Difluorobenzyl)piperidin-4-yl)isoxazol-3(2H)-one;
5-((2R,4R)-2-(3,5-Difluorobenzyl)piperidin-4-yl)isoxazol-3(2H)-one;
5-((2R,4S)-2-(2,4-Difluorobenzyl)piperidin-4-yl)isoxazol-3(2H)-one;
5-((2S,4R)-2-(2,4-Difluorobenzyl)piperidin-4-yl)isoxazol-3(2H)-one;
5-(Trans-2-(2,4-difluorobenzyl)piperidin-4-yl)isoxazol-3(2H)-one;
5-((2R,4S)-2-(3-Fluoro-5-(trifluoromethyl)benzyl)piperidin-4-yl)isoxazol-3(2H)-one;
5-((2S,4R)-2-(3-Fluoro-5-(trifluoromethyl)benzyl)piperidin-4-yl)isoxazol-3(2H)-one;

5-(Trans-2-(3-fluoro-5-(trifluoromethyl)benzyl)piperidin-4-yl)isoxazol-3(2H)-one;
5-((2R,4S)-2-(3-Fluoro-4-(trifluoromethyl)benzyl)piperidin-4-yl)isoxazol-3(2H)-one;
5-((2S,4R)-2-(3-Fluoro-4-(trifluoromethyl)benzyl)piperidin-4-yl)isoxazol-3(2H)-one;
5-(Trans-2-(3-fluoro-4-(trifluoromethyl)benzyl)piperidin-4-yl)isoxazol-3(2H)-one;
5-((2R,4S)-2-(3,4,5-Trifluorobenzyl)piperidin-4-yl)isoxazol-3(2H)-one;
5-((2S,4R)-2-(3,4,5-Trifluorobenzyl)piperidin-4-yl)isoxazol-3(2H)-one;
5-(Trans-2-(3,4,5-trifluorobenzyl)piperidin-4-yl)isoxazol-3(2H)-one;
5-((2R,4S)-2-(3,5-Di-tert-butylbenzyl)piperidin-4-yl)isoxazol-3(2H)-one;
5-((2S,4R)-2-(3,5-Di-tert-butylbenzyl)piperidin-4-yl)isoxazol-3(2H)-one;
5-(Trans-2-(3,5-di-tert-butylbenzyl)piperidin-4-yl)isoxazol-3(2H)-one;
5-((2R,4S)-2-Benzyl-2,3,4,5,6-$d_5$-piperidin-4-yl)isoxazol-3(2H)-one;
5-((2S,4R)-2-Benzyl-2,3,4,5,6-$d_5$-piperidin-4-yl)isoxazol-3(2H)-one; and
5-(Trans-2-benzyl-2,3,4,5,6-$d_5$-piperidin-4-yl)isoxazol-3(2H)-one;
and pharmaceutically acceptable salts thereof.

2. A pharmaceutical composition comprising:
a compound or pharmaceutically acceptable salt thereof according to claim 1, and
a pharmaceutically acceptable carrier or diluent.

3. 5-((2R,4S)-2-neopentylpiperidin-4-yl)isoxazol-3(2H)-one, or a pharmaceutically acceptable salt thereof.

4. A pharmaceutical composition comprising 5-((2R,4S)-2-neopentylpiperidin-4-yl)isoxazol-3(2H)-one, or a pharmaceutically acceptable salt thereof, and a pharmaceutically acceptable carrier or diluent.

* * * * *